United States Patent
Howorka et al.

(10) Patent No.: US 12,275,761 B2
(45) Date of Patent: Apr. 15, 2025

(54) MUTANT CsgG PORES

(71) Applicants: Oxford Nanopore Technologies PLC, Oxford (GB); VIB VZW, Ghent (BE); Vrije Universiteit Brussel, Brussels (BE)

(72) Inventors: Stefan Howorka, London (GB); Han Remaut, Roosbeek (BE); Lakmal Jayasinghe, Oxford (GB); Elizabeth Jayne Wallace, Oxford (GB); James Clarke, Oxford (GB); Richard George Hambley, Oxford (GB); Jonathan Bankes Pugh, Oxford (GB)

(73) Assignees: VIB VZW, Ghent (BE); Vrije Universiteit Brussel, Brussels (BE); Oxford Nanopore Technologies PLC, Oxford (GB)

( * ) Notice: Subject to any disclaimer, the term of this patent is extended or adjusted under 35 U.S.C. 154(b) by 1066 days.

(21) Appl. No.: 17/194,821

(22) Filed: Mar. 8, 2021

(65) Prior Publication Data

US 2021/0292376 A1  Sep. 23, 2021

Related U.S. Application Data

(63) Continuation of application No. 16/522,591, filed on Jul. 25, 2019, now Pat. No. 11,034,734, which is a continuation of application No. 15/507,947, filed as application No. PCT/EP2015/069965 on Sep. 1, 2015, now Pat. No. 10,400,014.

(30) Foreign Application Priority Data

Dec. 11, 2014 (GB) .................................. 1422079
Apr. 21, 2015 (GB) .................................. 1506754
May 14, 2015 (GB) .................................. 1508287

(51) Int. Cl.
| | | |
|---|---|---|
| *C07K 14/245* | (2006.01) | |
| *C12Q 1/68* | (2018.01) | |
| *C12Q 1/6869* | (2018.01) | |
| *C12Q 1/6874* | (2018.01) | |
| *G01N 27/447* | (2006.01) | |

(52) U.S. Cl.
CPC .......... *C07K 14/245* (2013.01); *C12Q 1/6869* (2013.01); *C12Q 1/6874* (2013.01); *G01N 27/447* (2013.01); *C07K 2319/22* (2013.01); *C12Q 1/68* (2013.01); *C12Q 2565/631* (2013.01)

(58) Field of Classification Search
CPC ...... C12Q 1/6869; C12Q 1/6874; C12Q 1/68; C12Q 2565/631; C12Q 2563/116; C12P 19/34
USPC ..... 435/6.1, 91.1, 91.31, 455, 458; 536/23.1
See application file for complete search history.

(56) References Cited

U.S. PATENT DOCUMENTS

| | | |
|---|---|---|
| 5,795,782 A | 8/1998 | Church et al. |
| 6,015,714 A | 1/2000 | Baldarelli et al. |
| 6,114,121 A | 9/2000 | Fujiwara et al. |
| 6,150,112 A | 11/2000 | Weissman et al. |
| 6,362,002 B1 | 3/2002 | Denison et al. |
| 6,426,231 B1 | 7/2002 | Bayley et al. |
| 6,627,067 B1 | 9/2003 | Branton et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 9,073,990 B2 | 7/2015 | Paas et al. |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,562,887 B2 | 2/2017 | Maglia et al. |
| 9,580,480 B2 | 2/2017 | Lu et al. |
| 9,588,079 B2 | 3/2017 | Gundlach et al. |
| 9,732,381 B2 | 8/2017 | Stoddart et al. |
| 9,751,915 B2 | 9/2017 | Clarke et al. |
| 9,777,049 B2 | 10/2017 | Bruce et al. |
| 10,006,905 B2 | 6/2018 | Maglia et al. |
| 10,167,503 B2 | 1/2019 | Clarke et al. |
| 10,266,885 B2 | 4/2019 | Jayasinghe et al. |
| 10,385,389 B2 | 8/2019 | Heron et al. |
| 10,400,014 B2 | 9/2019 | Howorka et al. |
| 10,443,097 B2 | 10/2019 | Jayasinghe et al. |
| 10,472,673 B2 | 11/2019 | Maglia et al. |
| 10,514,378 B2 | 12/2019 | Maglia et al. |

(Continued)

FOREIGN PATENT DOCUMENTS

| | | |
|---|---|---|
| CA | 2381139 A1 | 3/2001 |
| CN | 102116783 A | 7/2011 |

(Continued)

OTHER PUBLICATIONS

Goyal et al (Nature, vol. 516, No. 11 (2014)) (Year: 2014).*

(Continued)

*Primary Examiner* — Jane J Zara

(74) *Attorney, Agent, or Firm* — Wolf, Greenfield & Sacks, P.C.

(57) ABSTRACT

The invention relates to mutant forms of CsgG. The invention also related to analyte detection and characterisation using CsgG.

5 Claims, 60 Drawing Sheets

Specification includes a Sequence Listing.

(56) References Cited

U.S. PATENT DOCUMENTS

| | | | |
|---|---|---|---|
| 10,669,581 B2 | 6/2020 | Stoddart et al. |
| 10,802,015 B2 | 10/2020 | Maglia et al. |
| 10,844,432 B2 | 11/2020 | Jayasinghe et al. |
| 10,882,889 B2 | 1/2021 | Bruce et al. |
| 10,975,428 B2 | 4/2021 | Jayasinghe et al. |
| 10,976,300 B2 | 4/2021 | Maglia et al. |
| 10,976,311 B2 | 4/2021 | Maglia et al. |
| 10,995,372 B2 | 5/2021 | Jayasinghe et al. |
| 11,021,747 B2 | 6/2021 | Garalde et al. |
| 11,034,734 B2 | 6/2021 | Howorka et al. |
| 11,104,709 B2 | 8/2021 | Maglia et al. |
| 11,169,138 B2 | 11/2021 | Maglia et al. |
| 11,186,868 B2 | 11/2021 | Jayasinghe et al. |
| 11,307,192 B2 | 4/2022 | Jayasinghe et al. |
| 11,572,387 B2 | 2/2023 | Remaut et al. |
| 11,597,970 B2 | 3/2023 | Jayasinghe et al. |
| 11,685,949 B2 | 6/2023 | Jayasinghe et al. |
| 11,725,235 B2 | 8/2023 | Heron et al. |
| 11,739,377 B2 | 8/2023 | Jayasinghe et al. |
| 11,761,956 B2 | 9/2023 | Maglia et al. |
| 11,845,780 B2 | 12/2023 | Bruce et al. |
| 11,939,359 B2 | 3/2024 | Jayasinghe et al. |
| 11,945,840 B2 | 4/2024 | Remaut et al. |
| 12,018,326 B2 | 6/2024 | Jayasinghe et al. |
| 12,024,541 B2 | 7/2024 | Remaut et al. |
| 12,084,477 B2 | 9/2024 | Remaut et al. |
| 2001/0044137 A1 | 11/2001 | Heyman et al. |
| 2002/0028458 A1 | 3/2002 | Lexow |
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |
| 2003/0211502 A1 | 11/2003 | Sauer et al. |
| 2003/0215881 A1 | 11/2003 | Bayley et al. |
| 2004/0209299 A1 | 10/2004 | Pinter et al. |
| 2004/0214177 A1 | 10/2004 | Bension |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0121534 A1 | 5/2008 | White et al. |
| 2008/0311582 A1 | 12/2008 | Bayley et al. |
| 2009/0111115 A1 | 4/2009 | Drmanac et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2009/0298188 A1 | 12/2009 | Peti-Peterdi |
| 2010/0075328 A1* | 3/2010 | Bjornson ............ C12Q 1/6874 435/5 |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0194324 A1 | 7/2014 | Gormley et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0152495 A1 | 6/2015 | Stava et al. |
| 2015/0175663 A1 | 6/2015 | Yokoi et al. |
| 2015/0177237 A1 | 6/2015 | Turner et al. |
| 2015/0191709 A1 | 7/2015 | Heron et al. |
| 2015/0218629 A1 | 8/2015 | Heron et al. |
| 2015/0346149 A1 | 12/2015 | Brown et al. |
| 2016/0005330 A1 | 1/2016 | Maglia et al. |
| 2016/0010147 A1 | 1/2016 | Heron et al. |
| 2016/0053300 A1 | 2/2016 | Maglia et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0209952 A1 | 7/2018 | Maglia et al. |
| 2018/0334707 A1 | 11/2018 | Stoddart et al. |
| 2018/0335425 A1 | 11/2018 | Maglia et al. |
| 2018/0364214 A1 | 12/2018 | Maglia et al. |
| 2019/0071721 A1 | 3/2019 | Jayasinghe et al. |
| 2019/0202876 A1 | 7/2019 | Jayasinghe et al. |
| 2019/0300582 A1 | 10/2019 | Jayasinghe et al. |
| 2019/0330282 A1 | 10/2019 | Jayasinghe et al. |
| 2019/0346431 A1 | 11/2019 | Maglia et al. |
| 2020/0017556 A1 | 1/2020 | Howorka et al. |
| 2020/0072824 A1 | 3/2020 | Maglia et al. |
| 2020/0087724 A1 | 3/2020 | Heron et al. |
| 2020/0224262 A1 | 7/2020 | Jayasinghe et al. |
| 2020/0299336 A9 | 9/2020 | Jayasinghe et al. |
| 2020/0299337 A9 | 9/2020 | Jayasinghe et al. |
| 2020/0407785 A1 | 12/2020 | Stoddart et al. |
| 2021/0139972 A1 | 5/2021 | Jayasinghe et al. |
| 2021/0147486 A1 | 5/2021 | Remaut et al. |
| 2021/0147490 A1 | 5/2021 | Remaut et al. |
| 2021/0269872 A1 | 9/2021 | Jayasinghe et al. |
| 2021/0284696 A1 | 9/2021 | Remaut et al. |
| 2021/0317520 A1 | 10/2021 | Jayasinghe et al. |
| 2021/0324020 A1 | 10/2021 | Bruce et al. |
| 2021/0395811 A1 | 12/2021 | Garalde et al. |
| 2021/0405039 A1 | 12/2021 | Maglia et al. |
| 2022/0024985 A9 | 1/2022 | Remaut et al. |
| 2022/0056517 A1 | 2/2022 | Remaut et al. |
| 2022/0064230 A1 | 3/2022 | Jayasinghe et al. |
| 2022/0091096 A1 | 3/2022 | Maglia et al. |
| 2022/0119879 A1 | 4/2022 | Jayasinghe et al. |
| 2022/0154269 A9 | 5/2022 | Jayasinghe et al. |
| 2022/0162264 A9 | 5/2022 | Remaut et al. |
| 2022/0283141 A1 | 9/2022 | Jayasinghe et al. |
| 2023/0079731 A1 | 3/2023 | Remaut et al. |
| 2023/0295715 A1 | 9/2023 | Jayasinghe et al. |
| 2024/0026441 A1 | 1/2024 | Heron et al. |
| 2024/0044881 A1 | 2/2024 | Maglia et al. |
| 2024/0060126 A1 | 2/2024 | Jayasinghe et al. |
| 2024/0117422 A1 | 4/2024 | Jayasinghe et al. |
| 2024/0199711 A1 | 6/2024 | Bruce et al. |
| 2024/0254172 A1 | 8/2024 | Maglia et al. |

FOREIGN PATENT DOCUMENTS

| | | |
|---|---|---|
| CN | 102174554 A | 9/2011 |
| CN | 102216783 A | 10/2011 |
| CN | 102317310 A | 1/2012 |
| CN | 103460040 A | 12/2013 |
| CN | 102245760 A | 5/2014 |
| EP | 2194123 B1 | 8/2012 |
| EP | 2682460 A1 | 1/2014 |
| GB | 2453377 A | 4/2009 |
| GB | 1314695.6 | 8/2013 |
| JP | H10-146190 A | 6/1998 |
| JP | 2005-253427 A | 9/2005 |
| JP | 2015-514128 A | 5/2015 |
| WO | WO 1999/005167 A1 | 2/1999 |
| WO | WO 2000/028312 A1 | 5/2000 |
| WO | WO 2001/042782 A1 | 6/2001 |
| WO | WO 2001/059453 A2 | 8/2001 |
| WO | WO 2002/042496 A2 | 5/2002 |
| WO | WO 2003/095669 A1 | 11/2003 |
| WO | WO 2005/013666 A2 | 2/2005 |
| WO | WO 2005/076010 A2 | 8/2005 |

(56) References Cited

FOREIGN PATENT DOCUMENTS

| | | | |
|---|---|---|---|
| WO | WO 2006/028508 A2 | 3/2006 | |
| WO | WO 2006/100484 A2 | 9/2006 | |
| WO | 2007/119880 * | 4/2007 | ............ C12P 19/34 |
| WO | WO 2007/057668 A1 | 5/2007 | |
| WO | WO 2007/075987 A1 | 7/2007 | |
| WO | WO 2007/084103 A2 | 7/2007 | |
| WO | WO 2008/102120 A1 | 8/2008 | |
| WO | WO 2008/102121 A1 | 8/2008 | |
| WO | WO 2008/124107 A1 | 10/2008 | |
| WO | WO 2009/020682 A2 | 2/2009 | |
| WO | WO 2009/024775 A1 | 2/2009 | |
| WO | WO 2009/035647 A1 | 3/2009 | |
| WO | WO 2009/044170 A1 | 4/2009 | |
| WO | WO 2009/077734 A2 | 6/2009 | |
| WO | WO 2009/143425 A1 | 11/2009 | |
| WO | WO 2010/004265 A1 | 1/2010 | |
| WO | WO 2010/004273 A1 | 1/2010 | |
| WO | WO 2010/034018 A2 | 3/2010 | |
| WO | WO 2010/055307 A1 | 5/2010 | |
| WO | WO 2010/086602 A1 | 8/2010 | |
| WO | WO 2010/086603 A1 | 8/2010 | |
| WO | WO 2010/086622 A1 | 8/2010 | |
| WO | WO 2010/122293 A1 | 10/2010 | |
| WO | WO 2010/148126 A1 | 12/2010 | |
| WO | WO 2011/067559 A1 | 6/2011 | |
| WO | WO 2012/005857 A1 | 1/2012 | |
| WO | WO 2012/042226 A1 | 4/2012 | |
| WO | WO 2012/042226 A2 | 4/2012 | |
| WO | WO 2012/107778 A2 | 8/2012 | |
| WO | WO 2012/164270 A1 | 12/2012 | |
| WO | WO 2013/014451 A1 | 1/2013 | |
| WO | WO 2013/041878 A1 | 3/2013 | |
| WO | WO 2013/057495 A1 | 4/2013 | |
| WO | WO 2013/057495 A2 | 4/2013 | |
| WO | WO 2013/098561 A1 | 7/2013 | |
| WO | WO 2013/098562 A1 | 7/2013 | |
| WO | WO 2013/098562 A2 | 7/2013 | |
| WO | WO 2013/109970 A1 | 7/2013 | |
| WO | 2013153359 A1 † | 10/2013 | |
| WO | WO 2014/078489 A1 | 10/2013 | |
| WO | WO 2014/013259 A1 | 1/2014 | |
| WO | WO 2014/013260 A1 | 1/2014 | |
| WO | WO 2014/013262 A1 | 1/2014 | |
| WO | WO 2014/064443 A1 | 5/2014 | |
| WO | WO 2014/064444 A1 | 5/2014 | |
| WO | WO 2014/122654 A2 | 8/2014 | |
| WO | WO 2014/135838 A1 | 9/2014 | |
| WO | WO 2014/142850 A1 | 9/2014 | |
| WO | WO 2014/153047 A1 | 9/2014 | |
| WO | WO 2014/153625 A1 | 10/2014 | |
| WO | WO 2014/187924 A1 | 11/2014 | |
| WO | WO 2015/022544 A1 | 2/2015 | |
| WO | WO 2015/051378 A1 | 4/2015 | |
| WO | WO 2015/055981 A1 | 4/2015 | |
| WO | WO 2015/055981 A2 | 4/2015 | |
| WO | WO 2015/097289 A1 | 7/2015 | |
| WO | WO 2015/110777 A1 | 7/2015 | |
| WO | WO 2015/124935 A1 | 8/2015 | |
| WO | WO 2015/150786 A1 | 10/2015 | |
| WO | WO 2015/150787 A1 | 10/2015 | |
| WO | WO 2015/166275 A1 | 11/2015 | |
| WO | WO 2015/166276 A1 | 11/2015 | |
| WO | WO 2016/034591 A2 | 3/2016 | |
| WO | WO 2016/055778 A1 | 4/2016 | |
| WO | WO 2016/166232 A1 | 10/2016 | |
| WO | WO 2017/149316 A1 | 9/2017 | |
| WO | WO 2017/149317 A1 | 9/2017 | |
| WO | WO 2017/149318 A1 | 9/2017 | |
| WO | WO 2018/146491 A1 | 8/2018 | |
| WO | WO 2018/211241 A1 | 11/2018 | |
| WO | WO 2019/002893 A1 | 1/2019 | |

OTHER PUBLICATIONS

Howorka et al (Nature, vol. 19, pp. 636-639 (2002)) (Year: 2002).*
Goyal et al., Structural and mechanistic insights in the bacterial amyloid secretion channel CsgG, Nature, vol. 516, pp. 250-253 (2014)).*
International Search Report and Written Opinion for Application No. PCT/EP2015/069965, mailed Apr. 25, 2016.
International Preliminary Report on Patentability for Application No. PCT/EP2015/069965, mailed Mar. 16, 2017.
[No Author Listed] EBI Accession No. GSP:AXX09397. May 13, 2010.
[No Author Listed] EBI Accession No. A0A085GH19. Oct. 29, 2014.
[No Author Listed] EBI Accession No. A0A0DILDB9. Apr. 29, 2015.
[No Author Listed] EBI Accession No. EMBLCDS:ABV05494. Sep. 11, 2007.
[No Author Listed] Enterobacteria phage vB_EcoM-ACG-C40, complete genome. Genbank Acc. No. NC 019399.1. 2 pages.
[No Author Listed] Helicos BioSciences Corporation, "Helicos Genetic Analysis System," Specification Sheet retrieved online at: www.helicosbio.com/Portals/0/Documents/Helicos_SalesSpec.pdf, 4 pages (2008).
[No Author Listed] Uniprot Accession No. A0A081NL13. Oct. 29, 2014. 4 pages.
[No Author Listed] Uniprot Accession No. A0A0P7DN88. Jan. 20, 2016. 4 pages.
[No Author Listed] Uniprot Accession No. Q8Z727. Oct. 24, 2003. 6 pages.
[No Author Listed], *Escherichia coli* HS curli production assembly/transport subunit. Accession No. ABV05494. Sep. 11, 2007. 2 pages.
Ahern, Biochemical, reagents kits offer scientists good return on investment. The Scientist. Jul. 24, 1995;9(15):20.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Aoki et al., Single channel properties of lysenin measured in artificial lipid bilayers and their applications to biomolecule detection. Proc Jpn Acad Ser B Phys Biol Sci. 2010;86(9):920-5.
Aravind et al., The DNA-Repair Protein AlkB, EGL-9, and Leprecan Define New Families of 2-oxoglutarate-andIron-Dependent Dioxygenases. Genome Biology. 2001;2:1-8.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Ashton et al., MinION Nanopore Sequencing Identifies the Position and Structure of a Bacterial antibiotic Resistance Island. Nat Biotechnol. Mar. 2015;33(3):296-302.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Atkins et al., Structure-function relationships of a novel bacterial toxin, hemolysin E. The role of alpha G. J Biol Chem. Dec. 29, 2000;275(52):41150-5.
Avrameas, Coupling of enzymes to proteins with glutaraldehyde. Use of the conjugates for the detection of antigens and antibodies. Immunochemistry. Jan. 1969;6(1):43-52.
Bayley et al., Stochastic sensors inspired by biology. Nature. Sep. 13, 2001;413(6852):226-30.
Bayley et al., Wrestling with native chemical ligation. ACS Chem Biol. Dec. 18, 2009;4(12):983-5. doi: 10.1021/cb900304p.
Bayley, Membrane-protein structure: Piercing insights. Nature. Jun. 4, 2009;459(7247):651-2. doi: 10.1038/459651a.

(56) References Cited

OTHER PUBLICATIONS

Bayley, Nanopore Sequencing: From Imagination to Reality. Clin Chem. 2015;61(1):25-31.
Bayley, Sequencing single molecules of DNA. Curr Opin Chem Biol. Dec. 2006; 10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bezrukov et al., Counting Polymers Moving Through a Single Ion Channel. Nature. Jul. 28, 1994;370:279-81.
Bianco et al., Helicase unwinding: active or merely perfect? J Mol Biol. Jul. 13, 2012;420(3):139-40. doi: 10.1016/j.jmb.2012.04.030. Epub May 2, 2012.
Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.
Bleijlevens et al., Dynamic States of the DNA Repair Enzyme AlkB regulate Product Release. Eur Mol Biol Org. Jul. 11, 2008;9(9):872-77.
Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.
Bourdon et al., Molecular cloning and sequence analysis of a chondroitin sulfate proteoglycan cDNA. Proc Natl Acad Sci U S A. Mar. 1985;82(5):1321-5.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 3, 20080;105(52):20647-52. doi: 10.1073/pnas.0807514106. Epub Dec. 19, 2008.
Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.
Cao et al., Structure of the nonameric bacterial amyloid secretion channel. Proc Natl Acad Sci USA. Dec. 1, 20146;111(50):E5439-44. doi: 10.1073/pnas.1411942111. Epub Dec. 1, 2014.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997; 10(12):1433-43.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.
Chin et al., The Metabolite alpha-Ketoglutarate Extends Lifespan by Inhibiting ATP Synthase and TOR. Nature. Jul. 19, 2014;510:397-401.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., A Novel DNA Sensing Technique Using Nanopore MSPA. 54th Annual Meeting of the Biophysical Society, Poster 2182-Plat, 2 pages (2010).
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eifier et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
Engelhardt et al., A tetrameric porin limits the cell wall permeability of *Mycobacterium smegmatis*. J Biol Chem. Oct. 4, 2002;277(40):37567-72. Epub Jul. 18, 2002.
Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.
Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.
Franceschini et al., A nanopore machine promotes the vectorial transport of DNA across membranes. 2013 Sept; Nat Commun. 2013;4:2415. doi: 10.1038/ncomms3415.
Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.
Freedman et al., Single Molecule Unfolding and Stretching of Protein Domains Inside a Solid-State Nanopore by Electric Field. Scientific Reports. Apr. 10, 2013;3(1638):1-8.

(56) References Cited

OTHER PUBLICATIONS

Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gilbert et al., Two Structural Transitions in Membrane Pore Formation by Pneumolysin, the Pore-Forming Toxin of *Streptococcus Pneumoniae*. Cell. May 28, 1999;97:647-655.
Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.
Gouridis et al., Conformational Dynamics in Substrate-Binding Domains Influences Transport in the ABC Importer GinPQ. Nat Stuct Mol Biol. Dec. 8, 2014;22(1):57-66.
Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.
Goyal et al., Structural and mechanistic insights into the bacterial amyloid secretion channel CsgG. Nature. Dec. 11, 2014;516(7530):250-3. doi: 10.1038/nature13768. Epub Sep. 14, 2014.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Interaction of the noncovalent molecular adapter, beta-cyclodextrin, with the staphylococcal alpha-hemolysin pore. Biophys J. Oct. 2000;79(4):1967-75.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Guasch et al., Detailed architecture of a DNA translocating machine: the high-resolution structure of the bacteriophage phi29 connector particle. J Mol Biol. Jan. 25, 2002;315(4):663-76.
Guo et al., Nanopore sensor for copper ion detection using a polyamine decorated β-cyclodextrin as the recognition element. RSC Adv. 2017;7:15315. doi: 10.1039/c7ra00454k. 6 pages.
Hall et al., Hybrid pore formation by directed insertion of ?-haemolysin into solid-state nanopores. Nat Nanotechnol. Dec. 2010;5(12):874-7. doi: 10.1038/nnano.2010.237. Epub Nov. 28, 2010.
Han et al., Characterization and optimization of an entropic trap for DNA separation. Anal Chem. Jan. 1, 20025;74(2):394-401.
Han et al., RecJ exonuclease: substrates, products and interaction with SSB. Nucleic Acids Res. Feb. 18, 2006;34(4):1084-91. Print 2006.
Haque et al., Solid-State and Biological Nanopore for Real-Time Sensing of Single Chemical and Sequencing of DNA. Nano Today. Feb. 2013;8(1):56-74.
He et al. 2012; The T4 phage SF1 B helicase dda is structurally optimized to perform DNA strand separation. Structure. 20:1189-1200.
Henrickson et al., Driven DNA transport into an asymmetric nanometer-scale pore. Phys Rev Lett. Oct. 2, 2000;85(14):3057-60.
Heron et al., Direct detection of membrane channels from gels using water-in-oil droplet bilayers. J Am Chem Soc. Dec. 26, 2007;129(51):16042-7. Epub Dec. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{ 1, pt. 2):508a, No. 2482-Plat (2002).
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Nanopore Analytics: Sensing of Single Molecules. The Royal Society of Chemistry. Jun. 15, 2009;38:2360-84.
Howorka et al., Nanopores as protein sensors. Nat Biotechnol. Jun. 7, 2012;30(6):506-7. doi: 10.1038/nbt.2264.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Huff et al., Functions of the periplasmic loop of the porin MspA from *Mycobacterium smegmatis*. J Biol Chem. Apr. 1, 20090;284(15):10223-31. doi: 10.1074/jbc.M808599200. Epub Feb. 10, 2009.
Hwang et al., Electrical behavior of droplet interface bilayer networks: experimental analysis and modeling. J Am Chem Soc. Sep. 26, 2007;129(38):11854-64. Epub Sep. 1, 2007.
Iacovache et al., Structure and assembly of pore-forming proteins. Curr Opin Struct Biol. Apr. 2010;20(2):241-6. doi:10.1016/j.sbi.2010.01.013. Epub Feb. 19, 2010.
Ide et al., Lysenin forms a voltage-dependent channel in artificial lipid bilayer membranes. Biochem Biophys Res Commun. Jul. 2, 20061;346(1):288-92. Epub May 26, 2006.
Ivanov et al., DNA tunneling detector embedded in a nanopore. Nano Lett. Jan. 12, 2011;11(1):279-85. doi: 10.1021/nl103873a. Epub Dec. 6, 2010.
Jayasinghe et al., The leukocidin pore: evidence for an octamer with four LukF subunits and four LukS subunits alternating around a central axis. Protein Sci. Oct. 2005;14(10):2550-61.
Johnston et al., Coexpression of proteins in bacteria using T7-based expression plasmids: expression of heteromeric cell-cycle and transcriptional regulatory complexes. Protein Expr Purif. Dec. 2000;20(3):435-43.
Jung et al., The internal cavity of the staphylococcal alpha-hemolysin pore accommodates approximately 175 exogenous amino acid residues. Biochemistry. Jun. 28, 2005;44(25):8919-29.
Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.

(56) References Cited

OTHER PUBLICATIONS

Khulbe et al., DNA translocation through a-hemolysin nanopores with potential application to macromolecular data storage. Journal Applied Physics, vol. 97(104317):1-7 (2005).

Kobayashi et al., Comparative Physiology and Biochemistry, 2005, vol. 22, No. 3-4, pp. 139-148.

Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.

Krylova et al., DNA aptamers for as analytical tools for the quantitative analysis of DNA-dealkylating enzymes. Anal Biochem. 2011;414(2):261-265. doi:10.1016/j.ab.2011.03.010.

Kumar et al., PEG-labeled nucleotides and nanopore detection for single molecule DNA sequencing by synthesis. Sci Rep. 2012;2:684. Epub Sep. 21, 2012.

Langecker et al., Synthetic lipid membrane channels formed by designed DNA nanostructures. Science. Nov. 16, 2012;338(6109):932-6. doi: 10.1126/science.1225624.

Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.

Li et al., DNA molecules and configurations in a solid-state nanopore microscope. Nat Mater. Sep. 2003;2(9):611-5. Epub Aug. 24, 2003.

Lieberman et al., Processive replication of single DNA molecules in a nanopore catalyzed by phi29 DNA polymerase. J Am Chem Soc. Dec. 2, 20102;132(50):17961-72. doi: 10.1021/ja1087612. Epub Dec. 1, 2010.

Lu et al., Protein Motion and Configurations in a Form-Fitting Nanopore: Avidin in ClyA. Biophys J. Sep. 4, 2018; 115(5): 801-808. Epub Aug. 4, 2018. doi: 10.1016/j.bpj.2018.07.024.

Luchian et al., Single-Molecule Covalent Chemistry with Spatially Separated Reactants. Angew. Chem. Int. Ed. 2003;42:3766-771.

Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.

Luo et al., Influence of polymer-pore interactions on translocation. Phys Rev Lett. Oct. 5, 2007;99(14):148102. Epub Oct. 1, 2007.

Maglia et al., DNA strands from denatured duplexes are translocated through engineered protein nanopores at alkaline pH. Nano Lett. Nov. 2009;9(11):3831-6. doi: 10.1021/nl9020232.

Maglia et al., Engineering a Biomimetic Biological Nanopore to Selectively Capture Folded Target Proteins. Biophysical J. Feb. 5, 2013;104(2):518a.

Maglia et al., Enhanced translocation of single DNA molecules through alpha-hemolysin nanopores by manipulation of internal charge. Proc Natl Acad Sci U S A. Dec. 16, 2008;105(50):19720-5. doi: 10.1073/pnas.0808296105. Epub Dec. 5, 2008.

Makaram et al., Trends in Nanomaterial-Based Non-Invasive Diabetes Sensing Technologies. Diagnostics. Apr. 21, 2014;4:27-46.

Manrao et al., Nucleotide Discrimination with DNA Immobilized in the MspA Nanopore. PLoS One, vol. 6(10):e25723, 7 pages (2011).

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Manrao et al., Single Nucleotide Discrimination in Single Stranded DNA Immobilized within Biological Nanopre MSPA. 54th Annual Meeting of the Biophysical Society, 3 pages (2010).

Martin et al., Nanoscale protein pores modified with PAMAM dendrimers. J Am Chem Soc. Aug. 8, 2007;129(31):9640-9. Epub Jul. 18, 2007.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Mikheyev et al., A First Look at the Oxford Nanopore MinION Sequencer. Mol Ecol Res. 2014;14:1097-1102.

Miles et al., The Staphylococcal Leukocidin Bicomponent Toxin Forms Large Ionic Channels. Biochemistry. Jun. 28, 2001;40:8514-522.

Mitchell et al., Chemical tags facilitate the sensing of individual DNA strands with nanopores. Angew Chem Int Ed Engl. 2008;47(30):5565-8. doi:10.1002/anie.200800183.

Miyazaki et al., MEGAWHOP Cloning: A Method of Creating Random Mutagenesis Libraries via Megaprimer PCR of Whole Plasmids. Methods in Enzymology. 2011;498:399-406.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Moreau et al., Coupling ion channels to receptors for biomolecule sensing. Nat Nanotechnol. Oct. 2008;3(10):620-5. doi: 10.1038/nnano.2008.242. Epub Sep. 7, 2008.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Moyer et al., Correlation Between Sweat Glucose and Blood Glucose in Subjects with Diabetes. Diabetes Technol Ther. 2012:14(5):398-402.

Mueller et al., RCSB Protein Data Bank No. 2WCD. Mar. 11, 2009. doi: 10.2210/pdb2WCD/pdb. 5 pages.

Mueller et al., The Structure of Cytolytic alpha-Helical Toxin Pore Reveals its Assembly Mechanism. Nature. Jun. 4, 2009;459:726-731.

Mueller et al., The Structure of Cytolytic alpha-Helical Toxin Pore Reveals its Assembly Mechanism. Nature. Jun. 4, 2009;459:Supplemental Information.

Muller et al., DNA-directed assembly of artificial multienzyme complexes. Biochem Biophys Res Commun. Dec. 5, 2008;377(1):62-7. doi: 10.1016/j.bbrc.2008.09.078. Epub Sep. 25, 2008.

Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R 1365-R1393 (2003).

Niedzwiecki et al., Inspection of the Engineered FhuA deltaC/delta4L Protein Nanopore by Polymer Exclusion. Biophys J. Nov. 2012;103:2115-124.

Nikolaidou et al., alpha-Ketoglutarate: Biological Effects of a Novel Biomarker of Heart Failure. Heart. Sep. 2010;96(17). 2 pages.

Nivala et al., Unfoldase-mediated protein translocation through an α-hemolysin nanopore. Nat Biotechnol. Mar. 2013;31(3):247-50. doi: 10.1038/nbt.2503. Epub Feb. 3, 2013.

Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. 2009Nov;32(11):1819-18223.

(56) References Cited

OTHER PUBLICATIONS

Oukhaled et al., Dynamics of Completely Unfolded and Native Proteins through Solid-State Nanopores as a Function of Electric Driving Force. Am Chem Soc. 2011 Arp 8;5(5):3628-38.
Pavlenok et al., Hetero-oligomeric MspA pores in *Mycobacterium smegmatis*. FEMS Microbiol Lett. Apr. 2016;363(7). pii: fnw046. doi:10.1093/femsle/fnw046. Epub Feb. 23, 2016.
Pavlenok et al., MspA nanopores from subunit dimers. PLoS One. 2012;7(6):e38726. doi: 10.1371/journal.pone.0038726. Epub Jun. 18, 2012.
Pfeiffer et al., Bivalent cholesterol-based coupling of oligonucleotides to lipid membrane assemblies. J Am Chem Soc. Aug. 25, 2004;126(33):10224-5.
Plesa et al., Fast Translocation of Proteins through Solid State Nanopores. Nano Lett. Jan. 23, 2013:13:658-663.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Quick et al., A reference Bacterial Genome Dataset Generated on the MinION Portable Single-Molecule Nanopore Sequencer. GigaScience. 2014;3(22):1-6.
Rajagopalan et al., Interaction of Dihydrofolate Reductase with Methotrexate: Ensemble and Single-Molecule Kinetics. PNAS. Oct. 15, 2002;99(21):13481-6.
Rasko et al., The pangenome structure of *Escherichia coli*: comparative genomic analysis of *E. coli* commensal and pathogenic isolates. J Bacteriol. Oct. 2008;190(20):6881-93. doi:10.1128/JB.00619-08. Epub Aug. 1, 2008.
Rhee et al., Nanopore sequencing technology: research trends and applications. Trends Biotechnol. Dec. 2006;24(12):580-6. Epub Oct. 19, 2006.
Robinson et al., Secretion of curli fibre subunits is mediated by the outer membrane-localized CsgG protein. Mol Microbiol. Feb. 2006;59(3):870-81.
Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.
Rotem et al., Protein detection by nanopores equipped with aptamers. J Am Chem Soc. Feb. 8, 2012;134(5):2781-7. doi:10.1021/ja2105653. Epub Jan. 26, 2012.
Rucker et al., Recombinant ferritin: modulation of subunit stoichiometry in bacterial expression systems. Protein Eng. 1997;10(8):967-973. doi: 10.1093/protein/10.8.967.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon end DNA hairpin substrates. Nucleic Acids Res. Jun. 6, 2006;34(10):3139-49.
Sanchez-Quesada et al., Cyclic Peptides as Molecular Adaptors for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Skocaj et al., The sensing of membrane microdomains based on pore-forming toxins. Curr Med Chem. 2013;20(4):491-501.
Smeets et al., Salt dependence of ion transport and DNA translocation through solid-state nanopores. Nano Lett. Jan. 2006;6(1):89-95.
Soni et al., Synchronous optical and electrical detection of biomolecules traversing through solid-state nanopores. Rev Sci Instrum. Jan. 2010;81(1):014301. doi: 10.1063/1.3277116.
Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012.
Soskine et al., Single-Molecule Analyte Recognition with ClyA Nanopores Equipped with Internal Protein Adaptors. J Am Chem Soc. 2015;137:5793-97.
Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Taylor et al., Atomic resolution insights into curli fiber biogenesis. Structure. Sep. 7, 2011;19(9):1307-16. doi: 10.1016/j.str.2011.05.015.
Trewick et al., Oxidative Demethylation by *Escherichia coli* AlkB Directly Reverts DNA Base Damage. Nature. Sep. 12, 2002:419:174-78.
Van De Goor, Nanopore Detection: Threading DNA Through a Tiny Hole. PharmaGenomics, vol. 4 (3):28-30 (2004).
Van Gerven et al., Secretion and functional display of fusion proteins through the curlibiogenesis pathway. Mol Microbiol. Mar. 2014;91(5):1022-35. doi:10.1111/mmi.12515. Epub Feb. 12, 2014.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Van Meervelt et al., Detection of Two Isomeric Binding Configurations in a Protein-Aptamer Complex with a Biological Nanopore. Am Chem Soc. Dec. 10, 2014;8(12):12826-35.
Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wallace et al., *E. coli* hemolysin E (HlyE, ClyA, SheA): X-ray crystal structure of the toxin and observation of membrane pores by electron microscopy. Cell. Jan. 21, 2000;100(2):265-76.
Wang et al., Nanopores with a spark for single-molecule detection. Nat Biotechnol. Jul. 2001;19(7):622-3.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wanunu, Nanopores: A journey towards DNA sequencing. Phys Life Rev. Jun. 2012;9(2):125-58. doi:10.1016/j.plrev.2012.05.010. Epub May 18, 2012.
Welford et al., The Selectivity and Inhibition of AlkB. J. Biol. Chem. Mar. 21, 2003;278(12):10157-161.
Wendell et al., Translocation of double-stranded DNA through membrane-adapted phi29 motor protein nanopores. Nat Nanotechnol. 2009;4(11):765-772. doi: 10.1038/nnano.2009.259.
White et al., Single Ion-Channel Recordings Using Glass Nanopore Membranes. J Am Chem Soc. 2007;129:11766-775.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.

(56) References Cited

OTHER PUBLICATIONS

Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.
Yoo et al., Glucose Biosensors: An Overview of Use in Clinical Practice. Sensores. May 4, 2010;10:4558-4576.
Zernia et al., Current Blockades of Proteins inside Nanopores for Real-Time Metabolome Analysis. ACS Nano. Feb. 25, 2020; 14(2): 2296-2307. EPub Jan. 31, 2020. doi: 10.1021/acsnano.9b09434.
Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano.9b09434. 19 pages.
Zhou et al., Ion Channel Probes for Scanning Ion Conductance Microscopy. Langmuir. Nov. 25, 2014;30:15351-355.
Epstein, Assembly, Spatial Distribution, and Secretion Activity of the Curlin Secretion Lipoprotein, CsgG. Dissertation. The University of Michigan. 2008. 167 pages.
Heng et al., Sizing DNA using a nanometer-diameter pore. Biophys J. Oct. 2004;87(4):2905-11. doi: 10.1529/biophysj.104.041814. Epub Aug. 23, 2004.
Sivanathan et al., Generating extracellular amyloid aggregates using *E. coli* cells. Genes Dev. Dec. 1, 2012;26(23):2659-67. doi: 10.1101/gad.205310.112. Epub Nov. 19, 2012.
Third Party Observation for Application No. EP 15759438.3 mailed Sep. 17, 2021. 21 pages.
Wang et al., Engineering of protein nanopores for sequencing, chemical or protein sensing and disease diagnosis. Curr Opin Biotechnol. Jun. 2018;51:80-89. doi: 10.1016/j.copbio.2017.11.006. Epub Dec. 10, 2017.
[No Author Listed] NCBI Genbank Accession No. ABV05494. Jan. 31, 2014, 1 page.
[No Author Listed] Nextera™ DNA Sample Preparation Kits (Illumina) Oct. 2011. (2 pages).
[No Author Listed] Oxford Nanopore "Product" brochure (2020) https://nanoporetech.com/sites/default/files/s3/literature/product-brochure.Pdf (36 pages).
[No Author Listed] Protein Databank entries of AlphaFold structure prediction for POAE98 and POA202, 2 pages.
[No Author Listed] Uniprot Accession No. POAE98 and POA202 search results, last accessed Mar. 29, 2022. 4 pages.
[No Author Listed] UniProt, "SubName: Full=Curli production assembly/transport component {ECO:0000313:EMBL:CTR43957.1};", XP002783536, retrieved from EBI accession No. UNIPROT:A0A0K3UZP3, Nov. 11, 2015.
[No Author Listed] UniprotKB Accession No. N2DXI0, Jun. 26, 2013, 1 page.
Afonine et al., Real-space refinement in PHENIX for cryo-EM and crystallography. Acta Crystallogr D Struct Biol. 2018;74(Pt 6):531-544. doi:10.1107/S2059798318006551.
Altschul et al. Basic local alignment search tool. J Mol Biol. Oct. 5, 1990;215(3):403-10. doi: 10.1016/S0022-2836(05)80360-2.
Altschul, A protein alignment scoring system sensitive at all evolutionary distances. J Mol Evol. Mar. 1993;36(3):290-300. doi: 10.1007/BF00160485.
Ayub et al., Engineered transmembrane pores. Curr Opin Chem Biol. 2016;34:117-126. doi:10.1016/j.cbpa.2016.08.005. Author Manuscript, 16 pages.
Brown et al., Tools for macromolecular model building and refinement into electron cryo-microscopy reconstructions. Acta Crystallogr D Biol Crystallogr. 2015;71(Pt 1):136-153. doi:10.1107/S1399004714021683.
Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.
Cao et al., Mapping the sensing spots of aerolysin for single oligonucleotides analysis. Nat Commun. Jul. 19, 2018;9(1):2823. doi: 10.1038/s41467-018-05108-5. 9 pages.

Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.
Chapman et al., Role of *Escherichia coli* curli operons in directing amyloid fiber formation. Science. 2002;295(5556):851-855. doi:10.1126/science.1067484. Author Manuscript, 9 pages.
Chin et al., Addition of a photocrosslinking amino acid to the genetic code of *Escherichia coli*. Proc Natl Acad Sci U S A. Aug. 20, 2002;99(17):11020-4. doi: 10.1073/pnas.172226299. Epub Aug. 1, 2002.
Colas et al., Microscopical investigations of nisin-loaded nanoliposomes prepared by Mozafari method and their bacterial targeting. Micron. 2007;38(8):841-7. doi: 10.1016/j.micron.2007.06.013. Epub Jul. 3, 2007.
De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.
Devereux et al., A comprehensive set of sequence analysis programs for the VAX. Nucleic Acids Res. Jan. 11, 1984;12(1 Pt 1):387-95. doi: 10.1093/nar/12.1part1.387.
Devos et al., Practical limits of function prediction. Proteins. Oct. 1, 2000;41(1):98-107.
Dong et al., Oroxylin A inhibits hemolysis via hindering the self-assembly of α-hemolysin heptameric transmembrane pore. PLoS Comput Biol. 2013;9(1):e1002869. doi: 10.1371/journal.pcbi.1002869. Epub Jan. 17, 2013.
Fiaschi et al., Auto-Assembling Detoxified *Staphylococcus aureus* Alpha-Hemolysin Mimicking the Wild-Type Cytolytic Toxin. Clin Vaccine Immunol. Jun. 6, 2016;23(6):442-50. doi: 10.1128/CVI.00091-16.
Fiume et al., Savant: genome browser for high-throughput sequencing data. Bioinformatics. Aug. 15, 2010;26(16):1938-44. doi: 10.1093/bioinformatics/btq332. Epub Jun. 20, 2010.
Fleckenstein et al., "UPI0002CA1AFE" Uniprot Accession Number, https://www.uniprot.org/uniparc/UPI0002CA1AFE, Jun. 26, 2013 (Jun. 26, 2013).
Ghanem et al., Chimeric mutants of staphylococcal hemolysin, which act as both one-component and two-component hemolysin, created by grafting the stem domain. FEBS J. Jun. 2022;289(12):3505-3520. doi: 10.1111/febs.16354. Epub Feb. 16, 2022.
Gibson et al., AgfC and AgfE facilitate extracellular thin aggregative fimbriae synthesis in *Salmonella enteritidis*. Microbiology. Apr. 2007;153(Pt 4):1131-1140. doi: 10.1099/mic.0.2006/000935-0.
González-Pérez et al., Biomimetic triblock copolymer membrane arrays: a stable template for functional membrane proteins. Langmuir. Sep. 15, 2009;25(18):10447-50. doi: 10.1021/la902417m.
Goryshin et al., Tn5 in vitro transposition. J Biol Chem. Mar. 27, 1998;273(13):7367-74. doi: 10.1074/jbc.273.13.7367.
Goyal et al., Crystallization and preliminary X-ray crystallographic analysis of the curli transporter CsgG. Acta Crystallographica Section F: Structural Biology and Crystallization Communications. Dec. 1, 2013;69(12):1349-53.
Hammar et al., Expression of two csg operons is required for production of fibronectin- and congo red-binding curli polymers in *Escherichia coli* K-12. Mol Microbiol. Nov. 1995;18(4):661-70. doi: 10.1111/j.1365-2958.1995.mmi_18040661.x..
Haque et al., DNA-associated click chemistry. Science China Chemistry. Feb. 2014;57(2):215-231. doi:10.1007/s11426-013-5035-1.
Higgins et al., DNA-joining enzymes: a review. Methods Enzymol. 1979;68:50-71. doi: 10.1016/0076-6879(79)68006-0.
Ho et al., Engineering a nanopore with co-chaperonin function. Sci Adv. Dec. 11, 2015;1(11):e1500905. doi: 10.1126/sciadv.1500905. 9 pages.
Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17 (1):256.
Juncker et al., Prediction of lipoprotein signal peptides in Gram-negative bacteria. Protein Sci. 2003;12(8):1652-1662. doi:10.1110/ps.0303703.

(56) References Cited

OTHER PUBLICATIONS

Kanaan et al., UPF1-like helicase grip on nucleic acids dictates processivity. Nat Commun. Sep. 1, 2018;9(1):3752. doi: 10.1038/s41467-018-06313-y.

Kimanius et al., Accelerated cryo-EM structure determination with parallelisation using GPUs in RELION-2. Elife. 2016;5:e18722. Published Nov. 15, 2016. doi: 10.7554/eLife.18722. 21 pages.

Kisselev, Polypeptide release factors in prokaryotes and eukaryotes: same function, different structure. Structure. Jan. 2002;10(1):8-9. doi: 10.1016/s0969-2126(01)00703-1.

Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.

Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.

Li et al., ChIA-PET tool for comprehensive chromatin interaction analysis with paired-end tag sequencing. Genome Biol. 2010;11(2):R22. doi: 10.1186/GB-2010-11-2-r22. Epub Feb. 25, 2010.

Li, Minimap2: pairwise alignment for nucleotide sequences. Bioinformatics. 2018;34(18):3094-3100. doi: 10.1093/bioinformatics/bty191.

Loferer et al., Availability of the fibre subunit CsgA and the nucleator protein CsgB during assembly of fibronectin-binding curli is limited by the intracellular concentration of the novel lipoprotein CsgG. Mol Microbiol. 1997;26(1):11-23. doi:10.1046/j.1365-2958.1997.5231883.x.

Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.

Lu et al., Expression, purification and structural analysis of csgF gene of curli systems from *Escherichia coli* CFT073. Microbiol China. 2016, 43(9):2063-2071. doi:10.13344/j.microbiol.china.150752.

Ludtke, Single-Particle Refinement and Variability Analysis in EMAN2.1. Methods Enzymol. 2016;579:159-89. doi: 10.1016/bs.mie.2016.05.001. Epub Jul. 1, 2016.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Nivala et al., Unfoldase-mediated protein translocation through an α-hemolysin nanopore. Nat Biotechnol. Mar. 2013;31(3):247-50. doi: 10.1038/nbt.2503. Epub Feb. 3, 2013. Author Manuscript, 10 pages.

Peabody et al., Type II protein secretion and its relationship to bacterial type IV pili and archaeal flagella. Microbiology. Nov. 2003;149(Pt 11):3051-3072. doi: 10.1099/mic.0.26364-0.

Pud et al., Mechanical Trapping of DNA in a Double-Nanopore System. Nano Lett. 2016;16(12):8021-8028. doi:10.1021/acs.nanolett.6b04642.

Reznikoff, Tn5 as a model for understanding DNA transposition. Mol Microbiol. Mar. 2003;47(5):1199-206. doi: 10.1046/j.1365-2958.2003.03382.x.

Rhee et al., Comprehensive genome-wide protein-DNA interactions detected at single-nucleotide resolution. Cell. Dec. 9, 2011;147(6):1408-19. doi: 10.1016/j.cell.2011.11.013.

Rohou et al., CTFFIND4: Fast and accurate defocus estimation from electron micrographs. J Struct Biol. Nov. 2015;192(2):216-21. doi: 10.1016/j.jsb.2015.08.008. Epub Aug. 13, 2015.

Scheres, Relion: implementation of a Bayesian approach to cryo-EM structure determination. J Struct Biol. Dec. 2012;180(3):519-30. doi: 10.1016/j.jsb.2012.09.006. Epub Sep. 19, 2012.

Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.

Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.

Taylor et al., New insight into the molecular control of bacterial functional amyloids. Front Cell Infect Microbiol. Apr. 8, 2015;5:33. doi: 10.3389/fcimb.2015.00033.

Third Party Observation for Application No. EP 15759438.3, mailed Oct. 20, 2022. 11 pages.

Tuteja et al., Helicases as molecular motors: An insight. Physica A. Dec. 1, 2006;372(1):70-83. doi: 10.1016/j.physa.2006.05.014. Epub Jun. 5, 2006.

Van Der Verren et al., A dual-constriction biological nanopore resolves homonucleotide sequences with high fidelity. Nat Biotechnol. Dec. 2020;38(12):1415-1420. doi: 10.1038/s41587-020-0570-8. Epub Jul. 6, 2020. Author Manuscript, 25 pages.

Van Gerven et al., Bacterial amyloid formation: structural insights into curli biogenesis. Trends Microbiol. Nov. 2015; 23(11): 693-706. EPub Oct. 1, 2015. doi: 10.1016/j.tim.2015.07.010. Author Manuscript, 24 pages.

Walker et al., Assembly of the oligomeric membrane pore formed by Staphylococcal alpha-hemolysin examined by truncation mutagenesis. J Biol Chem. Oct. 25, 1992;267(30):21782-6.

Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.

Wang et al., Protein engineering with non-natural amino acids. InTechOpen; Feb. 24, 2012. DOI: 10.5772/28719.

Whisstock et al., Prediction of protein function from protein sequence and structure. Q Rev Biophys. Aug. 2003;36(3):307-40. doi: 10.1017/s0033583503003901.

Wiedmann et al., Ligase chain reaction (LCR)—overview and applications. PCR Methods Appl. Feb. 1994;3(4):S51-64. doi: 10.1101/gr.3.4.s51.

Wilkinson et al., Bacterial DNA ligases. Mol Microbiol. Jun. 2001;40(6):1241-8. doi: 10.1046/j.1365-2958.2001.02479.x.

Willems et al., Single-molecule nanopore enzymology. Philos Trans R Soc Lond B Biol Sci. Aug. 5, 2017;372(1726):20160230. doi: 10.1098/rstb.2016.0230. 11 pages.

Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

Wu et al., Sequence-specific capture of protein-DNA complexes for mass spectrometric protein identification. PLoS One. 2011;6(10):e26217. doi: 10.1371/journal.pone.0026217. Epub Oct. 20, 2011.

Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.

Zheng et al., MotionCor2: anisotropic correction of beam-induced motion for improved cryo-electron microscopy. Nat Methods. Apr. 2017;14(4):331-332. doi: 10.1038/nmeth.4193. Epub Feb. 27, 2017.

Sequence Listing, N2DXI0_ECOLX, Unreviewed; 277 AA; N2DXI0; Jun. 26, 2013, integrated into UniProtKB/TrEMBL; Jun. 26, 2013, sequence version 1; Jun. 26, 2013, entry version 1; SubName: Full=Curli production assembly/transport component CsgG family protein; ORFNames=EC2735000_1161; *Escherichia coli* 2735000; Bacteria; Proteobacteria; Gammaproteobacteria; Enterobacteriales; Enterobacteriaceae; Escherichia; NCBI_TaxID=1116008.†

Sequence Listing, ABV05494; SV 1; linear; genomic DNA; STD; PRO; 834 BP., CP000802.1, Project: PRJNA13959; Sep. 11, 2007 (Rel. 93, Created), May 15, 2014 (Rel. 120, Last updated, Version 7), *Escherichia coli* HS curli production assembly/transport subunit CsgG, *Escherichia coli* HS, Bacteria; Proteobacteria; Gammaproteobacteria; Enterobacterales; Enterobacteriaceae; Escherichia.†

Sivanathan et al., Generating extracellular amyloid aggregates using *E. coli* cells, 10 pages, Nov. 19, 2012, published online.†

Van Gerven et al., Secretion and functional display of fusion proteins through the curli biogenesis pathway 14 pages, Feb. 12, 2014, published online.†

(56) References Cited

OTHER PUBLICATIONS

Robinson et al., Secretion of curli fibre subunits is mediated by the outer membrane-localized CsgG protein 19 pages, Feb. 2006, Mol Microbiol., National Institutes of Health.†

\* cited by examiner
† cited by third party

MUTANT CsgG PORES

This application is a continuation of U.S. application Ser. No. 16/522,591, filed Jul. 25, 2019, which is a continuation of U.S. application Ser. No. 15/507,947, filed on Mar. 1, 2017, now U.S. Pat. No. 10,400,014, which is a national stage filing under 35 U.S.C. § 371 of PCT International Application No. PCT/EP2015/069965, which has an international filing date of Sep. 1, 2015, and claims foreign priority benefits under 35 U.S.C. § 119 (a)-(d) or 35 U.S.C. § 365(b) of United Kingdom application number 1415455.3, filed Sep. 1, 2014, United Kingdom application number 1422079.2, filed Dec. 11, 2014, United Kingdom application number 1506489.2, filed Apr. 16, 2015, United Kingdom application number 1506754.9, filed Apr. 21, 2015, United Kingdom application number 1508287.8, filed May 14, 2015, United Kingdom application number 1511203.0, filed Jun. 25, 2015, and United Kingdom application number 1515240.8, filed Aug. 27, 2015. The contents of the aforementioned applications are herein incorporated by reference in their entireties.

FIELD OF THE INVENTION

The present invention relates to novel protein pores and their uses. In particular it relates to biological nanopores in nucleic acid sequencing applications, and molecular sensing.

The invention relates to mutant forms of CsgG. The invention also relates to analyte detection and characterisation using CsgG.

BACKGROUND OF THE INVENTION

Protein pores are membrane spanning polypeptides and complexes that form a channel in the membrane through which ions and certain molecules may pass. The minimum diameter of the channel is typically in the nanometre ($10^{-9}$ metre) range hence giving certain of these polypeptides the name "nanopores".

Nanopores have great potential as biological sensors. When an electrical potential is applied across a membrane-bound nanopore, ions flow through the channel. This flow of ions can be measured as an electrical current. Suitable electrical measurement techniques using single channel recording equipment are described in, for example, WO 2000/28312 and D. Stoddart et al., Proc. Natl. Acad. Sci., 2010, 10 7702-7. Mufti-channel recording techniques are described, for example, hi WO 2009/077734.

A molecule translating though the pore, or binding in or near the pore acts to obstruct and thereby reduce the ion flow through the channel. The degree of reduction in ion flow, as measured by the reduction in electrical current, is indicative of the size of the obstruction within, or in the vicinity of, the pore. The measured electrical current can therefore be used as a measure of the size or degree of obstruction to the channel. The changes in electrical current can be used to identify that a molecule, or part of a molecule, has bound at or near the pore (molecular sensing), or in certain systems, it can be used to determine the identity of a molecule that is present within the pore based on its size (nucleic acid sequencing).

The "Strand Sequencing" method is known for sequencing nucleic acids using biological nanopores. On passing a single polynucleotide strand through a nanopore, the bases on individual nucleotides are determined by the changes in measured electrical current as they pass transiently through the channel of the nanopore. This method offers significant time and cost savings over historic methods of nucleic acid sequencing.

Previously reported protein nanopores, such as the mutant MspA (Manrao et al., Nature Biotechnology, 2012, 30(4), 349-353) and alpha-hemolysin nanopores (Nat. Nanotechnol., 2009, 4(4), 265-70) have been used for nucleic acid sequencing using the "Strand Sequencing" approach. Similarly, for protein 40 sensing other pores such as alpha-hemolysin (J Am Chem Soc., 2012, 134(5), 2781-7) and ClyA (Am. Chem. Soc. Nano. 2014, 8(12), 12826-35) (J. Am. Chem. Soc., 2013, 135(36), 13456-63) have also been adapted.

There remains a need for new nanopores that overcome the deficiencies of the prior art, not least in optimising the dimensions and characteristics of the pore for molecular sensing applications, and for example, nucleic acid sequencing applications.

Nanopore sensing is an approach to sensing that relies on the observation of individual binding or interaction events between analyte molecules and a receptor. Nanopore sensors can be created by placing a single pore of nanometer dimensions in an insulating membrane and measuring voltage-driven ionic transport through the pore in the presence of analyte molecules. The identity of an analyte is revealed through its distinctive current signature, notably the duration and extent of current block and the variance of current levels.

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required.

Two of the essential components of sequencing nucleic acids using nanopore sensing are (1) the control of nucleic acid movement through the pore and (2) the discrimination of nucleotides as the nucleic acid polymer is moved through the pore. In the past, to achieve nucleotide discrimination the nucleic acid has been passed through a mutant of hemolysin. This has provided current signatures that have been shown to be sequence dependent. It has also been shown that a large number of nucleotides contribute to the observed current when a hemolysin pore is used, making a direct relationship between observed current and polynucleotide challenging.

While the current range for nucleotide discrimination has been improved through mutation of the hemolysin pore, a sequencing system would have higher performance if the current differences between nucleotides could be improved further. In addition, it has been observed that when the nucleic acids are moved through a pore, some current states show high variance. It has also been shown that some mutant hemolysin pores exhibit higher variance than others. While the variance of these states may contain sequence specific information, it is desirable to produce pores that have low variance to simplify the system. It is also desirable to reduce the number of nucleotides that contribute to the observed current.

SUMMARY OF THE INVENTION

The inventors have identified the structure of the bacterial amyloid secretion channel CsgG. The CsgG channel is a trans-membrane oligomeric protein that forms a channel with a minimum diameter of approximately 0.9 nm. The structure of the CsgG nanopore renders it suitable for use in protein sensing applications, in particular in nucleic acid sequencing. Modified versions of the CsgG polypeptide may serve to further enhance the suitability of the channel for such particular applications.

The CsgG pore offers an advantage over existing protein pores such as ClyA or alpha-hemolysin in that the structure is favourable for DNA sequencing applications. The CsgG pore has a more favourable aspect ratio comprising a shorter trans-membrane channel than ClyA. The CsgG pore also has a wider channel opening compared to the alpha-hemolysin pore. This can facilitate the attachment of enzymes for certain applications, for example nucleic acid sequencing applications. In these embodiments, it can also minimize the length of the nucleic acid strand section positioned between the enzyme and the reading head (defined as the narrowest pore section) leading to an improved read-out signal. The narrow inner constriction of the channel of the CsgG pore also facilitates the translocation of single stranded DNA in embodiments of the invention involving nucleic acid sequencing. The constriction is composed of two annular rings formed by juxtaposition of tyrosine residues at position 51 (Tyr 51) in the adjacent protein monomers, and also the phenylalanine and asparagine residues at positions 56 and 55 respectively (Phe 56 and Asn 55). The dimensions of the constriction can be modified. ClyA has a much wider inner constriction which allows the passage of double stranded DNA which is currently not used for sequencing. The alpha-hemolysin pore has one 1.3 nm-wide inner constriction but also a 2 nm-wide beta barrel which features additional reading heads.

In a first aspect, the invention relates to a method for molecular sensing comprising:
 a) providing a CsgG biological pore formed of at least one CsgG monomer within an insulating layer;
 b) applying an electrical potential across the insulating layer thereby establishing flow of electrical current through the biological pore;
 c) contacting the CsgG biological pore with a test substrate; and
 d) measuring the electrical current flow through the biological pore.

Typically, the insulating layer is a membrane, such as a lipid bilayer. In an embodiment, the electrical current through the pore is carried by a flow of soluble ions from a first side of the insulating layer to the second side of the insulating layer.

In an embodiment of the invention, the molecular sensing is analyte detection. In a specific embodiment, the method for analyte detection comprises after step (d) the further step of determining the presence of the test substrate by a reduction in electrical current through the biological pore compared to the electrical current through the biological pore when the test substrate is absent.

In an alternative embodiment of the invention, the molecular sensing is nucleic acid sequencing. Typically, the type of nucleic acid sequenced by said method is DNA or RNA. In specific embodiments of the invention, the CsgG biological pore is adapted to accommodate additional accessory proteins. Typically, the additional accessory proteins are nucleic acid-processing enzymes selected from the group consisting of: DNA or RNA polymerases; isomerases; topoisomerases; gyrases; telomerases; exonucleases; and helicases.

In embodiments of the invention, the CsgG biological pore is a modified CsgG pore, wherein the modified CsgG pore has at least one modification to the monomeric wild-type E-coli CsgG polypeptide sequence in at least one of the CsgG monomers forming the CsgG pore. Typically, the same modification is made to all the CsgG monomers forming the CsgG pore. In specific embodiments of the invention, the modified CsgG monomer has a polypeptide sequence from positions 38 to 63 according to SEQ ID NOs 4 to 388.

In a second aspect, the invention relates to modified CsgG biological pore comprising at least one CsgG monomer, wherein the modified CsgG biological pore has no more than one channel constriction with a diameter in the range from 0.5 nm to 1.5 nm. Typically, the modification is between positions 38 to 63 of the CsgG monomeric polypeptide sequence. Suitably, the modification is at a position selected from: Tyr51; Asn55; and Phe 56. In specific embodiments, the modification is at position Tyr 51, or at both of positions Asn55 and Phe56.

In embodiments of the invention, the modification to the CsgG monomer is selected from the group consisting of substitution of the naturally occurring amino acid; deletion of the naturally occurring amino acid; and modification of the naturally-occurring amino acid side chain. Suitably, the modification reduces or removes the steric encumbrance of the unmodified amino acid. In specific embodiments, at least one CsgG monomer of the pore has a polypeptide sequence from positions 38 to 63 according to SEQ ID NOs 4 to 388.

In a third aspect, the invention relates to the isolated polypeptide encoding the at least one CsgG monomer of the modified CsgG biological pore of the second aspect of the invention.

In a fourth aspect, the invention relates to isolated nucleic acids encoding the isolated polypeptides of the third aspect of the invention.

In a fifth aspect, the invention relates to a biosensor comprising:
 a) An insulating layer;
 b) A CsgG biological pore within the insulating layer; and
 c) Apparatus for measuring an electrical current through the biological pore.

In specific embodiments, the CsgG biological pore in the biosensor is a modified CsgG biological pore according to the second aspect of the invention.

In a sixth aspect, the invention relates to the use of a CsgG biological pore for biological sensing applications, wherein the biological sensing application is analyte detection or nucleic acid sequencing. In an embodiment of the sixth aspect of the invention, the nucleic acid sequencing is DNA sequencing or RNA sequencing.

The inventors have surprisingly demonstrated that CsgG and novel mutants thereof may be used to characterise analytes, such as polynucleotides. The invention concerns mutant CsgG monomers in which one or more modifications have been made to improve the ability of the monomer to interact with an analyte, such as a polynucleotide. The inventors have also surprisingly demonstrated that pores comprising the novel mutant monomers have an enhanced ability to interact with analytes, such as polynucleotides, and therefore display improved properties for estimating the characteristics of analytes, such as the sequence of polynucleotides. The mutant pores surprisingly display improved nucleotide discrimination. In particular, the mutant pores surprisingly display an increased current range, which makes it easier to discriminate between different nucleotides, and a reduced variance of states, which increases the signal-to-noise ratio. In addition, the number of nucleotides contributing to the current as the polynucleotide moves through the pore is decreased. This makes it easier to identify a direct relationship between the observed current as the polynucleotide moves through the pore and the polynucleotide. In addition, the mutant pores may display an increased throughput, i.e. are more likely to interact with an analyte, such as a polynucleotide. This makes it easier to characterise analytes using the pores. The mutant pores may insert into a membrane more easily.

Accordingly, the invention provides a mutant CsgG monomer comprising a variant of the sequence shown in SEQ ID NO: 390, wherein the variant comprises a mutation at one or more of positions Y51, N55 and F56.

Accordingly, the invention provides a mutant CsgG monomer comprising a variant of the sequence shown in SEQ ID NO: 390, wherein the variant comprises one or more of the following: (i) one or more mutations at the following positions (i.e. mutations at one or more of the following positions) N40, D43, E44, S54, S57, Q62, R97, E101, E124, E131, R142, T150 and R192; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57.

The invention also provides:
  a construct comprising two or more covalently attached CsgG monomers, wherein at least one of the monomers is a mutant monomer of the invention;
  a polynucleotide which encodes a mutant monomer of the invention or a construct of the invention;
  a homo-oligomeric pore derived from CsgG comprising identical mutant monomers of the invention or identical constructs of the invention;
  a hetero-oligomeric pore derived from CsgG comprising at least one mutant monomer of the invention or at least one construct of the invention;
  a method for determining the presence, absence or one or more characteristics of a target analyte, comprising:
    a) contacting the target analyte with a CsgG pore or a mutant thereof such that the target analyte moves with respect to the pore; and
    b) taking one or more measurements as the analyte moves with respect to the pore and thereby determining the presence, absence or one or more characteristics of the analyte;
  a method of forming a sensor for characterising a target polynucleotide, comprising forming a complex between a CsgG pore or a mutant thereof and a polynucleotide binding protein and thereby forming a sensor for characterising the target polynucleotide;
  a sensor for characterising a target polynucleotide, comprising a complex between a CsgG pore or a mutant thereof and a polynucleotide binding protein;
  use of a CsgG pore or a mutant thereof to determine the presence, absence or one or more characteristics of a target analyte;
  a kit for characterising a target analyte comprising (a) a CsgG pore or a mutant thereof and (b) the components of a membrane;
  an apparatus for characterising target analytes in a sample, comprising (a) a plurality of a CsgG pores or mutants thereof and (b) a plurality of membranes;
  a method of characterising a target polynucleotide, comprising:
    a) contacting the polynucleotide with a CsgG pore or a mutant thereof, a polymerase and labelled nucleotides such that phosphate labelled species are sequentially added to the target polynucleotide by the polymerase, wherein the phosphate species contain a label specific for each nucleotide; and
    b) detecting the phosphate labelled species using the pore and thereby characterising the polynucleotide; and
  a method of producing a mutant monomer of the invention or a construct of the invention, comprising expressing a polynucleotide of the invention in a suitable host cell and thereby producing a mutant monomer of the invention or a construct.

DESCRIPTION OF THE FIGURES

FIG. 42 shows X-ray structure of $CsgG_{C1S}$ in pre-pore conformation. a, Ribbon diagram of the $CsgG_{C1S}$ monomer coloured as a blue to red rainbow from N terminus to C terminus. Secondary structure elements are labelled according to the ABD-like fold, with the additional N-terminal and C-terminal α-helices and the extended loop connecting β1 and α1 labelled αN, αC and C-loop (CL), respectively. b, Side view of the $CsgG_{C1S}$ C8 octamer with subunits differentiated by colour and one subunit oriented and coloured as in a.

FIG. 47) at higher protein concentration. These dimers can also be observed in single-channel recordings. The upper panel shows the single channel current trace of a stacked CsgG pore at +50, 0 and −50 mV (left to right). The lower left panel shows a current histogram of dimeric CsgG pores recorded at +50 and −50 mV. The experimental conductances of +16.2±1.8 and −16.0±3.0 pA (n=15) at +50 and −50 mV, respectively, are near the theoretically calculated value of 23 pA. The lower right panel shows an I-V curve for the stacked CsgG pores. The data represent averages and standard deviations from six independent recordings. d, The ability of CsgE to bind and block stacked CsgG pores was tested by electrophysiology. Shown are single-channel current traces of stacked CsgG pore in the presence of 10 or 100 nM CsgE at +50 mV (upper) and −50 mV (lower). The current traces indicate that otherwise saturating concentrations of CsgE do not lead to pore closure for stacked CsgG dimers. These observations are in good agreement with the mapping of the CsgG-CsgE contact zone to helix 2 and the mouth of the CsgG periplasmic cavity as discerned by EM and site-directed mutagenesis (FIG. 45 and FIG. 52).

DESCRIPTION OF THE SEQUENCE LISTING

Figure 1:
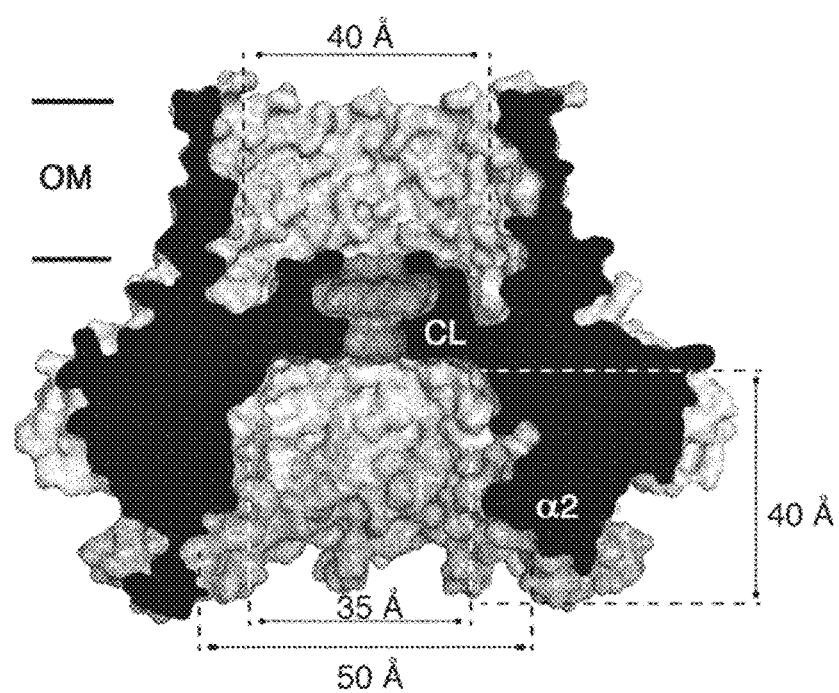
FIG. 1 shows a side cross-sectional view of the structure of a CsgG nonamer in its channel conformation in ribbon and surface representation.

SEQ ID NO: 1 shows amino acid sequence of wild-type *E. coli* CsgG including signal sequence (Uniprot accession number P0AEA2).

SEQ ID NO: 2 shows polynucleotide sequence of wild-type *E. coli* CsgG including signal sequence (Gene ID: 12932538).

SEQ ID NO: 3 shows the amino acid sequence of the wild-type *E. coli* CsgG from positions 53 to 77 of SEQ ID NO:2. This corresponds to the amino acid sequence from positions 38 to 63 of the mature wild-type *E. coli* CsgG monomer (i.e. lacking the signal sequence).

SEQ ID NOs 4 to 388 show the amino acid sequence from positions 38 to 63 of the modified monomers of CsgG lacking the signal sequence.

SEQ ID NO: 389 shows the codon optimised polynucleotide sequence encoding the wild-type CsgG monomer from *Escherichia coli* Str. K-12 substr. MC4100. This monomer lacks the signal sequence.

SEQ ID NO: 390 shows the amino acid sequence of the mature form of the wild-type CsgG monomer from *Escherichia coli* Str. K-12 substr. MC4100. This monomer lacks the signal sequence. The abbreviation used for this CsgG=CsgG-Eco.

SEQ ID NO: 391 shows the amino acid sequence of YP_001453594.1: 1-248 of hypothetical protein CKO_02032 [*Citrobacter koseri* ATCC BAA-895], which is 99% identical to SEQ ID NO: 390.

SEQ ID NO: 392 shows the amino acid sequence of WP_001787128.1: 16-238 of curli production assembly/transport component CsgG, partial [*Salmonella enterica*], which is 98% to SEQ ID NO: 390.

SEQ ID NO: 393 shows the amino acid sequence of KEY44978.11: 16-277 of curli production assembly/transport protein CsgG [*Citrobacter amalonaticus*], which is 98% identical to SEQ ID NO: 390.

SEQ ID NO: 394 shows the amino acid sequence of YP_003364699.1: 16-277 of curli production assembly/transport component [*Citrobacter rodentium* ICC168], which is 97% identical to SEQ ID NO: 390.

SEQ ID NO: 395 shows the amino acid sequence of YP_004828099.1: 16-277 of curli production assembly/transport component CsgG [*Enterobacter asburiae* LF7a], which is 94% identical to SEQ ID NO: 390.

SEQ ID NO: 396 shows the polynucleotide sequence encoding the Phi29 DNA polymerase.

SEQ ID NO: 397 shows the amino acid sequence of the Phi29 DNA polymerase.

SEQ ID NO: 398 shows the codon optimised polynucleotide sequence derived from the sbcB gene from *E. coli*. It encodes the exonuclease I enzyme (EcoExo I) from *E. coli*.

SEQ ID NO: 399 shows the amino acid sequence of exonuclease I enzyme (EcoExo I) from *E. coli*.

SEQ ID NO: 400 shows the codon optimised polynucleotide sequence derived from the xthA gene from *E. coli*. It encodes the exonuclease III enzyme from *E. coli*.

SEQ ID NO: 401 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 402 shows the codon optimised polynucleotide sequence derived from the recJ gene from *T. thermophilus*. It encodes the RecJ enzyme from *T. thermophilus* (TthRecJ-cd).

SEQ ID NO: 403 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 404 shows the codon optimised polynucleotide sequence derived from the bacteriophage lambda exo (redX) gene. It encodes the bacteriophage lambda exonuclease.

SEQ ID NO: 405 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 406 shows the amino acid sequence of Hel308 Mbu.

SEQ ID NO: 407 shows the amino acid sequence of Hel308 Csy.

SEQ ID NO: 408 shows the amino acid sequence of Hel308 Tga.

SEQ ID NO: 409 shows the amino acid sequence of Hel308 Mhu.

SEQ ID NO: 410 shows the amino acid sequence of Tral Eco.

SEQ ID NO: 411 shows the amino acid sequence of XPD Mbu.

SEQ ID NO: 412 shows the amino acid sequence of Dda 1993.

SEQ ID NO: 413 shows the amino acid sequence of Trwc Cba.

SEQ ID NO: 414 shows the amino acid sequence of WP_006819418.1: 19-280 of transporter [*Yokenella regensburgei*], which is 91% identical to SEQ ID NO: 390.

SEQ ID NO: 415 shows the amino acid sequence of WP_024556654.1: 16-277 of curli production assembly/transport protein CsgG [*Cronobacter pulveris*], which is 89% identical to SEQ ID NO: 390.

SEQ ID NO: 416 shows the amino acid sequence of YP_005400916.1:16-277 of curli production assembly/transport protein CsgG [*Rahnella aquatilis* HX2], which is 84% identical to SEQ ID NO: 390.

SEQ ID NO: 417 shows the amino acid sequence of KFC99297.1: 20-278 of CsgG family curli production assembly/transport component [*Kluyvera ascorbata* ATCC 33433], which is 82% identical to SEQ ID NO: 390.

SEQ ID NO: 418 shows the amino acid sequence of KFC86716.11:16-274 of CsgG family curli production assembly/transport component [*Hafnia alvei* ATCC 13337], which is 81% identical to SEQ ID NO: 390.

SEQ ID NO: 419 shows the amino acid sequence of YP_007340845.11:16-270 of uncharacterised protein involved in formation of curli polymers [Enterobacteriaceae bacterium strain FGI 57], which is 76% identical to SEQ ID NO: 390.

SEQ ID NO: 420 shows the amino acid sequence of WP_010861740.1: 17-274 of curli production assembly/transport protein CsgG [*Plesiomonas shigelloides*], which is 70% identical to SEQ ID NO: 390.

SEQ ID NO: 421 shows the amino acid sequence of YP_205788.1: 23-270 of curli production assembly/transport outer membrane lipoprotein component CsgG [*Vibrio fischeri* ES114], which is 60% identical to SEQ ID NO: 390.

SEQ ID NO: 422 shows the amino acid sequence of WP_017023479.1: 23-270 of curli production assembly protein CsgG [*Aliivibrio logei*], which is 59% identical to SEQ ID NO: 390.

SEQ ID NO: 423 shows the amino acid sequence of WP_007470398.1: 22-275 of Curti production assembly/transport component CsgG [*Photobacterium* sp. AK15], which is 57% identical to SEQ ID NO: 390.

SEQ ID NO: 424 shows the amino acid sequence of WP_021231638.1: 17-277 of curli production assembly protein CsgG [*Aeromonas veronii*], which is 56% identical to SEQ ID NO: 390.

SEQ ID NO: 425 shows the amino acid sequence of WP_033538267.1: 27-265 of curli production assembly/transport protein CsgG [*Shewanella* sp. ECSMB14101], which is 56% identical to SEQ ID NO: 390.

SEQ ID NO: 426 shows the amino acid sequence of WP_003247972.1: 30-262 of curli production assembly protein CsgG [*Pseudomonas putida*], which is 54% identical to SEQ ID NO: 390.

SEQ ID NO: 427 shows the amino acid sequence of YP_003557438.1: 1-234 of curli production assembly/transport component CsgG [*Shewanella violacea* DSS12], which is 53% identical to SEQ ID NO: 390.

SEQ ID NO: 428 shows the amino acid sequence of WP_027859066.1: 36-280 of curli production assembly/transport protein CsgG [*Marinobacterium jannaschii*], which is 53% identical to SEQ ID NO: 390.

SEQ ID NO: 429 shows the amino acid sequence of CEJ70222.1: 29-262 of Curli production assembly/transport component CsgG [*Chryseobacterium oranimense* G311], which is 50% identical to SEQ ID NO: 390.

SEQ ID NO: 430 shows a polynucleotide sequence used in Example 18.

SEQ ID NO: 431 shows a polynucleotide sequence used in Example 18.

SEQ ID NO: 432 shows a polynucleotide sequence used in Example 18.

SEQ ID NO: 433 shows a polynucleotide sequence used in Example 18.

SEQ ID NO: 434 shows a polynucleotide sequence used in Example 18. Attached to the 3' end of SEQ ID NO: 434 is six iSp18 spacers which are attached at the opposite end to two thymines and a 3' cholesterol TEG.

SEQ ID NO: 435 shows the amino acid sequence of StepII(C).

SEQ ID NO: 436 shows the amino acid sequence of Pro.

SEQ ID NO: 437 to 440 show primers from example 1.

SEQ ID NO: 441 shows the Hairpin from example 21.

Figure 4:
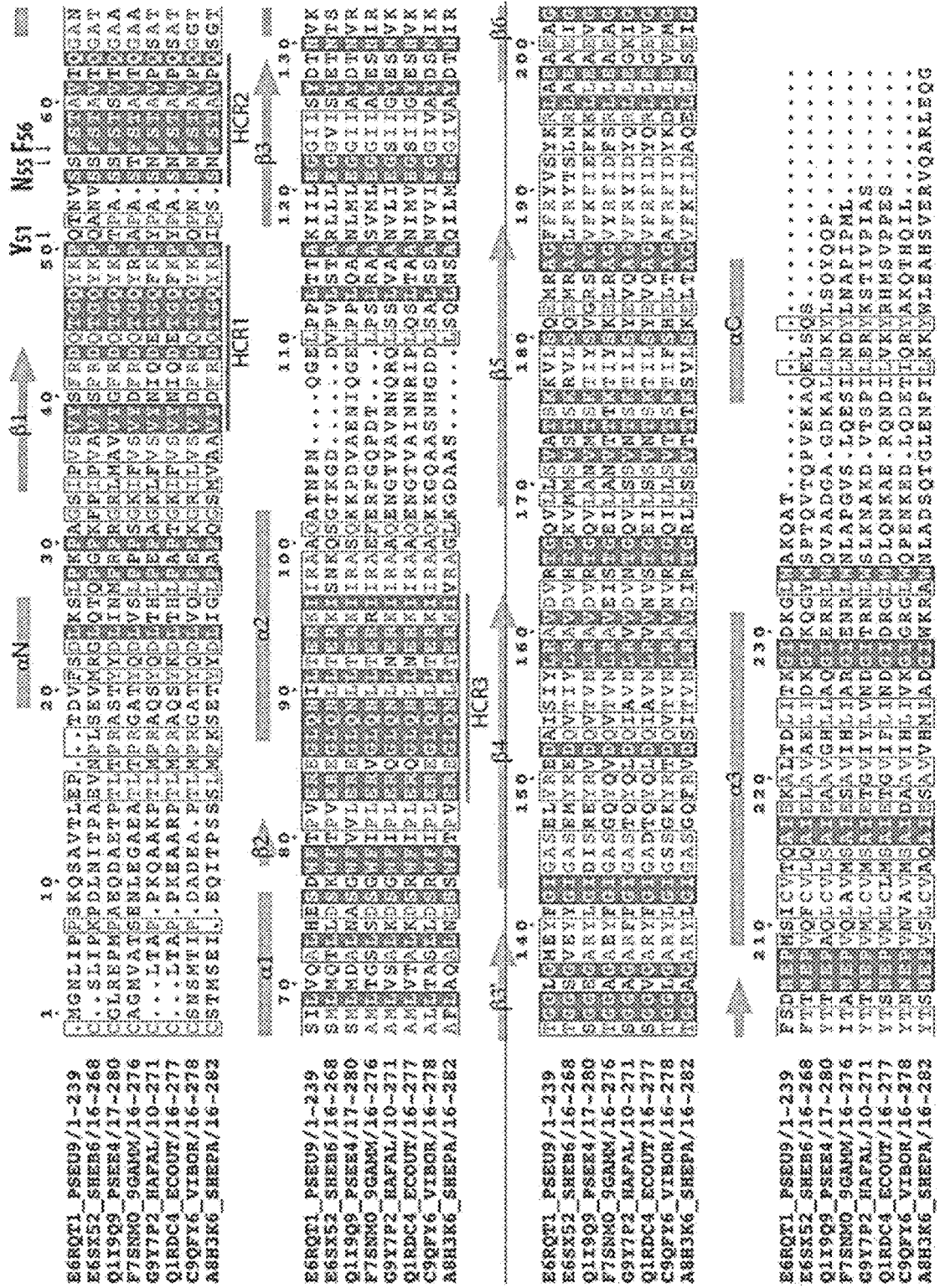
FIG. 4 shows the sequence homology in CsgG homologues, including the multiple sequence alignment of CsgG-like proteins (SEQ ID NO: 442 to SEQ ID NO: 448). The selected sequences were chosen from monophyletic clades across the phylogenetic tree of CsgG-like sequences (not shown), to give a representative view of sequence diversity. Secondary structure elements are shown as arrows or bars for β-strands and α-helices, respectively, and are based on the *E. coli* CsgG crystal structure. Importantly, the residues equivalent to *E. coli* Tyr 51, Asn55 and Phe 56 are highlighted by arrows. These residues form the pore's inner constriction, i.e. the pore reading head in the context of nanopore sensing applications.

SEQ ID NO: 442 to 448 show the sequences from FIG. 4.

Figure 43:
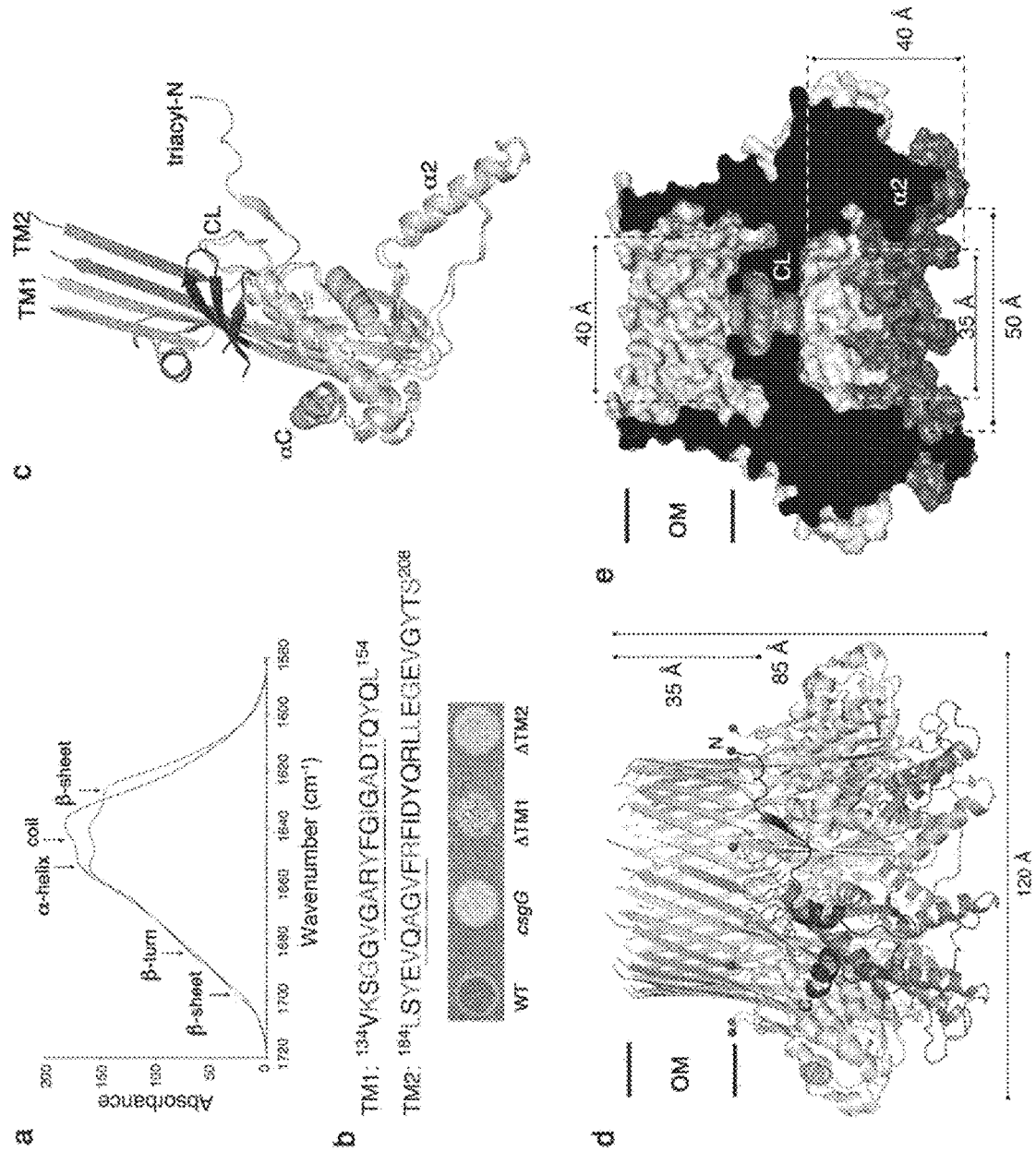
FIG. 43 shows the structure of CsgG in its channel conformation. a, Amide I region (1,700-1,600 cm$^{-1}$) of ATR-FTIR spectra of CsgGC1S (blue) and membrane extracted CsgG (red). b, TM1 and TM2 sequence (SEQ ID NO: 449 and SEQ ID NO: 450) (bilayer-facing residues in blue) and Congo red binding of *E. coli* BW25141ΔcsgG complemented with wild-type csgG (WT), empty vector or csgG lacking the underlined fragments of TM1 or TM2. Data are representative of three biological replicates. c, Overlay of CsgG monomer in pre-pore (light blue; TM1 pink, TM2 purple) and channel conformation (tan; TM1 green, TM2 orange). CL, C-loop. d, e, Side view (d) and cross-sectional view (e) of CsgG nonamers in ribbon and surface representation; helix 2, the core domain and TM hairpins are shown in blue, light blue and tan, respectively. A single protomer is coloured as in FIG. 42a. Magenta spheres show the position of Leu 2. OM, outer membrane.

SEQ ID NO: 449 and 450 show the sequences from FIG. 43.

DETAILED DESCRIPTION OF THE INVENTION

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, N.Y.; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Prior to setting forth the invention, a number of definitions are provided that will assist in the understanding of the invention. All references cited herein are incorporated by reference in their entirety.

Unless otherwise defined, all technical and scientific terms used herein have the same meaning as commonly understood by one of ordinary skill in the art to which this invention belongs.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "nucleic acid" as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may include DNA and RNA, and may be manufactured synthetically in vitro or isolated from natural sources. Nucleic acids may further include modified DNA or RNA, for example DNA or RNA that has been methylated, or RNA that has been subject to post-translational modification, for example 5'-capping with 7-methylguanosine, 3'-processing such as cleavage and polyadenylation, and splicing. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Sizes of nucleic acids, also referred to herein as "polynucleotides" are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called "oligonucleotides" and may comprise primers for use in manipulation of DNA such as via polymerase chain reaction (PCR).

The term "amino acid" in the context of the present invention is used in its broadest sense and is meant to include naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

A "polypeptide" is a polymer of amino acid residues joined by peptide bonds, whether produced naturally or in vitro by synthetic means. Polypeptides of less than around 12 amino acid residues in length are typically referred to as "peptides" and those between about 12 and about 30 amino acid residues in length may be referred to as "oligopeptides". The term "polypeptide" as used herein denotes the product of a naturally occurring polypeptide, precursor form or proprotein. Polypeptides can also undergo maturation or post-translational modification processes that may include, but are not limited to: glycosylation, proteolytic cleavage, lipidization, signal peptide cleavage, propeptide cleavage, phosphorylation, and such like. The term "protein" is used herein to refer to a macromolecule comprising one or more polypeptide chains.

A "biological pore" is a trans-membrane protein structure defining a channel or hole that allows the translocation of molecules and ions from one side of the membrane to the other. The translocation of ionic species through the pore may be driven by an electrical potential difference applied to either side of the pore. A "nanopore" is a biological pore in which the minimum diameter of the channel through which molecules or ions pass is in the order of nanometres ($10^{-9}$ metres).

For all aspects and embodiments of the present invention, a polynucleotide can comprise a polynucleotide that has at least 50%, 60%, 70%, 80%, 90%, 95% or 99% complete sequence identity to wild-type E. coli CsgG as shown in SEQ ID NO: 2. Likewise, the polypeptide can comprise a polypeptide that has at least 50%, 60%, 70%, 80%, 90%, 95% or 99% complete sequence identity to wild-type E. coli CsgG as shown in SEQ ID NO: 1. A polypeptide can comprise a polypeptide that contains the PFAM domain PF03783, which is characteristic for CsgG-like proteins. A list of presently known CsgG homologues and CsgG architectures can be found at http://pfam.xfam.org//family/PF03783. Sequence identity can thus also be to a fragment or portion of the full length polynucleotide or polypeptide. Hence, a sequence may have only 50% overall sequence identity with a sequence of the invention but a particular region, domain or subunit could share 80%, 90%, or as much as 99% sequence identity with sequences of the invention. According to the present invention, homology to the nucleic acid sequence of SEQ ID NO: 2 is not limited simply to sequence identity. Many nucleic acid sequences can demonstrate biologically significant homology to each other despite having apparently low sequence identity. In the present invention homologous nucleic acid sequences are considered to be those that will hybridise to each other under conditions of low stringency (M. R. Green, J. Sambrook, 2012, Molecular Cloning: A Laboratory Manual, Fourth Edition, Books 1-3, Cold Spring Harbor Laboratory Press, Cold Spring Harbor, N.Y.).

The term "vector" is used to denote a DNA molecule that is either linear or circular, into which another nucleic acid (typically DNA) sequence fragment of appropriate size can be integrated. Such DNA fragment(s) can include additional segments that provide for transcription of a gene encoded by the DNA sequence fragment. The additional segments can include and are not limited to: promoters, transcription terminators, enhancers, internal ribosome entry sites, untranslated regions, polyadenylation signals, selectable markers, origins of replication and such like. A variety of suitable promoters for prokaryotic (e.g., the [beta]-lactamase and lactose promoter systems, alkaline phosphatase, the tryptophan (trp) promoter system, lac, tac, T3, T7 promoters for E. coli) and eukaryotic (e.g., simian virus 40 early or late promoter, Rous sarcoma virus long terminal repeat promoter, cytomegalovirus promoter, adenovirus late promoter, EG-1a promoter) hosts are available. Expression vectors are often derived from plasmids, cosmids, viral vectors and yeast artificial chromosomes; vectors are often recombinant molecules containing DNA sequences from several sources. Specific embodiments of the present invention provide for an expression vector that encodes a wild type or modified CsgG polypeptide as described herein. The term "operably linked", when applied to DNA sequences, for example in an nucleic acid vector such as mentioned above, indicates that the sequences are arranged so that they function cooperatively in order to achieve their intended purposes, i.e. a promoter sequence allows for initiation of transcription that proceeds through an associated coding sequence as far as a termination sequence.

The trans-membrane protein structure of a biological pore may be monomeric or oligomeric in nature. Typically, the pore comprises a plurality of polypeptide subunits arranged around a central axis thereby forming a protein-lined channel that extends substantially perpendicular to the membrane in which the nanopore resides. The number of polypeptide subunits is not limited. Typically, the number of subunits is from 5 to up to 30, suitably the number of subunits is from 6 to 10. Alternatively, the number of subunits is not defined as in the case of perfringolysin or related large membrane pores. The portions of the protein subunits within the nanopore that form protein-lined channel typically comprise secondary structural motifs that may include one or more trans-membrane β-barrel, and/or α-helix sections.

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "a polynucleotide binding protein" includes two or more such proteins, reference to "a helicase" includes two or more helicases, reference to "a monomer" refers to two or more monomers, reference to "a pore" includes two or more pores and the like.

All publications, patents and patent applications cited herein, whether supra or infra, are hereby incorporated by reference in their entirety.

The present invention relates in part to the bacterial amyloid secretion channel (CsgG), its method of manufacture and its use in nucleic acid sequencing applications, and molecular sensing.

Figure 42:
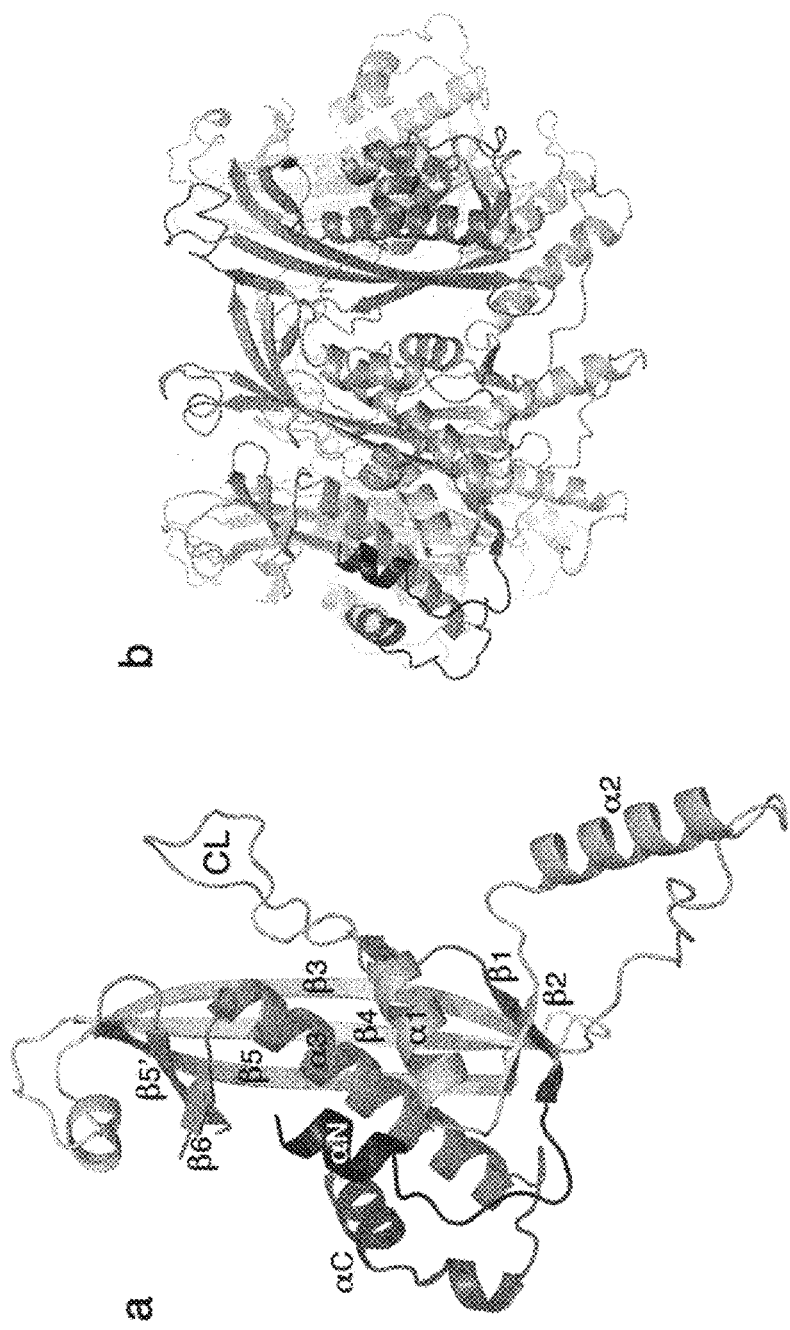

CsgG is a membrane lipoprotein present in the outer membrane of *E. coli* (Uniprot accession no. P0AEA2; Gene ID: 12932538). In the outer lipid membrane, CsgG forms a nanopore comprising an oligomeric complex of nine CsgG monomer subunits. By virtue of the type II (lipoprotein) signal sequence, the CsgG preprotein is translocated across the SEC translocon and subsequently becomes triacylated at the N-terminal Cys residue of the mature CsgG (i.e. CsgG with cleaved type II signal sequence). Triacylated, or "lipidated" CsgG is transported to the outer membrane of a Gram-negative host, where it inserts into the bilayer as a nonameric pore. A non-lipidated form of CsgG, e.g. $CsgG_{C1S}$, exists in the periplasm as a soluble protein in a pre-pore conformation (FIG. 42).

Figure 2:
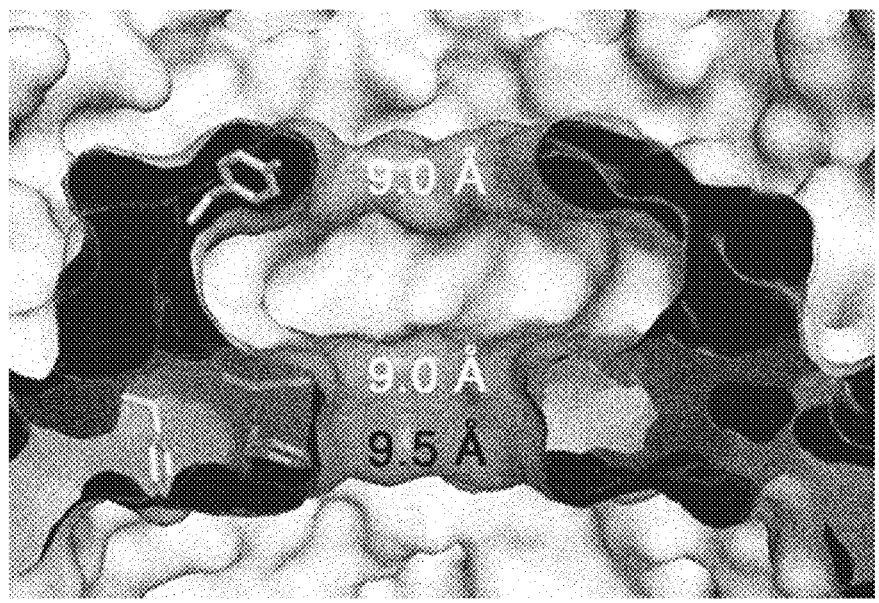
FIG. 2 shows a cross-section of CsgG channel constriction (i.e. the pore reading head in the context of nanopore sensing applications) and relevant diameter measurements.
Figure 3:
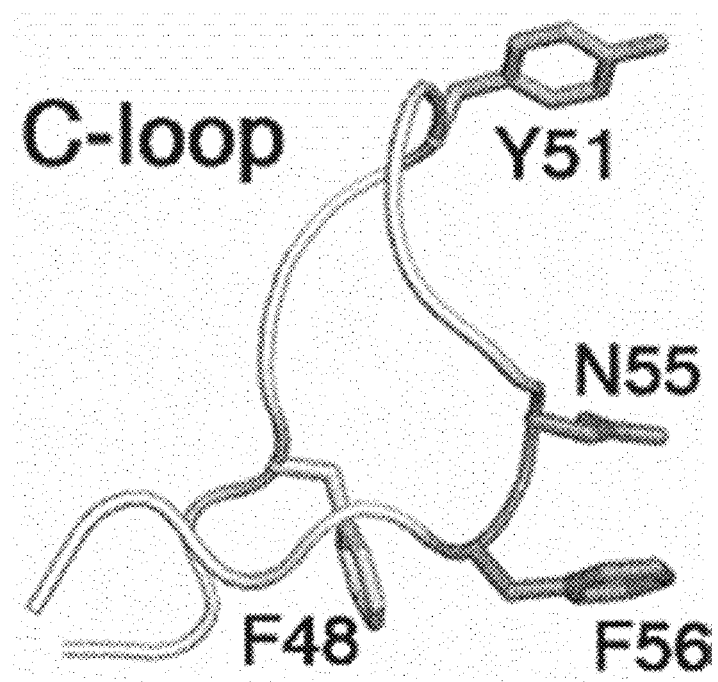
FIG. 3 shows the structural motif that contributes to the pore constriction comprising three stacked concentric side-chain layers: Tyr 51, Asn 55 and Phe 56.

The X-ray structure of the wild type CsgG nanopore (Goyal et al., Nature, 2014, 516(7530), 250-3) shows that it has a width of 120 Å and a height of 85 Å (hereinafter, the term "width" of the nanopore will relate to its dimension parallel with the membrane surface, and the term "height" of the nanopore will relate to its dimension perpendicular to the membrane). The CsgG pore complex traverses the membrane through a 36-stranded β-barrel to provide a 40 Å inner diameter channel (FIG. 1). The assembled monomers of the CsgG channel each possess a conserved 12-residue loop (C-loop, "CL"; FIG. 2), which co-operate so as to form a constriction in the channel to a diameter of approximately 9.0 Å (FIGS. 1 and 2). The constriction in the wild type CsgG nanopore is composed of three stacked concentric rings formed by the side chains of amino acid residues Tyr51, Asn55 and Phe56 of each of the CsgG monomers present in the CsgG oligomer (FIG. 3). This numbering of residues is based upon the mature protein which lacks the native 15 amino acid signal sequence at the N-terminal. The mature protein therefore corresponds to residues 16 to 277 of SEQ ID NO:1. Tyr51 is at position 66 in SEQ ID NO:1, Asn is at position 70 in SEQ ID NO:1 and Phe56 is at position 71 in SEQ ID NO:1.

Figure 5:
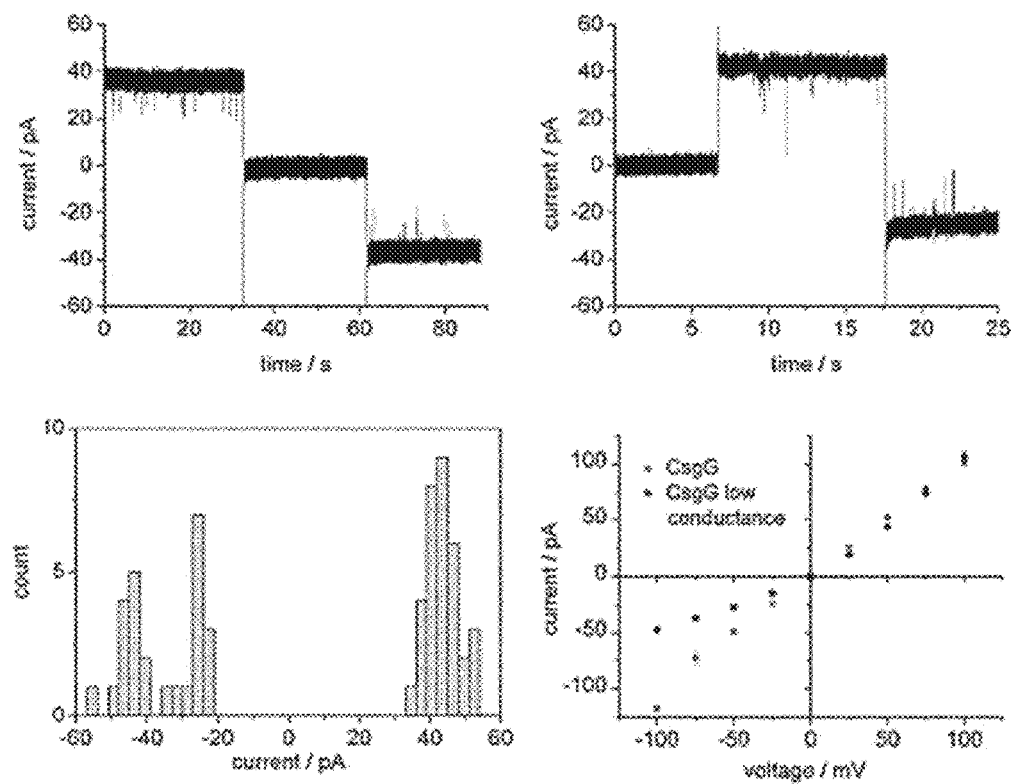
FIG. 5 shows representative single-channel current recordings (a) and conductance histogram (b) of CsgG reconstituted in planar phospholipid bilayers and measured under an electrical field of +50 mV (n=33) or −50 mV (n=13).

The constriction acts to limit the passage of ions and other molecules through the CsgG channel. Single-channel current recordings of CsgG reconstituted in planar phospholipid bilayers led to a steady current of 43.1±4.5 pA (n=33) or −45.1±4.0 pA (n=13) using standard electrolyte conditions and a potential of +50 mV or −50 mV, respectively (FIG. 5).

Current flow through the CsgG channel can be effectively blocked by the addition of stoichiometric quantities of the periplasmic factor CsgE (Uniprot accession no. P0AE95; Examples 10 to 12). Without wishing to be bound by theory, current evidence points to a mechanism whereby CsgE forms a complex with the CsgG pore acting to cap one end of the channel. The significant reduction in the flow of ions through the CsgG channel may be measured using standard single-channel recording techniques (Examples 12 and 13, FIG. 6). The inventors have found that measured parameters for the current flow (maximum current, and ability to monitor current variation) render the nanopore suitable for use in nucleic acid sequencing and molecular sensing applications according to one embodiment of the invention.

Accordingly, the present invention relates in part to methods and uses of the CsgG nanopore protein complex in nucleic acid sequencing based on variations of electrical measurements of the current flowing through a nanopore.

Nucleic acids are particularly suitable for nanopore sequencing. The naturally-occurring nucleic acid bases in DNA and RNA may be distinguished by their physical size. As a nucleic acid molecule, or individual base, passes through the channel of a nanopore, the size differential between the bases causes a directly correlated reduction in the ion flow through the channel. The variation in ion flow may be recorded. Suitable electrical measurement techniques for recording ion flow variations are described in, for example, WO 2000/28312 and D. Stoddart et al., Proc. Natl. Acad. Sci., 2010, 106, pp 7702-7 (single channel recording equipment); and, for example, in WO 2009/077734 (multi-channel recording techniques). Through suitable calibration, the characteristic reduction in ion flow can be used to identify the particular nucleotide and associated base traversing the channel in real-time.

The size of the narrowest constriction in a transmembrane channel is typically a key factor in determining suitability of a nanopore for nucleic acid sequencing applications. If the constriction is too small, the molecule to be sequenced will not be able to pass through. However, to achieve a maximal effect on ion flow through the channel, at its narrowest point (i.e. at a constriction) the channel should not be too large. Ideally, any constriction should be as close as possible in diameter to the size of the base passing through. For sequencing of nucleic acids and nucleic acid bases, suitable constriction diameters are in the nanometre range ($10^{-9}$ metre range). Suitably, the diameter should be in the region of 0.5 to 1.5 nm, typically, the diameter is in the region of 0.7 to 1.2 nm. The constriction in wild type *E. coli* CsgG has a diameter of approximately 9 Å (0.9 nm). The inventors have deduced that the size and configuration of the constriction in the CsgG channel is suitable for nucleic acid sequencing.

For applications related to nucleic acid sequencing, the CsgG nanopore may be used in wild-type form or may be further modified, such as by directed mutagenesis of particular amino acid residues, to further enhance the desired properties of the nanopore in use. For example, in embodiments of the present invention mutations are contemplated to alter the number, size, shape, placement or orientation of the constriction within the channel. Modified mutant CsgG nanopore complex may be prepared by known genetic engineering techniques that result in the insertion, substitution and/or deletion of specific targeted amino acid residues in the polypeptide sequence. In the case of the oligomeric CsgG nanopore, the mutations may be made in each monomeric polypeptide subunit, or any one of the monomers, or all of the monomers. Suitably, in one embodiment of the invention the mutations described are made to all monomeric polypeptides within the oligomeric protein structure.

According to an embodiment of the invention, a modified mutant CsgG nanopore is provided where the number of channel constrictions within the pore is reduced.

The wild type *E. coli* CsgG pore includes two channel constrictions (see FIG. 1). These are formed by (i) amino acid residues Phe56 and Asn55, and (ii) amino acid residue Tyr 51, as part of a wider structure comprising additional amino acids from position 54 and to 53, as well as the C-loop motif (FIGS. 2 and 3).

In typical nanopore nucleic acid sequencing, the open-channel ion flow is reduced as the individual nucleotides of the nucleic sequence of interest sequentially pass through the channel of the nanopore due to the partial blockage of the channel by the nucleotide. It is this reduction in ion flow that is measured using the suitable recording techniques described above. The reduction in ion flow may be calibrated to the reduction in measured ion flow for known nucleotides through the channel resulting in a means for determining which nucleotide is passing through the channel, and therefore, when done sequentially, a way of determining the nucleotide sequence of the nucleic acid passing through the nanopore. For the accurate determination of individual nucleotides, it has typically required for the reduction in ion flow through the channel to be directly correlated to the size of the individual nucleotide passing through the single constriction (or "reading head"). It will be appreciated that sequencing may be performed upon an intact nucleic acid polymer that is 'threaded' through the pore via the action of an associated polymerase, for example. Alternatively, sequences may be determined by passage of nucleotide triphosphate bases that have been sequentially removed from a target nucleic acid in proximity to the pore (see for example WO 2014/187924).

When two or more constrictions are present and spaced apart each constriction may interact or "read" separate nucleotides within the nucleic acid strand at the same time. In this situation, the reduction in ion flow through the channel will be the result of the combined restriction in flow of all the constrictions containing nucleotides. Hence, in some instances a double constriction may lead to a composite current signal. In certain circumstances, the current read-out for one constriction, or "reading head", may not be able to be determined individually when two such reading heads are present.

The wild-type pore structure of CsgG may be re-engineered via recombinant genetic techniques to widen, alter, or remove one of the two constrictions to leave a single constriction within the channel, thus, defining a single reading head. The constriction motif in the CsgG oligomeric pore is located at amino acid residues at position 38 to 63 in the wild type monomeric *E. coli* CsgG polypeptide. The wild-type amino acid sequence of this region is provided as SEQ ID NO: 3. In considering this region, mutations at any of the amino acid residue positions 50 to 53, 54 to 56 and 58 to 59 are contemplated as within the remit of the present invention. Based on sequence similarity with CsgG homologues (FIG. 4), amino acid residue positions 38 to 49, 53, 57, and 61 to 63 are considered to be highly conserved and therefore may be less suitable for substitution or other modification. Due to the key positioning of the sidechains of Tyr51, Asn55, and Phe56 within the channel of the wild-type CsgG structure, mutation at these positions may be advantageous in order to modify or alter the characteristics of the reading head.

Mutations at a given position of the monomeric CsgG protein may result in the substitution of the wild-type amino acid at that position with any other natural or unnatural amino acid. In one embodiment of the invention, it is desirable to widen or remove a constriction; suitably the amino acid sidechain in the modified CsgG protein will be selected so as to be less sterically encumbering than the amino acid sidechain in the wild type structure which it replaces. The replacement amino acid residue at a given position may have similar electrostatic properties, or it may have different electrostatic properties. Suitably, the replacement amino acid sidechain will possess a similar electrostatic charge to the amino acid sidechain in the wild type structure which it replaces in order to minimise disruption to secondary structure or the properties of the channel.

The selection of replacement amino acid may be based on a BLOSUM62 matrix which provides a standard methodology for calculating the likelihood of an amino acid being substituted for another based on a large multiple sequence alignment. Examples of BLOSUM62 matrices are freely available to the skilled person on the Internet; see for example the website of the National Center for Biotechnology Information (http://www.ncbi.nlm.nih.gov/Class/Structure/aa/aa_explorer.cgi).

For Tyr51 in the wild-type CsgG structure, which acts to form a first constriction in the CsgG channel, substitution with any amino acid is provided. In particular, in certain embodiments of the invention Tyr51 may be substituted with alanine, glycine, valine, leucine, isoleucine, asparagine, glutamine, and phenylalanine (SEQ ID: 39-318). In embodiments of the invention, substitution of Tyr51 with alanine or glycine is particularly suitable (SEQ ID: 39-108). In embodiments, residues 50 to 53 (PYPA in the wild-type sequence) may be replaced with glycine-glycine (GG) (SEQ ID: 354-388).

For Asn55, which contributes to the second constriction in the CsgG channel, substitution with any amino acid is provided. In particular, in certain embodiments of the invention Asn55 may be substituted with alanine, glycine, valine, serine or threonine (SEQ ID: 9-33, 44-68, 79-103 114-138, 149-173, 184-208, 219-243, 254-278, 289-313 and 324-348).

For Phe56 which forms part of the second constriction in the CsgG channel, substitution with any amino acid is provided. In particular, in certain embodiments of the invention Phe56 may be substituted with alanine, glycine, valine, leucine, isoleucine, asparagine, and glutamine (SEQ ID: 5-13, 15-18, 20-23, 25-28, 30-33, 40-43, 45-48, 50-53, 55-58, 60-63, 65-68, 75-78, 80-83, 85-88, 90-93, 95-98, 100-103, 110-113, 115-118, 120-123, 125-128, 130-133, 135-138, 145-148, 150-153, 155-158, 160-163, 165-168, 170-173, 180-183, 185-188, 190-193, 195-198, 200-203, 205-208, 215-218, 220-223, 225-228, 230-233, 235-238, 240-243, 250-253, 255-258, 260-263, 265-268, 270-273, 275-578, 285-288, 290-293, 295-298, 300-303, 305-308, 310-313, 320-323, 325-328, 330-333, 335-338, 340-343 and 345-348). In embodiments of the invention, substitution of Phe56 with alanine and glycine is particularly suitable (SEQ ID: 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 6, 11, 16, 21, 26, 31, 36, 41, 46, 51, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 206, 211, 216, 221, 226, 231, 236, 241, 246, 251, 256, 261, 266, 271, 276, 281, 286, 291, 296, 301, 306, 311, 316, 321, 326, 331, 336, 341 346, 351, 356, 361, 366, 371, 376, 381 and 386).

In a given mutant CsgG protein, substitution of Tyr51 may be performed at the same time as either one of positions 55 and 56 (SEQ ID: 44, 49, 54, 59, 64, 79, 84, 89, 94, 99, 114, 119, 124, 129, 134, 149, 154, 159, 164, 169, 184, 189, 194, 199, 204, 219, 224, 229, 234, 239, 254, 259, 264, 269, 274, 289, 294, 299, 304, 309, 359, 364, 369, 374, 379, 40, 41, 42, 75, 76 77, 110, 111, 112, 145, 146, 147, 180, 181, 182, 215, 216, 217, 250, 251, 252, 285, 286 and 287), wherein at least one constriction of suitable dimensions within the channel is maintained. Alternatively, substitution of Tyr51 is mutually exclusive to substitution at both of positions Asn55 and Phe56 (SEQ ID: 39, 74, 109, 144, 179, 214, 249, 284, 354, 10, 11, 12, 15, 16, 17, 20, 21, 22, 25, 26, 27, 30, 31 and 32

Alternatively, one or more of the Tyr51, Asn55 or Phe56 in the wild type CsgG protein may be deleted (SEQ ID: 319-353, 34-38, 69-73, 104-108, 139-143, 174-178, 209-213, 244-248, 279-283, 314-318, 384-388, 8, 13, 18, 23, 28, 33, 43, 48, 53, 58, 63, 68, 78, 83, 88, 93, 98, 103, 113, 118, 123, 128, 133, 138, 148, 153, 158, 163, 168, 173, 183, 188, 193, 198, 203, 208, 218, 223, 228, 233, 238, 243, 253, 258, 263, 268, 273, 278, 288, 293, 298, 303, 308 and 313). To maintain at least one constriction in the channel, in a given embodiment, deletion of amino acid residue Tyr51 is mutually exclusive to deletion of both amino acid residues Asn55 and Phe56 (SEQ ID: 319-322, 324-327, 329-332, 334-337, 339-342, 344-347, 38, 73, 108, 143, 178, 213, 248, 283 and 318). Certain neighbouring amino acid residues at positions 53 and 54 and 48 and 49 may also be deleted.

It is to be understood that the present invention provides embodiments where the above modifications may be made in isolation, or in any combination.

Removal of either the constriction at Tyr51 or the constriction at Asn55/Tyr56 results in a single constriction within the CsgG channel. Without wishing to be bound by theory, it is postulated that the constriction at Asn55/Tyr56 would have higher conformational stability than the constriction at Tyr51 which may be desirable. However, the Asn55/Tyr56 constriction could be too high (as measured along the central pore axis) in comparison to the nucleotides. This may lead to poor resolution of individual base pairs in translocating DNA strands.

The opposite is likely true for the Tyr51 constriction. After the removal of the Asn55/Tyr56 constriction, the remaining ring of Tyr51 residues in the oligomer may be conformationally less stable than in the native structure. However, the Tyr51 constriction is shorter (when measured along the central pore axis) and likely more capable of providing a constriction within the channel that may distinguish between individual bases.

In either embodiment, the presence of a single narrow constriction (when measured along the central pore axis) is likely to reduce the complexity of the electrical current readings when the pore is utilised in nucleic acid sequencing applications. Modulations in the observed electrical current occurring during nucleic acid translocation through the pore will, hence, solely reflect the passage of separate nucleotides through a single constriction, or "reading head".

The effective removal of one constriction may also increase the open-channel current of the pore variant. An increased open-channel current would be advantageous as a higher background conductance leads to better resolved current blockade levels for the different nucleic acid base pair signals. In this way, modifications to the reading head can improve the suitability of the biological pore for both nucleic acid sequencing and other molecular sensing applications.

As an alternative embodiment, or in addition to the sequence modifications described above, it is also provided that the Asn55/Phe56 constriction may be further adapted to tune its height (as measured along the central pore axis). Such further adaptation of the Asn55/Phe56 constriction may or may not be accompanied by mutations of the Tyr51 or other positions within the CsgG channel. Suitably, further adaptation of the Asn55/Phe56 constriction is contemplated as part of mutations that widen or remove the constriction formed by the Tyr51 residue.

In the wild-type form, the Asn55/Phe56 channel constriction is composed of two amino acid rings positioned vertically adjacent to each other. The constriction, as a result, has a length of more than 1 nm. A 1 nm long constriction may not allow the resolution of the electrical signals generated from the ion flow to the separate bases in translocating nucleic acid strands. Typically, the constriction(s) of known nanopores used for nucleic acid sequencing typically has a length less than 1 nm. For example, the MspA nanopore which is used for DNA sequencing has a constriction height of 0.6 nm (as measured along the central pore axis; Manrao et al., Nature Biotechnology, 2012, 30(4), 349-353).

To reduce the height of the Asn55/Phe56 constriction (as measured along the central pore axis), either of the two residues may be substituted or deleted leading to a widening of the top or bottom of the constriction.

For Asn55, which forms part of the second constriction in the CsgG channel, substitution with any amino acid is contemplated. In particular, substitution with alanine, glycine, valine, serine or threonine (SEQ ID: 9-33, 44-68, 79-103 114-138, 149-173, 184-208, 219-243, 254-278, 289-313 and 324-348).

For Phe 56 which forms part of the second constriction in the CsgG channel, substitution with any amino acid is contemplated. In particular, substitution with alanine, glycine, valine, leucine, isoleucine, asparagine, and glutamine (SEQ ID: 5-13, 15-18, 20-23, 25-28, 30-33, 40-43, 45-48, 50-53, 55-58, 60-63, 65-68, 75-78, 80-83, 85-88, 90-93, 95-98, 100-103, 110-113, 115-118, 120-123, 125-128, 130-133, 135-138, 145-148, 150-153, 155-158, 160-163, 165-168, 170-173, 180-183, 185-188, 190-193, 195-198, 200-203, 205-208, 215-218, 220-223, 225-228, 230-233, 235-238, 240-243, 250-253, 255-258, 260-263, 265-268, 270-273, 275-578, 285-288, 290-293, 295-298, 300-303, 305-308, 310-313, 320-323, 325-328, 330-333, 335-338, 340-343 and 345-348). In embodiments of the invention, substitution of Phe56 with alanine and glycine is particularly suitable (SEQ ID: 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 6, 11, 16, 21, 26, 31, 36, 41, 46, 51, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 206, 211, 216, 221, 226, 231, 236, 241, 246, 251, 256, 261, 266, 271, 276, 281, 286, 291, 296, 301, 306, 311, 316, 321, 326, 331, 336, 341 346, 351, 356, 361, 366, 371, 376, 381 and 386).

Modifications to tune the minimum diameter of the constriction of the wild-type CsgG pore are also contemplated. The minimum diameter of both constrictions in the CsgG pore is approximately 0.9 nm (9 Å), which is less than the diameter of 1.2 nm for the constriction in the known MspA nanopore that shows utility for DNA sequencing (Manrao et al., Nature Biotechnology, 2012, 30(4), 349-353). Any of the above mutations above that provide the remaining constriction in the modified CsgG pore with a minimum diameter of 0.5 to 1.5 nm would be suitable.

Any of the modifications listed above may beneficially alter the hydrophilicity and charge distribution of the amino acids at the constriction to improve the passage and non-covalent interaction with the translocating nucleic acid strand in order to improve the current read-out. Any of the mutations listed above may also beneficially alter the hydrophilicity and charge distribution close to the channel constriction in order to optimise the flow of electrolyte ions through the constriction and achieve a better discrimination among the passing nucleotides of the translocating nucleic acid strand.

Further modifications of the CsgG protein are contemplated that may result in changing the surface charge distribution within the channel lumen. In one embodiment of the invention, these modifications may be made to avoid undesired electrostatic adsorption of the translocating nucleic acid to the channel wall. Since a nucleic acid is negatively charged and the CsgG channel lumen contains some positive charges (FIG. 1), it is postulated that electrostatic interaction may interfere with the threading or translocation during nucleic acid sequencing. Suitably positively charged amino acid residues such as lysine, histidine and arginine may be substituted with neutral or negatively charged side chains in order to further improve the efficiency of nucleic acid translocation through the pore, and thus the clarity of electrical current readout.

Modification of the channel lumen of wild-type E. coli CsgG or mutant CsgG to facilitate the translocation or threading of a nucleic acid strand (or individual nucleotides) into the pore constriction is also provided by an embodiment of the present invention. The membrane-spanning section of CsgG with the inner constriction resembles a barrel with a lid featuring a central hole. The threading could be facilitated by adding additional loops into the pore lumen which is closest to the barrel and lid.

A specific embodiment of the invention provides that the CsgG pore may be comprised of one or more monomers, dimers or oligomers that are covalently attached. By way of non-limiting example, monomers may be genetically fused in any configuration, such as by their terminal amino acids. In this instance, the amino terminus of one monomer may be fused to the carboxy terminus of another monomer.

According to an embodiment of the invention, it is also provided that the CsgG pore may be adapted to accommodate additional accessory proteins that may have beneficial properties on the passage of molecules through the pore. The adaptations to the pore may facilitate anchoring of nucleic acid-processing enzymes. Nucleic acid-processing enzymes may include DNA or RNA polymerases; isomerases; topoisomerases; gyrases; telomerases; and helicases. Associated of one or more of these enzymes with the nanopore can have benefits in terms of enhanced threading of the nucleic acid into the pore, and in controlling the speed at which a nucleic acid strand translates through the pore (Manrao et al., Nature Biotechnology, 2012, 30(4), 349-353). Controlling the translocation speed of the nucleic acid strand through the pore has the advantage of providing an improved response in terms of the electrical current measurement of the ion flow that is more suitable for reading and more uniform.

In embodiments of the invention, it is envisaged that modifications in the extra-membranous regions of the nanopore may help facilitate the docking of a suitable nucleic acid-processing enzyme, such as a DNA-polymerase, inside or adjacent to the lumen of the channel via the provision of one or more binding/anchoring sites. Suitable anchoring sites may comprise electrostatic patches for electrostatic binding of the enzyme; one or more cysteine residues to allow for covalent coupling; and/or an altered inner width of the transmembrane channel section to provide a steric anchor.

Further adaptations of the CsgG wild type pore for use in nucleic acid sequencing that are provided by the present invention in specific embodiments that are set out in more detail below.

In embodiments of the invention, the extra-membranous region of the CsgG pore (bottom portion as shown in FIG. 1) may be truncated or removed to facilitate the exit of the nucleic strand on the other side of the channel lumen. Truncation or removal of the extra-membranous region can also improve the current resolution of the electrical signal from the ion flow in the channel. The latter benefit is brought about by lowering the resistance caused to ion flow by the extra-membranous region. In the present CsgG pore, the transmembrane channel, the inner constriction, and cap region represent three areas of resistance in series. Removing or lowering the contribution of one of these will increase the open-channel current and hence improve the electrical current resolution. Such alteration can include the deletion of α-helix 2 (α2), the C-terminal a-helix (αC) (FIG. 1), and/or a combination thereof.

In further embodiments of the invention, the membrane facing amino acids on the outer face of the wild-type E. coli CsgG pore may be modified to facilitate the insertion of the pore into the membrane. In certain embodiments, it is provided that single amino-acid substitutions may replace wild-type residues with suitable more hydrophobic analogues. For example, one or more of the residues Ser136, Gly138, Gly140, Ala148, Ala 188 or Gly202 could be changed to Ala, Val, Leu, or Ile. In addition, aromatic residues such as tyrosine or tryptophan can substitute appropriate wild-type amino-acid so that they are positioned at the interface the hydrophobic membrane and the hydrophilic solvent. For example, one or more of the residues Leu154 or Leu182 could be substituted by Tyr, Phe or Trp.

In embodiments of the invention, the thermal stability of the protein pore may be increased. This results in an advantageous increase in the shelf-life of the nanopore in sequencing devices. In embodiments, an increase in thermal stability of the protein pore is attained by the modification of beta-turn sequences or improving electrostatic interactions at the protein surface. In one embodiment, the β-hairpin in the trans-membrane regions could be stabilized by a covalent disulfide formation across two adjacent β-strands within or between adjacent β-hairpins. Examples of such cross-strand cysteine pairs could be: Val139-Asp203; Gly139-Gly205; Lys135-Thr207; Glu201-Ala141; Gly147-Gly189; Asp149-Gln187; Gln151-Glu185; Thr207-Glu185; Gly205-Gln187; Asp203-Gly189; Ala153-Lys135; Gly137-Gln151; Val139-Asp149 or Ala141-Gly147.

In further embodiments of the invention, the codon usage of the polypeptide sequence may be modified to allow expression of the CsgG protein at high level and with a low error rate according to the methods described in Biotechnol. J., 2011, 6(6), 650-659. The modification may also target any secondary structures of the mRNA.

The present invention also provides for the alteration of the protein sequence to improve its protease stability. This may be achieved by removal of flexible loop regions, for example the deletion of α-helix 2 (α2), the C-terminal a-helix (αC) (FIG. 1), and/or a combination thereof.

In embodiments of the invention, the CsgG polypeptide sequence/expression system is altered to avoid the possible aggregation of the protein.

The present invention also provides for the alteration of the polypeptide sequence to improve the folding efficiency of the protein. Suitable techniques are provided in Biotechnol. J., 2011, 6(6), 650-659.

One embodiment of the invention further provides for the replacement of or addition of a bioaffinity tag to facilitate the purification of the CsgG protein. The published structure of the CsgG pore contains a StrepII tag (Goyal et al., Nature, 2014, 516(7530), 250-3). Embodiments of the invention comprise other bioaffinity tags, such as Histidine-tag to facilitate the purification via metal chelate affinity chromatography. In alternative embodiments of the invention, the tag may include a FLAG-tag or an epitope tag, such as a Myo- or HA-tag. In a further embodiment of the invention, the nanopore may be modified by biotinylation with biotin or an analogue thereof (e.g. desthiobiotin), thereby facilitating purification via interaction with streptavidin.

In embodiments of the invention, negative charges at the protein terminus may be added to increase the net charge of the polypeptide and facilitate the migration of the protein in polyacrylamide gel electrophoresis. This may lead to the improved separation of heteroligomers of the CsgG in the case where these species are of interest (see Howorka et al. Proc. Nat. Acad. Sci., 2001, 98(23), 12996-13001). A heterooligomer can be useful to introduce a single-cysteine residue per pore which may be advantageous in facilitating the attachment of a suitable nucleic acid-processing enzyme, such as a DNA-polymerase as described above.

The present invention relates in part to the use of the wild type or modified CsgG nanopore in molecular sensing applications based on variations of electrical measurements of current flowing through a nanopore.

The binding of a molecule in the channel of the CsgG pore, or in the vicinity of either opening of the channel will have an effect on the open-channel ion flow through the pore. In a similar manner to the nucleic acid sequencing application described above, variation in the open-channel ion flow can be measured using suitable measurement techniques by the change in electrical current (for example, WO 2000/28312 and D. Stoddart et al., Proc. Natl. Acad. Sci., 2010, 106, 7702-7 or WO 2009/077734). The degree of reduction in ion flow, as measured by the reduction in electrical current, is related to the size of the obstruction within, or in the vicinity of, the pore. Binding of a molecule of interest, also referred to as an analyte, in or near the pore therefore provides a detectable and measurable event, thereby forming the basis of a biological sensor. Suitable molecules for nanopore sensing include nucleic acids; proteins; peptides; and small molecules such as pharmaceuticals, toxins or cytokines.

Detecting the presence of biological molecules finds application in personalised drug development, medicine, diagnostics, life science research, environmental monitoring and in the security and/or the defence industry.

In embodiments of the invention, the wild type or modified *E. coli* CsgG nanopore, or homologue thereof, disclosed herein may serve as a molecular sensor. Procedures for analyte detection are described in Howorka et al. Nature Biotechnology (2012) June 7; 30(6):506-7. The analyte molecule that is to be detected may bind to either face of the channel, or within the lumen of the channel itself. The position of binding may be determined by the size of the molecule to be sensed. The wild-type CsgG pore may act as sensor, or embodiments of the invention, the CsgG pore is modified via recombinant or chemical methods to increase the strength of binding, the position of binding, or the specificity of binding of the molecule to be sensed. Typical modifications include addition of a specific binding moiety complimentary to the structure of the molecule to be sensed. Where the analyte molecule comprises a nucleic acid, this binding moiety may comprise a cyclodextrin or an oligonucleotide; for small molecules this may be a known complimentary binding region, for example the antigen binding portion of an antibody or of a non-antibody molecule, including a single chain variable fragment (scFv) region or an antigen recognition domain from a T-cell receptor (TCR); or for proteins, it may be a known ligand of the target protein. In this way the wild type or modified *E. coli* CsgG nanopore, or homologue thereof, may be rendered capable of acting as a molecular sensor for detecting presence in a sample of suitable antigens (including epitopes) that may include cell surface antigens, including receptors, markers of solid tumours or haematologic cancer cells (e.g. lymphoma or leukaemia), viral antigens, bacterial antigens, protozoal antigens, allergens, allergy related molecules, albumin (e.g. human, rodent, or bovine), fluorescent molecules (including fluorescein), blood group antigens, small molecules, drugs, enzymes, catalytic sites of enzymes or enzyme substrates, and transition state analogues of enzyme substrates.

Modifications may be achieved using known genetic engineering and recombinant DNA techniques. The positioning of any adaptation would be dependent on the nature of the molecule to be sensed, for example, the size, three-dimensional structure, and its biochemical nature. The choice of adapted structure may make use of computational structural design. A series of bespoke CsgG nanopores is envisaged each adapted specifically to the sensing application to which it is destined. Determination and optimization of protein-protein interactions or protein—small molecule interactions can be investigated using technologies such as a BIAcore® which detects molecular interactions using surface plasmon resonance (BIAcore, Inc., Piscataway, N.J.; see also www.biacore.com).

In an embodiment, the CsgG pore can be that of the water soluble, octameric form where the N-terminal Cys residue is replaced by an alternative aminoacid in order to prevent the lipidation of the protein N-terminus. In an alternative embodiment, the protein can be expressed in the cytoplasm by removal of the N-terminal leader sequence in order to avoid processing by the bacterial lipidation pathway.

The method of manufacture of the CsgG monomeric soluble protein, octameric soluble protein and the oligomeric lipidated CsgG pore is described in Goyal et al. (Nature, 2014; 516(7530): 250-3), which is incorporated herein by reference, and in Examples 1 and 2.

Mutant CsgG Monomers

The present invention provides mutant CsgG monomers. The mutant CsgG monomers may be used to form the pores of the invention. A mutant CsgG monomer is a monomer whose sequence varies from that of a wild-type CsgG monomer and which retains the ability to form a pore. Methods for confirming the ability of mutant monomers to form pores are well-known in the art and are discussed in more detail below.

The mutant monomers have improved polynucleotide reading properties i.e. display improved polynucleotide capture and nucleotide discrimination. In particular, pores constructed from the mutant monomers capture nucleotides and polynucleotides more easily than the wild type. In addition, pores constructed from the mutant monomers display an increased current range, which makes it easier to discriminate between different nucleotides, and a reduced variance of states, which increases the signal-to-noise ratio. In addition, the number of nucleotides contributing to the current as the polynucleotide moves through pores constructed from the mutants is decreased. This makes it easier to identify a direct relationship between the observed current as the polynucleotide moves through the pore and the polynucleotide sequence. In addition, pores constructed from the mutant monomers may display an increased throughput, i.e. are more likely to interact with an analyte, such as a polynucleotide. This makes it easier to characterise analytes using the pores. Pores constructed from the mutant monomers may insert into a membrane more easily.

A mutant monomer of the invention comprises a variant of the sequence shown in SEQ ID NO: 390. SEQ ID NO: 390 is the wild-type CsgG monomer from *Escherichia coli* Str. K-12 substr. MC4100. A variant of SEQ ID NO: 390 is a polypeptide that has an amino acid sequence which varies from that of SEQ ID NO: 390 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state.

In all of the discussion herein, the standard one letter codes for amino acids are used. These are as follows: alanine (A), arginine (R), asparagine (N), aspartic acid (D), cysteine (C), glutamic acid (E), glutamine (0), glycine (G), histidine (H), isoleucine (I), leucine (L), lysine (K), methionine (M), phenylalanine (F), proline (P), serine (S), threonine (T), tryptophan (W), tyrosine (Y) and valine (V). Standard substitution notation is also used, i.e. Q42R means that Q at position 42 is replaced with R.

In one embodiment, the mutant monomers of the invention comprise a variant of SEQ ID NO: 390 comprising one or more of the following (i) one or more mutations at the following positions (i.e. mutations at one or more of the following positions) N40, D43, E44, S54, S57, Q62, R97, E101, E124, E131, R142, T150 and R192, such as one or more mutations at the following positions (i.e. mutations at one or more of the following positions) N40, D43, E44, S54, S57, Q62, E101, E131 and T150 or N40, D43, E44, E101 and E131; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, 0149Q or 0149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any combination of (i) to (xi). In particular, the variant may comprise {i} {ii} {iii} {iv} {v} {vii} {viii} {ix} {x} {xi} {i,iii} {i,v} {i,viii} {i,x} {i,xi} {ii,iii} {ii,iv} {ii,v} {ii,vi} {ii,vii} {ii,xi} {iii,x} {iii,xi} {iv,v} {iv,vi} {iv,vii} {iv,x} {iv,xi} {v,vi} {v,vii} {v,viii} {v,ix} {v,x} {v,xi} {vi,vii} {vi,viii} {vi,ix} {vi,x} {vi,xi} {vii,viii} {vii,ix} {vii,x} {vii,xi} {viii,ix} {viii,x} {viii,xi} {ix,x} {ix,xi} {x,xi} {i,ii,iii} {i,ii,iv} {i,ii,v} {i,ii,vi} {i,ii,viii} {i,ii,ix} {i,iv,viii} {i,iv,ix} {i,iv,x} {i,iv,xi} {i,v,vi} {i,v,vii} {i,v,viii} {i,v,ix} {i,v,x} {i,v,xi} {i,vi,vii} {i,vi,viii} {i,vi,ix} {i,vi,x}{i,vi,xi} {i,vii,viii} {i,vii,ix} {i,vii,x} {i,vii,xi} {i,viii,ix} {i,viii,x} {i,ix,x} {i,ix,xi} {i,x,xi} {ii,iii,iv} {ii,iii,v} {ii,iii,vi} {ii,iii,vii} {ii, iii,viii} {ii,iii,ix} {ii,iii,x} {ii,iii,xi} {ii,iv,v} {ii,iv,vi} {ii,iv, vii} {ii,iv,viii} {ii,iv,ix} {ii,iv,x} {ii,iv,xi} {ii,v,vi}{ii,v,vii} {ii,v,viii} {ii,v,ix} {ii,v,x} {ii,v,xi} {ii,vi,vii} {ii,vi,viii} {ii,vi,ix} {ii,vi,x} {ii,vi,xi} {ii,vii,viii} {ii,vii,ix} {ii,vii, x}{ii,vii,xi} {ii,viii,ix} {ii,viii,x} {ii,viii,xi} {ii,ix,x} {ii,ix, xi} {ii,x,xi} {iii,iv,v} {iii,iv,vi} {iii,iv,vii} {iii,iv,viii} {iii, iv,ix}{iii,iv,x} {iii,iv,xi} {iii,v,vi} {iii,v,vii} {iii,v,viii} {iii, v,ix} {iii,v,x} {iii,v,xi} {iii,vi,vii} {iii,vi,viii} {iii,vi,ix} {iii,vi,x} {iii,vi,xi}{iii,vii,viii} {iii,vii,ix} {iii,vii,x} {iii,vii, xi} {iii,viii,ix} {iii,viii,x} {i,ii,iii,iv} {i,ii,iii,v} {i,ii,iii,vi} {i,ii,iii,vii} {i,ii,iii,viii}{i,ii,iii,ix} {i,ii,iii,x} {i,ii,iii,xi} {i,ii, iv,v} {i,ii,iv,vi} {i,ii,iv,vii} {i,ii,iv,viii} {i,ii,iv,ix} {i,ii,iv,x} {i,ii,iv,xi} {i,ii,v,vi} {i,ii,v,vii}{i,ii,v,viii} {i,ii,v,ix} {i,ii,v, x} {i,ii,v,xi} {i,ii,vi,vii} {i,ii,vi,viii} {i,ii,vi,ix} {i,ii,vi,x} {i,ii,vi,xi} {i,ii,vii,viii} {i,ii,vii,ix}{i,ii,vii,x} {i,ii,vii,xi} {i,ii,viii,ix} {i,ii,viii,x} {i,ii,viii,xi} {i,ii,ix,x} {i,ii,ix,xi} {i,ii,x,xi} {i,iii,iv,v} {i,iii,iv,vi} {i,iii,iv,vii}{i,iii,iv,viii} {i,iii,iv,ix} {i,iii,iv,x} {i,iii,iv,xi} {i,iii,v,vi} {i,iii,v,vii} {i,iii,v,viii} {i,iii,v,ix} {i,iii,v,x} {i,iii,v,xi} {i,iii,vi,vii}{i,iii, vi,viii} {i,iii,vi,ix} {i,iii,vi,x} {i,iii,vi,xi} {i,iii,vii,viii} {i,iii, vii,ix} {i,iii,vii,x} {i,iii,vii,xi} {i,iii,viii,ix} {i,iii,viii,x}{i, iii,viii,xi} {i,iii,ix,x} {i,iii,ix,xi} {i,iii,x,xi} {i,iv,v,vi} {i,iv, v,vii} {i,iv,v,viii} {i,iv,v,ix} {i,iv,v,x} {i,iv,v,xi} {i,iv,vi, vii}{i,iv,vi,viii} {i,iv,vi,ix} {i,iv,vi,x} {i,iv,vi,xi} {i,iv,vii, viii} {i,iv,vii,ix} {i,iv,vii,x} {i,iv,vii,xi} {i,iv,viii,ix} {i,iv, viii,x}{i,iv,viii,xi} {i,iv,ix,x} {i,iv,ix,xi} {i,iv,x,xi} {i,v,vi, vii} {i,v,vi,viii} {i,v,vi,ix} {i,v,vi,x} {i,v,vi,xi} {i,v,vii,viii} {i,v,vii,ix}{i,v,vii,x} {i,v,vii,xi} {i,v,viii,ix} {i,v,viii,x} {i,v, viii,xi} {i,v,ix,x} {i,v,ix,xi} {i,v,x,xi} {i,vi,vii,viii} {i,vi,vii, ix} {i,vi,vii,x}{i,vi,vii,xi} {i,vi,viii,ix} {i,vi,viii,x} {i,vi, viii,xi} {i,vi,ix,x} {i,vi,ix,xi} {i,vi,x,xi} {i,vii,viii,ix} {i,vii, viii,x} {i,vii,viii,xi}{i,vii,ix,x} {i,vii,ix,xi} {i,vii,x,xi} {i,viii,ix,x} {i,viii,ix,xi} {i,viii,x,xi} {i,ix,x,xi} {ii,iii,iv,v} {ii,iii,iv,vi} {ii,iii,iv,vii}{ii,iii,iv,viii} {ii,iii,iv,ix} {ii,iii,iv, x} {ii,iii,iv,xi} {ii,iii,v,vi} {ii,iii,v,vii} {ii,iii,v,viii} {ii,iii,v, ix} {ii,iii,v,x} {ii,iii,v,xi}{ii,iii,vi,vii} {ii,iii,vi,viii} {ii,iii,vi, ix} {ii,iii,vi,x} {ii,iii,vi,xi} {ii,iii,vii,viii} {ii,iii,vii,ix} {ii, iii,vii,x} {ii,iii,vii,xi} {ii,iii,viii,ix}{ii,iii,viii,x} {ii,iii,viii, xi} {ii,iii,ix,x} {ii,iii,ix,xi} {ii,iii,x,xi} {ii,iv,v,vi} {ii,iv,v, vii} {ii,iv,v,viii} {ii,iv,v,ix} {ii,iv,v,x}{ii,iv,v,xi} {ii,iv,vi, vii} {ii,iv,vi,viii} {ii,iv,vi,ix} {ii,iv,vi,x} {ii,iv,vi,xi} {ii,iv, vii,viii} {ii,iv,vii,ix} {ii,iv,vii,x} {ii,iv,vii,xi}{ii,iv,viii,ix} {ii,iv,viii,x} {ii,iv,viii,xi} {ii,iv,ix,x} {ii,iv,ix,xi} {ii,iv,x,xi} {ii,v,vi,vii} {ii,v,vi,viii} {ii,v,vi,ix} {ii,v,vi,x}{ii,v,vi,xi} {ii, v,vii,viii} {ii,v,vii,ix} {ii,v,vii,x} {ii,v,vii,xi} {ii,v,viii,ix} {ii,v,viii,x} {ii,v,viii,xi} {ii,v,ix,x} {ii,v,ix,xi}{ii,v,x,xi} {ii, vi,vii,viii} {ii,vi,vii,ix} {ii,vi,vii,x} {ii,vi,vii,xi} {ii,vi,viii, ix} {ii,vi,viii,x} {ii,vi,viii,xi} {ii,vi,ix,x} {ii,vi,ix,xi}{ii,vi, x,xi} {ii,vii,viii,ix} {ii,vii,viii,x} {ii,vii,viii,xi} {ii,vii,ix,x} {ii,vii,ix,xi} {ii,vii,x,xi} {ii,viii,ix,x} {ii,viii,ix,xi}{ii,viii, xi} {ii,ix,x,xi} {iii,iv,v,vi} {iii,iv,v,vii} {iii,iv,v,viii} {iii,iv, v,ix} {iii,iv,v,x} {iii,iv,v,xi} {iii,iv,vi,vii} {iii,iv,vi,viii}{iii, iv,vi,ix} {iii,iv,vi,x} {iii,iv,vi,xi} {iii,iv,vii,viii} {iii,iv,vii, ix} {iii,iv,vii,x} {iii,iv,vii,xi} {iii,iv,viii,ix} {iii,iv,viii,x}{iii, iv,viii,xi} {iii,iv,ix,x} {iii,iv,ix,xi} {iii,iv,x,xi} {iii,v,vi,vii} {iii,v,vi,viii} {iii,v,vi,ix} {iii,v,vi,x} {iii,v,vi,xi} {iii,v,vii, viii}{iii,v,vii,ix} {iii,v,vii,x} {iii,v,vii,xi} {iii,v,viii,ix} {iii, v,viii,x} {iii,v,viii,xi} {iii,v,ix,x} {iii,v,ix,xi} {iii,v,x,xi} {iii, vi,vii,viii}{iii,vi,vii,ix} {iii,vi,vii,x} {iii,vi,vii,xi} {iii,vi, viii,ix} {iii,vi,viii,x} {iii,vi,viii,xi} {iii,vi,ix,x} {iii,vi,ix,xi} {iii,vi,x,xi}{iii,vii,viii,ix} {iii,vii,viii,x} {iii,vii,viii,xi} {iii, vii,ix,x} {iii,vii,ix,xi} {iii,vii,x,xi} {iii,viii,ix,x} {iii,viii,ix, xi} {iii,viii,x,xi}{iii,ix,x,xi} {iv,v,vi,vii} {iv,v,vi,viii} {iv,v, vi,ix} {iv,v,vi,x} {iv,v,vi,xi} {iv,v,vii,viii} {iv,v,vii,ix} {iv, v,vii,x} {iv,v,vii,xi}{iv,v,viii,ix} {iv,v,viii,x} {iv,v,viii,xi} {iv,v,ix,x} {iv,v,ix,xi} {iv,v,x,xi} {iv,v,vii,viii} {iv,vi,vii, ix} {iv,vi,vii,x}{iv,vi,vii,xi} {iv,vi,viii,ix} {iv,vi,viii,x} {iv, vi,viii,xi} {iv,vi,ix,x} {iv,vi,ix,xi} {iv,vi,x,xi} {iv,vii,viii,x} {iv,vii,viii,xi} {iv,vii,ix,x} {iv,vii,ix,xi} {iv, {vii,x,xi} {iv,viii,ix,x} {iv,viii,ix,xi} {iv,viii,x,xi} {iv,ix,x,xi} {v,vi,vii,viii}{v,vi,vii,ix} {v,vi,vii,x} {v,vi,vii,xi} {v,vi,viii,ix} {v,vi,viii,x} {v,vi,viii,xi} {v,vi,ix,x} {v,vi,ix,xi} {v,vi,x,xi} {v,vii,viii,ix}{v,vii,viii,x} {v,vii,viii,xi} {v,vii,ix,x} {v,vii,ix,xi} {v,vii,x,xi} {v,viii,ix,x} {v,viii,ix,xi} {v,viii,x,xi} {v,ix,x,xi} {vi,vii,viii,ix} {vi,vii,viii,x} {vi,vii,viii,xi} {vi,vii,ix,x} {vi,vii,ix,xi} {vi,vii,x,xi} {vi,viii,ix,x} {vi,viii,ix,xi}{vi,viii,x,xi}{vi,ix,x,xi} {vii,viii,ix,x} {vii,viii,ix,xi} {vii,viii,x,xi} {vii,ix,x,xi} {viii,ix,x,xi} {i,ii,iii,iv,v} {i,ii,iii,iv,vi} {i,ii,iii,iv,vii} {i,ii,iii,iv,viii} {i,ii,iii,iv,ix} {i,ii,iii,iv,x} {i,ii,iii,iv,xi} {i,ii,iii,v,vi} {i,ii,iii,v,vii} {i,ii,iii,v,viii} {i,ii,iii,v,ix} {i,ii,iii,v,x}{i,ii,iii,v,xi} {i,ii,iii,vi,vii} {i,ii,iii,vi,viii} {i,ii,iii,vi,ix} {i,ii,iii,vi,x} {i,ii,iii,vi,xi} {i,ii,iii,vii,viii} {i,ii,iii,vii,ix} {i,ii,iii,vii,x}{i,ii,iii,vii,xi} {i,ii,iii,viii,ix} {i,ii,iii,viii,x} {i,ii,iii,viii,xi} {i,ii,iii,ix,x} {i,ii,iii,ix,xi} {i,ii,iii,x,xi} {i,ii,iv,v,vi} {i,ii,iv,v,vii}{i,ii,iv,v,viii} {i,ii,iv,v,ix} {i,ii,iv,v,x} {i,ii,iv,v,xi} {i,ii,iv,vi,vii} {i,ii,iv,vi,viii} {i,ii,iv,vi,ix} {i,ii,iv,vi,x} {i,ii,iv,vi,xi} {i,ii,iv,vii,viii} {i,ii,iv,vii,ix} {i,ii,iv,vii,x} {i,ii,iv,vii,xi} {i,ii,iv,viii,ix} {i,ii,iv,viii,x} {i,ii,iv,viii,xi} {i,ii,iv,ix,x} {i,ii,iv,ix,xi}{i,ii,iv,x,xi} {i,ii,v,vi,vii} {i,ii,v,vi,viii} {i,ii,v,vi,ix} {i,ii,v,vi,x} {i,ii,v,vi,xi} {i,ii,v,vii,viii} {i,ii,v,vii,ix} {i,ii,v,vii,x}{i,ii,v,vii,xi} {i,ii,v,viii,ix} {i,ii,v,viii,x} {i,ii,v,viii,xi} {i,ii,v,ix,x} {i,ii,v,ix,xi} {i,ii,v,x,xi} {i,ii,vi,vii,viii} {i,ii,vi,vii,ix} {i,ii,vi,vii,x} {i,ii,vi,vii,xi} {i,ii,vi,viii,ix} {i,ii,vi,viii,x} {i,ii,vi,viii,xi} {i,ii,vi,ix,x} {i,ii,vi,ix,xi} {i,ii,vi,x,xi} {i,ii,vii,viii,ix} {i,ii,vii,viii,x} {i,ii,vii,viii,xi} {i,ii,vii,ix,x} {i,ii,vii,ix,xi} {i,ii,vii,x,xi} {i,ii,viii,ix,x} {i,ii,viii,ix,xi} {i,ii,viii,x,xi} {i,ii,ix,x,xi}{i,iii,iv,v,vi} {i,iii,iv,v,vii} {i,iii,iv,v,viii} {i,iii,iv,v,ix} {i,iii,iv,v,x} {i,iii,iv,v,xi} {i,iii,iv,vi,vii} {i,iii,iv,vi,viii} {i,iii,iv,vi,ix}{i,iii,iv,vi,x} {i,iii,iv,vi,xi} {i,iii,iv,vii,viii} {i,iii,iv,vii,ix} {i,iii,iv,vii,x} {i,iii,iv,vii,xi} {i,iii,iv,viii,ix} {i,iii,iv,viii,x}{i,iii,iv,viii,xi} {i,iii,iv,ix,x} {i,iii,iv,ix,xi} {i,iii,iv,x,xi} {i,iii,v,vi,vii} {i,iii,v,vi,viii} {i,iii,v,vi,ix} {i,iii,v,vi,x} {i,iii,v,vi,xi}{i,iii,v,vii,viii} {i,iii,v,vii,ix} {i,iii,v,vii,x} {i,iii,v,vii,xi} {i,iii,v,viii,ix} {i,iii,v,viii,x} {i,iii,v,viii,xi} {i,iii,v,ix,x} {i,iii,v,ix,xi}{i,iii,v,x,xi} {i,iii,vi,vii,viii} {i,iii,vi,vii,ix} {i,iii,vi,vii,x} {i,iii,vi,vii,xi} {i,iii,vi,viii,ix} {i,iii,vi,viii,x} {i,iii,vi,viii,xi}{i,iii,vi,ix,x} {i,iii,vi,ix,xi} {i,iii,vi,x,xi} {i,iii,vii,viii,ix} {i,iii,vii,viii,x} {i,iii,vii,viii,xi} {i,iii,vii,ix,x} {i,iii,vii,ix,xi}{i,iii,vii,x,xi} {i,iii,viii,ix,x} {i,iii,viii,ix,xi} {i,iii,viii,x,xi} {i,iii,ix,x,xi} {i,iv,v,vi,vii} {i,iv,v,vi,viii} {i,iv,v,vi,ix} {i,iv,v,vi,x}{i,iv,v,vi,xi} {i,iv,v,vii,viii} {i,iv,v,vii,ix} {i,iv,v,vii,x} {i,iv,v,vii,xi} {i,iv,v,viii,ix} {i,iv,v,viii,x} {i,iv,v,viii,xi} {i,iv,v,ix,x} {i,iv,v,ix,xi} {i,iv,v,x,xi} {i,iv,vi,vii,viii} {i,iv,vi,vii,ix} {i,iv,vi,vii,x} {i,iv,vi,vii,xi} {i,iv,vi,viii,ix} {i,iv,vi,viii,x} {i,iv,vi,viii,xi} {i,iv,vi,ix,x} {i,iv,vi,ix,xi} {i,iv,vi,x,xi} {i,iv,vii,viii,ix} {i,iv,vii,viii,x} {i,iv,vii,viii,xi}{i,iv,vii,ix,x} {i,iv,vii,ix,xi} {i,iv,vii,x,xi} {i,iv,viii,ix,x} {i,iv,viii,ix,xi} {i,iv,viii,x,xi} {i,iv,ix,x,xi} {i,v,vi,vii,viii}{i,v,vi,vii,ix} {i,v,vi,vii,x} {i,v,vi,vii,xi} {i,v,vi,viii,ix} {i,v,vi,viii,x} {i,v,vi,viii,xi} {i,v,vi,ix,x} {i,v,vi,ix,xi} {i,v,vi,x,xi} {i,v,vii,viii,ix} {i,v,vii,viii,x} {i,v,vii,viii,xi} {i,v,vii,ix,x} {i,v,vii,ix,xi} {i,v,vii,x,xi} {i,v,viii,ix,x} {i,v,viii,ix,xi}{i,v,viii,x,xi} {i,v,ix,x,xi} {i,vi,vii,viii,ix} {i,vi,vii,viii,x} {i,vi,vii,viii,xi} {i,vi,vii,ix,x} {i,vi,vii,ix,xi} {i,vi,vii,x,xi}{i,vi,viii,ix,x} {i,vi,viii,ix,xi} {i,vi,viii,x,xi} {i,vi,ix,x,xi} {i,vii,viii,ix,x} {i,vii,viii,ix,xi} {i,vii,viii,x,xi} {i,vii,ix,x,xi}{i,viii,ix,x,xi} {ii,iii,iv,v,vi} {ii,iii,iv,v,vii} {ii,iii,iv,v,viii} {ii,iii,iv,v,ix} {ii,iii,iv,v,x} {ii,iii,iv,v,xi} {ii,iii,iv,vi,vii}{ii,iii,iv,vi,viii} {ii,iii,iv,vi,ix} {ii,iii,iv,vi,x} {ii,iii,iv,vi,xi}{ii,iii,iv,vii,viii} {ii,iii,iv,vii,ix} {ii,iii,iv,vii,x} {ii,iii,iv,vii,xi} {ii,iii,iv,viii,ix} {ii,iii,iv,viii,x} {ii,iii,iv,viii,xi} {ii,iii,iv,ix,x} {ii,iii,iv,ix,xi} {ii,iii,iv,x,xi} {ii,iii,v,vi,vii} {ii,iii,v,vi,viii} {ii,iii,v,vi,ix} {ii,iii,v,vi,x} {ii,iii,v,vi,xi} {ii,iii,v,vii,viii} {ii,iii,v,vii,ix} {ii,iii,v,vii,x} {ii,iii,v,vii,xi} {ii,iii,v,viii,ix} {ii,iii,v,viii,x}{ii,iii,v,viii,xi} {ii,iii,v,ix,x} {ii,iii,v,ix,xi} {ii,iii,v,x,xi} {ii,iii,vi,vii,viii} {ii,iii,vi,vii,ix} {ii,iii,vi,vii,x}{ii,iii,vi,vii,xi} {ii,iii,vi,viii,ix} {ii,iii,vi,viii,x} {ii,iii,vi,viii,xi} {ii,iii,vi,ix,x} {ii,iii,vi,ix,xi} {ii,iii,vi,x,xi} {ii,iii,vii,viii,ix} {ii,iii,vii,viii,x} {ii,iii,vii,viii,xi} {ii,iii,vii,ix,x} {ii,iii,vii,ix,xi} {ii,iii,vii,x,xi} {ii,iii,viii,ix,x} {ii,iii,viii,ix,xi}{ii,iii,viii,x,xi} {ii,iii,ix,x,xi} {ii,iv,v,vi,vii} {ii,iv,v,vi,viii} {ii,iv,v,vi,ix} {ii,iv,v,vi,x} {ii,iv,v,vi,xi} {ii,iv,v,vii,viii} {ii,iv,v,vii,ix} {ii,iv,v,vii,x} {ii,iv,v,vii,xi} {ii,iv,v,viii,ix} {ii,iv,v,viii,x} {ii,iv,v,viii,xi} {ii,iv,v,ix,x} {ii,iv,v,ix,xi} {ii,iv,v,x,xi}{ii,iv,vi,vii,viii} {ii,iv,vi,vii,ix} {ii,iv,vi,vii,x} {ii,iv,vi,vii,xi} {ii,iv,vi,viii,ix} {ii,iv,vi,viii,x} {ii,iv,vi,viii,xi} {ii,iv,vi,ix,x}{ii,iv,vi,ix,xi} {ii,iv,vi,x,xi} {ii,iv,vii,viii,ix} {ii,iv,vii,viii,x} {ii,iv,vii,viii,xi} {ii,iv,vii,ix,x} {ii,iv,vii,ix,xi} {ii,iv,vii,x,xi} {ii,iv,viii,ix,x} {ii,iv,viii,ix,xi} {ii,iv,viii,x,xi} {ii,iv,ix,x,xi} {ii,v,vi,vii,viii} {ii,v,vi,vii,ix} {ii,v,vi,vii,x} {ii,v,vi,vii,xi}{ii,v,vi,viii,ix} {ii,v,vi,viii,x} {ii,v,vi,viii,xi} {ii,v,vi,ix,x} {ii,v,vi,ix,xi} {ii,v,vi,x,xi} {ii,v,vii,viii,ix} {ii,v,vii,viii,x}{ii,v,vii,viii,xi} {ii,v,vii,ix,x} {ii,v,vii,ix,xi} {ii,v,vii,x,xi} {ii,v,viii,ix,x} {ii,v,viii,ix,xi} {ii,v,viii,x,xi} {ii,v,ix,x,xi}{ii,vi,vii,viii,ix} {ii,vi,vii,viii,x} {ii,vi,vii,viii,xi} {ii,vi,vii,ix,x} {ii,vi,vii,ix,xi} {ii,vi,vii,x,xi} {ii,vi,viii,ix,x} {ii,vi,viii,ix,xi}{ii,vi,viii,x,xi} {ii,vi,ix,x,xi} {ii,vii,viii,ix,x} {ii,vii,viii,ix,xi} {ii,vii,viii,x,xi} {ii,vii,ix,x,xi} {ii,viii,ix,x,xi} {iii,iv,v,vi,vii} {iii,iv,v,vi,viii} {iii,iv,v,vi,ix} {iii,iv,v,vi,x} {iii,iv,v,vi,xi} {iii,iv,v,vii,viii} {iii,iv,v,vii,ix} {iii,iv,v,vii,x} {iii,iv,v,vii,xi} {iii,iv,v,viii,ix} {iii,iv,v,viii,x} {iii,iv,v,viii,xi} {iii,iv,v,ix,x} {iii,iv,v,ix,xi} {iii,iv,v,x,xi} {iii,iv,vi,vii,viii} {iii,iv,vi,vii,ix} {iii,iv,vi,vii,x} {iii,iv,vi,vii,xi} {iii,iv,vi,viii,ix} {iii,iv,vi,viii,x} {iii,iv,vi,viii,xi} {iii,iv,vi,ix,x} {iii,iv,vi,ix,xi} {iii,iv,vi,x,xi} {iii,iv,vii,viii,ix} {iii,iv,vii,viii,x} {iii,iv,vii,viii,xi} {iii,iv,vii,ix,x} {iii,iv,vii,ix,xi} {iii,iv,vii,x,xi} {iii,iv,viii,ix,x}{iii,iv,viii,ix,xi} {iii,iv,viii,x,xi} {iii,iv,ix,x,xi} {iii,v,vi,vii,viii} {iii,v,vi,vii,ix} {iii,v,vi,vii,x} {iii,v,vi,vii,xi} {iii,v,vi,viii,ix}{iii,v,vi,viii,x} {iii,v,vi,viii,xi} {iii,v,vi,ix,x} {iii,v,vi,ix,xi} {iii,v,vi,x,xi} {iii,v,vii,viii,ix} {iii,v,vii,viii,x} {iii,v,vii,viii,xi}{iii,v,vii,ix,x} {iii,v,vii,ix,xi} {iii,v,vii,x,xi} {iii,v,viii,ix,x} {iii,v,viii,ix,xi} {iii,v,viii,x,xi} {iii,v,ix,x,xi} {iii,vi,vii,viii,ix}{iii,vi,vii,viii,x} {iii,vi,vii,viii,xi} {iii,vi,vii,ix,x} {iii,vi,vii,ix,xi} {iii,vi,vii,x,xi} {iii,vi,viii,ix,x} {iii,vi,viii,ix,xi}{iii,vi,viii,x,xi} {iii,vi,ix,x,xi} {iii,vii,viii,ix,x} {iii,vii,viii,ix,xi} {iii,vii,viii,x,xi} {iii,vii,ix,x,xi} {iii,viii,ix,x,xi} {iv,v,vi,vii,viii} {iv,v,vi,vii,ix} {iv,v,vi,vii,x} {iv,v,vi,vii,xi} {iv,v,vi,viii,ix} {iv,v,vi,viii,x} {iv,v,vi,viii,xi} {iv,v,vi,ix,x} {iv,v,vi,ix,xi} {iv,v,vi,x,xi} {iv,v,vii,viii,ix} {iv,v,vii,viii,x} {iv,v,vii,viii,xi} {iv,v,vii,ix,x} {iv,v,vii,ix,xi} {iv,v,vii,x,xi} {iv,v,viii,ix,x} {iv,v,viii,ix,xi} {iv,v,viii,x,xi} {iv,v,ix,x,xi} {iv,vi,vii,viii,ix} {iv,vi,vii,viii,x} {iv,vi,vii,viii,xi}{iv,vi,vii,ix,x} {iv,vi,vii,ix,xi} {iv,vi,vii,x,xi} {iv,vi,viii,ix,x} {iv,vi,viii,ix,xi} {iv,vi,viii,x,xi} {iv,vi,ix,x,xi} {iv,vii,viii,ix,x} {iv,vii,viii,ix,xi} {iv,vii,viii,x,xi} {iv,vii,ix,x,xi} {iv,viii,ix,x,xi} {v,vi,vii,viii,ix} {v,vi,vii,viii,x}{v,vi,vii,viii,xi} {v,vi,vii,ix,x} {v,vi,vii,ix,xi} {v,vi,vii,x,xi} {v,vi,viii,ix,x} {v,vi,viii,ix,xi} {v,vi,viii,x,xi} {v,vi,ix,x,xi}{v,vii,viii,ix,x} {v,vii,viii,ix,xi} {v,vii,viii,x,xi} {v,vii,ix,x,xi} {v,viii,ix,x,xi} {vi, vii, viii,ix,x} {vi,vii,viii,ix,xi}{vi,vii,viii,x,xi} {vi,vii,ix,x,xi} {vi,viii,ix,x,xi} {vii,viii,ix,x,xi} {i,ii,iii,iv,v,vi} {i,ii,iii,iv,v,vii} {i,ii,iii,iv,v,viii}{i,ii,iii,iv,v,ix} {i,ii,iii,iv,v,x} {i,ii,iii,iv,v,xi} {i,ii,iii,iv,vi,vii} {i,ii,iii,iv,vi,viii} {i,ii,iii,iv,vi,ix} {i,ii,iii,iv,vi,x} {i,ii,iii,iv,vi,xi}{i,ii,iii,iv,vii,viii} {i,ii,iii,iv,vii,ix} {i,ii,iii,iv,vii,x} {i,ii,iii,iv,vii,xi} {i,ii,iii,iv,viii,ix} {i,ii,iii,iv,viii,x} {i,ii,iii,iv,viii,xi} {i,ii,iii,iv,ix,x} {i,ii,iii,iv,ix,xi} {i,ii,iii,iv,x,xi} {i,ii,iii,v,vi,vii} {i,ii,iii,v,vi,viii} {i,ii,iii,v,vi,ix} {i,ii,iii,v,vi,x} {i,ii,iii,v,vi,xi} {i,ii,iii,v, vii, viii} {i,ii,iii,v,vii,ix} {i,ii,iii,v,vii,x} {i,ii,iii,v,vii,xi} {i,ii,iii,v,viii,ix} {i,ii,iii,v,viii,x} {i,ii,iii,v,viii,xi} {i,ii,iii,v,ix,x} {i,ii,iii,v,ix,xi} {i,ii,iii,v,x,xi} {i,ii,iii,vi,vii,viii} {i,ii,iii,vi,vii,ix} {i,ii,iii,vi,vii,x}

{i,ii,iii,vi,vii,xi}{i,ii,iii,vi,viii,ix} {i,ii,iii,vi,viii,x} {i,ii,iii, vi,viii,xi} {i,ii,iii,vi,ix,x} {i,ii,iii,vi,ix,xi} {i,ii,iii,vi,x,xi} {i,ii,iii,vii,viii,ix}{i,ii,iii,vii,viii,x} {i,ii,iii,vii,viii,xi} {i,ii, iii,vii,ix,x} {i,ii,iii,vii,ix,xi} {i,ii,iii,vii,x,xi} {i,ii,iii,viii,ix, x} {i,ii,iii,viii,ix,xi}{i,ii,iii,viii,x,xi} {i,ii,iii,ix,x,xi} {i,ii, v,vi,vii} {i,ii,iv,v,vi,viii} {i,ii,iv,v,vi,ix} {i,ii,iv,v,vi,x} {i,ii, iv,v,vi,xi}{i,ii,iv,v,vii,viii} {i,ii,iv,v,vii,ix} {i,ii,iv,v,vii,x} {i,ii,iv,v,vii,xi} {i,ii,iv,v,viii,ix} {i,ii,iv,v,viii,x} {i,ii,iv,v,viii, xi}{i,ii,iv,v,ix,x} {i,ii,iv,v,ix,xi} {i,ii,iv,v,x,xi} {i,ii,iv,vi,vii, viii} {i,ii,iv,vi,vii,ix} {i,ii,iv,vi,vii,x} {i,ii,iv,vi,vii,xi}{i,ii, iv,vi,viii,ix} {i,ii,iv,vi,viii,x} {i,ii,iv,vi,viii,xi} {i,ii,iv,vi,ix, x} {i,ii,iv,vi,ix,xi} {i,ii,iv,vi,x,xi} {i,ii,iv,vii,viii,ix}{i,ii,iv, vii,viii,x} {i,ii,iv,vii,viii,xi} {i,ii,iv,vii,ix,x} {i,ii,iv,vii,ix,xi} {i,ii,iv,vii,x,xi} {i,ii,iv,viii,ix,x} {i,ii,iv,viii,ix,xi}{i,ii,iv,viii, x,xi} {i,ii,iv,ix,x,xi} {i,ii,v,vi,vii,viii} {i,ii,v,vi,vii,ix} {i,ii, v,vi,vii,x} {i,ii,v,vi,vii,xi} {i,ii,v,vi,viii,ix} {i,ii,v,vi,viii,x} {i,ii,v,vi,viii,xi} {i,ii,v,vi,ix,x} {i,ii,v,vi,ix,xi} {i,ii,v,vi,x,xi} {i,ii,v, vii, viii, ix} {i, ii,v, vii,viii, x}{i,ii,v,vii,viii,xi} {i,ii, v,vii,ix,x} {i,ii,v,vii,ix,xi} {i,ii,v,vii,x,xi} {i,ii,v,viii,ix,x} {i,ii,v,viii,ix,xi} {i,ii,v,viii,x,xi}{i,ii,v,ix,x,xi} {i,ii,vi,vii, viii,ix} {i,ii,vi,vii,viii,x} {i,ii,vi,vii,viii,xi} {i,ii,vi,vii,ix,x} {i,ii,vi,vii,ix,xi} {i,ii,vi,vii,x,xi}{i,ii,vi,viii,ix,x} {i,ii,vi,viii, ix,xi} {i,ii,vi,viii,x,xi} {i,ii,vi,ix,x,xi} {i,ii,vii,viii,ix,x} {i,ii, vii,viii,ix,xi} {i,ii,vii,viii,x,xi} {i,ii,vii,ix,x,xi} {i,ii,viii,ix,x, xi} {i,iii,iv,v,vi,vii} {i,iii,iv,v,vi,viii} {i,iii,iv,v,vi,ix} {i,iii, iv,v,vi,x} {i,iii,iv,v,vi,xi} {i,iii,iv,v,vii,viii} {i,iii,iv,v,vii,ix} {i,iii,iv,v,vii,x} {i,iii,iv,v,vii,xi} {i,iii,iv,v,viii,ix} {i,iii,iv,v, viii,x} {i,iii,iv,v,viii,xi}{i,iii,iv,v,ix,x} {i,iii,iv,v,ix,xi} {i,iii, iv,v,x,xi} {i,iii,iv,vi,vii,viii} {i,iii,iv,vi,vii,ix} {i,iii,iv,vi,vii, x} {i,iii,iv,vi,vii,xi}{i,iii,iv,vi,viii,ix} {i,iii,iv,vi,viii,x} {i,iii, iv,vi,viii,xi} {i,iii,iv,vi,ix,x} {i,iii,iv,vi,ix,xi} {i,iii,iv,vi,x,xi} {i,iii,iv,vii,viii,ix}{i,iii,iv,vii,viii,x} {i,iii,iv,vii,viii,xi} {i,iii, iv,vii,ix,x} {i,iii,iv,vii,ix,xi} {i,iii,iv,vii,x,xi} {i,iii,iv,viii,ix, x} {i,iii,iv,viii,ix,xi}{i,iii,iv,viii,x,xi} {i,iii,iv,ix,x,xi} {i,iii, v,vi,vii,viii} {i,iii,v,vi,vii,ix} {i,iii,v,vi,vii,x} {i,iii,v,vi,vii, xi} {i,iii,v,vi,viii,ix}{i,iii,v,vi,viii,x} {i,iii,v,vi,viii,xi} {i,iii, v,vi,ix,x} {i,iii,v,vi,ix,xi} {i,iii,v,vi,x,xi} {i,iii,v,vii,viii,ix} {i,iii,v,vii,viii,x}{i,iii,v,vii,viii,xi} {i,iii,v,vii,ix,x} {i,iii,v, vii,ix,xi} {i,iii,v,vii,x,xi} {i,iii,v,viii,ix,x} {i,iii,v,viii,ix,xi} {i,iii,v,viii,x,xi}{i,iii,v,ix,x,xi} {i,iii,vi,vii,viii,ix} {i,iii,vi, vii,viii,x} {i,iii,vi,vii,viii,xi} {i,iii,vi,vii,ix,x} {i,iii,vi,vii,ix, xi} {i,iii,vi,vii,x,xi}{i,iii,vi,viii,ix,x} {i,iii,vi,viii,ix,xi} {i,iii,vi,viii,x,xi} {i,iii,vi,ix,x,xi} {i,iii,vii,viii,ix,x} {i,iii,vii, viii,ix,xi} {i,iii,vii,viii,x,xi} {i,iii,vii,ix,x,xi} {i,iii,viii,ix,x, xi} {i,iv,v,vi,vii,viii} {i,iv,v,vi,vii,ix} {i,iv,v,vi,vii,x} {i,iv,v, vi,vii,xi} {i,iv,v,vi,viii,ix}{i,iv,v,vi,viii,x} {i,iv,v,vi,viii,xi} {i,iv,v,vi,ix,x} {i,iv,v,vi,ix,xi} {i,iv,v,vi,x,xi} {i,iv,v,vii,viii, ix} {i,iv,v,vii,viii,x}{i,iv,v,vii,viii,xi} {i,iv,v,vii,ix,x} {i,iv, v,vii,ix,xi} {i,iv,v,vii,x,xi} {i,iv,v,viii,ix,x} {i,iv,v,viii,ix,xi} {i,iv,v,viii,x,xi}{i,iv,v,ix,x,xi} {i,iv,vi,vii,viii,ix} {i,iv,vi,vii, viii,x} {i,iv,vi,vii,viii,xi} {i,iv,vi,vii,ix,x} {i,iv,vi,vii,ix,xi} {i,iv,vi,vii,x,xi}{i,iv,vi,viii,ix,x} {i,iv,vi,viii,ix,xi} {i,iv,vi, viii,x,xi} {i,iv,vi,ix,x,xi} {i,iv,vii,viii,ix,x} {i,iv,vii,viii,ix, xi} {i,iv,vii,viii,x,xi}{i,iv,vii,ix,x,xi} {i,iv,viii,ix,x,xi} {i,v, vi,vii,viii,ix} {i,v,vi,vii,viii,x} {i,v,vi,vii,viii,xi} {i,v,vi,vii, ix,x} {i,v,vi,vii,ix,xi}{i,v,vi,vii,x,xi} {i,v,vi,viii,ix,x} {i,v,vi, viii,ix,xi} {i,v,vi,viii,x,xi} {i,v,vi,ix,x,xi} {i,v,vii,viii,ix,x} {i,v,vii,viii,ix,xi}{i,v,vii,viii,x,xi} {i,v,vii,ix,x,xi} {i,v,viii, ix,x,xi} {i,vi,vii,viii,ix,x} {i,vi,vii,viii,ix,xi} {i,vi,vii,viii,x, xi} {i,vi,vii,ix,x,xi}{i,vi,viii,ix,x,xi} {i,vii,viii,ix,x,xi} {ii, iii,iv,v,vi,vii} {ii,iii,iv,v,vi,viii} {ii,iii,iv,v,vi,ix} {ii,iii,iv,v, vi,x} {ii,iii,iv,v,vi,xi} {ii,iii,iv,v,vii,viii} {ii,iii,iv,v,vii,ix} {ii, iii,iv,v,vii,x} {ii,iii,iv,v,vii,xi} {ii,iii,iv,v,viii,ix} {ii,iii,iv,v, viii,x} {ii,iii,iv,v,viii,xi} {ii,iii,iv,v,ix,x} {ii,iii,iv,v,ix,xi} {ii, iii,iv,v,x,xi} {ii,iii,iv,vi,vii,viii} {ii,iii,iv,vi,vii,ix} {ii,iii,iv, vi,vii,x} {ii,iii,iv,vi,viii,xi} {ii,iii,iv,vi,ix,x} {ii,iii,iv,vi,ix,xi} {ii, iii,iv,vi,x,xi} {ii,iii,iv,vii,viii,ix} {ii,iii,iv,vii,viii,x} {ii,iii,iv, vii,viii,xi} {ii,iii,iv,vii,ix,x} {ii,iii,iv,vii,ix,xi} {ii,iii,iv,vii,x, xi} {ii,iii,iv,viii,ix,x} {ii,iii,iv,viii,ix,xi}{ii,iii,iv,viii,x,xi} {ii,iii, iv,ix,x,xi} {ii,iii,v,vi,vii,viii} {ii,iii,v,vi,vii,ix} {ii,iii,v, vi,vii,x} {ii,iii,v,vi,vii,xi} {ii,iii,v,vi,viii,ix}{ii,iii,v,vi,viii,x} {ii,iii,v,vi,viii,xi} {ii,iii,v,vi,ix,x} {ii,iii,v,vi,ix,xi} {ii,iii,v, vi,x,xi} {ii,iii,v,vii,viii,ix} {ii,iii,v,vii,viii,x}{ii,iii,v,vii,viii, xi} {ii,iii,v,vii,ix,x} {ii,iii,v,vii,ix,xi} {ii,iii,v,vii,x,xi} {ii,iii, v,viii,ix,x} {ii,iii,v,viii,ix,xi} {ii,iii,v,viii,x,xi}{ii,iii,v,ix,x, xi} {ii,iii,vi,vii,viii,ix} {ii,iii,vi,vii,viii,x} {ii,iii,vi,vii,viii, xi} {ii,iii,vi,vii,ix,x} {ii,iii,vi,vii,ix,xi} {ii,iii,vi,vii,x,xi}{ii, iii,vi,viii,ix,x} {ii,iii,vi,viii,ix,xi} {ii,iii,vi,viii,x,xi} {ii,iii,vi, ix,x,xi} {ii,iii,vii,viii,ix,x} {ii,iii,vii,viii,ix,xi} {ii,iii,vii,viii, x,xi} {ii,iii,vii,ix,x,xi} {ii,iii,viii,ix,x,xi} {ii,iv,v,vi,vii,viii} {ii,iv,v,vi,vii,ix} {ii,iv,v,vi,vii,x} {ii,iv,v,vi,vii,xi}{ii,iv,v,vi, viii,ix} {ii,iv,v,vi,viii,x} {ii,iv,v,vi,viii,xi} {ii,iv,v,vi,ix,x} {ii,iv,v,vi,ix.xi} {ii,iv,v,vi,x,xi} {ii,iv,v,vii,viii,ix} {ii,iv,v,vii, viii,x} {ii,iv,v,vii,viii,xi} {ii,iv,v,vii,ix,x} {ii,iv,v,vii,ix,xi} {ii,iv,v,vii,x,xi} {ii,iv,v,viii,ix,x} {ii,iv,v,viii,ix,xi}{ii,iv,v, viii,x,xi} {ii,iv,v,ix,x,xi} {ii,iv,vi,vii,viii,ix} {ii,iv,vi,vii,viii, x} {ii,iv,vi,vii,viii,xi} {ii,iv,vi,vii,ix,x} {ii,iv,vi,vii,ix,xi}{ii, iv,vi,vii,x,xi} {ii,iv,vi,viii,ix,x} {ii,iv,vi,viii,ix,xi} {ii,iv,vi, viii,x,xi} {ii,iv,vi,ix,x,xi} {ii,iv,vii,viii,ix,x} {ii,iv,vii,viii,ix, xi} {ii,iv,vii,viii,x,xi} {ii,iv,vii,ix,x,xi} {ii,iv,viii,ix,x,xi} {ii, v,vi,vii,viii,ix} {ii,v,vi,vii,viii,x} {ii,v,vi,vii,viii,xi} {ii,v,vi, vii,ix,x} {ii,v,vi,vii,ix,xi} {ii,v,vi,vii,x,xi} {ii,v,vi,viii,ix,x} {ii,v,vi,viii,ix,xi} {ii,v,vi,viii,x,xi}{ii,v,vi,ix,x,xi} {ii,v,vii, viii,ix,x} {ii,v,vii,viii,ix,xi} {ii,v,vii,viii,x,xi} {ii,v,vii,ix,x, xi} {ii,v,viii,ix,x,xi} {ii,vi,vii,viii,ix,x}{ii,vi,vii,viii,ix,xi} {ii,vi,vii,viii,x,xi} {ii,vi,vii,ix,x,xi} {ii,vi,viii,ix,x,xi} {ii,vii, viii,ix,x,xi} {iii,iv,v,vi,vii,viii}{iii,iv,v,vi,vii,ix} {iii,iv,v,vi, vii,x} {iii,iv,v,vi,vii,xi} {iii,iv,v,vi,viii,ix} {iii,iv,v,vi,viii,x} {iii,iv,v,vi,viii,xi} {iii,iv,v,vi,ix,x}{iii,iv,v,vi,ix,xi} {iii,iv,v, vi,x,xi} {iii,iv,v,vii,viii,ix} {iii,iv,v,vii,viii,x} {iii,iv,v,vii, viii,xi} {iii,iv,v,vii,ix,x}{iii,iv,v, vii, ix,xi} {iii,iv,v,vii,x,xi} {iii,iv,v,viii,ix,x} {iii,iv,v,viii,ix,xi} {iii,iv,v,viii,x,xi} {iii,iv, v,ix,x,xi}{iii,iv,vi,vii,viii,ix} {iii,iv,vi,vii,viii,x} {iii,iv,vi, vii,viii,xi} {iii,iv,vi,vii,ix,x} {iii,iv,vi,vii,ix,xi} {iii,iv,vi,vii, x,xi}{iii,iv,vi,viii,ix,x} {iii,iv,vi,viii,ix,xi} {iii,iv,vi,viii,x, xi} {iii,iv,vi,ix,x,xi} {iii,iv,vii,viii,ix,x} {iii,iv,vii,viii,ix, xi}{iii,iv,vii,viii,x,xi} {iii,iv,vii,ix,x,xi} {iii,iv,viii,ix,x,xi} {iii,v,vi,vii,viii,ix} {iii,v,vi,vii,viii,x} {iii,v,vi,vii,viii,xi}{iii, v,vi,vii,ix,x} {iii,v,vi,vii,ix,xi} {iii,v,vi,vii,x,xi} {iii,v,vi,viii, ix,x} {iii,v,vi,viii,ix,xi} {iii,v,vi,viii,x,xi} {iii,v,vi,ix,x,xi} {iii,v,vii,viii,ix,x} {iii,v,vii,viii,ix,xi} {iii,v,vii,viii,x,xi}{iii, v,vii,ix,x,xi} {iii,v,viii,ix,x,xi} {iii,vi,vii,viii,ix,x}{iii,vi, vii,viii,ix,xi} {iii,vi,vii,viii,x,xi} {iii,vi,vii,ix,x,xi} {iii,vi, viii,ix,x,xi} {iii,vii,viii,ix,x,xi} {iv,v,vi,vii,viii,ix}{iv,v,vi, vii,viii,x} {iv,v,vi,vii,viii,xi} {iv,v,vi,vii,ix,x} {iv,v,vi,vii,ix, xi} {iv,v,vi,vii,x,xi} {iv,v,vi,viii,ix,x}{iv,v,vi,viii,ix,xi} {iv, v,vi,viii,x,xi} {iv,v,vi,ix,x,xi} {iv,v,vii,viii,ix,x} {iv,v,vii, viii,ix,xi} {iv,v,vii,viii,x,xi}{iv,v,vii,ix,x,xi} {iv,v,viii,ix,x, xi} {iv,vi,vii,viii,ix,x} {iv,vi,vii,viii,ix,xi} {iv,vi,vii,viii,x, xi} {iv,vi,vii,ix,x,xi}{iv,vi,viii,ix,x,xi} {iv,vii,viii,ix,x,xi} {v,vi,vii,viii,ix,x} {v,vi,vii,viii,ix,xi} {v,vi,vii,viii,x,xi} {v,vi,vii,ix,x,xi}{v,vi,viii,ix,x,xi} {v,vii,viii,ix,x,xi} {vi,vii, viii,ix,x,xi} {i,ii,iii,iv,v,vi,vii} {i,ii,iii,iv,v,vi,viii} {i,ii,iii,iv, v,vi,ix}{i,ii,iii,iv,v,vi,x} {i,ii,iii,iv,v,vi,xi} {i,ii,iii,iv,v,vii, viii} {i,ii,iii,iv,v,vii,ix} {i,ii,iii,iv,v,vii,x} {i,ii,iii,iv,v,vii, xi}{i,ii,iii,iv,v,viii,ix} {i,ii,iii,iv,v,viii,x} {i,ii,iii,iv,v,viii,xi} {i,ii,iii,iv,v,ix,x} {i,ii,iii,iv,v,ix,xi} {i,ii,iii,iv,v,x,xi}{i,ii,iii, iv,vi,vii,viii} {i,ii,iii,iv,vi,vii,ix} {i,ii,iii,iv,vi,vii,x} {i,ii,iii, iv,vi,vii,xi} {i,ii,iii,iv,vi,viii,ix} {i,ii,iii,iv,vi,viii,x}{i,ii,iii, iv,vi,viii,xi} {i,ii,iii,iv,vi,ix,x} {i,ii,iii,iv,vi,ix,xi} {i,ii,iii,iv, vi,x,xi} {i,ii,iii,iv,vii,viii,ix} {i,ii,iii,iv,vii,viii,x} {i,ii,iii,iv,vii,viii,xi}{i,ii,iii,iv,vii,ix,x} {i,ii,iii,iv,vii,ix,xi} {i,ii,iii,iv,vii, x,xi} {i,ii,iii,iv,viii,ix,x} {i,ii,iii,iv,viii,ix,xi} {i,ii,iii,iv,viii,x, xi} {i,ii,iii,iv,ix,x,xi} {i,ii,iii,v,vi,vii,viii} {i,ii,iii,v,vi,vii,ix}
{i,ii,iii,v,vi,vii,x} {i,ii,iii,v,vi,vii,xi}{i,ii,iii,v,vi,viii,ix} {i,ii,
iii,v,vi,viii,x} {i,ii,iii,v,vi,viii,xi} {i,ii,iii,v,vi,ix,x} {i,ii,iii,v,
vi,ix,xi} {i,ii,iii,v,vi,x,xi} {i,ii,iii,v,vii,viii,ix} {i,ii,iii,v,vii,
viii,x} {i,ii,iii,v,vii,viii,xi} {i,ii,iii,v,vii,ix,x} {i,ii,iii,v,vii,ix,
xi} {i,ii,iii,v,vii,x,xi}{i,ii,iii,v,viii,ix,x} {i,ii,iii,v,viii,ix,xi}
{i,ii,iii,v,viii,x,xi} {i,ii,iii,v,ix,x,xi} {i,ii,iii,vi,vii,viii,ix}
{i,ii,iii,vi,vii,viii,x}{i,ii,iii,vi,vii,viii,xi} {i,ii,iii,vi,vii,ix,x}
{i,ii,iii,vi,vii,ix,xi} {i,ii,iii,vi,vii,x,xi} {i,ii,iii,vi,viii,ix,x}
{i,ii,iii,vi,viii,ix,xi}{i,ii,iii,vi,viii,x,xi} {i,ii,iii,vi,ix,x,xi}
{i,ii,iii,vii,viii,ix,x} {i,ii,iii,vii,viii,ix,xi} {i,ii,iii,vii,viii,x,
xi} {i,ii,iii,vii,ix,x,xi}{i,ii,iii,viii,ix,x,xi} {i,ii,iv,v,vi,vii,
viii} {i,ii,iv,v,vi,vii,ix} {i,ii,iv,v,vi,vii,x} {i,ii,iv,v,vi,vii,xi}
{i,ii,iv,v,vi,viii,ix}{i,ii,iv,v,vi,viii,x} {i,ii,iv,v,vi,viii,xi} {i,ii,
iv,v,vi,ix,x} {i,ii,iv,v,vi,ix,xi} {i,ii,iv,v,vi,x,xi} {i,ii,iv,v,vii,
viii,ix}{i,ii,iv,v,vii,viii,x} {i,ii,iv,v,vii,viii,xi} {i,ii,iv,v,vii,ix,
x} {i,ii,iv,v,vii,ix,xi} {i,ii,iv,v,vii,x,xi} {i,ii,iv,v,viii,ix,x} {i,
ii,iv,v,viii,ix,xi} {i,ii,iv,v,viii,x,xi} {i,ii,iv,v,ix,x,xi} {i,ii,iv,
vi,vii,viii,ix} {i,ii,iv,vi,vii,viii,x} {i,ii,iv,vi,vii,viii,xi}{i,ii,iv,
vi,vii,ix,x} {i,ii,iv,vi,vii,ix,xi} {i,ii,iv,vi,vii,x,xi} {i,ii,iv,vi,
viii,ix,x} {i,ii,iv,vi,viii,ix,xi} {i,ii,iv,vi,viii,x,xi}{i,ii,iv,vi,ix,
x,xi} {i,ii,iv,vii,viii,ix,x} {i,ii,iv,vii,viii,ix,xi} {i,ii,iv,vii,viii,
x,xi} {i,ii,iv,vii,ix,x,xi} {i,ii,iv,viii,ix,x,xi}{i,ii,v,vi,vii,viii,
ix} {i,ii,v,vi,vii,viii,x} {i,ii,v,vi,vii,viii,xi} {i,ii,v,vi,vii,ix,x}
{i,ii,v,vi,vii,ix,xi} {i,ii,v,vi,vii,x,xi}{i,ii,v,vi,viii,ix,x} {i,ii,v,
vi,viii,ix,xi} {i,ii,v,vi,viii,x,xi} {i,ii,v,vi,ix,x,xi} {i,ii,v,vii,
viii,ix,x} {i,ii,v,vii,viii,ix,xi}{i,ii,v,vii,viii,x,xi} {i,ii,v,vii,ix,
x,xi} {i,ii,v,viii,ix,x,xi} {i,ii,vi,vii,viii,ix,x} {i,ii,vi,vii,viii,
ix,xi} {i,ii,vi,vii,viii,x,xi} {i,ii,vi,vii,ix,x,xi} {i,ii,vi,viii,ix,x,
xi} {i,ii,vii,viii,ix,x,xi} {i,iii,iv,v,vi,vii,viii} {i,iii,iv,v,vi,vii,
ix} {i,iii,iv,v,vi,vii,x} {i,iii,iv,v,vi,vii,xi} {i,iii,iv,v,vi,viii,ix}
{i,iii,iv,v,vi,viii,x} {i,iii,iv,v,vi,viii,xi} {i,iii,iv,v,vi,ix,x}
{i,iii,iv,v,vi,ix,xi} {i,iii,iv,v,vi,x,xi} {i,iii,iv,v,vii,viii,ix}
{i,iii,iv,v,vii,viii,x} {i,iii,iv,v,vii,viii,xi} {i,iii,iv,v,vii,ix,x}
{i,iii,iv,v,vii,ix,xi}{i,iii,iv,v,vii,x,xi} {i,iii,iv,v,viii,ix,x}
{i,iii,iv,v,viii,ix,xi} {i,iii,iv,v,viii,x,xi} {i,iii,iv,v,ix,x,xi}
{i,iii,iv,vi,vii,viii,ix}{i,iii,iv,vi,vii,viii,x} {i,iii,iv,vi,vii,viii,
xi} {i,iii,iv,vi,vii,ix,x} {i,iii,iv,vi,vii,ix,xi} {i,iii,iv,vi,vii,x,
xi} {i,iii,iv,vi,viii,ix,x}{i,iii,iv,vi,viii,ix,xi} {i,iii,iv,vi,viii,x,
xi} {i,iii,iv,vi,ix,x,xi} {i,iii,iv,vii,viii,ix,x} {i,iii,iv,vii,viii,ix,
xi} {i,iii,iv,vii,viii,x,xi}{i,iii,iv,vii,ix,x,xi} {i,iii,iv,viii,ix,x,
xi} {i,iii,v,vi,vii,viii,ix} {i,iii,v,vi,vii,viii,x} {i,iii,v,vi,vii,
viii,xi} {i,iii,v,vi,vii,ix,x}{i,iii,v,vi,vii,ix,xi} {i,iii,v,vi,vii,x,
xi} {i,iii,v,vi,viii,ix,x} {i,iii,v,vi,viii,ix,xi} {i,iii,v,vi,viii,x,
xi} {i,iii,v,vi,ix,x,xi}{i,iii,v,vii,viii,ix,x} {i,iii,v,vii,viii,ix,
xi} {i,iii,v,vii,viii,x,xi} {i,iii,v,vii,ix,x,xi} {i,iii,v,viii,ix,x,
xi} {i,iii,vi,vii,viii,ix,x} {i,iii,vi,vii,viii,ix,xi} {i,iii,vi,vii,viii,x,
xi} {i,iii,vi,vii,ix,x,xi} {i,iii,vi,viii,ix,x,xi} {i,iii,vii,viii,ix,
x,xi} {i,iv,v,vi,vii,viii,ix} {i,iv,v,vi,vii,viii,x} {i,iv,v,vi,vii,
viii,xi} {i,iv,v,vi,vii,ix,x} {i,iv,v,vi,vii,ix,xi} {i,iv,v,vi,vii,x,
xi} {i,iv,v,vi,viii,ix,x}{i,iv,v,vi,viii,ix,xi} {i,iv,v,vi,viii,x,xi}
{i,iv,v,vi,ix,x,xi} {i,iv,v,vii,viii,ix,x} {i,iv,v,vii,viii,ix,xi}
{i,iv,v,vii,viii,x,xi}{i,iv,v,vii,ix,x,xi} {i,iv,v,viii,ix,x,xi}
{i,iv,vi,vii,viii,ix,x} {i,iv,vi,vii,viii,ix,xi} {i,iv,vi,vii,viii,x,
xi} {i,iv,vi,vii,ix,x,xi}{i,iv,vi,viii,ix,x,xi} {i,iv,vii,viii,ix,x,
xi} {i,v,vi,vii,viii,ix,x} {i,v,vi,vii,viii,ix,xi} {i,v,vi,vii,viii,x,
xi} {i,v,vi,vii,ix,x,xi}{i,v,vi,viii,ix,x,xi} {i,v,vii,viii,ix,x,xi}
{i,vi,vii,viii,ix,x,xi} {ii,iii,iv,v,vi,vii,viii} {ii,iii,iv,v,vi,vii,
ix} {ii,iii,iv,v,vi,vii,x}{ii,iii,iv,v,vi,vii,xi} {ii,iii,iv,v,vi,viii,
ix} {ii,iii,iv,v,vi,viii,x} {ii,iii,iv,v,vi,viii,xi} {ii,iii,iv,v,vi,ix,
x} {ii,iii,iv,v,vi,ix,xi}{ii,iii,iv,v,vi,x,xi} {ii,iii,iv,v,vii,viii,ix}
{ii,iii,iv,v,vii,viii,x} {ii,iii,iv,v,vii,viii,xi} {ii,iii,iv,v,vii,ix,x}
{ii,iii,iv,v,vii,ix,xi}{ii,iii,iv,v,vii,x,xi} {ii,iii,iv,v,viii,ix,x}
{ii,iii,iv,v,viii,ix,xi} {ii,iii,iv,v,viii,x,xi} {ii,iii,iv,v,ix,x,xi}
{ii,iii,iv,vi,vii,viii,ix}{ii,iii,iv,vi,vii,viii,x} {ii,iii,iv,vi,vii,
viii,xi} {ii,iii,iv,vi,vii,ix,x} {ii,iii,iv,vi,vii,ix,xi} {ii,iii,iv,vi,
vii,x,xi} {ii,iii,iv,vi,viii,ix,x}{ii,iii,iv,vi,viii,ix,xi} {ii,iii,
iv,vi,viii,x,xi} {ii,iii,iv,vi,ix,x,xi} {ii,iii,iv,vii,viii,ix,x} {ii,iii,
iv,vii,viii,ix,xi} {ii,iii,iv,vii,viii,x,xi}{ii,iii,iv,vii,ix,x,xi} {ii,
iii,iv,viii,ix,x,xi} {ii,iii,v,vi,vii,viii,ix} {ii,iii,v,vi,vii,viii,x}
{ii,iii,v,vi,vii,viii,xi} {ii,iii,v,vi,vii,ix,x} {ii,iii,v,vi,vii,ix,xi}
{ii,iii,v,vi,vii,x,xi} {ii,iii,v,vi,viii,ix,x} {ii,iii,v,vi,viii,ix,xi}
{ii,iii,v,vi,viii,x,xi} {ii,iii,v,vi,ix,x,xi} {ii,iii,v,vii,viii,ix,x}
{ii,iii,v,vii,viii,ix,xi} {ii,iii,v,vii,viii,x,xi} {ii,iii,v,vii,ix,x,xi}
{ii,iii,v,viii,ix,x,xi} {ii,iii,vi,vii,viii,ix,x} {ii,iii,vi,vii,viii,ix,
xi} {ii,iii,vi,vii,viii,x,xi} {ii,iii,vi,vii,ix,x,xi} {ii,iii,vi,viii,ix,
x,xi} {ii,iii,vii,viii,ix,x,xi} {ii,iv,v,vi,vii,viii,ix}{ii,iv,v,vi,
vii,viii,x} {ii,iv,v,vi,vii,viii,xi} {ii,iv,v,vi,vii,ix,x} {ii,iv,v,vi,
vii,ix,xi} {ii,iv,v,vi,vii,x,xi} {ii,iv,v,vi,viii,ix,x}{ii,iv,v,vi,
viii,ix,xi} {ii,iv,v,vi,viii,x,xi} {ii,iv,v,vi,ix,x,xi} {ii,iv,v,vii,
viii,ix,x} {ii,iv,v,vii,viii,ix,xi} {ii,iv,v,vii,viii,x,xi}{ii,iv,v,
vii,ix,x,xi} {ii,iv,v,viii,ix,x,xi} {ii,iv,vi,vii,viii,ix,x} {ii,iv,
vi,vii,viii,ix,xi} {ii,iv,vi,vii,viii,x,xi} {ii,iv,vii,viii,ix,x,xi}{ii,iv,
vi,viii,ix,x,xi} {ii,iv,vii,viii,ix,x,xi} {ii,v,vi,vii,viii,ix,x} {ii,
v,vi,vii,viii,ix,xi} {ii,v,vi,vii,viii,x,xi} {ii,v,vi,vii,ix,x,xi}{ii,
v,vi,viii,ix,x,xi} {ii,v,vii,viii,ix,x,xi} {ii,vi,vii,viii,ix,x,xi}
{iii,iv,v,vi,vii,viii,ix} {iii,iv,v,vi,vii,viii,x}{iii,iv,v,vi,vii,viii,
xi} {iii,iv,v,vi,vii,ix,x} {iii,iv,v,vi,vii,ix,xi} {iii,iv,v,vi,vii,x,
xi} {iii,iv,v,vi,viii,ix,x} {iii,iv,v,vi,viii,ix,xi} {iii,iv,v,vi,viii,
x,xi} {iii,iv,v,vi,ix,x,xi} {iii,iv,v,vii,viii,ix,x} {iii,iv,v,vii,
viii,ix,xi} {iii,iv,v,vii,viii,x,xi} {iii,iv,v,vii,ix,x,xi}{iii,iv,v,
viii,ix,x,xi} {iii,iv,vi,vii,viii,ix,x} {iii,iv,vi,vii,viii,ix,xi} {iii,iv,
vi,vii,viii,x,xi} {iii,iv,vi,vii,ix,x,xi}{iii,iv,vi,viii,ix,x,xi} {iii,iv,vii,viii,ix,x,xi}
{iii,v,vi,vii,viii,ix,x} {iii,v,vi,vii,viii,ix,xi} {iii,v,vi,vii,viii,
ix,xi} {iii,v,vi,vii,viii,x,xi}{iii,v,vi,vii,ix,x,xi} {iii,v,vi,viii,
ix,x,xi} {iii,v,vii,viii,ix,x,xi} {iii,vi,vii,viii,ix,x,xi} {iv,v,vi,
vii,viii,ix,x}{iv,v,vi,vii,viii,ix,xi} {iv,v,vi,vii,viii,x,xi} {iv,v,
vi,vii,ix,x,xi} {iv,v,vi,viii,ix,x,xi} {iv,v,vii,viii,ix,x,xi}{iv,
vi,vii,viii,ix,x,xi} {v,vi,vii,viii,ix,x,xi} {i,ii,iii,iv,v,vi,vii,
viii} {i,ii,iii,iv,v,vi,vii,ix} {i,ii,iii,iv,v,vi,vii,x} {i,ii,iii,iv,v,vi,
vii,xi} {i,ii,iii,iv,v,vi,viii,ix} {i,ii,iii,iv,v,vi,viii,x} {i,ii,iii,iv,
v,vi,viii,xi} {i,ii,iii,iv,v,vi,ix,x}{i,ii,iii,iv,v,vi,ix,xi} {i,ii,iii,
iv,v,vi,x,xi} {i,ii,iii,iv,v,vii,viii,ix} {i,ii,iii,iv,v,vii,viii,x}
{i,ii,iii,iv,v,vii,viii,xi} {i,ii,iii,iv,v,vii,ix,x} {i,ii,iii,iv,v,vii,ix,
xi} {i,ii,iii,iv,v,vii,x,xi} {i,ii,iii,iv,v,viii,ix,x} {i,ii,iii,iv,v,viii,
ix,xi}{i,ii,iii,iv,v,viii,x,xi} {i,ii,iii,iv,v,ix,x,xi} {i,ii,iii,iv,vi,
vii,viii,ix} {i,ii,iii,iv,vi,vii,viii,x} {i,ii,iii,iv,vi,vii,viii,xi}{i,
ii,iii,iv,vi,vii,ix,x} {i,ii,iii,iv,vi,vii,ix,xi} {i,ii,iii,iv,vi,vii,x,
xi} {i,ii,iii,iv,vi,viii,ix,x} {i,ii,iii,iv,vi,viii,ix,xi}{i,ii,iii,iv,vi,
viii,x,xi} {i,ii,iii,iv,vi,ix,x,xi} {i,ii,iii,iv,vii,viii,ix,x} {i,ii,iii,
iv,vii,viii,ix,xi} {i,ii,iii,iv,vii,viii,x,xi} {i,ii,iii,iv,vii,ix,x,xi}
{i,ii,iii,iv,viii,ix,x,xi} {i,ii,iii,v,vi,vii,viii,ix} {i,ii,iii,v,vi,vii,
viii,x} {i,ii,iii,v,vi,vii,viii,xi}{i,ii,iii,v,vi,vii,ix,x} {i,ii,iii,v,
vi,vii,ix,xi} {i,ii,iii,v,vi,vii,x,xi} {i,ii,iii,v,vi,viii,ix,x} {i,ii,
iii,v,vi,viii,ix,xi} {i,ii,iii,v,vi,viii,x,xi} {i,ii,iii,v,vi,ix,x,xi}
{i,ii,iii,v,vii,viii,ix,x} {i,ii,iii,v,vii,viii,ix,xi} {i,ii,iii,v,vii,
viii,x,xi}{i,ii,iii,v,vii,ix,x,xi} {i,ii,iii,v,viii,ix,x,xi} {i,ii,iii,
vi,vii,viii,ix,x} {i,ii,iii,vi,vii,viii,ix,xi} {i,ii,iii,vi,vii,viii,x,
xi}{i,ii,iii,vi,vii,ix,x,xi} {i,ii,iii,vi,viii,ix,x,xi} {i,ii,iii,vii,
viii,ix,x,xi} {i,ii,iv,v,vi,vii,viii,ix} {i,ii,iv,v,vi,vii,viii,x} {i,
ii,iv,v,vi,vii,viii,xi} {i,ii,iv,v,vi,vii,ix,x} {i,ii,iv,v,vi,vii,ix,xi}
{i,ii,iv,v,vi,vii,x,xi} {i,ii,iv,v,vi,viii,ix,x} {i,ii,iv,v,vi,viii,ix,
xi} {i,ii,iv,v,vi,viii,x,xi} {i,ii,iv,v,vi,ix,x,xi} {i,ii,iv,v,vii,viii,
ix,x} {i,ii,iv,v,vii,viii,ix,xi} {i,ii,iv,v,vii,viii,x,xi} {i,ii,iv,v,
vii,ix,x,xi} {i,ii,iv,v,viii,ix,x,xi} {i,ii,iv,vi,vii,viii,ix,x} {i,ii,
iv,vi,vii,viii,ix,xi}{i,ii,iv,vi,vii,viii,x,xi} {i,ii,iv,vi,vii,ix,x,xi}
{i,ii,iv,vi,viii,ix,x,xi} {i,ii,iv,vii,viii,ix,x,xi} {i,ii,v,vi,vii,
viii,ix,x}{i,ii,v,vi,vii,viii,ix,xi} {i,ii,v,vi,vii,viii,x,xi} {i,ii,v,
vi,vii,ix,x,xi} {i,ii,v,vi,viii,ix,x,xi} {i,ii,v,vii,viii,ix,x,xi} {i,
ii,vi,vii,viii,ix,x,xi} {i,iii,iv,v,vi,vii,viii,ix} {i,iii,iv,v,vi,vii,
viii,x} {i,iii,iv,v,vi,vii,viii,xi} {i,iii,iv,v,vi,vii,ix,x} {i,iii,iv,v,
vi,vii,ix,xi} {i,iii,iv,v,vi,vii,x,xi}{i,iii,iv,v,vi,viii,ix,x} {i,iii,
iv,v,vi,viii,ix,xi} {i,iii,iv,v,vi,viii,x,xi} {i,iii,iv,v,vi,ix,x,xi}
{i,iii,iv,v,vii,viii,ix,x} {i,iii,iv,v,vii,viii,ix,xi} {i,iii,iv,v,vii,
viii,ix,x} {i,iii,iv,v,vii,viii,ix,xi} {i,iii,iv,v,vii, viii,x,xi} {i,iii,iv,v,vii,ix,x,xi}{i,iii,iv,v,viii,ix,x,xi} {i,iii,iv, vi,vii,viii,ix,x} {i,iii,iv,vi,vii,viii,ix,xi} {i,iii,iv,vi,vii,viii,x, xi} {i,iii,iv,vi,vii,ix,x,xi}{i,iii,iv,vi,viii,ix,x,xi} {i,iii,iv,vii, viii,ix,x,xi} {i,iii,v,vi,vii,viii,ix,x} {i,iii,v,vi,vii,viii,ix,xi} {i,iii,v,vi,vii,viii,x,xi}{i,iii,v,vi,vii,ix,x,xi} {i,iii,v,vi,viii,ix, x,xi} {i,iii,v,vii,viii,ix,x,xi} {i,iii,vi,vii,viii,ix,x,xi} {i,iv,v, vi,vii,viii,ix,x}{i,iv,v,vi,vii,viii,ix,xi} {i,iv,v,vi,vii,viii,x,xi} {i,iv,v,vi,vii,ix,x,xi} {i,iv,v,vi,viii,ix,x,xi} {i,iv,v,vii,viii,ix, x,xi}{i,iv,vi,vii,viii,ix,x,xi} {i,v,vi,vii,viii,ix,x,xi} {ii,iii,iv,v, vi,vii,viii,ix}  {ii,iii,iv,v,vi,vii,viii,x}  {ii,iii,iv,v,vi,vii,viii, xi}{ii,iii,iv,v,vi,vii,ix,x} {ii,iii,iv,v,vi,vii,ix,xi} {ii,iii,iv,v,vi, vii,x,xi} {ii,iii,iv,v,vi,viii,ix,x} {ii,iii,iv,v,vi,viii,ix,xi}{ii,iii, iv,v,vi,viii,x,xi} {ii,iii,iv,v,vi,ix,x,xi} {ii,iii,iv,v,vii,viii,ix,x} {ii,iii,iv,v,vii,viii,ix,xi} {ii,iii,iv,v,vii,viii,x,xi}{ii,iii,iv,v,vii, ix,x,xi} {ii,iii,iv,v,viii,ix,x,xi} {ii,iii,iv,vi,vii,viii,ix,x} {ii,iii, iv,vi,vii,viii,ix,xi}   {ii,iii,iv,vi,vii,viii,x,xi}{ii,iii,iv,vi,vii,ix, x,xi} {ii,iii,iv,vi,viii,ix,x,xi} {ii,iii,iv,vii,viii,ix,x,xi} {ii,iii,v, vi,vii,viii,ix,x}   {ii,iii,v,vi,vii,viii,ix,xi}{ii,iii,v,vi,vii,viii,x, xi} {ii,iii,v,vi,vii,ix,x,xi} {ii,iii,v,vi,viii,ix,x,xi} {ii,iii,v,vii, viii,ix,x,xi}    {ii,iii,vi,vii,viii,ix,x,xi}{ii,iv,v,vi,vii,viii,ix,x} {ii,iv,v,vi,vii,viii,ix,xi} {ii,iv,v,vi,vii,viii,x,xi} {ii,iv,v,vi,vii, ix,x,xi} {ii,iv,v,vi,viii,ix,x,xi}{ii,iv,v,vii,viii,ix,x,xi} {ii,iv, vi,vii,viii,ix,x,xi} {ii,v,vi,vii,viii,ix,x,xi} {iii,iv,v,vi,vii,viii, ix,x} {iii,iv,v,vi,vii,viii,ix,xi} {iii,iv,v,vi,vii,viii,x,xi} {iii,iv, v,vi,vii,ix,x,xi} {iii,iv,v,vi,viii,ix,x,xi} {iii,iv,v,vii,viii,ix,x, xi} {iii,iv,vi,vii,viii,ix,x,xi} {iii,v,vi,vii,viii,ix,x,xi} {iv,v,vi, vii,viii,ix,x,xi} {i,ii,iii,iv,v,vi,vii,viii,ix} {i,ii,iii,iv,v,vi,vii, viii,x} {i,ii,iii,iv,v,vi,vii,viii,xi}{i,ii,iii,iv,v,vi,vii,ix,x} {i,ii, iii,iv,v,vi,vii,ix,xi} {i,ii,iii,iv,v,vi,vii,x,xi} {i,ii,iii,iv,v,vi,viii, ix,x} {i,ii,iii,iv,v,vi,viii,ix,xi} {i,ii,iii,iv.v.vi,viii,x,xi} {i,ii,iii, iv,v,vi,ix,x,xi} {i,ii,iii,iv,v,vii,viii,ix,x} {i,ii,iii,iv,v,vii,viii, ix,xi} {i,ii,iii,iv,v,vii,viii,x,xi}{i,ii,iii,iv,v,vii,ix,x,xi} {i,ii,iii, iv,v,viii,ix,x,xi} {i,ii,iii,iv,vi,vii,viii,ix,x} {i,ii,iii,iv,vi,vii, viii,ix,xi}   {i,ii,iii,iv,vi,vii,viii,x,xi}{i,ii,iii,iv,vi,vii,ix,x,xi} {i,ii,iii,iv,vi,viii,ix,x,xi} {i,ii,iii,iv,vii,viii,ix,x,xi} {i,ii,iii,v, vi,vii,viii,ix,x} {i,ii,iii,v,vi,vii,viii,ix,xi}{i,ii,iii,v,vi,vii,viii, x,xi} {i,ii,iii,v,vi,vii,ix,x,xi} {i,ii,iii,v,vi,viii,ix,x,xi} {i,ii,iii, v,vii,viii,ix,x,xi}     {i,ii,iii,vi,vii,viii,ix,x,xi}{i,ii,iv,v,vi,vii, viii,ix,x} {i,ii,iv,v,vi,vii,viii,ix,xi} {i,ii,iv,v,vi,vii,viii,x,xi} {i,ii,iv,v,vi,vii,ix,x,xi}     {i,ii,iv,v,vi,viii,ix,x,xi}{i,ii,iv,v,vii, viii,ix,x,xi} {i,ii,iv,vi,vii,viii,ix,x,xi} {i,ii,v,vi,vii,viii,ix,x, xi} {i,iii,iv,v,vi,vii,viii,ix,x} {i,iii,iv,v,vi,vii,viii,ix,xi}{i,iii, iv,v,vi,vii,viii,x,xi} {i,iii,iv,v,vi,vii,ix,x,xi} {i,iii,iv,v,vi,viii, ix,x,xi} {i,iii,iv,v,vii,viii,ix,x,xi}    {i,iii,iv,vi,vii,viii,ix,x, xi}{i,iii,iv,v,vi,vii,viii,ix,x,xi} {i,iv,v,vi,vii,viii,ix,x,xi} {ii,iii, iv,v,vi,vii,viii,ix,x}    {ii,iii,iv,v,vi,vii,viii,ix,xi}{ii,iii,iv,v,vi, vii,viii,x,xi} {ii,iii,iv,v,vi,vii,ix,x,xi} {ii,iii,iv,v,vi,viii,ix,x, xi} {ii,iii,iv,v,vii,viii,ix,x,xi}{ii,iii,iv,vi,vii,viii,ix,x,xi} {ii, iii,v,vi,vii,viii,ix,x,xi} {ii,iv,v,vi,vii,viii,ix,x,xi} {iii,iv,v,vi, vii,viii,ix,x,xi}{i,ii,iii,iv,v,vi,vii,viii,ix,x} {i,ii,iii,iv,v,vi,vii, viii,ix,xi} {i,ii,iii,iv,v,vi,vii,viii,x,xi} {i,ii,iii,iv,v,vi,vii,ix,x, xi}{i,ii,iii,iv,v,vi,viii,ix,x,xi}    {i,ii,iii,iv,v,vii,viii,ix,x,xi} {i,ii,iii,iv,vi,vii,viii,ix,x,xi} {i,ii,iii,v,vi,vii,viii,ix,x,xi}{i,ii, iv,v,vi,vii,viii,ix,x,xi} {i,iii,iv,v,vi,vii,viii,ix,x,xi} {ii,iii,iv,v, vi,vii,viii,ix,x,xi} or {i,ii,iii,iv,v,vi,vii,viii,ix,x,xi}.

If the variant comprises any one of (i) and (iii) to (xi), it may further comprise a mutation at one or more of Y51, N55 and F56, such as at Y51, N55, F56, Y51/N55, Y51/F56, N55/F56 or Y51/N55/F56.

In (i), the variant may comprises mutations at any number and combination of N40, D43, E44, S54, S57, Q62, R97, E101, E124, E131, R142, T150 and R192. In (i), the variant preferably comprises one or more mutations at at the following positions (i.e. mutations at one or more of the following positions) N40, D43, E44, S54, S57, Q62, E101, E131 and T150. In (i), the variant preferably comprises one or more mutations at the following positions (i.e. mutations at one or more of the following positions) N40, D43, E44, E101 and E131. In (i), the variant preferably comprises a mutation at S54 and/or S57. In (i), the variant more preferably comprises a mutation at (a) S54 and/or S57 and (b) one or more of Y51, N55 and F56, such as at Y51, N55, F56, Y51/N55, Y51/F56, N55/F56 or Y51/N55/F56. If S54 and/or S57 are deleted in (xi), it/they cannot be mutated in (i) and vice versa. In (i), the variant preferably comprises a mutation at T150, such as T150I. Alternatively the variant preferably comprises a mutation at (a) T150 and (b) one or more of Y51, N55 and F56, such as at Y51, N55, F56, Y51/N55, Y51/F56, N55/F56 or Y51/N55/F56. In (i), the variant preferably comprises a mutation at Q62, such as Q62R or Q62K. Alternatively the variant preferably comprises a mutation at (a) Q62 and (b) one or more of Y51, N55 and F56, such as at Y51, N55, F56, Y51/N55, Y51/F56, N55/F56 or Y51/N55/F56. The variant may comprise a mutation at D43, E44, Q62 or any combination thereof, such as D43, E44, Q62, D43/E44, D43/Q62, E44/Q62 or D43/E44/Q62. Alternatively the variant preferably comprises a mutation at (a) D43, E44, Q62, D43/E44, D43/Q62, E44/Q62 or D43/E44/Q62 and (b) one or more of Y51, N55 and F56, such as at Y51, N55, F56, Y51/N55, Y51/F56, N55/F56 or Y51/N55/F56.

In (ii) and elsewhere in this application, the / symbol means "and" such that Y51/N55 is Y51 and N55. In (ii), the variant preferably comprises mutations at Y51/N55. It has been proposed that the constriction in CsgG is composed of three stacked concentric rings formed by the side chains of residues Y51, N55 and F56 (Goyal et al, 2014, Nature, 516, 250-253). Mutation of these residues in (ii) may therefore decrease the number of nucleotides contributing to the current as the polynucleotide moves through the pore and thereby make it easier to identify a direct relationship between the observed current (as the polynucleotide moves through the pore) and the polynucleotide. Y56 may be mutated in any of the ways discussed below with reference to variants and pores useful in the method of the invention.

In (v), the variant may comprise N102R, N102F, N102Y or N102W. The variant preferably comprises (a) N102R, N102F, N102Y or N102W and (b) a mutation at one or more of Y51, N55 and F56, such as at Y51, N55, F56, Y51/N55, Y51/F56, N55/F56 or Y51/N55/F56.

In (xi), any number and combination of K49, P50, Y51, P52, A53, S54, N55, F56 and S57 may be deleted. Preferably one or more of K49, P50, Y51, P52, A53, S54, N55 and S57 may be deleted. If any of Y51, N55 and F56 are deleted in (xi), it/they cannot be mutated in (ii) and vice versa.

In (i), the variant preferably comprises one of more of the following substitutions N40R, N40K, D43N, D43Q, D43R, D43K, E44N, E44Q, E44R, E44K, S54P, S57P, Q62R, Q62K, R97N, R97G, R97L, E101N, E101Q, E101R, E101K, E101F, E101Y, E101W, E124N, E124Q, E124R, E124K, E124F, E124Y, E124W, E131D, R142E, R142N, T150I, R192E and R192N, such as one or more of N40R, N40K, D43N, D43Q, D43R, D43K, E44N, E44Q, E44R, E44K, S54P, S57P, Q62R, Q62K, E101N, E101Q, E101R, E101K, E101F, E101Y, E101W, E131D and T150I, or one or more of N40R, N40K, D43N, D43Q, D43R, D43K, E44N, E44Q, E44R, E44K, E101N, E101Q, E101R, E101K, E101F, E101Y, E101W and E131D. The variant may comprise any number and combination of these substitutions. In (i), the variant preferably comprises S54P and/or S57P. In (i), the variant preferably comprises (a) S54P and/or S57P and (b) a mutation at one or more of Y51, N55 and F56, such as at Y51, N55, F56, Y51/N55, Y51/F56, N55/F56 or Y51/N55/F56. The mutations at one or more of Y51, N55 and F56 may be any of those discussed below. In (i), the variant preferably comprises F56A/S57P or S54P/F56A. The variant preferably comprises T150I. Alternatively the variant preferably comprises a mutation at (a) T150I and (b) one or more of Y51, N55 and F56, such as at Y51, N55, F56, Y51/N55, Y51/F56, N55/F56 or Y51/N55/F56.

In (i), the variant preferably comprises Q62R or Q62K. Alternatively the variant preferably comprises (a) Q62R or Q62K and (b) a mutation at one or more of Y51, N55 and F56, such as at Y51, N55, F56, Y51/N55, Y51/F56, N55/F56 or Y51/N55/F56. The variant may comprise D43N, E44N, Q62R or Q62K or any combination thereof, such as D43N, E44N, Q62R, Q62K, D43N/E44N, D43N/Q62R, D43N/Q62K, E44N/Q62R, E44N/Q62K, D43N/E44N/Q62R or D43N/E44N/Q62K. Alternatively the variant preferably comprises (a) D43N, E44N, Q62R, Q62K, D43N/E44N, D43N/Q62R, D43N/Q62K, E44N/Q62R, E44N/Q62K, D43N/E44N/Q62R or D43N/E44N/Q62K and (b) a mutation at one or more of Y51, N55 and F56, such as at Y51, N55, F56, Y51/N55, Y51/F56, N55/F56 or Y51/N55/F56.

In (i), the variant preferably comprises D43N.

In (i), the variant preferably comprises E101R, E101S, E101F or E101N.

In (i), the variant preferably comprises E124N, E124Q, E124R, E124K, E124F, E124Y, E124W or E124D, such as E124N.

In (i), the variant preferably comprises R142E and R142N.

In (i), the variant preferably comprises R97N, R97G or R97L.

In (i), the variant preferably comprises R192E and R192N.

In (ii), the variant preferably comprises F56N/N55Q, F56N/N55R, F56N/N55K, F56N/N55S, F56N/N55G, F56N/N55A, F56N/N55T, F56Q/N55Q, F56Q/N55R, F56Q/N55K, F56Q/N55S, F56Q/N55G, F56Q/N55A, F56Q/N55T, F56R/N55Q, F56R/N55R, F56R/N55K, F56R/N55S, F56R/N55G, F56R/N55A, F56R/N55T, F56S/N55Q, F56S/N55R, F56S/N55K, F56S/N55S, F56S/N55G, F56S/N55A, F56S/N55T, F56G/N55Q, F56G/N55R, F56G/N55K, F56G/N55S, F56G/N55G, F56G/N55A, F56G/N55T, F56A/N55Q, F56A/N55R, F56A/N55K, F56A/N55S, F56A/N55G, F56A/N55A, F56A/N55T, F56K/N55Q, F56K/N55R, F56K/N55K, F56K/N55S, F56K/N55G, F56K/N55A, F56K1N55T, F56N/Y51L, F56N/Y51V, F56N/Y51A, F56N/Y51N, F56N/Y51Q, F56N/Y51S, F56N/Y51G, F56Q/Y51L, F56Q/Y51V, F56Q/Y51A, F56Q/Y51N, F56Q/Y51Q, F56Q/Y51S, F56Q/Y51G, F56R/Y51L, F56R/Y51V, F56R/Y51A, F56R/Y51N, F56R/Y51Q, F56R/Y51S, F56R/Y51G, F56S/Y51L, F56S/Y51V, F56S/Y51A, F56S/Y51N, F56S/Y51Q, F56S/Y51S, F56S/Y51G, F56G/Y51L, F56G/Y51V, F56G/Y51A, F56G/Y51N, F56G/Y51Q, F56G/Y51S, F56G/Y51G, F56A/Y51L, F56A/Y51V, F56A/Y51A, F56A/Y51N, F56A/Y51Q, F56A/Y51S, F56A/Y51G, F56K/Y51L, F56K/Y51V, F56K/Y51A, F56K1Y51N, F56K/Y51Q, F56K/Y51S, F56K/Y51G, N55Q/Y51L, N55Q/Y51V, N55Q/Y51A, N55Q/Y51N, N55Q/Y51Q, N55Q/Y51S, N55Q/Y51G, N55R/Y51L, N55R/Y51V, N55R/Y51A, N55R/Y51N, N55R/Y51Q, N55R/Y51S, N55R/Y51G, N55K/Y51L, N55K/Y51V, N55K/Y51A, N55K/Y51N, N55K/Y51Q, N55K/Y51S, N55K/Y51G, N55S/Y51L, N55S/Y51V, N55S/Y51A, N55S/Y51N, N55S/Y51Q, N55S/Y51S, N55S/Y51G, N55G/Y51L, N55G/Y51V, N55G/Y51A, N55G/Y51N, N55G/Y51Q, N55G/Y51S, N55G/Y51G, N55A/Y51L, N55A/Y51V, N55A/Y51A, N55A/Y51N, N55A/Y51Q, N55A/Y51S, N55A/Y51G, N55T/Y51L, N55T/Y51V, N55T/Y51A, N55T/Y51N, N55T/Y51Q, N55T/Y51S, N55T/Y51G, F56N/N55Q/Y51L, F56N/N55Q/Y51V, F56N/N55Q/Y51A, F56N/N55Q/Y51N, F56N/N55Q/Y51Q, F56N/N55Q/Y51S, F56N/N55Q/Y51G, F56N/N55R/Y51L, F56N/N55R/Y51V, F56N/N55R/Y51A, F56N/N55R/Y51N, F56N/N55R/Y51Q, F56N/N55R/Y51S, F56N/N55R/Y51G, F56N/N55K/Y51L, F56N/N55K/Y51V, F56N/N55K/Y51A, F56N/N55K/Y51N, F56N/N55K/Y51Q, F56N/N55K/Y51S, F56N/N55K/Y51G, F56N/N55S/Y51L, F56N/N55S/Y51V, F56N/N55S/Y51A, F56N/N55S/Y51N, F56N/N55S/Y51Q, F56N/N55S/Y51S, F56N/N55S/Y51G, F56N/N55G/Y51L, F56N/N55G/Y51V, F56N/N55G/Y51A, F56N/N55G/Y51N, F56N/N55G/Y51Q, F56N/N55G/Y51S, F56N/N55G/Y51G, F56N/N55A/Y51L, F56N/N55A/Y51V, F56N/N55A/Y51A, F56N/N55A/Y51N, F56N/N55A/Y51Q, F56N/N55A/Y51S, F56N/N55A/Y51G, F56N/N55T/Y51L, F56N/N55T/Y51V, F56N/N55T/Y51A, F56N/N55T/Y51N, F56N/N55T/Y51Q, F56N/N55T/Y51S, F56N/N55T/Y51G, F56Q/N55Q/Y51L, F56Q/N55Q/Y51V, F56Q/N55Q/Y51A, F56Q/N55Q/Y51N, F56Q/N55Q/Y51Q, F56Q/N55Q/Y51S, F56Q/N55Q/Y51G, F56Q/N55R/Y51L, F56Q/N55R/Y51V, F56Q/N55R/Y51A, F56Q/N55R/Y51N, F56Q/N55R/Y51Q, F56Q/N55R/Y51S, F56Q/N55R/Y51G, F56Q/N55K/Y51L, F56Q/N55K/Y51V, F56Q/N55K/Y51A, F56Q/N55K/Y51N, F56Q/N55K/Y51Q, F56Q/N55K/Y51S, F56Q/N55K/Y51G, F56Q/N55S/Y51L, F56Q/N55S/Y51V, F56Q/N55S/Y51A, F56Q/N55S/Y51N, F56Q/N55S/Y51Q, F56Q/N55S/Y51S, F56Q/N55S/Y51G, F56Q/N55G/Y51L, F56Q/N55G/Y51V, F56Q/N55G/Y51A, F56Q/N55G/Y51N, F56Q/N55G/Y51Q, F56Q/N55G/Y51S, F56Q/N55G/Y51G, F56Q/N55A/Y51L, F56Q/N55A/Y51V, F56Q/N55A/Y51A, F56Q/N55A/Y51N, F56Q/N55A/Y51Q, F56Q/N55A/Y51S, F56Q/N55A/Y51G, F56Q/N55T/Y51L, F56Q/N55T/Y51V, F56Q/N55T/Y51A, F56Q/N55T/Y51N, F56Q/N55T/Y51Q, F56Q/N55T/Y51S, F56Q/N55T/Y51G, F56R/N55Q/Y51L, F56R/N55Q/Y51V, F56R/N55Q/Y51A, F56R/N55Q/Y51N, F56R/N55Q/Y51Q, F56R/N55Q/Y51S, F56R/N55Q/Y51G, F56R/N55R/Y51L, F56R/N55R/Y51V, F56R/N55R/Y51A, F56R/N55R/Y51N, F56R/N55R/Y51Q, F56R/N55R/Y51S, F56R/N55K/Y51L, F56R/N55K/Y51V, F56R/N55K/Y51L, F56R/N55K/Y51A, F56R/N55K/Y51N, F56R/N55K/Y51Q, F56R/N55K/Y51S, F56R/N55K/Y51G, F56R/N55S/Y51L, F56R/N55S/Y51V, F56R/N55S/Y51A, F56R/N55S/Y51N, F56R/N55S/Y51Q, F56R/N55S/Y51S, F56R/N55S/Y51G, F56R/N55G/Y51L, F56R/N55G/Y51V, F56R/N55G/Y51A, F56R/N55G/Y51N, F56R/N55G/Y51Q, F56R/N55G/Y51S, F56R/N55G/Y51G, F56R/N55A/Y51L, F56R/N55A/Y51V, F56R/N55A/Y51A, F56R/N55A/Y51N, F56R/N55A/Y51Q, F56R/N55A/Y51S, F56R/N55A/Y51G, F56R/N55T/Y51L, F56R/N55T/Y51V, F56R/N55T/Y51A, F56R/N55T/Y51N, F56R/N55T/Y51Q, F56R/N55T/Y51S, F56R/N55T/Y51G, F56S/N55Q/Y51L, F56S/N55Q/Y51V, F56S/N55Q/Y51A, F56S/N55Q/Y51N, F56S/N55Q/Y51Q, F56S/N55Q/Y51S, F56S/N55Q/Y51G, F56S/N55R/Y51L, F56S/N55R/Y51V, F56S/N55R/Y51A, F56S/N55R/Y51N, F56S/N55R/Y51Q, F56S/N55R/Y51S, F56S/N55R/Y51G, F56S/N55K/Y51L, F56S/N55K/Y51V, F56S/N55K/Y51A, F56S/N55K/Y51N, F56S/N55K/Y51Q, F56S/N55K/Y51S, F56S/N55K/Y51G, F56S/N55S/Y51L, F56S/N55S/Y51V, F56S/N55S/Y51A, F56S/N55S/Y51N, F56S/N55S/Y51Q, F56S/N55S/Y51S, F56S/N55S/Y51G, F56S/N55G/Y51L, F56S/N55G/Y51V, F56S/N55G/Y51A, F56S/N55G/Y51N, F56S/N55G/Y51Q, F56S/N55G/Y51S, F56S/N55G/Y51G, F56S/N55A/Y51L, F56S/N55A/Y51V, F56S/N55A/Y51A, F56S/N55A/Y51N, F56S/N55A/Y51Q, F56S/N55A/Y51S, F56S/N55A/Y51G, F56S/N55T/Y51L, F56S/N55T/Y51V, F56S/N55T/Y51A, F56S/N55T/Y51N, F56S/N55T/Y51Q, F56S/N55T/Y51S, F56S/N55T/Y51G, F56G/N55Q/Y51L, F56G/N55Q/Y51V, F56G/N55Q/Y51A, F56G/N55Q/Y51N, F56G/N55Q/Y51Q, F56G/N55Q/Y51S, F56G/N55Q/Y51G, F56G/N55R/Y51L, F56G/N55R/Y51V, F56G/N55R/Y51A, F56G/N55R/Y51N, F56G/N55R/Y51Q, F56G/N55R/Y51S, F56G/N55R/Y51G, F56G/N55K/Y51L, F56G/N55K/Y51V, F56G/N55K/Y51A, F56G/N55K/Y51N, F56G/N55K/Y51Q, F56G/N55K/Y51S, F56G/N55K/Y51G, F56G/N55S/Y51L, F56G/N55S/Y51V, F56G/N55S/Y51A, F56G/N55S/Y51N, F56G/N55S/Y51Q, F56G/N55S/Y51S, F56G/N55S/Y51G, F56G/N55G/Y51L, F56G/N55G/Y51V, F56G/N55G/Y51A, F56G/N55G/Y51N, F56G/N55G/Y51Q, F56G/N55G/Y51S, F56G/N55G/Y51G, F56G/N55A/Y51L, F56G/N55A/Y51V, F56G/N55A/Y51A, F56G/N55A/Y51N, F56G/N55A/Y51Q, F56G/N55A/Y51S, F56G/N55A/Y51G, F56G/N55T/Y51L, F56G/N55T/Y51V, F56G/N55T/Y51A, F56G/N55T/Y51N, F56G/N55T/Y51Q, F56G/N55T/Y51S, F56G/N55T/Y51G, F56A/N55Q/Y51L, F56A/N55Q/Y51V, F56A/N55Q/Y51A, F56A/N55Q/Y51N, F56A/N55Q/Y51Q, F56A/N55Q/Y51S, F56A/N55Q/Y51G, F56A/N55R/Y51L, F56A/N55R/Y51V, F56A/N55R/Y51A, F56A/N55R/Y51N, F56A/N55R/Y51Q, F56A/N55R/Y51S, F56A/N55R/Y51G, F56A/N55K/Y51L, F56A/N55K/Y51V, F56A/N55K/Y51A, F56A/N55K/Y51N, F56A/N55K/Y51Q, F56A/N55K/Y51S, F56A/N55K/Y51G, F56A/N55S/Y51L, F56A/N55S/Y51V, F56A/N55S/Y51A, F56A/N55S/Y51N, F56A/N55S/Y51Q, F56A/N55S/Y51S, F56A/N55S/Y51G, F56A/N55G/Y51L, F56A/N55G/Y51V, F56A/N55G/Y51A, F56A/N55G/Y51N, F56A/N55G/Y51Q, F56A/N55G/Y51S, F56A/N55G/Y51G, F56A/N55A/Y51L, F56A/N55A/Y51V, F56A/N55A/Y51A, F56A/N55A/Y51N, F56A/N55A/Y51Q, F56A/N55A/Y51S, F56A/N55A/Y51G, F56A/N55T/Y51L, F56A/N55T/Y51V, F56A/N55T/Y51A, F56A/N55T/Y51N, F56A/N55T/Y51Q, F56A/N55T/Y51S, F56A/N55T/Y51G, F56K/N55Q/Y51L, F56K/N55Q/Y51V, F56K/N55Q/Y51A, F56K/N55Q/Y51N, F56K/N55Q/Y51Q, F56K/N55Q/Y51S, F56K/N55Q/Y51G, F56K/N55R/Y51L, F56K/N55R/Y51V, F56K/N55R/Y51A, F56K/N55R/Y51N, F56K/N55R/Y51Q, F56K/N55R/Y51S, F56K/N55R/Y51G, F56K/N55K/Y51L, F56K/N55K/Y51V, F56K/N55K/Y51A, F56K/N55K/Y51N, F56K/N55K/Y51Q, F56K/N55K/Y51S, F56K/N55K/Y51G, F56K/N55S/Y51L, F56K/N55S/Y51V, F56K/N55S/Y51A, F56K/N55S/Y51N, F56K/N55S/Y51Q, F56K/N55S/Y51S, F56K/N55S/Y51G, F56K/N55G/Y51L, F56K/N55G/Y51V, F56K/N55G/Y51A, F56K/N55G/Y51N, F56K/N55G/Y51Q, F56K/N55G/Y51S, F56K/N55G/Y51G, F56K/N55A/Y51L, F56K/N55A/Y51V, F56K/N55A/Y51A, F56K/N55A/Y51N, F56K/N55A/Y51Q, F56K/N55A/Y51S, F56K/N55A/Y51G, F56K/N55T/Y51L, F56K/N55T/Y51V, F56K/N55T/Y51A, F56K/N55T/Y51N, F56K/N55T/Y51Q, F56K/N55T/Y51S, F56K/N55T/Y51G, F56E/N55R, F56E/N55K, F56D/N55R, F56D/N55K, F56R/N55E, F56R/N55D, F56K/N55E or F56K/N55D.

In (ii), the variant preferably comprises Y51R/F56Q, Y51N/F56N, Y51M/F56Q, Y51L/F56Q, Y51I/F56Q, Y51V/F56Q, Y51A/F56Q, Y51P/F56Q, Y51G/F56Q, Y51C/F56Q, Y51Q/F56Q, Y51N/F56Q, Y51S/F56Q, Y51E/F56Q, Y51D/F56Q, Y51K/F56Q or Y51H/F56Q.

In (ii), the variant preferably comprises Y51T/F56Q, Y51Q/F56Q or Y51A/F56Q.

In (ii), the variant preferably comprises Y51T/F56F, Y51T/F56M, Y51T/F56L, Y51T/F56I, Y51T/F56V, Y51T/F56A, Y51T/F56P, Y51T/F56G, Y51T/F56C, Y51T/F56Q, Y51T/F56N, Y51T/F56T, Y51T/F56S, Y51T/F56E, Y51T/F56D, Y51T/F56K, Y51T/F56H or Y51T/F56R.

In (ii), the variant preferably comprises Y51T/N55Q, Y51T/N55S or Y51T/N55A.

In (ii), the variant preferably comprises Y51A/F56F, Y51A/F56L, Y51A/F56I, Y51A/F56V, Y51A/F56A, Y51A/F56P, Y51A/F56G, Y51A/F56C, Y51A/F56Q, Y51A/F56N, Y51A/F56T, Y51A/F56S, Y51A/F56E, Y51A/F56D, Y51A/F56K, Y51A/F56H or Y51A/F56R.

In (ii), the variant preferably comprises Y51C/F56A, Y51E/F56A, Y51D/F56A, Y51K/F56A,
Y51H/F56A, Y51Q/F56A, Y51N/F56A, Y51S/F56A, Y51P/F56A or Y51V/F56A.

In (xi), the variant preferably comprises deletion of Y51/P52, Y51/P52/A53, P50 to P52, P50 to A53, K49 to Y51, K49 to A53 and replacement with a single proline (P), K49 to S54 and replacement with a single P, Y51 to A53, Y51 to S54, N55/F56, N55 to S57, N55/F56 and replacement with a single P, N55/F56 and replacement with a single glycine (G), N55/F56 and replacement with a single alanine (A), N55/F56 and replacement with a single P and Y51N, N55/F56 and replacement with a single P and Y51Q, N55/F56 and replacement with a single P and Y51S, N55/F56 and replacement with a single G and Y51N, N55/F56 and replacement with a single G and Y51Q, N55/F56 and replacement with a single G and Y51S, N55/F56 and replacement with a single A and Y51N, N55/F56 and replacement with a single A/Y51Q or N55/F56 and replacement with a single A and Y51S.

The variant more preferably comprises D195N/E203N, D195Q/E203N, D195N/E203Q, D195Q/E203Q, E201N/E203N, E201Q/E203N, E201N/E203Q, E201Q/E203Q, E185N/E203Q, E185Q/E203Q, E185N/E203N, E185Q/E203N, D195N/E201N/E203N, D195Q/E201N/E203N, D195N/E201Q/E203N, D195N/E201N/E203Q, D195Q/E201Q/E203N, D195Q/E201N/E203Q, D195N/E201Q/E203Q, D195Q/E201Q/E203Q, D149N/E201N, D149Q/E201N, D149N/E201Q, D149Q/E201Q, D149N/E201N/D195N, D149Q/E201N/D195N, D149N/E201Q/D195N, D149N/E201N/D195Q, D149Q/E201N/D195Q, D149Q/E201Q/D195N, D149Q/E201Q/D195Q, D149N/E203N, D149Q/E203N, D149N/E203Q, D149Q/E203Q, D149N/E185N/E201N, D149Q/E185N/E201N, D149N/E185Q/E201N, D149N/E185N/E201Q, D149Q/E185Q/E201N, D149Q/E185N/E201Q, D149N/E185Q/E201Q, D149Q/E185Q/E201Q, D149N/E185N/E203N, D149Q/E185N/E203N, D149N/E185Q/E203N, D149N/E185N/E203Q, D149Q/E185Q/E203N, D149Q/E185N/E203Q, D149N/E185Q/E203Q, D149Q/E185Q/E203Q, D149N/E185N/E201N/E203N, D149Q/E185N/E201N/E203N, D149N/E185Q/E201N/E203N, D149N/E185N/E201Q/E203N, D149N/E185N/E201N/E203Q, D149Q/E185Q/E201N/E203N, D149Q/E185N/E201Q/E203N, D149Q/E185N/E201N/E203Q, D149N/E185Q/E201Q/E203N, D149N/E185Q/E201N/E203Q, D149N/E185N/E201Q/E203Q, D149Q/E185Q/E201Q/E203N, D149Q/E185Q/E201N/E203Q, D149Q/E185N/E201Q/E203Q, D149N/E185Q/E201Q/E203Q, D149Q/E185Q/E201Q/E203Q, D149N/E185N/D195N/E201N/E203N, D149N/E185Q/D195N/E201N/E203N, D149N/E185N/D195Q/E201N/E203N, D149N/E185N/D195N/E201Q/E203N, D149N/E185N/D195N/E201N/E203Q, D149N/

E185N/D195N/E201N/E203Q, D149Q/E185Q/D195N/E201N/E203N, D149Q/E185N/D195Q/E201N/E203N, D149Q/E185N/D195N/E201Q/E203N, D149Q/E185N/D195N/E201N/E203Q, D149N/E185Q/D195Q/E201N/E203N, D149N/E185Q/D195N/E201Q/E203N, D149N/E185Q/D195N/E201N/E203Q, D149N/E185N/D195Q/E201Q/E203N, D149N/E185N/D195Q/E201N/E203Q, D149N/E185N/D195N/E201Q/E203Q, D149Q/E185Q/D195Q/E201N/E203N, D149Q/E185Q/D195N/E201Q/E203N, D149Q/E185Q/D195N/E201N/E203Q, D149Q/E185N/D195Q/E201Q/E203N, D149Q/E185N/D195Q/E201N/E203Q, D149Q/E185N/D195N/E201Q/E203Q, D149N/E185Q/D195Q/E201Q/E203N, D149N/E185Q/D195Q/E201N/E203Q, D149N/E185Q/D195N/E201Q/E203Q, D149N/E185N/D195Q/E201Q/E203Q, D149Q/E185Q/D195Q/E201Q/E203N, D149Q/E185Q/D195Q/E201N/E203Q, D149Q/E185Q/D195N/E201Q/E203Q, D149Q/E185N/D195Q/E201Q/E203Q, D149N/E185Q/D195Q/E201Q/E203Q, D149N/E185Q/D195Q/E201Q/E203Q, D149N/E185R/E201N/E203N, D149Q/E185R/E201N/E203N, D149N/E185R/E201Q/E203N, D149N/E185R/E201N/E203Q, D149Q/E185R/E201Q/E203N, D149Q/E185R/E201N/E203Q, D149N/E185R/E201Q/E203Q, D149Q/E185R/E201Q/E203Q, D149Q/E185N/E201N/E203N, D149R/E185Q/E201N/E203N, D149R/E185N/E201Q/E203N, D149R/E185N/E201N/E203Q, D149R/E185Q/E201Q/E203N, D149R/E185Q/E201N/E203Q, D149R/E185N/E201Q/E203Q, D149R/E185Q/E201Q/E203Q, D149R/E185N/D195N/E201N/E203N, D149R/E185Q/D195N/E201N/E203N, D149R/E185N/D195Q/E201N/E203N, D149R/E185N/D195N/E201Q/E203N, D149R/E185N/D195N/E201N/E203Q, D149R/E185Q/D195Q/E201N/E203N, D149R/E185Q/D195N/E201Q/E203N, D149R/E185Q/D195N/E201N/E203Q, D149R/E185N/D195Q/E201Q/E203N, D149R/E185N/D195Q/E201N/E203Q, D149R/E185N/D195N/E201Q/E203Q, D149R/E185Q/D195Q/E201Q/E203N, D149R/E185Q/D195Q/E201N/E203Q, D149R/E185Q/D195N/E201Q/E203Q, D149R/E185N/D195Q/E201Q/E203Q, D149R/E185Q/D195Q/E201Q/E203Q, D149N/E185R/D195N/E201N/E203N, D149Q/E185R/D195N/E201N/E203N, D149N/E185R/D195Q/E201N/E203N, D149N/E185R/D195N/E201Q/E203N, D149N/E185R/D195N/E201N/E203Q, D149Q/E185R/D195N/E201N/E203N, D149Q/E185R/D195N/E201Q/E203N, D149Q/E185R/D195N/E201N/E203Q, D149N/E185R/D195Q/E201Q/E203N, D149N/E185R/D195Q/E201N/E203Q, D149N/E185R/D195N/E201Q/E203Q, D149Q/E185R/D195Q/E201N/E203N, D149Q/E185R/D195Q/E201N/E203Q, D149Q/E185R/D195N/E201Q/E203Q, D149N/E185R/D195Q/E201Q/E203Q, D149Q/E185R/D195Q/E201Q/E203Q, D149N/E185R/D195N/E201R/E203N, D149Q/E185R/D195N/E201R/E203N, D149N/E185R/D195Q/E201R/E203N, D149N/E185R/D195N/E201R/E203Q, D149Q/E185R/D195Q/E201R/E203N, D149Q/E185R/D195N/E201R/E203Q, D149N/E185R/D195Q/E201R/E203Q, D149Q/E185R/D195Q/E201R/E203Q, E131D/K49R, E101N/N102F, E101N/N102Y, E101N/N102W, E101F/N102F, E101F/N102Y, E101F/N102W, E101Y/N102F, E101Y/N102Y, E101Y/N102W, E101W/N102F, E101W/N102Y, E101W/N102W, E101N/N102R, E101F/N102R, E101Y/N102R or E101W/N102F.

Preferred variants of the invention which form pores in which fewer nucleotides contribute to the current as the polynucleotide moves through the pore comprise Y51A/F56A, Y51A/F56N, Y51I/F56A, Y51L/F56A, Y51T/F56A, Y51I/F56N, Y51L/F56N or Y51T/F56N or more preferably Y51I/F56A, Y51L/F56A or Y51T/F56A. As discussed above, this makes it easier to identify a direct relationship between the observed current (as the polynucleotide moves through the pore) and the polynucleotide.

Preferred variants which form pores displaying an increased range comprise mutations at the following positions:
  Y51, F56, D149, E185, E201 and E203;
  N55 and F56;
  Y51 and F56;
  Y51, N55 and F56; or
  F56 and N102.

Preferred variants which form pores displaying an increased range comprise:
  Y51N, F56A, D149N, E185R, E201N and E203N;
  N55S and F56Q;
  Y51A and F56A;
  Y51A and F56N;
  Y51I and F56A;
  Y51 L and F56A;
  Y51T and F56A;
  Y51I and F56N;
  Y51L and F56N;
  Y51T and F56N;
  Y51T and F56Q;
  Y51A, N55S and F56A;
  Y51A, N55S and F56N;
  Y51T, N55S and F56Q; or
  F56Q and N102R.

Preferred variants which form pores in which fewer nucleotides contribute to the current as the polynucleotide moves through the pore comprise mutations at the following positions:
  N55 and F56, such as N55X and F56Q, wherein X is any amino acid; or
  Y51 and F56, such as Y51X and F56Q, wherein X is any amino acid.

Preferred variants which form pores displaying an increased throughput comprise mutations at the following positions:
  D149, E185 and E203;
  D149, E185, E201 and E203; or
  D149, E185, D195, E201 and E203.

Preferred variants which form pores displaying an increased throughput comprise:
  D149N, E185N and E203N;
  D149N, E185N, E201N and E203N;
  D149N, E185R, D195N, E201N and E203N; or
  D149N, E185R, D195N, E201R and E203N.

Preferred variants which form pores in which capture of the polynucleotide is increased comprise the following mutations:
  D43N/Y51T/F56Q;
  E44N/Y51T/F56Q;
  D43N/E44N/Y51T/F56Q;
  Y51T/F56Q/Q62R;
  D43N/Y51T/F56Q/Q62R;
  E44N/Y51T/F56Q/Q62R; or
  D43N/E44N/Y51T/F56Q/Q62R.

Preferred variants comprise the following mutations:
  D149R/E185R/E201R/E203R or Y51T/F56Q/D149R/E185R/E201R/E203R;
  D149N/E185N/E201N/E203N or Y51T/F56Q/D149N/E185N/E201N/E203N;
  E201R/E203R or Y51T/F56Q/E201R/E203R
  E201N/E203R or Y51T/F56Q/E201N/E203R;
  E203R or Y51T/F56Q/E203R;

E203N or Y51T/F56Q/E203N;
E201R or Y51T/F56Q/E201R;
E201N or Y51T/F56Q/E201N;
E185R or Y51T/F56Q/E185R;
E185N or Y51T/F56Q/E185N;
D149R or Y51T/F56Q/D149R;
D149N or Y51T/F56Q/D149N;
R142E or Y51T/F56Q/R142E;
R142N or Y51T/F56Q/R142N;
R192E or Y51T/F56Q/R192E; or
R192N or Y51T/F56Q/R192N.

Preferred variants comprise the following mutations:
Y51A/F56Q/E101N/N102R;
Y51A/F56Q/R97N/N102G;
Y51A/F56Q/R97N/N102R;
Y51A/F56Q/R97N;
Y51A/F56Q/R97G;
Y51A/F56Q/R97L;
Y51A/F56Q/N102R;
Y51A/F56Q/N102F;
Y51A/F56Q/N102G;
Y51A/F56Q/E101R;
Y51A/F56Q/E101F;
Y51A/F56Q/E101N; or
Y51A/F56Q/E101G The invention also provides a mutant CsgG monomer comprising a variant of the sequence shown in SEQ ID NO: 390, wherein the variant comprises a mutation at T150. A preferred variant which forms a pore displaying an increased insertion comprises T150I. A mutation at T150, such as T150I, may be combined with any of the mutations or combinations of mutations discussed above.

The invention also provides a mutant CsgG monomer comprising a variant of the sequence shown in SEQ ID NO: 390 comprising the combination of mutations present in a variant disclosed in the Examples.

Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. The polynucleotide can then be expressed as discussed below.

Methods for introducing or substituting non-naturally-occurring amino acids are also well known in the art. For instance, non-naturally-occurring amino acids may be introduced by including synthetic aminoacyl-tRNAs in the IVTT system used to express the mutant monomer. Alternatively, they may be introduced by expressing the mutant monomer in *E. coli* that are auxotrophic for specific amino acids in the presence of synthetic (i.e. non-naturally-occurring) analogues of those specific amino acids. They may also be produced by naked ligation if the mutant monomer is produced using partial peptide synthesis.

Other Monomers of the Invention

In another embodiment, the invention provides a mutant CsgG monomer comprising a variant of the sequence shown in SEQ ID NO: 390, wherein the variant comprises a mutation at one or more of positions Y51, N55 and F56. The variant may comprise a mutation at Y51; N55; F56; Y51/N55; Y51/F56; N55/F56; or Y51/N55/F56. The variant preferably comprises a mutation at Y51, N55 or F56. The variant may comprise any of the specific mutations at one or more of positions Y51, N55 and F56 discussed above and in any combination. One or more Y51, N55 and F56 may be substituted with any amino acid. Y51 may be substituted with F, M, L, I, V, A, P, G, C, Q, N, T, S, E, D, K, H or R, such as A, S, T, N or Q. N55 may be substituted with F, M, L, I, V, A, P, G, C, Q, T, S, E, D, K, H or R, such as A, S, T or Q. F56 may be substituted with M, L, I, V, A, P, G, C, Q, N, T, S, E, D, K, H or R, such as A, S, T, N or Q.

The variant may further comprise one or more of the following: (i) one or more mutations at the following positions (i.e. mutations at one or more of the following positions) (i) N40, D43, E44, S54, S57, Q62, R97, E101, E124, E131, R142, T150 and R192; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any of the combinations of (i) and (iii) to (xi) discussed above. The variant may comprise any of the embodiments discussed above for (i) and (iii) to (xi).

Variants

In addition to the specific mutations discussed above, the variant may include other mutations. Over the entire length of the amino acid sequence of SEQ ID NO: 390, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 390 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 390 is the wild-type CsgG monomer from *Escherichia coli* Str. K-12 substr. MC4100. The variant of SEQ ID NO: 390 may comprise any of the substitutions present in another CsgG homologue. Preferred CsgG homologues are shown in SEQ ID NOs: 391 to 395 and 414 to 429. The variant may comprise combinations of one or more of the substitutions present in SEQ ID NOs: 391 to 395 and 414 to 429 compared with SEQ ID NO: 390.

Amino acid substitutions may be made to the amino acid sequence of SEQ ID NO: 390 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can also be determined by reference to the hydropathy scale for amino acid side chains in Table 2.

TABLE 1

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| | | Val | aliphatic, hydrophobic, neutral |
| Ile | aliphatic, hydrophobic, neutral | Trp | aromatic, hydrophobic, neutral |
| Lys | polar, hydrophilic, charged(+) | Tyr | aromatic, polar, hydrophobic |
| Leu | aliphatic, hydrophobic, neutral | | |

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 390 may additionally be deleted from the polypeptides described above. Up to 1, 2, 3, 4, 5, 10, 20 or 30 or more residues may be deleted.

Variants may include fragments of SEQ ID NO: 390. Such fragments retain pore forming activity. Fragments may be at least 50, at least 100, at least 150, at least 200 or at least 250 amino acids in length. Such fragments may be used to produce the pores. A fragment preferably comprises the membrane spanning domain of SEQ ID NO: 390, namely K135-Q153 and S183-S208.

One or more amino acids may be alternatively or additionally added to the polypeptides described above. An extension may be provided at the amino terminal or carboxy terminal of the amino acid sequence of SEQ ID NO: 390 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 390 and which retains its ability to form a pore. A variant typically contains the regions of SEQ ID NO: 390 that are responsible for pore formation. The pore forming ability of CsgG, which contains a β-barrel, is provided by β-sheets in each subunit. A variant of SEQ ID NO: 390 typically comprises the regions in SEQ ID NO: 390 that form β-sheets, namely K135-Q153 and S183-S208. One or more modifications can be made to the regions of SEQ ID NO: 390 that form β-sheets as long as the resulting variant retains its ability to form a pore. A variant of SEQ ID NO: 390 preferably includes one or more modifications, such as substitutions, additions or deletions, within its α-helices and/or loop regions.

The monomers derived from CsgG may be modified to assist their identification or purification, for example by the addition of a streptavidin tag or by the addition of a signal sequence to promote their secretion from a cell where the monomer does not naturally contain such a sequence. Other suitable tags are discussed in more detail below. The monomer may be labelled with a revealing label. The revealing label may be any suitable label which allows the monomer to be detected. Suitable labels are described below.

The monomer derived from CsgG may also be produced using D-amino acids. For instance, the monomer derived from CsgG may comprise a mixture of L-amino acids and D-amino acids. This is conventional in the art for producing such proteins or peptides.

The monomer derived from CsgG contains one or more specific modifications to facilitate nucleotide discrimination. The monomer derived from CsgG may also contain other non-specific modifications as long as they do not interfere with pore formation. A number of non-specific side chain modifications are known in the art and may be made to the side chains of the monomer derived from CsgG. Such modifications include, for example, reductive alkylation of amino acids by reaction with an aldehyde followed by reduction with $NaBH_4$, amidination with methylacetimidate or acylation with acetic anhydride.

The monomer derived from CsgG can be produced using standard methods known in the art. The monomer derived from CsgG may be made synthetically or by recombinant means. For example, the monomer may be synthesised by in vitro translation and transcription (IVTT). Suitable methods for producing pores and monomers are discussed in International Application Nos. PCT/GB09/001690 (published as WO 2010/004273), PCT/GB09/001679 (published as WO 2010/004265) or PCT/GB101000133 (published as WO 2010/086603). Methods for inserting pores into membranes are discussed.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant monomer may be chemically modified by the attachment of any molecule. For instance, the mutant monomer may be chemically modified by attachment of a dye or a fluorophore.

In some embodiments, the mutant monomer is chemically modified with a molecular adaptor that facilitates the interaction between a pore comprising the monomer and a target nucleotide or target polynucleotide sequence. The presence of the adaptor improves the host-guest chemistry of the pore and the nucleotide or polynucleotide sequence and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore.

The molecular adaptor is preferably a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor preferably has eight-fold or nine-fold symmetry since CsgG typically has eight or nine subunits around a central axis. This is discussed in more detail below.

The adaptor typically interacts with the nucleotide or polynucleotide sequence via host-guest chemistry. The adaptor is typically capable of interacting with the nucleotide or polynucleotide sequence. The adaptor comprises one or more chemical groups that are capable of interacting with the nucleotide or polynucleotide sequence. The one or more chemical groups preferably interact with the nucleotide or polynucleotide sequence by non-covalent interactions, such as hydrophobic interactions, hydrogen bonding, Van der Waal's forces, n-cation interactions and/or electrostatic forces. The one or more chemical groups that are capable of interacting with the nucleotide or polynucleotide sequence are preferably positively charged. The one or more chemical groups that are capable of interacting with the nucleotide or polynucleotide sequence more preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of eight amino groups. A ring of protonated amino groups may interact with negatively charged phosphate groups in the nucleotide or polynucleotide sequence.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, π-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide sequence can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H.-J. (1994) *J. Am. Chem. Soc.* 116, 6081-6088. The adaptor is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). The guanidino group in $gu_7$-βCD has a much higher pKa than the primary amines in $am_7$-βCD and so it is more positively charged. This $gu_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanoyl-β-cyclodextrin ($am_6amPDP_1$-βCD).

More suitable adaptors include α-cyclodextrins, which comprise 9 sugar units (and therefore have nine-fold symmetry). The γ-cyclodextrin may contain a linker molecule or may be modified to comprise all or more of the modified sugar units used in the β-cyclodextrin examples discussed above.

The molecular adaptor is preferably covalently attached to the mutant monomer. The adaptor can be covalently attached to the pore using any method known in the art. The adaptor is typically attached via chemical linkage. If the molecular adaptor is attached via cysteine linkage, the one or more cysteines have preferably been introduced to the mutant, for instance in the barrel, by substitution. The mutant monomer may be chemically modified by attachment of a molecular adaptor to one or more cysteines in the mutant monomer. The one or more cysteines may be naturally-occurring, i.e. at positions 1 and/or 215 in SEQ ID NO: 390. Alternatively, the mutant monomer may be chemically modified by attachment of a molecule to one or more cysteines introduced at other positions. The cysteine at position 215 may be removed, for instance by substitution, to ensure that the molecular adaptor does not attach to that position rather than the cysteine at position 1 or a cysteine introduced at another position.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the mutant monomer before a linker is attached.

The molecule may be attached directly to the mutant monomer. The molecule is preferably attached to the mutant monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and Maleimide-based linkers.

In other embodiment, the monomer may be attached to a polynucleotide binding protein. This forms a modular sequencing system that may be used in the methods of sequencing of the invention. Polynucleotide binding proteins are discussed below.

The polynucleotide binding protein is preferably covalently attached to the mutant monomer. The protein can be covalently attached to the monomer using any method known in the art. The monomer and protein may be chemically fused or genetically fused. The monomer and protein are genetically fused if the whole construct is expressed from a single polynucleotide sequence. Genetic fusion of a monomer to a polynucleotide binding protein is discussed in International Application No. PCT/GB09/001679 (published as WO 2010/004265).

If the polynucleotide binding protein is attached via cysteine linkage, the one or more cysteines have preferably been introduced to the mutant by substitution. The one or more cysteines are preferably introduced into loop regions which have low conservation amongst homologues indicating that mutations or insertions may be tolerated. They are therefore suitable for attaching a polynucleotide binding protein. In such embodiments, the naturally-occurring cysteine at position 251 may be removed. The reactivity of cysteine residues may be enhanced by modification as described above.

The polynucleotide binding protein may be attached directly to the mutant monomer or via one or more linkers. The molecule may be attached to the mutant monomer using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The mutant monomer may be chemically modified with a molecular adaptor and a polynucleotide binding protein.

The molecule (with which the monomer is chemically modified) may be attached directly to the monomer or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the mutant monomers and pores of the invention, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the mutant monomers and pores of the invention, may be labelled with a revealing label. The revealing label may be any suitable label which allows the protein to be detected. Suitable labels include, but are not limited to, fluorescent molecules, radioisotopes, e.g. $^{125}I$, $^{35}S$, enzymes, antibodies, antigens, polynucleotides and ligands such as biotin.

Any of the proteins described herein, such as the monomers or pores of the invention, may be made synthetically or by recombinant means. For example, the protein may be synthesised by in vitro translation and transcription (IVTT). The amino acid sequence of the protein may be modified to include non-naturally occurring amino acids or to increase the stability of the protein. When a protein is produced by synthetic means, such amino acids may be introduced during production. The protein may also be altered following either synthetic or recombinant production.

Proteins may also be produced using D-amino acids. For instance, the protein may comprise a mixture of L-amino acids and D-amino acids. This is conventional in the art for producing such proteins or peptides.

The protein may also contain other non-specific modifications as long as they do not interfere with the function of the protein. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins described herein, including the monomers and pores of the invention, can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Constructs

The invention also provides a construct comprising two or more covalently attached CsgG monomers, wherein at least one of the monomers is a mutant monomer of the invention.

The construct of the invention retains its ability to form a pore. This may be determined as discussed above. One or more constructs of the invention may be used to form pores for characterising, such as sequencing, polynucleotides. The construct may comprise at least 2, at least 3, at least 4, at least 5, at least 6, at least 7, at least 8, at least 9 or at least 10 monomers. The construct preferably comprises two monomers. The two or more monomers may be the same or different.

At least one monomer in the construct is a mutant monomer of the invention. 2 or more, 3 or more, 4 or more, 5 or more, 6 or more, 7 or more, 8 or more, 9 or more or 10 or more monomers in the construct may be mutant monomers of the invention. All of the monomers in the construct are preferably mutant monomers of the invention. The mutant monomers may be the same or different. In a preferred embodiment, the construct comprises two mutant monomers of the invention.

The mutant monomers of the invention in the construct are preferably approximately the same length or are the same length. The barrels of the mutant monomers of the invention in the construct are preferably approximately the same length or are the same length. Length may be measured in number of amino acids and/or units of length.

The construct may comprise one or more monomers which are not mutant monomers of the invention. CsgG mutant monomers which are non mutant monomers of the invention include monomers comprising SEQ ID NO: 390, 391, 392, 393, 394, 395, 414, 415, 416, 417, 418, 419, 420, 421, 422, 423, 424, 425, 426, 427, 428 or 429 or a comparative variant of SEQ ID NO: 390, 391, 392, 393, 394, 395, 414, 415, 416, 417, 418, 419, 420, 421, 422, 423, 424, 425, 426, 427, 428 or 429 in which none of the amino acids/positions discussed above have been mutated. At least one monomer in the construct may comprise SEQ ID NO: 390, 391, 392, 393, 394, 395, 414, 415, 416, 417, 418, 419, 420, 421, 422, 423, 424, 425, 426, 427, 428 or 429 or a comparative variant of the sequence shown in SEQ ID NO: 390, 391, 392, 393, 394, 395, 414, 415, 416, 417, 418, 419, 420, 421, 422, 423, 424, 425, 426, 427, 428 or 429. A comparative variant of SEQ ID NO: 390, 391, 392, 393, 394, 395, 414, 415, 416, 417, 418, 419, 420, 421, 422, 423, 424, 425, 426, 427, 428 or 429 is at least 50% homologous to 390, 391, 392, 393, 394, 395, 414, 415, 416, 417, 418, 419, 420, 421, 422, 423, 424, 425, 426, 427, 428 or 429, 40 or 41 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 390, 391, 392, 393, 394, 395, 414, 415, 416, 417, 418, 419, 420, 421, 422, 423, 424, 425, 426, 427, 428 or 429 over the entire sequence.

The monomers in the construct are preferably genetically fused. Monomers are genetically fused if the whole construct is expressed from a single polynucleotide sequence. The coding sequences of the monomers may be combined in any way to form a single polynucleotide sequence encoding the construct.

The monomers may be genetically fused in any configuration. The monomers may be fused via their terminal amino acids. For instance, the amino terminus of the one monomer may be fused to the carboxy terminus of another monomer. The second and subsequent monomers in the construct (in the amino to carboxy direction) may comprise a methionine at their amino terminal ends (each of which is fused to the carboxy terminus of the previous monomer). For instance, if M is a monomer (without an amino terminal methionine) and mM is a monomer with an amino terminal methionine, the construct may comprise the sequence M-mM, M-mM-mM or M-mM-mM-mM. The presences of these methionines typically results from the expression of the start codons (i.e. ATGs) at the 5' end of the polynucleotides encoding the second or subsequent monomers within the polynucleotide encoding entire construct. The first monomer in the construct (in the amino to carboxy direction) may also comprise a methionine (e.g. mM-mM, mM-mM-mM or mM-mM-mM-mM).

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed above may be used.

In another preferred embodiment, the monomers are chemically fused. Two monomers are chemically fused if the two parts are chemically attached, for instance via a chemical crosslinker. Any of the chemical crosslinkers discussed above may be used. The linker may be attached to one or more cysteine residues introduced into a mutant monomer of the invention. Alternatively, the linker may be attached to a terminus of one of the monomers in the construct.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described in International Application No. PCT/GB10/000132 (published as WO 2010/086602).

Polynucleotides

The present invention also provides polynucleotide sequences which encode a mutant monomer of the invention. The mutant monomer may be any of those discussed above. The polynucleotide sequence preferably comprises a sequence at least 50%, 60%, 70%, 80%, 90% or 95% homologous based on nucleotide identity to the sequence of SEQ ID NO: 389 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 389 on the basis of the degeneracy of the genetic code.

The present invention also provides polynucleotide sequences which encode any of the genetically fused constructs of the invention. The polynucleotide preferably comprises two or more variants of the sequence shown in SEQ ID NO: 389. The polynucleotide sequence preferably comprises two or more sequences having at least 50%, 60%, 70%, 80%, 90% or 95% homology to SEQ ID NO: 389 based on nucleotide identity over the entire sequence. There may be at least 80%, for example at least 85%, 90% or 95% nucleotide identity over a stretch of 600 or more, for example 750, 900, 1050 or 1200 or more, contiguous nucleotides ("hard homology"). Homology may be calculated as described above.

Polynucleotide sequences may be derived and replicated using standard methods in the art. Chromosomal DNA encoding wild-type CsgG may be extracted from a pore producing organism, such as *Escherichia coli*. The gene encoding the pore subunit may be amplified using PCR involving specific primers. The amplified sequence may then undergo site-directed mutagenesis. Suitable methods of site-directed mutagenesis are known in the art and include, for example, combine chain reaction. Polynucleotides encoding a construct of the invention can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct of the invention can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane.

Alternatively, the recombinant pore produced in this manner may be removed from the host cell and inserted into another membrane. When producing pores comprising at least two different monomers or constructs, the different monomers or constructs may be expressed separately in different host cells as described above, removed from the host cells and assembled into a pore in a separate membrane, such as a rabbit cell membrane or a synthetic membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the monomer or construct at a high level. Host cells transformed with a polynucleotide sequence will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter. In addition to the conditions listed above any of the methods cited in Cao et al, 2014, PNAS, Structure of the nonameric bacterial amyloid secretion channel, doi-1411942111 and Goyal et al, 2014, Nature, 516, 250-253 structural and mechanistic insights into the bacterial amyloid secretion channel CsgG may be used to express the CsgG proteins.

The invention also comprises a method of producing a mutant monomer of the invention or a construct of the invention. The method comprises expressing a polynucleotide of the invention in a suitable host cell. The polynucleotide is preferably part of a vector and is preferably operably linked to a promoter.

Pores

The invention also provides various pores. The pores of the invention are ideal for characterising, such as sequencing, polynucleotide sequences because they can discriminate between different nucleotides with a high degree of sensitivity. The pores can surprisingly distinguish between the four nucleotides in DNA and RNA. The pores of the invention can even distinguish between methylated and unmethylated nucleotides. The base resolution of pores of the invention is surprisingly high. The pores show almost complete separation of all four DNA nucleotides. The pores further discriminate between deoxycytidine monophosphate (dCMP) and methyl-dCMP based on the dwell time in the pore and the current flowing through the pore.

The pores of the invention can also discriminate between different nucleotides under a range of conditions. In particular, the pores will discriminate between nucleotides under conditions that are favourable to the characterising, such as sequencing, of nucleic acids. The extent to which the pores of the invention can discriminate between different nucleotides can be controlled by altering the applied potential, the salt concentration, the buffer, the temperature and the presence of additives, such as urea, betaine and DTT. This allows the function of the pores to be fine-tuned, particularly when sequencing.

This is discussed in more detail below. The pores of the invention may also be used to identify polynucleotide polymers from the interaction with one or more monomers rather than on a nucleotide by nucleotide basis.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, a pore of the invention may be present in a membrane. Suitable membranes are discussed below.

A pore of the invention may be present as an individual or single pore. Alternatively, a pore of the invention may be present in a homologous or heterologous population of two or more pores.

Homo-Oligomeric Pores

The invention also provides a homo-oligomeric pore derived from CsgG comprising identical mutant monomers of the invention. The homo-oligomeric pore may comprise any of the mutants of the invention. The homo-oligomeric pore of the invention is ideal for characterising, such as sequencing, polynucleotides. The homo-oligomeric pore of the invention may have any of the advantages discussed above.

The homo-oligomeric pore may contain any number of mutant monomers. The pore typically comprises at least 7, at least 8, at least 9 or at least 10 identical mutant monomers, such as 7, 8, 9 or 10 mutant monomers. The pore preferably comprises eight or nine identical mutant monomers. One or more, such as 2, 3, 4, 5, 6, 7, 8, 9 or 10, of the mutant monomers is preferably chemically modified as discussed above.

Methods for making pores are discussed in more detail below.

Hetero-Oligomeric Pores

The invention also provides a hetero-oligomeric pore derived from CsgG comprising at least one mutant monomer of the invention. The hetero-oligomeric pore of the invention is ideal for characterising, such as sequencing, polynucleotides. Hetero-oligomeric pores can be made using methods known in the art (e.g. Protein Sci. 2002 July; 11(7):1813-24).

The hetero-oligomeric pore contains sufficient monomers to form the pore. The monomers may be of any type. The pore typically comprises at least 7, at least 8, at least 9 or at least 10 monomers, such as 7, 8, 9 or 10 monomers. The pore preferably comprises eight or nine monomers.

In a preferred embodiment, all of the monomers (such as 10, 9, 8 or 7 of the monomers) are mutant monomers of the invention and at least one of them differs from the others. In a more preferred embodiment, the pore comprises eight or nine mutant monomers of the invention and at least one of them differs from the others. They may all differ from one another.

The mutant monomers of the invention in the pore are preferably approximately the same length or are the same length. The barrels of the mutant monomers of the invention in the pore are preferably approximately the same length or are the same length. Length may be measured in number of amino acids and/or units of length.

In another preferred embodiment, at least one of the mutant monomers is not a mutant monomer of the invention. In this embodiment, the remaining monomers are preferably mutant monomers of the invention. Hence, the pore may comprise 9, 8, 7, 6, 5, 4, 3, 2 or 1 mutant monomers of the invention. Any number of the monomers in the pore may not be a mutant monomer of the invention. The pore preferably comprises seven or eight mutant monomers of the invention and a monomer which is not a monomer of the invention. The mutant monomers of the invention may be the same or different.

The mutant monomers of the invention in the construct are preferably approximately the same length or are the same length. The barrels of the mutant monomers of the invention in the construct are preferably approximately the same length or are the same length. Length may be measured in number of amino acids and/or units of length.

The pore may comprise one or more monomers which are not mutant monomers of the invention. CsgG monomers which are not mutant monomers of the invention include monomers comprising SEQ ID NO: 390, 391, 392, 393, 394, 395, 414, 415, 416, 417, 418, 419, 420, 421, 422, 423, 424, 425, 426, 427, 428 or 429 or a comparative variant of SEQ ID NO: 390, 391, 392, 393, 394, 395, 414, 415, 416, 417, 418, 419, 420, 421, 422, 423, 424, 425, 426, 427, 428 or 429 in which none of the amino acids/positions discussed above in relation to the invention have been mutated/substituted. A comparative variant of SEQ ID NO: 390, 391, 392, 393, 394, 395, 414, 415, 416, 417, 418, 419, 420, 421, 422, 423, 424, 425, 426, 427, 428 or 429 is typically at least 50% homologous to SEQ ID NO: 390, 391, 392, 393, 394, 395, 414, 415, 416, 417, 418, 419, 420, 421, 422, 423, 424, 425, 426, 427, 428 or 429 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 390, 391, 392, 393, 394, 395, 414, 415, 416, 417, 418, 419, 420, 421, 422, 423, 424, 425, 426, 427, 428 or 429 over the entire sequence.

In all the embodiments discussed above, one or more, such as 2, 3, 4, 5, 6, 7, 8, 9 or 10, of the mutant monomers is preferably chemically modified as discussed above.

Methods for making pores are discussed in more detail below.

Construct-Containing Pores

The invention also provides a pore comprising at least one construct of the invention. A construct of the invention comprises two or more covalently attached monomers derived from CsgG wherein at least one of the monomers is a mutant monomer of the invention. In other words, a construct must contain more than one monomer. The pore contains sufficient constructs and, if necessary, monomers to form the pore. For instance, an octameric pore may comprise (a) four constructs each comprising two constructs, (b) two constructs each comprising four monomers or (b) one construct comprising two monomers and six monomers that do not form part of a construct. For instance, an nonameric pore may comprise (a) four constructs each comprising two constructs and one monomer that does not form part of a construct, (b) two constructs each comprising four monomers and a monomer that does not form part of a construct or (b) one construct comprising two monomers and seven monomers that do not form part of a construct. Other combinations of constructs and monomers can be envisaged by the skilled person.

At least two of the monomers in the pore are in the form of a construct of the invention. The construct, and hence the pore, comprises at least one mutant monomer of the invention. The pore typically comprises at least 7, at least 8, at least 9 or at least 10 monomers, such as 7, 8, 9 or 10 monomers, in total (at least two of which must be in a construct). The pore preferably comprises eight or nine monomers (at least two of which must be in a construct).

The construct containing pore may be a homo-oligomer (i.e. include identical constructs) or be a hetero-oligomer (i.e. where at least one construct differs from the others).

A pore typically contains (a) one construct comprising two monomers and (b) 5, 6, 7 or 8 monomers. The construct may be any of those discussed above. The monomers may be any of those discussed above, including mutant monomers of the invention, monomers comprising SEQ ID NO: 390, 391, 392, 393, 394, 395, 414, 415, 416, 417, 418, 419, 420, 421, 422, 423, 424, 425, 426, 427, 428 or 429 and mutant monomers comprising a comparative variant of SEQ ID NO: 390, 391, 392, 393, 394, 395, 414, 415, 416, 417, 418, 419, 420, 421, 422, 423, 424, 425, 426, 427, 428 or 429 as discussed above.

Another typical pore comprises more than one construct of the invention, such as two, three or four constructs of the invention. If necessary, such pores further comprise sufficient additional monomers or constructs to form the pore. The additional monomer(s) may be any of those discussed above, including mutant monomers of the invention, monomers comprising SEQ ID NO: 390, 391, 392, 393, 394, 395, 414, 415, 416, 417, 418, 419, 420, 421, 422, 423, 424, 425, 426, 427, 428 or 429 and mutant monomers comprising a comparative variant of SEQ ID NO: 390, 391, 392, 393, 394, 395, 414, 415, 416, 417, 418, 419, 420, 421, 422, 423, 424, 425, 426, 427, 428 or 429 as discussed above. The additional construct(s) may be any of those discussed above or may be a construct comprising two or more covalently attached CsgG monomers each comprising a monomer comprising SEQ ID NO: 390, 391, 392, 393, 394, 395, 414, 415, 416, 417, 418, 419, 420, 421, 422, 423, 424, 425, 426, 427, 428 or 429 or a comparative variant of SEQ ID NO: 390, 391, 392, 393, 394, 395, 414, 415, 416, 417, 418, 419, 420, 421, 422, 423, 424, 425, 426, 427, 428 or 429 as discussed above.

A further pore of the invention comprises only constructs comprising 2 monomers, for example a pore may comprise 4, 5, 6, 7 or 8 constructs comprising 2 monomers. At least one construct is a construct of the invention, i.e. at least one monomer in the at least one construct, and preferably each monomer in the at least one construct, is a mutant monomer of the invention. All of the constructs comprising 2 monomers may be constructs of the invention.

A specific pore according to the invention comprises four constructs of the invention each comprising two monomers, wherein at least one monomer in each construct, and preferably each monomer in each construct, is a mutant monomer of the invention. The constructs may oligomerise into a pore with a structure such that only one monomer of each construct contributes to the channel of the pore. Typically the other monomers of the construct will be on the outside of the channel of the pore.

For example, pores of the invention may comprise 7, 8, 9 or 10 constructs comprising 2 monomers where the channel comprises 7, 8, 9 or 10 monomers.

Mutations can be introduced into the construct as described above. The mutations may be alternating, i.e. the mutations are different for each monomer within a two monomer construct and the constructs are assembled as a homo-oligomer resulting in alternating modifications. In other words, monomers comprising MutA and MutB are fused and assembled to form an A-B:A-B:A-B:A-B pore. Alternatively, the mutations may be neighbouring, i.e. identical mutations are introduced into two monomers in a construct and this is then oligomerised with different mutant monomers or constructs. In other words, monomers comprising MutA are fused follow by oligomerisation with MutB-containing monomers to form A-A:B:B:B:B:B:B.

One or more of the monomers of the invention in a construct-containing pore may be chemically-modified as discussed above.

Analyte Characterisation

The invention provides a method of determining the presence, absence or one or more characteristics of a target analyte. The method involves contacting the target analyte with a CsgG pore or a mutant thereof, such as a pore of the invention, such that the target analyte moves with respect to, such as through, the pore and taking one or more measurements as the analyte moves with respect to the pore and thereby determining the presence, absence or one or more characteristics of the analyte. The target analyte may also be called the template analyte or the analyte of interest.

The method comprises contacting the target analyte with a CsgG pore or a mutant thereof, such as a pore of the invention, such that the target analyte moves through the pore. The pore typically comprises at least 7, at least 8, at least 9 or at least 10 monomers, such as 7, 8, 9 or 10 monomers. The pore preferably comprises eight or nine identical monomers. One or more, such as 2, 3, 4, 5, 6, 7, 8, 9 or 10, of the monomers is preferably chemically modified as discussed above.

The CsgG pore may be derived from any organism. The CsgG pore may comprise monomers comprising the sequence shown in SEQ ID NO: 390, 391, 392, 393, 394, 395, 414, 415, 416, 417, 418, 419, 420, 421, 422, 423, 424, 425, 426, 427, 428 or 429. The CsgG pore may comprise at least 7, at least 8, at least 9 or at least 10 monomers, such as 7, 8, 9 or 10 monomers, each comprising the sequence shown in SEQ ID NO: 390, 391, 392, 393, 394, 395, 414, 415, 416, 417, 418, 419, 420, 421, 422, 423, 424, 425, 426, 427, 428 or 429 (i.e. the pore is a homo-oligomer comprising identical monomers from the same organism). The CsgG may comprise any combination of monomers each comprising a sequence shown in SEQ ID NO: 390, 391, 392, 393, 394, 395, 414, 415, 416, 417, 418, 419, 420, 421, 422, 423, 424, 425, 426, 427, 428 or 429. For instance, the pore may comprise 7 monomers comprising the sequence shown in SEQ ID NO: 390 and two monomers comprising the sequence shown in SEQ ID NO: 391.

The CsgG mutant may comprise any number of mutant monomers, such as at least 7, at least 8, at least 9 or at least 10 monomers, such as 7, 8, 9 or 10 monomers. The mutant monomers may comprise a comparative variant of the sequence shown in SEQ ID NO: 390, 391, 392, 393, 394, 395, 414, 415, 416, 417, 418, 419, 420, 421, 422, 423, 424, 425, 426, 427, 428 or 429. Comparative variants are discussed above. Comparative variants must be capable of forming a pore and may have any of the % homologies discussed above with reference to the pores of the invention.

The CsgG mutant preferably comprises nine monomers and at least one of the monomers is a variant of the sequence shown in SEQ ID NO: 390 comprising (a) mutations at one or more of the following positions N40, Q42, D43, E44, K49, Y51, S54, N55, F56, S57, Q62, E101, N102, E124, E131, R142, D149, T150, E185, R192, D195, E201 and E203, such as mutations at one or more of the following positions N40, Q42, D43, E44, K49, Y51, S54, N55, F56, S57, Q62, E101, N102, E131, D149, T150, E185, D195, E201 and E203 or one or mutations at one or more of the following positions N40, Q42, D43, E44, K49, Y51, N55, F56, E101, N102, E131, D149, T150, E185, D195, E201 and E203; and/or (b) deletion of one or more of the following positions F48, K49, P50, Y51, P52, A53, S54, N55, F56 and S57. The variant may comprise (a); (b); or (a) and (b). In (a), any number and combination of positions N40, Q42, D43, E44, K49, Y51, S54, N55, F56, S57, Q62, E101, N102, R124, E131, R142, D149, E185, R192, D195, E201 and E203 may be mutated. As discussed above, mutating one or more of Y51, N55 and F56 may decrease the number of nucleotides contributing to the current as the polynucleotide moves through the pore and thereby make it easier to identify a direct relationship between the observed current as the polynucleotide moves through the pore and the polynucleotide.

In (b), any number and combination of F48, K49, P50, Y51, P52, A53, S54, N55, F56 and S57 may be deleted. The variant may comprise any of the specific mutations/substitutions or combinations thereof discussed above with reference to the mutant monomers of the invention.

Preferred variants for use in the method of the invention comprise one or more of the following substitutions (a) F56N, F56Q, F56R, F56S, F56G, F56A or F56K or F56A, F56P, F56R, F56H, F56S, F56Q, F56I, F56L, F56T or F56G; (b) N55Q, N55R, N55K, N55S, N55G, N55A or N55T; (c) Y51L, Y51V, Y51A, Y51N, Y51Q, Y51S or Y51G; (d) T150I; (e) S54P; and (f) S57P. The variant may comprise any number and combination of (a) to (f).

Preferred variants for use in the method of the invention comprise Q62R or Q62K.

Preferred variants for use in the method of the invention comprise mutations at D43, E44, Q62 or any combination thereof, such as D43, E44, Q62, D43/E44, D43/Q62, E44/Q62 or D43/E44/Q62.

The variant may comprise a mutation at the following positions:
- Y51, F56, D149, E185, E201 and E203, such as Y51N, F56A, D149N, E185R, E201N and E203N;
- N55, such as N55A or N55S;
- Y51, such as Y51N or Y51T;
- S54, such as S54P;
- S57, such as S57P;
- F56, such as F56N, F56Q, F56R, F56S, F56G, F56A or F56K or F56A, F56P, F56R, F56H, F56S, F56Q, F56I, F56L, F56T or F56G;
- Y51 and F56, such as Y51A and F56A, Y51A and F56N, Y51I and F56A, Y51L and F56A, Y51T and F56A, Y51T and F56Q, Y51I and F56N, Y51L and F56N or Y51T and F56N, preferably, Y51I and F56A, Y51L and F56A or Y51T and F56A, more preferably Y51T and F56Q or more preferably Y51X and F56Q, wherein X is any amino acid;
- N55 and F56, such as N55X and F56Q, wherein X is any amino acid;
- Y51, N55 and F56, such as Y51A, N55S and F56A, Y51A, N55S and F56N or Y51T, N55S and F56Q;
- S54 and F56, such as S54P and F56A or S54P and F56N;
- F56 and S57, such as F56A and S57P or F56N and S57P;
- D149, E185 and E203, such as D149N, E185N and E203N;
- D149, E185, E201 and E203, such as D149N, E185N, E201N and E203N;
- D149, E185, D195, E201 and E203, such as D149N, E185R, D195N, E201N and E203N or D149N, E185R, D195N, E201R and E203N;
- F56 and N102, such as F56Q and N102R;
- (a) Q62, such as Q62R or Q62K, and (b) one or more of Y51, N55 and F56, such as at Y51, N55, F56, Y51/N55, Y51/F56, N55/F56 or Y51/N55/F56, such as Y51T/F56Q/Q62R;
- (i) D43, E44, Q62 or any combination thereof, such as D43, E44, Q62, D43/E44, D43/Q62, E44/Q62 or D43/E44/Q62 and (ii) one or more of Y51, N55 and F56, such as at Y51, N55, F56, Y51/N55, Y51/F56, N55/F56 or Y51/N55/F56, such as D43N/Y51T/F56Q, E44N/Y51T/F56Q, D43N/E44N/Y51T/F56Q, D43N/Y51T/F56Q/Q62R, E44N/Y51T/F56Q/Q62R or D43N/E44N/Y51T/F56Q/Q62R; or
- T150, such as T150I.

Preferred pores for use in the method of the invention comprise at least 7, at least 8, at least 9 or at least 10 monomers, such as 7, 8, 9 or 10 monomers, each of which comprises a variant of SEQ ID NO: 390 which comprises one or more of the following substitutions (a) F56N, F56Q, F56R, F56S, F56G, F56A or F56K or F56A, F56P, F56R, F56H, F56S, F56Q, F56I, F56L, F56T or F56G; (b) N55Q, N55R, N55K, N55S, N55G, N55A or N55T; (c) Y51L, Y51V, Y51A, Y51N, Y51Q, Y51S or Y51G; (d) T150I; (e) S54P; and (f) S57P. The variants may comprise any number and combination of (a) to (f). The monomers are preferably identical in these preferred pores.

Preferred pores for use in the method of the invention comprise at least 7, at least 8, at least 9 or at least 10 monomers, such as 7, 8, 9 or 10 monomers, each of which comprises a variant of SEQ ID NO: 390 which comprises:
- Y51N, F56A, D149N, E185R, E201N and E203N;
- N55A;
- N55S;
- Y51N;
- S54P;
- S57P;
- F56N, F56Q, F56R, F56S, F56G, F56A or F56K;
- F56A, F56P, F56R, F56H, F56S, F56Q, F56I, F56L, F56T or F56G;
- Y51A and F56A;
- Y51A and F56N;
- Y51I and F56A;
- Y51 L and F56A;
- Y51T and F56A;
- Y51T and F56Q;
- Y51I and F56N;
- Y51 L and F56N;
- Y51T and F56N;
- N55S and F56Q;
- Y51A, N55S and F56A;
- Y51A, N55S and F56N;
- Y51T, N55S and F56Q;
- S54P and F56A;
- S54P and F56N;
- F56A and S57P;
- F56N and S57P;
- D149N, E185N and E203N;
- D149N, E185N, E201N and E203N;
- D149N, E185R, D195N, E201N and E203N;
- D149N, E185R, D195N, E201R and E203N;
- T150I;
- F56Q and N102R;
- F56 and N102, such as F56Q and N102R;
- Y51T/F56Q/Q62R;
- D43N/Y51T/F56Q;
- E44N/Y51T/F56Q;
- D43N/E44N/Y51T/F56Q
- D43N/Y51T/F56Q/Q62R;
- E44N/Y51T/F56Q/Q62R; or
- D43N/E44N/Y51T/F56Q/Q62R.

The CsgG mutant for use in the method of the invention preferably comprises nine monomers and at least one of the monomers is a variant of the sequence shown in SEQ ID NO: 390 comprising a mutation at one or more of positions Y51, N55 and F56. Preferred pores for use in the method of the invention comprise at least 7, at least 8, at least 9 or at least 10 monomers, such as 7, 8, 9 or 10 monomers, each of which comprises a variant of SEQ ID NO: 390 comprising a mutation at one or more of positions Y51, N55 and F56. The monomers are preferably identical in these preferred pores. The variant may comprise a mutation at Y51; N55; F56; Y51/N55; Y51/F56; N55/F56; or Y51/N55/F56. The variant may comprise any of the specific mutations at one or more of positions Y51, N55 and F56 discussed above and in any combination. One or more Y51, N55 and F56 may be substituted with any amino acid. Y51 may be substituted with F, M, L, I, V, A, P, G, C, Q, N, T, S, E, D, K, H or R, such as A, S, T, N or Q. N55 may be substituted with F, M, L, I, V, A, P, G, C, Q, T, S, E, D, K, H or R, such as A, S, T or Q. F56 may be substituted with M, L, I, V, A, P, G, C, Q, N, T, S, E, D, K, H or R, such as A, S, T, N or Q. The variant may further comprise one or more of the following: (i) one or more mutations at the following positions (i.e.

mutations at one or more of the following positions) (i) N40, D43, E44, S54, S57, Q62, R97, E101, E124, E131, R142, T150 and R192; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any of the combinations of (i) and (iii) to (xi) discussed above. The variant may comprise any of the embodiments discussed above for (i) and (iii) to (xi).

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise: Y51R/F56Q, Y51N/F56N, Y51M/F56Q, Y51L/F56Q, Y51I/F56Q, Y51V/F56Q, Y51A/F56Q, Y51P/F56Q, Y51G/F56Q, Y51C/F56Q, Y51Q/F56Q, Y51N/F56Q, Y51S/F56Q, Y51E/F56Q, Y51D/F56Q, Y51K/F56Q or Y51H/F56Q.

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise: Y51T/F56Q, Y51Q/F56Q or Y51A/F56Q.

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise: Y51T/F56F, Y51T/F56M, Y51T/F56L, Y51T/F56I, Y51T/F56V, Y51T/F56A, Y51T/F56P, Y51T/F56G, Y51T/F56C, Y51T/F56Q, Y51T/F56N, Y51T/F56T, Y51T/F56S, Y51T/F56E, Y51T/F56D, Y51T/F56K, Y51T/F56H or Y51T/F56R.

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise: Y51T/N55Q, Y51T/N55S or Y51T/N55A.

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise: Y51A/F56F, Y51A/F56L, Y51A/F56I, Y51A/F56V, Y51A/F56A, Y51A/F56P, Y51A/F56G, Y51A/F56C, Y51A/F56Q, Y51A/F56N, Y51A/F56T, Y51A/F56S, Y51A/F56E, Y51A/F56D, Y51A/F56K, Y51A/F56H or Y51A/F56R.

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise: Y51C/F56A, Y51E/F56A, Y51D/F56A, Y51K/F56A, Y51H/F56A, Y51Q/F56A, Y51N/F56A, Y51S/F56A, Y51P/F56A or Y51V/F56A.

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise:
D149R/E185R/E201R/E203R or Y51T/F56Q/D149R/E185R/E201R/E203R;
D149N/E185N/E201N/E203N or Y51T/F56Q/D149N/E185N/E201N/E203N;
E201R/E203R or Y51T/F56Q/E201R/E203R
E201N/E203R or Y51T/F56Q/E201N/E203R;
E203R or Y51T/F56Q/E203R;
E203N or Y51T/F56Q/E203N;
E201R or Y51T/F56Q/E201R;
E201N or Y51T/F56Q/E201N;
E185R or Y51T/F56Q/E185R;
E185N or Y51T/F56Q/E185N;
D149R or Y51T/F56Q/D149R;
D149N or Y51T/F56Q/D149N;
R142E or Y51T/F56Q/R142E;
R142N or Y51T/F56Q/R142N;
R192E or Y51T/F56Q/R192E; or
R192N or Y51T/F56Q/R192N.

(1) Preferred variants for use in the method of the invention comprise or (2) preferred pores for use in the method of the invention comprise at least 7, at least 8, at least 9 or at least 10 monomers, such as 7, 8, 9 or 10 monomers, each of which comprises a variant of SEQ ID NO: 390 which comprise:
Y51A/F56Q/E101N/N102R;
Y51A/F56Q/R97N/N102G;
Y51A/F56Q/R97N/N102R;
Y51A/F56Q/R97N;
Y51A/F56Q/R97G;
Y51A/F56Q/R97L;
Y51A/F56Q/N102R;
Y51A/F56Q/N102F;
Y51A/F56Q/N102G;
Y51A/F56Q/E101R;
Y51A/F56Q/E101F;
Y51A/F56Q/E101N; or
Y51A/F56Q/E101G.

The monomers are preferably identical in these preferred pores.

Preferred pores for use in the method of the invention comprise at least 7, at least 8, at least 9 or at least 10 monomers, such as 7, 8, 9 or 10 monomers, each of which comprises a variant of SEQ ID NO: 390 which comprises F56A, F56P, F56R, F56H, F56S, F56Q, F56I, F56L, F56T or F56G. The monomers are preferably identical in these preferred pores.

The CsgG mutant may comprise any of the variants of SEQ ID NO: 390 disclosed in the Examples or may be any of the pores disclosed in the Examples.

The CsgG mutant is most preferably a pore of the invention.

Steps (a) and (b) are preferably carried out with a potential applied across the pore. As discussed in more detail below, the applied potential typically results in the formation of a complex between the pore and a polynucleotide binding protein. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The method is for determining the presence, absence or one or more characteristics of a target analyte. The method may be for determining the presence, absence or one or more characteristics of at least one analyte. The method may concern determining the presence, absence or one or more characteristics of two or more analytes. The method may comprise determining the presence, absence or one or more characteristics of any number of analytes, such as 2, 5, 10, 15, 20, 30, 40, 50, 100 or more analytes. Any number of characteristics of the one or more analytes may be determined, such as 1, 2, 3, 4, 5, 10 or more characteristics.

The target analyte is preferably a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The method may concern determining the presence, absence or one or more characteristics of two or more analytes of the same type, such as two or more proteins, two or more nucleotides or two or more pharmaceuticals. Alternatively, the method may concern determining the presence, absence or one or more characteristics of two or more analytes of different types, such as one or more proteins, one or more nucleotides and one or more pharmaceuticals.

The target analyte can be secreted from cells. Alternatively, the target analyte can be an analyte that is present inside cells such that the analyte must be extracted from the cells before the invention can be carried out.

The analyte is preferably an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. For the purposes of the invention, it is to be understood that the target analyte can be modified by any method available in the art.

The protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-γ, and other cytokines such as TNF-α. The protein may be a bacterial protein, a fungal protein, a virus protein or a parasite-derived protein.

The target analyte is preferably a nucleotide, an oligonucleotide or a polynucleotide.

Nucleotides and polynucleotides are discussed below. Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed below, including the abasic and modified nucleotides.

The target analyte, such as a target polynucleotide, may be present in any of the suitable samples discussed below.

The pore is typically present in a membrane as discussed below. The target analyte may be coupled or delivered to the membrane using of the methods discussed below.

Any of the measurements discussed below can be used to determine the presence, absence or one or more characteristics of the target analyte. The method preferably comprises contacting the target analyte with the pore such that the analyte moves with respect to, such as moves through, the pore and measuring the current passing through the pore as the analyte moves with respect to the pore and thereby determining the presence, absence or one or more characteristics of the analyte.

The target analyte is present if the current flows through the pore in a manner specific for the analyte (i.e. if a distinctive current associated with the analyte is detected flowing through the pore). The analyte is absent if the current does not flow through the pore in a manner specific for the nucleotide. Control experiments can be carried out in the presence of the analyte to determine the way in which if affects the current flowing through the pore.

The invention can be used to differentiate analytes of similar structure on the basis of the different effects they have on the current passing through a pore. Individual analytes can be identified at the single molecule level from their current amplitude when they interact with the pore. The invention can also be used to determine whether or not a particular analyte is present in a sample. The invention can also be used to measure the concentration of a particular analyte in a sample. Analyte characterisation using pores other than CsgG is known in the art.

Polynucleotide Characterisation

The invention provides a method of characterising a target polynucleotide, such as sequencing a polynucleotide. There are two main strategies for characterising or sequencing polynucleotides using nanopores, namely strand characterisation/sequencing and exonuclease characterisation/sequencing. The method of the invention may concern either method.

In strand sequencing, the DNA is translocated through the nanopore either with or against an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In one embodiment, the method of characterising a target polynucleotide involves contacting the target sequence with a pore and a helicase enzyme. Any helicase may be used in the method. Suitable helicases are discussed below. Helicases may work in two modes with respect to the pore. First, the method is preferably carried out using a helicase such that it controls movement of the target sequence through the pore with the field resulting from the applied voltage. In this mode the 5' end of the DNA is first captured in the pore, and the enzyme controls movement of the DNA into the pore such that the target sequence is passed through the pore with the field until it finally translocates through to the trans side of the bilayer. Alternatively, the method is preferably carried out such that a helicase enzyme controls movement of the target sequence through the pore against the field resulting from the applied voltage. In this mode the 3' end of the DNA is first captured in the pore, and the enzyme controls movement of the DNA through the pore such that the target sequence is pulled out of the pore against the applied field until finally ejected back to the cis side of the bilayer.

In exonuclease sequencing, an exonuclease releases individual nucleotides from one end of the target polynucleotide and these individual nucleotides are identified as discussed below. In another embodiment, the method of characterising a target polynucleotide involves contacting the target sequence with a pore and an exonuclease enzyme. Any of the exonuclease enzymes discussed below may be used in the method. The enzyme may be covalently attached to the pore as discussed below.

Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves contacting the polynucleotide with the exonuclease so that the nucleotides are digested from the end of the polynucleotide at a rate that allows characterisation or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of the invention involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

In the strand characterisation embodiment, the method comprises contacting the polynucleotide with a CsgG pore or mutant thereof, such as a pore of the invention, such that the polynucleotide moves with respect to, such as through, the pore and taking one or more measurements as the polynucleotide moves with respect to the pore, wherein the measurements are indicative of one or more characteristics of the polynucleotide, and thereby characterising the target polynucleotide.

In the exonucleotide characterisation embodiment, the method comprises contacting the polynucleotide with a CsgG pore or mutant thereof, such as a pore of the invention, and an exonucleoase such that the exonuclease digests individual nucleotides from one end of the target polynucleotide and the individual nucleotides move with respect to, such as through, the pore and taking one or more measurements as the individual nucleotides move with respect to the pore, wherein the measurements are indicative of one or more characteristics of the individual nucleotides, and thereby characterising the target polynucleotide.

An individual nucleotide is a single nucleotide. An individual nucleotide is one which is not bound to another nucleotide or polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand. The nucleotide can be any of those discussed below.

The individual nucleotides may interact with the pore in any manner and at any site. The nucleotides preferably reversibly bind to the pore via or in conjunction with an adaptor as discussed above. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane.

During the interaction between the individual nucleotide and the pore, the nucleotide typically affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample. The ratio of different nucleotides within a sample can also be calculated. For instance, the ratio of dCMP to methyl-dCMP can be calculated.

The method involves measuring one or more characteristics of the target polynucleotide. The target polynucleotide may also be called the template polynucleotide or the polynucleotide of interest.

This embodiment also uses a CsgG pore or mutant thereof, such as a pore of the invention. Any of the pores and embodiments discussed above with reference to the target analyte may be used.

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety. Bridged nucleic acids (BNAs) are modified RNA nucleotides. They may also be called constrained or inaccessible RNA. BNA monomers can contain a five-membered, six-membered or even a seven-membered bridged structure with a "fixed" C3'-endo sugar puckering. The bridge is synthetically incorporated at the 2',4'-position of the ribose to produce a 2',4'-BNA monomer.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated. For instance, the method of the invention may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

Sample

The polynucleotide is typically present in any suitable sample. The invention is typically carried out on a sample that is known to contain or suspected to contain the polynucleotide. Alternatively, the invention may be carried out on a sample to confirm the identity of a polynucleotide whose presence in the sample is known or expected.

The sample may be a biological sample. The invention may be carried out in vitro using a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum.

Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The may be measured immediately upon being taken. The sample may also be typically stored prior to assay, preferably below −70° C.

Characterisation

The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,iii}, {ii,iii}, {ii,iv}, {iii,iv}, {iii,v}, {iv,v}, {i,ii,iii}, {i,ii,v}, {i,iii,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The target polynucleotide is contacted with a CsgG pore or mutant thereof, such as a pore of the invention. The pore is typically present in a membrane. Suitable membranes are discussed below. The method may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in International Application No. PCT/GB08/000562 (WO 2008/102120).

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85), and FET measurements (International Application WO 2005/124888). Optical measurements may be combined with electrical measurements (Sony G V et al., Rev Sci Instrum. 2010 January; 81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et at, J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The method may involve measuring the current passing through the pore as the polynucleotide moves with respect to the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The method is typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Polynucleotide Binding Protein

The strand characterisation method preferably comprises contacting the polynucleotide with a polynucleotide binding protein such that the protein controls the movement of the polynucleotide with respect to, such as through, the pore.

More preferably, the method comprises (a) contacting the polynucleotide with a CsgG pore or mutant thereof, such as a pore of the invention, and a polynucleotide binding protein such that the protein controls the movement of the polynucleotide with respect to, such as through, the pore and (b) taking one or more measurements as the polynucleotide moves with respect to the pore, wherein the measurements are indicative of one or more characteristics of the polynucleotide, and thereby characterising the polynucleotide.

More preferably, the method comprises (a) contacting the polynucleotide with a CsgG pore or mutant thereof, such as a pore of the invention, and a polynucleotide binding protein such that the protein controls the movement of the polynucleotide with respect to, such as through, the pore and (b) measuring the current through the pore as the polynucleotide moves with respect to the pore, wherein the current is indicative of one or more characteristics of the polynucleotide, and thereby characterising the polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The protein may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 399), exonuclease III enzyme from *E. coli* (SEQ ID NO: 401), RecJ from *T. thermophilus* (SEQ ID NO: 403) and bacteriophage lambda exonuclease (SEQ ID NO: 405), TatD exonuclease and variants thereof. Three subunits comprising the sequence shown in SEQ ID NO: 403 or a variant thereof interact to form a trimer exonuclease. These exonucleases can also be used in the exonuclease method of the invention. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 397) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 406), Hel308 Csy (SEQ ID NO: 407), Hel308 Tga (SEQ ID NO: 408), Hel308 Mhu (SEQ ID NO: 409), TraI Eco (SEQ ID NO: 410), XPD Mbu (SEQ ID NO: 411) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736.

The helicase preferably comprises the sequence shown in SEQ ID NO: 413 (Trwc Cba) or as variant thereof, the sequence shown in SEQ ID NO: 406 (Hel308 Mbu) or a variant thereof or the sequence shown in SEQ ID NO: 412 (Dda) or a variant thereof. Variants may differ from the native sequences in any of the ways discussed below for transmembrane pores. A preferred variant of SEQ ID NO: 412 comprises (a) E94C and A360C or (b) E94C, A360C, C109A and C136A and then optionally (ΔM1)G1G2 (i.e. deletion of M1 and then addition G1 and G2).

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NOs: 397, 399, 401, 403, 405, 406, 407, 408, 409, 410, 411, 412 or 413 is an enzyme that has an amino acid sequence which varies from that of SEQ ID NO: 397, 399, 401, 403, 405, 406, 407, 408, 409, 410, 411, 412 or 413 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 397, 399, 401, 403, 405, 406, 407, 408, 409, 410, 411, 412 or 413, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 397, 399, 401, 403, 405, 406, 407, 408, 409, 410, 411, 412 or 413 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 390 above. The enzyme may be covalently attached to the pore. Any method may be used to covalently attach the enzyme to the pore.

A preferred molecular brake is TrwC Cba-Q594A (SEQ ID NO: 413 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises:
(a) providing the polynucleotide with one or more helicases and one or more molecular brakes attached to the polynucleotide;
(b) contacting the polynucleotide with a CsgG pore or mutant thereof, such as a pore of the invention, and applying a potential across the pore such that the one or more helicases and the one or more molecular brakes are brought together and both control the movement of the polynucleotide with respect to, such as through, the pore;
(c) taking one or more measurements as the polynucleotide moves with respect to the pore wherein the measurements are indicative of one or more characteristics of the polynucleotide and thereby characterising the polynucleotide.

This type of method is discussed in detail in the International Application PCT/GB2014/052737

The one or more helicases may be any of those discussed above. The one or more molecular brakes may be any compound or molecule which binds to the polynucleotide and slows the movement of the polynucleotide through the pore. The one or more molecular brakes preferably comprise one or more compounds which bind to the polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-monoamino-β-cyclodextrin ($am_1$-□CD) or heptakis-(6-deoxy-6-guanidino)-cyclodextrin ($gu_7$-βCD).

The one or more molecular brakes are preferably one or more single stranded binding proteins (SSB). The one or more molecular brakes are more preferably a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably one of the SSBs disclosed in International Application No. PCT/GB2013/051924 (published as WO 2014/013259).

The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 396) which act as molecular brakes are disclosed in U.S. Pat. No. 5,576,204. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are be used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucleotide binding domain through which in at least one conformational state the polynucleotide can unbind from the helicase. This is disclosed in WO 2014/013260.

Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

If the one or more helicases are used in the active mode (i.e. when the one or more helicases are provided with all the necessary components to facilitate movement, e.g. ATP and $Mg^{2+}$), the one or more molecular brakes are preferably (a) used in an inactive mode (i.e. are used in the absence of the necessary components to facilitate movement or are incapable of active movement), (b) used in an active mode where the one or more molecular brakes move in the opposite direction to the one or more helicases or (c) used in an active mode where the one or more molecular brakes move in the same direction as the one or more helicases and more slowly than the one or more helicases.

If the one or more helicases are used in the inactive mode (i.e. when the one or more helicases are not provided with all the necessary components to facilitate movement, e.g. ATP and $Mg^{2+}$ or are incapable of active movement), the one or more molecular brakes are preferably (a) used in an inactive mode (i.e. are used in the absence of the necessary components to facilitate movement or are incapable of active movement) or (b) used in an active mode where the one or more molecular brakes move along the polynucleotide in the same direction as the polynucleotide through the pore.

The one or more helicases and one or more molecular brakes may be attached to the polynucleotide at any positions so that they are brought together and both control the movement of the polynucleotide through the pore. The one or more helicases and one or more molecular brakes are at least one nucleotide apart, such as at least 5, at least 10, at least 50, at least 100, at least 500, at least 1000, at least 5000, at least 10,000, at least 50,000 nucleotides or more apart. If the method concerns characterising a double stranded polynucleotide provided with a Y adaptor at one end and a hairpin loop adaptor at the other end, the one or more helicases are preferably attached to the Y adaptor and the one or more molecular brakes are preferably attached to the hairpin loop adaptor. In this embodiment, the one or more molecular brakes are preferably one or more helicases that are modified such that they bind the polynucleotide but do not function as a helicase. The one or more helicases attached to the Y adaptor are preferably stalled at a spacer as discussed in more detail below. The one or more molecular brakes attach to the hairpin loop adaptor are preferably not stalled at a spacer. The one or more helicases and the one or more molecular brakes are preferably brought together when the one or more helicases reach the hairpin loop. The one or more helicases may be attached to the Y adaptor before the Y adaptor is attached to the polynucleotide or after the Y adaptor is attached to the polynucleotide. The one or more molecular brakes may be attached to the hairpin loop adaptor before the hairpin loop adaptor is attached to the polynucleotide or after the hairpin loop adaptor is attached to the polynucleotide.

The one or more helicases and the one or more molecular brakes are preferably not attached to one another. The one or more helicases and the one or more molecular brakes are more preferably not covalently attached to one another. The one or more helicases and the one or more molecular brakes are preferably not attached as described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

Spacers

The one or more helicases may be stalled at one or more spacers as discussed in International Application No. PCT/GB2014/050175. Any configuration of one or more helicases and one or more spacers disclosed in the International Application may be used in this invention.

When a part of the polynucleotide enters the pore and moves through the pore along the field resulting from the applied potential, the one or more helicases are moved past the spacer by the pore as the polynucleotide moves through the pore. This is because the polynucleotide (including the one or more spacers) moves through the pore and the one or more helicases remain on top of the pore.

The one or more spacers are preferably part of the polynucleotide, for instance they interrupt(s) the polynucleotide sequence. The one or more spacers are preferably not part of one or more blocking molecules, such as speed bumps, hybridised to the polynucleotide.

There may be any number of spacers in the polynucleotide, such as 1, 2, 3, 4, 5, 6, 7, 8, 9, 10 or more spacers. There are preferably two, four or six spacers in the polynucleotide. There may be one or more spacers in different regions of the polynucleotide, such as one or more spacers in the Y adaptor and/or hairpin loop adaptor.

The one or more spacers each provides an energy barrier which the one or more helicases cannot overcome even in the active mode. The one or more spacers may stall the one or more helicases by reducing the traction of the helicase (for instance by removing the bases from the nucleotides in the polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the polynucleotide. It is straightforward to determine whether or not the one or more helicases are stalled at one or more spacers in the absence of a transmembrane pore and an applied potential. For instance, the ability of a helicase to move past a spacer and displace a complementary strand of DNA can be measured by PAGE.

The one or more spacers typically comprise a linear molecule, such as a polymer. The one or more spacers typically have a different structure from the polynucleotide. For instance, if the polynucleotide is DNA, the one or more spacers are typically not DNA. In particular, if the polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA) or a synthetic polymer with nucleotide side chains. The one or more spacers may comprise one or more nucleotides in the opposite direction from the polynucleotide. For instance, the one or more spacers may comprise one or more nucleotides in the 3' to 5' direction when the polynucleotide is in the 5' to 3' direction. The nucleotides may be any of those discussed above.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies®).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSp18 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

The one or more helicases may be stalled by (i.e. before) or on each linear molecule spacers. If linear molecule spacers are used, the polynucleotide is preferably provided with a double stranded region of polynucleotide adjacent to the end of each spacer past which the one or more helicases are to be moved. The double stranded region typically helps to stall the one or more helicases on the adjacent spacer. The presence of the double stranded region(s) is particularly preferred if the method is carried out at a salt concentration of about 100 mM or lower. Each double stranded region is typically at least 10, such as at least 12, nucleotides in length. If the polynucleotide used in the invention is single stranded, a double stranded region may be formed by hybridising a shorter polynucleotide to a region adjacent to a spacer. The shorter polynucleotide is typically formed from the same nucleotides as the polynucleotide, but may be formed from different nucleotides. For instance, the shorter polynucleotide may be formed from LNA.

If linear molecule spacers are used, the polynucleotide is preferably provided with a blocking molecule at the end of each spacer opposite to the end past which the one or more helicases are to be moved. This can help to ensure that the one or more helicases remain stalled on each spacer. It may also help retain the one or more helicases on the polynucleotide in the case that it/they diffuse(s) off in solution. The blocking molecule may be any of the chemical groups discussed below which physically cause the one or more helicases to stall. The blocking molecule may be a double stranded region of polynucleotide.

The one or more spacers preferably comprise one or more chemical groups which physically cause the one or more helicases to stall. The one or more chemical groups are preferably one or more pendant chemical groups. The one or more chemical groups may be attached to one or more nucleobases in the polynucleotide. The one or more chemical groups may be attached to the polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzyl-cyclooctyne groups.

Different spacers in the polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more abasics and a fluorophore.

Suitable spacers can be designed depending on the type of polynucleotide and the conditions under which the method of the invention is carried out. Most helicases bind and move along DNA and so may be stalled using anything that is not DNA. Suitable molecules are discussed above.

The method of the invention is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the method of the invention is carried out in the presence of free nucleotides and a helicase cofactor as discussed below (such that the one of more helicases are in the active mode), one or more longer spacers are typically used to ensure that the one or more helicases are stalled on the polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method of the invention, the shorter the one or more spacers that are typically used and vice versa.

Preferred combinations of features are shown in Table 3 below.

TABLE 3

| Polynucleotide | Spacer composition* | Spacer length (i.e. number of *) | Salt [ ] | Free nucleotides? | Helicase cofactor? |
| --- | --- | --- | --- | --- | --- |
| DNA | iSpC3 | 4 | 1M | Yes | Yes |
| DNA | iSp18 | 4 | 100-1000 mM | Yes | Yes |

TABLE 3-continued

| Polynucleotide | Spacer composition* | Spacer length (i.e. number of *) | Salt [ ] | Free nucleotides? | Helicase cofactor? |
|---|---|---|---|---|---|
| DNA | iSp18 | 6 | <100-1000 mM | Yes | Yes |
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

The method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 3 above may be increased 1.5 fold, 2 fold, 2.5 fold or 3 fold.

Membrane

The pore of the invention may be present in a membrane. In the methods of the invention, the polynucleotide is typically contacted with the CsgG pore or mutant thereof, such as a pore of the invention, in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. PCT/GB2013/052766 or PCT/GB2013/052767.

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s-1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In another preferred embodiment, the membrane comprises a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647). If the membrane comprises a solid state layer, the pore is typically present in an amphiphilic membrane or layer contained within the solid state layer, for instance within a hole, well, gap, channel, trench or slit within the solid state layer. The skilled person can prepare suitable solid state/amphiphilic hybrid systems. Suitable systems are disclosed in WO 2009/020682 and WO 2012/005857. Any of the amphiphilic membranes or layers discussed above may be used.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Coupling

The polynucleotide is preferably coupled to the membrane comprising the pore. The method may comprise coupling the polynucleotide to the membrane comprising the pore. The polynucleotide is preferably coupled to the membrane using one or more anchors. The polynucleotide may be coupled to the membrane using any known method.

Each anchor comprises a group which couples (or binds) to the polynucleotide and a group which couples (or binds) to the membrane. Each anchor may covalently couple (or bind) to the polynucleotide and/or the membrane. If a Y adaptor and/or a hairpin loop adaptors are used, the polynucleotide is preferably coupled to the membrane using the adaptor(s).

The polynucleotide may be coupled to the membrane using any number of anchors, such as 2, 3, 4 or more anchors. For instance, a polynucleotide may be coupled to the membrane using two anchors each of which separately couples (or binds) to both the polynucleotide and membrane.

The one or more anchors may comprise the one or more helicases and/or the one or more molecular brakes.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut to broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane or may be used to couple (or bind) to the polynucleotide. This is discussed in more detail below.

Crosslinkage of polynucleotides can be avoided using a "lock and key" arrangement. Only one end of each linker may react together to form a longer linker and the other ends of the linker each react with the polynucleotide or membrane respectively. Such linkers are described in International Application No. PCT/GB10/000132 (published as WO 2010/086602).

The use of a linker is preferred in the sequencing embodiments discussed below. If a polynucleotide is permanently coupled directly to the membrane in the sense that it does not uncouple when interacting with the pore (i.e. does not uncouple in step (b) or (e)), then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

For certain applications, such as aptamer detection, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 4 below.

TABLE 4

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." Anal Biochem 169(2): 376-82). Streptavidin/biotin and/or streptavidin/desthiobiotin coupling may be used for any other polynucleotide. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the polynucleotide to the membrane via hybridisation. Hybridisation in the one or more anchors allows coupling in a transient manner as discussed above. The hybridisation may be present in any part of the one or more anchors, such as between the one or more anchors and the polynucleotide, within the one or more anchors or between the one or more anchors and the membrane. For instance, a linker may comprise two or more polynucleotides, such as 3, 4 or 5 polynucleotides, hybridised together. The one or more anchors may hybridise to the polynucleotide. The one or more anchors may hybridise directly to the polynucleotide or directly to a Y adaptor and/or leader sequence attached to the polynucleotide or directly to a hairpin loop adaptor attached to the polynucleotide (as discussed below). Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a hairpin loop adaptor attached to the polynucleotide (as discussed below).

The one or more anchors may comprise a single stranded or double stranded polynucleotide. One part of the anchor may be ligated to a single stranded or double stranded polynucleotide. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the a double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalising the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-0'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2,6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before contacting with the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein), Ni-NTA (for binding to poly-histidine or poly-histidine tagged proteins) or a peptides (such as an antigen).

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Double Stranded Polynucleotide

The polynucleotide may be double stranded. If the polynucleotide is double stranded, the method preferably further comprises before the contacting step ligating a bridging moiety, such as a hairpin loop, to one end of the polynucleotide. The two strands of the polynucleotide may then be separated as or before the polynucleotide is contacted with the pore in accordance with the invention. The two strands may be separated as the polynucleotide movement through the pore is controlled by a polynucleotide binding protein, such as a helicase, or molecular brake.

Linking and interrogating both strands on a double stranded construct in this way increases the efficiency and accuracy of characterisation.

The bridging moiety is capable of linking the two strands of the target polynucleotide. The bridging moiety typically covalently links the two strands of the target polynucleotide. The bridging moiety can be anything that is capable of linking the two strands of the target polynucleotide, provided that the bridging moiety does not interfere with movement of the single stranded polynucleotide through the transmembrane pore.

The bridging moiety may be linked to the target polynucleotide by any suitable means known in the art. The bridging moiety may be synthesised separately and chemically attached or enzymatically ligated to the target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the target polynucleotide Suitable bridging moieties include, but are not limited to a polymeric linker, a chemical linker, a polynucleotide or a polypeptide. Preferably, the bridging moiety comprises DNA, RNA, modified DNA (such as abasic DNA), RNA, PNA, LNA or PEG. The bridging moiety is more preferably DNA or RNA.

The bridging moiety is most preferably a hairpin loop or a hairpin loop adaptor. Suitable hairpin adaptors can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin adaptor may be ligated to either end of the first and/or second polynucleotide, i.e. the 5' or the 3' end. The hairpin adaptor may be ligated to the first and/or second polynucleotide using any method known in the art. The hairpin adaptor may be ligated using a ligase, such as T4 DNA ligase, E. coli DNA ligase, Taq DNA ligase, Tma DNA ligase and 9° N DNA ligase.

The two strands of the polynucleotide may be separated using any method known in the art. For instance, they may be separated by a polynucleotide binding protein or using conditions which favour dehybridisation (examples of conditions which favour dehybridisation include, but are not limited to, high temperature, high pH and the addition of agents that can disrupt hydrogen bonding or base pairing, such as formamide and urea).

The hairpin adaptor preferably comprises a selectable binding moiety. This allows the first and/or second polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin adaptor and/or the selectable binding moiety may comprise a region that can be cut, nicked, cleaved or hydrolysed. Such a region can be designed to allow the first and/or second polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The double stranded target polynucleotide preferably comprises a leader sequence at the opposite end of the bridging moiety, such as a hairpin loop or hairpin loop adaptor. Leader sequences are discussed in more detail below.

Round the Corner Sequencing

In a preferred embodiment, a target double stranded polynucleotide is provided with a bridging moiety, such as a hairpin loop or hairpin loop adaptor, at one end and the method comprises contacting the polynucleotide with the pore such that both strands of the polynucleotide move through the pore and taking one or more measurements as the both strands of the polynucleotide move with respect to the pore wherein the measurements are indicative of one or more characteristics of the strands of the polynucleotide and thereby characterising the target double stranded polynucleotide. In another preferred embodiment, a target double stranded polynucleotide is provided with a bridging moiety, such as a hairpin loop or hairpin loop adaptor, at one end and the method comprises contacting the polynucleotide with the pore and exonuclease such that both strands of the polynucleotide are digested to form individual nucleotides. Any of the embodiments discussed above equally apply to this embodiment.

Leader Sequence

Before the contacting step in the strand characterisation/sequencing method, the method preferably comprises attaching to the polynucleotide a leader sequence which preferentially threads into the pore. The leader sequence facilitates the method of the invention. The leader sequence is designed to preferentially thread into the pore and thereby facilitate the movement of polynucleotide through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The leader sequence is preferably part of a Y adaptor as defined below.

Double Coupling

The method of the invention may involve double coupling of a double stranded polynucleotide. In a preferred embodiment, the method of the invention comprises:

(a) providing the double stranded polynucleotide with a Y adaptor at one end and a bridging moiety adaptor, such as a hairpin loop adaptor, at the other end, wherein the Y adaptor comprises one or more first anchors for coupling the polynucleotide to the membrane, wherein the bridging moiety adaptor comprises one or more second anchors for coupling the polynucleotide to the membrane and wherein the strength of coupling of the bridging moiety adaptor to the membrane is greater than the strength of coupling of the Y adaptor to the membrane;

(b) contacting the polynucleotide provided in step (a) with a CsgG pore or mutant thereof, such as a pore the invention, such that the polynucleotide moves with respect to, such as through, the pore; and (c) taking one or more measurements as the polynucleotide moves with respect to the pore, wherein the measurements are indicative of one or more characteristics of the polynucleotide, and thereby characterising the target polynucleotide.

This type of method is discussed in detail in the UK Application No. 1406147.7.

The double stranded polynucleotide is provided with a Y adaptor at one end and a bridging moiety adaptor at the other end. The Y adaptor and/or the bridging moiety adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail above.

The Y adaptor preferably comprises a leader sequence which preferentially threads into the pore. This is discussed above.

The bridging moiety adaptor preferably comprises a selectable binding moiety as discussed above. The bridging moiety adaptor and/or the selectable binding moiety may comprise a region that can be cut, nicked, cleaved or hydrolysed as discussed above.

If one or more helicases and one or more molecular brakes are used as discussed above, the Y adaptor preferably comprises the one or more helicases and the bridging moiety adaptor preferably comprises the one or more molecular brakes.

The Y adaptor and/or the bridging moiety adaptor may be ligated to the polynucleotide using any method known in the art. One or both of the adaptors may be ligated using a ligase, such as T4 DNA ligase, E. coli DNA ligase, Taq DNA ligase, Tma DNA ligase and 9° N DNA ligase. Alternatively, the adaptors may be added to the polynucleotide using the methods of the invention discussed below.

In a preferred embodiment, step a) of the method comprises modifying the double stranded polynucleotide so that it comprises the Y adaptor at one end and the bridging moiety adaptor at the other end. Any manner of modification can be used. The method preferably comprises modifying the double stranded polynucleotide in accordance with the invention. This is discussed in more detail below. The methods of modification and characterisation may be combined in any way.

The strength of coupling (or binding) of the bridging moiety adaptor to the membrane is greater than the strength of coupling (or binding) of the Y adaptor to the membrane.

This can be measured in any way. A suitable method for measuring the strength of coupling (or binding) is disclosed in the Examples of the UK Application No. 1406147.7.

The strength of coupling (or binding) of the bridging moiety adaptor is preferably at least 1.5 times the strength of coupling (or binding) of the Y adaptor, such as at least twice, at least three times, at least four times, at least five or at least ten times the strength of coupling (or binding) of the anchor adaptor. The affinity constant (Kd) of the bridging moiety adaptor for the membrane is preferably at least 1.5 times the affinity constant of the Y adaptor, such as at least twice, at least three times, at least four times, at least five or at least ten times the strength of coupling of the Y adaptor.

There are several ways in which the bridging moiety adaptor couples (or binds) more strongly to the membrane than the Y adaptor. For instance, the bridging moiety adaptor may comprise more anchors than the Y adaptor. For instance, the bridging moiety adaptor may comprise 2, 3 or more second anchors whereas the Y adaptor may comprise one first anchor.

The strength of coupling (or binding) of the one or more second anchors to the membrane may be greater than the strength of coupling (or binding) of the one or more first anchors to the membrane. The strength of coupling (or binding) of the one or more second anchors to the bridging moiety adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used in the invention. Strength of coupling (or binding) may be measure using known techniques in the art.

The one or more second anchors preferably comprise one or more groups which couple(s) (or bind(s)) to the membrane with a greater strength than the one or more groups in the one or more first anchors which couple(s) (or bind(s)) to the membrane. In preferred embodiments, the bridging moiety adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the bridging moiety adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine.

Adding Hairpin Loops and Leader Sequences

Before provision, a double stranded polynucleotide may be contacted with a MuA transposase and a population of double stranded MuA substrates, wherein a proportion of the substrates in the population are Y adaptors comprising the leader sequence and wherein a proportion of the substrates in the population are hairpin loop adaptors. The transposase fragments the double stranded polynucleotide analyte and ligates MuA substrates to one or both ends of the fragments. This produces a plurality of modified double stranded polynucleotides comprising the leader sequence at one end and the hairpin loop at the other. The modified double stranded polynucleotides may then be investigated using the method of the invention.

Each substrate in the population preferably comprises at least one overhang of universal nucleotides such that the transposase fragments the template polynucleotide and ligates a substrate to one or both ends of the double stranded fragments and thereby produces a plurality of fragment/substrate constructs and wherein the method further comprises ligating the overhangs to the fragments in the constructs and thereby producing a plurality of modified double stranded polynucleotides. Suitable universal nucleotides are discussed above. The overhang is preferably five nucleotides in length.

Alternatively, each substrate in population preferably comprises (i) at least one overhang and (ii) at least one nucleotide in the same strand as the at least one overhang which comprises a nucleoside that is not present in the template polynucleotide such that the transposase fragments the template polynucleotide and ligates a substrate to one or both ends of the double stranded fragments and thereby produces a plurality of fragment/substrate constructs, and wherein the method further comprises (a) removing the overhangs from the constructs by selectively removing the at least one nucleotide and thereby producing a plurality of double stranded constructs comprising single stranded gaps and (b) repairing the single stranded gaps in the constructs and thereby producing a plurality of modified double stranded polynucleotides. The polynucleotide typically comprises the nucleosides deoxyadenosine (dA), deoxyuridine (dU) and/or thymidine (dT), deoxyguanosine (dG) and deoxycytidine (dC). The nucleoside that is not present in the polynucleotide is preferably abasic, adenosine (A), uridine (U), 5-methyluridine ($m^5U$), cytidine (C) or guanosine (G) or comprises urea, 5,6 dihydroxythymine, thymine glycol, 5-hydroxy-5 methylhydanton, uracil glycol, 6-hydroxy-5,6-dihdrothimine, methyltartronylurea, 7,8-dihydro-8-oxoguanine (8-oxoguanine), 8-oxoadenine, fapy-guanine, methyfapy-guanine, fapy-adenine, aflatoxin B1-fapy-guanine, 5-hydroxy-cytosine, 5-hydroxy-uracil, 3-methyladenine, 7-methylguanine, 1,N6-ethenoadenine, hypoxanthine, 5-hydroxyuracil, 5-hydroxymethyluracil, 5-formyluracil or a cis-syn-cyclobutane pyrimidine dimer. The at least one nucleotide preferably is 10 nucleotides or fewer from the overhang. The at least one nucleotide is the first nucleotide in the overhang. All of the nucleotides in the overhang preferably comprise a nucleoside that is not present in the template polynucleotide.

These MuA based methods are disclosed in International Application No. PCT/GB2014/052505. They are also discussed in detail in the UK Application No. 1406147.7.

One or more helicases may be attached to the MuA substrate Y adaptors before they are contacted with the double stranded polynucleotide and MuA transposase. Alternatively, one or more helicases may be attached to the MuA substrate Y adaptors before they are contacted with the double stranded polynucleotide and MuA transposase.

One or more molecular brakes may be attached to the MuA substrate hairpin loop adaptors before they are contacted with the double stranded polynucleotide and MuA transposase. Alternatively, one or more molecular brakes may be attached to the MuA substrate hairpin loop adaptors before they are contacted with the double stranded polynucleotide and MuA transposase.

Uncoupling

The method of the invention may involve characterising multiple target polynucleotides and uncoupling of the at least the first target polynucleotide.

In a preferred embodiment, the invention involves characterising two or more target polynucleotides. The method comprises:

(a) providing a first polynucleotide in a first sample;
(b) providing a second polynucleotide in a second sample;

(c) coupling the first polynucleotide in the first sample to a membrane using one or more anchors;
(d) contacting the first polynucleotide with CsgG pore or mutant thereof, such as a pore of the invention, such that the polynucleotide moves with respect to, such as through, the pore;
(e) taking one or more measurements as the first polynucleotide moves with respect to the pore wherein the measurements are indicative of one or more characteristics of the first polynucleotide and thereby characterising the first polynucleotide;
(f) uncoupling the first polynucleotide from the membrane;
(g) coupling the second polynucleotide in the second sample to the membrane using one or more anchors;
(h) contacting the second polynucleotide with the CsgG pore or mutant thereof, such as a pore of the invention, such that the second polynucleotide moves with respect to, such as through, the pore; and
(i) taking one or more measurements as the second polynucleotide moves with respect to the pore wherein the measurements are indicative of one or more characteristics of the second polynucleotide and thereby characterising the second polynucleotide.

This type of method is discussed in detail in the UK Application No. 1406155.0.

Step (f) (i.e. uncoupling of the first polynucleotide) may be performed before step (g) (i.e. before coupling the second polynucleotide to the membrane). Step (g) may be performed before step (f). If the second polynucleotide is coupled to the membrane before the first polynucleotide is uncoupled, step (f) preferably comprises selectively uncoupling the first polynucleotide from the membrane (i.e. uncoupling the first polynucleotide but not the second polynucleotide from the membrane). A skilled person can design a system in which selective uncoupling is achieved. Steps (f) and (g) may be performed at the same time. This is discussed in more detail below.

In step (f), at least 10% of the first polynucleotide is preferably uncoupled from the membrane. For instance, at least 20%, at least 30%, at least 40%, at least 50%, at least 60%, at least 70%, at least 80%, at least 90% or at least 95% of the first polynucleotide may be uncoupled from the membrane. Preferably, all of the first polynucleotide is uncoupled from the membrane. The amount of the first polynucleotide uncoupled from the membrane can be determined using the pore. This is disclosed in the Examples.

The first polynucleotide and second polynucleotide may be different from one another. Alternatively, the first and second polynucleotides may be different polynucleotides. In such instances, there may be no need to remove at least part of the first sample before adding the second polynucleotide. This is discussed in more detail below. If the method concerns investigating three or more polynucleotides, they may all be different from one another or some of them may be different from one another.

The first polynucleotide and the second polynucleotide may be two instances of the same polynucleotide. The first polynucleotide may be identical to the second polynucleotide. This allows proof reading. If the method concerns investigating three or more polynucleotides, they may all be three or more instances of the same polynucleotide or some of them may be separate instances of the same polynucleotide.

The first sample and second sample may be different from one another. For instance, the first sample may be derived from a human and the second sample may be derived from a virus. If the first and second samples are different from one another, they may contain or be suspected of containing the same first and second polynucleotides. If the method concerns investigating three or more samples, they may all be different from one another or some of them may be different from one another.

The first sample and the second sample are preferably two instances of the same sample. The first sample is preferably identical to the second sample. This allows proof reading. If the method concerns investigating three or more samples, they may all be three or more instances of the same sample or some of them may be separate instances of the same sample.

Any number of polynucleotides can be investigated. For instance, the method of the invention may concern characterising 3, 4, 5, 6, 7, 8, 9, 10, 20, 30, 50, 100 or more polynucleotides. If three or more polynucleotides are investigated using the method of the invention, the second polynucleotide is also uncoupled from the membrane and the requisite number of steps are added for the third polynucleotide. The same is true for four or more polynucleotides.

The method of the invention involves uncoupling the first polynucleotide from the membrane. The method of the invention may involve uncoupling the second polynucleotide from the membrane if three or more polynucleotides are being investigated.

The first polynucleotide can be uncoupled from the membrane using any known method. The first polynucleotide is preferably not uncoupled from the membrane in step (f) using the transmembrane pore. The first polynucleotide is preferably not uncoupled from the membrane using a voltage or an applied potential.

Step (f) preferably comprises uncoupling the first polynucleotide from the membrane by removing the one or more anchors from the membrane. If the anchors are removed, the second polynucleotide is coupled to the membrane using other (or separate) anchors. The anchors used to couple the second polynucleotide may be the same type of anchors used to couple the first polynucleotide or different type of anchors.

Step (f) more preferably comprises contacting the one or more anchors with an agent which has a higher affinity for the one or more anchors than the anchors have for the membrane. A variety of protocols for competitive binding or immunoradiometric assays to determine the specific binding capability of molecules are well known in the art (see for example Maddox et al, *J. Exp. Med.* 158, 1211-1226, 1993). The agent removes the anchor(s) from the membrane and thereby uncouples the first polynucleotide. The agent is preferably a sugar. Any sugar which binds to the one or more anchors with a higher affinity than the one or more anchors have for the membrane may be used. The sugar may be a cyclodextrin or derivative thereof as discussed below.

If one or more anchors comprise a hydrophobic anchor, such as cholesterol, the agent is preferably a cyclodextrin or a derivative thereof or a lipid. The cyclodextrin or derivative thereof may be any of those disclosed in Eliseev, A. V., and Schneider, H-J. (1994) *J. Am. Chem. Soc.* 116, 6081-6088.

The agent is more preferably heptakis-6-amino-β-cyclodextrin ($am_7$-βCD), 6-monodeoxy-6-monoamino-3-cyclodextrin ($am_1$-☐CD) or heptakis-(6-deoxy-6-guanidino)-cyclodextrin ($gu_7$-βCD). Any of the lipids disclosed herein may be used.

If an anchor comprise(s) streptavidin, biotin or desthiobiotin, the agent is preferably biotin, desthiobiotin or streptavidin. Both biotin and desthiobiotin bind to streptavidin with a higher affinity than streptavidin binds to the membrane and vice versa. Biotin has a stronger affinity for streptavidin than desthiobiotin. An anchor comprising streptavidin may therefore be removed from the membrane using biotin or streptavidin and vice versa.

If an anchor comprises a protein, the agent is preferably an antibody or fragment thereof which specifically binds to the protein. An antibody specifically binds to a protein if it binds to the protein with preferential or high affinity, but does not bind or binds with only low affinity to other or different proteins. An antibody binds with preferential or high affinity if it binds with a Kd of $1\times10^{-6}$ M or less, more preferably $1\times10^{-7}$ M or less, $5\times10^{-8}$ M or less, more preferably $1\times10^{-8}$ M or less or more preferably $5\times10^{-9}$ M or less. An antibody binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more. Any method may be used to detect binding or specific binding. Methods of quantitatively measuring the binding of an antibody to a protein are well known in the art. The antibody may be a monoclonal antibody or a polyclonal antibody. Suitable fragments of antibodies include, but are not limited to, Fv, F(ab') and F(ab')$_2$ fragments, as well as single chain antibodies. Furthermore, the antibody or fragment thereof may be a chimeric antibody or fragment thereof, a CDR-grafted antibody or fragment thereof or a humanised antibody or fragment thereof.

Step (f) preferably comprises contacting the one or more anchors with an agent which reduces ability of the one or more anchors to couple to the membrane. For instance, the agent could interfere with the structure and/or hydrophobicity of the one or more anchors and thereby reduce their ability to couple to the membrane. If an anchor comprises cholesterol, the agent is preferably cholesterol dehydrogenase. If an anchor comprises a lipid, the agent is preferably a phospholipase. If an anchor comprises a protein, the agent is preferably a proteinase or urea. Other combination of suitable anchors and agents will be clear to a person skilled in the art.

Step (f) preferably comprises uncoupling the first polynucleotide from the membrane by separating the first polynucleotide from the one or more anchors. This can be done in any manner. For instance, the linker could be cut in an anchor comprising a linker. This embodiment is particularly applicable to anchors which involve linkage via hybridisation. Such anchors are discussed above.

Step (f) more preferably comprises uncoupling the first polynucleotide from the membrane by contacting the first polynucleotide and the one or more anchors with an agent which competes with the first polynucleotide for binding to one or more anchors. Methods for determining and measuring competitive binding are known in the art. The agent is preferably a polynucleotide which competes with the first polynucleotide for hybridisation to the one or more anchors. For instance, if the first polynucleotide is coupled to the membrane using one or more anchors which involve hybridisation, the polynucleotide can be uncoupled by contacting the one or more anchors with a polynucleotide which also hybridises to the site of hybridisation. The polynucleotide agent is typically added at a concentration that is higher than the concentration of the first polynucleotide and one or more anchors. Alternatively, the polynucleotide agent may hybridise more strongly to the one or more anchors than the first polynucleotide.

Step (f) more preferably comprises (i) contacting the first polynucleotide and the one or more anchors with urea, tris(2-carboxyethyl)phosphine (TCEP), dithiothreitol (DTT), streptavidin or biotin, UV light, an enzyme or a binding agent; (ii) heating the first polynucleotide and the one or more anchors; or (iii) altering the pH. Urea, tris(2-carboxyethyl)phosphine (TCEP) or dithiothreitol (DTT) are capable of disrupting anchors and separating the first polynucleotide from the membrane. If an anchor comprises a streptavidin-biotin link, then a streptavidin agent will compete for binding to the biotin. If an anchor comprises a streptavidin-desthiobiotin link, then a biotin agent will compete for binding to the streptavidin. UV light can be used to breakdown photolabile groups. Enzymes and binding agents can be used to cut, breakdown or unravel the anchor. Preferred enzymes include, but are not limited to, an exonuclease, an endonuclease or a helicase. Preferred binding agents include, but are not limited to, an enzyme, an antibody or a fragment thereof or a single-stranded binding protein (SSB). Any of the enzymes discussed below or antibodies discussed above may be used. Heat and pH can be used to disrupt hybridisation and other linkages.

If the first polynucleotide is uncoupled from the membrane by separating the first polynucleotide from the one or more anchors, the one or more anchors will remain in the membrane. Step (g) preferably comprises coupling the second polynucleotide to the membrane using the one or more anchors that was separated from the first polynucleotide. For instance, the second polynucleotide may also be provided with one or more polynucleotides which hybridise(s) to the one or more anchors that remain in the membrane. Alternatively, step (g) preferably comprises coupling the second polynucleotide to the membrane using one or more separate anchors from the ones separated from the first polynucleotide (i.e. one or more other anchors). The one or more separate anchors may be the same type of anchors used to couple the first polynucleotide to the membrane or may be different types of anchors. Step (g) preferably comprises coupling the second polynucleotide to the membrane using one or more different anchors from the one or more anchors separated from the first polynucleotide.

In a preferred embodiment, steps (f) and (g) comprise uncoupling the first polynucleotide from the membrane by contacting the membrane with the second polynucleotide such that the second polynucleotide competes with the first polynucleotide for binding to the one or more anchors and replaces the first polynucleotide. For instance, if the first polynucleotide is coupled to the membrane using one or more anchors which involve hybridisation, the first polynucleotide can be uncoupled by contacting the anchors with the second polynucleotide attached to polynucleotides which also hybridise to the sites of hybridisation in the one or more anchors. The second polynucleotide is typically added at a concentration that is higher than the concentration of the first polynucleotide and the one or more anchors. Alternatively, the second polynucleotide may hybridise more strongly to the one or more anchors than the first polynucleotide.

Removal or Washing

Although the first polynucleotide is uncoupled from the membrane in step (f), it is not necessarily removed or washed away. If the second polynucleotide can be easily distinguished from the first polynucleotide, there is no need to remove the first polynucleotide.

Between steps (f) and (g), the method preferably further comprises removing at least some of the first sample from the membrane. At least 10% of the first sample may be removed, such as at least 20%, at least 30%, at least 40%, at least 50%, at least 60%, at least 70%, at least 80% or at least 90% of the first sample may be removed.

The method more preferably further comprises removing all of the first sample from the membrane. This can be done in any way. For instance, the membrane can be washed with a buffer after the first polynucleotide has been uncoupled. Suitable buffers are discussed below.

Modified Polynucleotides

Before characterisation, a target polynucleotide may be modified by contacting the polynucleotide with a polymerase and a population of free nucleotides under conditions in which the polymerase forms a modified polynucleotide using the target polynucleotide as a template, wherein the polymerase replaces one or more of the nucleotide species in the target polynucleotide with a different nucleotide species when forming the modified polynucleotide. The modified polynucleotide may then be provided with one or more helicases attached to the polynucleotide and one or more molecular brakes attached to the polynucleotide. This type of modification is described in UK Application No. 1403096.9. Any of the polymerases discussed above may be used. The polymerase is preferably Klenow or 90 North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 90 North. A primer or a 3' hairpin is typically used as the nucleation point for polymerase extension.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the target polynucleotide with different nucleotide species in the modified polynucleotide, the modified polynucleotide contains k-mers which differ from those in the target polynucleotide. The different k-mers in the modified polynucleotide are capable of producing different current measurements from the k-mers in the target polynucleotide and so the modified polynucleotide provides different information from the target polynucleotide. The additional information from the modified polynucleotide can make it easier to characterise the target polynucleotide. In some instances, the modified polynucleotide itself may be easier to characterise. For instance, the modified polynucleotide may be designed to include k-mers with an increased separation or a clear separation between their current measurements or k-mers which have a decreased noise.

The polymerase preferably replaces two or more of the nucleotide species in the target polynucleotide with different nucleotide species when forming the modified polynucleotide. The polymerase may replace each of the two or more nucleotide species in the target polynucleotide with a distinct nucleotide species. The polymerase may replace each of the two or more nucleotide species in the target polynucleotide with the same nucleotide species.

If the target polynucleotide is DNA, the different nucleotide species in the modified typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the target polynucleotide is RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcytidine. The different nucleotide species may be any of the universal nucleotides discussed above.

The polymerase may replace the one or more nucleotide species with a different nucleotide species which comprises a chemical group or atom absent from the one or more nucleotide species.

The chemical group may be a propynyl group, a thio group, an oxo group, a methyl group, a hydroxymethyl group, a formyl group, a carboxy group, a carbonyl group, a benzyl group, a propargyl group or a propargylamine group.

The polymerase may replace the one or more nucleotide species with a different nucleotide species which lacks a chemical group or atom present in the one or more nucleotide species. The polymerase may replace the one or more of the nucleotide species with a different nucleotide species having an altered electronegativity. The different nucleotide species having an altered electronegativity preferably comprises a halogen atom.

The method preferably further comprises selectively removing the nucleobases from the one or more different nucleotides species in the modified polynucleotide.

Analyte Delivery

The target analyte is preferably attached to a microparticle which delivers the analyte towards the membrane. This type of delivery is disclosed in UK Application No. 1418469.1. Any type of microparticle and attachment method may be used.

Other Characterisation Method

In another embodiment, a polynucleotide is characterised by detecting labelled species that are added to the target polynucleotide by a polymerase and then released. The polymerase uses the polynucleotide as a template. Each labelled species is specific for each nucleotide. The polynucleotide is contacted with a CsgG pore or mutant thereof, such as a pore of the invention, a polymerase and labelled nucleotides such that phosphate labelled species are sequentially added to the polynucleotide by the polymerase, wherein the phosphate species contain a label specific for each nucleotide. The labelled species may be detected using the pore before they are released from the nucleotides (i.e. as they are added to the target polynucleotide) or after they are released from the nucleotides.

The polymerase may be any of those discussed above. The phosphate labelled species are detected using the pore and thereby characterising the polynucleotide. This type of method is disclosed in European Application No. 13187149.3 (published as EP 2682460). Any of the embodiments discussed above equally apply to this method.

Examples of labelled species include, but are not limited to, polymers, polyethylene glycols, sugars, cyclodextrins, fluorophores, drugs, metabolites, peptides. A non-limiting example of such tags can be found in the work of Kumar et al. Sci Rep. 2012; 2:684. Epub 2012 Sep. 21.

Methods of Forming Sensors

The invention also provides a method of forming a sensor for characterising a target polynucleotide. The method comprises forming a complex between a CsgG pore or mutant thereof, such as a pore of the invention, and a polynucleotide binding protein, such as a helicase or an exonuclease. The complex may be formed by contacting the pore and the protein in the presence of the target polynucleotide and then applying a potential across the pore. The applied potential may be a chemical potential or a voltage potential as described above. Alternatively, the complex may be formed by covalently attaching the pore to the protein. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a CsgG pore or mutant thereof, such as a pore of the invention, and a helicase. Any of the embodiments discussed above equally apply to this method.

The invention also provides a sensor for characterising a target polynucleotide. The sensor comprises a complex between a CsgG pore or mutant thereof, such as a pore of the invention, and a polynucleotide binding protein. Any of the embodiments discussed above equally apply to the sensor of the invention.

Kits

The present invention also provides a kit for characterising a target polynucleotide. The kit comprises a CsgG pore or mutant thereof, such as a pore of the invention, and the components of a membrane. The membrane is preferably formed from the components. The pore is preferably present in the membrane. The kit may comprise components of any of the membranes disclosed above, such as an amphiphilic layer or a triblock copolymer membrane.

The kit may further comprise a polynucleotide binding protein. Any of the polynucleotide binding proteins discussed above may be used.

The kit may further comprise one or more anchors for coupling the polynucleotide to the membrane.

The kit is preferably for characterising a double stranded polynucleotide and preferably comprises a Y adaptor and a hairpin loop adaptor. The Y adaptor preferably has one or more helicases attached and the hairpin loop adaptor preferably has one or more molecular brakes attached. The Y adaptor preferably comprises one or more first anchors for coupling the polynucleotide to the membrane, the hairpin loop adaptor preferably comprises one or more second anchors for coupling the polynucleotide to the membrane and the strength of coupling of the hairpin loop adaptor to the membrane is preferably greater than the strength of coupling of the Y adaptor to the membrane.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

Apparatus

The invention also provides an apparatus for characterising a target analyte, such as a target polynucleotide. The apparatus comprises a plurality of CsgG pores or mutants thereof and a plurality of membranes. The plurality of pores are preferably present in the plurality of membranes. The number of pores and membranes is preferably equal. Preferably, a single pore is present in each membrane.

The apparatus preferably further comprises instructions for carrying out the method of the invention. The apparatus may be any conventional apparatus for analyte analysis, such as an array or a chip. Any of the embodiments discussed above with reference to the methods of the invention are equally applicable to the apparatus of the invention. The apparatus may further comprise any of the features present in the kit of the invention.

The apparatus is preferably set up to carry out the method of the invention.

The apparatus preferably comprises:
  a sensor device that is capable of supporting the plurality of pores and membranes and being operable to perform analyte characterisation using the pores and membranes; and
  at least one port for delivery of the material for performing the characterisation.

Alternatively, the apparatus preferably comprises:
  a sensor device that is capable of supporting the plurality of pores and membranes being operable to perform analyte characterisation using the pores and membranes; and
  at least one reservoir for holding material for performing the characterisation.

The apparatus more preferably comprises:
  a sensor device that is capable of supporting the membrane and plurality of pores and membranes and being operable to perform analyte characterising using the pores and membranes;
  at least one reservoir for holding material for performing the characterising;
  a fluidics system configured to controllably supply material from the at least one reservoir to the sensor device; and
  one or more containers for receiving respective samples, the fluidics system being configured to supply the samples selectively from one or more containers to the sensor device.

The apparatus may be any of those described in International Application No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

The following Examples illustrate the invention.

EXAMPLES

Example 1: Cloning and Strains of CsgG

Expression constructs for the production of outer membrane localized C-terminally StrepII-tagged CsgG (pPG1) and periplasmic C-terminally StrepII-tagged $CsgG_{C1S}$ (pPG2) have been described (Goyal, P. et al., Acta Crystallogr. F. Struct. Biol. Cryst. Commun. 2013, 69, 1349-1353). For selenomethionine labelling, StrepII-tagged $CsgG_{C1S}$ was expressed in the cytoplasm because of increased yields. Therefore, pPG2 was altered to remove the N-terminal signal peptide using inverse PCR with primers 5'-TCT TTA AC CGC CCC GCC TAA AG-3' (forward) (SEQ ID NO: 437) and 5'-CAT TTT TTG CCC TCG TTA TC-3' (reverse) (pPG3) (SEQ ID NO: 438). For phenotypic assays, a csgG deletion mutant of *E. coli* BW25141 (*E. coli* NVG2) was constructed by the method described [Datsenko, K. A. et al, Proc. Natl Acad. Sci. USA 97, 6640-6645 (2000)] (with primers 5'-AAT AAC TCA ACC GAT TTT TAA GCC CCA GCT TCA TAA GGA AAA TAA TCG TGT AGG CTG GAG CTG CTT C-3' (SEQ ID NO: 439) and 5'-CGC TTA AAC AGT AAA ATG CCG GAT GAT AAT TCC GGC TTT TTT ATC TGC ATA TGA ATA TCC TCC TTA G-3' (SEQ ID NO: 440)). The various CsgG substitution mutants used for Cys accessibility assays and for phenotypic probing of the channel constriction were constructed by site-directed mutagenesis (QuikChange protocol; Stratagene) starting from pMC2, a pTRC99a vector containing csgG under control of the trc promoter (Robinson, L. S., et al, Mol. Microbiol., 2006, 59, 870-881).

Example 2: Protein Expression and Purification

CsgG and CsgG$_{C1S}$ were expressed and purified as described (Robinson, L. S., et al, Mol. Microbiol., 2006, 59, 870-881). In brief, CsgG was recombinantly produced in *E. coli* BL 21 (DE3) transformed with pPG1 and extracted from isolated outer membranes with the use of 1% n-dodecyl-β-D-maltoside (DDM) in buffer A (50 mM Tris-HCl pH 8.0, 500 mM NaCl, 1 mM EDTA, 1 mM dithiothreitol (DTT)). StrepII-tagged CsgG was loaded onto a 5 ml Strep-Tactin Sepharose column (Iba GmbH) and detergent-exchanged by washing with 20 column volumes of buffer A supplemented with 0.5% tetraethylene glycol monooctyl ether (C8E4; Affymetrix) and 4 mM lauryldimethylamine-N-oxide (LDAO; Affymetrix). The protein was eluted by the addition of 2.5 mM D-desthiobiotin and concentrated to 5 mg ml$^{-1}$ for crystallization experiments. For selenomethionine labelling, CsgG$_{C1S}$ was produced in the Met auxotrophic strain B834 (DE3) transformed with pPG3 and grown on M9 minimal medium supplemented with 40 mg l$^{-1}$ L-selenomethionine. Cell pellets were resuspended in 50 mM Tris-HCl pH 8.0, 150 mM NaCl, 1 mM EDTA, 5 mM DTT, supplemented with cOmplete Protease Inhibitor Cocktail (Roche) and disrupted by passage through a TS series cell disruptor (Constant Systems Ltd) operated at 20×10$^3$ lb in$^{-2}$. Labelled CsgG$_{C1S}$ was purified as described (Robinson, L. S., et al, Mol. Microbiol., 2006, 59, 870-881). DTT (5 mM) was added throughout the purification procedure to avoid oxidation of selenomethionine.

CsgE was produced in *E. coli* NEBC2566 cells harbouring pNH27 (Nenninger, A. A. et al., Mol. Microbial. 2011, 81, 486-499). Cell lysates in 25 mM Tris-HCl pH 8.0, 150 mM NaCl, 25 mM imidazole, 5% (v/v) glycerol were loaded on a HisTrap FF (GE Healthcare). CsgE-his was eluted with a linear gradient to 500 mM imidazole in 20 mM Tris-HCl pH 8.0, 150 mM NaCl, 5% (v/v) glycerol buffer. Fractions containing CsgE were supplemented with 250 mM (NH$_4$)$_2$SO$_4$ and applied to a 5 ml HiTrap Phenyl HP column (GE Healthcare) equilibrated with 20 mM Tris-HCl pH 8.0, 100 mM NaCl, 250 mM (NH$_4$)$_2$SO$_4$, 5% (v/v) glycerol. A linear gradient to 20 mM Tris-HCl pH 8.0, 10 mM NaCl, 5% (v/v) glycerol was applied for elution. CsgE containing fractions were loaded onto a Superose 6 Prep Grade 10/600 (GE Healthcare) column equilibrated in 20 mM Tris-HCl pH 8.0, 100 mM NaCl, 5% (v/v) glycerol.

Example 3: In-Solution Oligomeric State Assessment

Figure 7:
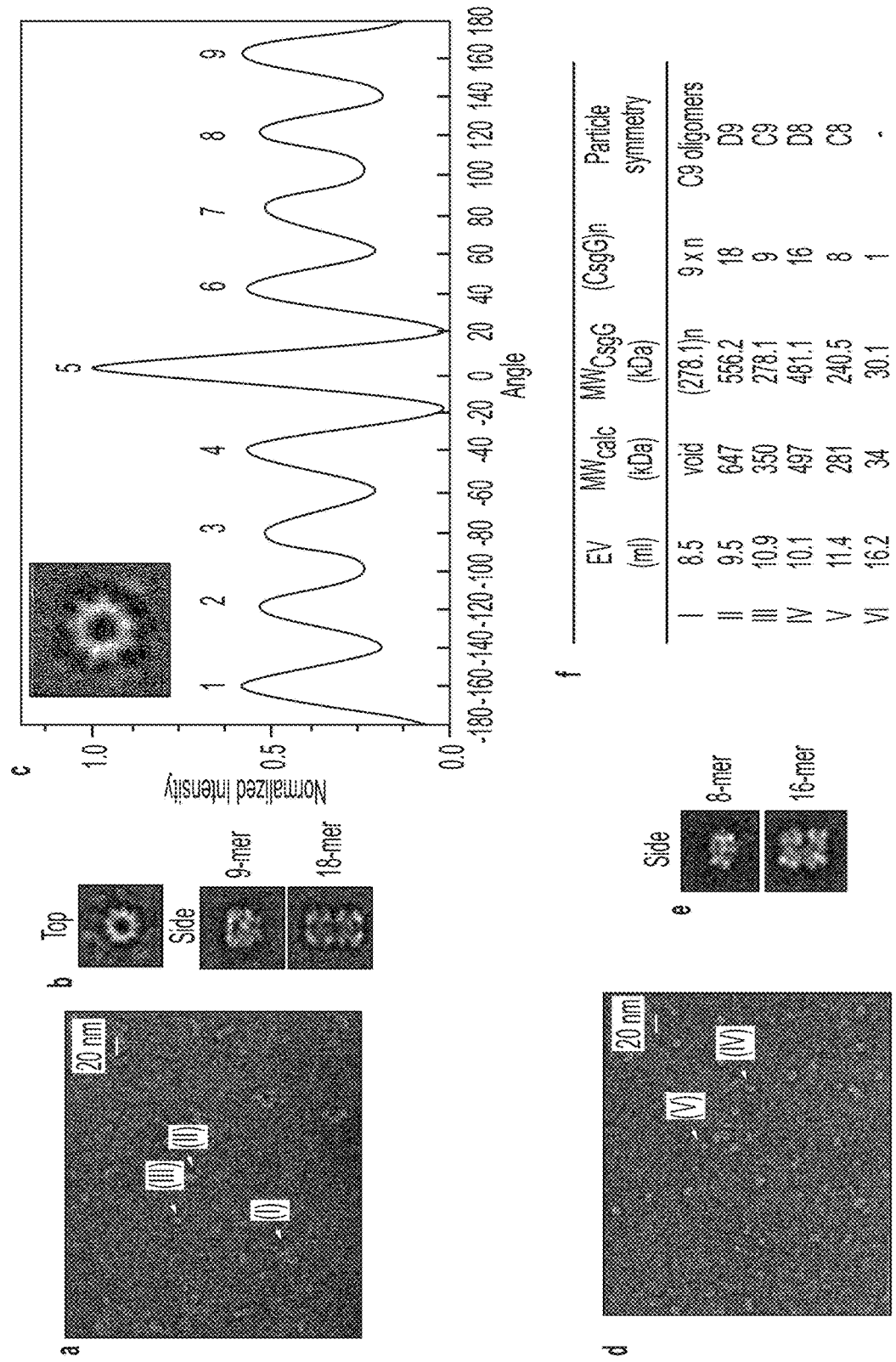
FIG. 7 shows a, Raw negative-stain EM image of C8E4/LDAO-solubilized CsgG. Arrows indicate the different particle populations as labelled in the size exclusion profile shown in g, being (I) aggregates of CsgG nonamers, (II) CsgG octadecamers and (III) CsgG nonamers. Scale bar, 20 nm. b, Representative class average for top and side views of the indicated oligomeric states. c, Rotational autocorrelation function graph of LDAO-solubilized CsgG in top view, showing nine-fold symmetry. d, Raw negative-stain EM image of $CsgG_{C1S}$. Arrows indicate the hexadecameric (IV) and octameric (V) particles observed by size-exclusion chromatography in g. e, Representative class average for side views of $CsgG_{C1S}$ oligomers. No top views were observed for this construct. f, Table of elution volumes (EV) of $CsgG_{C1S}$ and CsgG particles observed by size-exclusion chromatography shown in g, calculated molecular mass (MW) expected molecular mass ($MW_{csgG}$) corresponding CsgG oligomerization state ($CsgG_n$) and the particles' symmetry as observed by negative-stain EM and X-ray crystallography. g, Size-exclusion chromatogram of $CsgG_{C1S}$ (black) and C8E4/LDAO-solubilized CsgG (grey) run on Superdex 200 10/300 GL (GE Healthcare). h, i, Ribbon representation of crystallized oligomers in top and side view, showing the $D_8$ hexadecamers for $CsgG_{C1S}$ (h) and $D_9$ octadecamers for membrane-extracted CsgG (i). One protomer is coloured in rainbow from N terminus (blue) to C terminus (red). The two $C_8$ octamers ($CsgG_{C1S}$) or $C_9$ nonamers (CsgG) that form the tail-to-tail dimers captured in the crystals are coloured blue and tan. r and ° give radius and interprotomer rotation, respectively.
Figure 7:
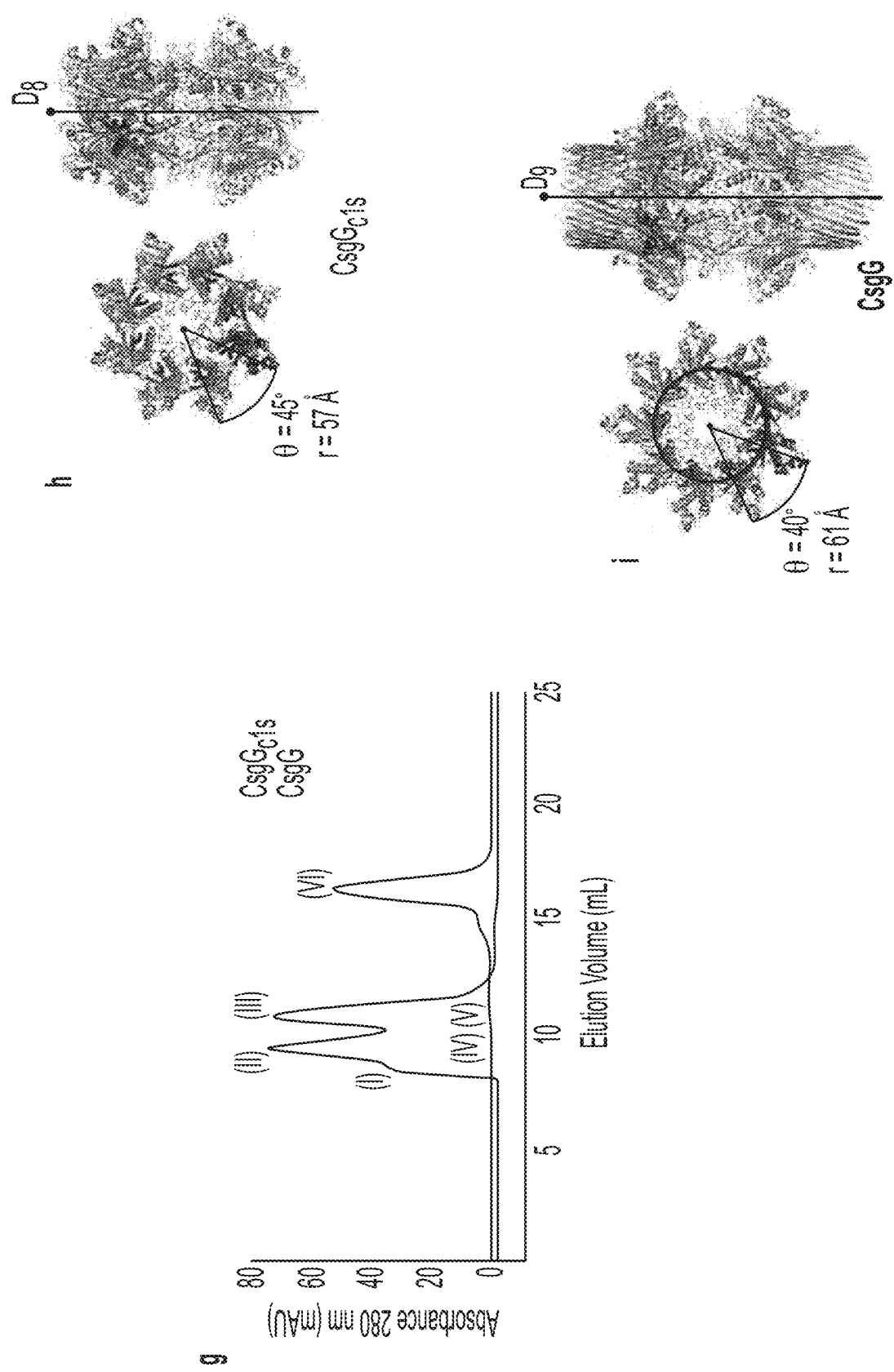

About 0.5 mg each of detergent-solubilized CsgG (0.5% C8E4, 4 mM LDAO) and CsgG$_{C1S}$ were applied to a Superdex 200 10/300 GL analytical gel filtration column (GE Healthcare) equilibrated with 25 mM Tris-HCl pH 8.0, 500 mM NaCl, 1 mM DTT, 4 mM LDAO and 0.5% C8E4 (CsgG) or with 25 mM Tris-HCl pH 8.0, 200 mM NaCl (CsgG$_{C1S}$), and run at 0.7 ml min$^{-1}$. The column elution volumes were calibrated with bovine thyroglobulin, bovine γ-globulin, chicken ovalbumin, horse myoglobulin and vitamin B$_{12}$ (Bio-Rad) (FIG. 7). Membrane-extracted CsgG, 20 µg of the detergent-solubilized protein was also run on 3-10% blue native PAGE using the procedure described in Swamy, M., et al., Sci. STKE 2006, p 14, [http://dx.doi.org/10.1126/stke.3452006pl4(2006)] (FIG. 7). NativeMark (Life Technologies) unstained protein standard (7 µl) was used for molecular mass estimation. Mature CsgG is predominantly found as discrete nonameric poreforming particles with C9 symmetry, as well as tail-to-tail dimers of nonameric pores (i.e. octadecamers with D9 symmetry). For the purpose of nanopore sensing applications, a preferred state of the proteins is a single nonameric pore. The population of nonameric versus D9 octadecameric pores can be increased by heating samples prior to size exclusion chromatography and/or insertion in a lipid bilayer for nanopore sensing applications.

Example 4: Crystallization, Data Collection and Structure Determination

Selenomethionine-labelled CsgG$_{C1S}$ was concentrated to 3.8 mg ml$^{-1}$ and crystallized by sitting-drop vapour diffusion against a solution containing 100 mM sodium acetate pH 4.2, 8% PEG 4000 and 100 mM sodium malonate pH 7.0. Crystals were incubated in crystallization buffer supplemented with 15% glycerol and flash-frozen in liquid nitrogen. Detergent-solubilized CsgG was concentrated to 5 mg ml$^{-1}$ and crystallized by hanging-drop vapour diffusion against a solution containing 100 mM Tris-HCl pH 8.0, 8% PEG 4000, 100 mM NaCl and 500 mM MgCl$_2$. Crystals were flash-frozen in liquid nitrogen and cryoprotected by the detergent present in the crystallization solution. For optimization of crystal conditions and screening for crystals with good diffraction quality, crystals were analysed on beamlines Proxima-1 and Proxima-2a (Soleil, France), PX-I (Swiss Light Source, Switzerland), 102, 103, 104 and 124 (Diamond Light Source, UK) and ID14eh2, ID23eh1 and ID23eh2 (ESRF, France). Final diffraction data used for structure determination of CsgG$_{C1S}$ and CsgG were collected at beamlines I04 and I03, respectively (Table 5).

TABLE 5

| | CsgG$_{C1S}$ | CsgG |
|---|---|---|
| Data collection and refinement statistics | | |
| Data collection | | |
| Space group | P1 | C2 |

TABLE 5-continued

Data collection and refinement statistics

|  | $CsgG_{C18}$ | CsgG |
|---|---|---|
| Cell dimensions | | |
| a, b, c (Å) | 101.3, 103.6. 141.7 | 161.9, 372.8, 161.9 |
| α, β, γ (°) | 111.3, 90,5, 118.2 | 90.0, 92.9, 90.0 |
| Resolution (Å)* | 30-2.8 (2.9-2.8) | 30-3.6 (3.7-3.6) |
|  |  | 30-3.6 (a*), −3.7 (b+), −3.8 (c*) † |
| Rmeas * | 15.1 (81.8) | 16.2 (90.6) † |
| I/σI* | 9.82 (2.03) | 6.80 (1.89) † |
| Completeness (%)* | 98.7 (98.3) | 91.57 (27.26) |
|  |  | 99.9 (99.1) † |
| Redundancy* | 11.2 (7.0) | 4.4 (4.3) |
| Wilson B (Å$^2$) | 46.7 | 101.0 |
| Refinement | | |
| Resolution (Å)* | 30-2.8 (2.9-2.8) | 30-3.6 (3.7-3.6) |
|  |  | 30-3.6 (a+), −3.7 (b+), −3.8 (c*) † |
| No. reflections* | 112419 (11159) | 102130 (11094) |
| $R_{work}/R_{free}$ | 0.1881/0.2337 | 0.3024/0.3542 |
| No. atoms | | |
| Protein | 28853 | 34165 |
| Ligand/ion |  | 0 |
| Water | 0 | 0 |
| B-factors (Å$^2$) | | |
| Protein | 57.3 | 116.7 |
| Ligand/ion | | |
| Water | | |
| R.m.s deviations | | |
| Bond lengths (Å) | 0.01 | 0.03 |
| Bond angles (°) | 1.31 | 1.87 |

Data statistics for $CsgG_{C18}$ and membrane-extracted CsgG, collected from a single crystal each.
*Highest resolution shell is shown in parenthesis.
† Values corrected for anisotropic truncation along reciprocal directions a*, b* and c*.

Diffraction data for $CsgG_{C1S}$ were processed using Xia2 and the XDS package (Winter, G., J. Appl. Cryst., 2010, 43, 186-190; Kabsch, W., Acta Crystallogr. D Biol. Crystallogr. 2010, 66, 125-132). Crystals of $CsgG_{C1S}$ belonged to space group P1 with unit cell dimensions of a=101.3 Å, b=103.6 Å, c=141.7 Å, α=111.3°, β=90.5°, γ=118.2°, containing 16 protein copies in the asymmetric unit. For structure determination and refinement, data collected at 0.9795 Å wavelength were truncated at 2.8 Å on the basis of an I/σI cutoff of 2 in the highest-resolution shell. The structure was solved using experimental phases calculated from a single anomalous dispersion (SAD) experiment. A total of 92 selenium sites were located in the asymmetric unit by using ShelxC and ShelxD (Sheldrick, G. M., Acta Crystallogr. D Biol. Crystallogr. 2010, 66, 479-485), and were refined and used for phase calculation with Sharp (Bricogne, G., Acta Crystallogr. D Biol. Crystallogr. 2003, 59, 2023-2030) (phasing power 0.79, Figure of merit (FOM) 0.25). Experimental phases were density modified and averaged by non-crystallographic symmetry (NCS) using Parrot (Cowtan, K., Acta Crystallogr. D Biol. Crystallogr. 2010, 66, 470-478 (FIG. 7; FOM 0.85). An initial model was built with Buccaneer (Cowtan, K., Acta Crystallogr. D Biol. Crystallogr. 2006, 62, 1002-1011) and refined by iterative rounds of maximum-likelihood refinement with Phenix refine (Adams, P. D. et al. Acta Crystallogr. D Biol. Crystallogr. 2010, 66, 213-221) and manual inspection and model (re)building in Coot (Emsley, P. et al., Acta Crystallogr. D Biol. Crystallogr. 2010, 66, 486-501). The final structure contained 28,853 atoms in 3,700 residues belonging to 16 $CsgG_{C1S}$ chains (FIG. 7), with a molprobity (Davis, I. W. et al., Nucleic Acids Res. 35 (Suppl 2), W375-W383) score of 1.34; 98% of the residues lay in favoured regions of the Ramachandran plot (99.7% in allowed regions). Electron density maps showed no unambiguous density corresponding to possible solvent molecules, and no water molecules or ions were therefore built in. Sixteenfold NCS averaging was maintained throughout refinement, using strict and local NCS restraints in early and late stages of refinement, respectively.

Figure 8:
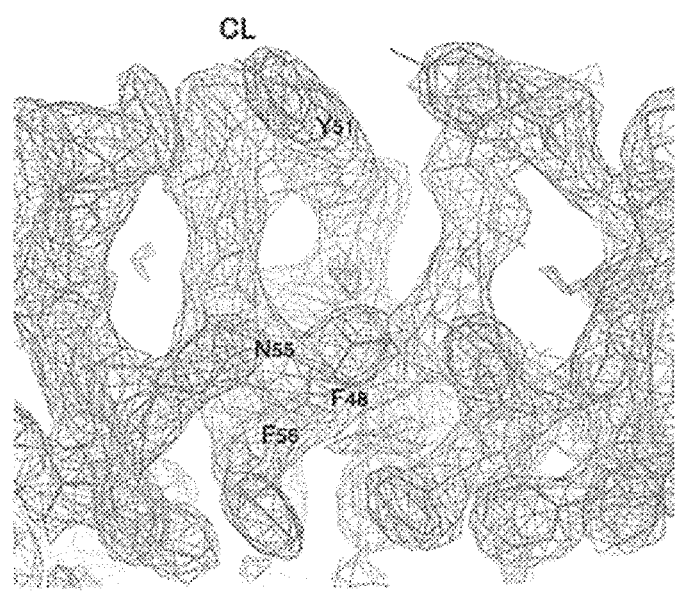
FIG. 8 shows an electron density map at 2.8 Å for $CsgG_{C1S}$ calculated using NCS-averaged and density-modified experimental SAD phases, and contoured at 1.5 g. The map shows the region of the channel construction (CL; a single protomer is labelled) and is overlaid on the final refined model. $CsgG_{C1S}$ is a mutant CsgG where the N-terminal Cys of the mature CsgG sequence, i.e. Cys 1, is replaced by Ser, resulting in lack of lipid modification by the E. coli LOL pathway. This results in a soluble homooctameric oligomer that is present in a pre-pore conformation (see FIG. 42) contrary to the membrane-targeted homononameric pore formed by native, lipid-modified CsgG (FIG. 43).

Diffraction data for CsgG were collected from a single crystal at 0.9763 Å wavelength and were indexed and scaled, using the XDS package (Winter, G., J. Appl. Cryst. 2010, 43, 186-190; Kabsch, W., Acta Crystallogr. D Biol. Crystallogr. 2010, 66, 125-132), in space group C2 with unit-cell dimensions a=161.7 Å, b=372.3 Å, c=161.8 Å and p=92.9°, encompassing 18 CsgG copies in the asymmetric unit and a 72% solvent content. Diffraction data for structure determination and refinement were elliptically truncated to resolution limits of 3.6 Å, 3.7 Å and 3.8 Å along reciprocal cell directions a*, b* and c* and scaled anisotropically with the Diffraction Anisotropy Server (Strong, M. et al., Proc. Natl Acad. Sci. USA 2006, 103, 8060-8065). Molecular replacement using the $CsgG_{C1S}$ monomer proved unsuccessful. Analysis of the self rotation function revealed $D_9$ symmetry in the asymmetric unit (not shown). On the basis of on the $CsgG_{C1S}$ structure, a nonameric search model was generated in the assumption that after going from a $C_9$ to $C_9$ oligomer, the interprotomer arc at the particle circumference would stay approximately the same as the interprotomer angle changed from 45° to 40°, giving a calculated increase in radius of about 4 Å. Using the calculated nonamer as search model, a molecular replacement solution containing two copies was found with Phaser (McCoy, A. J. et al., J. Appl. Cryst. 2007, 40, 658-674). Inspection of density-modified and NCS-averaged electron density maps (Parrot [Cowtan, K., Acta Crystallogr. D Biol. Crystallogr. 2010, 66, 470-478]; FIG. 8) allowed manual building of the TM1 and TM2 and remodelling of adjacent residues in the protein core, as well as the building of residues 2-18, which were missing from the $CsgG_{C1S}$ model and linked the α1 helix to the N-terminal lipid anchor. Refinement of the CsgG model was performed with Buster-TNT (Smart, O. S. et al., Acta Crystallogr. D Biol. Crystallogr. 2012, 68, 368-380) and Refmac5 (Murshudov, G. N. et al., Acta Crystallogr. D Biol. Crystallogr., 2011, 67, 355-367) for initial and final refinement rounds, respectively. Eighteenfold local NCS restraints were applied throughout refinement, and Refmac5 was run employing a jelly-body refinement with sigma 0.01 and hydrogen-bond restraints generated by Prosmart (Nicholls, R. A., Long, F. & Murshudov, G. N., Acta Crystallogr. D Biol. Crystallogr. 2011, 68, 404-417). The final structure contained 34,165 atoms in 4,451 residues belonging to 18 CsgG chains (FIG. 7), with a molprobity score of 2.79; 93.0% of the residues lay in favoured regions of the Ramachandran plot (99.3% in allowed regions). No unambiguous electron density corresponding the N-terminal lipid anchor could be discerned.

Example 5: Congo Red Assay

For analysis of Congo red binding, a bacterial overnight culture grown at 37° C. in Lysogeny Broth (LB) was diluted in LB medium until a $D_{600}$ of 0.5 was reached. A 5 µl sample was spotted on LB agar plates supplemented with ampicillin (100 mg l$^{-1}$), Congo red (100 mg l$^{-1}$) and 0.1% (w/v) isopropyl β-D-thiogalactoside (IPTG). Plates were incubated at room temperature (20 to 22° C.) for 48 h to induce curli expression. The development of the colony morphology and dye binding were observed at 48 h.

Example 6: Cysteine Accessibility Assays

Cysteine mutants were generated in pMC2 using site-directed mutagenesis and expressed in E. coli LSR12 (Chapman, M. R. et al., Science, 2002, 295, 851-855). Bacterial cultures grown overnight were spotted onto LB agar plates containing 1 mM IPTG and 100 mg l$^{-1}$ ampicillin. Plates were incubated at room temperature and cells were scraped after 48 h, resuspended in 1 ml of PBS and normalized using $D_{600}$. The cells were lysed by sonication and centrifuged for 20 s at 3,000 g at 4° C. to remove unbroken cells from cell lysate and suspended membranes. Proteins in the supernatant were labelled with 15 mM methoxypolyethylene glycol-maleimide (MAL-PEG 5 kDa) for 1 h at room temperature. The reaction was stopped with 100 mM DTT and centrifuged at 40,000 r.p.m. (100,000 g) in a 50.4 Ti rotor for 20 min at 4° C. to pellet total membranes. The pellet was washed with 1% sodium lauroyl sarcosinate to solubilize cytoplasmic membranes and centrifuged again. The resulting outer membranes were resuspended and solubilized using PBS containing 1% DDM. Metal-affinity pulldowns with nickel beads were used for SDS-PAGE and anti-His western blots. E. coli LSR12 cells with empty pMC2 vector were used as negative control.

Example 7: ATR-FTIR Spectroscopy

ATR-FTIR measurements were performed on an Equinox 55 infrared spectrophotometer (Bruker), continuously purged with dried air, equipped with a liquid-nitrogen-refrigerated mercury cadmium telluride detector and a Golden Gate reflectance accessory (Specac). The internal reflection element was a diamond crystal (2 mm×2 mm) and the beam incidence angle was 45°. Each purified protein sample (1 µl) was spread at the surface of the crystal and dried under a gaseous nitrogen flow to form a film. Each spectrum, recorded at 2 cm$^{-1}$ resolution, was an average of 128 accumulations for improved signal-to-noise ratio. All the spectra were treated with water vapour contribution subtraction, smoothed at a final resolution of 4 cm$^{-1}$ by apodization and normalized on the area of the Amide I band (1,700-1,600 cm$^{-1}$) to allow their comparison (Goormaghtigh, E.; Ruysschaert, J. M., Spectrochim. Acta, 1994, 50A, 2137-2144).

Example 8: Negative Stain EM and Symmetry Determination

Negative stain EM was used to monitor in-solution oligomerization states of CsgG, $CsgG_{C1S}$ and CsgE. CsgE, $CsgG_{C1S}$ and amphipol-bound CsgG were adjusted to a concentration of 0.05 mg ml$^{-1}$ and applied to glow-discharged carbon-coated copper grids (CF-400; Electron Microscopy Sciences). After 1 min incubation, samples were blotted, then washed and stained in 2% uranyl acetate. Images were collected on a Tecnai T12 BioTWIN LaB6 microscope operating at a voltage of 120 kV, at a magnification of ×49,000 and defocus between 800 and 2,000 nm. Contrast transfer function (CTF), phase flipping and particle selection were performed as described for cryo-EM. For membrane-extracted CsgG, octadecameric particles (1,780 in all) were analysed separately from nonamers and top views. For purified CsgE a total of 2,452 particles were analysed. Three-dimensional models were obtained as described for the CsgG-CsgE cryo-EM analysis below and refined by several rounds of multi-reference alignment (MRA), multi-statistical analysis (MSA) and anchor set refinement. In all cases, after normalization and centring, images were classified using IMAGIC-4D as described in the cryo-EM section. The best classes corresponding to characteristic views were selected for each set of particles. Symmetry determination of CsgG top views was performed using the best class averages with roughly 20 images per class. The rotational autocorrelation function was calculated using IMAGIC and plotted.

Example 9: Negative Stain EM and Symmetry Determination

Negative stain EM was used to monitor in-solution oligomerization states of CsgG, CsgGC1S and CsgE. CsgE, CsgGC1S and amphipol-bound CsgG were adjusted to a concentration of 0.05 mg ml−1 and applied to glow-discharged carbon-coated copper grids (CF-400; Electron Microscopy Sciences). After 1 min incubation, samples were blotted, then washed and stained in 2% uranyl acetate. Images were collected on a Tecnai T12 BioTWIN LaB6 microscope operating at a voltage of 120 kV, at a magnification of ×49,000 and defocus between 800 and 2,000 nm. Contrast transfer function (CTF), phase flipping and particle selection were performed as described for cryo-EM. For membrane-extracted CsgG, octadecameric particles (1,780 in all) were analysed separately from nonamers and top views. For purified CsgE a total of 2,452 particles were analysed. Three-dimensional models were obtained as described for the CsgG-CsgE cryo-EM analysis below and refined by several rounds of multi-reference alignment (MRA), multi-statistical analysis (MSA) and anchor set refinement. In all cases, after normalization and centring, images were classified using IMAGIC-4D as described in the cryo-EM section. The best classes corresponding to characteristic views were selected for each set of particles. Symmetry determination of CsgG top views was performed using the best class averages with roughly 20 images per class. The rotational autocorrelation function was calculated using IMAGIC and plotted.

Example 10: CsgG-CsgE Complex Formation

For CsgG-CsgE complex formation, the solubilizing detergents in purified CsgG were exchanged for Amphipols A8-35 (Anatrace) by adding 120 ml of CsgG (24 mg ml$^{-1}$ protein in 0.5% C8E4, 4 mM LDAO, 25 mM Tris-HCl pH 8.0, 500 mM NaCl, 1 mM DTT) to 300 ml of detergent-destabilized liposomes (1 mg ml$^{-1}$ 1,2-dimyristoyl-sn-glycero-3-phosphocholine (DMPC) and 0.4% LDAO) and incubating for 5 min on ice before the addition of 90 ml of A8-35 amphipols at 100 mg ml$^{-1}$ stock. After an additional 15 min incubation on ice, the sample was loaded on a Superose 6 10/300 GL (GE Healthcare) column and gel filtration was performed in 200 mM NaCl, 2.5% xylitol, 25 mM Tris-HCl pH 8, 0.2 mM DTT. An equal volume of purified monomeric CsgE in 200 mM NaCl, 2.5% xylitol, 25 mM Tris-HCl pH 8, 0.2 mM DTT was added to the amphipol-solubilized CsgG at final protein concentrations of 15 and 5 mM for CsgE and CsgG, respectively, and the sample was run at 125 V at 18° C. on a 4.5% native PAGE in 0.5×TBE buffer. For the second, denaturing dimension, the band corresponding to the CsgG-CsgE complex was cut out of unstained lanes run in parallel on the same gel, boiled for 5 min in Laemmli buffer (60 mM Tris-HCl pH 6.8, 2% SDS, 10% glycerol, 5% 2-mercaptoethanol, 0.01% bromophenol blue) and run on 4-20% SDS-PAGE. Purified CsgE and CsgG were run alongside the complex as control samples. Gels were stained with InstantBlue Coomassie for visual inspection or SYPRO orange for stoichiometry assessment of the CsgG-CsgE complex by fluorescence detection (Typhoon FLA 9000) of the CsgE and CsgG bands on SDS-PAGE, yielding a CsgG/CsgE ratio of 0.97.

Example 11: CsgG-CsgE Cryo-EM

Cryo-electron microscopy was used to determine the in-solution structure of the $C_9$ CsgG-CsgE complex. CsgG-CsgE complex prepared as described above was bound and eluted from a HisTrap FF (GE Healthcare) to remove unbound CsgG, and on elution it was immediately applied to Quantifoil R2/2 carbon coated grids (Quantifoil Micro Tools GmbH) that had been glow-discharged at 20 mA for 30 s. Samples were plunge-frozen in liquid nitrogen using an automated system (Leica) and observed under a FEI F20 microscope operating at a voltage of 200 kV, a nominal magnification of ×50,000 under low-dose conditions and a defocus range of 1.4-3 mm. Image frames were recorded on a Falcon II detector. The pixel size at the specimen level was 1.9 Å per pixel. The CTF parameters were assessed using CTFFIND3 (Mindell, J. A. & Grigorieff, N., J. Struct. Biol. 2003, 142, 334-347), and the phase flipping was done in SPIDER (Shaikh, T. R. et al., Nature Protocols, 2008, 3, 1941-1974). Particles were automatically selected from CTF-corrected micrographs using BOXER (EMAN2; Tang, G. et al., J. Struct. Biol., 2007, 157, 38-46). Images with an astigmatism of more than 10% were discarded. A total of 1,221 particles were selected from 75 micrographs and windowed into 128-pixel×128-pixel boxes. Images were normalized to the same mean and standard deviation and high-pass filtered at a low-resolution cut-off of −200 Å. They were centred and then subjected to a first round of MSA. An initial reference set was obtained using reference free classification in IMAGIC-4D (Image Science Software). The best classes corresponding to characteristic side views of the $C_9$ cylindrical particles were used as references for the MRA. For CsgG-CsgE complex, the first three-dimensional model was calculated from the best 125 characteristic views (with good contrast and well-defined features) encompassing 1,221 particles of the complex with orientations determined by angular reconstitution (Image Science Software). The three-dimensional map was refined by iterative rounds of MRA, MSA and anchor set refinement. The resolution was estimated to be 24 Å by Fourier shell correlation (FSC) according to the 0.5 criteria level (FIG. 5). Visualization of the map and Figures was performed in UCSF Chimera (Pettersen, E. F. et al., J. Comput. Chem., 2004, 25, 1605-1612).

Example 12: Single-Channel Current Analysis of CsgG and CsgG+CsgE Pores

Under negative field potential, CsgG pores show two conductance states. FIG. 5 shows representative single-channel current traces of, respectively, the normal (measured at +50, 0 and −50 mV) and the low-conductance forms (measured at 0, +50 and −50 mV). No conversions between both states were observed during the total observation time (n=22), indicating that the conductance states have long lifetimes (second to minute timescale). The lower left panel shows a current histogram for the normal and low-conductance forms of CsgG pores acquired at +50 and −50 mV (n=33). I-V curves for CsgG pores with regular and low conductance are shown in the lower right panel. The data represent averages and standard deviations from at least four independent recordings. The nature or physiological existence of the low-conductance form is unknown.

Figure 6:
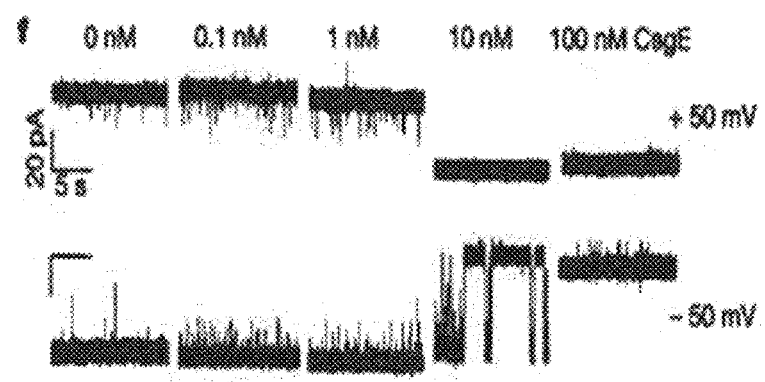
FIG. 6 shows single-channel current recordings of PPB-reconstituted CsgG at +50 mV or −50 mV and supplemented with incremental concentrations of CsgE. Horizontal scale bars lie at 0 pA.

FIG. 6 shows the results of electrophysiology of CsgG channels titrated with the accessory factor CsgE. The plots display the fraction of open, intermediate and closed channels as a function of CsgE concentration. Open and closed states of CsgG are illustrated in FIG. 6 (0 nM and 100 nM CsgE respectively). Increasing the concentration of CsgE to more than 10 nM leads to the closure of CsgG pores. The effect occurs at +50 mV (left) and −50 mV (right), ruling out the possibility that the pore blockade is caused by electrophoresis of CsgE (calculated pI 4.7) into the CsgG pore. An infrequent (<5%) intermediate state has roughly half the conductance of the open channel. It may represent CsgE-induced incomplete closures of the CsgG channel; alternatively, it could represent the temporary formation of a CsgG dimer caused by the binding of residual CsgG monomer from the electrolyte solution to the membrane-embedded pore. The fraction for the three states was obtained from all-point histogram analysis of single-channel current traces. The histograms yielded peak areas for up to three states, and the fraction for a given state was obtained by dividing the corresponding peak area by the sum of all other states in the recording. Under negative field potential, two open conductance states are discerned, similar to the observations for CsgG (see a). Because both open channel variations were blocked by higher CsgE concentrations, the 'open' traces in FIG. 6 (0 nM) combine both conductance forms. The data in the plot represent averages and standard deviations from three independent recordings.

The crystal structure, size-exclusion chromatography and EM show that detergent extracted CsgG pores form non-native tail-to-tail stacked dimers (for example, two nonamers as D9 particle, FIG. 7) at higher protein concentration. These dimers can also be observed in single-channel recordings. The upper panel shows the single-channel current trace of a stacked CsgG pore at +50, 0 and −50 mV (left to right). The lower left panel shows a current histogram of dimeric CsgG pores recorded at +50 and −50 mV. The experimental conductances of +16.2±1.8 and −16.0±3.0 pA (n=15) at +50 and −50 mV, respectively, are near the theoretically calculated value of 23 pA. The lower right panel shows an I-V curve for the stacked CsgG pores. The data represent averages and standard deviations from six independent recordings.

The ability of CsgE to bind and block stacked CsgG pores was tested by electrophysiology. Shown are single-channel current traces of stacked CsgG pore in the presence of 10 or 100 nM CsgE at +50 mV (upper) and −50 mV (lower) are shown. The current traces indicate that otherwise saturating concentrations of CsgE do not lead to pore closure for stacked CsgG dimers. These observations are in good agreement with the mapping of the CsgG-CsgE contact zone to helix 2 and the mouth of the CsgG periplasmic cavity as discerned by EM and site-directed mutagenesis (FIGS. 5 and 6).

Example 13: Bile Salt Toxicity Assay

Outer-membrane permeability was investigated by decreased growth on agar plates containing bile salts. Ten-fold serial dilutions of *E. coli* LSR12 (Chapman, M. R. et al., Science, 2002, 295, 851-855) cells (5 ml) harbouring both pLR42 (Nenninger, A. A. et al., Mol. Microbiol., 2011, 81, 486-499) and pMC2 (Robinson, L. S. et al., Mol. Microbiol., 2006, 59, 870-881) (or derived helix 2 mutants) were spotted on McConkey agar plates containing 100 mg l$^{-1}$ ampicillin, 25 mg l$^{-1}$ chloramphenicol, 1 mM IPTG with or without 0.2% (w/v) L-arabinose. After incubation overnight at 37° C., colony growth was examined.

Example 14: Single-Channel Current Recordings

Single-channel current recordings were performed using parallel high-resolution electrical recording with the Orbit 16 kit from Nanion. In brief, horizontal bilayers of 1,2-diphytanoyl-sn-glycero-3-phosphocholine (Avanti Polar Lipids) were formed over microcavities (of subpicolitre volume) in a 16-channel multielectrode cavity array (MECA) chip (Ionera) (del Rio Martinez, J. M., ACS NanoSmall, 2014, 5, 8080-8088). Both the cis and trans cavities above and below the bilayer contained 1.0 M KCl, 25 mM Tris-HCl pH 8.0. To insert channels into the membrane, CsgG dissolved in 25 mM Tris-HCl pH 8.0, 500 mM NaCl, 1 mM DTT, 0.5% C8E4, 5 mM LDAO was added to the cis compartment to a final concentration of 90-300 nM. To test the interaction of the CsgG channel with CsgE, a solution of the latter protein dissolved in 25 mM Tris-HCl pH 8.0, 150 mM NaCl was added to the cis compartment to final concentrations of 0.1, 1, 10 and 100 nM. Transmembrane currents were recorded at a holding potential of +50 mV and −50 mV (with the cis side grounded) using a Tecella Triton 16-channel amplifier at a low-pass filtering frequency of 3 kHz and a sampling frequency of 10 kHz. Current traces were analysed using the Clampfit of the pClamp suite (Molecular Devices). Plots were generated using Origin 8.6 (Microcal) (Movileanu, L., Nature Biotechnol., 2000, 18, 1091-1095).

Measured currents were compared with those calculated based on the pore dimensions of the CsgG X-ray structure, modelled to be composed of three segments: the transmembrane section, the periplasmic vestibule, and the inner channel constriction connecting the two. The first two segments were modeled to be of conical shape while the constriction was represented as a cylinder. The corresponding resistances $R_1$, $R_2$ and $R_3$, respectively, were calculated as $$R_1 = L_1/(\pi D_1 d_1 \kappa)$$

$$R_2 = L_2/(\pi D_2 d_2 \kappa)$$

$$R_3 = L_3/(\pi d_1 d_2 \kappa)$$

where $L_1$, $L_2$ and $L_3$ are the axial lengths of the segments, measuring 3.5, 4.0 and 2.0 nm, respectively, and $D_1$, $d_1$, $D_2$ and $d_2$ are the maximum and minimum diameters of segments 1 and 2, measuring 4.0, 0.8, 3.4 and 0.8 nm, respectively. The conductivity $\kappa$ has a value of 10.6 S m$^{-1}$. The current was calculated by inserting $R_1$, $R_2$ and $R_3$ and voltage V=50 mV into $$I = V/(R_1 + R_2 + R_3)$$

Access resistance was not found to alter the predicted current significantly.

Single channel current recordings such as those described above may be made in the presence of analytes, thereby allowing the channel to assume the role of a biosensor.

Figures 9A, 9B, 9C:
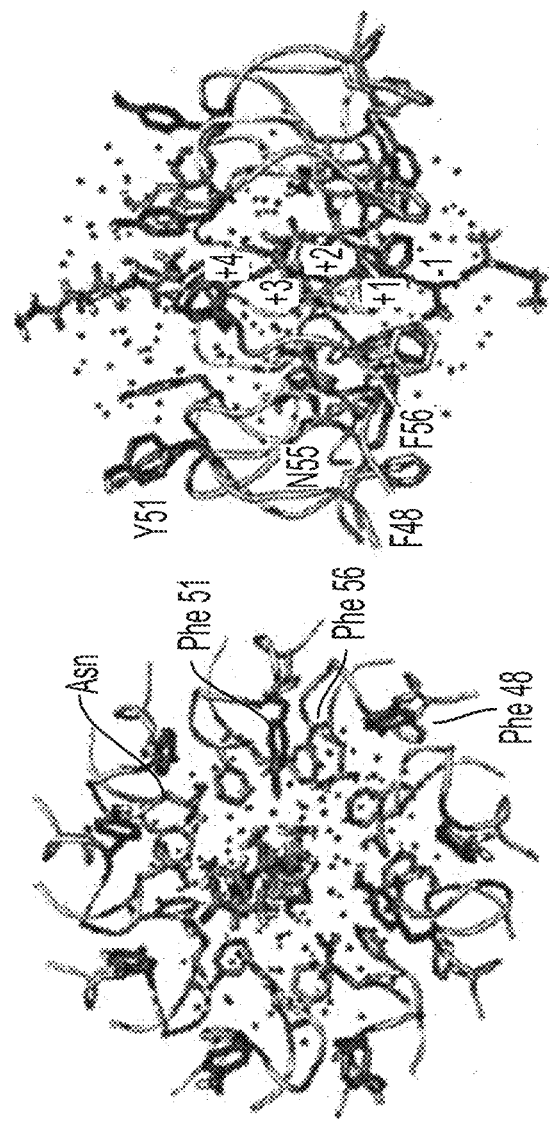
FIG. 9A-9C shows top (FIG. 9a) and side (FIG. 9b) views of the CsgG constriction modelled with a polyalanine chain threaded through the channel in an extended conformation, shown in a C-terminal to N-terminal direction. The modelled solvation of the polyalanine chain, position as in FIG. 9b, is shown in FIG. 9c with C-loops removed for clarity (shown solvent molecules are those within 10 Å of the full polyalanine chain).
Figure 10:
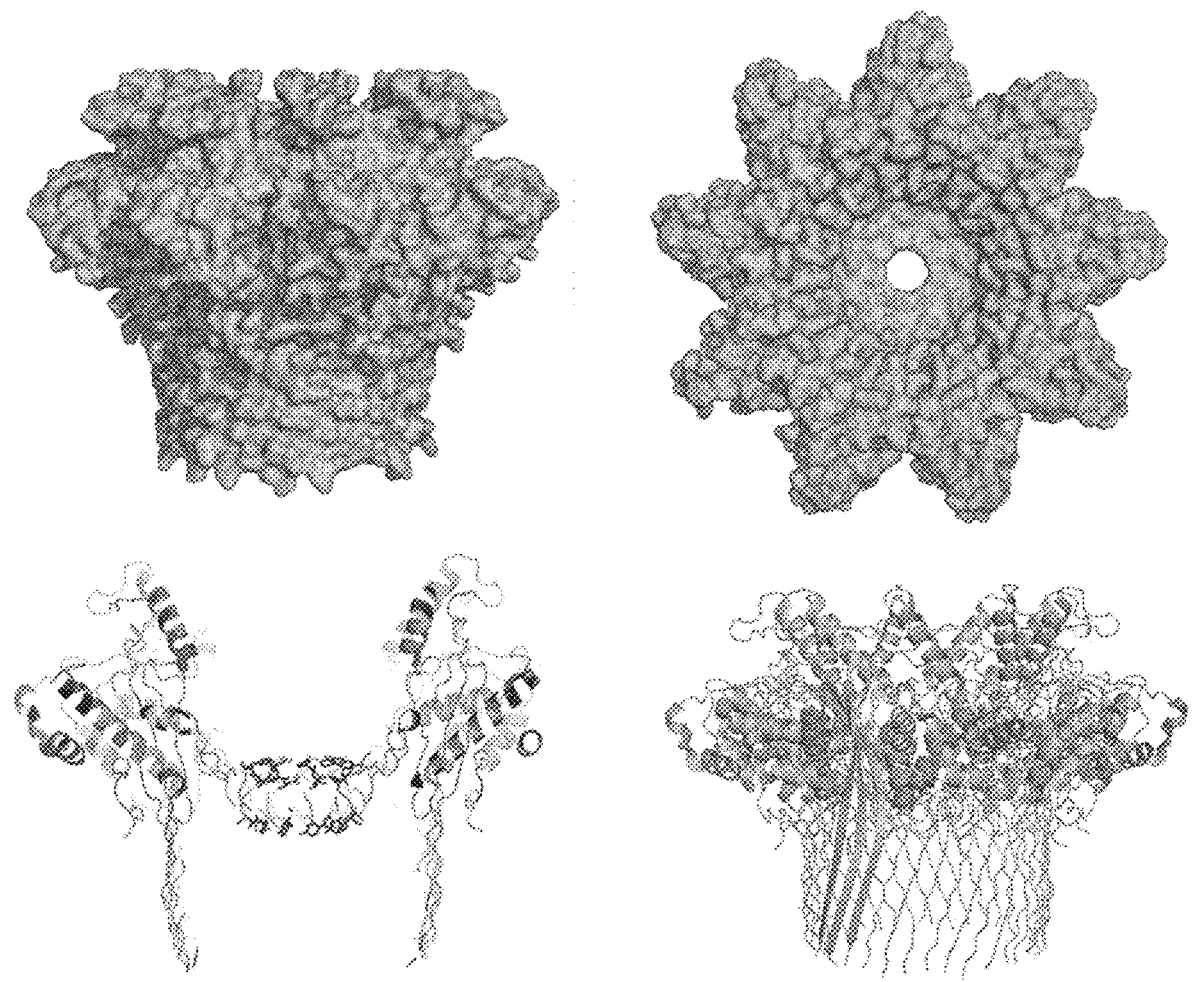
FIG. 10: Illustrates CsgG from E. coli.
Figure 11:
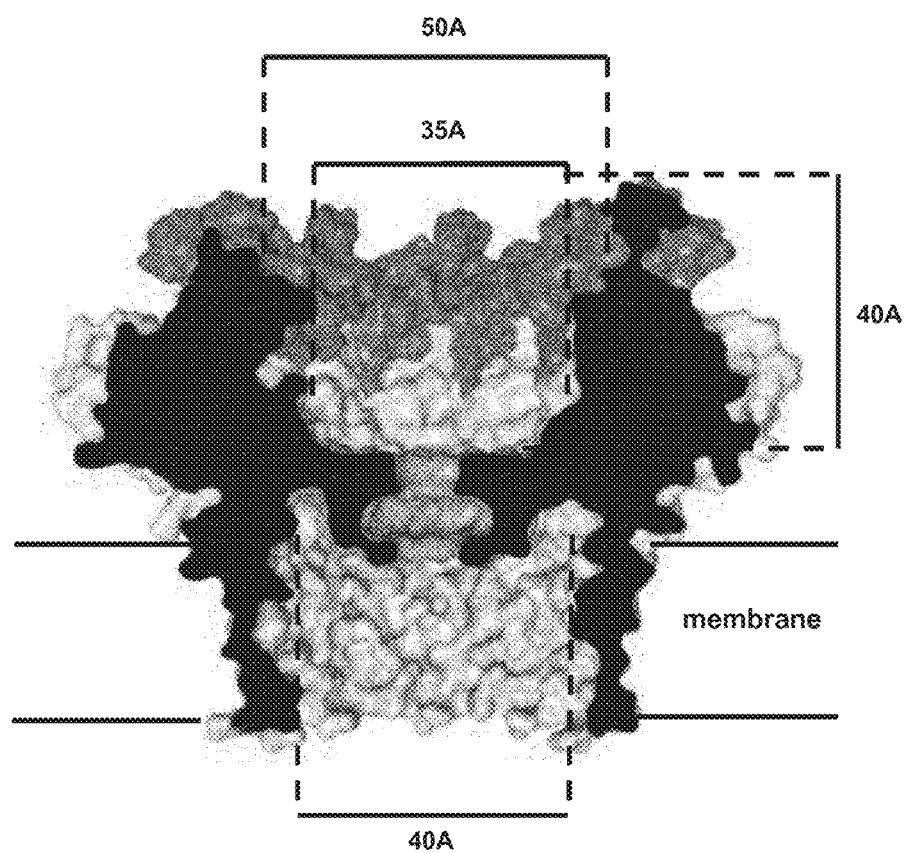
FIG. 11: Illustrates the dimensions of CsgG.

Example 15: Molecular Dynamics Simulation of CsgG Constriction with Model Polyalanine Chain The CsgG constriction has been modelled with a polyalanine chain threaded through the channel in an extended conformation, shown in FIG. 9 in a C-terminal to N-terminal direction. Substrate passage through the CsgG transporter is itself not sequence specific (Nenninger, A. A. et al., Mol. Microbiol., 2011, 81, 486-499; Van Gerven, N. et al., Mol. Microbiol. 2014, 91, 1022-1035 2014). For clarity, a polyalanine chain was used for modelling the putative interactions of a passing polypeptide chain. The modelled area is composed of nine concentric CsgG C-loops, each comprising residues 47-58. Side chains lining the constriction are shown in stick representation with Asn 55 and Phe 56 marked. Solvent molecules (water) within 10 Å of the polyalanine residues inside the constriction (residues labelled+1 to +5) are shown as dots. FIG. 9c shows the modelled solvation of the polyalanine chain, positioned as shown in FIG. 9b and with C-loops removed for clarity (shown solvent molecules are those within 10 Å of the full polyalanine chain). At the height of ring of Asn 55 and Phe 56, the solvation of the polyalanine chain is reduced to a single water shell that bridges the peptide backbone and amide-clamp side chains. Most side chains in the Tyr 51 ring have rotated towards the solvent in comparison with their inward, centre-pointing position observed in the CsgG (and the CsgG$_{C1S}$) X-ray structure. The model is the result of a 40 ns all-atom explicit solvent molecular dynamics simulation with GROMACS (Pronk, S. et al., Bioinformatics, 2013, 29, 845-854) using the AMBER99SB-ILDN (Lindorff-Larsen, K. et al., Proteins 2010, 78, 1950-1958) force field and with the Ca atoms of the residues at the extremity of the C-loop (Gln 47 and Thr 58) positionally restricted.

Example 16: Use of the CsgG Nanopore for Nucleic Acid Sequencing

The Phi29 DNA polymerase (DNAP) may be used as a molecular motor with a mutant or wild type CsgG nanopore located within a membrane to allow controlled movement of an oligomeric probe DNA strand through the pore. A voltage may be applied across the pore and a current generated from the movement of ions in a salt solution on either side of the nanopore. As the probe DNA moves through the pore, the ionic flow through the pore changes with respect to the DNA. This information has been shown to be sequence dependent and allows for the sequence of the probe to be read with accuracy from current measurements such as those described above in Example 14.

Example 17

This Example describes the simulations which were run to investigate DNA behaviour within CsgG.

Materials and Methods

Steered molecular dynamics simulations were performed to investigate the magnitude of the energetic barrier of CsgG-Eco and various mutants to DNA translocation. Simulations were performed using the GROMACS package version 4.0.5, with the GROMOS 53α6 forcefield and the SPC water model. The structure of CsgG-Eco (SEQ ID NO: 390) was taken from the protein data bank, accession code 4UV3. In order to make models of the CsgG-Eco mutants, the wild-type protein structure was mutated using PyMOL. The mutants studied were CsgG-Eco-(F56A) (SEQ ID NO: 390 with mutation F56A), CsgG-Eco-(F56A-N55S) (SEQ ID NO: 390 with mutations F56A/N55S) and CsgG-Eco-(F56A-N55S-Y51A) (SEQ ID NO: 390 with mutations F56A/N55S/Y51A).

DNA was then placed into the pores. Two different systems were set up:
 i. A single guanine nucleotide was placed into the pore, just above the constriction region (approximately 5-10 Angstroms above the residue 56 ring)
 ii. A single strand of DNA (ssDNA) was placed along the pore axis, with the 5' end towards the beta-barrel side of the pore. In this set up, the ssDNA was pre-threaded through the entire length of the pore.

The simulation box was then solvated and then energy minimised using the steepest descents algorithm.

Each system was simulated in the NPT ensemble, using the Berendsen thermostat and Berendsen barostat to 300 K. Throughout the simulation, restraints were applied to the backbone of the pore.

In order to pull the DNA through the pore, a pulling force was applied to the phosphorus atom in the single guanine simulations. In the ssDNA simulations the pulling force was applied to the phosphorus atom at the 5' end of the strand. The pulling force was applied at a constant velocity by connecting a spring between the DNA phosphorus atom mentioned above and an imaginary point travelling at a constant velocity parallel to the pore axis. Note that the spring does not have any shape nor does it undergo any hydrodynamic drag. The spring constant was equal to 5 $kJmol^{-1}A^{-2}$.

Results

Single G Translocation

Figure 12:
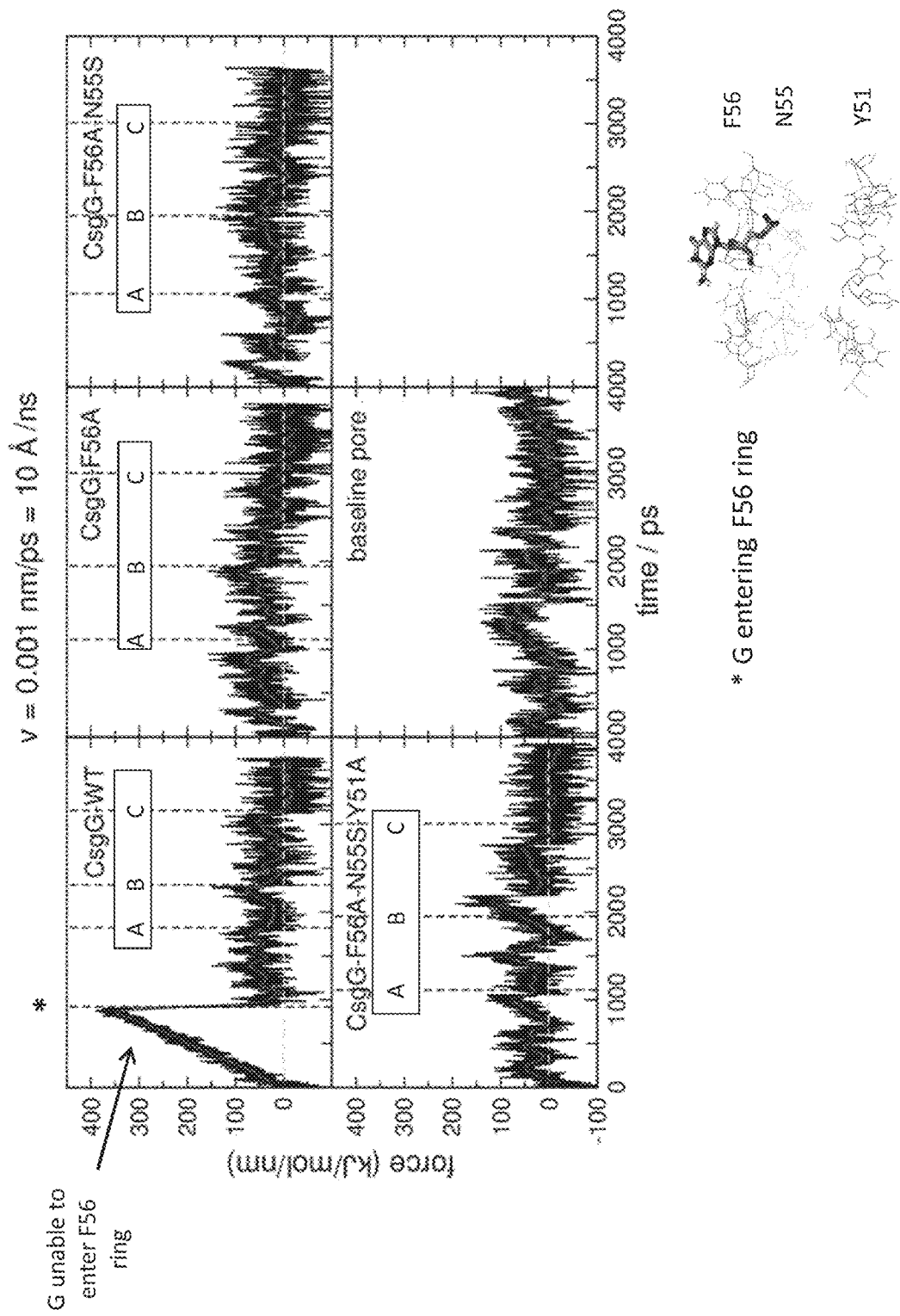
FIG. 12: Illustrates single G translocation at 10 Å/ns. There is a large barrier for entry of guanine into F56 ring in CsgG-Eco. *=G enters F56 ring. A=G stops interacting with 56 ring. B=G stops interacting with 55 ring. C=G stops interacting with 51 ring.

As shown in FIG. 12, a plot of the pulling force versus time shows that there is a large barrier for nucleotide entry into the ring of phenylalanine residues F56 in the wild type CsgG-Eco pore. There was no significant barrier to guanine translocation observed for the CsgG-Eco mutants studied.

ssDNA Translocation

Figure 13:
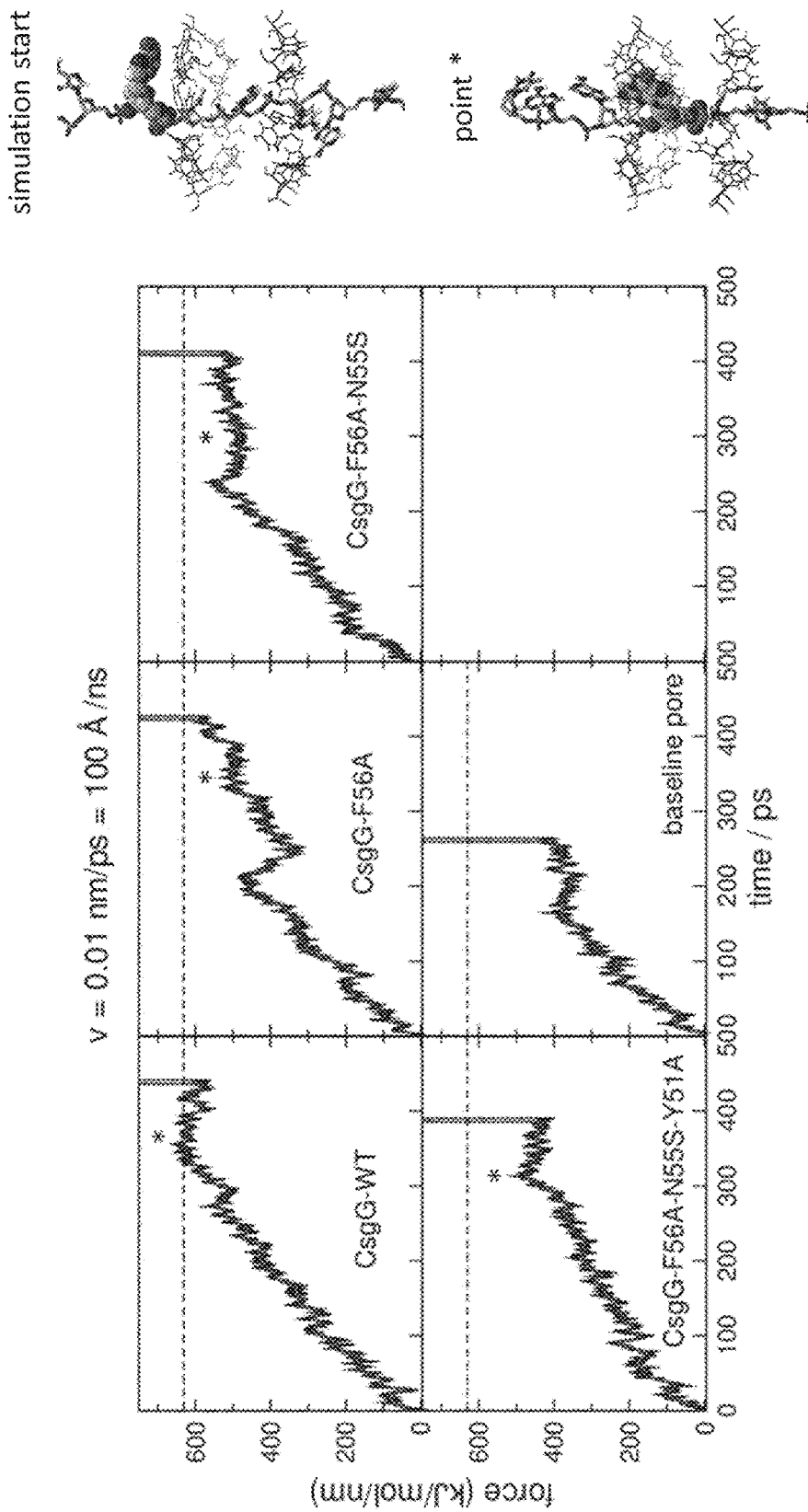
FIG. 13: Illustrates ssDNA translocation at 100 Å/ns. A larger force is required to pull the DNA through the constriction for CsgG-Eco.
Figure 14:
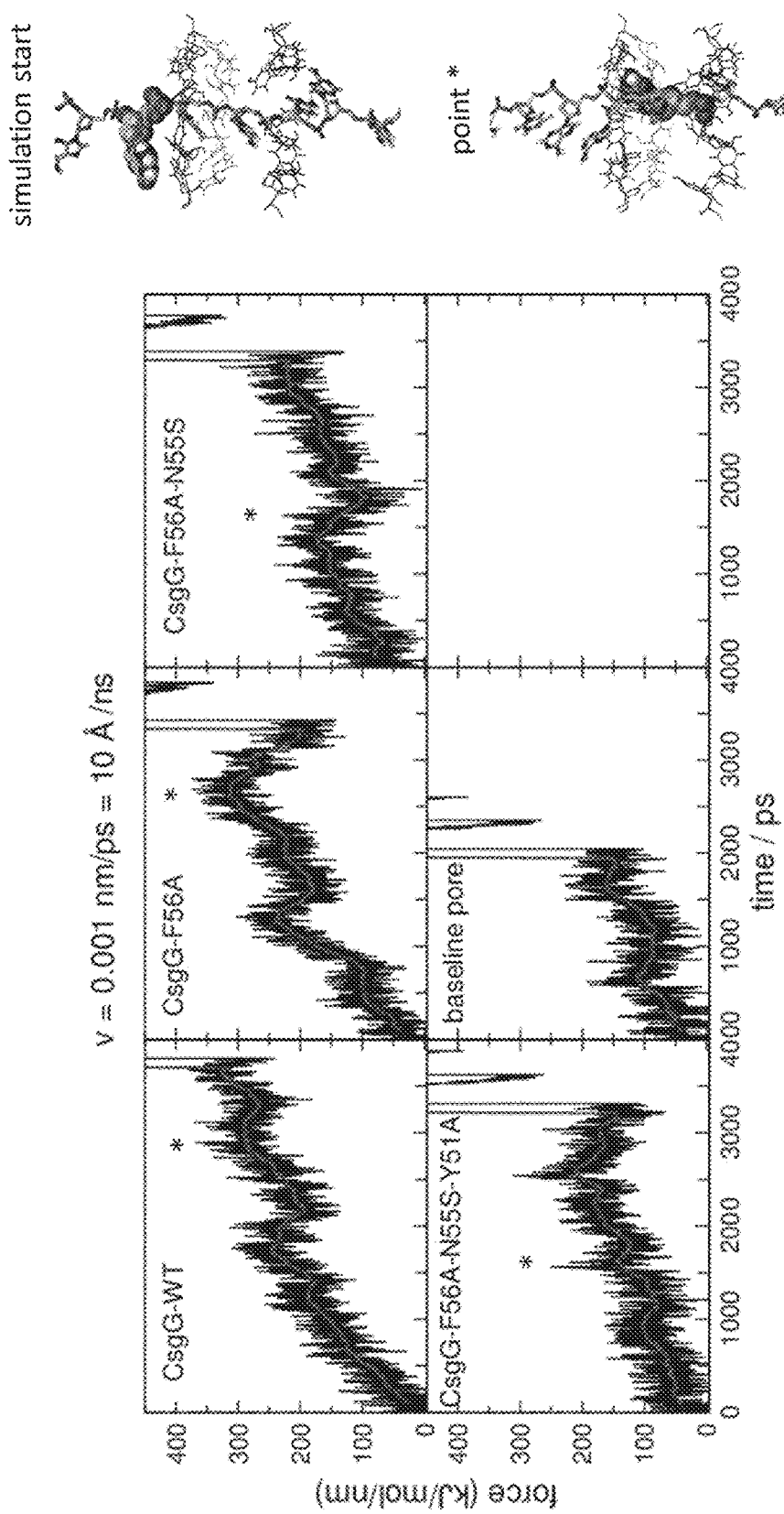
FIG. 14: Illustrates ssDNA translocation at 10 Å/ns. CsgG-F56A-N55S and CsG-F56A-N55S-Y51A mutants both have a lower barrier for ssDNA translocation.
Figure 15:
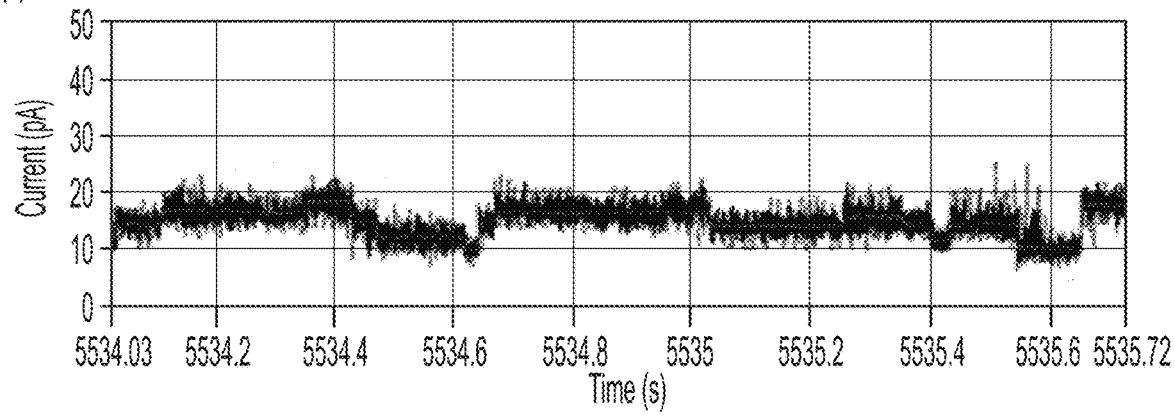
FIGS. 15 to 17: Mutant pores showing increased range compared with wild-type (WT).
Figure 15:
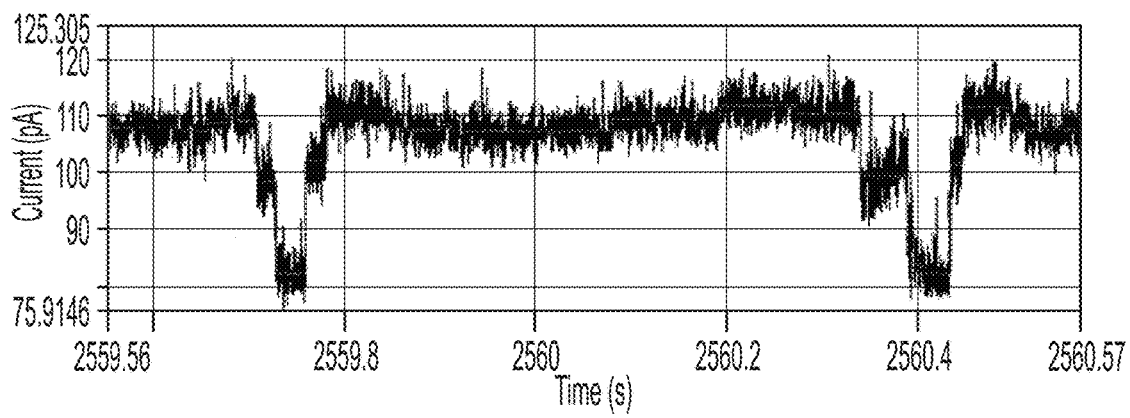
Figure 15:
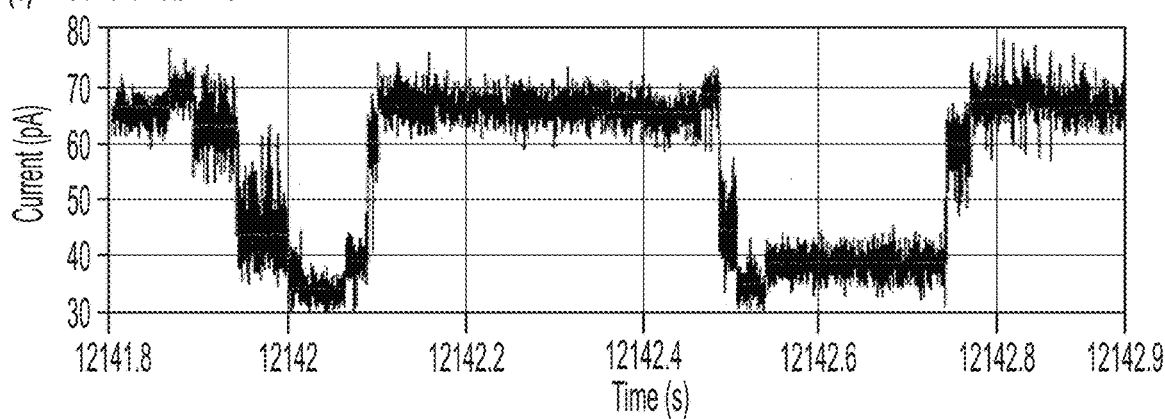
Figure 16:
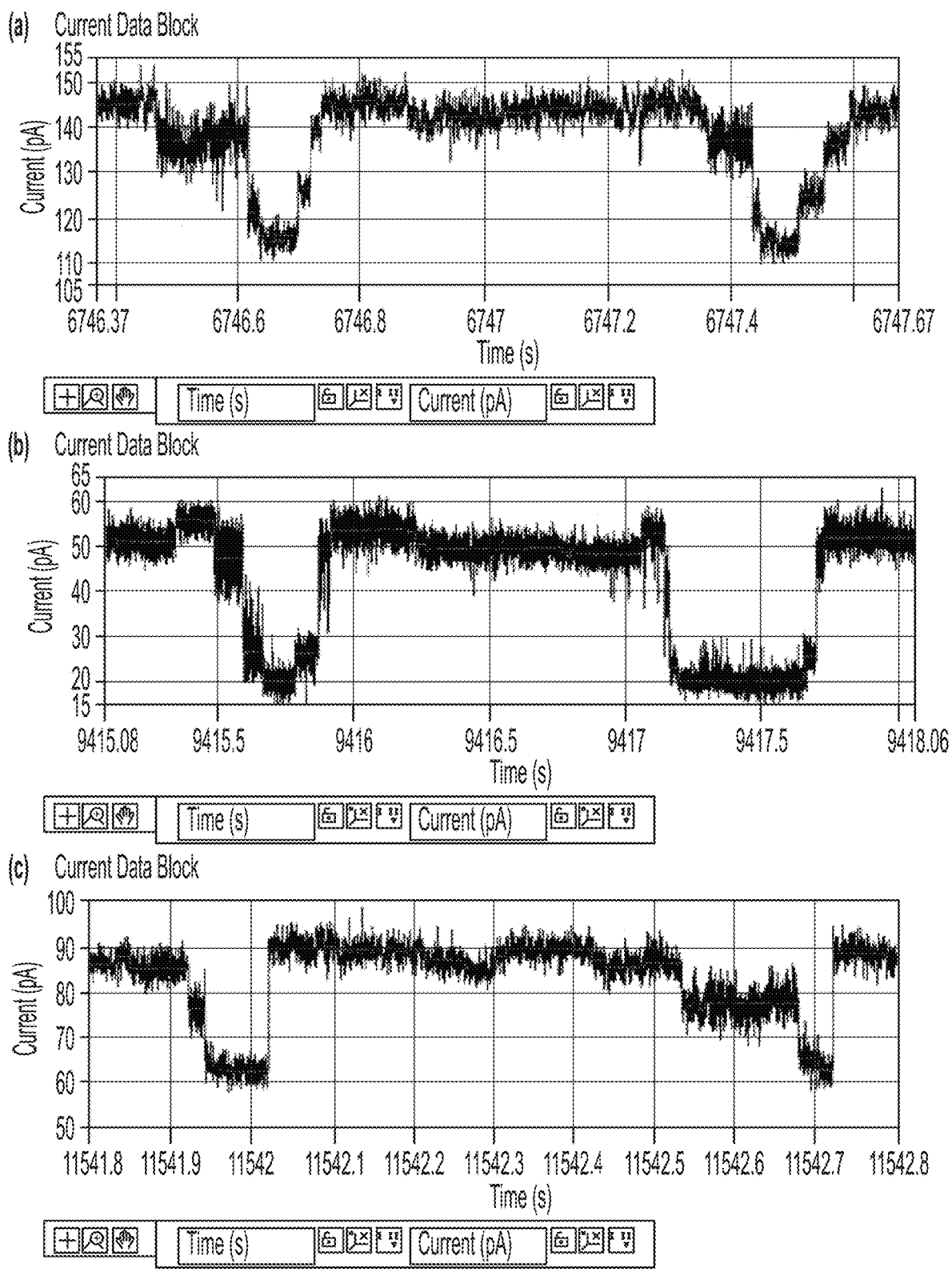
Figure 17:
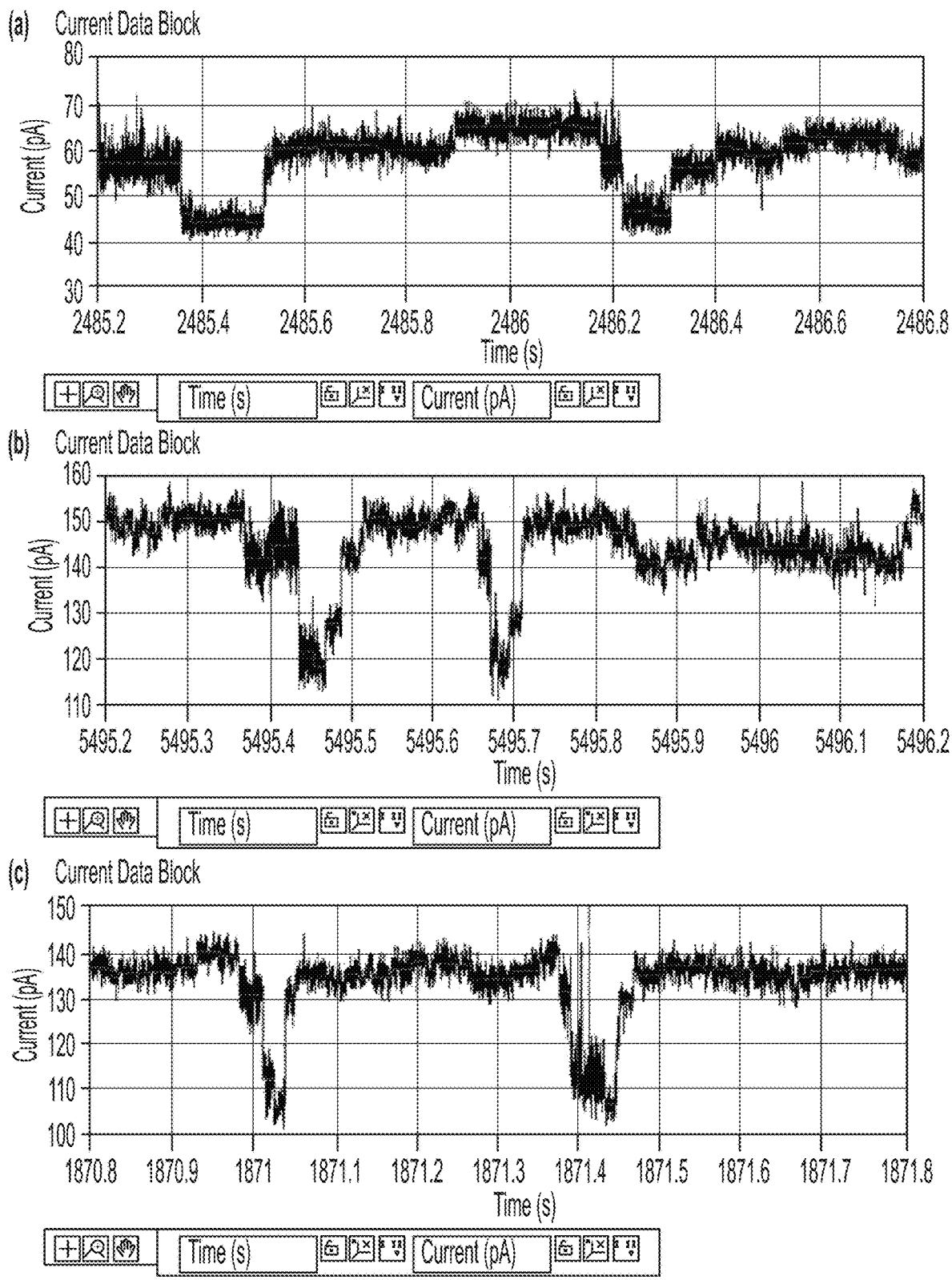

For ssDNA translocation, two simulations were run per pore with each run having a different applied pulling velocity (100 Å/ns and 10 Å/ns). As shown in FIG. 13, which illustrates the faster pulling velocity simulations, the CsgG wild-type pore required the largest pulling force to enable ssDNA translocation. As shown in FIG. 14, which illustrates the slower pulling velocity simulations, both the CsgG-Eco (wild-type, SEQ ID NO: 390) and CsgG-Eco-(F56A) pores required the largest applied force to enable ssDNA translocation. Comparisons between the pulling force required for ssDNA translocation through CsgG and MspA baseline pore, suggest that mutation of the CsgG pore is required to allow a similar level of ssDNA translocation.

Example 18

This Example describes the characterisation of several CsgG mutants.

Materials and Methods

Figure 22:
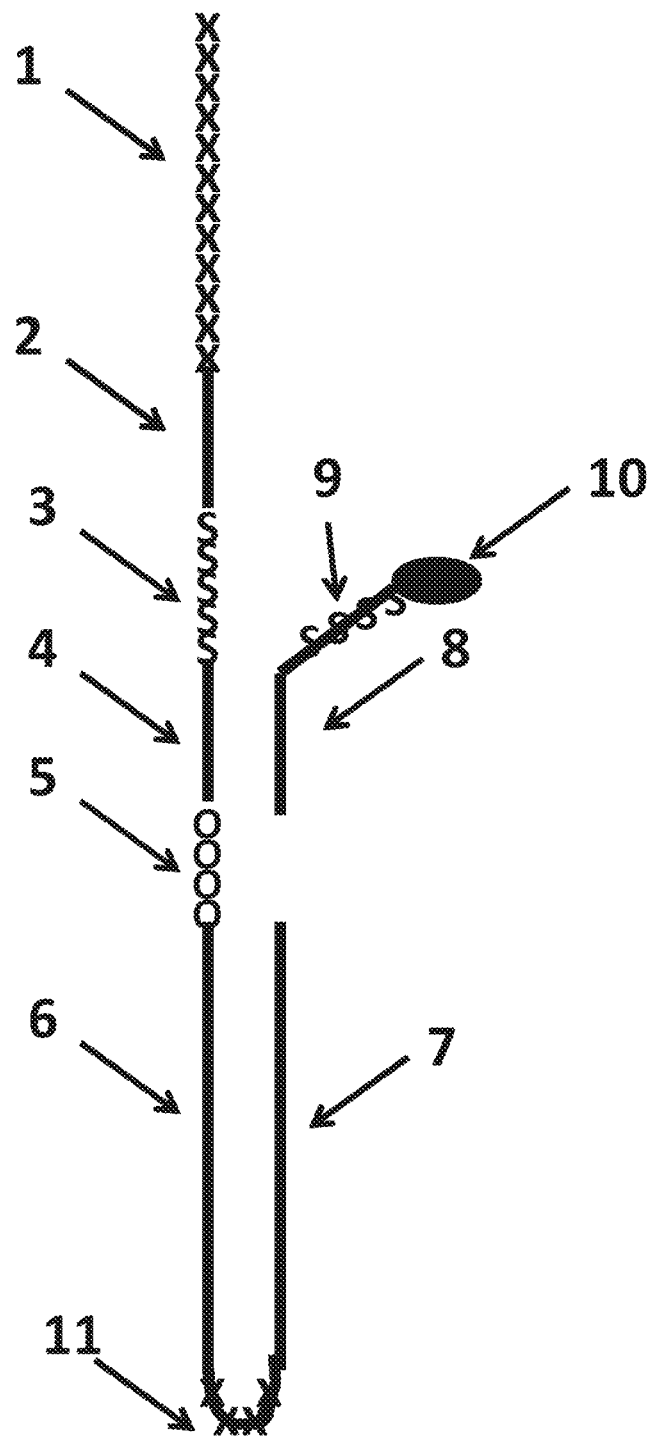
FIG. 22: shows the DNA construct X used in Example 18. The region labelled 1 corresponded to 30 SpC3 spacers. The region labelled 2 corresponded to SEQ ID NO: 415. The region labelled 3 corresponded to four iSp18 spacers. The region labelled 4 corresponded to SEQ ID NO: 416. The section labelled 5 corresponded to four 5-nitroindoles. The region labelled 6 corresponded to SEQ ID NO: 417. The region labelled 7 corresponded to SEQ ID NO: 418. The region labelled 8 corresponded to SEQ ID NO: 419 which had four iSp18 spacers (the region labelled 9) attached at the 3' end of SEQ ID NO: 419. At the opposite end of the iSp18 spacers was a 3' cholesterol tether (labelled 10). The region labelled 11 corresponded to four SpC3 spacers.

Prior to setting up the experiment, DNA construct X (final concentration 0.1 nM, see FIG. 22 for cartoon representation of construct X and description) was pre-incubated at room temperature for five minutes with T4 Dda-E94C/C109A/C136A/A360C (SEQ ID NO: 412 with mutations E94C/C109A/C136A/A360C, final concentration added to the nanopore system 10 nM, which was provided in buffer (151.5 mM KCl, 25 mM potassium phosphate, 5% glycerol, pH 7.0, 1 mM EDTA)). After five minutes, TMAD (100 µM) was added to the pre-mix and the mixture incubated for a further 5 minutes. Finally, MgCl2 (1.5 mM final concentration added to the nanopore system), ATP (1.5 mM final concentration added to the nanopore system), KCl (500 mM final concentration added to the nanopore system) and potassium phosphate buffer (25 mM final concentration added to the nanopore system) were added to the pre-mix.

Electrical measurements were acquired from a variety of single CsgG nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess CsgG nanopores. 150 uL of 500 mM KCl, 25 mM K Phosphate, 1.5 mM MgCl2, 1.5 mM ATP, pH8.0 was then flowed through the system. After 10 minutes a 150 uL of 500 mM KCl, 25 mM potassium phosphate, 1.5 mM MgCl2, 1.5 mM ATP, pH8.0 was flowed through the system and then the enzyme (T4 Dda-E94C/C109A/C136A/A360C, 10 nM final concentration), DNA construct X (0.1 nM final concentration), fuel (MgCl2 1.5 mM final concentration, ATP 1.5 mM final concentration) pre-mix (150 µL total) was then flowed into the single nanopore experimental system. The experiment was run at −120 mV and helicase-controlled DNA movement monitored.

Results

Pores showing increased range (FIGS. 15 to 17, and 27 to 39)

CsgG-Eco-(StrepII(C)) (SEQ ID NO: 390 where StepII (C) is SEQ ID NO: 435 and is attached at the C-terminus)

has a range of ~10 pA (see FIG. 15(a)) whereas the CsgG-Eco pore mutants below exhibited an increased current range—

1—CsgG-Eco-(Y51N-F56A-D149N-E185R-E201N-E203N-StrepII(C))9 (SEQ ID NO: 390 with mutations Y51N/F56A/D149N/E185R/E201N/E203N where StepII(C) is SEQ ID NO: 435 and is attached at the C-terminus) exhibited a range of −30 pA (See FIG. 15(b)).

2—CsgG-Eco-(N55A-StrepII(C))9 (SEQ ID NO: 390 with mutation N55A where StepII(C) is has SEQ ID NO: 435 and is attached at the C-terminus) exhibited a range of 35 pA (see FIG. 15(c)).

3—CsgG-Eco-(N55S-StrepII(C))9 (SEQ ID NO: 390 with mutations N55S where StepII(C) is SEQ ID NO: 435 and is attached at the C-terminus) exhibited a range of 40 pA (see FIG. 16(a)).

4—CsgG-Eco-(Y51N-StrepII(C))9 (SEQ ID NO: 390 with mutation Y51N where StepII(C) is SEQ ID NO: 435 and is attached at the C-terminus) exhibited a range of 40 pA (see FIG. 16(b)).

5—CsgG-Eco-(Y51A-F56A-StrepII(C))9 (SEQ ID NO: 390 with mutations Y51A/F56A where StepII(C) is SEQ ID NO: 435 and is attached at the C-terminus) exhibited a range of 30 pA (see FIG. 16(c)).

6—CsgG-Eco-(Y51A-F56N-StrepII(C))9 (SEQ ID NO: 390 with mutations Y51A/F56N where StepII(C) is SEQ ID NO: 435 and is attached at the C-terminus) exhibited a range of 20 pA (see FIG. 17(a)).

7—CsgG-Eco-(Y51A-N55S-F56A-StrepII(C))9 (SEQ ID NO: 390 with mutations Y51A/N55S/F56A where StepII(C) is SEQ ID NO: 435 and is attached at the C-terminus) exhibited a range of 30 pA (see FIG. 17(b)).

8—CsgG-Eco-(Y51A-N55S-F56N-StrepII(C))9 (SEQ ID NO: 390 with mutations Y51A/N55S/F56N where StepII(C) is SEQ ID NO: 435 and is attached at the C-terminus) exhibited a range of −30 pA (see FIG. 17(c)).

Figure 27:
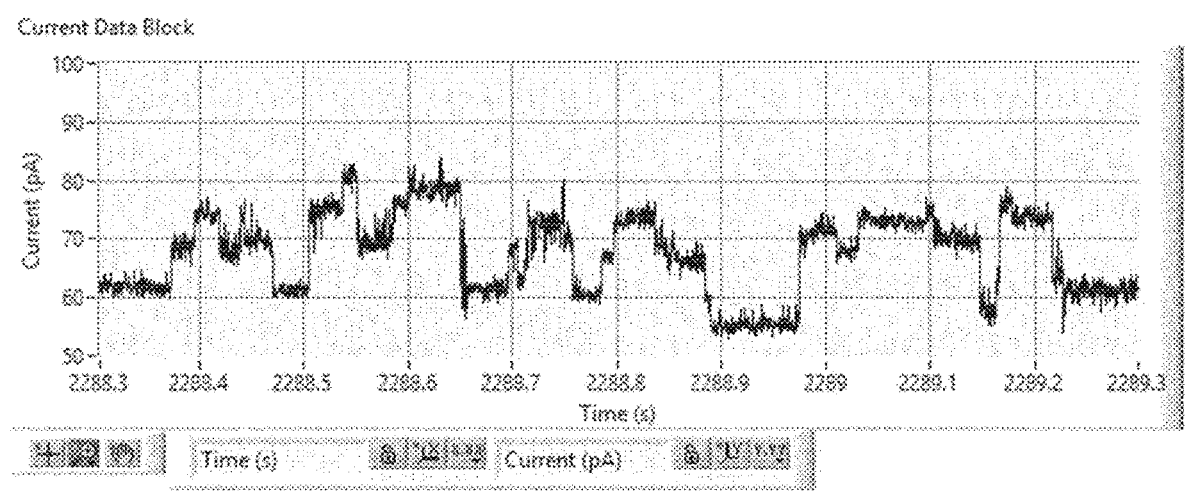
FIGS. 27 to 33: Mutant pores showing increased range compared with wild-type (WT).

13—CsgG-Eco-(F56H-StrepII(C))9 (SEQ ID NO: 390 with mutation F56H where StepII(C) is SEQ ID NO: 435 and is attached at the C-terminus) exhibited a range of −35 pA (see FIG. 27).

Figure 28:
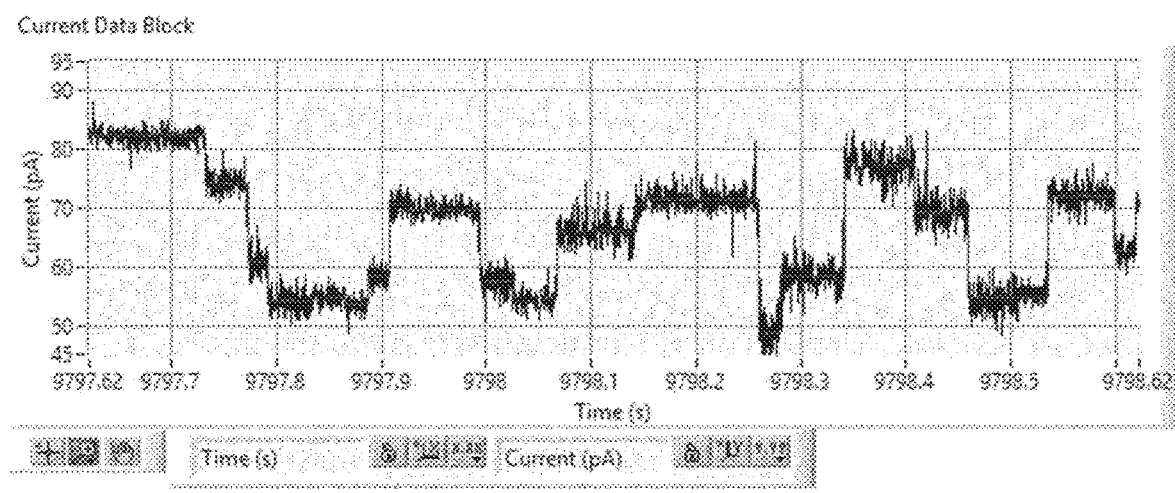

14—CsgG-Eco-(F56Q-StrepII(C))9 (SEQ ID NO: 390 with mutation F56Q where StepII(C) is SEQ ID NO: 435 and is attached at the C-terminus) exhibited a range of −40 pA (see FIG. 28).

Figure 29:
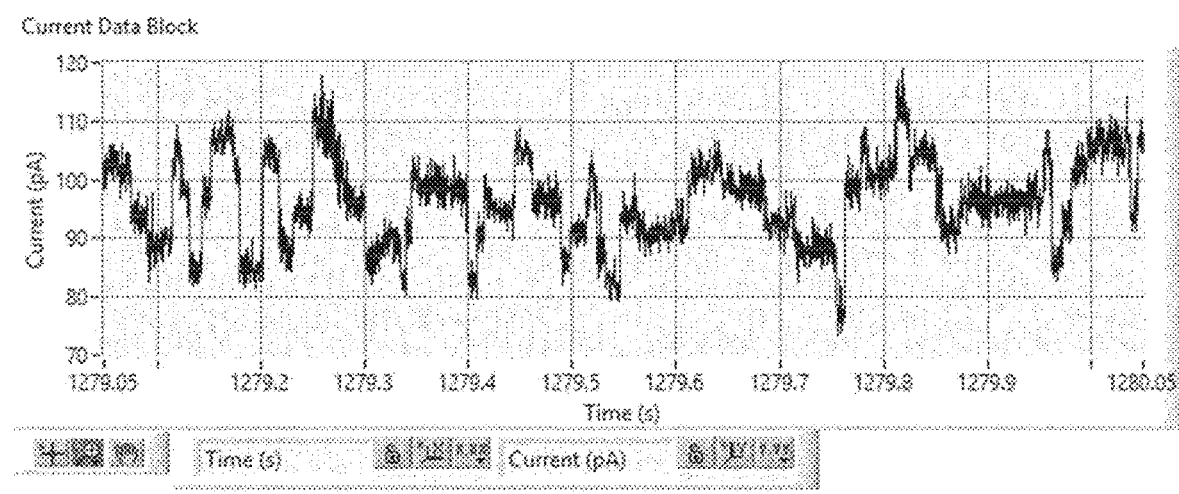

15—CsgG-Eco-(F56T-StrepII(C))9 (SEQ ID NO: 390 with mutation F56T where StepII(C) is SEQ ID NO: 435 and is attached at the C-terminus) exhibited a range of −35 pA (see FIG. 29).

Figure 30:
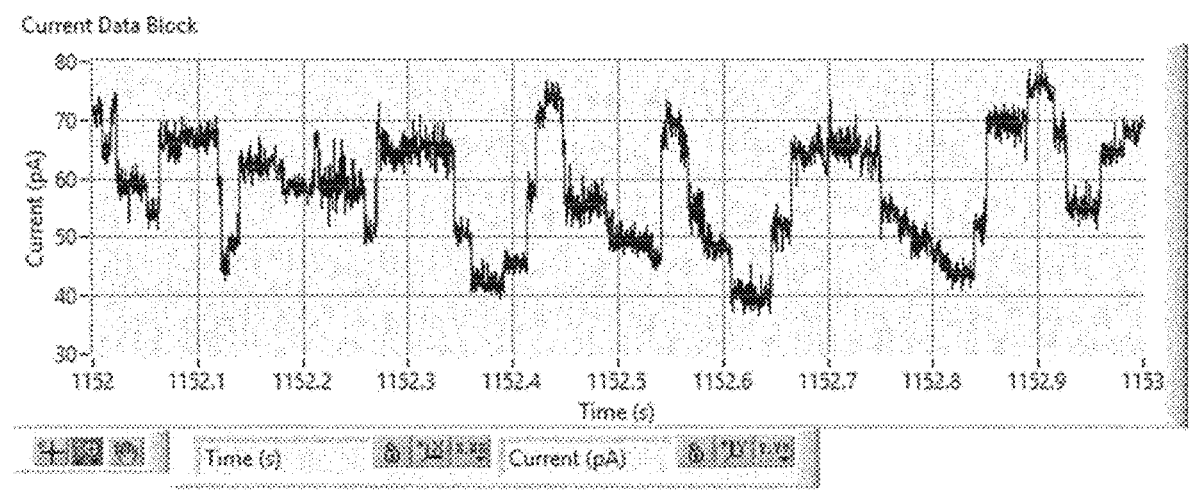

16—CsgG-Eco-(S54P/F56A-StrepII(C))9 (SEQ ID NO: 390 with mutation S54P/F56A where StepII(C) is SEQ ID NO: 435 and is attached at the C-terminus) exhibited a range of −35 pA (see FIG. 30).

Figure 31:
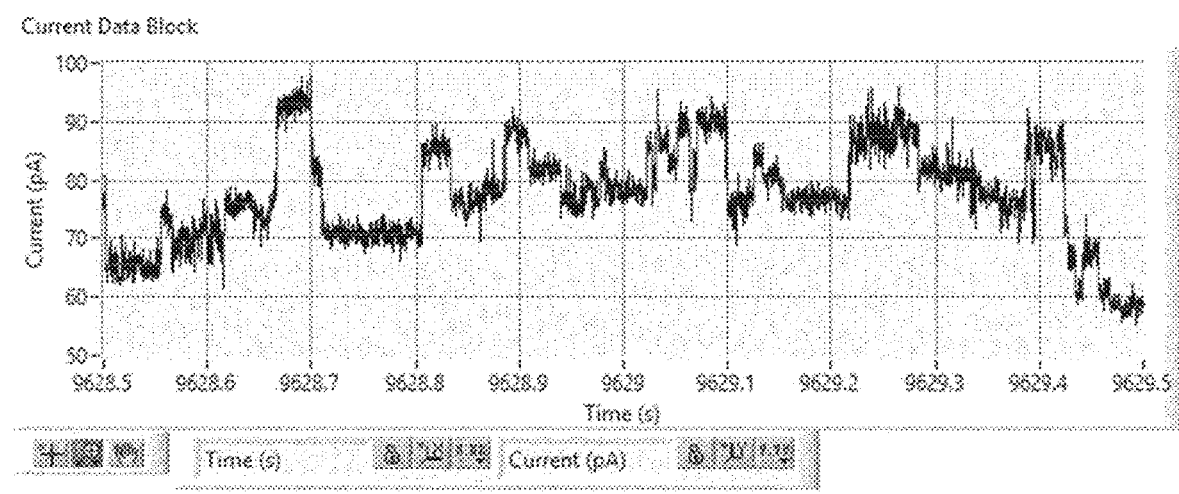

17—CsgG-Eco-(Y51T/F56A-StrepII(C))9 (SEQ ID NO: 390 with mutation Y51T/F56A where StepII(C) is SEQ ID NO: 435 and is attached at the C-terminus) exhibited a range of −30 pA (see FIG. 31).

Figure 32:
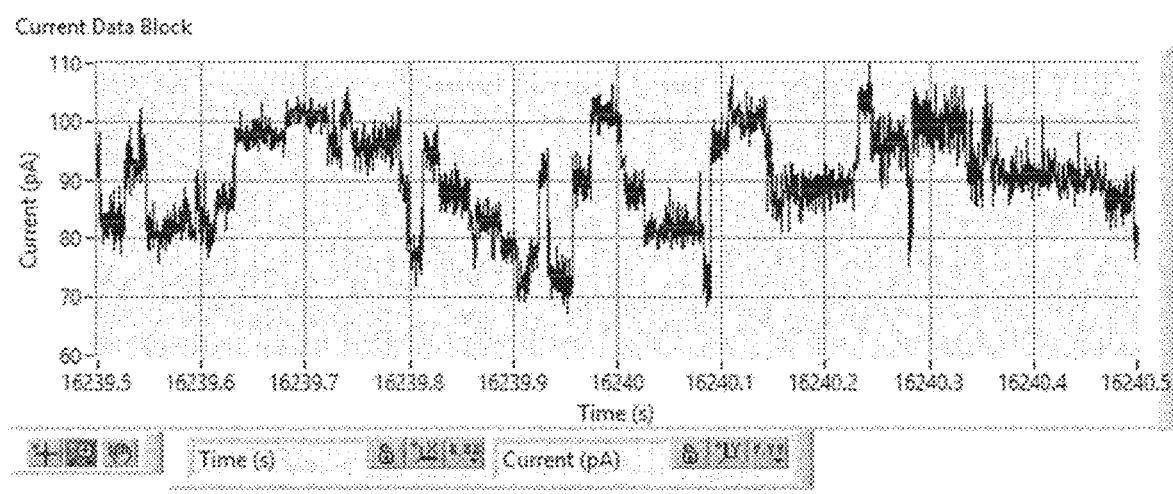

18—CsgG-Eco-(F56P-StrepII(C))9 (SEQ ID NO: 390 with mutation F56P where StepII(C) is SEQ ID NO: 435 and is attached at the C-terminus) exhibited a range of −30 pA (see FIG. 32).

Figure 33:
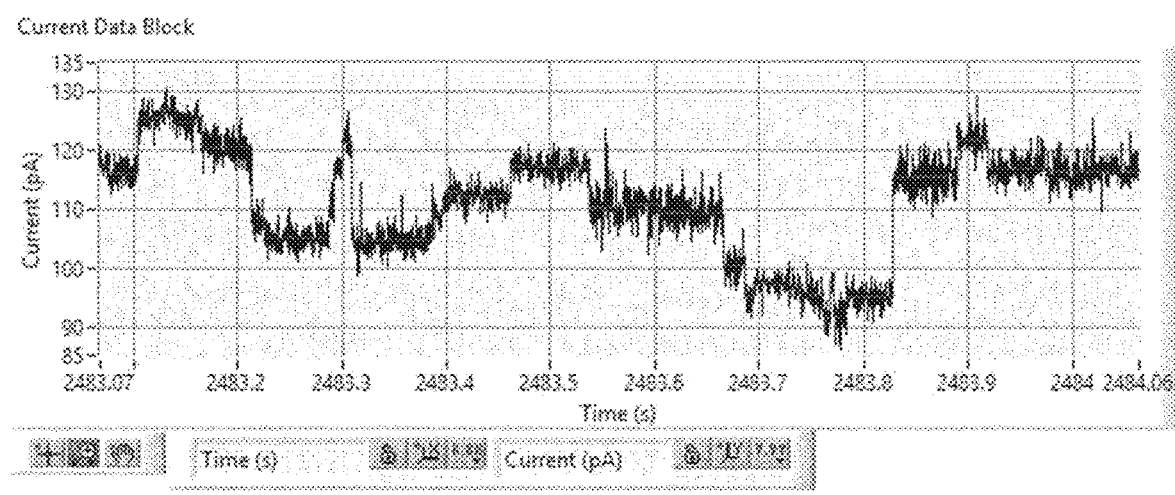

19—CsgG-Eco-(F56A-StrepII(C))9 (SEQ ID NO: 390 with mutation F56A where StepII(C) is SEQ ID NO: 435 and is attached at the C-terminus) exhibited a range of −40 pA (see FIG. 33).

Figure 34:
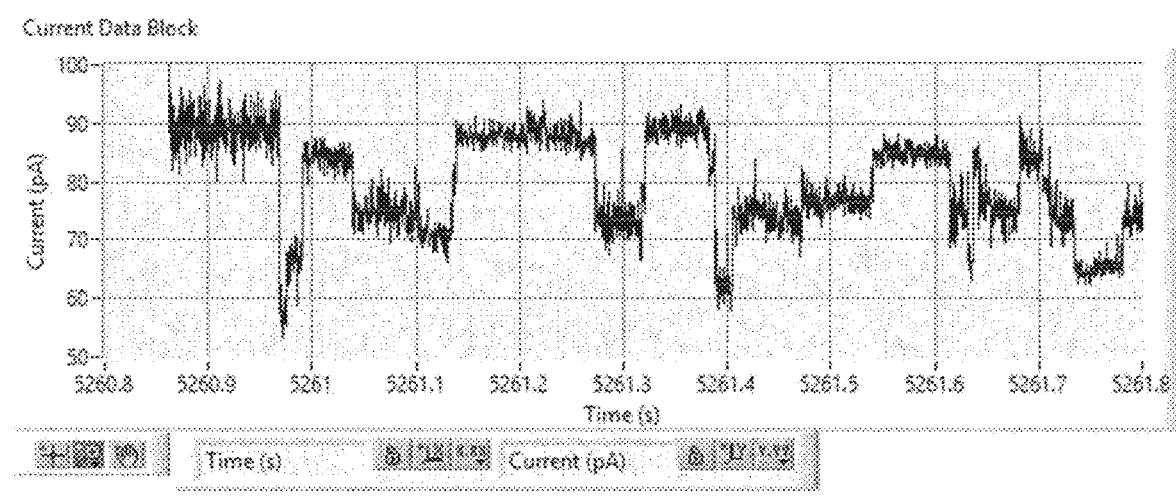
FIGS. 34 to 39: Mutant pores showing increased range compared with wild-type (WT).

20—CsgG-Eco-(Y51T/F56Q-StrepII(C))9 (SEQ ID NO: 390 with mutations Y51T/F56Q where StepII(C) is SEQ ID NO: 435 and is attached at the C-terminus) exhibited a range of −30 pA (see FIG. 34).

Figure 35:
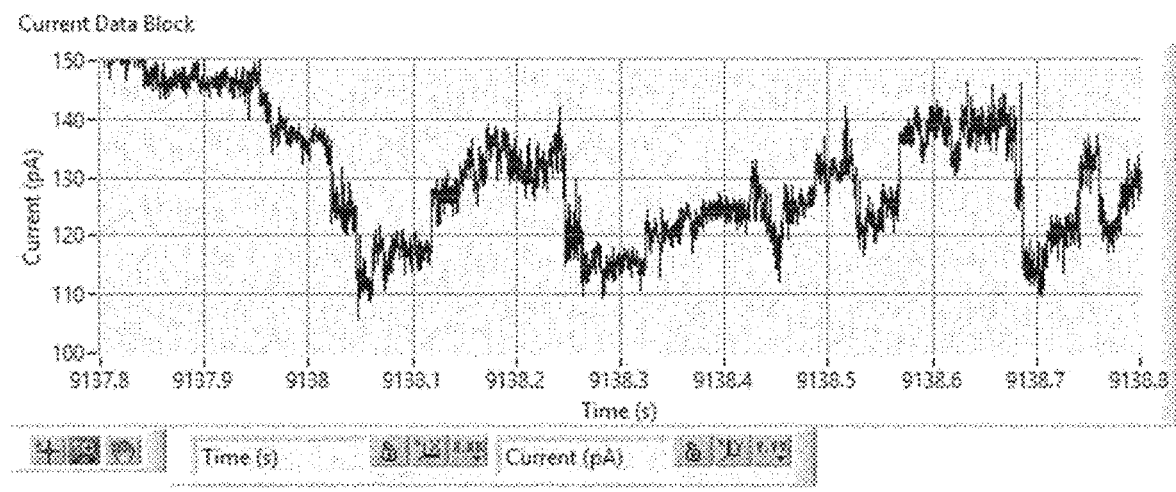

21—CsgG-Eco-(N55S/F56Q-StrepII(C))9 (SEQ ID NO: 390 with mutations N55S/F56Q where StepII(C) is SEQ ID NO: 435 and is attached at the C-terminus) exhibited a range of −35 pA (see FIG. 35).

Figure 36:
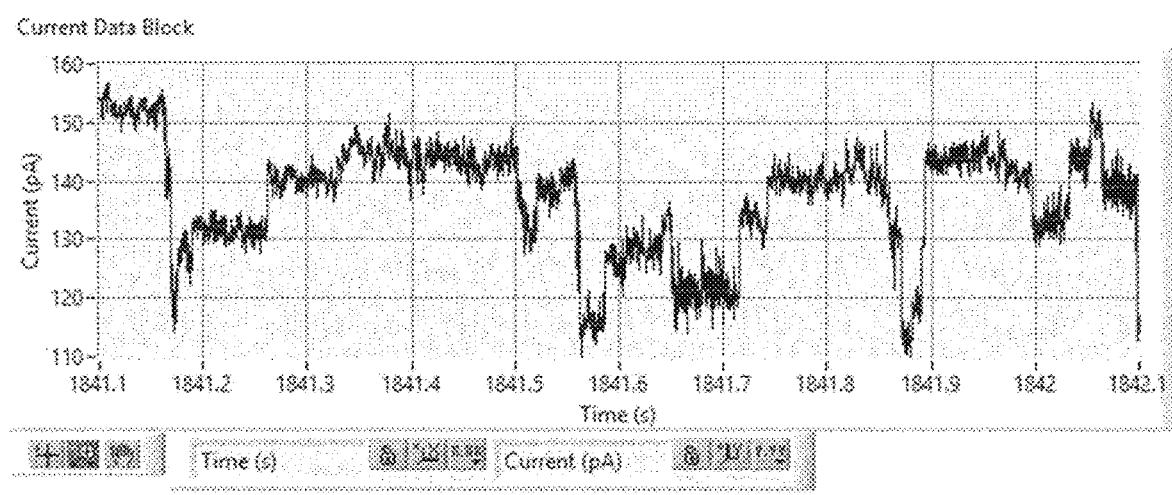

22—CsgG-Eco-(Y51T/N55S/F56Q-StrepII(C))9 (SEQ ID NO: 390 with mutations Y51T/N55S/F56Q where StepII(C) is SEQ ID NO: 435 and is attached at the C-terminus) exhibited a range of 35 pA (see FIG. 36).

Figure 37:
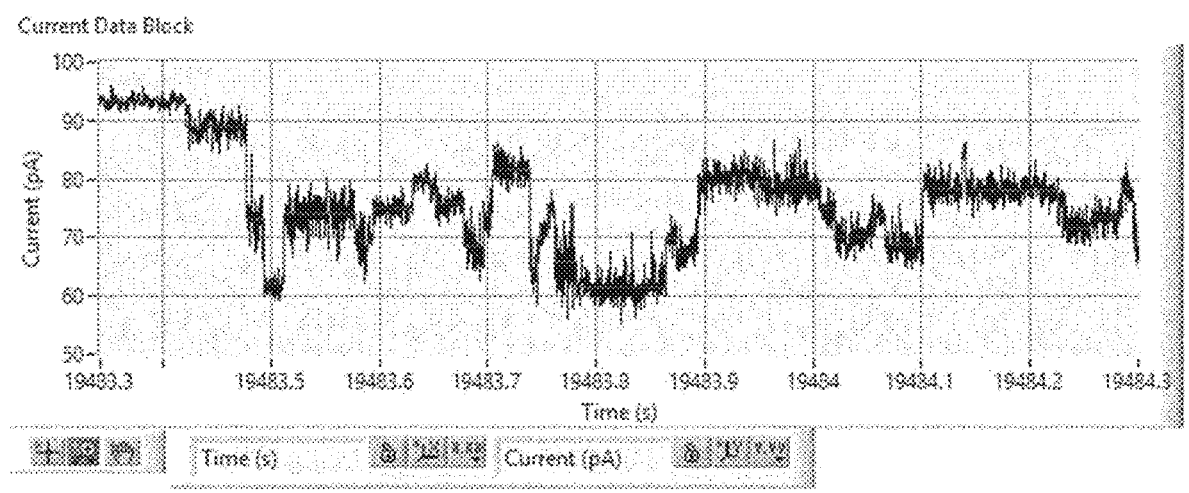

23—CsgG-Eco-(F56Q/N102R-StrepII(C))9 (SEQ ID NO: 390 with mutations F56Q/N102R where StepII(C) is SEQ ID NO: 435 and is attached at the C-terminus) exhibited a range of −30 pA (see FIG. 37).

Figure 38:
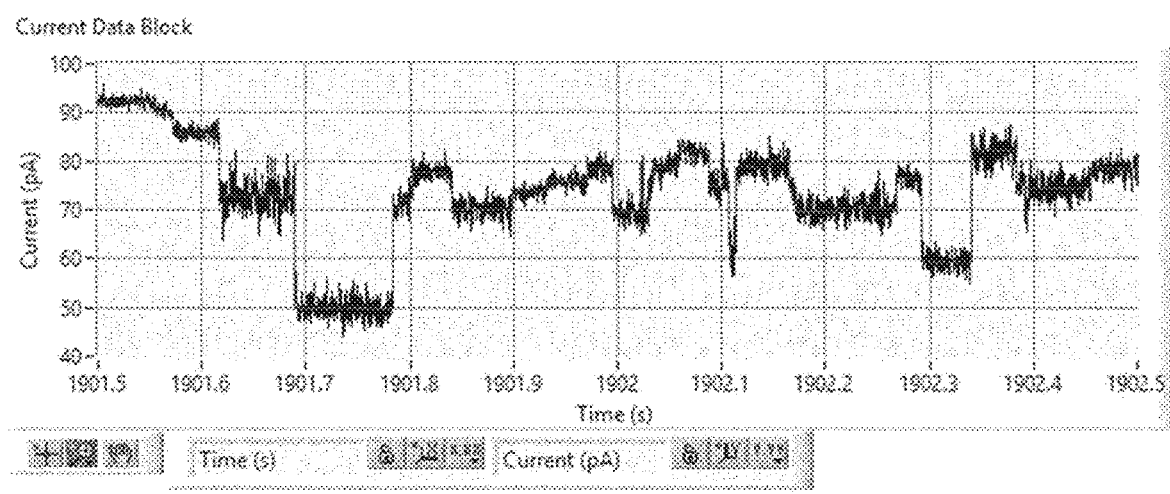

24—CsgG-Eco-(Y51Q/F56Q-StrepII(C))9 (SEQ ID NO: 390 with mutations Y51Q/F56Q where StepII(C) is SEQ ID NO: 435 and is attached at the C-terminus) exhibited a range of −40 pA (see FIG. 38).

Figure 39:
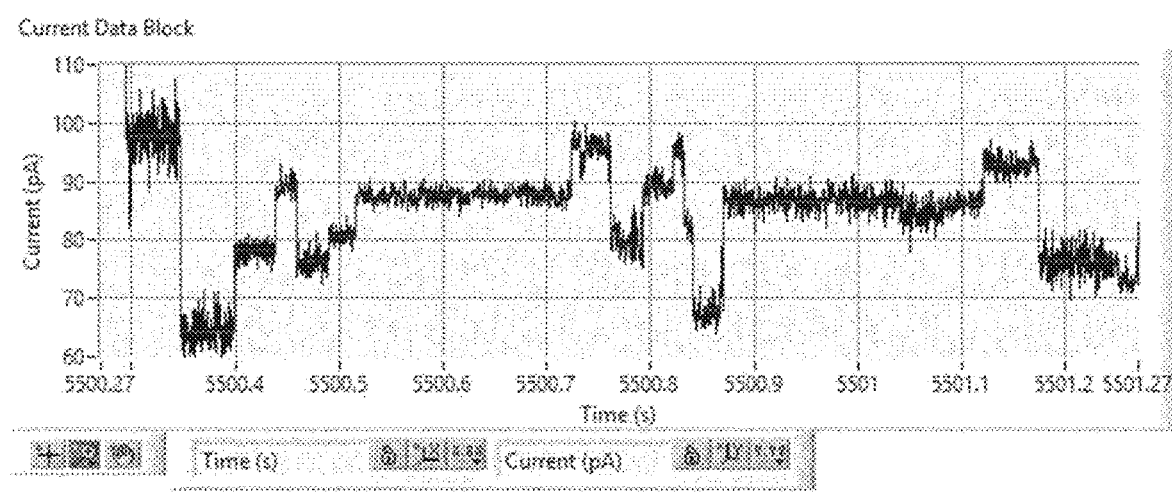

25—CsgG-Eco-(Y51A/F56Q-StrepII(C))9 (SEQ ID NO: 390 with mutations Y51A/F56Q where StepII(C) is SEQ ID NO: 435 and is attached at the C-terminus) exhibited a range of −35 pA (see FIG. 39).

Figure 18:
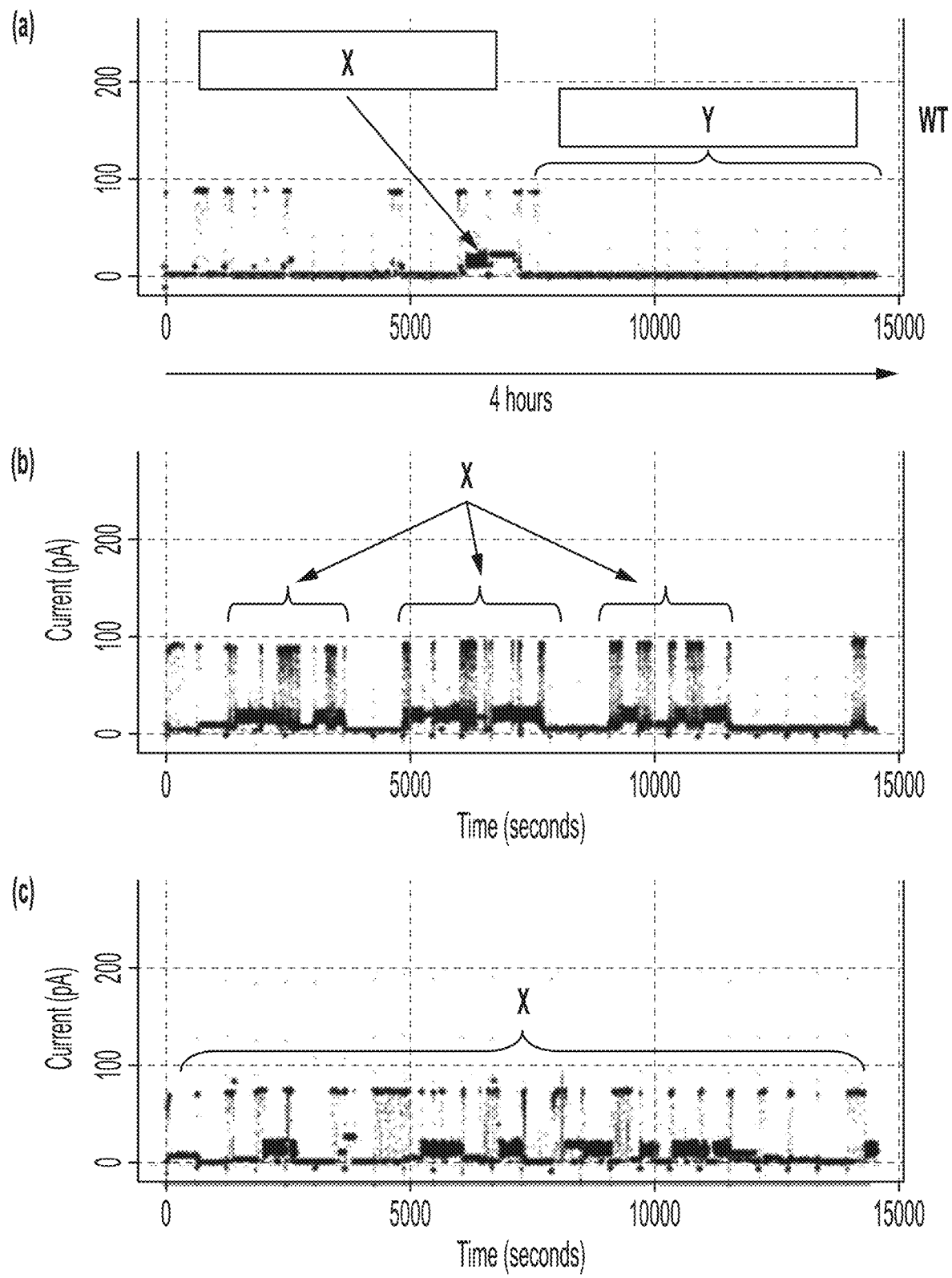
FIGS. 18 and 19: Mutant pores showing increased throughput compared with wild-type (WT).
Figure 19:
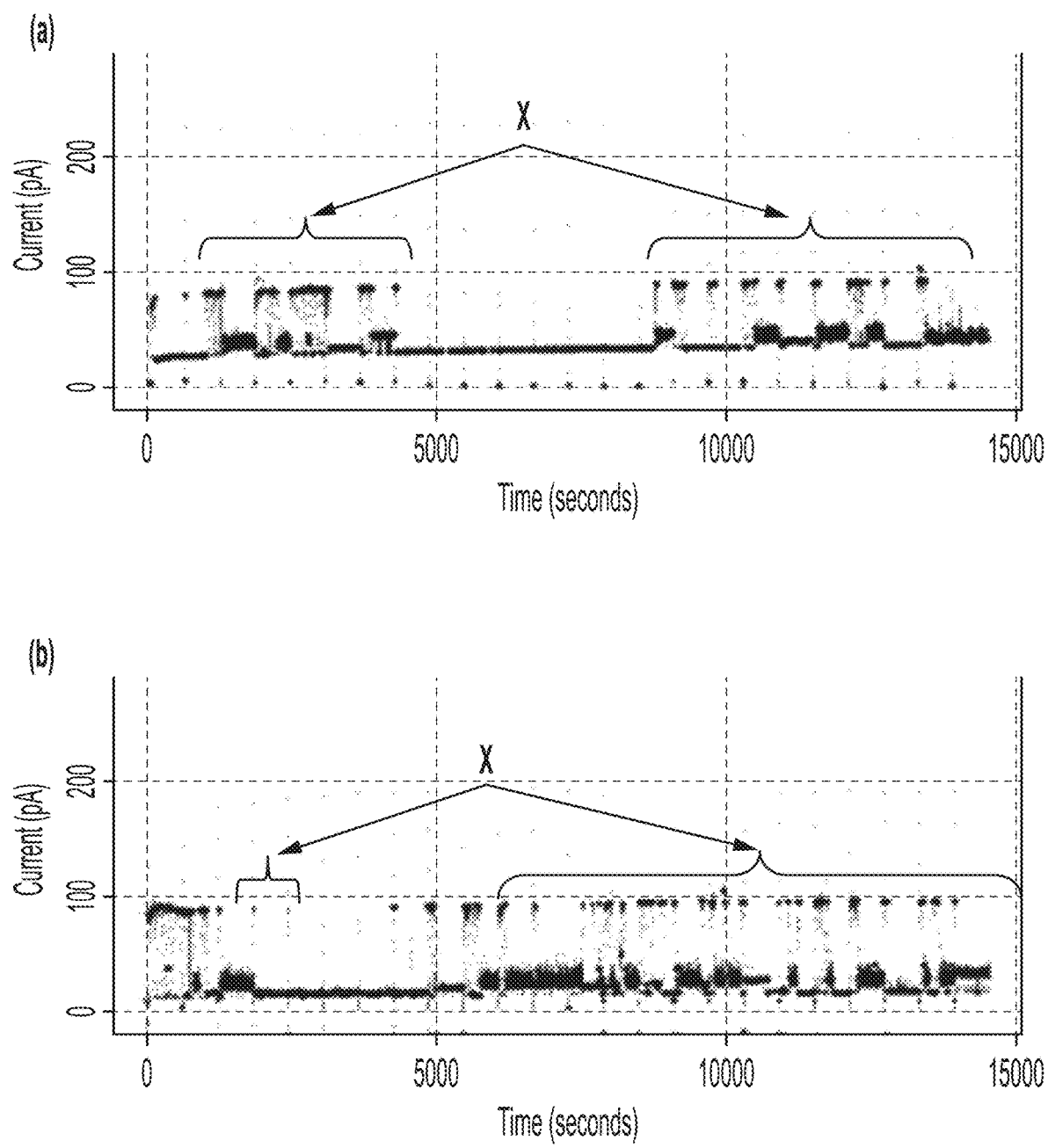

Pores Showing Increased Throughput (FIGS. 18 and 19)

As can be seen from FIGS. 18 and 19, the following mutant pores (9-12 below) exhibited multiple helicase controlled DNA movements (Labelled as X in FIGS. 18 and 19) per channel in 4 hours, whereas CsgG-Eco-(StrepII(C)) (SEQ ID NO: 390 where StepII(C) is SEQ ID NO: 435 and is attached at the C-terminus) shown in FIG. 18(a) frequently exhibited only 1 or 2 helicase controlled DNA movements (labelled as X in FIG. 18(a)) per channel in 4 hours and instead exhibited prolonged block regions (labelled as Y in FIG. 18(a)).

9—CsgG-Eco-(D149N-E185N-E203N-StrepII(C))9 (SEQ ID NO: 390 with mutations D149N/E185N/E203N where StepII(C) is SEQ ID NO: 435 and is attached at the C-terminus) (FIG. 18(b))

10—CsgG-Eco-(D149N-E185N-E201N-E203N-StrepII(C))9 (SEQ ID NO: 390 with mutations D149N/E185N/E201N/E203N where StepII(C) is SEQ ID NO: 435 and is attached at the C-terminus) (FIG. 18(c))

11—CsgG-Eco-(D149N-E185R-D195N-E201N-E203N)-StrepII(C))9 (SEQ ID NO: 390 with mutations D149N/E185R/D195N/E201N/E203N where StepII(C) is SEQ ID NO: 435 and is attached at the C-terminus) (FIG. 19(a))

12—CsgG-Eco-(D149N-E185R-D195N-E201R-E203N)-StrepII(C))9 (SEQ ID NO: 390 with mutations D149N/E185R/D195N/E201R/E203N where StepII(C) is SEQ ID NO: 435 and is attached at the C-terminus) (FIG. 19(b))

Figure 20:
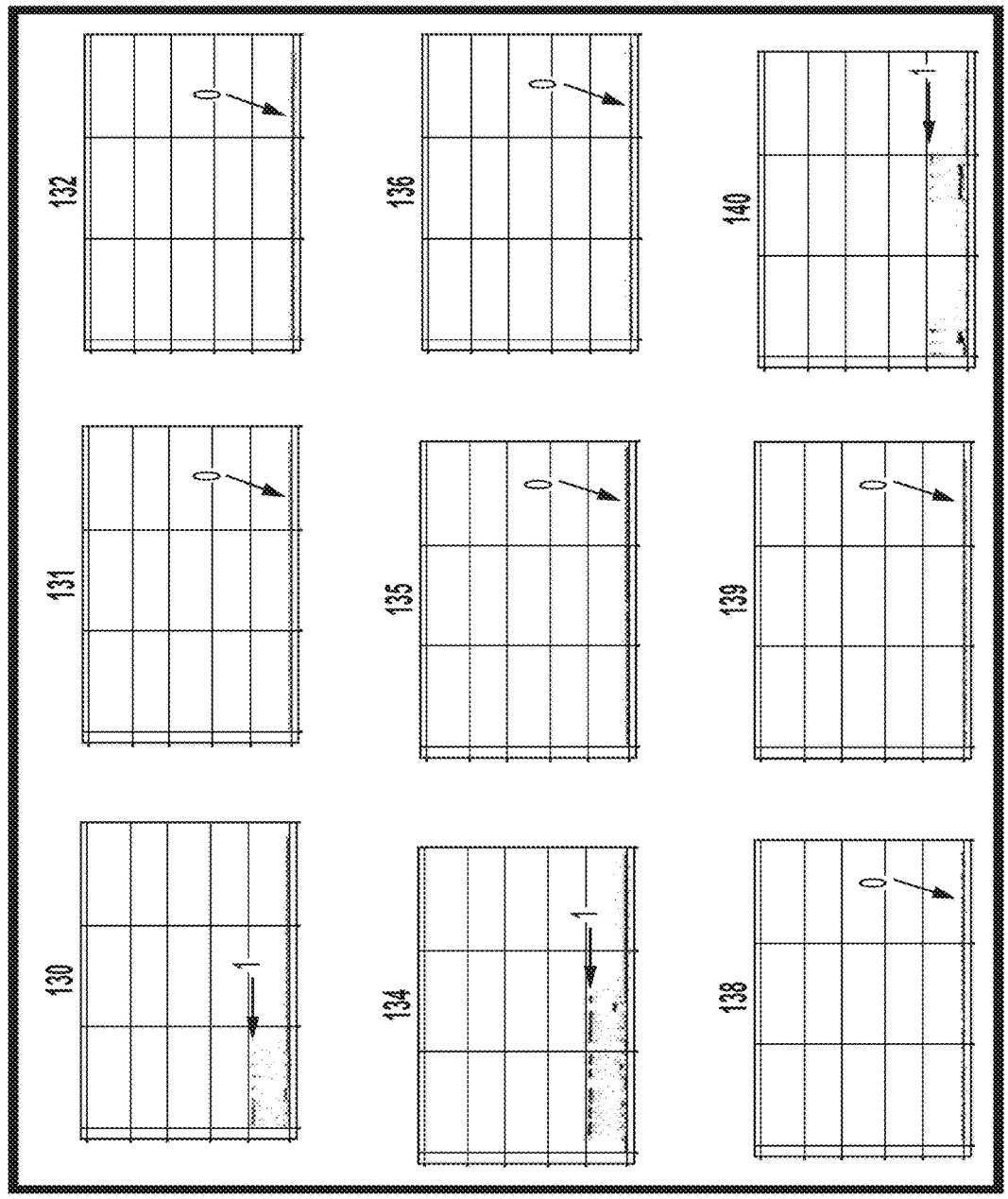
FIGS. 20 and 21: Mutant pore showing increased insertion compared with wild-type (WT).
Figure 21:
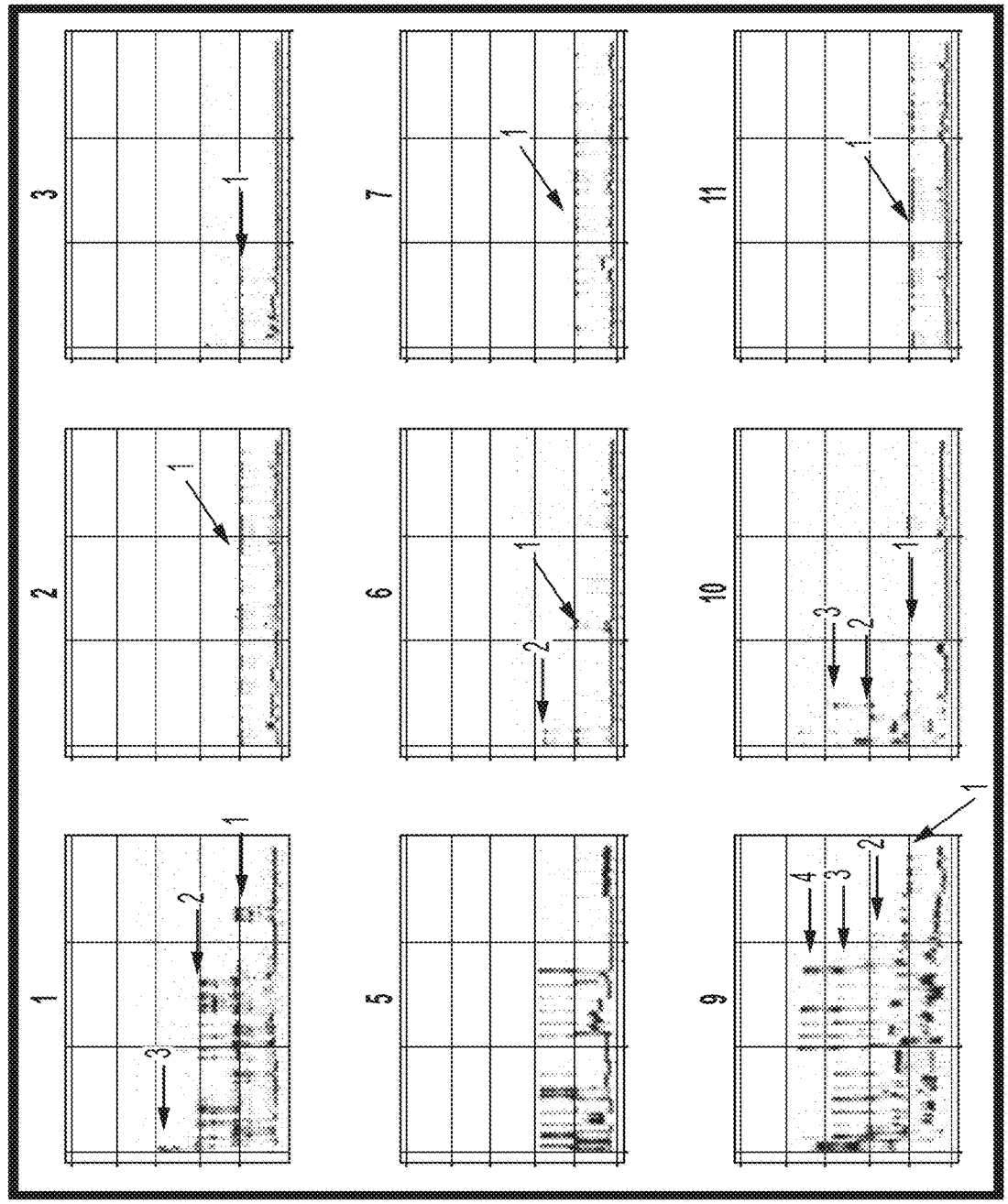

Pore Showing Increased Insertion (FIGS. 20 and 21)

As can be seen by comparing FIGS. 20 and 21, the mutant pore CsgG-Eco-(T150I-StrepII(C))9 (SEQ ID NO: 390 with mutations T150I where StepII(C) is SEQ ID NO: 435 and is attached at the C-terminus) shown in FIG. 21. was present in the membrane in increased pore numbers (~4-5 fold) compared with the CsgG-Eco-(StrepII(C)) (SEQ ID NO: 390 where StepII(C) is SEQ ID NO: 435 and is attached at the C-terminus) pore (shown in FIG. 20). Arrows in FIGS. 20 and 21 illustrated the number of CsgG-Eco nanopores which inserted into the block co-polymer in a 4 hour experiment (130-140 in FIGS. 20 and 1-11 in FIG. 21 each corresponded to a separate nanopore experiment). For CsgG-Eco-(StrepII(C)) (SEQ ID NO: 390 where StepII(C)

is SEQ ID NO: 435 and is attached at the C-terminus) three experiments showed insertion of one nanopore, whereas for the mutant pore (CsgG-Eco-(T150I-StrepII(C))9) each experiment showed insertion of at least one nanopore and several experiments showed multiple pore insertions.

Example 19

This example described an *E. Coli* purification method developed to purify the CsgG pore.

Materials and Methods

DNA encoding the polypeptide Pro-CsgG-Eco-(StrepII (C)) (SEQ ID NO: 390 where StepII(C) is SEQ ID NO: 435 and is attached at the C-terminus and where Pro is SEQ ID NO: 436 and is attached at the N-terminus) was synthesised in GenScript USA Inc. and cloned into a pT7 vector containing ampicillin resistance gene. Protein expression of the pT7 vector was induced by Isopropyl β-D-1-thiogalactopyranoside (IPTG). The concentration of the DNA solution was adjusted to 400 ng/uL. DNA (1 μl) was used to transform Lemo21(DE3) competent *E. coli* cells (50 μl, NEB, catalogue number C2528H). Prior to transformation, the CsgG gene was knocked out from Lemo21(DE3) cells (Gene Bridges GmbH, Germany). The cells were then plated out on LB agar containing ampicillin (0.1 mg/mL) and incubated for approx 16 hours at 37° C.

Bacterial colonies grown on LB plates, containing ampicillin, incorporated the CsgG plasmid. One such colony was used to inoculate a starter culture of LB media (100 mL) containing carbenicillin (0.1 mg/mL). The starter culture was grown at 37° C. with agitation until OD600 was reached to 1.0-1.2. The starter culture was used to inoculate a fresh 500 mL of LB media containing carbenicillin (0.1 mg/mL) and Rhamnose (500 μM) to an O.D. 600 of 0.1. The culture was grown at 37° C. with agitation until OD600 reached 0.6. The temperature of the culture was then adjusted to 18° C. and induction was initiated by the addition of IPTG (0.2 mM final concentration). Induction was carried out for approximately 18 hours with agitation at 18° C.

Following induction, the culture was pelleted by centrifugation at 6,000 g for 30 minutes. The pellet was resuspended in 50 mM Tris, 300 mM NaCl, containing protease inhibitors (Merck Millipore 539138), benzonase nuclease (Sigma E1014) and 1× bugbuster (Merck Millipore 70921) pH8.0 (approximately 10 mL of buffer per gram of pellet). Suspension was mixed well until it was fully homogeneous, the sample was then transferred to roller mixer at 4° c. for approx 5 hours. Lysate was pelleted by centrifugation at 20,000 g for 45 minutes and the supernatant was filtered through 0.22 μM PES syringe filter. Supernatant which contained CsgG (known as sample 1) was taken forward for purification by column chromatography.

Figure 23:
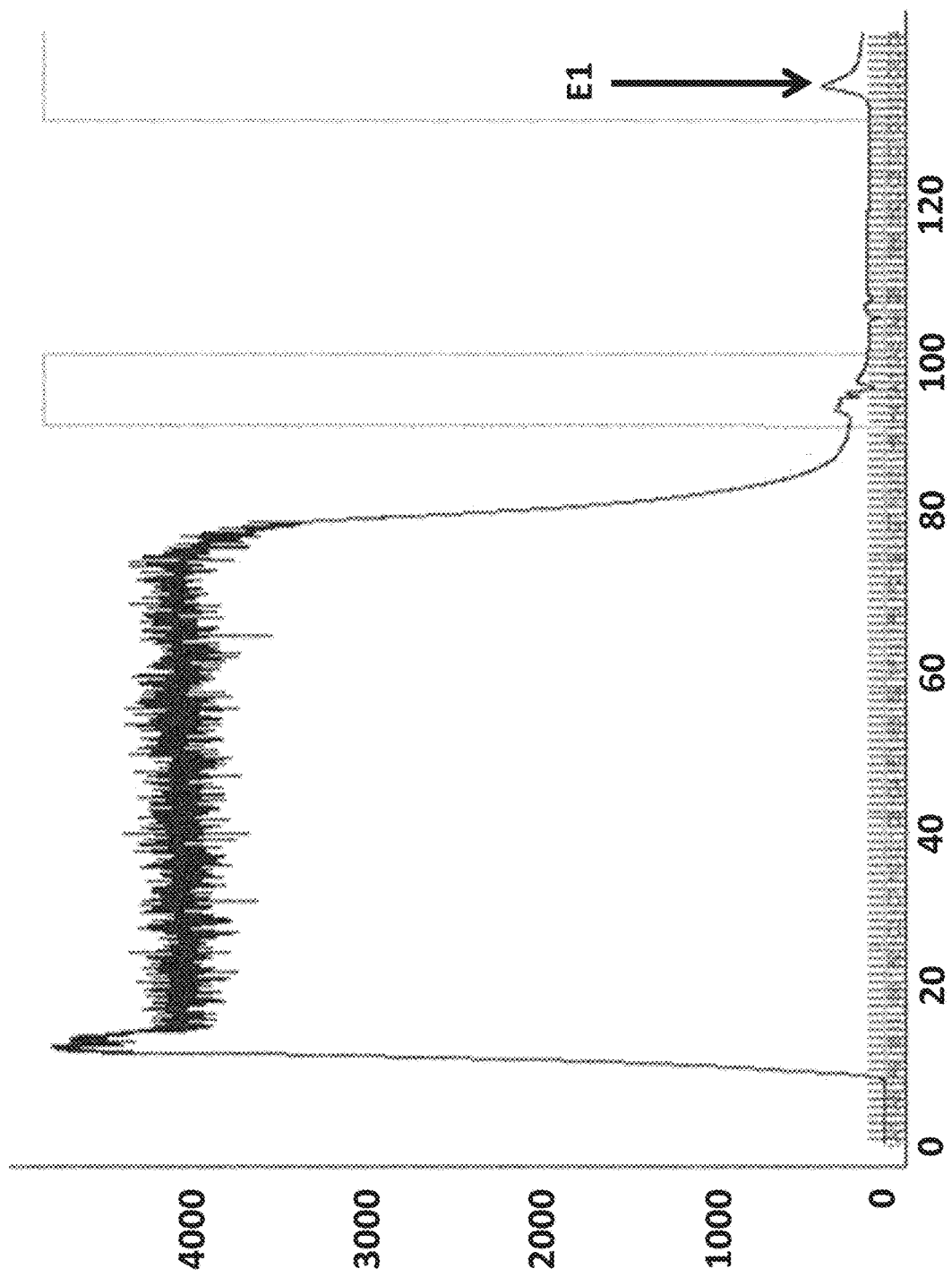
FIG. 23: shows an example chromatography trace of Strep trap (GE Healthcare) purification of CsgG protein (x-axis label=elution volume (mL), Y-axis label=Absorbance (mAu)). The sample was loaded in 25 mM Tris, 150 mM NaCl, 2 mM EDTA, 0.01% DDM and eluted with 10 mM desthiobiotin. The elution peak in which CsgG protein eluted is labelled as E1.
Figure 24:
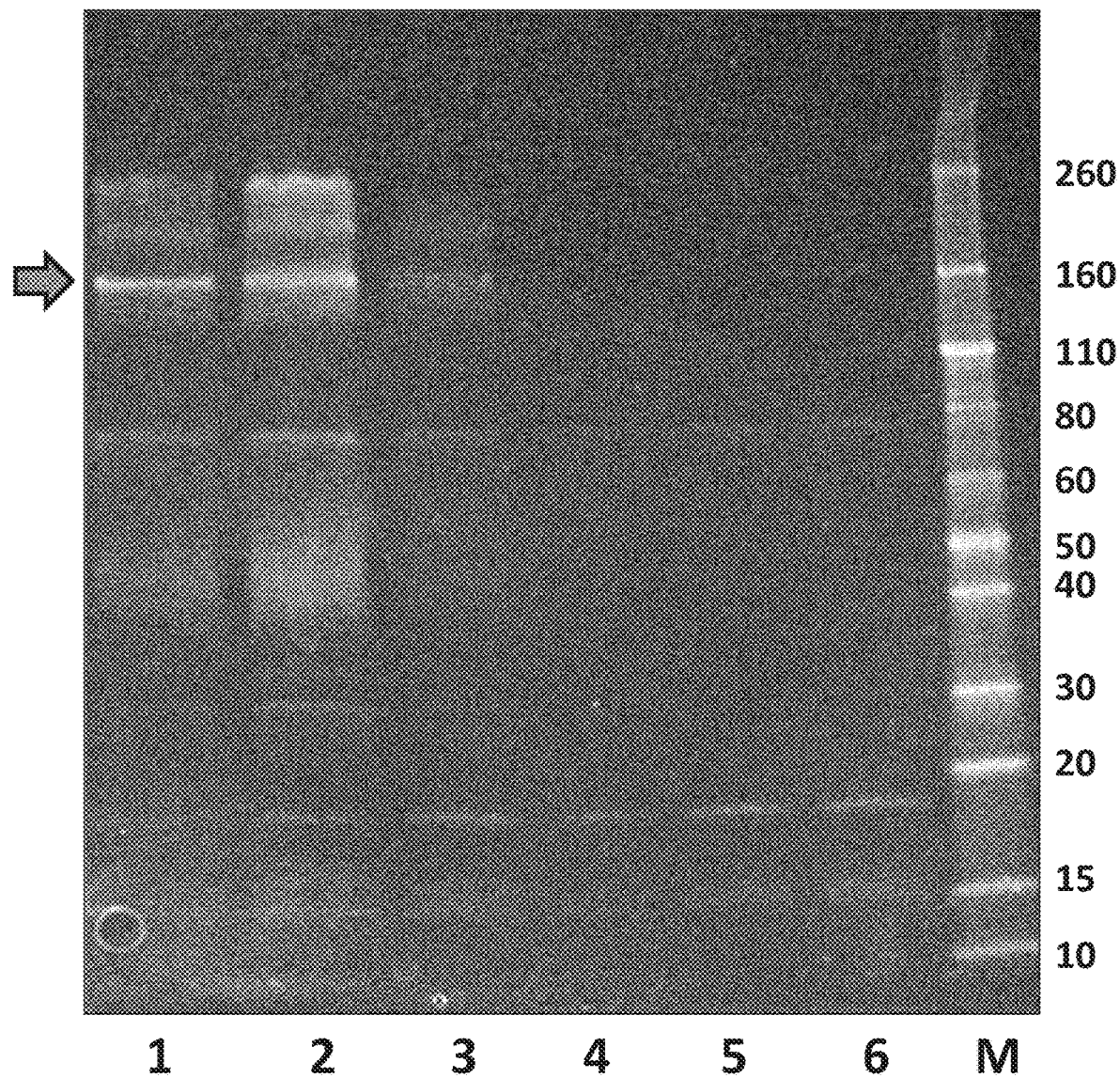
FIG. 24: shows an example of a typical SDS-PAGE visualisation of CsgG protein after the initial strep purification. A 4-20% TGX Gel (Bio Rad) was run at 300 V for 22 minutes in 1×TGS buffer. The gel was stained with Sypro Ruby stain. Lanes 1-3 show the main elution peak (labelled E1 in FIG. 23) which contained CsgG protein as indicated by the arrow. Lanes 4-6 corresponded to elution fractions of the tail of the main elution peak (labelled E1 in FIG. 23) which contained contaminants. M shows the molecular weight marker used which was a Novex Sharp Unstained (unit=kD).

Sample 1 was applied to a 5 mL Strep Trap column (GE Healthcare). The column was washed with 25 mM Tris, 150 mM NaCl, 2 mM EDTA, 0.01% DDM pH8 until a stable baseline of 10 column volumes was maintained. The column was then washed with 25 mM Tris, 2M NaCl, 2 mM EDTA, 0.01% DDM pH8 before being returned to the 150 mM buffer. Elution was carried out with 10 mM desthiobiotin. An example of a chromatography trace of Strep trap (GE Healthcare) purification of a CsgG protein is shown in FIG. 23. The elution peak is labelled E1. FIG. 24 shows an example of a typical SDS-PAGE visualization of CsgG-Eco protein after the initial Strep purification. Lanes 1-3 shows the main elution peak (labelled E1 in FIG. 23) which contained CsgG protein as indicated by the arrow. Lanes 4-6 corresponded to elution fractions of the tail of the main elution peak (labelled E1 in FIG. 23) which contained contaminants.

Figure 25:
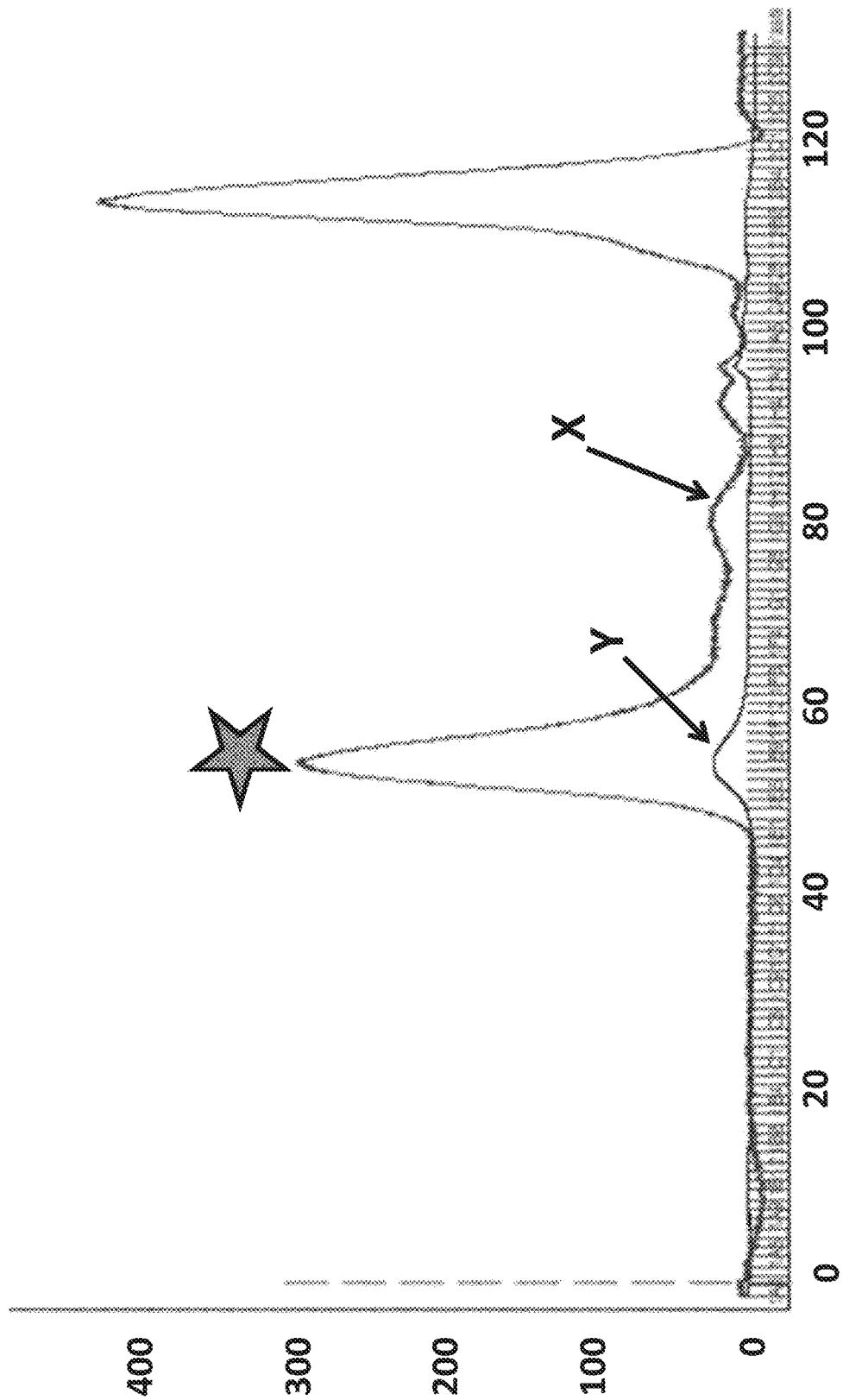
FIG. 25: Shows an example of a size exclusion chromatogram (SEC) of CsgG protein (120 mL S200 GE healthcare, x-axis label=elution volume (mL), y-axis label=absorbance (mAu)). The SEC was carried out after strep purification and heating the protein sample. The running buffer for SEC was 25 mM Tris, 150 mM NaCl, 2 mM EDTA, 0.01% DDM, 0.1% SDS, pH 8.0 and the column was run at 1 mL/minute rate. The trace labelled X shows absorbance at 220 nm and the trace labelled Y shows absorbance at 280 nm. The peak labelled with a star was collected.
Figure 26:
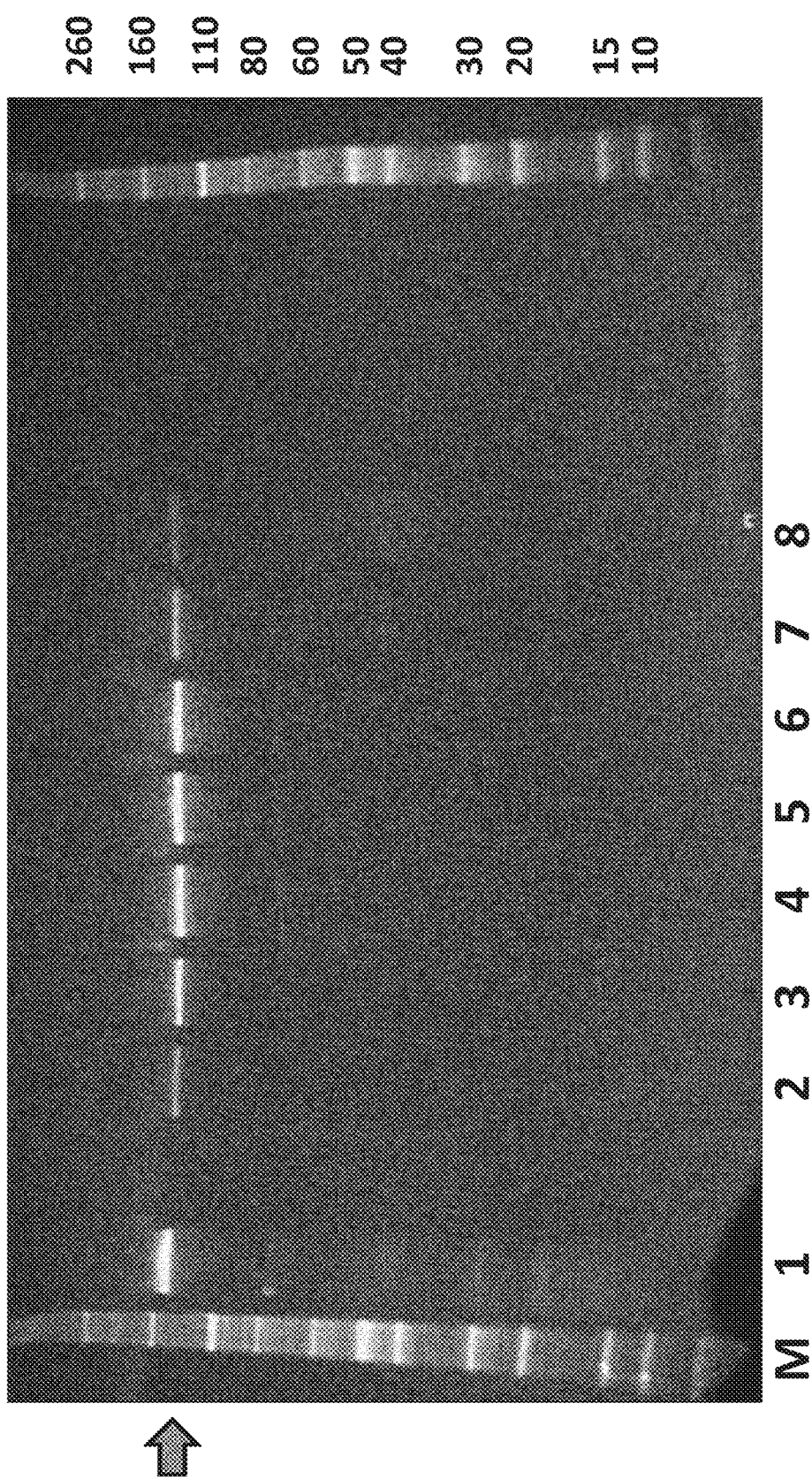
FIG. 26: shows an example of a typical SDS-PAGE visualisation of CsgG protein after SEC. A 4-20% TGX Gel (Bio Rad) was run at 300V for 22 minutes in 1×TGS buffer and the gel was stained with Sypro Ruby stain. Lane 1 shows CsgG protein sample after strep purification and heating but before SEC. Lanes 2-8 show fractions collected across the peak running approximately 48 mL-60 mL of FIG. 25 (mid peak=55 mL) and labelled with a star in FIG. 25. M shows the molecular weight marker used which was a Novex Sharp Unstained (unit=kD). The bar corresponding to the CsgG-Eco pore is indicated by an arrow.

The elution peak was pooled and heated to 65° C. for 15 minutes to remove heat unstable contaminated proteins. The heated solution was subjected to centrifugation at 20,000 g for 10 minutes and the pellet was discarded. The supernatant was subjected to gel filtration on a 120 mL Sephadex S200 column (GE Healthcare) in 25 mM Tris, 150 mM NaCl, 2 mM EDTA, 0.01% DDM, 0.1% SDS pH8. Monitoring was carried out at 220 nM due to low Tryptophan component of protein. The sample was eluted at approximately 55 mL volume (FIG. 25 shows the size exclusion column trace with the 55 mL sample peak labelled with a star). The elution peak was run on a 4-20% TGX (see FIG. 26, Bio Rad) to confirm the presence of the pore of interest CsgG-Eco-(StrepII(C)) (SEQ ID NO: 390 where StepII(C) is SEQ ID NO: 435 and is attached at the C-terminus). Identified fractions were pooled and concentrated by 50 kD Amicon spin column.

Example 20

This example describes the simulations which were run to investigate the interaction between CsgG-Eco-(Y51T/F56Q)-StrepII(C))9 (SEQ ID NO: 390 with mutations Y51T/F56Q where StepII(C) is SEQ ID NO: 435 and is attached at the C-terminus pore mutant No. 20) with T4 Dda-(E94C/C109A/C136A/A360C) (SEQ ID NO: 412 with mutations E94C/C109A/C136A/A360C and then (ΔM1) G1G2).

Simulation Methods

Simulations were performed using the GROMACS package version 4.0.5, with the GROMOS 53a6 forcefield and the SPC water model.

The CsgG-Eco-(Y51T/F56Q)-StrepII(C))9 (SEQ ID NO: 390 with mutations Y51T/F56Q where StepII(C) is SEQ ID NO: 435 and is attached at the C-terminus pore mutant No. 20) model was based on the crystal structures of CsgG found in the protein data bank, accession codes 4UV3 and 4Q79. The relevant mutations were made using PyMOL. The resultant pore model was then energy minimised using the steepest descents algorithm. The T4 Oda-(E94C/C109A/C136A/A360C) (SEQ ID NO: 412 with mutations E94C/C109A/C136A/A360C and then (ΔM1)G1G2) model was based on the Dda1993 structure found in the protein data bank, accession code 3UPU. Again, relevant mutations were made using PyMOL, and the model was energy minimised using the steepest descents algorithm.

Figure 40:
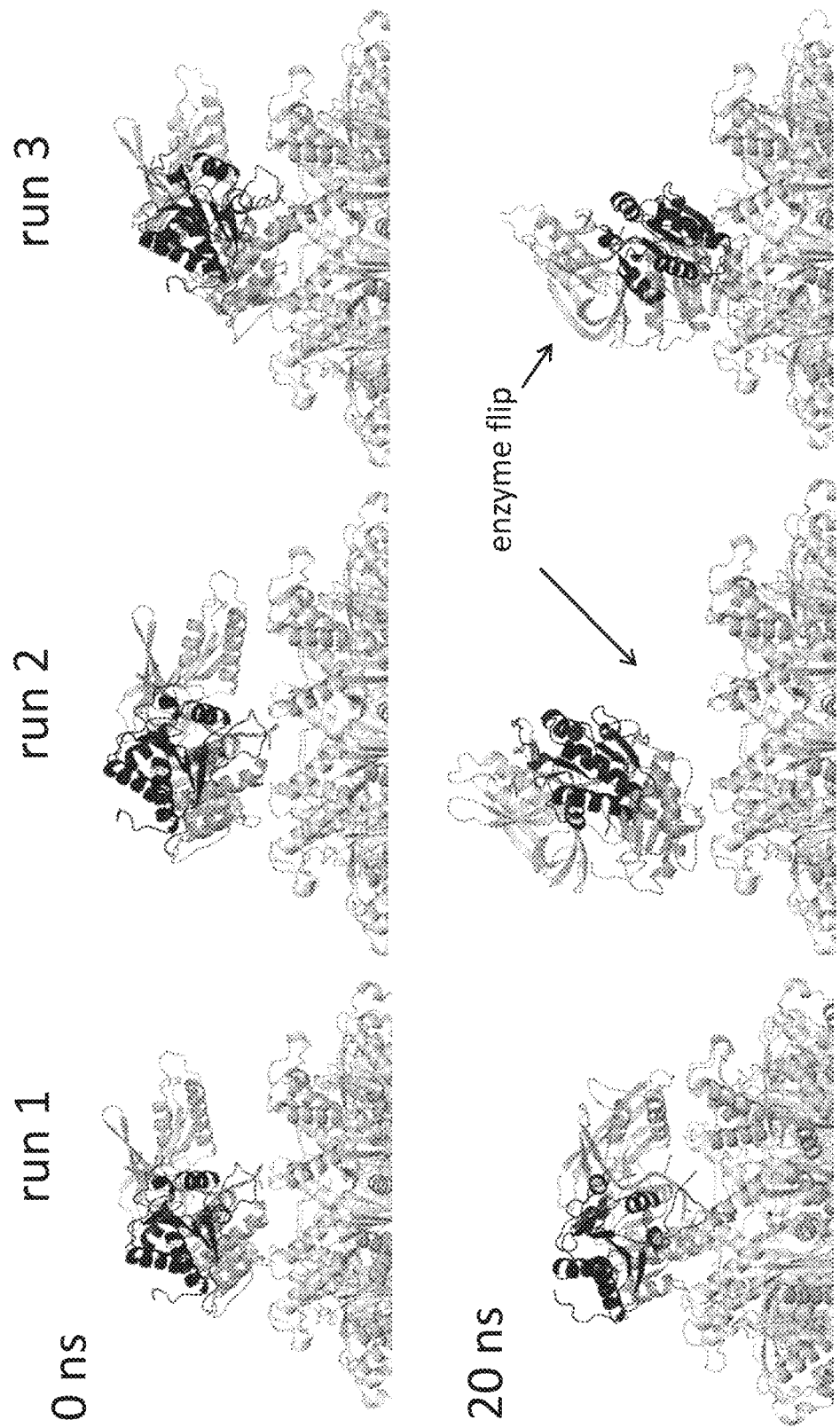
FIG. 40 shows snap shots of the enzyme (T4 Dda-(E94C/C109A/C136A/A360C) (SEQ ID NO: 412 with mutations E94C/C109A/C136A/A360C and then (ΔM1)G1G2)) on top of the pore (CsgG-Eco-(Y51T/F56Q)-StrepII(C))9 (SEQ ID NO: 390 with mutations Y51T/F56Q where StepII(C) is SEQ ID NO: 435 and is attached at the C-terminus pore mutant No. 20)) taken at 0 and 20 ns during the simulations (Runs 1 to 3).

The T4 Dda-(E94C/C109A/C136A/A360C) (SEQ ID NO: 412 with mutations E94C/C 109A/C136A/A360C and then (ΔM1)G1G2) model was then placed above CsgG-Eco-(Y51T/F56Q)-StrepII(C))9 (SEQ ID NO: 390 with mutations Y51T/F56Q where StepII(C) is SEQ ID NO: 435 and is attached at the C-terminus pore mutant No. 20). Three simulations were performed with a different initial enzyme conformation (Runs 1 to 3 (0 ns), see FIG. 40):

In all enzyme conformations, the enzyme was oriented such that the 5' end of the DNA was pointing towards the pore, and the enzyme was unrestrained throughout the simulation. The pore backbone was restrained and the simulation box was solvated. The system was simulated in the NPT ensemble for 40 ns, using the Berendsen thermostat and Berendsen barostat to 300 K.

Figure 41:
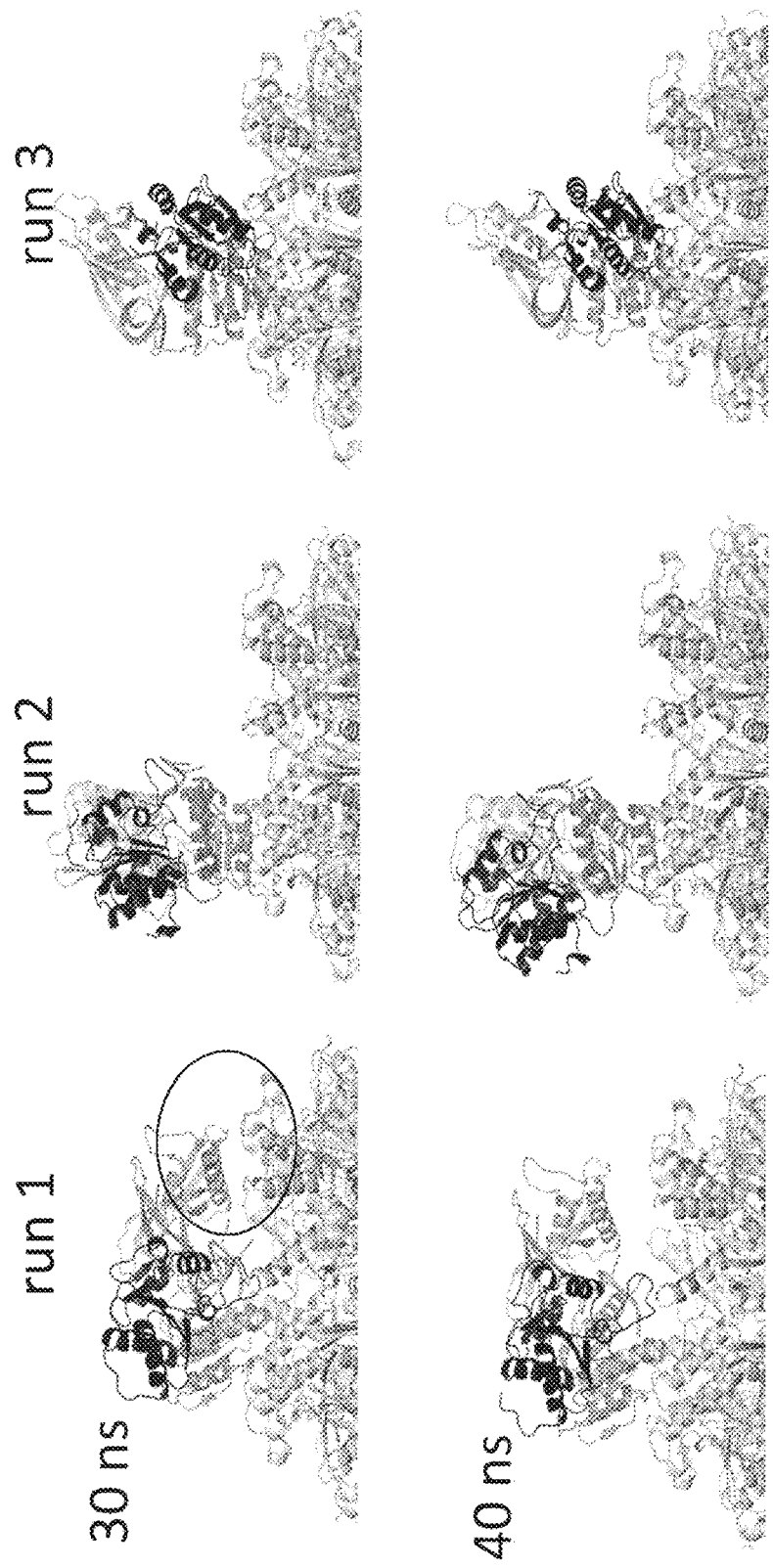
FIG. 41 shows snap shots of the enzyme (T4 Dda-(E94C/C109A/C136A/A360C) (SEQ ID NO: 412 with mutations E94C/C109A/C136A/A360C and then (ΔM1)G1G2)) on top of the pore (CsgG-Eco-(Y51T/F56Q)-StrepII(C))9 (SEQ ID NO: 390 with mutations Y51T/F56Q where StepII(C) is SEQ ID NO: 435 and is attached at the C-terminus pore mutant No. 20)) taken at 30 and 40 ns during the simulations (Runs 1 to 3).

The contacts between the enzyme and pore were analysed using both GROMACS analysis software and also locally written code. The tables below show the number of contacts observed for both pore and enzyme amino acids. Tables 6-8 show the amino acid contact points on pore which interact with the amino acid contact points on the enzyme. In two out of the three simulations the enzyme tilts on top of the pore (see run 2 and 3 (20, 30 and 40 ns), FIGS. 40 and 41). Run 1 shows that the enzyme has not tilted and so points that are shown to have high interaction in table 6 can be optimised in order to increase enzyme stability on the pore cap.

TABLE 6 run 1 enzyme and pore contact interactions

| Pore | Enzyme | # contacts |
| --- | --- | --- |
| ASN 102 | ASP 198 | 8200 |
| ASN 102 | TYR 438 | 8130 |
| GLN 100 | ASP 212 | 7369 |
| GLU 101 | TRP 195 | 5979 |
| ARG 97 | TYR 350 | 4873 |
| GLU 101 | LEU 215 | 4851 |
| ASN 102 | TRP 195 | 3988 |
| ARG 97 | TYR 415 | 3798 |
| GLU 101 | TYR 350 | 3759 |
| LEU 113 | ASP 212 | 3718 |
| ASN 102 | LYS 358 | 3124 |
| ARG 97 | GLY 211 | 2765 |
| GLU 101 | CYS 412 | 2715 |
| ARG 97 | GLY 193 | 2708 |
| ASN 102 | ILE 196 | 2342 |
| GLU 101 | TYR 415 | 2268 |
| GLU 101 | ARG 216 | 2158 |
| ARG 110 | THR 213 | 2094 |
| ARG 110 | ASP 212 | 2066 |
| GLY 103 | ARG 216 | 1456 |
| GLU 101 | TYR 318 | 1333 |
| ASN 102 | GLU 347 | 1316 |
| GLU 101 | LYS 194 | 1310 |
| ARG 97 | PRO 411 | 1203 |
| GLU 101 | LYS 358 | 1161 |
| ASN 102 | ARG 216 | 1132 |
| ARG 97 | TRP 195 | 888 |
| LYS 94 | TYR 415 | 793 |
| ASN 102 | PRO 315 | 696 |
| ASN 102 | LYS 247 | 541 |
| GLU 101 | ALA 214 | 449 |
| ASN 102 | ASP 346 | 440 |
| ARG 97 | ALA 214 | 366 |
| ARG 97 | LYS 194 | 336 |
| GLU 101 | ASP 212 | 302 |
| ARG 97 | VAL 439 | 267 |
| ARG 110 | THR 210 | 263 |
| ARG 97 | THR 210 | 259 |
| ARG 97 | GLN 422 | 257 |
| GLU 101 | TYR 409 | 228 |
| ALA 98 | TRP 195 | 207 |
| GLU 101 | LYS 247 | 201 |
| ASN 102 | GLU 317 | 179 |
| ARG 110 | ARG 216 | 147 |
| ARG 97 | ASP 212 | 108 |
| ASN 102 | VAL 314 | 87 |
| GLU 101 | THR 213 | 72 |
| ASN 102 | LYS 255 | 70 |
| VAL 105 | ARG 216 | 69 |
| ASN 102 | LEU 215 | 59 |
| ASN 102 | THR 210 | 55 |
| ILE 111 | ASP 212 | 48 |
| ARG 97 | HIS 414 | 48 |
| THR 104 | ARG 216 | 36 |
| ASN 102 | TYR 197 | 32 |
| GLN 100 | THR 213 | 30 |
| ASN 102 | GLU 361 | 28 |
| ARG 97 | VAL 418 | 28 |
| ALA 98 | TYR 415 | 27 |
| GLU 101 | LEU 354 | 17 |
| GLU 101 | TYR 197 | 16 |
| ASN 102 | GLY 316 | 16 |
| ARG 97 | GLU 361 | 16 |
| ARG 97 | GLU 347 | 14 |

TABLE 6-continued run 1 enzyme and pore contact interactions

| Pore | Enzyme | # contacts |
| --- | --- | --- |
| ILE 107 | ARG 216 | 12 |
| ASN 102 | GLY 208 | 12 |
| ARG 97 | TYR 409 | 11 |
| ARG 97 | LYS 247 | 11 |
| GLU 101 | LYS 364 | 8 |
| ARG 97 | PHE 209 | 7 |
| LYS 94 | GLU 419 | 6 |
| GLU 101 | PRO 411 | 5 |
| GLU 101 | GLU 317 | 5 |
| ASN 102 | ILE 251 | 5 |
| ARG 97 | LEU 354 | 5 |
| LYS 94 | VAL 418 | 3 |
| ASN 102 | ARG 321 | 3 |
| ARG 97 | LYS 243 | 3 |
| LYS 94 | CYS 412 | 2 |
| LEU 113 | THR 210 | 2 |
| GLY 103 | GLU 317 | 2 |
| GLU 101 | LYS 351 | 2 |
| ASN 102 | TYR 318 | 2 |
| ASN 102 | MET 219 | 2 |
| ASN 102 | LYS 194 | 2 |
| ARG 97 | VAL 314 | 2 |
| ARG 97 | LYS 364 | 2 |
| THR 104 | PRO 315 | 1 |
| GLY 103 | THR 213 | 1 |
| GLU 101 | PRO 315 | 1 |

TABLE 7 run 2 enzyme and pore contact

| Pore | Enzyme | # contacts |
| --- | --- | --- |
| GLU 101 | THR 210 | 14155 |
| SER 115 | ASP 202 | 9477 |
| ARG 97 | THR 210 | 9064 |
| ASN 102 | VAL 200 | 5323 |
| THR 104 | ASP 202 | 4476 |
| ASN 102 | ASN 221 | 3422 |
| GLU 101 | PHE 437 | 3171 |
| ARG 97 | ASP 217 | 2698 |
| GLU 101 | ARG 216 | 2198 |
| ARG 97 | GLY 208 | 1730 |
| GLU 101 | LYS 199 | 1710 |
| SER 115 | SER 224 | 1440 |
| ASN 102 | LYS 199 | 1351 |
| ASN 102 | ASP 212 | 1298 |
| ASN 102 | ARG 405 | 1219 |
| GLU 101 | ARG 207 | 1180 |
| ASN 102 | SER 224 | 1150 |
| ASN 102 | LYS 255 | 1114 |
| ARG 97 | ASP 198 | 946 |
| GLU 101 | PHE 209 | 931 |
| ARG 97 | THR 213 | 791 |
| ARG 97 | ARG 216 | 599 |
| ASN 102 | THR 210 | 589 |
| GLN 114 | ASP 202 | 530 |
| ASN 102 | ASP 202 | 492 |
| ARG 97 | ASP 212 | 490 |
| GLY 103 | ARG 405 | 474 |
| THR 104 | SER 224 | 451 |
| GLU 101 | LYS 255 | 429 |
| ASN 102 | ASP 198 | 405 |
| ASN 102 | PHE 209 | 400 |
| ASN 102 | ARG 178 | 316 |
| ARG 110 | GLU 258 | 309 |
| ASN 102 | ASN 180 | 257 |
| GLN 100 | PHE 223 | 256 |
| GLU 101 | TYR 197 | 220 |
| GLN 114 | SER 228 | 212 |
| LEU 113 | PHE 223 | 210 |
| ASN 102 | ILE 225 | 204 |
| GLN 114 | LYS 227 | 194 |

TABLE 7-continued run 2 enzyme and pore contact

| Pore | Enzyme | # contacts |
| --- | --- | --- |
| GLU 101 | GLY 211 | 189 |
| GLU 101 | ASP 212 | 174 |
| LEU 113 | SER 224 | 159 |
| LEU 113 | GLY 203 | 145 |
| ARG 97 | VAL 220 | 134 |
| GLU 101 | THR 213 | 133 |
| THR 104 | SER 228 | 125 |
| ARG 97 | TYR 197 | 123 |
| LYS 94 | ASP 212 | 118 |
| ASN 102 | ARG 216 | 110 |
| ASN 102 | ASN 235 | 108 |
| ASN 102 | GLY 211 | 104 |
| GLU 101 | ARG 405 | 79 |
| GLN 114 | SER 224 | 69 |
| ASN 102 | VAL 220 | 63 |
| LEU 113 | LYS 227 | 49 |
| ASN 102 | VAL 201 | 42 |
| ARG 97 | PHE 209 | 42 |
| GLU 101 | ASN 180 | 40 |
| ARG 97 | TYR 438 | 38 |
| ARG 97 | ARG 207 | 32 |
| ASN 102 | PHE 407 | 28 |
| SER 115 | ASN 221 | 23 |
| ARG 110 | HIS 204 | 22 |
| GLU 101 | PHE 223 | 21 |
| ARG 97 | ASP 189 | 19 |
| ARG 110 | PHE 223 | 16 |
| THR 104 | ILE 225 | 13 |
| GLY 103 | ASN 180 | 11 |
| ARG 97 | LYS 194 | 11 |
| GLU 101 | PHE 407 | 10 |
| ARG 97 | MET 219 | 9 |
| THR 104 | ASN 235 | 8 |
| ARG 110 | ARG 405 | 8 |
| ARG 97 | TRP 195 | 7 |
| ILE 111 | PHE 223 | 6 |
| GLU 101 | GLY 208 | 6 |
| LEU 113 | ASP 202 | 5 |
| GLU 101 | ARG 178 | 5 |
| ASN 102 | THR 213 | 5 |
| ALA 98 | ARG 216 | 5 |
| ASN 102 | ASP 217 | 4 |
| ARG 97 | LYS 199 | 4 |
| THR 104 | LEU 229 | 3 |
| THR 104 | ARG 405 | 3 |
| GLU 101 | VAL 201 | 3 |
| GLU 101 | MET 219 | 3 |
| ARG 110 | ASP 202 | 3 |
| ARG 110 | ARG 207 | 2 |
| THR 104 | VAL 201 | 1 |
| GLY 103 | SER 224 | 1 |
| GLY 103 | LYS 255 | 1 |
| GLY 103 | GLU 258 | 1 |
| GLY 103 | ASN 235 | 1 |
| GLU 101 | ASP 198 | 1 |
| ASN 102 | PHE 437 | 1 |
| ARG 97 | PHE 437 | 1 |
| ARG 110 | LYS 227 | 1 |

TABLE 8 run 3 enzyme and pore contact interactions

| Pore | Enzyme | # contacts |
| --- | --- | --- |
| ARG 97 | THR 174 | 15557 |
| GLN 100 | ASP 5 | 10353 |
| GLU 101 | LYS 177 | 9238 |
| ARG 97 | SER 179 | 6630 |
| LEU 116 | ASP 202 | 6545 |
| GLU 101 | TYR 434 | 6524 |
| SER 115 | ASP 202 | 5693 |
| GLU 101 | HIS 204 | 5457 |
| ARG 97 | GLN 10 | 5106 |
| ARG 93 | ASP 202 | 4646 |
| ARG 93 | GLU 8 | 4446 |
| SER 115 | LYS 11 | 4342 |
| LEU 113 | ASP 5 | 3871 |
| ASN 102 | SER 224 | 3605 |
| GLU 101 | ASN 12 | 3344 |
| GLU 101 | GLN 10 | 3327 |
| ARG 97 | GLU 175 | 3096 |
| GLU 101 | SER 224 | 3028 |
| LEU 116 | GLU 8 | 2936 |
| LYS 94 | ASP 185 | 2708 |
| ARG 97 | ASN 180 | 2700 |
| GLU 101 | PHE 3 | 2500 |
| THR 104 | LYS 11 | 2352 |
| SER 115 | GLU 8 | 2323 |
| ARG 93 | ASN 180 | 1912 |
| ASN 102 | LYS 177 | 1838 |
| LYS 94 | ASP 198 | 1828 |
| ARG 110 | ASP 5 | 1714 |
| ALA 98 | GLY 203 | 1701 |
| ASN 102 | ASN 12 | 1695 |
| GLU 101 | TYR 169 | 1691 |
| ARG 97 | THR 7 | 1593 |
| ARG 110 | ASP 4 | 1404 |
| ARG 97 | ASP 212 | 1381 |
| ASN 102 | HIS 204 | 1226 |
| ASN 102 | ASN 15 | 1173 |
| ARG 97 | VAL 176 | 1096 |
| ALA 98 | HIS 204 | 998 |
| ARG 97 | ASP 202 | 875 |
| ASN 102 | TYR 434 | 850 |
| ALA 98 | ASN 12 | 716 |
| GLU 101 | THR 213 | 702 |
| GLU 101 | ARG 178 | 642 |
| GLU 101 | ASN 221 | 600 |
| ASN 102 | LYS 11 | 588 |
| ARG 97 | ASP 217 | 585 |
| ARG 97 | ARG 207 | 537 |
| GLU 101 | ARG 207 | 525 |
| ARG 97 | PHE 437 | 511 |
| GLU 101 | ARG 216 | 510 |
| ASN 102 | LYS 19 | 482 |
| ARG 97 | HIS 204 | 473 |
| LEU 113 | LYS 11 | 409 |
| ARG 97 | THR 213 | 358 |
| ARG 93 | ASP 212 | 354 |
| ARG 97 | TYR 169 | 316 |
| ARG 97 | GLY 203 | 308 |
| ARG 97 | ASP 435 | 300 |
| GLN 87 | LYS 199 | 249 |
| THR 104 | ASN 15 | 221 |
| ARG 97 | ALA 181 | 220 |
| ASN 102 | LYS 227 | 198 |
| LYS 94 | ARG 178 | 184 |
| ASN 102 | GLU 8 | 183 |
| LEU 113 | LEU 6 | 182 |
| ARG 93 | SER 179 | 179 |
| LEU 90 | ASN 180 | 172 |
| LEU 90 | ASP 202 | 144 |
| ARG 97 | ILE 225 | 138 |
| GLU 101 | ASN 15 | 135 |
| GLU 101 | LYS 19 | 113 |
| LYS 94 | ASN 180 | 109 |
| LYS 94 | GLU 175 | 105 |
| ARG 93 | THR 7 | 81 |
| LYS 94 | ARG 207 | 77 |
| GLN 100 | PHE 3 | 72 |
| ASN 102 | ARG 216 | 66 |
| ARG 97 | LYS 177 | 62 |
| GLU 101 | THR 210 | 59 |
| ARG 97 | ARG 178 | 56 |
| LYS 94 | ASP 212 | 55 |
| ARG 97 | GLU 172 | 53 |
| GLU 101 | VAL 176 | 51 |
| ALA 98 | ARG 207 | 49 |

TABLE 8-continued run 3 enzyme and pore contact interactions

| Pore | Enzyme | # contacts |
|---|---|---|
| ARG 110 | PHE 3 | 48 |
| ALA 98 | ASP 202 | 47 |
| ARG 97 | VAL 200 | 40 |
| ALA 98 | VAL 201 | 36 |
| LYS 94 | THR 210 | 35 |
| ILE 111 | ASP 5 | 32 |
| ARG 97 | ARG 405 | 27 |
| LEU 90 | VAL 200 | 26 |
| ARG 97 | THR 210 | 26 |
| GLY 103 | PHE 3 | 25 |
| GLU 101 | PHE 209 | 25 |
| ARG 97 | ARG 216 | 22 |
| ASN 102 | VAL 220 | 21 |
| LYS 94 | GLY 211 | 19 |
| ARG 97 | PHE 209 | 17 |
| GLU 101 | LYS 227 | 15 |
| GLN 114 | LYS 11 | 15 |
| GLY 103 | LYS 19 | 13 |
| ARG 97 | PHE 3 | 13 |
| GLU 101 | THR 2 | 12 |
| GLU 101 | ILE 225 | 12 |
| ARG 97 | ILE 184 | 12 |
| ALA 98 | GLU 8 | 12 |
| ALA 98 | ARG 178 | 12 |
| ASN 102 | ILE 225 | 11 |
| LYS 94 | LYS 199 | 10 |
| GLU 101 | ARG 433 | 8 |
| ARG 97 | ASN 221 | 8 |
| LYS 94 | VAL 200 | 7 |
| ASN 102 | ASP 202 | 7 |
| ASN 102 | ASN 221 | 7 |
| ARG 97 | LEU 173 | 7 |
| SER 115 | HIS 204 | 6 |
| ASN 102 | GLY 203 | 6 |
| GLU 101 | CVS 171 | 5 |
| ARG 97 | ASN 12 | 5 |
| ASN 102 | PHE 223 | 4 |
| ASN 102 | LYS 166 | 4 |
| ARG 97 | GLY 211 | 4 |
| ARG 97 | GLN 170 | 4 |
| GLU 101 | ARG 405 | 3 |
| ASN 102 | PHE 3 | 3 |
| GLU 101 | GLU 175 | 2 |
| ARG 97 | VAL 220 | 2 |
| ARG 93 | GLY 203 | 2 |
| LYS 94 | THR 174 | 1 |
| LEU 90 | LYS 199 | 1 |
| LEU 116 | ASN 180 | 1 |
| LEU 113 | ASP 212 | 1 |
| LEU 113 | ASP 202 | 1 |
| GLY 103 | ASN 15 | 1 |
| GLU 101 | THR 7 | 1 |
| GLU 101 | PHE 437 | 1 |
| GLN 114 | ASP 202 | 1 |
| ASN 102 | ARG 405 | 1 |
| ARG 97 | TYR 434 | 1 |
| ARG 97 | PRO 182 | 1 |
| ARG 97 | GLY 9 | 1 |
| ARG 97 | GLU 8 | 1 |
| ALA 99 | ASP 202 | 1 |

Figure 56:
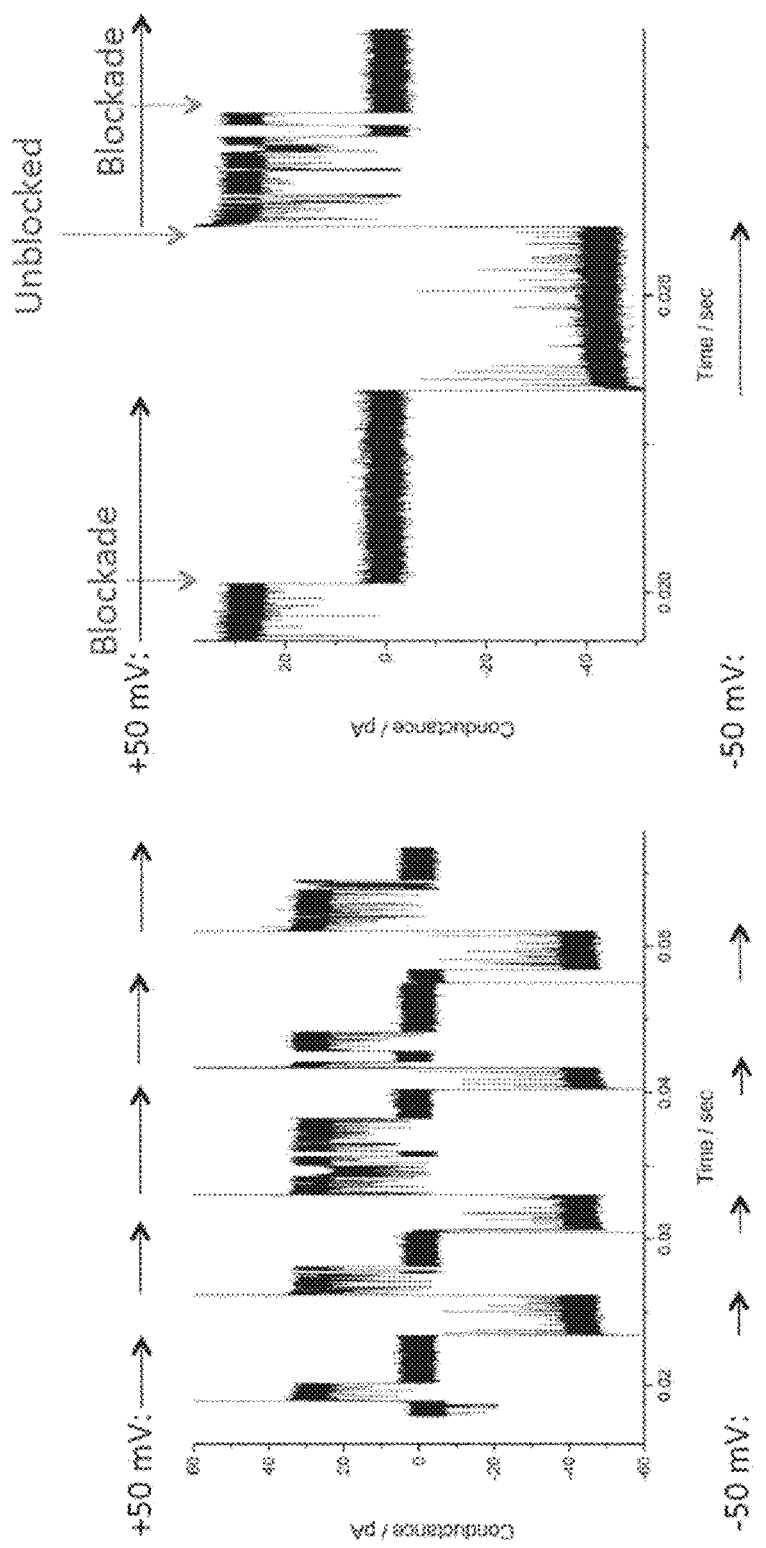
FIG. 56 shows a single channel current trace (left) and zoomed region thereof (right) of a CsgG WT protein interacting with a DNA hairpin carrying a single-stranded DNA overhang. The trace shows the current which alters in response to the potential measured at +50 mV or −50 mV intervals (indicated by arrows). The downward current blockades in the last +50 mV segment represent the simultaneous lodging of the hairpin duplex inside the pore lumen and threading of the single-stranded hairpin end into inner pore construction leading to an almost complete current blockade. Reversal of the electrical field to −50 mV results in the electrophoretic unblocking of the pore. A new +50 mV episode results again in DNA hairpin lodging/threading and pore blockage. On the +50 mV segments, unfolding of the hairpin structure can lead to the termination of the current blockade indicated by the reversal of the current blockade. The hairpin with the sequence was 3' GCGGGGA GCGT-ATT AGAGTTG GATCGGATGCA GCTGGC-TACTGACGTCA TGACGTCAGTAGCCAGCATG-CATCCGATC-5' was added to the cis side of the chamber at a final concentration of 10 nM.

Example 21: Ability of the CsgG Nanopore to the Capture Nucleic Acids in the Channel Constriction The use of nanopores for nucleic acid sequencing requires the capture and threading of single stranded DNA by the nanopore. In this example, single channel current traces of a CsgG WT protein were followed in presence of a DNA hairpin carrying a single-stranded DNA overhang. The example trace presented in FIG. 56 shows the current which alters in response to the potential measured at +50 mV or −50 mV intervals (indicated by arrows). The downward current blockades in the last +50 mV segment represent the threading of the single-stranded hairpin end into inner pore construction leading to an almost complete current blockade. Reversal of the electrical field to −50 mV results in the electrophoretic unblocking of the pore. A new +50 mV epoxide results again in DNA hairpin binding and pore blockage. On the +50 mV segments, unfolding of the hairpin structure can lead to the termination of the current blockade indicated by the reversal of the current blockade. The hairpin with the sequence 3' GCGGGGA GCGTATTAGAGTTG-GATCGGATGCAGCTGGCTACTGACGT-CATGACGTCAGTAGCCAGCATGCATC CGATC-5' (SEQ ID NO: 441) was added to the cis side of the chamber at a final concentration of 10 nM.

Figure 57:
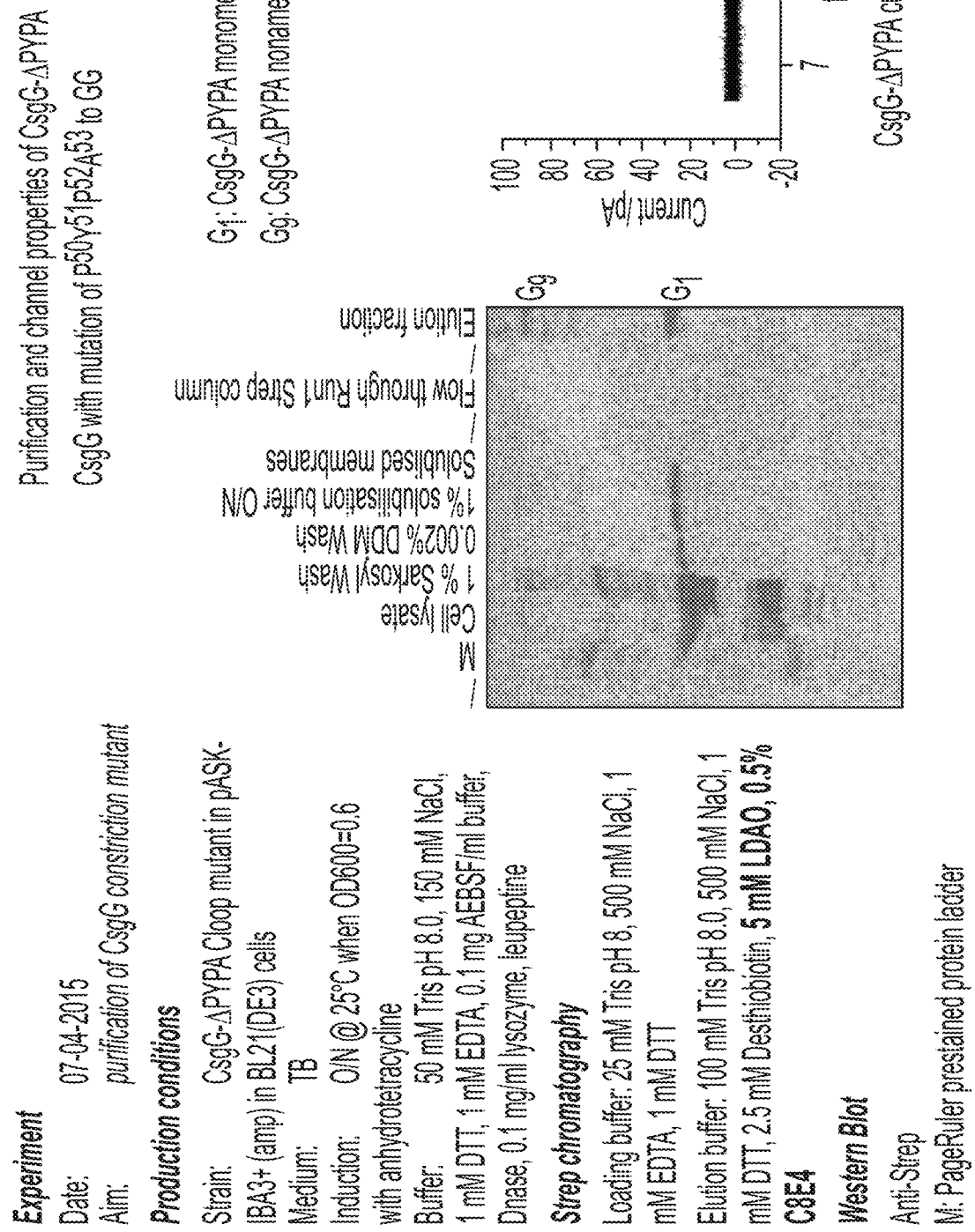
FIG. 57 shows the purification and channel properties of CsgG-ΔPYPA, a mutant CsgG pore where the PYPA sequence (residues 50-53) at the constriction residue Y51 is mutated to GG.

Example 22. This Example Describes the Generation of a Mutant CsgG Pore with an Altered Inner Constriction In this example, the stability and channel properties are demonstrated for CsgG-ΔPYPA, a mutant CsgG pore where the sequence PYPA (residues 50-53) in the constriction loop is replaced by GG. For this mutant, the constriction motif from position 38 to 63 corresponds to SEQ ID NO: 354. This mutation foresees in the removal of Y51 from the pore constriction and the shortening of the constriction loop in order to reduce complexity in the pore reading head, i.e. the narrowest part of the pore where the conductivity measured during sensing applications is most sensitive to the nature of the substrate binding or threading the pore. Replacement of the PYPA sequence retains stability of the CsgG nonamer and results in a pore with increase conductivity as shown in FIG. 57.

The CsgG-ΔPYPA pore mutant was analysed with single-channel current recordings using parallel high-resolution electrical recording with the Orbit 16 kit from Nanion (Munich, Germany). Briefly, horizontal bilayers of 1,2-diphytanoyl-sn-glycero-3-phosphocholine (Avanti Polar Lipids) were formed over microcavities (of sub-picoliter volume) in a 16-channel multielectrode cavity array (MEGA) chip (Ionera, Freiburg, Germany) 51. Both the cis and trans cavities above and below the bilayer contained 1.0 M KCl, 25 mM Tris-HCl, pH 8.0. To insert channels into the membrane, CsgG dissolved in 25 mM Tris pH 8.0, 500 mM NaCl, 1 mM DTT, 0.5% C8E4, 5 mM LDAO was added to the cis compartment to a final concentration of 100 nM. HTransmembrane currents were recorded at a holding potential of +50 mV and −50 mV (with the cis side grounded) using a Tecella Triton 16 channel amplifier at a low-pass filtering frequency of 3 kHz and a sampling frequency of 10 kHz. Current traces were analyzed using the Clampfit of the pClamp suite (Molecular Devices, USA).

Example 23

This example describes the structural and mechanistic insights into the bacterial amyloid secretion channel CsgG.

Curli are functional amyloid fibres that constitute the major protein component of the extracellular matrix in pellicle biofilms formed by Bacteroidetes and Proteobacteria (predominantly of the a and c classes)[1-3]. They provide a fitness advantage in pathogenic strains and induce a strong pro-inflammatory response during bacteraemia[1,4,5]. Curli formation requires a dedicated protein secretion machinery comprising the outer membrane lipoprotein CsgG and two soluble accessory proteins, CsgE and CsgF[6,7]. Here we report the X-ray structure of *Escherichia coli* CsgGin a non-lipidated, soluble form as well as in its Native membrane-extracted conformation. CsgG forms an oligomeric transport complex composed of nine anticodon-binding-domain-like units that give rise to a 36-stranded β-barrel that traverses the bilayer and is connected to a cage-like vestibule in the periplasm. The transmembrane and periplasmic domains are separated by a 0.9-nm channel constriction composed of three stacked concentric phenylalanine, asparagine and tyrosine rings that may guide the extended polypeptide substrate through the secretion pore. The specificity factor CsgE forms a nonameric adaptor that binds and closes off the periplasmic face of the secretion channel, creating a 24,000 Å$^3$ pre-constriction chamber. Our structural, functional and electrophysiological analyses imply that CsgG is an ungated, non-selective protein secretion channel that is expected to employ a diffusion-based, entropy-driven transport mechanism.

Curli are bacterial surface appendages that have structural and physical characteristics of amyloid fibrils, best known from human degenerative diseases[7-9]. However, the role of bacterial amyloids such as curli are to facilitate biofilmformation[4,10]. Unlike pathogenic amyloids, which are the product of protein misfolding, curli formation is coordinated by proteins encoded in two dedicated operons, csgBAC (curli specific genes BAC) and csgDEFG in *Escherichia coli* (FIG. 46)[6,17]. After secretion, CsgB nucleates CsgA subunits into curli fibres[7,11,12]. Secretion and extracellular deposition of CsgA and CsgB are dependent on two soluble accessory factors, respectively CsgE and CsgF, as well as CsgG, a 262-residue lipoprotein located in the outer membrane[13-16]. Because of the lack of hydrolysable energy sources or ion gradients at the outer membrane, CsgG falls into a specialized class of protein translocators that must operate through an alternatively energized transport mechanism. In the absence of a structural model, the dynamic workings of how CsgG promotes the secretion and assembly of highly stable amyloid like fibres in a regulated fashion across a biological membrane has so far remained enigmatic.

Figure 46:
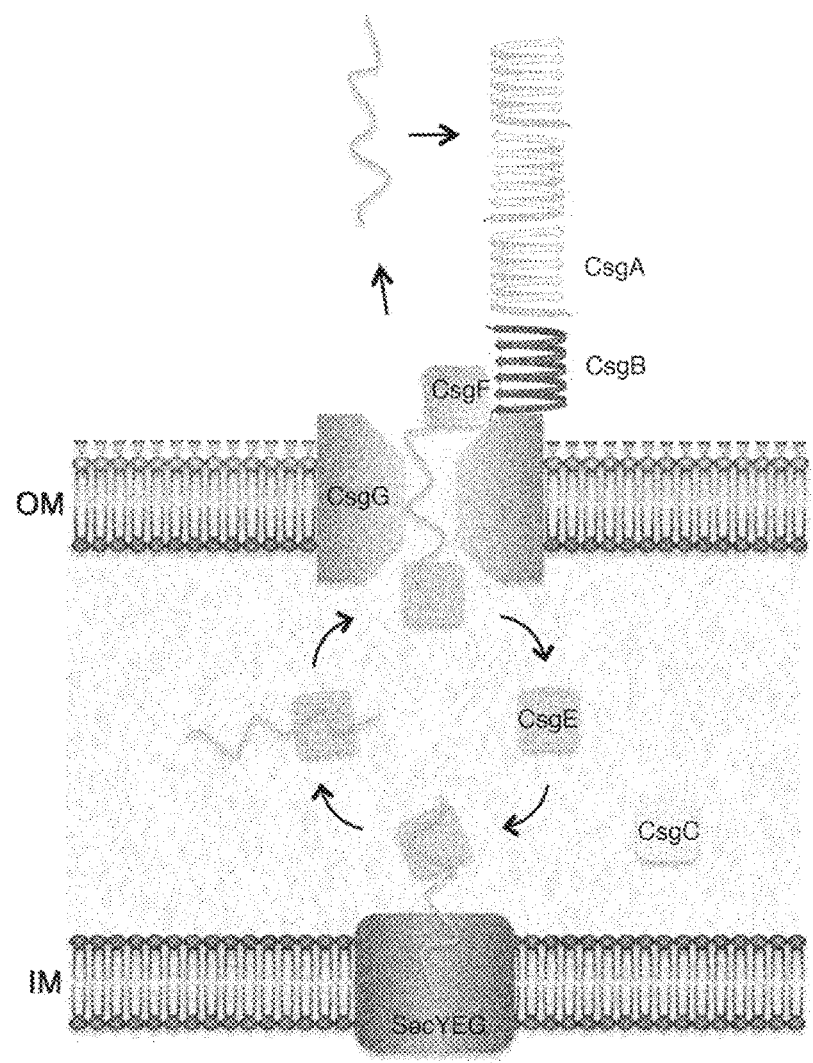
FIG. 46 shows the Curli biosynthesis pathway in *E. coli*. The major curli subunit CsgA (light green) is secreted from the cell as a soluble monomeric protein. The minor curli subunit CsgB (dark green) is associated with the outer membrane (OM) and acts as a nucleator for the conversion of CsgA from a soluble protein to amyloid deposit. CsgG (orange) assembles into an oligomeric curli-specific translocation channel in the outer membrane. CsgE (purple) and CsgF (light blue) form soluble accessory proteins required for productive CsgA and CsgB transport and deposition. CsgC forms a putative oxidoreductase of unknown function. All curli proteins have putative Sec signal sequences for transport across the cytoplasmic (inner) membrane (IM).
Figure 47:
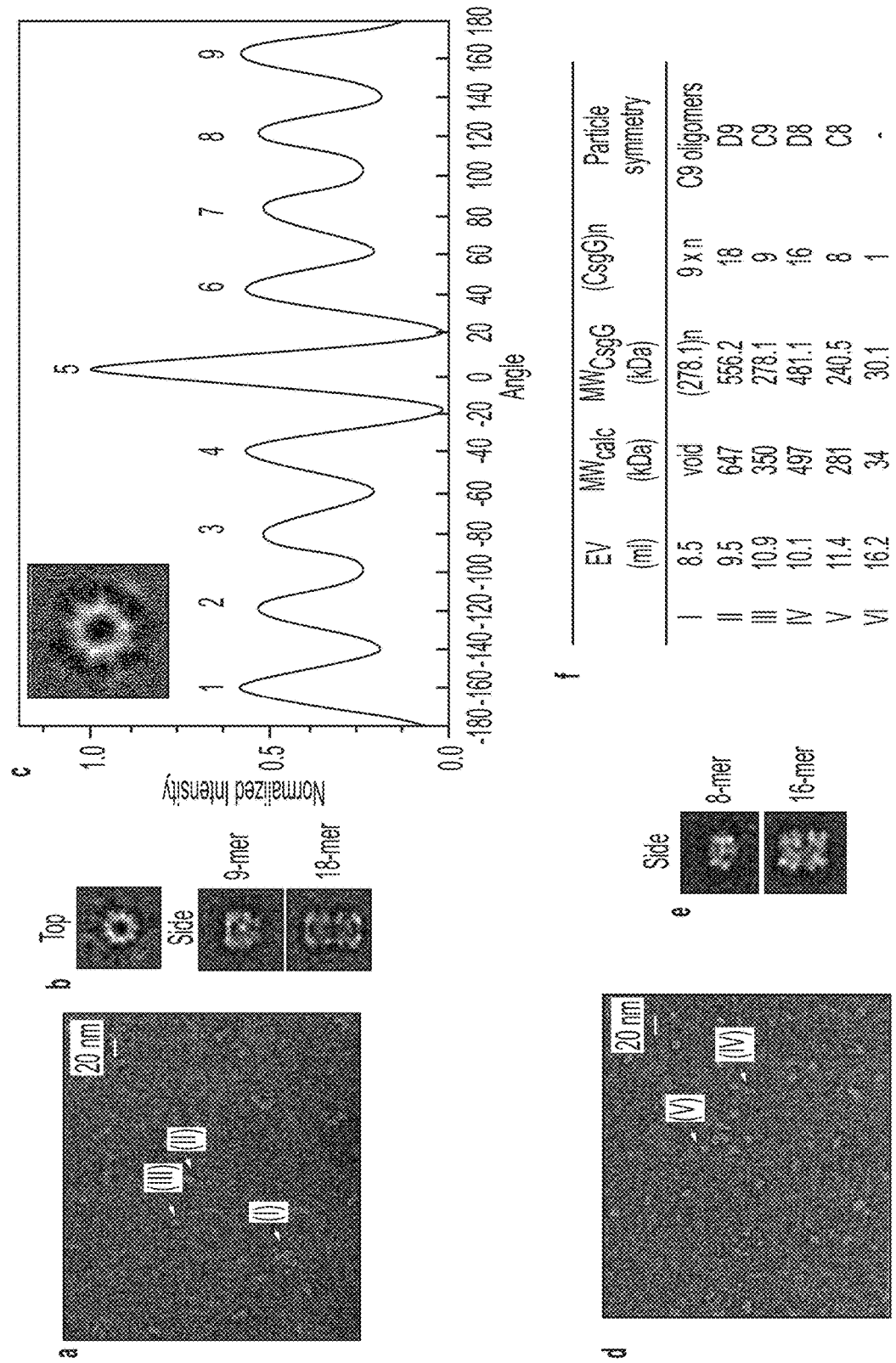
FIG. 47 shows the in-solution oligomerization states of CsgG and CsgG$_{C1S}$ analysed by size-exclusion chromatography and negative-stain electron microscopy. a, Raw negative-stain EM image of C8E4/LDAO solubilized CsgG. Arrows indicate the different particle populations as labeled in the size exclusion profile shown in g, being (I) aggregates of CsgG nonamers, (II) CsgG octadecamers and (III) CsgG nonamers. Scale bar, 20 nm. b, Representative class average for top and side views of the indicated oligomeric states. c, Rotational autocorrelation function graph of LDAO solubilized CsgG in top view, showing nine-fold symmetry. d, Raw negative stain EM image of CsgG$_{C1S}$. Arrows indicate the hexadecameric (IV) and octameric (V) particles observed by size-exclusion chromatography in g. e, Representative class average for side views of CsgG$_{C1S}$ oligomers. No top views were observed for this construct. f, Table of elution volumes (EV) of CsgG$_{C1S}$ and CsgG particles observed by size-exclusion chromatography shown in g, calculated molecular mass (MWcalc), expected molecular mass (MWCsgG) corresponding CsgG oligomerization state (CsgG$_n$) and the particles' symmetry as observed by negative-stain EM and X-ray crystallography. g, Size-exclusion chromatogram of CsgG$_{C1S}$ (black) and C8E4/LDAO-solubilized CsgG (grey) run on Superdex 200 10/300 GL (GE Healthcare). h, i, Ribbon representation of crystallized oligomers in top and side view, showing the D8 hexadecamers for CsgG$_{C1S}$ (h) and D9 octadecamers for membrane-extracted CsgG (i). One protomer is coloured in rainbow from N terminus (blue) to C terminus (red). The two C8 octamers (CsgG$_{C1S}$) or C9 nonamers (CsgG) that form the tail-to-tail dimers captured in the crystals are coloured blue and tan. r and h give radius and interprotomer rotation, respectively.
Figure 47:
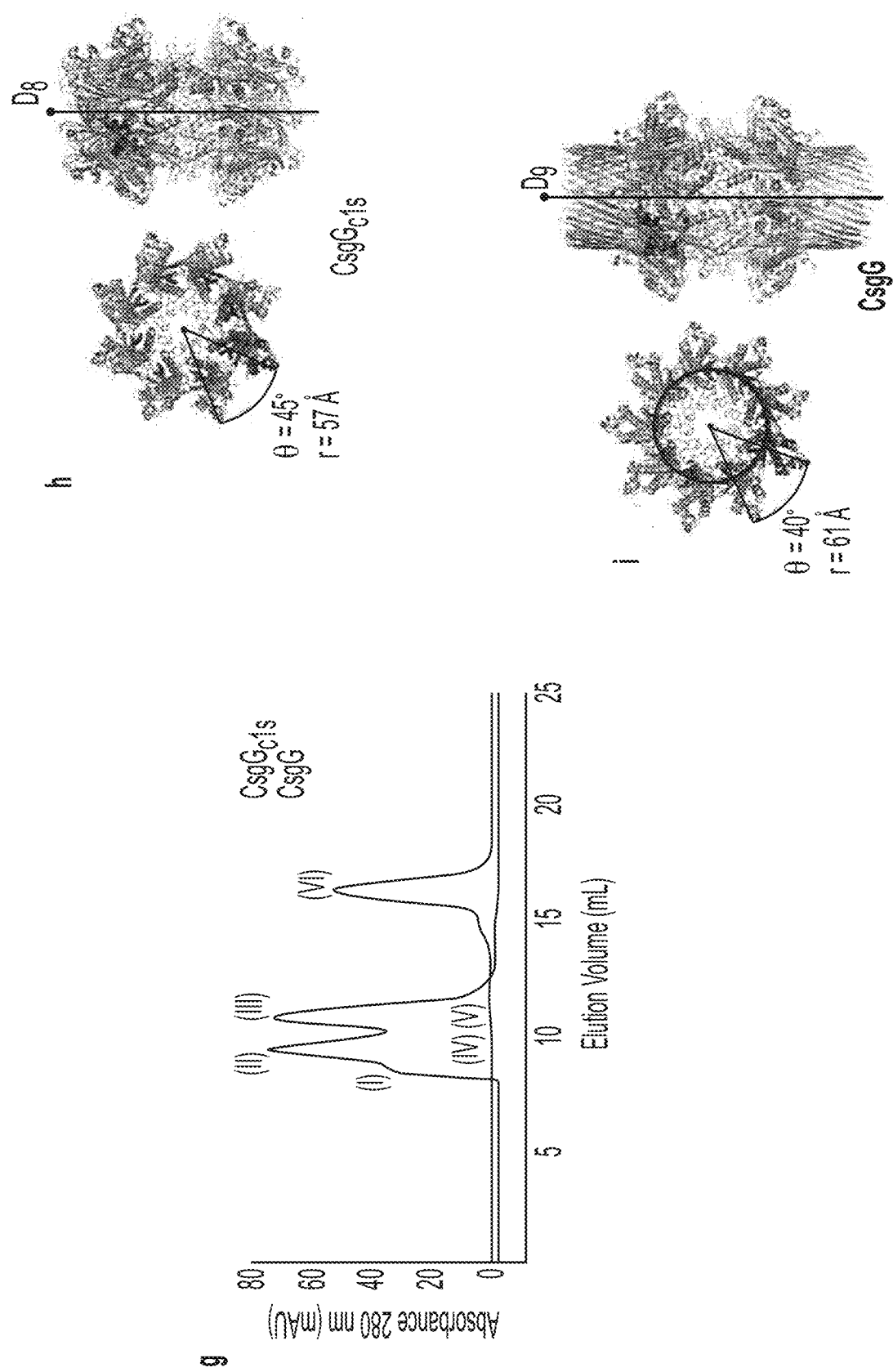
Figure 48:
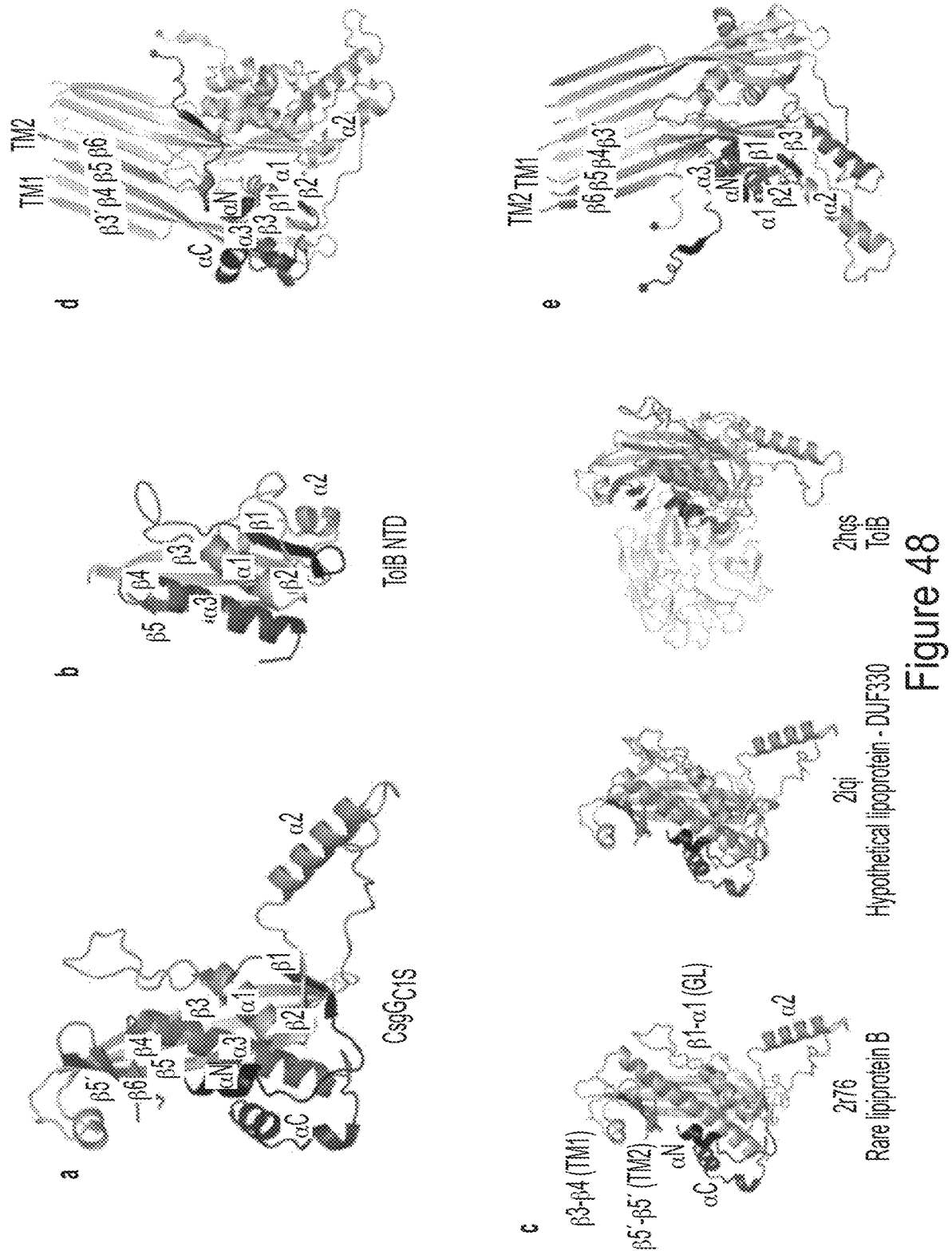
FIG. 48 shows a comparison of CsgG with structural homologues and interprotomer contacts in CsgG. a, b, Ribbon diagram for the CsgG$_{C1S}$ monomer (for example CsgG in pre-pore conformation) (a) and the nucleotide-binding-domain-like domain of TolB (b) (PDB 2hqs), both coloured in rainbow from N terminus (blue) to C terminus (red). Common secondary structure elements are labelled equivalently. c, CsgG$_{C1S}$ (grey) in superimposition with, from left to right, *Xanthomonas campestris* rare lipoprotein B (PDB 2r76, coloured pink), *Shewanella oneidensis* hypothetical lipoprotein DUF330 (PDB 2iqi, coloured pink) and *Escherichia coli* TolB (PDB 2hqs, coloured pink and yellow for the N-terminal and b-propeller domains, respectively). CsgG-specific structural elements are labelled and coloured as in the upper left panel. d, e, Ribbon diagram of two adjacent protomers as found in the CsgG structure, viewed along the plane of the bilayer, either from outside (c) or inside (d) the oligomer. One protomer is shown in rainbow (dark blue to red) from N terminus to C terminus; a second protomer is shown in light blue (core domain), blue (helix 2) and tan (TM domain). Four main oligomerization interfaces are apparent: b6-b39 main-chain interactions inside the b-barrel, the constriction loop (CL), side-chain packing of helix 1 (α1) against b1-b3-b4-b5, and helix-helix packing of helix 2 (α2). The 18-residue N-terminal loop connecting the lipid anchor (a magenta sphere shows the Ca position of Leu 2) and N-terminal helix (αN) is also seen to wrap over the adjacent two protomers. The projected position of the lipid anchor is expected to lie against the TM1 and TM2 hairpins of the +2 protomer (not shown for clarity).

Before insertion into the outer membrane, lipoproteins are piloted across the periplasm by means of the lipoprotein localization (Lol) pathway[17]. We observed that non-lipidated CsgG (CsgG$_{C1S}$) could be isolated as a soluble periplasmic intermediate, analogous to the pre-pore forms observed in poreforming proteins and toxins[19]. CsgG$_{C1S}$ was found predominantly as monomers, in addition to a minor fraction of discrete oligomeric complexes (FIG. 47)[19]. The soluble CsgG$_{C1S}$ oligomers were crystallized and their structure was determined to 2.8 Å, revealing a hexadecameric particle with eight-fold dihedral symmetry (D8), consisting of two ring-shaped octameric complexes (C8) that are joined in a tail-to-tail interaction (FIG. 47 and FIG. 46). The CsgG$_{C1S}$ protomer shows an anticodon-binding domain (ABD)-like fold that is extended with two α-helices at the amino and carboxy termini (αN and αC, respectively; FIG. 42 and FIG. 48a-c). Additional CsgG-specific elements are an extended loop linking β1 and α1, two insertions in the loops connecting β3-β4 and β5-α3 and an extended α2 helix that is implicated in CsgG oligomerization by packing between adjacent monomers (FIG. 42b). Further inter-protomer contacts are formed between the back of the β3-β5 sheet and the extended β1-α1 loop (FIG. 48d, e).

Figure 49:
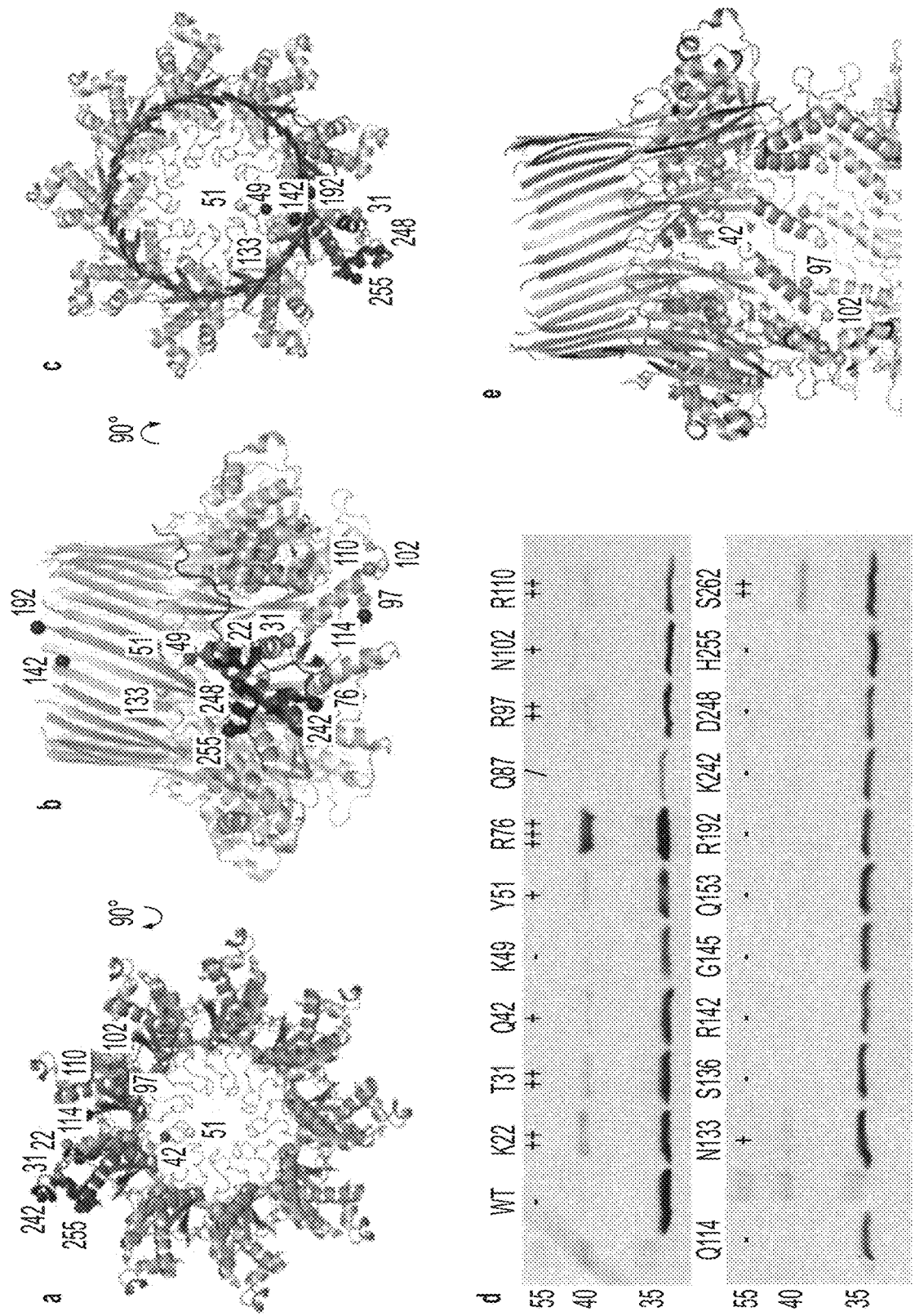
FIG. 49 shows Cys accessibility assays for selected surface residues in the CsgG oligomers. a-c, Ribbon representation of CsgG nonamers shown in periplasmic (a), side (b) and extracellular (c) views. One protomer is coloured in rainbow from N terminus (blue) to C terminus (red). Cysteine substitutions are labelled and the equivalent locations of the S atoms are shown as spheres, coloured according to accessibility to MAL-PEG (5,000 Da) labelling in *E. coli* outer membranes. d, Western blot of MAL-PEG reacted samples analysed on SDS-PAGE, showing 5 kDa increase on MALPEG binding of the introduced cysteine. Accessible (11 and 111), moderately accessible (1) and inaccessible (2) sites are coloured green, orange and red, respectively, in a-e. For Arg 97 and Arg 110 a second species at 44 kDa is present, corresponding to a fraction of protein in which both the introduced and native cysteine became labelled. Data are representative of four independent experiments from biological replicates. e, Side view of the dimerization interface in the D9 octadecamer as present in the X-ray structure. Introduced cysteines in the dimerization interface or inside the lumen of the D9 particle are labelled. In membrane-bound CsgG, these residues are accessible to MAL-PEG, demonstrating that the D9 particles are an artifact of concentrated solutions of membrane-extracted CsgG and that the C9 complex forms the physiologically relevant species. Residues in the C-terminal helix (aC; Lys 242, Asp 248 and His 255) are found to be inaccessible to poorly accessible, indicating that aC may form additional contacts with the *E. coli* cell envelope, possibly the peptidoglycan layer.

In the CsgG$_{C1S}$ structure, residues 1-17, which would link α1 to the N-terminal lipid anchor, are disordered and no obvious transmembrane (TM) domain can be discerned (FIG. 42). Attenuated total reflection Fourier transform infrared spectroscopy (ATR-FTIR) of CsgG$_{C1S}$ and native, membrane-extracted CsgG revealed that the latter has a higher absorption in the β-sheet region (1,625-1,630 cm$^{-1}$) and a concomitant reduction in the random coil and α-helical regions (1,645-1,650 cm$^{-1}$ and 1,656 cm$^{-1}$, respectively; FIG. 43a), suggesting that membrane-associated CsgG contains a β-barrel domain. Candidate sequence stretches for β-strand formation are found in the poorly ordered, extended loops connecting β3-β4 (residues 134-154) and β5-α3 (residues 184-204); deletion of these resulted in the loss of curli formation (FIG. 43b). The crystal structure of detergent-extracted CsgG confirmed a conformational rearrangement of both regions into two adjacent β-hairpins, extending the β-sheet formed by β3-β4 (TM1) and β5-α5 (TM2) (FIG. 43c). Their juxtaposition in the CsgG oligomer gave rise to a composite 36-stranded (β-barrel (FIG. 43d). Whereas the crystallized CsgG$_{C1S}$ oligomers showed a D8 symmetry, the CsgG structure showed D9 symmetry, with CsgG protomers retaining equivalent interprotomer contacts, except for a 5° rotation relative to the central axis and a 4 Å translation along the radial axes FIG. 47). This observation is reconciled in the in-solution oligomeric states revealed by single-particle electron microscopy, which exclusively found C9 and D9 symmetries for membrane-extracted CsgG (FIG. 47). The predominant presence of monomers in the non-lipidated sample and the symmetry mismatch with the membrane-bound protein argue that before membrane insertion, CsgG is targeted to the outer membrane in a monomeric, LolA-bound form and that the C8 and D8 particles are an artefact of highly concentrated solutions of CsgG$_{C1S}$. Furthermore, we show that the C9 nonamer rather than the D9 complex forms the physiologically relevant particle, because in isolated *E. coli* outer membranes, cysteine substitutions in residues enclosed by the observed tail-to-tail dimerization are accessible to labelling with maleimidepolyethylene glycol (PEG, 5 kDa; FIG. 49).

Figure 44:
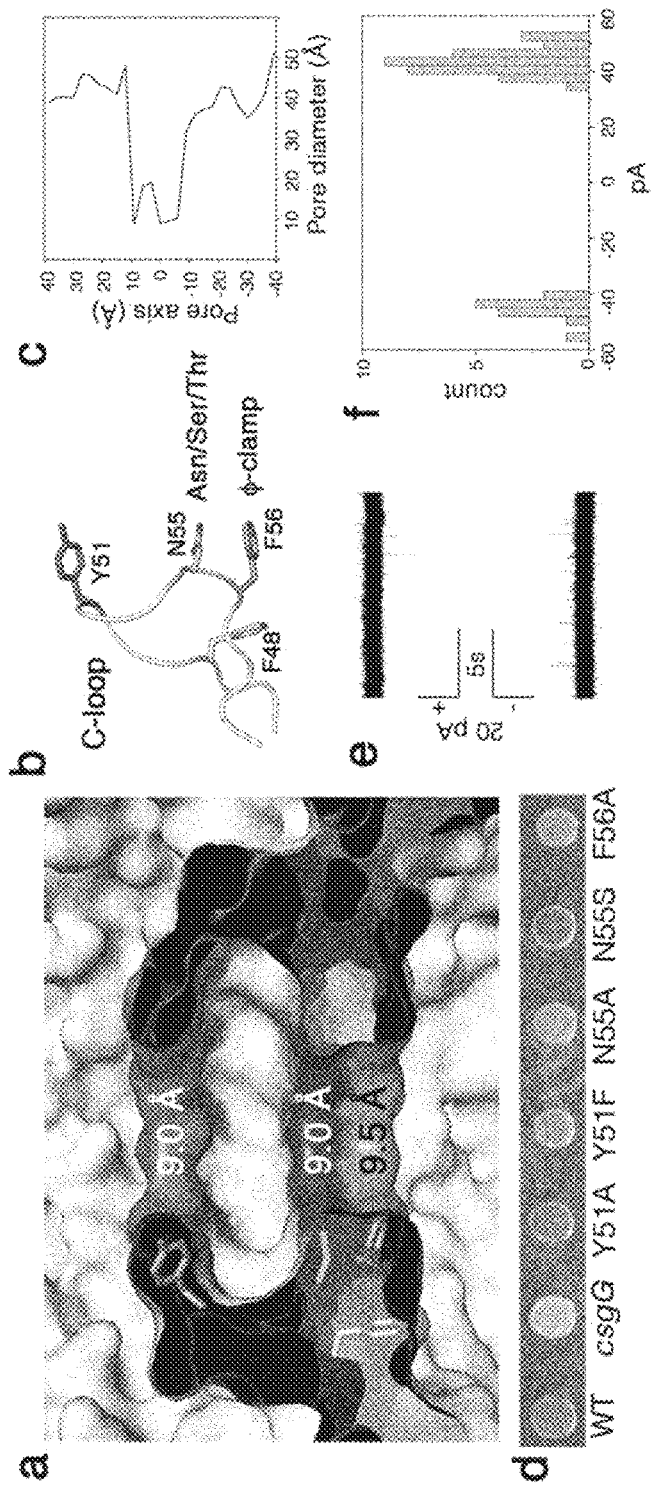
FIG. 44 shows the CsgG channel constriction. a, Cross-section of CsgG channel constriction and its solvent-excluded diameters. b, The constriction is composed of three stacked concentric side-chain layers: Tyr 51, Asn 55 and Phe 56, preceded by Phe 48 from the periplasmic side. c, CsgG channel topology. d, Congo red binding of *E. coli* BW25141ΔcsgG complemented with csgG (WT), empty vector or csgG carrying indicated constrictions mutants. Data are representative of six biological replicates. e, f, Representative single channel current recordings (e) and conductance histogram (f) of CsgG reconstituted in planar phospholipid bilayers and measured under an electrical field of +50 mV (n=33) or −50 mV (n=13).
Figure 50:
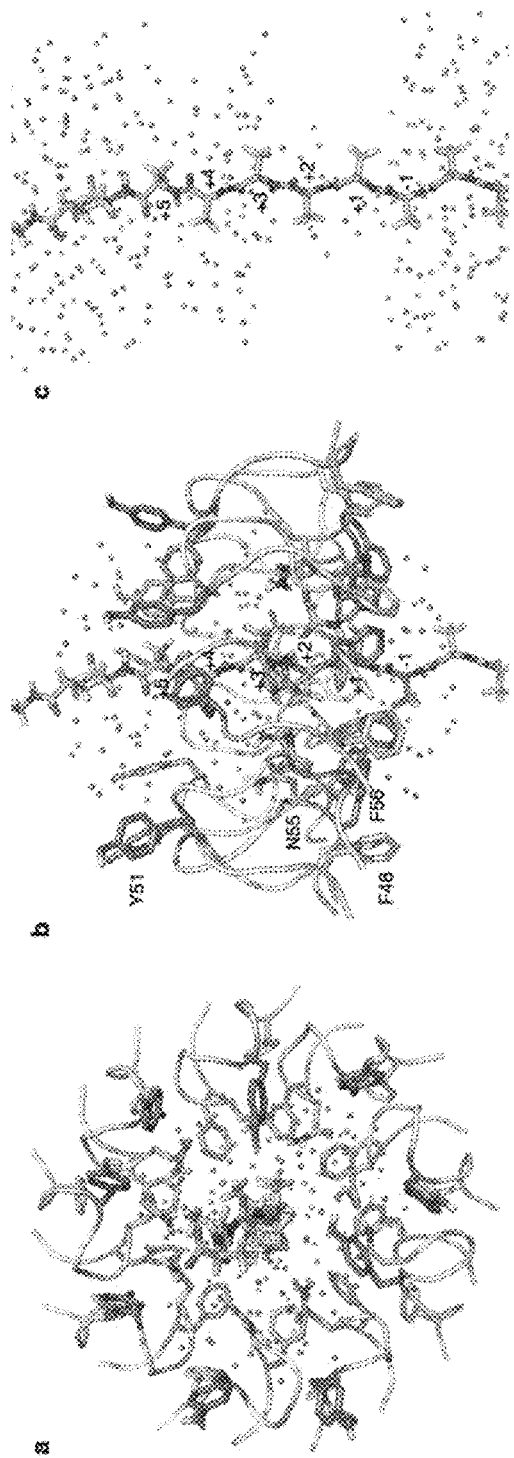
FIG. 50 shows molecular dynamics simulation of CsgG constriction with model polyalanine chain. a, b, Top (a) and side (b) views of the CsgG constriction modelled with a polyalanine chain threaded through the channel in an extended conformation, here shown in a C-terminal to N-terminal direction. Substrate passage through the CsgG transporter is itself not sequence specific$^{ref16,23}$. For clarity, a polyalanine chain was used for modelling the putative interactions of a passing polypeptide chain. The modelled area is composed of nine concentric CsgG C-loops, each comprising residues 47-58. Side chains lining the constriction are shown in stick representation, with Phe 51 coloured slate blue, Asn 55 (amide-clamp) cyan, and Phe 48 and Phe 56 (φ-clamp) in light and dark orange, respectively. N, O and H atoms (only hydroxyl or side-chain amide H atoms are shown) are coloured blue, red and white, respectively. The polyalanine chain is coloured green, blue, red and white for C, N, O and H atoms, respectively. Solvent molecules (water) within 10 Å of the polyalanine residues inside the constriction (residues labelled 11 to 15) are shown as red dots. c, Modelled solvation of the polyalanine chain, position as in b and with C-loops removed for clarity (shown solvent molecules are those within 10 Å of the full polyalanine chain). At the height of the amide-clamp and φ-clamp, the solvation of the polyalanine chain is reduced to a single water shell that bridges the peptide backbone and amide-clamp side chains. Most side chains in the Tyr 51 ring have rotated towards the solvent in comparison with their inward, centre-pointing position observed in the CsgG (and the CsgG$_{C1S}$) X-ray structure. The model is the result of a 40 ns all-atom explicit solvent molecular dynamics simulation with GROMACS$^{ref53}$ using the AMBER99SB-ILDN54 force field and with the Ca atoms of the residues at the extremity of the C-loop (Gln 47 and Thr 58) positionally restricted.
Figure 51:
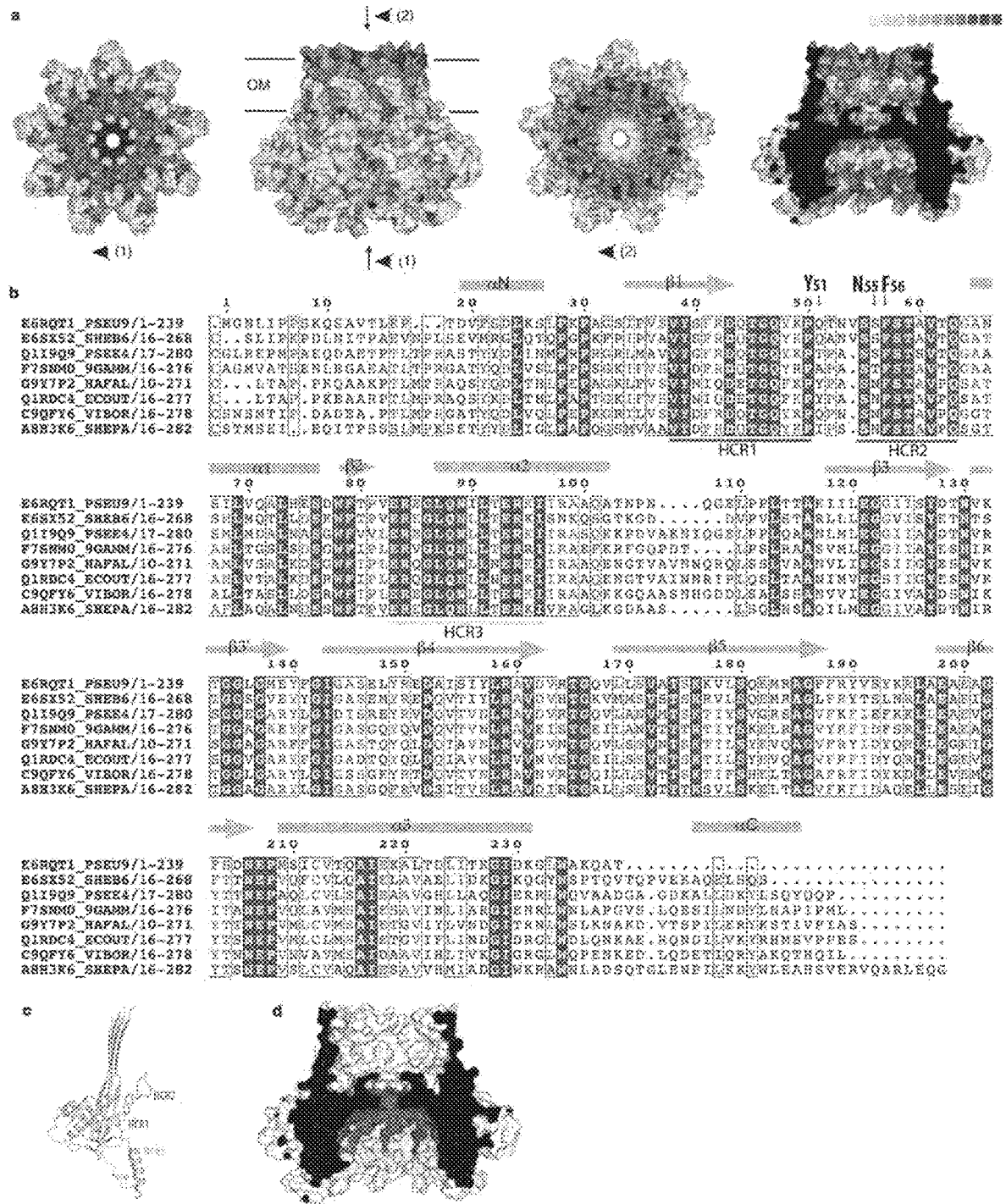
FIG. 51 shows sequence conservation in CsgG homologues. a, Surface representation of the CsgG nonamer coloured according to sequence similarity (coloured yellow to blue from low to high conservation score) and viewed from the periplasm (far left), the side (middle left), the extracellular milieu (middle right) or as a cross-sectional side view (far right). The figures show that the regions of highest sequence conservation map to the entry of the periplasmic vestibule, the vestibular side of the constriction loop and the luminal surface of the TM domain. b, Multiple sequence alignment of CsgGlike lipoproteins. The selected sequences were chosen from monophyletic clades across the phylogenetic three of CsgG-like sequences (not shown), to give a representative view of sequence diversity. Secondary structure elements are shown as arrows or bars for β-strands and α-helices, respectively, and are based on the *E. coli* CsgG crystal structure. c, d, CsgG protomer in secondary structure representation (c) and a cross-sectional side view (d) of the CsgG nonamer in surface representation, both coloured grey and with three continuous blocks of high sequence conservation coloured red (HCR1), blue (HCR2) and yellow (HCR3). HCR1 and HCR2 shape the vestibular side of the constriction loop; HCR3 corresponds to helix 2, lying at the entry of the periplasmic vestibule. Inside the constriction, Phe 56 is 100% conserved, whereas Asn 55 can be conservatively replaced by Ser or Thr, for example by a small polar side chain that can act as hydrogen-bond donor/acceptor. The concentric side-chain ring at the exit of the constriction (Tyr 51) is not conserved. The presence of the Phe-ring at the entrance of the constriction is topologically similar to the Phe 427-ring (referred to as the φ-clamp) in the anthrax protective antigen PA63, in which it was shown to catalyse polypeptide capture and passage$^{ref20}$. MST of toxB superfamily proteins reveals a conserved motif D(D/Q)(F)(S/N)S at the height of the Phe-ring. This is similar to the S(Q/N/T)(F)ST motif seen in curli-like transporters. Although an atomic resolution structure of PA63 in pore conformation is not yet available, available structures suggest the Phe-ring may similarly be followed by a conserved hydrogen-bond donor/acceptor (Ser/Asn 428) as a subsequent concentric ring in the translocation channel (note that the orientation of the element is inverted in both transporters).

Thus, CsgG forms a nonameric transport complex 120 Å in width and 85 Å in height. The complex traverses the outer membrane through a 36-stranded β-barrel with an inner diameter of 40 Å (FIG. 43e). The N-terminal lipid anchor is separated from the core domain by an 18-residue linker that wraps over the adjacent protomer (FIG. 48d). The diacylglycerol- and amide-linked acyl chain on the N-terminal Cys are not resolved in the electron density maps, but on the basis of the location of Leu 2 the lipid anchor is expected to flank the outer wall of the β-barrel. On the periplasmic side, the transporter forms a large solvent-accessible cavity with an inner diameter of 35 Å and a height of 40 Å that opens to the periplasmin a 50 Å mouth formed by helix 2 (FIG. 43e). At its apex, this periplasmic vestibule is separated from the TM channel by a conserved 12-residue loop connecting β1 to α1 (C-loop; FIGS. 43e and 44a, b), which constricts the secretion conduit to a solvent-excluded diameter of 9.0 Å (FIG. 44a, c). These pore dimensions would be compatible with the residence of one or two (for example a looped structure) extended polypeptide segments, with five residues spanning the height of the constriction (FIG. 50). The luminal lining of the constriction is composed of three stacked concentric rings formed by the side chains of residues Tyr 51, Asn 55 and Phe 56 (FIG. 44a, b). In the anthrax PA63 toxin, a topologically equivalent concentric Phe ring (referred to as a φ-clamp) lines the entry of the translocation channel and catalyses polypeptide capture and passage[20-22]. Multiple sequence alignment of CsgG-like translocators shows the absolute conservation of Phe 56 and the conservative variation of Asn 55 to Ser or Thr (FIG. 51). Mutation of Phe 56 or Asn 55 to Ala leads to a near loss of curli production (FIG. 44d), whereas a Asn 55→Ser substitution retains wild-type secretion levels, together alluding to the requirement of the stacked configuration of a φ-clamp followed by a hydrogen-bond donor/acceptor in the CsgG constriction (FIG. 44b and FIG. 51).

Figure 52:
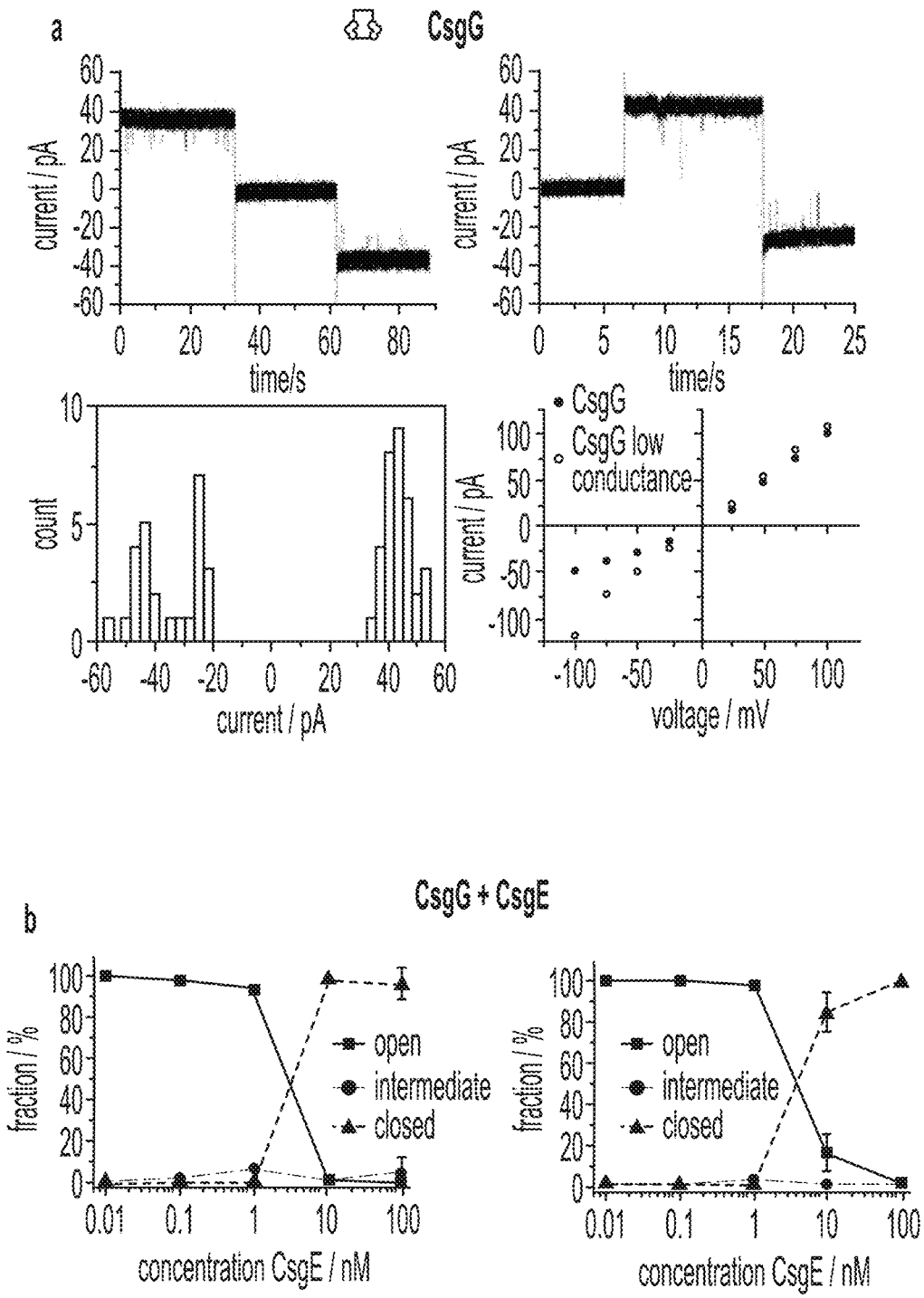
FIG. 52 shows single-channel current analysis of CsgG and CsgG:CsgE pores. a, Under negative field potential, CsgG pores show two conductance states. The upper left and right panels show a representative single-channel current trace of, respectively, the normal (measured at +50, 0 and −50 mV) and the low-conductance forms (measured at 0, +50 and −50 mV). No conversions between both states were observed during the total observation time (n=22), indicating that the conductance states have long lifetimes (second to minute timescale). The lower left panel shows a current histogram for the normal and low-conductance forms of CsgG pores acquired at +50 and −50 mV (n=33). I-V curves for CsgG pores with regular and low conductance are shown in the lower right panel. The data represent averages and standard deviations from at least four independent recordings. The nature or physiological existence of the low-conductance form is unknown. b, Electrophysiology of CsgG channels titrated with the accessory factor CsgE. The plots display the fraction of open, intermediate and closed channels as a function of CsgE concentration. Open and closed states of CsgG are illustrated in FIG. 45f. Increasing the concentration of CsgE to more than 10 nM leads to the closure of CsgG pores. The effect occurs at +50 mV (left) and −50 mV (right), ruling out the possibility that the pore blockade is caused by electrophoresis of CsgE (calculated pI 4.7) into the CsgG pore. An infrequent (5%) intermediate state has roughly half the conductance of the open channel. It may represent CsgE-induced incomplete closures of the CsgG channel; alternatively, it could represent the temporary formation of a CsgG dimer caused by the binding of residual CsgG monomer from the electrolyte solution to the membrane-embedded pore. The fraction for the three states was obtained from all-point histogram analysis of single-channel current traces. The histograms yielded peak areas for up to three states, and the fraction for a given state was obtained by dividing the corresponding peak area by the sum of all other states in the recording. Under negative field potential, two open conductance states are discerned, similar to the observations for CsgG (see a). Because both open channel variations were blocked by higher CsgE concentrations, the 'open' traces in b combine both conductance forms. The data in the plot represent averages and standard deviations from three independent recordings. c, The crystal structure, size-exclusion chromatography and EM show that detergent extracted CsgG pores form non-native tail-to-tail stacked dimers (for example, two nonamers as D9 particle.
Figure 52:
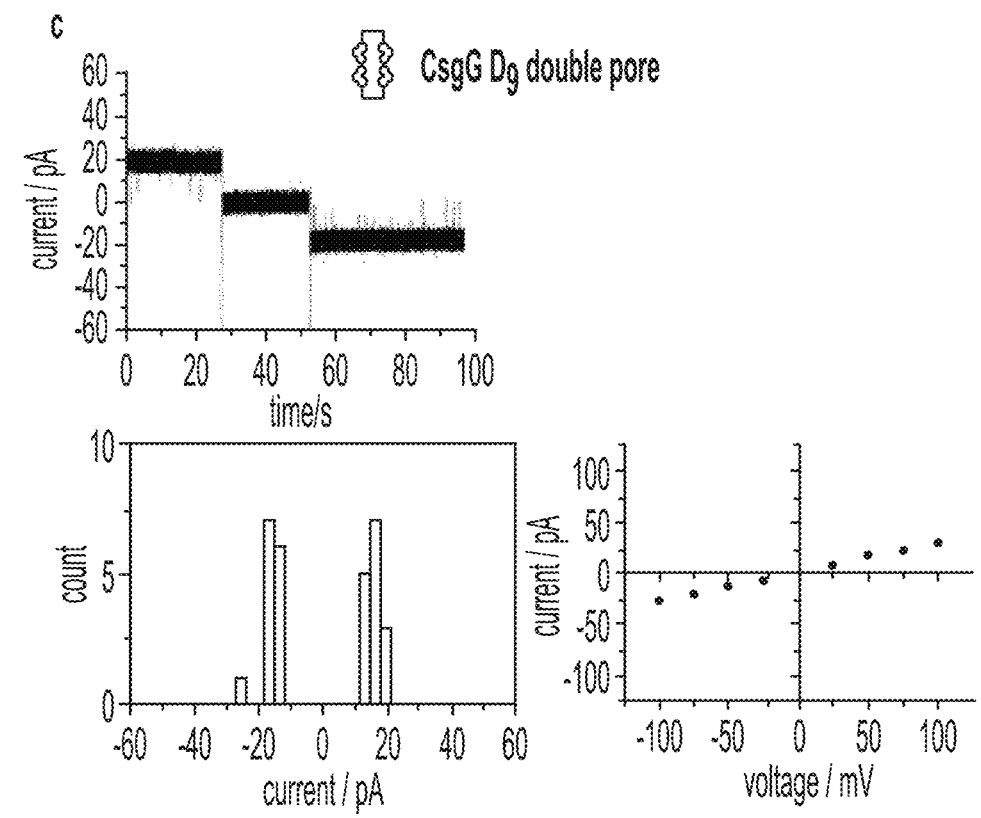
Figure 52:
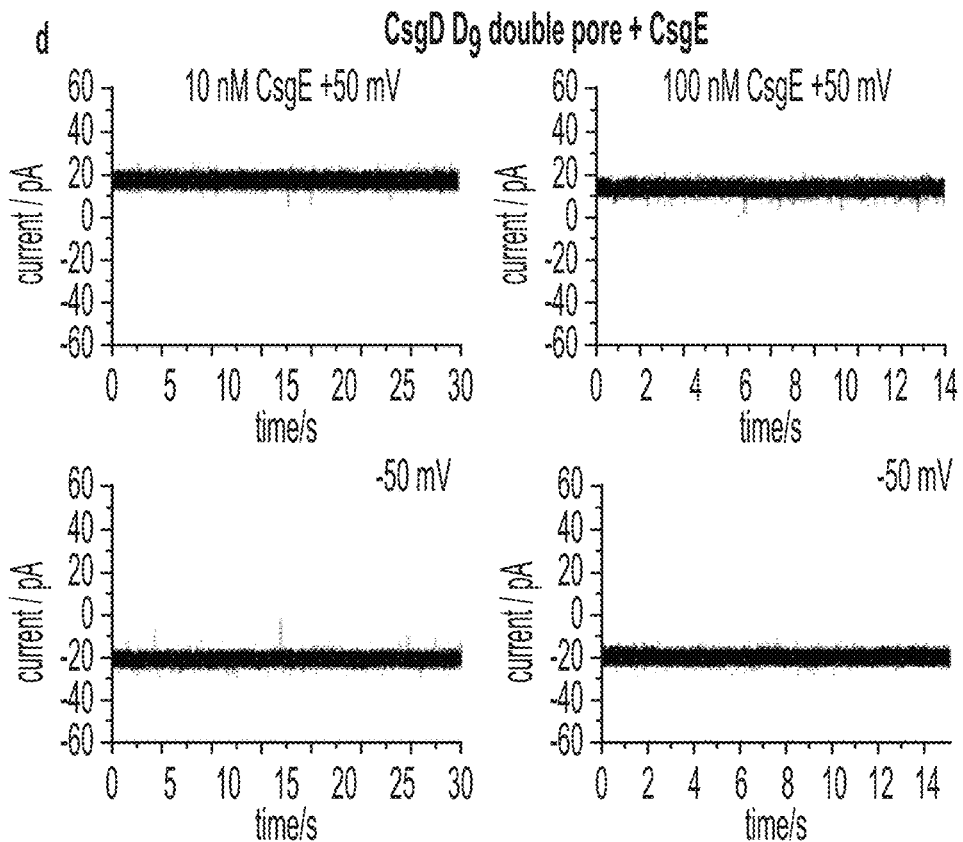

Single-channel current recordings of CsgG reconstituted in planar phospholipid bilayers led to a steady current of 43.1±4.5 pA (n=33) or −45.1±4.0 pA (n=13) using standard electrolyte conditions and a potential of +50 mV or −50 mV, respectively (FIG. 44e, f and FIG. 52). The observed current was in good agreement with the predicted value of 46.6 pA calculated on the basis of a simple three-segment pore model and the dimensions of the central constriction seen in the X-ray structure (FIG. 44c). A second, low-conductance conformation can also be observed under negative electrical field potential (−26.2±3.6 pA (n=13); FIG. 52). It is unclear, however, whether this species is present under physiological conditions.

Figure 45:
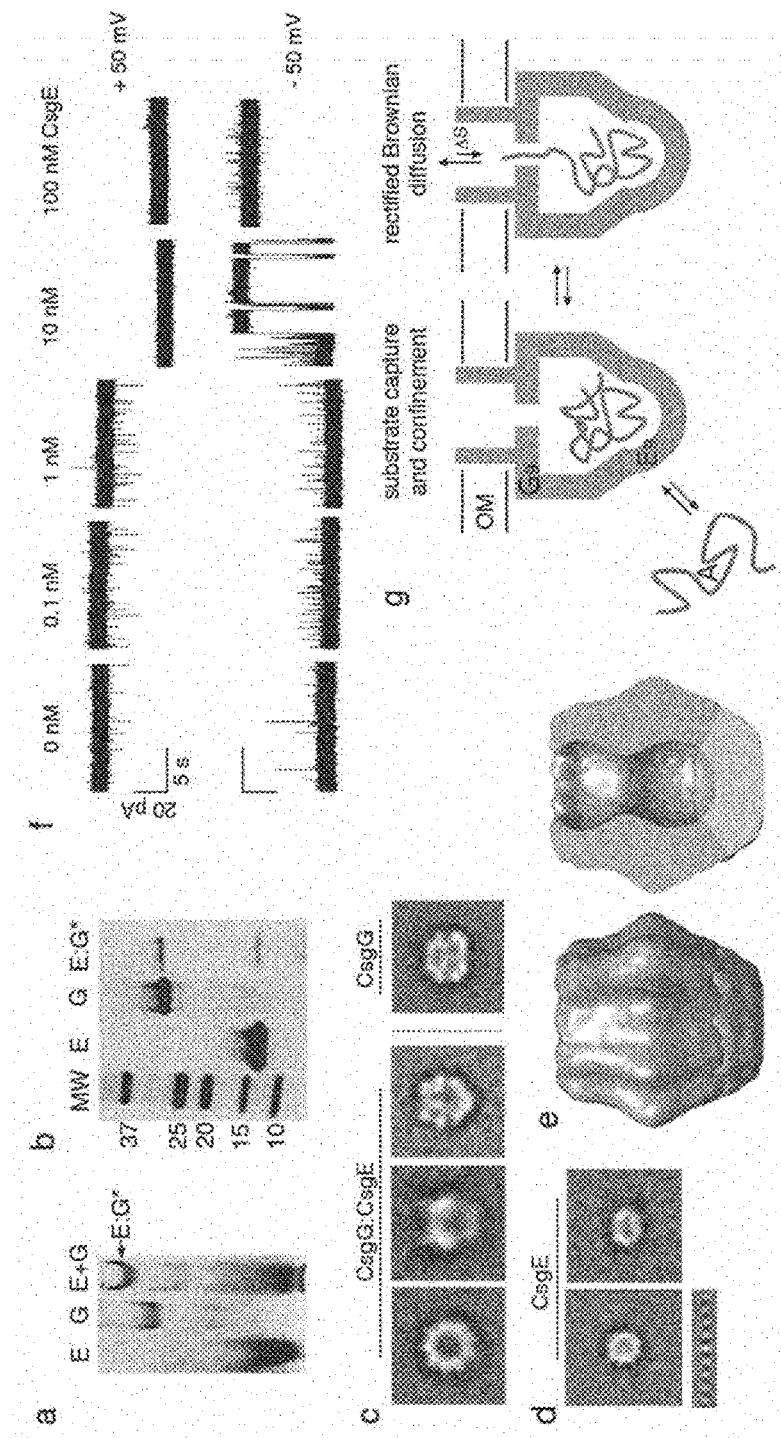
FIG. 45 shows a model of CsgG transport mechanism. a, NativePAGE of CsgE (E), CsgG (G) and CsgG supplemented with excess CsgE (E+G), showing the formation of a CsgG-CsgE complex (E–G*). Data are representative of seven experiments, encompassing four protein batches. b, SDS-PAGE of CsgE (E), CsgG (G) and the E–G* complex recovered from native PAGE. Data are representative of two repetitions. M, molecular mass markers. c, Selected class averages of CsgG-CsgE particles. From left to right: top and side view visualized by cryo-EM, and comparison of negatively stained side views with CsgG nonamers. d, Cryo-EM averages of top and tilted side-viewed CsgE particles. Rotational autocorrelation shows nine-fold symmetry. e, Three-dimensional reconstruction of CsgG-CsgE (24Å° resolution, 1,221 single particles) shows a nonameric particle comprising CsgG (blue) and an additional density assigned as a CsgE nonamer (orange). f, Single-channel current recordings of PPB reconstituted CsgG at +50 mV or −50 mV and supplemented with incremental concentrations of CsgE. Horizontal scale bars lie at 0 pA. g, Tentative model for CsgG-mediated protein secretion. CsgG and CsgE are proposed to form a secretion complex that entraps CsgA (discussed in FIG. 54), generating an entropic potential over the channel. After capture of CsgA in the channel constriction, a DS-rectified Brownian diffusion facilitates the progressive translocation of the polypeptide across the outer membrane.
Figure 53:
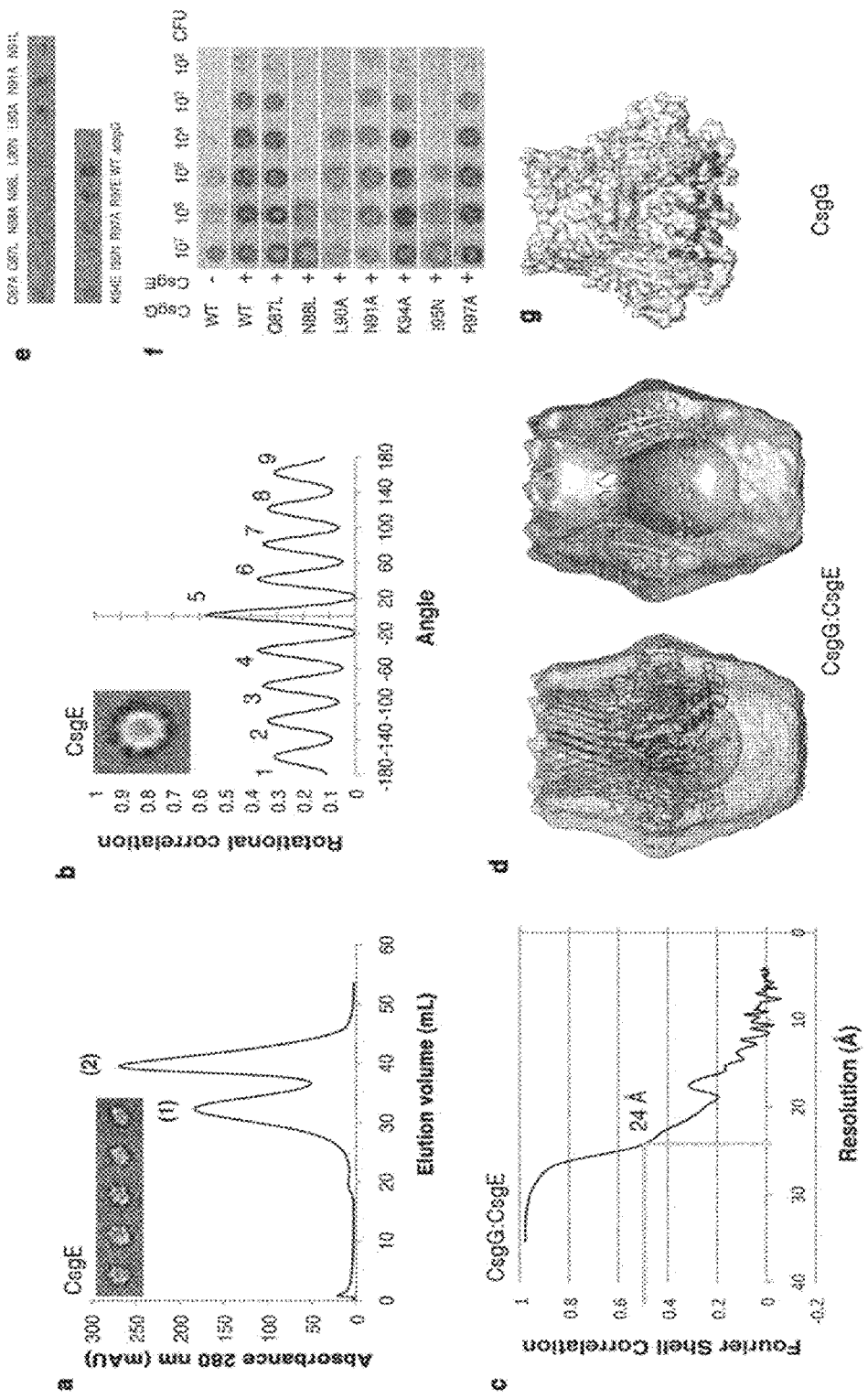
FIG. 53 shows CsgE oligomer and CsgG-CsgE complex. a, Size exclusion chromatography of CsgE (Superose 6, 16/600; running buffer 20 mM Tris-HCl pH8, 100 mM NaCl, 2.5% glycerol) shows an equilibrium of two oligomeric states, 1 and 2, with an apparent molecular mass ratio of 9.16:1. Negative-stain EM inspection of peak 1 shows discrete CsgE particles (five representative class averages are shown in the inset, ordered by increasing tilt angles) compatible in size with nine CsgE copies. b, Selected class average of CsgE oligomer observed in top view by cryo-EM and its rotational autocorrelation show the presence of C9 symmetry. c, FSC analysis of CsgG-CsgE cryo-EMmodel. Three-dimensional reconstruction achieved a resolution of 24 Å as determined by FSC at a threshold of 0.5 correlation using 125 classes corresponding to 1,221 particles. d, Overlay of CsgG-CsgE cryo-EM density and the CsgG nonamer observed in the X-ray structure. The overlays are shown viewed from the side as semi-transparent density (left) or as across-sectional view. e, Congo red binding of *E. coli* BW25141ΔcsgG complemented with wild-type csgG (WT), empty vector (ΔcsgG) or csgGhelix 2 mutants (single amino acid replacements labelled in single-letter code). Data are representative of four biological replicates. f, Effect of bile salt toxicity on *E. coli* LSR12 complemented with csgG (WT) or on csgG carrying different helix 2 mutations, complemented with (1) or without (2) csgE. Tenfold serial dilution starting from 107 bacteria were spotted on McConkey agar plates. Expression of the CsgG pore in the outer membrane leads to an increased bile salt sensitivity that can be blocked by co-expression of CsgE (n=6, three biological replicates, with two repetitions each). g, Cross-sectional view of CsgG X-ray structure in molecular surface representation. CsgG mutants without an effect on Congo red binding or toxicity are shown in blue; mutants that interfere with CsgE-mediated rescue of bile salt sensitivity are indicated in red.

Our structural data and single-channel recordings imply that CsgG forms an ungated peptide diffusion channel. In $PA_{63}$, a model peptide diffusion channel, polypeptide passage depends on a ΔpH-driven Brownian ratchet that rectifies the diffusive steps in the translocation channel[20-22]. However, such proton gradients are not present at the outer membrane, requiring an alternative driving force. Whereas at elevated concentrations CsgG facilitates a non-selective diffusive leakage of periplasmic polypeptides, secretion is specific for CsgA under native conditions and requires the periplasmic factor CsgE[16,23]. In the presence of excess CsgE, purified CsgG forms a more slowly migrating species on native PAGE (FIG. 45a). SDS-PAGE analysis shows this new species consists of a CsgG-CsgE complex that is present in a 1:1 stoichiometry (FIG. 45b). Cryoelectron microscopy (cryo-EM) visualization of CsgG-CsgE isolated by pull-down affinity purification revealed a nine-fold symmetrical particle corresponding to the CsgG nonamer and an additional capping density at the entrance to the periplasmic vestibule, similar in size and shape to a C9 CsgE oligomer also observed by single-particle EM and size-exclusion chromatography (FIG. 45c-e and FIG. 53). The location of the observed CsgG-CsgE contact interface was corroborated by blocking point mutations in CsgG helix 2 (FIG. 53). In agreement with a capping function, single-channel recordings showed that CsgE binding to the translocator led to the specific silencing of its ion conductance (FIG. 45f and FIG. 52). This CsgE capping of the channel seemed to be an all-or-none response in function of CsgE nomamerbinding. At saturation, CsgE binding induced full blockage of the channel, whereas at about 10 nM, an equilibrium between CsgE binding and dissociation events resulted in an intermittently blocked or fully open translocator. At 1 nM or below, transient (<1 ms) partial blockage events may have stemmed from short-lived encounters with monomeric CsgE.

Figure 54:
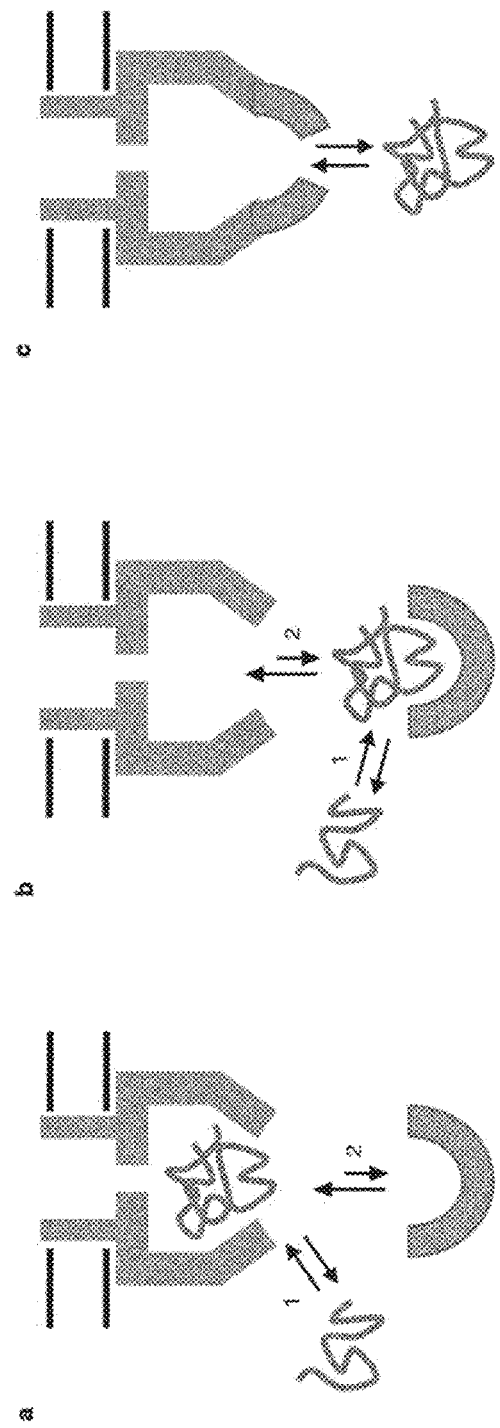
FIG. 54 shows assembly and substrate recruitment of the CsgG secretion complex. The curli transporter CsgG and the soluble secretion cofactor CsgE form a secretion complex with 9:9 stoichiometry that encloses a, 24,000 Å$^3$ chamber that is proposed to entrap the CsgA substrate and facilitate its entropy-driven diffusion across the outer membrane (OM; see the text and FIG. 45). On theoretical grounds, three putative pathways (a-c) for substrate recruitment and assembly of the secretion complex can be envisaged. a, A 'catch-and-cap' mechanism entails the binding of CsgA to the apo CsgG translocation channel (1), leading to a conformational change in the latter that exposes a high-affinity binding platform for CsgE binding (2). CsgE binding leads to capping of the substrate cage. On secretion of CsgA, CsgG would fall back into its low-affinity conformation, leading to CsgE dissociation and liberation of the secretion channel for a new secretion cycle. b, In a 'dock and-trap' mechanism, periplasmic CsgA is first captured by CsgE (1), causing the latter to adopt a high-affinity complex that docks onto the CsgG translocation pore (2), enclosing CsgA in the secretion complex. CsgA binding could be directly to CsgE oligomers or to CsgE monomers, the latter leading to subsequent oligomerization and CsgG binding. Secretion of CsgA leads CsgE to fall back into its low-affinity conformation and to dissociate from the secretion channel. c, CsgG and CsgE form a constitutive complex, in which CsgE conformational dynamics cycle between open and closed forms in the course of CsgA recruitment and secretion. Currently published or available data do not allow us to discriminate between these the putative recruitment modes or derivatives thereof, or to put forward one of them.

Thus, CsgG and CsgE seem to form an encaging complex enclosing a central cavity of ~24,000 Å$^3$, reminiscent in appearance to the substrate binding cavity and encapsulating lid structure seen in the GroEL chaperonin and GroES co-chaperonin[24]. The CsgG-CsgE enclosure would be compatible with the full or partial entrapment of the 129-residue CsgA. The caging of a translocation substrate has recently been observed in ABC toxins[25]. Spatial confinement of an unfolded polypeptide leads to a decrease in its conformational space, creating an entropic potential that has been shown to favour polypeptide folding in the case of chaperonins[24,26]. Similarly, we speculate that in curli transport the local high concentration and conformational confinement of curli subunits in the CsgG vestibule would generate an entropic free-energy gradient over the translocation channel (FIG. 45g). On capture into the constriction, the polypeptide chain is then expected to move progressively outwards by Brownian diffusion, rectified by the entropic potential generated from the CsgE-mediated confinement and/or substrate trapping near the secretion channel. For full confinement in the pre-constriction cavity, the escape of an unfolded 129-residue polypeptide to the bulk solvent would correspond to an entropic free-energy release of up to −80 kcal mol$^{-1}$ (about 340 kJ mol$^{-1}$; ref. 27). The initial entropic cost of substrate docking and confinement are likely to be at least partly compensated for by binding energy released during assembly of the CsgG-CsgE-CsgA complex and an already lowered CsgA entropy in the periplasm. On theoretical grounds, three potential routes of CsgA recruitment to the secretion complex can be envisaged (FIG. 54).

Curli-induced biofilms form a fitness and virulence factor in pathogenic Enterobacteriaceae[4,5]. Their unique secretion and assembly properties are also rapidly gaining interest for (bio)technological application[23,28,29]. Our structural characterization and biochemical study of two key secretion components provide a tentative model of an iterative mechanism for the membrane translocation of unfolded protein substrates in the absence of a hydrolysable energy source, a membrane potential or an ion gradient (FIG. 45e and FIG. 54). The full validation and deconstruction of the contributing factors in the proposed secretion model will require the in vitro reconstitution of the translocator to allow transport kinetics to be followed accurately at the single-molecule level.

Methods

Cloning and strains. Expression constructs for the production of outer membrane localized C-terminally StrepII-tagged CsgG (pPG1) and periplasmic C-terminally StrepII-tagged $CsgG_{C1S}$ (pPG2) have been described in ref. 19. For selenomethionine labelling, StrepII-tagged $CsgG_{C1S}$ was expressed in the cytoplasm because of increased yields. Therefore, $_p$PG2 was altered to remove the N-terminal signal peptide using inverse PCR with primers 5'-TCTT-TAACCGCCCCGCCTAAAG-3' (forward) and 5'-CAT-TTTTTGCCCTCGTTATC-3' (reverse) (pPG3). For phenotypic assays, a csgG deletion mutant of E. coli BW25141 (E. coli NVG2) was constructed by the method described in ref. 30 (with primers 5'-AATAACTCAACC GAT TTT TAA GCC CCA GCT TCA TAA GGA AAA TAA TCG TGT AGG CTG GAG CTG CTT C-3' and 5'-CGC TTA AAC AGT AAA ATG CCG GAT GAT AAT TCC GGC TTT TTT ATC TGC ATA TGA ATA TCC TCC TTA G-3'). The various CsgG substitution mutants used for Cys accessibility assays and for phenotypic probing of the channel constriction were constructed by site-directed mutagenesis (QuikChange protocol; Stratagene) starting from pMC2, a pTRC99a vector containing csgG under control of the trc promoter[14].

Protein expression and purification. CsgG and $CsgG_{C1S}$ were expressed and purified as described[19]. In brief, CsgG was recombinantly produced in E. coli BL 21 (DE3) transformed with pPG1 and extracted from isolated outer membranes with the use of 1% n-dodecyl-b-D-maltoside (DDM) in buffer A (50 mM Tris-HCl pH 8.0, 500 mM NaCl, 1 mM EDTA, 1 mM dithiothreitol (DTT)). StrepII-tagged CsgG was loaded onto a 5 ml Strep-Tactin Sepharose column (Iba GmbH) and detergent exchanged by washing with 20 column volumes of buffer A supplemented with 0.5% tetraethylene glycol monooctyl ether (C8E4; Affymetrix) and 4 mM lauryldimethylamine-N-oxide (LDAO; Affymetrix). The protein was eluted by the addition of 2.5 mM D-desthiobiotin and concentrated to 5 mg ml$^{-1}$ for crystallization experiments. For selenomethionine labelling, $CsgG_{C1S}$ was produced in the Met auxotrophic strain B834 (DE3) transformed with pPG3 and grown on M9 minimal medium supplemented with 40 mg l$^{-1}$ L-selenomethionine. Cell pellets were resuspended in 50 mM Tris-HCl pH 8.0, 150 mM NaCl, 1 mM EDTA, 5 mM DTT, supplemented with cOmplete Protease Inhibitor Cocktail (Roche) and disrupted by passage through a TS series cell disruptor (Constant Systems Ltd) operated at 20×10$^3$ lb in$^{-2}$. Labelled CsgG$_{C1S}$ was purified as described[19]. DTT (5 mM) was added throughout the purification procedure to avoid oxidation of selenomethionine. CsgE was produced in E. coli NEBC2566 cells harbouring pNH27 (ref. 16). Cell lysates in 25 mM Tris-HCl pH 8.0, 150 mM NaCl, 25 mM imidazole, 5% (v/v) glycerol were loaded on a HisTrap FF (GE Healthcare). CsgE-his was eluted with a linear gradient to 500 mM imidazole in 20 mM Tris-HCl pH 8.0, 150 mM NaCl, 5% (v/v) glycerol buffer. Fractions containing CsgE were supplemented with 250 mM $(NH_4)_2SO_4$ and applied to a 5 ml HiTrap Phenyl HP column (GE Healthcare) equilibrated with 20 mM Tris-HCl pH 8.0, 100 mM NaCl, 250 mM $(NH_4)_2SO_4$, 5% (v/v) glycerol. A linear gradient to 20 mM Tris-HCl pH 8.0, 10 mM NaCl, 5% (v/v) glycerol was applied for elution. CsgE containing fractions were loaded onto a Superose 6 Prep Grade 10/600 (GE Healthcare) column equilibrated in 20 mM Tris-HCl pH 8.0, 100 mM NaCl, 5% (v/v) glycerol.

In-solution oligomeric state assessment. About 0.5 mg each of detergent-solubilized CsgG (0.5% C8E4, 4 mM LDAO) and CsgG$_{C1S}$ were applied to a Superdex 200 10/300 GL analytical gel filtration column (GE Healthcare) equilibrated with 25 mM Tris-HCl pH 8.0, 500 mM NaCl, 1 mM DTT, 4 mM LDAO and 0.5% C8E4 (CsgG) or with 25 mM Tris-HCl pH 8.0, 200 mM NaCl (CsgG$_{C1S}$), and run at 0.7 ml min$^{-1}$. The column elution volumes were calibrated with bovine thyroglobulin, bovine γ-globulin, chicken ovalbumin, horse myoglobulin and vitamin B12 (Bio-Rad) (FIG. 47). Membrane-extracted CsgG, 20 mg of the detergent-solubilized protein was also run on 3-10% blue native PAGE using the procedure described in ref. 31 (FIG. 47). NativeMark (Life Technologies) unstained protein standard (7 ml) was used for molecular mass estimation.

Crystallization, data collection and structure determination. Selenomethionine-labelled CsgG$_{C1S}$ was concentrated to 3.8 mg ml$^{-1}$ and crystallized by sitting-drop vapour diffusion against a solution containing 100 mM sodium acetate pH 4.2, 8% PEG 4000 and 100 mM sodium malonate pH 7.0. Crystals were incubated in crystallization buffer supplemented with 15% glycerol and flash-frozen in liquid nitrogen. Detergent-solubilized CsgG was concentrated to 5 mg ml$^{-1}$ and crystallized by hanging-drop vapour diffusion against a solution containing 100 mM Tris-HCl pH 8.0, 8% PEG 4000, 100 mM NaCl and 500 mM MgCl$_2$. Crystals were flash-frozen in liquid nitrogen and cryoprotected by the detergent present in the crystallization solution. For optimization of crystal conditions and screening for crystals with good diffraction quality, crystals were analysed on beamlines Proxima-1 and Proxima-2a (Soleil, France), PX-I (Swiss Light Source, Switzerland), 102, 103, 104 and 124 (Diamond Light Source, UK) and ID14eh2, ID23eh1 and ID23eh2 (ESRF, France). Final diffraction data used for structure determination of CsgG$_{C1S}$ and CsgG were collected at beamlines 104 and 103, respectively (see FIG. 55a for data collection and refinement statistics). Diffraction data for CsgG$_{C1S}$ were processed using Xia2 and the XDS package[32,33]. Crystals of CsgG$_{C1S}$ belonged to space group P1 with unit cell dimensions of a=101.3 Å, b=103.6 Å, c=141.7 Å, α=111.3°, β=90.5°, γ=118.2°, containing 16 protein copies in the asymmetric unit. For structure determination and refinement, data collected at 0.9795 Å wavelength were truncated at 2.8 Å on the basis of an I/δI cutoff of 2 in the highest-resolution shell. The structure was solved using experimental phases calculated from a single anomalous dispersion (SAD) experiment. A total of 92 selenium sites were located in the asymmetric unit by using ShelxC and ShelxD[34], and were refined and used for phase calculation with Sharp[35] (phasing power 0.79, figure of merit (FOM) 0.25). Experimental phases were density modified and averaged by non-crystallographic symmetry (NCS) using Parrot[36] (FIG. 55; FOM 0.85). An initial model was built with Buccaneer[37] and refined by iterative rounds of maximum-likelihood refinement with Phenix refine[33] and manual inspection and model (re)building in Coot[39]. The final structure contained 28,853 atoms in 3,700 residues belonging to 16 CsgG$_{C1S}$ chains (FIG. 47), with a molprobity[40] score of 1.34; 98% of the residues lay in favoured regions of the Ramachandran plot (99.7% in allowed regions). Electron density maps showed no unambiguous density corresponding to possible solvent molecules, and no water molecules or ions were therefore built in. Sixteenfold NCS averaging was maintained throughout refinement, using strict and local NCS restraints in early and late stages of refinement, respectively.

Figure 55:
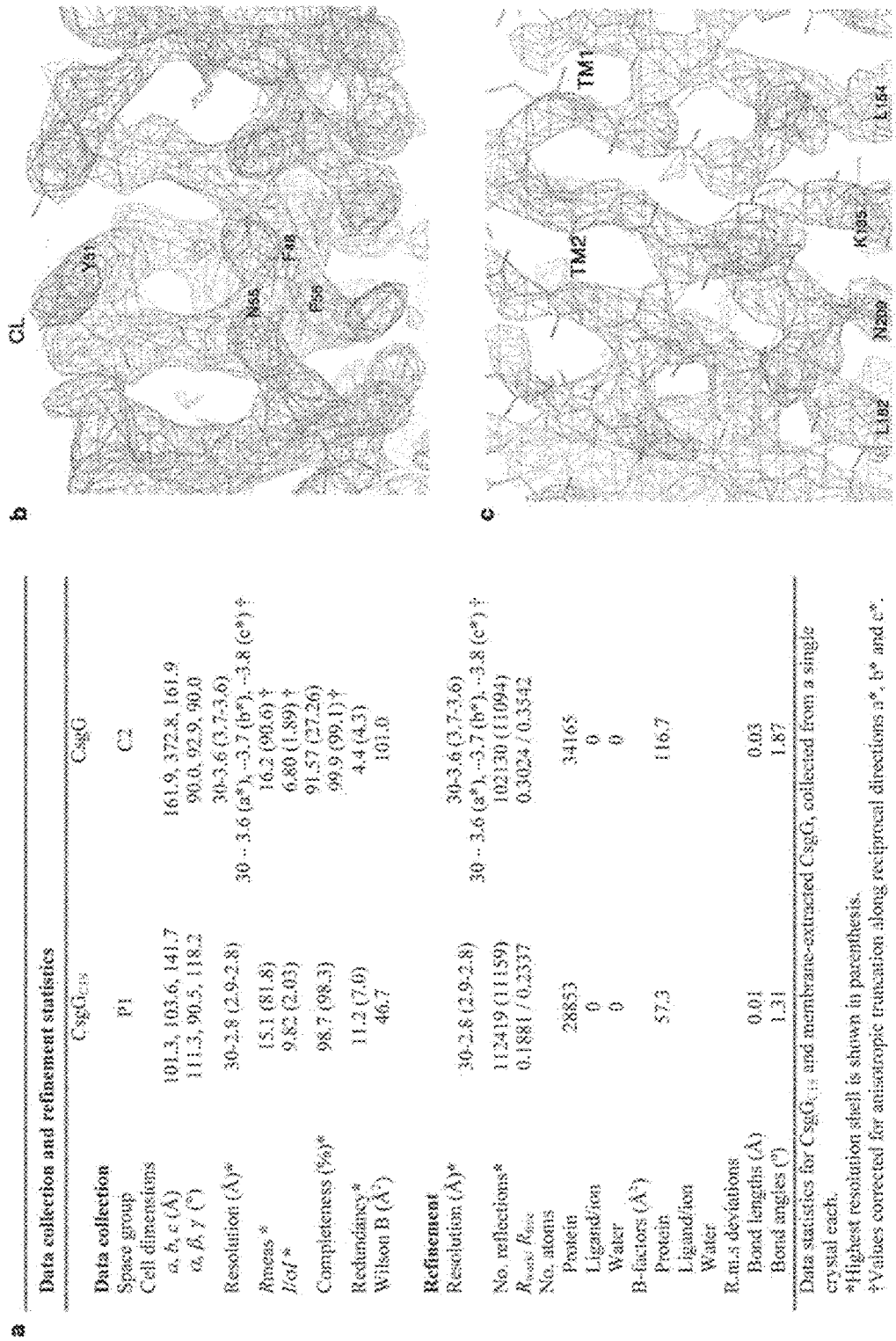
FIG. 55 shows data collection statistics and electron density maps of $CsgG_{C1S}$ and CsgG. a, Data collection statistics for $CsgG_{C1S}$ and CsgG X-ray structures. b, Electron density map at 2.8 Å for $CsgG_{C1S}$ calculated using NCS-averaged and density-modified experimental SAD phases, and contoured at 1.5σ. The map shows the region of the channel construction (CL; a single protomer is labelled) and is overlaid on the final refined model. c, Electron density map (resolutions 3.6, 3.7 and 3.8 Å along reciprocal vectors a*, b* and c*, respectively) in the CsgG TM domain region, calculated from NCS averaged and density-modified molecular replacement phases (TM loops were absent from the input model); B-factor sharpened by −20 Å$^2$ and contoured at 1.0σ. The figure shows the TM1 (Lys 135-Leu 154) and TM2 (Leu 182-Asn 209) region of a single CsgG protomer, overlaid on the final refined model.

Diffraction data for CsgG were collected from a single crystal at 0.9763 Å wavelength and were indexed and scaled, using the XDS package[32,33], in space group C2 with unit-cell dimensions a=161.7 Å, b=372.3 Å, c=161.8 Å and β=92.9°, encompassing 18 CsgG copies in the asymmetric unit and a 72% solvent content. Diffraction data for structure determination and refinement were elliptically truncated to resolution limits of 3.6 Å, 3.7 Å and 3.8 Å along reciprocal cell directions a*, b* and c* and scaled anisotropically with the Diffraction Anisotropy Server[41]. Molecular replacement using the CsgG$_{C1S}$ monomer proved unsuccessful. Analysis of the self rotation function revealed D$_9$ symmetry in the asymmetric unit (not shown). On the basis of on the CsgG$_{C1S}$ structure, a nonameric search model was generated in the assumption that after going from a C$_8$ to C$_9$ oligomer, the interprotomer arc at the particle circumference would stay approximately the same as the interprotomer angle changed from 45° to 40°, giving a calculated increase in radius of about 4 Å. Using the calculated nonamer as search model, a molecular replacement solution containing two copies was found with Phaser[42]. Inspection of density-modified and NCS-averaged electron density maps (Parrot[36]; FIG. 55) allowed manual building of the TM1 and TM2 and remodelling of adjacent residues in the protein core, as well as the building of residues 2-18, which were missing from the CsgG$_{C1S}$ model and linked the α1 helix to the N-terminal lipid anchor. Refinement of the CsgG mode I was performed with Buster-TNT[43] and Refmac5 (ref. 44) for initial and final refinement rounds, respectively. Eighteenfold local NCS restraints were applied throughout refinement, and Refmac5 was run employing a jelly-body refinement with sigma 0.01 and hydrogen-bond restraints generated by Prosmart[45]. The final structure contained 34,165 atoms in 4,451 residues belonging to 18 CsgG chains (FIG. 47), with a molprobity score of 2.79; 93.0% of the residues lay in favoured regions of the Ramachandran plot (99.3% in allowed regions). No unambiguous electron density corresponding the N-terminal lipid anchor could be discerned.

Congo red assay. For analysis of Congo red binding, a bacterial overnight culture grown at 37° C. in Lysogeny Broth (LB) was diluted in LB medium until a D$_{600}$ of 0.5 was reached. A 5 µl sample was spotted on LB agar plates supplemented with ampicillin (100 mg l$^{-1}$), Congo red (100 mg l$^{-1}$) and 0.1% (w/v) isopropyl β-D-thiogalactoside (IPTG). Plates were incubated at room temperature (20-22° C.) for 48 h to induce curli expression. The development of the colony morphology and dye binding were observed at 48 h.

Cysteine accessibility assays. Cysteine mutants were generated in pMC2 using site-directed mutagenesis and expressed in E. coli LSR12 (ref. 7). Bacterial cultures grown overnight were spotted onto LB agar plates containing 1 mM IPTG and 100 mg l$^{-1}$ ampicillin. Plates were incubated at room temperature and cells were scraped after 48 h, resuspended in 1 ml of PBS and normalized using $D_{600}$.

The cells were lysed by sonication and centrifuged for 20 s at 3,000 g at 4° C. to remove unbroken cells from cell lysate and suspended membranes. Proteins in the supernatant were labelled with 15 mM methoxypolyethylene glycol-maleimide (MAL-PEG 5 kDa) for 1 h at room temperature. The reaction was stopped with 100 mM DTT and centrifuged at 40,000 r.p.m. (~100,000 g) in a 50.4 Ti rotor for 20 min at 4° C. to pellet total membranes. The pellet was washed with 1% sodiumlauroyl sarcosinate to solubilize cytoplasmic membranes and centrifuged again. The resulting outer membranes were resuspended and solubilized using PBS containing 1% DDM. Metal affinity pulldowns with nickel beads were used for SDS-PAGE and anti-His western blots. E. coli LSR12 cells with empty pMC2 vector were used as negative control.

ATR-FTIR spectroscopy. ATR-FTIR measurements were performed on an Equinox 55 infrared spectrophotometer (Bruker), continuously purged with dried air, equipped with a liquid-nitrogen-refrigerated mercury cadmium telluride detector and a Golden Gate reflectance accessory (Specac). The internal reflection element was a diamond crystal (2 mm×2 mm) and the beam incidence angle was 45°. Each purified protein sample (1 µl) was spread at the surface of the crystal and dried under a gaseous nitrogen flow to form a film. Each spectrum, recorded at 2 cm$^{-1}$ resolution, was an average of 128 accumulations for improved signal-to-noise ratio. All the spectra were treated with water vapour contribution subtraction, smoothed at a final resolution of 4 cm$^{-1}$ by apodization and normalized on the area of the Amide I band (1,700-1,600 cm$^{-1}$) to allow their comparison[46].

Negative stain EM and symmetry determination. Negative stain EM was used to monitor in-solution oligomerization states of CsgG, $CsgG_{C1S}$ and CsgE. CsgE, $CsgG_{C1S}$ and amphipol-bound CsgG were adjusted to a concentration of 0.05 mg ml$^{-1}$ and applied to glow-discharged carbon-coated copper grids (CF-400; Electron Microscopy Sciences). After 1 min incubation, samples were blotted, then washed and stained in 2% uranyl acetate. Images were collected on a Tecnai T12 BioTWIN LaB6 microscope operating at a voltage of 120 kV, at a magnification of X49,000 and defocus between 800 and 2,000 nm. Contrast transfer function (CTF), phase flipping and particle selection were performed as described for cryo-EM. For membrane extracted CsgG, octadecameric particles (1,780 in all) were analysed separately from nonamers and top views. For purified CsgE a total of 2,452 particles were analysed. Three-dimensional models were obtained as described for the CsgG-CsgE cryo-EManalysis below and refined by several rounds of multi-reference alignment (MRA), multi-statistical analysis (MSA) and anchor set refinement. In all cases, after normalization and centring, images were classified using IMAGIC-4D as described in the cryo-EM section. The best classes corresponding to characteristic views were selected for each set of particles. Symmetry determination of CsgG top views was performed using the best class averages with roughly 20 images per class. The rotational autocorrelation function was calculated using IMAGIC and plotted.

CsgG-CsgE complex formation. For CsgG-CsgE complex formation, the solubilizing detergents in purified CsgG were exchanged for Amphipols A8-35 (Anatrace) by adding 120 µl of CsgG (24 mg ml$^{-1}$ protein in 0.5% C8E4, 4 mM LDAO, 25 mM Tris-HCl pH 8.0, 500 mM NaCl, 1 mM DTT) to 300 µl of detergent-destabilized liposomes (1 mg ml$^{-1}$ 1,2-dimyristoyl-sn-glycero-3-phosphocholine (DMPC) and 0.4% LDAO) and incubating for 5 min on ice before the addition of 90 ml of A8-35 amphipols at 100 mg ml$^{-1}$ stock. After an additional 15 min incubation on ice, the sample was loaded on a Superose 6 10/300 GL (GE Healthcare) column and gel filtration was performed in 200 mM NaCl, 2.5% xylitol, 25 mM Tris-HCl pH 8, 0.2 mM DTT. An equal volume of purified monomeric CsgE in 200 mM NaCl, 2.5% xylitol, 25 mM Tris-HCl pH 8, 0.2 mM DTT was added to the amphipol-solubilized CsgG at final protein concentrations of 15 and 5 µM for CsgE and CsgG, respectively, and the sample was run at 125V at 18° C. on a 4.5% native PAGE in 0.5×TBE buffer. For the second, denaturing dimension, the band corresponding to the CsgG-CsgE complex was cut out of unstained lanes run in parallel on the same gel, boiled for 5 min in Laemmli buffer (60 mM Tris-HCl pH 6.8, 2% SDS, 10% glycerol, 5% 2-mercaptoethanol, 0.01% bromophenol blue) and run on 4-20% SDS-PAGE. Purified CsgE and CsgG were run alongside the complex as control samples. Gels were stained with InstantBlue Coomassie for visual inspection or SYPRO orange for stoichiometry assessment of the CsgG-CsgE complex by fluorescence detection (Typhoon FLA 9000) of the CsgE and CsgG bands on SDS-PAGE, yielding a CsgG/CsgE ratio of 0.97.

CsgG-CsgE Cryo-EM. Cryo-electron microscopy was used to determine the in-solution structure of the $C_9$ CsgG-CsgE complex. CsgG-CsgE complex prepared as described above was bound and eluted from a HisTrap FF (GE Healthcare) to remove unbound CsgG, and on elution it was immediately applied to Quantifoil R2/2 carbon coated grids (Quantifoil Micro Tools GmbH) that had been glow-discharged at 20 mA for 30 s. Samples were plunge-frozen in liquid nitrogen using an automated system (Leica) and observed under a FEI F20 microscope operating at a voltage of 200 kV, a nominal magnification of X50,000 under low-dose conditions and a defocus range of 1.4-3 µm. Image frames were recorded on a Falcon II detector. The pixel size at the specimen level was 1.9 Å per pixel. The CTF parameters were assessed using CTFFIND3 (ref. 47), and the phase flipping was done in SPIDER[48]. Particles were automatically selected from CTF-corrected micrographs using BOXER (EMAN2; ref. 49). Images with an astigmatism of more than 10% were discarded. A total of 1,221 particles were selected from 75 micrographs and windowed into 128-pixel X 128-pixel boxes. Images were normalized to the same mean and standard deviation and high-pass filtered at a low-resolution cut-off of ~200 Å. They were centred and then subjected to a first round of MSA. An initial reference set was obtained using reference free classification in IMAGIC-4D (Image Science Software). The best classes corresponding to characteristic side views of the $C_9$ cylindrical particles were used as references for the MRA. For CsgG-CsgE complex, the first three-dimensional model was calculated from the best 125 characteristic views (with good contrast and well-defined features) encompassing 1,221 particles of the complex with orientations determined by angular reconstitution (Image Science Software). The three-dimensional map was refined by iterative rounds of MRA, MSA and anchor set refinement. The resolution was estimated to be 24 Å by Fourier shell correlation (FSC) according to the 0.5 criteria level FIG. 52). Visualization of the map and figures was performed in UCSF Chimera[50].

Bile salt toxicity assay. Outer-membrane permeability was investigated by decreased growth on agar plates containing bile salts. Tenfold serial dilutions of *E. coli* LSR12 (ref. 7) cells (5 µl) harbouring both pLR42 (ref. 16) and pMC2 (ref. 14) (or derived helix 2 mutants) were spotted on McConkey agar plates containing 100 µg l$^{-1}$ ampicillin, 25 µg chloramphenicol, 1 mM IPTG with or without 0.2% (w/v) L-arabinose. After incubation overnight at 37° C., colony growth was examined.

Single-channel current recordings. Single-channel current recordings were performed using parallel high-resolution electrical recording with the Orbit 16 kit from Nanion. In brief, horizontal bilayers of 1,2-diphytanoyl-sn-glycero-3-phosphocholine (Avanti Polar Lipids) were formed over microcavities (of subpicolitre volume) in a 16-channel multielectrode cavity array (MECA) chip (Ionera)[51]. Both the cis and trans cavities above and below the bilayer contained 1.0 M KCl, 25 mM Tris-HCl pH 8.0. To insert channels into the membrane, CsgG dissolved in 25 mM Tris-HCl pH 8.0, 500 mM NaCl, 1 mM DTT, 0.5% C8E4, 5 mM LDAO was added to the cis compartment to a final concentration of 90-300 nM. To test the interaction of the CsgG channel with CsgE, a solution of the latter protein dissolved in 25 mM Tris-HCl pH 8.0, 150 mM NaCl was added to the cis compartment to final concentrations of 0.1, 1, 10 and 100 nM. Transmembrane currents were recorded at a holding potential of +50 mV and −50 mV (with the cis side grounded) using a Tecella Triton 16-channel amplifier at a low-pass filtering frequency of 3 kHz and a sampling frequency of 10 kHz. Current traces were analysed using the Clampfit of the pClamp suite (Molecular Devices). Plots were generated using Origin 8.6 (Microcal)[52].

Measured currents were compared with those calculated based on the pore dimensions of the CsgG X-ray structure, modelled to be composed of three segments: the transmembrane section, the periplasmic vestibule, and the inner channel constriction connecting the two. The first two segments were modelled to be of conical shape; the constriction was represented as a cylinder. The corresponding resistances R1, R2 and R3, respectively, were calculated as $R1 = L1/(\pi D_1 d_1 \kappa)$ $R2 = L2/(\pi D_2 d_2 \kappa)$ $R3 = L3/(\pi D_1 d_2 \kappa)$ where L1, L2 and L3 are the axial lengths of the segments, measuring 3.5, 4.0 and 2.0 nm, respectively, and D1, d1, D2 and d2 are the maximum and minimum diameters of segments 1 and 2, measuring 4.0, 0.8, 3.4 and 0.8 nm, respectively. The conductivity κ has a value of 10.6 Sm$^{-1}$. The current was calculated by inserting R1, R2 and R3 and voltage V=50 mV into $I = V/(R1+R2+R3)$ Access resistance was not found to alter the predicted current significantly.

REFERENCES

1. Olsen, A., Jonsson, A. & Normark, S. Fibronectin binding mediated by a novel class of surface organelles on *Escherichia coli*. Nature 338, 652-655 (1989).
2. Collinson, S. K. et al. Thin, aggregative fimbriae mediate binding of *Salmonella enteritidis* to fibronectin. J. Bacterial. 175, 12-18 (1993).
3. Dueholm, M. S., Albertsen, M., Otzen, D. & Nielsen, P. H. Curli functional amyloid systems are phylogenetically widespread and display large diversity in operon and protein structure. PLoS ONE 7, e51274 (2012).
4. Cegelski, L. et al. Small-molecule inhibitors target *Escherichia coli* amyloid biogenesis and biofilm formation. Nature Chem. Biol. 5, 913-919 (2009).
5. Herwald, H. et al. Activation of the contact-phase system on bacterial surfaces—a clue to serious complications in infectious diseases. Nature Med. 4, 298-302 (1998).
6. Hammar, M., Arnqvist, A., Bian, Z., Olsen, A. & Normark, S. Expression of two csg operons is required for production of fibronectin- and Congo red-binding curli polymers in *Escherichia coli* K-12. Mol. Microbiol. 18, 661-670 (1995).
7. Chapman, M. R. et al. Role of *Escherichia coli* curli operons in directing amyloid fiber formation. Science 295, 851-855 (2002).
8. Wang, X., Smith, D. R., Jones, J. W. & Chapman, M. R. In vitro polymerization of a functional *Escherichia coli* amyloid protein. J. Biol. Chem. 282, 3713-3719 (2007).
9. Dueholm, M. S. et al. Fibrillation of the major curli subunit CsgA under a wide range of conditions implies a robust design of aggregation. Biochemistry 50, 8281-8290 (2011).
10. Hung, C. et al. *Escherichia coli* biofilms have an organized and complex extracellular matrix structure. MBio 4, e00645-13 (2013).
11. Hammar, M., Bian, Z.& Normark, S. Nucleator-dependent intercellular assembly of adhesive curli organelles in *Escherichia coli*. Proc. Natl Acad. Sci. USA 93, 6562-6566 (1996).
12. Bian, Z. & Normark, S. Nucleator function of CsgB for the assembly of adhesive surface organelles in *Escherichia coli*. EMBO J. 16, 5827-5836 (1997).
13. Loferer, H., Hammar, M. & Normark, S. Availability of the fibre subunit CsgA and the nucleator protein CsgB during assembly of fibronectin-binding curli is limited by the intracellular concentration of the novel lipoprotein CsgG. Mol. Microbiol. 26, 11-23 (1997).
14. Robinson, L. S., Ashman, E. M., Hultgren, S. J. & Chapman, M. R. Secretion of curli fibre subunits is mediated by the outer membrane-localized CsgG protein. Mol. Microbiol. 59, 870-881 (2006).
15. Nenninger, A. A., Robinson, L. S. & Hultgren, S. J. Localized and efficient curli nucleation requires the chaperone-like amyloid assembly protein CsgF. Proc. Natl Acad. Sci. USA 106, 900-905 (2009).
16. Nenninger, A. A. et al. CsgE is a curli secretion specificity factor that prevents amyloid fibre aggregation. Mol. Microbiol. 81, 486-499 (2011).
17. Okuda, S. & Tokuda, H. Lipoprotein sorting in bacteria. Annu. Rev. Microbiol. 65, 239-259 (2011).
18. Iacovache, I., Bischofberger, M. & van der Goot, F. G. Structure and assembly of poreforming proteins. Curr. Opin. Struct. Biol. 20, 241-246 (2010).
19. Goyal, P., Van Gerven, N., Jonckheere, W. & Remaut, H. Crystallization and preliminary X-ray crystallographic analysis of the curli transporter CsgG. Acta Crystallogr. F Struct. Biol. Cryst. Commun. 69, 1349-1353 (2013).
20. Krantz, B. A. et al. A phenylalanine clamp catalyzes protein translocation through the anthrax toxin pore. Science 309, 777-781 (2005).

21. Janowiak, B. E., Fischer, A. & Collier, R. J. Effects of introducing a single charged residue into the phenylalanine clamp of multimeric anthrax protective antigen. J. Biol. Chem. 285, 8130-8137 (2010).
22. Feld, G. K., Brown, M. J. & Krantz, B. A. Ratcheting up protein translocation with anthrax toxin. Protein Sci. 21, 606-624 (2012).
23. Van Gerven, N. et al. Secretion and functional display of fusion proteins through the curli biogenesis pathway. Mol. Microbiol. 91, 1022-1035 (2014).
24. Brinker, A. et al. Dual function of protein confinement in chaperonin-assisted protein folding. Cell 107, 223-233 (2001).
25. Busby, J. N., Panjikar, S., Landsberg, M. J., Hurst, M. R. & Lott, J. S. The BC component of ABC toxins is an RHS-repeat-containing protein encapsulation device. Nature 501, 547-550 (2013).
26. Takagi, F., Koga, N. & Takada, S. How protein thermodynamics and folding mechanisms are altered by the chaperonin cage:molecular simulations. Proc. Natl Acad. Sci. USA 100, 11367-11372 (2003).
27. Zhou, H. X. Protein folding in confined and crowded environments. Arch. Biochem. Biophys. 469, 76-82 (2008).
28. Chen, A. Y. et al. Synthesis and patterning of tunable multiscale materials with engineered cells. Nature Mater. 13, 515-523 (2014).
29. Sivanathan, V. & Hochschild, A. A bacterial export system for generating extracellular amyloid aggregates. Nature Protocols 8, 1381-1390 (2013).
30. Datsenko, K. A. & Wanner, B. L. One-step inactivation of chromosomal genes in *Escherichia coli* K-12 using PCR products. Proc. Natl Acad. Sci. USA 97, 6640-6645 (2000).
31. Swamy, M., Siegers, G. M., Minguet, S., Wollscheid, B. & Schamel, W. W. A. Blue native polyacrylamide gel electrophoresis (BN-PAGE) for the identification and analysis of multiprotein complexes. Sci. STKE 2006, p 14, http://dx.doi.org/10.1126/stke.3452006p14 (2006).
32. Winter, G. xia2: an expert system for macromolecular crystallography data reduction. J. Appl. Cryst. 43, 186-190 (2010).
33. Kabsch, W. Xds. Acta Crystallogr. D Biol. Crystallogr. 66, 125-132 (2010).
34. Sheldrick, G. M. Experimental phasing with SHELXC/D/E: combining chain tracing with density modification. Acta Crystallogr. D Biol. Crystallogr. 66, 479-485 (2010).
35. Bricogne, G., Vonrhein, C., Flensburg, C., Schiltz, M. & Paciorek, W. Generation, representation and flow of phase information in structure determination: recent developments in and around SHARP 2.0. Acta Crystallogr. D Biol. Crystallogr. 59, 2023-2030 (2003).
36. Cowtan, K. Recent developments in classical density modification. Acta Crystallogr. D Biol. Crystallogr. 66, 470-478 (2010).
37. Cowtan, K. The Buccaneer software for automated model building. 1. Tracing protein chains. Acta Crystallogr. D Biol. Crystallogr. 62, 1002-1011 (2006).
38. Adams, P. D. et al. PHENIX: a comprehensive Python-based system for macromolecular structure solution. Acta Crystallogr. D Biol. Crystallogr. 66, 213-221 (2010).
39. Emsley, P., Lohkamp, B., Scott, W. G. & Cowtan, K. Features and development of Coot. Acta Crystallogr. D Biol. Crystallogr. 66, 486-501 (2010).
40. Davis, I. W. et al. MolProbity: all-atom contacts and structure validation for proteins and nucleic acids. Nucleic Acids Res. 35 (Supp) 2), W375-W383 (2007).
41. Strong, M. et al. Toward the structural genomics of complexes: crystal structure of a PE/PPE protein complex from *Mycobacterium tuberculosis*. Proc. Natl Acad. Sci. USA 103, 8060-8065 (2006).
42. McCoy, A. J. et al. Phaser crystallographic software. J. Appl. Cryst. 40, 658-674 (2007).
43. Smart, O. S. et al. Exploiting structure similarity in refinement: automated NCS and target-structure restraints in BUSTER. Acta Crystallogr. D Biol. Crystallogr. 68, 368-380 (2012).
44. Murshudov, G. N. et al. REFMAC5 for the refinement of macromolecular crystal structures. Ada Crystallogr. D Biol. Crystallogr. 67, 355-367 (2011).
45. Nicholls, R. A., Long, F. & Murshudov, G. N. Low-resolution refinement tools in REFMAC5. Acta Crystallogr. D Biol. Crystallogr. 68, 404-417 (2012).
46. Goormaghtigh, E. & Ruysschaert, J. M. Subtraction of atmospheric water contribution in Fourier transform infrared spectroscopy of biological membranes and proteins. Spectrochim. Acta 50A, 2137-2144 (1994).
47. Mindell, J. A.& Grigorieff, N. Accurate determination of local defocus and specimen tilt in electron microscopy. J. Struct. Biol. 142, 334-347 (2003).
48. Shaikh, T. R. et al. SPIDER image processing for single-particle reconstruction of biological macromolecules from electron micrographs. Nature Protocols 3, 1941-1974 (2008).
49. Tang, G. et al. EMAN2: an extensible image processing suite for electron microscopy. J. Struct. Biol. 157, 38-46 (2007).
50. Pettersen, E. F. et al. UCSF Chimera—a visualization system for exploratory research and analysis. J. Comput. Chem. 25, 1605-1612 (2004).
51. Del Rio Martinez, J. M., Zaitseva, E., Petersen, S., Baaken, G. & Behrends, J. C. Automated formation of lipid membrane microarrays for ionic single molecule sensing with protein nanopores. Small http://dx.doi.org/10.1002/smll.201402016 (13 Aug. 2014).
52. Movileanu, L., Howorka, S., Braha, O. & Bayley, H. Detecting protein analytes that modulate transmembrane movement of a polymer chain within a single protein pore. Nature Biotechnol. 18, 1091-1095 (2000).
53. Pronk, S. et al. GROMACS 4.5: a high-throughput and highly parallel open source molecular simulation toolkit. Bioinformatics 29, 845-854 (2013).
54. Lindorff-Larsen, K. et al. Improved side-chain torsion potentials for the Amber ff99SB protein force field. Proteins 78, 1950-1958 (2010).
55. Capra, J. A. & Singh, M. Predicting functionally important residues from sequence conservation. Bioinformatics 23, 1875-1882 (2007).

The invention claimed is:

1. A method measuring a target analyte, comprising:
   (a) contacting the target analyte with a transmembrane pore comprising at least one CsgG monomer such that the target analyte moves through the pore; and
   (b) taking one or more electrical measurements as the target analyte moves through the pore.

2. The method of claim 1, wherein the at least one CsgG monomer is a variant of SEQ ID NO: 390, said variant comprising: (a) mutations at one or more of the following positions N40, Q42, D43, E44, K49, Y51, S54, N55, F56, S57, Q62, E101, N102, E124, E131, R142, D149, T150, E185, R192, D195, E201 and E203; and/or (b) deletion of one or more of the following positions F48, K49, P50, Y51, P52, A53, S54, N55, F56 and S57.

3. The method of claim 2, wherein the variant comprises any of the combinations of mutations/substitutions selected from the group consisting of: (i) one or more mutations at the following positions N40, D43, E44, S54, S57, Q62, R97, E101, E124, E131, R142, T150 and R192; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57.

4. The method of claim 1, wherein the target analyte is a target polynucleotide and step (a) further comprises contacting the polynucleotide with a polynucleotide binding protein such that the protein controls the movement of the polynucleotide through the pore.

5. The method of claim 4, wherein the polynucleotide binding protein is a helicase or is derived from a helicase.

* * * * *

SEQUENCE LISTING

<160> NUMBER OF SEQ ID NOS: 482

<210> SEQ ID NO 1

```
<211> LENGTH: 277
<212> TYPE: PRT
<213> ORGANISM: Escherichia coli

<400> SEQUENCE: 1

Met Gln Arg Leu Phe Leu Leu Val Ala Val Met Leu Leu Ser Gly Cys
1               5                   10                  15

Leu Thr Ala Pro Pro Lys Glu Ala Ala Arg Pro Thr Leu Met Pro Arg
            20                  25                  30

Ala Gln Ser Tyr Lys Asp Leu Thr His Leu Pro Ala Pro Thr Gly Lys
        35                  40                  45

Ile Phe Val Ser Val Tyr Asn Ile Gln Asp Glu Thr Gly Gln Phe Lys
50                  55                  60

Pro Tyr Pro Ala Ser Asn Phe Ser Thr Ala Val Pro Gln Ser Ala Thr
65                  70                  75                  80

Ala Met Leu Val Thr Ala Leu Lys Asp Ser Arg Trp Phe Ile Pro Leu
                85                  90                  95

Glu Arg Gln Gly Leu Gln Asn Leu Leu Asn Glu Arg Lys Ile Ile Arg
            100                 105                 110

Ala Ala Gln Glu Asn Gly Thr Val Ala Ile Asn Asn Arg Ile Pro Leu
        115                 120                 125

Gln Ser Leu Thr Ala Ala Asn Ile Met Val Glu Gly Ser Ile Ile Gly
130                 135                 140

Tyr Glu Ser Asn Val Lys Ser Gly Gly Val Gly Ala Arg Tyr Phe Gly
145                 150                 155                 160

Ile Gly Ala Asp Thr Gln Tyr Gln Leu Asp Gln Ile Ala Val Asn Leu
                165                 170                 175

Arg Val Val Asn Val Ser Thr Gly Glu Ile Leu Ser Ser Val Asn Thr
            180                 185                 190

Ser Lys Thr Ile Leu Ser Tyr Glu Val Gln Ala Gly Val Phe Arg Phe
        195                 200                 205

Ile Asp Tyr Gln Arg Leu Leu Glu Gly Glu Val Gly Tyr Thr Ser Asn
210                 215                 220

Glu Pro Val Met Leu Cys Leu Met Ser Ala Ile Glu Thr Gly Val Ile
225                 230                 235                 240

Phe Leu Ile Asn Asp Gly Ile Asp Arg Gly Leu Trp Asp Leu Gln Asn
                245                 250                 255

Lys Ala Glu Arg Gln Asn Asp Ile Leu Val Lys Tyr Arg His Met Ser
            260                 265                 270

Val Pro Pro Glu Ser
        275

<210> SEQ ID NO 2
<211> LENGTH: 834
<212> TYPE: DNA
<213> ORGANISM: Escherichia coli

<400> SEQUENCE: 2
atgcagcgct tatttctttt ggttgccgtc atgttactga gcggatgctt aaccgccccg      60
cctaaagaag ccgccagacc gacattaatg cctcgtgctc agagctacaa agatttgacc     120
catctgccag cgccgacggg taaaatcttt gtttcggtat acaacattca ggacgaaacc     180
gggcaattta acccctaccc ggcaagtaac ttctccactg ctgttccgca aagcgccacg     240
gcaatgctgg tcacggcact gaaagattct cgctggttta taccgctgga gcgcagggc      300 ttacaaaacc tgcttaacga gcgcaagatt attcgtgcgg cacaagaaaa cggcacggtt     360
```

```
gccattaata accgaatccc gctgcaatct ttaacggcgg caaatatcat ggttgaaggt    420
tcgattatcg gttatgaaag caacgtcaaa tctggcgggg ttggggcaag atattttggc    480
atcggtgccg acacgcaata ccagctcgat cagattgccg tgaacctgcg cgtcgtcaat    540
gtgagtaccg gcgagatcct ttcttcggtg aacaccagta agacgatact ttcctatgaa    600
gttcaggccg gggttttccg ctttattgac taccagcgct tgcttgaagg ggaagtgggt    660
tacacctcga cgaacctgt tatgctgtgc ctgatgtcgg ctatcgaaac aggggtcatt    720
ttcctgatta atgatggtat cgaccgtggt ctgtgggatt tgcaaaataa agcagaacgg    780
cagaatgaca ttctggtgaa ataccgccat atgtcggttc caccggaatc ctga          834
```

<210> SEQ ID NO 3
<211> LENGTH: 25
<212> TYPE: PRT
<213> ORGANISM: Escherichia coli

<400> SEQUENCE: 3

Val Tyr Asn Ile Gln Asp Glu Thr Gly Gln Phe Lys Pro Tyr Pro Ala
1               5                   10                  15

Ser Asn Phe Ser Thr Ala Val Pro Gln
            20                  25

<210> SEQ ID NO 4
<211> LENGTH: 25
<212> TYPE: PRT
<213> ORGANISM: Escherichia coli

<400> SEQUENCE: 4

Val Tyr Asn Ile Gln Asp Glu Thr Gly Gln Phe Lys Pro Tyr Pro Ala
1               5                   10                  15

Ser Asn Phe Ser Thr Ala Val Pro Gln
            20                  25

<210> SEQ ID NO 5
<211> LENGTH: 25
<212> TYPE: PRT
<213> ORGANISM: Escherichia coli

<400> SEQUENCE: 5

Val Tyr Asn Ile Gln Asp Glu Thr Gly Gln Phe Lys Pro Tyr Pro Ala
1               5                   10                  15

Ser Asn Ala Ser Thr Ala Val Pro Gln
            20                  25

<210> SEQ ID NO 6
<211> LENGTH: 25
<212> TYPE: PRT
<213> ORGANISM: Escherichia coli

<400> SEQUENCE: 6

Val Tyr Asn Ile Gln Asp Glu Thr Gly Gln Phe Lys Pro Tyr Pro Ala
1               5                   10                  15

Ser Asn Gly Ser Thr Ala Val Pro Gln
            20                  25

<210> SEQ ID NO 7
<211> LENGTH: 25
<212> TYPE: PRT
<213> ORGANISM: Escherichia coli

```
<400> SEQUENCE: 7

Val Tyr Asn Ile Gln Asp Glu Thr Gly Gln Phe Lys Pro Tyr Pro Ala
1               5                   10                  15

Ser Asn Val Ser Thr Ala Val Pro Gln
            20                  25

<210> SEQ ID NO 8
<211> LENGTH: 24
<212> TYPE: PRT
<213> ORGANISM: Escherichia coli

<400> SEQUENCE: 8

Val Tyr Asn Ile Gln Asp Glu Thr Gly Gln Phe Lys Pro Tyr Pro Ala
1               5                   10                  15

Ser Asn Ser Thr Ala Val Pro Gln
            20

<210> SEQ ID NO 9
<211> LENGTH: 25
<212> TYPE: PRT
<213> ORGANISM: Escherichia coli

<400> SEQUENCE: 9

Val Tyr Asn Ile Gln Asp Glu Thr Gly Gln Phe Lys Pro Tyr Pro Ala
1               5                   10                  15

Ser Ala Phe Ser Thr Ala Val Pro Gln
            20                  25

<210> SEQ ID NO 10
<211> LENGTH: 25
<212> TYPE: PRT
<213> ORGANISM: Escherichia coli

<400> SEQUENCE: 10

Val Tyr Asn Ile Gln Asp Glu Thr Gly Gln Phe Lys Pro Tyr Pro Ala
1               5                   10                  15

Ser Ala Ala Ser Thr Ala Val Pro Gln
            20                  25

<210> SEQ ID NO 11
<211> LENGTH: 25
<212> TYPE: PRT
<213> ORGANISM: Escherichia coli

<400> SEQUENCE: 11

Val Tyr Asn Ile Gln Asp Glu Thr Gly Gln Phe Lys Pro Tyr Pro Ala
1               5                   10                  15

Ser Ala Gly Ser Thr Ala Val Pro Gln
            20                  25

<210> SEQ ID NO 12
<211> LENGTH: 25
<212> TYPE: PRT
<213> ORGANISM: Escherichia coli

<400> SEQUENCE: 12

Val Tyr Asn Ile Gln Asp Glu Thr Gly Gln Phe Lys Pro Tyr Pro Ala
1               5                   10                  15

Ser Ala Val Ser Thr Ala Val Pro Gln
            20                  25
```

-continued

```
<210> SEQ ID NO 13
<211> LENGTH: 24
<212> TYPE: PRT
<213> ORGANISM: Escherichia coli

<400> SEQUENCE: 13

Val Tyr Asn Ile Gln Asp Glu Thr Gly Gln Phe Lys Pro Tyr Pro Ala
1               5                   10                  15

Ser Ala Ser Thr Ala Val Pro Gln
            20

<210> SEQ ID NO 14
<211> LENGTH: 25
<212> TYPE: PRT
<213> ORGANISM: Escherichia coli

<400> SEQUENCE: 14

Val Tyr Asn Ile Gln Asp Glu Thr Gly Gln Phe Lys Pro Tyr Pro Ala
1               5                   10                  15

Ser Gly Phe Ser Thr Ala Val Pro Gln
            20                  25

<210> SEQ ID NO 15
<211> LENGTH: 25
<212> TYPE: PRT
<213> ORGANISM: Escherichia coli

<400> SEQUENCE: 15

Val Tyr Asn Ile Gln Asp Glu Thr Gly Gln Phe Lys Pro Tyr Pro Ala
1               5                   10                  15

Ser Gly Ala Ser Thr Ala Val Pro Gln
            20                  25

<210> SEQ ID NO 16
<211> LENGTH: 25
<212> TYPE: PRT
<213> ORGANISM: Escherichia coli

<400> SEQUENCE: 16

Val Tyr Asn Ile Gln Asp Glu Thr Gly Gln Phe Lys Pro Tyr Pro Ala
1               5                   10                  15

Ser Gly Gly Ser Thr Ala Val Pro Gln
            20                  25

<210> SEQ ID NO 17
<211> LENGTH: 25
<212> TYPE: PRT
<213> ORGANISM: Escherichia coli

<400> SEQUENCE: 17

Val Tyr Asn Ile Gln Asp Glu Thr Gly Gln Phe Lys Pro Tyr Pro Ala
1               5                   10                  15

Ser Gly Val Ser Thr Ala Val Pro Gln
            20                  25

<210> SEQ ID NO 18
<211> LENGTH: 24
<212> TYPE: PRT
<213> ORGANISM: Escherichia coli

<400> SEQUENCE: 18

Val Tyr Asn Ile Gln Asp Glu Thr Gly Gln Phe Lys Pro Tyr Pro Ala
1               5                   10                  15
```

Ser Gly Ser Thr Ala Val Pro Gln
            20

<210> SEQ ID NO 19
<211> LENGTH: 25
<212> TYPE: PRT
<213> ORGANISM: Escherichia coli

<400> SEQUENCE: 19

Val Tyr Asn Ile Gln Asp Glu Thr Gly Gln Phe Lys Pro Tyr Pro Ala
1               5                   10                  15

Ser Val Phe Ser Thr Ala Val Pro Gln
            20                  25

<210> SEQ ID NO 20
<211> LENGTH: 25
<212> TYPE: PRT
<213> ORGANISM: Escherichia coli

<400> SEQUENCE: 20

Val Tyr Asn Ile Gln Asp Glu Thr Gly Gln Phe Lys Pro Tyr Pro Ala
1               5                   10                  15

Ser Val Ala Ser Thr Ala Val Pro Gln
            20                  25

<210> SEQ ID NO 21
<211> LENGTH: 25
<212> TYPE: PRT
<213> ORGANISM: Escherichia coli

<400> SEQUENCE: 21

Val Tyr Asn Ile Gln Asp Glu Thr Gly Gln Phe Lys Pro Tyr Pro Ala
1               5                   10                  15

Ser Val Gly Ser Thr Ala Val Pro Gln
            20                  25

<210> SEQ ID NO 22
<211> LENGTH: 25
<212> TYPE: PRT
<213> ORGANISM: Escherichia coli

<400> SEQUENCE: 22

Val Tyr Asn Ile Gln Asp Glu Thr Gly Gln Phe Lys Pro Tyr Pro Ala
1               5                   10                  15

Ser Val Val Ser Thr Ala Val Pro Gln
            20                  25

<210> SEQ ID NO 23
<211> LENGTH: 24
<212> TYPE: PRT
<213> ORGANISM: Escherichia coli

<400> SEQUENCE: 23

Val Tyr Asn Ile Gln Asp Glu Thr Gly Gln Phe Lys Pro Tyr Pro Ala
1               5                   10                  15

Ser Val Ser Thr Ala Val Pro Gln
            20

<210> SEQ ID NO 24
<211> LENGTH: 25
<212> TYPE: PRT
<213> ORGANISM: Escherichia coli

```
<400> SEQUENCE: 24

Val Tyr Asn Ile Gln Asp Glu Thr Gly Gln Phe Lys Pro Tyr Pro Ala
1               5                   10                  15

Ser Ser Phe Ser Thr Ala Val Pro Gln
            20                  25

<210> SEQ ID NO 25
<211> LENGTH: 25
<212> TYPE: PRT
<213> ORGANISM: Escherichia coli

<400> SEQUENCE: 25

Val Tyr Asn Ile Gln Asp Glu Thr Gly Gln Phe Lys Pro Tyr Pro Ala
1               5                   10                  15

Ser Ser Ala Ser Thr Ala Val Pro Gln
            20                  25

<210> SEQ ID NO 26
<211> LENGTH: 25
<212> TYPE: PRT
<213> ORGANISM: Escherichia coli

<400> SEQUENCE: 26

Val Tyr Asn Ile Gln Asp Glu Thr Gly Gln Phe Lys Pro Tyr Pro Ala
1               5                   10                  15

Ser Ser Gly Ser Thr Ala Val Pro Gln
            20                  25

<210> SEQ ID NO 27
<211> LENGTH: 25
<212> TYPE: PRT
<213> ORGANISM: Escherichia coli

<400> SEQUENCE: 27

Val Tyr Asn Ile Gln Asp Glu Thr Gly Gln Phe Lys Pro Tyr Pro Ala
1               5                   10                  15

Ser Ser Val Ser Thr Ala Val Pro Gln
            20                  25

<210> SEQ ID NO 28
<211> LENGTH: 24
<212> TYPE: PRT
<213> ORGANISM: Escherichia coli

<400> SEQUENCE: 28

Val Tyr Asn Ile Gln Asp Glu Thr Gly Gln Phe Lys Pro Tyr Pro Ala
1               5                   10                  15

Ser Ser Ser Thr Ala Val Pro Gln
            20

<210> SEQ ID NO 29
<211> LENGTH: 25
<212> TYPE: PRT
<213> ORGANISM: Escherichia coli

<400> SEQUENCE: 29

Val Tyr Asn Ile Gln Asp Glu Thr Gly Gln Phe Lys Pro Tyr Pro Ala
1               5                   10                  15

Ser Thr Phe Ser Thr Ala Val Pro Gln
            20                  25
```

```
<210> SEQ ID NO 30
<211> LENGTH: 25
<212> TYPE: PRT
<213> ORGANISM: Escherichia coli

<400> SEQUENCE: 30

Val Tyr Asn Ile Gln Asp Glu Thr Gly Gln Phe Lys Pro Tyr Pro Ala
1               5                   10                  15

Ser Thr Ala Ser Thr Ala Val Pro Gln
            20                  25

<210> SEQ ID NO 31
<211> LENGTH: 25
<212> TYPE: PRT
<213> ORGANISM: Escherichia coli

<400> SEQUENCE: 31

Val Tyr Asn Ile Gln Asp Glu Thr Gly Gln Phe Lys Pro Tyr Pro Ala
1               5                   10                  15

Ser Thr Gly Ser Thr Ala Val Pro Gln
            20                  25

<210> SEQ ID NO 32
<211> LENGTH: 25
<212> TYPE: PRT
<213> ORGANISM: Escherichia coli

<400> SEQUENCE: 32

Val Tyr Asn Ile Gln Asp Glu Thr Gly Gln Phe Lys Pro Tyr Pro Ala
1               5                   10                  15

Ser Thr Val Ser Thr Ala Val Pro Gln
            20                  25

<210> SEQ ID NO 33
<211> LENGTH: 24
<212> TYPE: PRT
<213> ORGANISM: Escherichia coli

<400> SEQUENCE: 33

Val Tyr Asn Ile Gln Asp Glu Thr Gly Gln Phe Lys Pro Tyr Pro Ala
1               5                   10                  15

Ser Thr Ser Thr Ala Val Pro Gln
            20

<210> SEQ ID NO 34
<211> LENGTH: 24
<212> TYPE: PRT
<213> ORGANISM: Escherichia coli

<400> SEQUENCE: 34

Val Tyr Asn Ile Gln Asp Glu Thr Gly Gln Phe Lys Pro Tyr Pro Ala
1               5                   10                  15

Ser Phe Ser Thr Ala Val Pro Gln
            20

<210> SEQ ID NO 35
<211> LENGTH: 24
<212> TYPE: PRT
<213> ORGANISM: Escherichia coli

<400> SEQUENCE: 35

Val Tyr Asn Ile Gln Asp Glu Thr Gly Gln Phe Lys Pro Tyr Pro Ala
```

```
1               5                   10                  15

Ser Ala Ser Thr Ala Val Pro Gln
            20

<210> SEQ ID NO 36
<211> LENGTH: 24
<212> TYPE: PRT
<213> ORGANISM: Escherichia coli

<400> SEQUENCE: 36

Val Tyr Asn Ile Gln Asp Glu Thr Gly Gln Phe Lys Pro Tyr Pro Ala
1               5                   10                  15

Ser Gly Ser Thr Ala Val Pro Gln
            20

<210> SEQ ID NO 37
<211> LENGTH: 24
<212> TYPE: PRT
<213> ORGANISM: Escherichia coli

<400> SEQUENCE: 37

Val Tyr Asn Ile Gln Asp Glu Thr Gly Gln Phe Lys Pro Tyr Pro Ala
1               5                   10                  15

Ser Val Ser Thr Ala Val Pro Gln
            20

<210> SEQ ID NO 38
<211> LENGTH: 23
<212> TYPE: PRT
<213> ORGANISM: Escherichia coli

<400> SEQUENCE: 38

Val Tyr Asn Ile Gln Asp Glu Thr Gly Gln Phe Lys Pro Tyr Pro Ala
1               5                   10                  15

Ser Ser Thr Ala Val Pro Gln
            20

<210> SEQ ID NO 39
<211> LENGTH: 25
<212> TYPE: PRT
<213> ORGANISM: Escherichia coli

<400> SEQUENCE: 39

Val Tyr Asn Ile Gln Asp Glu Thr Gly Gln Phe Lys Pro Ala Pro Ala
1               5                   10                  15

Ser Asn Phe Ser Thr Ala Val Pro Gln
            20                  25

<210> SEQ ID NO 40
<211> LENGTH: 25
<212> TYPE: PRT
<213> ORGANISM: Escherichia coli

<400> SEQUENCE: 40

Val Tyr Asn Ile Gln Asp Glu Thr Gly Gln Phe Lys Pro Ala Pro Ala
1               5                   10                  15

Ser Asn Ala Ser Thr Ala Val Pro Gln
            20                  25

<210> SEQ ID NO 41
<211> LENGTH: 25
<212> TYPE: PRT
```

```
<213> ORGANISM: Escherichia coli

<400> SEQUENCE: 41

Val Tyr Asn Ile Gln Asp Glu Thr Gly Gln Phe Lys Pro Ala Pro Ala
1               5                   10                  15

Ser Asn Gly Ser Thr Ala Val Pro Gln
            20                  25

<210> SEQ ID NO 42
<211> LENGTH: 25
<212> TYPE: PRT
<213> ORGANISM: Escherichia coli

<400> SEQUENCE: 42

Val Tyr Asn Ile Gln Asp Glu Thr Gly Gln Phe Lys Pro Ala Pro Ala
1               5                   10                  15

Ser Asn Val Ser Thr Ala Val Pro Gln
            20                  25

<210> SEQ ID NO 43
<211> LENGTH: 24
<212> TYPE: PRT
<213> ORGANISM: Escherichia coli

<400> SEQUENCE: 43

Val Tyr Asn Ile Gln Asp Glu Thr Gly Gln Phe Lys Pro Ala Pro Ala
1               5                   10                  15

Ser Asn Ser Thr Ala Val Pro Gln
            20

<210> SEQ ID NO 44
<211> LENGTH: 25
<212> TYPE: PRT
<213> ORGANISM: Escherichia coli

<400> SEQUENCE: 44

Val Tyr Asn Ile Gln Asp Glu Thr Gly Gln Phe Lys Pro Ala Pro Ala
1               5                   10                  15

Ser Ala Phe Ser Thr Ala Val Pro Gln
            20                  25

<210> SEQ ID NO 45
<211> LENGTH: 25
<212> TYPE: PRT
<213> ORGANISM: Escherichia coli

<400> SEQUENCE: 45

Val Tyr Asn Ile Gln Asp Glu Thr Gly Gln Phe Lys Pro Ala Pro Ala
1               5                   10                  15

Ser Ala Ala Ser Thr Ala Val Pro Gln
            20                  25

<210> SEQ ID NO 46
<211> LENGTH: 25
<212> TYPE: PRT
<213> ORGANISM: Escherichia coli

<400> SEQUENCE: 46

Val Tyr Asn Ile Gln Asp Glu Thr Gly Gln Phe Lys Pro Ala Pro Ala
1               5                   10                  15

Ser Ala Gly Ser Thr Ala Val Pro Gln
            20                  25
```

```
<210> SEQ ID NO 47
<211> LENGTH: 25
<212> TYPE: PRT
<213> ORGANISM: Escherichia coli

<400> SEQUENCE: 47

Val Tyr Asn Ile Gln Asp Glu Thr Gly Gln Phe Lys Pro Ala Pro Ala
1               5                   10                  15

Ser Ala Val Ser Thr Ala Val Pro Gln
            20                  25

<210> SEQ ID NO 48
<211> LENGTH: 24
<212> TYPE: PRT
<213> ORGANISM: Escherichia coli

<400> SEQUENCE: 48

Val Tyr Asn Ile Gln Asp Glu Thr Gly Gln Phe Lys Pro Ala Pro Ala
1               5                   10                  15

Ser Ala Ser Thr Ala Val Pro Gln
            20

<210> SEQ ID NO 49
<211> LENGTH: 25
<212> TYPE: PRT
<213> ORGANISM: Escherichia coli

<400> SEQUENCE: 49

Val Tyr Asn Ile Gln Asp Glu Thr Gly Gln Phe Lys Pro Ala Pro Ala
1               5                   10                  15

Ser Gly Phe Ser Thr Ala Val Pro Gln
            20                  25

<210> SEQ ID NO 50
<211> LENGTH: 25
<212> TYPE: PRT
<213> ORGANISM: Escherichia coli

<400> SEQUENCE: 50

Val Tyr Asn Ile Gln Asp Glu Thr Gly Gln Phe Lys Pro Ala Pro Ala
1               5                   10                  15

Ser Gly Ala Ser Thr Ala Val Pro Gln
            20                  25

<210> SEQ ID NO 51
<211> LENGTH: 25
<212> TYPE: PRT
<213> ORGANISM: Escherichia coli

<400> SEQUENCE: 51

Val Tyr Asn Ile Gln Asp Glu Thr Gly Gln Phe Lys Pro Ala Pro Ala
1               5                   10                  15

Ser Gly Gly Ser Thr Ala Val Pro Gln
            20                  25

<210> SEQ ID NO 52
<211> LENGTH: 25
<212> TYPE: PRT
<213> ORGANISM: Escherichia coli

<400> SEQUENCE: 52
```

Val Tyr Asn Ile Gln Asp Glu Thr Gly Gln Phe Lys Pro Ala Pro Ala
1               5                   10                  15

Ser Gly Val Ser Thr Ala Val Pro Gln
            20                  25

<210> SEQ ID NO 53
<211> LENGTH: 24
<212> TYPE: PRT
<213> ORGANISM: Escherichia coli

<400> SEQUENCE: 53

Val Tyr Asn Ile Gln Asp Glu Thr Gly Gln Phe Lys Pro Ala Pro Ala
1               5                   10                  15

Ser Gly Ser Thr Ala Val Pro Gln
            20

<210> SEQ ID NO 54
<211> LENGTH: 25
<212> TYPE: PRT
<213> ORGANISM: Escherichia coli

<400> SEQUENCE: 54

Val Tyr Asn Ile Gln Asp Glu Thr Gly Gln Phe Lys Pro Ala Pro Ala
1               5                   10                  15

Ser Val Phe Ser Thr Ala Val Pro Gln
            20                  25

<210> SEQ ID NO 55
<211> LENGTH: 25
<212> TYPE: PRT
<213> ORGANISM: Escherichia coli

<400> SEQUENCE: 55

Val Tyr Asn Ile Gln Asp Glu Thr Gly Gln Phe Lys Pro Ala Pro Ala
1               5                   10                  15

Ser Val Ala Ser Thr Ala Val Pro Gln
            20                  25

<210> SEQ ID NO 56
<211> LENGTH: 25
<212> TYPE: PRT
<213> ORGANISM: Escherichia coli

<400> SEQUENCE: 56

Val Tyr Asn Ile Gln Asp Glu Thr Gly Gln Phe Lys Pro Ala Pro Ala
1               5                   10                  15

Ser Val Gly Ser Thr Ala Val Pro Gln
            20                  25

<210> SEQ ID NO 57
<211> LENGTH: 25
<212> TYPE: PRT
<213> ORGANISM: Escherichia coli

<400> SEQUENCE: 57

Val Tyr Asn Ile Gln Asp Glu Thr Gly Gln Phe Lys Pro Ala Pro Ala
1               5                   10                  15

Ser Val Val Ser Thr Ala Val Pro Gln
            20                  25

<210> SEQ ID NO 58
<211> LENGTH: 24

```
<212> TYPE: PRT
<213> ORGANISM: Escherichia coli

<400> SEQUENCE: 58

Val Tyr Asn Ile Gln Asp Glu Thr Gly Gln Phe Lys Pro Ala Pro Ala
1               5                   10                  15

Ser Val Ser Thr Ala Val Pro Gln
            20

<210> SEQ ID NO 59
<211> LENGTH: 25
<212> TYPE: PRT
<213> ORGANISM: Escherichia coli

<400> SEQUENCE: 59

Val Tyr Asn Ile Gln Asp Glu Thr Gly Gln Phe Lys Pro Ala Pro Ala
1               5                   10                  15

Ser Ser Phe Ser Thr Ala Val Pro Gln
            20                  25

<210> SEQ ID NO 60
<211> LENGTH: 25
<212> TYPE: PRT
<213> ORGANISM: Escherichia coli

<400> SEQUENCE: 60

Val Tyr Asn Ile Gln Asp Glu Thr Gly Gln Phe Lys Pro Ala Pro Ala
1               5                   10                  15

Ser Ser Ala Ser Thr Ala Val Pro Gln
            20                  25

<210> SEQ ID NO 61
<211> LENGTH: 25
<212> TYPE: PRT
<213> ORGANISM: Escherichia coli

<400> SEQUENCE: 61

Val Tyr Asn Ile Gln Asp Glu Thr Gly Gln Phe Lys Pro Ala Pro Ala
1               5                   10                  15

Ser Ser Gly Ser Thr Ala Val Pro Gln
            20                  25

<210> SEQ ID NO 62
<211> LENGTH: 25
<212> TYPE: PRT
<213> ORGANISM: Escherichia coli

<400> SEQUENCE: 62

Val Tyr Asn Ile Gln Asp Glu Thr Gly Gln Phe Lys Pro Ala Pro Ala
1               5                   10                  15

Ser Ser Val Ser Thr Ala Val Pro Gln
            20                  25

<210> SEQ ID NO 63
<211> LENGTH: 24
<212> TYPE: PRT
<213> ORGANISM: Escherichia coli

<400> SEQUENCE: 63

Val Tyr Asn Ile Gln Asp Glu Thr Gly Gln Phe Lys Pro Ala Pro Ala
1               5                   10                  15

Ser Ser Ser Thr Ala Val Pro Gln
            20
```

<210> SEQ ID NO 64
<211> LENGTH: 25
<212> TYPE: PRT
<213> ORGANISM: Escherichia coli

<400> SEQUENCE: 64

Val Tyr Asn Ile Gln Asp Glu Thr Gly Gln Phe Lys Pro Ala Pro Ala
1               5                   10                  15

Ser Thr Phe Ser Thr Ala Val Pro Gln
            20                  25

<210> SEQ ID NO 65
<211> LENGTH: 25
<212> TYPE: PRT
<213> ORGANISM: Escherichia coli

<400> SEQUENCE: 65

Val Tyr Asn Ile Gln Asp Glu Thr Gly Gln Phe Lys Pro Ala Pro Ala
1               5                   10                  15

Ser Thr Ala Ser Thr Ala Val Pro Gln
            20                  25

<210> SEQ ID NO 66
<211> LENGTH: 25
<212> TYPE: PRT
<213> ORGANISM: Escherichia coli

<400> SEQUENCE: 66

Val Tyr Asn Ile Gln Asp Glu Thr Gly Gln Phe Lys Pro Ala Pro Ala
1               5                   10                  15

Ser Thr Gly Ser Thr Ala Val Pro Gln
            20                  25

<210> SEQ ID NO 67
<211> LENGTH: 25
<212> TYPE: PRT
<213> ORGANISM: Escherichia coli

<400> SEQUENCE: 67

Val Tyr Asn Ile Gln Asp Glu Thr Gly Gln Phe Lys Pro Ala Pro Ala
1               5                   10                  15

Ser Thr Val Ser Thr Ala Val Pro Gln
            20                  25

<210> SEQ ID NO 68
<211> LENGTH: 24
<212> TYPE: PRT
<213> ORGANISM: Escherichia coli

<400> SEQUENCE: 68

Val Tyr Asn Ile Gln Asp Glu Thr Gly Gln Phe Lys Pro Ala Pro Ala
1               5                   10                  15

Ser Thr Ser Thr Ala Val Pro Gln
            20

<210> SEQ ID NO 69
<211> LENGTH: 24
<212> TYPE: PRT
<213> ORGANISM: Escherichia coli

<400> SEQUENCE: 69

Val Tyr Asn Ile Gln Asp Glu Thr Gly Gln Phe Lys Pro Ala Pro Ala
1               5                   10                  15

Ser Phe Ser Thr Ala Val Pro Gln
            20

<210> SEQ ID NO 70
<211> LENGTH: 24
<212> TYPE: PRT
<213> ORGANISM: Escherichia coli

<400> SEQUENCE: 70

Val Tyr Asn Ile Gln Asp Glu Thr Gly Gln Phe Lys Pro Ala Pro Ala
1               5                   10                  15

Ser Ala Ser Thr Ala Val Pro Gln
            20

<210> SEQ ID NO 71
<211> LENGTH: 24
<212> TYPE: PRT
<213> ORGANISM: Escherichia coli

<400> SEQUENCE: 71

Val Tyr Asn Ile Gln Asp Glu Thr Gly Gln Phe Lys Pro Ala Pro Ala
1               5                   10                  15

Ser Gly Ser Thr Ala Val Pro Gln
            20

<210> SEQ ID NO 72
<211> LENGTH: 24
<212> TYPE: PRT
<213> ORGANISM: Escherichia coli

<400> SEQUENCE: 72

Val Tyr Asn Ile Gln Asp Glu Thr Gly Gln Phe Lys Pro Ala Pro Ala
1               5                   10                  15

Ser Val Ser Thr Ala Val Pro Gln
            20

<210> SEQ ID NO 73
<211> LENGTH: 23
<212> TYPE: PRT
<213> ORGANISM: Escherichia coli

<400> SEQUENCE: 73

Val Tyr Asn Ile Gln Asp Glu Thr Gly Gln Phe Lys Pro Ala Pro Ala
1               5                   10                  15

Ser Ser Thr Ala Val Pro Gln
            20

<210> SEQ ID NO 74
<211> LENGTH: 25
<212> TYPE: PRT
<213> ORGANISM: Escherichia coli

<400> SEQUENCE: 74

Val Tyr Asn Ile Gln Asp Glu Thr Gly Gln Phe Lys Pro Gly Pro Ala
1               5                   10                  15

Ser Asn Phe Ser Thr Ala Val Pro Gln
            20                  25

<210> SEQ ID NO 75

-continued

<211> LENGTH: 25
<212> TYPE: PRT
<213> ORGANISM: Escherichia coli

<400> SEQUENCE: 75

Val Tyr Asn Ile Gln Asp Glu Thr Gly Gln Phe Lys Pro Gly Pro Ala
1               5                   10                  15

Ser Asn Ala Ser Thr Ala Val Pro Gln
            20                  25

<210> SEQ ID NO 76
<211> LENGTH: 25
<212> TYPE: PRT
<213> ORGANISM: Escherichia coli

<400> SEQUENCE: 76

Val Tyr Asn Ile Gln Asp Glu Thr Gly Gln Phe Lys Pro Gly Pro Ala
1               5                   10                  15

Ser Asn Gly Ser Thr Ala Val Pro Gln
            20                  25

<210> SEQ ID NO 77
<211> LENGTH: 25
<212> TYPE: PRT
<213> ORGANISM: Escherichia coli

<400> SEQUENCE: 77

Val Tyr Asn Ile Gln Asp Glu Thr Gly Gln Phe Lys Pro Gly Pro Ala
1               5                   10                  15

Ser Asn Val Ser Thr Ala Val Pro Gln
            20                  25

<210> SEQ ID NO 78
<211> LENGTH: 24
<212> TYPE: PRT
<213> ORGANISM: Escherichia coli

<400> SEQUENCE: 78

Val Tyr Asn Ile Gln Asp Glu Thr Gly Gln Phe Lys Pro Gly Pro Ala
1               5                   10                  15

Ser Asn Ser Thr Ala Val Pro Gln
            20

<210> SEQ ID NO 79
<211> LENGTH: 25
<212> TYPE: PRT
<213> ORGANISM: Escherichia coli

<400> SEQUENCE: 79

Val Tyr Asn Ile Gln Asp Glu Thr Gly Gln Phe Lys Pro Gly Pro Ala
1               5                   10                  15

Ser Ala Phe Ser Thr Ala Val Pro Gln
            20                  25

<210> SEQ ID NO 80
<211> LENGTH: 25
<212> TYPE: PRT
<213> ORGANISM: Escherichia coli

<400> SEQUENCE: 80

Val Tyr Asn Ile Gln Asp Glu Thr Gly Gln Phe Lys Pro Gly Pro Ala
1               5                   10                  15

Ser Ala Ala Ser Thr Ala Val Pro Gln
            20                  25

<210> SEQ ID NO 81
<211> LENGTH: 25
<212> TYPE: PRT
<213> ORGANISM: Escherichia coli

<400> SEQUENCE: 81

Val Tyr Asn Ile Gln Asp Glu Thr Gly Gln Phe Lys Pro Gly Pro Ala
1               5                   10                  15

Ser Ala Gly Ser Thr Ala Val Pro Gln
            20                  25

<210> SEQ ID NO 82
<211> LENGTH: 25
<212> TYPE: PRT
<213> ORGANISM: Escherichia coli

<400> SEQUENCE: 82

Val Tyr Asn Ile Gln Asp Glu Thr Gly Gln Phe Lys Pro Gly Pro Ala
1               5                   10                  15

Ser Ala Val Ser Thr Ala Val Pro Gln
            20                  25

<210> SEQ ID NO 83
<211> LENGTH: 24
<212> TYPE: PRT
<213> ORGANISM: Escherichia coli

<400> SEQUENCE: 83

Val Tyr Asn Ile Gln Asp Glu Thr Gly Gln Phe Lys Pro Gly Pro Ala
1               5                   10                  15

Ser Ala Ser Thr Ala Val Pro Gln
            20

<210> SEQ ID NO 84
<211> LENGTH: 25
<212> TYPE: PRT
<213> ORGANISM: Escherichia coli

<400> SEQUENCE: 84

Val Tyr Asn Ile Gln Asp Glu Thr Gly Gln Phe Lys Pro Gly Pro Ala
1               5                   10                  15

Ser Gly Phe Ser Thr Ala Val Pro Gln
            20                  25

<210> SEQ ID NO 85
<211> LENGTH: 25
<212> TYPE: PRT
<213> ORGANISM: Escherichia coli

<400> SEQUENCE: 85

Val Tyr Asn Ile Gln Asp Glu Thr Gly Gln Phe Lys Pro Gly Pro Ala
1               5                   10                  15

Ser Gly Ala Ser Thr Ala Val Pro Gln
            20                  25

<210> SEQ ID NO 86
<211> LENGTH: 25
<212> TYPE: PRT
<213> ORGANISM: Escherichia coli

```
<400> SEQUENCE: 86

Val Tyr Asn Ile Gln Asp Glu Thr Gly Gln Phe Lys Pro Gly Pro Ala
1               5                   10                  15

Ser Gly Gly Ser Thr Ala Val Pro Gln
            20                  25

<210> SEQ ID NO 87
<211> LENGTH: 25
<212> TYPE: PRT
<213> ORGANISM: Escherichia coli

<400> SEQUENCE: 87

Val Tyr Asn Ile Gln Asp Glu Thr Gly Gln Phe Lys Pro Gly Pro Ala
1               5                   10                  15

Ser Gly Val Ser Thr Ala Val Pro Gln
            20                  25

<210> SEQ ID NO 88
<211> LENGTH: 24
<212> TYPE: PRT
<213> ORGANISM: Escherichia coli

<400> SEQUENCE: 88

Val Tyr Asn Ile Gln Asp Glu Thr Gly Gln Phe Lys Pro Gly Pro Ala
1               5                   10                  15

Ser Gly Ser Thr Ala Val Pro Gln
            20

<210> SEQ ID NO 89
<211> LENGTH: 25
<212> TYPE: PRT
<213> ORGANISM: Escherichia coli

<400> SEQUENCE: 89

Val Tyr Asn Ile Gln Asp Glu Thr Gly Gln Phe Lys Pro Gly Pro Ala
1               5                   10                  15

Ser Val Phe Ser Thr Ala Val Pro Gln
            20                  25

<210> SEQ ID NO 90
<211> LENGTH: 25
<212> TYPE: PRT
<213> ORGANISM: Escherichia coli

<400> SEQUENCE: 90

Val Tyr Asn Ile Gln Asp Glu Thr Gly Gln Phe Lys Pro Gly Pro Ala
1               5                   10                  15

Ser Val Ala Ser Thr Ala Val Pro Gln
            20                  25

<210> SEQ ID NO 91
<211> LENGTH: 25
<212> TYPE: PRT
<213> ORGANISM: Escherichia coli

<400> SEQUENCE: 91

Val Tyr Asn Ile Gln Asp Glu Thr Gly Gln Phe Lys Pro Gly Pro Ala
1               5                   10                  15

Ser Val Gly Ser Thr Ala Val Pro Gln
            20                  25
```

<210> SEQ ID NO 92
<211> LENGTH: 25
<212> TYPE: PRT
<213> ORGANISM: Escherichia coli

<400> SEQUENCE: 92

Val Tyr Asn Ile Gln Asp Glu Thr Gly Gln Phe Lys Pro Gly Pro Ala
1               5                   10                  15

Ser Val Val Ser Thr Ala Val Pro Gln
            20                  25

<210> SEQ ID NO 93
<211> LENGTH: 24
<212> TYPE: PRT
<213> ORGANISM: Escherichia coli

<400> SEQUENCE: 93

Val Tyr Asn Ile Gln Asp Glu Thr Gly Gln Phe Lys Pro Gly Pro Ala
1               5                   10                  15

Ser Val Ser Thr Ala Val Pro Gln
            20

<210> SEQ ID NO 94
<211> LENGTH: 25
<212> TYPE: PRT
<213> ORGANISM: Escherichia coli

<400> SEQUENCE: 94

Val Tyr Asn Ile Gln Asp Glu Thr Gly Gln Phe Lys Pro Gly Pro Ala
1               5                   10                  15

Ser Ser Phe Ser Thr Ala Val Pro Gln
            20                  25

<210> SEQ ID NO 95
<211> LENGTH: 25
<212> TYPE: PRT
<213> ORGANISM: Escherichia coli

<400> SEQUENCE: 95

Val Tyr Asn Ile Gln Asp Glu Thr Gly Gln Phe Lys Pro Gly Pro Ala
1               5                   10                  15

Ser Ser Ala Ser Thr Ala Val Pro Gln
            20                  25

<210> SEQ ID NO 96
<211> LENGTH: 25
<212> TYPE: PRT
<213> ORGANISM: Escherichia coli

<400> SEQUENCE: 96

Val Tyr Asn Ile Gln Asp Glu Thr Gly Gln Phe Lys Pro Gly Pro Ala
1               5                   10                  15

Ser Ser Gly Ser Thr Ala Val Pro Gln
            20                  25

<210> SEQ ID NO 97
<211> LENGTH: 25
<212> TYPE: PRT
<213> ORGANISM: Escherichia coli

<400> SEQUENCE: 97

Val Tyr Asn Ile Gln Asp Glu Thr Gly Gln Phe Lys Pro Gly Pro Ala
1               5                   10                  15

Ser Ser Val Ser Thr Ala Val Pro Gln
            20                  25

<210> SEQ ID NO 98
<211> LENGTH: 24
<212> TYPE: PRT
<213> ORGANISM: Escherichia coli

<400> SEQUENCE: 98

Val Tyr Asn Ile Gln Asp Glu Thr Gly Gln Phe Lys Pro Gly Pro Ala
1               5                   10                  15

Ser Ser Ser Thr Ala Val Pro Gln
            20

<210> SEQ ID NO 99
<211> LENGTH: 25
<212> TYPE: PRT
<213> ORGANISM: Escherichia coli

<400> SEQUENCE: 99

Val Tyr Asn Ile Gln Asp Glu Thr Gly Gln Phe Lys Pro Gly Pro Ala
1               5                   10                  15

Ser Thr Phe Ser Thr Ala Val Pro Gln
            20                  25

<210> SEQ ID NO 100
<211> LENGTH: 25
<212> TYPE: PRT
<213> ORGANISM: Escherichia coli

<400> SEQUENCE: 100

Val Tyr Asn Ile Gln Asp Glu Thr Gly Gln Phe Lys Pro Gly Pro Ala
1               5                   10                  15

Ser Thr Ala Ser Thr Ala Val Pro Gln
            20                  25

<210> SEQ ID NO 101
<211> LENGTH: 25
<212> TYPE: PRT
<213> ORGANISM: Escherichia coli

<400> SEQUENCE: 101

Val Tyr Asn Ile Gln Asp Glu Thr Gly Gln Phe Lys Pro Gly Pro Ala
1               5                   10                  15

Ser Thr Gly Ser Thr Ala Val Pro Gln
            20                  25

<210> SEQ ID NO 102
<211> LENGTH: 25
<212> TYPE: PRT
<213> ORGANISM: Escherichia coli

<400> SEQUENCE: 102

Val Tyr Asn Ile Gln Asp Glu Thr Gly Gln Phe Lys Pro Gly Pro Ala
1               5                   10                  15

Ser Thr Val Ser Thr Ala Val Pro Gln
            20                  25

<210> SEQ ID NO 103
<211> LENGTH: 24
<212> TYPE: PRT
<213> ORGANISM: Escherichia coli

<400> SEQUENCE: 103

Val Tyr Asn Ile Gln Asp Glu Thr Gly Gln Phe Lys Pro Gly Pro Ala
1               5                   10                  15

Ser Thr Ser Thr Ala Val Pro Gln
            20

<210> SEQ ID NO 104
<211> LENGTH: 24
<212> TYPE: PRT
<213> ORGANISM: Escherichia coli

<400> SEQUENCE: 104

Val Tyr Asn Ile Gln Asp Glu Thr Gly Gln Phe Lys Pro Gly Pro Ala
1               5                   10                  15

Ser Phe Ser Thr Ala Val Pro Gln
            20

<210> SEQ ID NO 105
<211> LENGTH: 24
<212> TYPE: PRT
<213> ORGANISM: Escherichia coli

<400> SEQUENCE: 105

Val Tyr Asn Ile Gln Asp Glu Thr Gly Gln Phe Lys Pro Gly Pro Ala
1               5                   10                  15

Ser Ala Ser Thr Ala Val Pro Gln
            20

<210> SEQ ID NO 106
<211> LENGTH: 24
<212> TYPE: PRT
<213> ORGANISM: Escherichia coli

<400> SEQUENCE: 106

Val Tyr Asn Ile Gln Asp Glu Thr Gly Gln Phe Lys Pro Gly Pro Ala
1               5                   10                  15

Ser Gly Ser Thr Ala Val Pro Gln
            20

<210> SEQ ID NO 107
<211> LENGTH: 24
<212> TYPE: PRT
<213> ORGANISM: Escherichia coli

<400> SEQUENCE: 107

Val Tyr Asn Ile Gln Asp Glu Thr Gly Gln Phe Lys Pro Gly Pro Ala
1               5                   10                  15

Ser Val Ser Thr Ala Val Pro Gln
            20

<210> SEQ ID NO 108
<211> LENGTH: 23
<212> TYPE: PRT
<213> ORGANISM: Escherichia coli

<400> SEQUENCE: 108

Val Tyr Asn Ile Gln Asp Glu Thr Gly Gln Phe Lys Pro Gly Pro Ala
1               5                   10                  15

Ser Ser Thr Ala Val Pro Gln
            20

<210> SEQ ID NO 109
<211> LENGTH: 25
<212> TYPE: PRT
<213> ORGANISM: Escherichia coli

<400> SEQUENCE: 109

Val Tyr Asn Ile Gln Asp Glu Thr Gly Gln Phe Lys Pro Val Pro Ala
1               5                   10                  15

Ser Asn Phe Ser Thr Ala Val Pro Gln
            20                  25

<210> SEQ ID NO 110
<211> LENGTH: 25
<212> TYPE: PRT
<213> ORGANISM: Escherichia coli

<400> SEQUENCE: 110

Val Tyr Asn Ile Gln Asp Glu Thr Gly Gln Phe Lys Pro Val Pro Ala
1               5                   10                  15

Ser Asn Ala Ser Thr Ala Val Pro Gln
            20                  25

<210> SEQ ID NO 111
<211> LENGTH: 25
<212> TYPE: PRT
<213> ORGANISM: Escherichia coli

<400> SEQUENCE: 111

Val Tyr Asn Ile Gln Asp Glu Thr Gly Gln Phe Lys Pro Val Pro Ala
1               5                   10                  15

Ser Asn Gly Ser Thr Ala Val Pro Gln
            20                  25

<210> SEQ ID NO 112
<211> LENGTH: 25
<212> TYPE: PRT
<213> ORGANISM: Escherichia coli

<400> SEQUENCE: 112

Val Tyr Asn Ile Gln Asp Glu Thr Gly Gln Phe Lys Pro Val Pro Ala
1               5                   10                  15

Ser Asn Val Ser Thr Ala Val Pro Gln
            20                  25

<210> SEQ ID NO 113
<211> LENGTH: 24
<212> TYPE: PRT
<213> ORGANISM: Escherichia coli

<400> SEQUENCE: 113

Val Tyr Asn Ile Gln Asp Glu Thr Gly Gln Phe Lys Pro Val Pro Ala
1               5                   10                  15

Ser Asn Ser Thr Ala Val Pro Gln
            20

<210> SEQ ID NO 114
<211> LENGTH: 25
<212> TYPE: PRT
<213> ORGANISM: Escherichia coli

<400> SEQUENCE: 114

Val Tyr Asn Ile Gln Asp Glu Thr Gly Gln Phe Lys Pro Val Pro Ala

```
                1               5                   10                  15
Ser Ala Phe Ser Thr Ala Val Pro Gln
            20                  25

<210> SEQ ID NO 115
<211> LENGTH: 25
<212> TYPE: PRT
<213> ORGANISM: Escherichia coli

<400> SEQUENCE: 115

Val Tyr Asn Ile Gln Asp Glu Thr Gly Gln Phe Lys Pro Val Pro Ala
1               5                   10                  15

Ser Ala Ala Ser Thr Ala Val Pro Gln
            20                  25

<210> SEQ ID NO 116
<211> LENGTH: 25
<212> TYPE: PRT
<213> ORGANISM: Escherichia coli

<400> SEQUENCE: 116

Val Tyr Asn Ile Gln Asp Glu Thr Gly Gln Phe Lys Pro Val Pro Ala
1               5                   10                  15

Ser Ala Gly Ser Thr Ala Val Pro Gln
            20                  25

<210> SEQ ID NO 117
<211> LENGTH: 25
<212> TYPE: PRT
<213> ORGANISM: Escherichia coli

<400> SEQUENCE: 117

Val Tyr Asn Ile Gln Asp Glu Thr Gly Gln Phe Lys Pro Val Pro Ala
1               5                   10                  15

Ser Ala Val Ser Thr Ala Val Pro Gln
            20                  25

<210> SEQ ID NO 118
<211> LENGTH: 24
<212> TYPE: PRT
<213> ORGANISM: Escherichia coli

<400> SEQUENCE: 118

Val Tyr Asn Ile Gln Asp Glu Thr Gly Gln Phe Lys Pro Val Pro Ala
1               5                   10                  15

Ser Ala Ser Thr Ala Val Pro Gln
            20

<210> SEQ ID NO 119
<211> LENGTH: 25
<212> TYPE: PRT
<213> ORGANISM: Escherichia coli

<400> SEQUENCE: 119

Val Tyr Asn Ile Gln Asp Glu Thr Gly Gln Phe Lys Pro Val Pro Ala
1               5                   10                  15

Ser Gly Phe Ser Thr Ala Val Pro Gln
            20                  25

<210> SEQ ID NO 120
<211> LENGTH: 25
<212> TYPE: PRT
```

<213> ORGANISM: Escherichia coli

<400> SEQUENCE: 120

Val Tyr Asn Ile Gln Asp Glu Thr Gly Gln Phe Lys Pro Val Pro Ala
1               5                   10                  15

Ser Gly Ala Ser Thr Ala Val Pro Gln
            20                  25

<210> SEQ ID NO 121
<211> LENGTH: 25
<212> TYPE: PRT
<213> ORGANISM: Escherichia coli

<400> SEQUENCE: 121

Val Tyr Asn Ile Gln Asp Glu Thr Gly Gln Phe Lys Pro Val Pro Ala
1               5                   10                  15

Ser Gly Gly Ser Thr Ala Val Pro Gln
            20                  25

<210> SEQ ID NO 122
<211> LENGTH: 25
<212> TYPE: PRT
<213> ORGANISM: Escherichia coli

<400> SEQUENCE: 122

Val Tyr Asn Ile Gln Asp Glu Thr Gly Gln Phe Lys Pro Val Pro Ala
1               5                   10                  15

Ser Gly Val Ser Thr Ala Val Pro Gln
            20                  25

<210> SEQ ID NO 123
<211> LENGTH: 24
<212> TYPE: PRT
<213> ORGANISM: Escherichia coli

<400> SEQUENCE: 123

Val Tyr Asn Ile Gln Asp Glu Thr Gly Gln Phe Lys Pro Val Pro Ala
1               5                   10                  15

Ser Gly Ser Thr Ala Val Pro Gln
            20

<210> SEQ ID NO 124
<211> LENGTH: 25
<212> TYPE: PRT
<213> ORGANISM: Escherichia coli

<400> SEQUENCE: 124

Val Tyr Asn Ile Gln Asp Glu Thr Gly Gln Phe Lys Pro Val Pro Ala
1               5                   10                  15

Ser Val Phe Ser Thr Ala Val Pro Gln
            20                  25

<210> SEQ ID NO 125
<211> LENGTH: 25
<212> TYPE: PRT
<213> ORGANISM: Escherichia coli

<400> SEQUENCE: 125

Val Tyr Asn Ile Gln Asp Glu Thr Gly Gln Phe Lys Pro Val Pro Ala
1               5                   10                  15

Ser Val Ala Ser Thr Ala Val Pro Gln
            20                  25

<210> SEQ ID NO 126
<211> LENGTH: 25
<212> TYPE: PRT
<213> ORGANISM: Escherichia coli

<400> SEQUENCE: 126

Val Tyr Asn Ile Gln Asp Glu Thr Gly Gln Phe Lys Pro Val Pro Ala
1               5                   10                  15

Ser Val Gly Ser Thr Ala Val Pro Gln
            20                  25

<210> SEQ ID NO 127
<211> LENGTH: 25
<212> TYPE: PRT
<213> ORGANISM: Escherichia coli

<400> SEQUENCE: 127

Val Tyr Asn Ile Gln Asp Glu Thr Gly Gln Phe Lys Pro Val Pro Ala
1               5                   10                  15

Ser Val Val Ser Thr Ala Val Pro Gln
            20                  25

<210> SEQ ID NO 128
<211> LENGTH: 24
<212> TYPE: PRT
<213> ORGANISM: Escherichia coli

<400> SEQUENCE: 128

Val Tyr Asn Ile Gln Asp Glu Thr Gly Gln Phe Lys Pro Val Pro Ala
1               5                   10                  15

Ser Val Ser Thr Ala Val Pro Gln
            20

<210> SEQ ID NO 129
<211> LENGTH: 25
<212> TYPE: PRT
<213> ORGANISM: Escherichia coli

<400> SEQUENCE: 129

Val Tyr Asn Ile Gln Asp Glu Thr Gly Gln Phe Lys Pro Val Pro Ala
1               5                   10                  15

Ser Ser Phe Ser Thr Ala Val Pro Gln
            20                  25

<210> SEQ ID NO 130
<211> LENGTH: 25
<212> TYPE: PRT
<213> ORGANISM: Escherichia coli

<400> SEQUENCE: 130

Val Tyr Asn Ile Gln Asp Glu Thr Gly Gln Phe Lys Pro Val Pro Ala
1               5                   10                  15

Ser Ser Ala Ser Thr Ala Val Pro Gln
            20                  25

<210> SEQ ID NO 131
<211> LENGTH: 25
<212> TYPE: PRT
<213> ORGANISM: Escherichia coli

<400> SEQUENCE: 131

Val Tyr Asn Ile Gln Asp Glu Thr Gly Gln Phe Lys Pro Val Pro Ala
1               5                   10                  15

Ser Ser Gly Ser Thr Ala Val Pro Gln
            20                  25

<210> SEQ ID NO 132
<211> LENGTH: 25
<212> TYPE: PRT
<213> ORGANISM: Escherichia coli

<400> SEQUENCE: 132

Val Tyr Asn Ile Gln Asp Glu Thr Gly Gln Phe Lys Pro Val Pro Ala
1               5                   10                  15

Ser Ser Val Ser Thr Ala Val Pro Gln
            20                  25

<210> SEQ ID NO 133
<211> LENGTH: 24
<212> TYPE: PRT
<213> ORGANISM: Escherichia coli

<400> SEQUENCE: 133

Val Tyr Asn Ile Gln Asp Glu Thr Gly Gln Phe Lys Pro Val Pro Ala
1               5                   10                  15

Ser Ser Ser Thr Ala Val Pro Gln
            20

<210> SEQ ID NO 134
<211> LENGTH: 25
<212> TYPE: PRT
<213> ORGANISM: Escherichia coli

<400> SEQUENCE: 134

Val Tyr Asn Ile Gln Asp Glu Thr Gly Gln Phe Lys Pro Val Pro Ala
1               5                   10                  15

Ser Thr Phe Ser Thr Ala Val Pro Gln
            20                  25

<210> SEQ ID NO 135
<211> LENGTH: 25
<212> TYPE: PRT
<213> ORGANISM: Escherichia coli

<400> SEQUENCE: 135

Val Tyr Asn Ile Gln Asp Glu Thr Gly Gln Phe Lys Pro Val Pro Ala
1               5                   10                  15

Ser Thr Ala Ser Thr Ala Val Pro Gln
            20                  25

<210> SEQ ID NO 136
<211> LENGTH: 25
<212> TYPE: PRT
<213> ORGANISM: Escherichia coli

<400> SEQUENCE: 136

Val Tyr Asn Ile Gln Asp Glu Thr Gly Gln Phe Lys Pro Val Pro Ala
1               5                   10                  15

Ser Thr Gly Ser Thr Ala Val Pro Gln
            20                  25

<210> SEQ ID NO 137
<211> LENGTH: 25

```
<212> TYPE: PRT
<213> ORGANISM: Escherichia coli

<400> SEQUENCE: 137

Val Tyr Asn Ile Gln Asp Glu Thr Gly Gln Phe Lys Pro Val Pro Ala
1               5                   10                  15

Ser Thr Val Ser Thr Ala Val Pro Gln
            20                  25

<210> SEQ ID NO 138
<211> LENGTH: 24
<212> TYPE: PRT
<213> ORGANISM: Escherichia coli

<400> SEQUENCE: 138

Val Tyr Asn Ile Gln Asp Glu Thr Gly Gln Phe Lys Pro Val Pro Ala
1               5                   10                  15

Ser Thr Ser Thr Ala Val Pro Gln
            20

<210> SEQ ID NO 139
<211> LENGTH: 24
<212> TYPE: PRT
<213> ORGANISM: Escherichia coli

<400> SEQUENCE: 139

Val Tyr Asn Ile Gln Asp Glu Thr Gly Gln Phe Lys Pro Val Pro Ala
1               5                   10                  15

Ser Phe Ser Thr Ala Val Pro Gln
            20

<210> SEQ ID NO 140
<211> LENGTH: 24
<212> TYPE: PRT
<213> ORGANISM: Escherichia coli

<400> SEQUENCE: 140

Val Tyr Asn Ile Gln Asp Glu Thr Gly Gln Phe Lys Pro Val Pro Ala
1               5                   10                  15

Ser Ala Ser Thr Ala Val Pro Gln
            20

<210> SEQ ID NO 141
<211> LENGTH: 24
<212> TYPE: PRT
<213> ORGANISM: Escherichia coli

<400> SEQUENCE: 141

Val Tyr Asn Ile Gln Asp Glu Thr Gly Gln Phe Lys Pro Val Pro Ala
1               5                   10                  15

Ser Gly Ser Thr Ala Val Pro Gln
            20

<210> SEQ ID NO 142
<211> LENGTH: 24
<212> TYPE: PRT
<213> ORGANISM: Escherichia coli

<400> SEQUENCE: 142

Val Tyr Asn Ile Gln Asp Glu Thr Gly Gln Phe Lys Pro Val Pro Ala
1               5                   10                  15

Ser Val Ser Thr Ala Val Pro Gln
```

```
<210> SEQ ID NO 143
<211> LENGTH: 23
<212> TYPE: PRT
<213> ORGANISM: Escherichia coli

<400> SEQUENCE: 143

Val Tyr Asn Ile Gln Asp Glu Thr Gly Gln Phe Lys Pro Val Pro Ala
1               5                   10                  15

Ser Ser Thr Ala Val Pro Gln
            20

<210> SEQ ID NO 144
<211> LENGTH: 25
<212> TYPE: PRT
<213> ORGANISM: Escherichia coli

<400> SEQUENCE: 144

Val Tyr Asn Ile Gln Asp Glu Thr Gly Gln Phe Lys Pro Leu Pro Ala
1               5                   10                  15

Ser Asn Phe Ser Thr Ala Val Pro Gln
            20                  25

<210> SEQ ID NO 145
<211> LENGTH: 25
<212> TYPE: PRT
<213> ORGANISM: Escherichia coli

<400> SEQUENCE: 145

Val Tyr Asn Ile Gln Asp Glu Thr Gly Gln Phe Lys Pro Leu Pro Ala
1               5                   10                  15

Ser Asn Ala Ser Thr Ala Val Pro Gln
            20                  25

<210> SEQ ID NO 146
<211> LENGTH: 25
<212> TYPE: PRT
<213> ORGANISM: Escherichia coli

<400> SEQUENCE: 146

Val Tyr Asn Ile Gln Asp Glu Thr Gly Gln Phe Lys Pro Leu Pro Ala
1               5                   10                  15

Ser Asn Gly Ser Thr Ala Val Pro Gln
            20                  25

<210> SEQ ID NO 147
<211> LENGTH: 25
<212> TYPE: PRT
<213> ORGANISM: Escherichia coli

<400> SEQUENCE: 147

Val Tyr Asn Ile Gln Asp Glu Thr Gly Gln Phe Lys Pro Leu Pro Ala
1               5                   10                  15

Ser Asn Val Ser Thr Ala Val Pro Gln
            20                  25

<210> SEQ ID NO 148
<211> LENGTH: 24
<212> TYPE: PRT
<213> ORGANISM: Escherichia coli

<400> SEQUENCE: 148
```

Val Tyr Asn Ile Gln Asp Glu Thr Gly Gln Phe Lys Pro Leu Pro Ala
1               5                   10                  15

Ser Asn Ser Thr Ala Val Pro Gln
            20

<210> SEQ ID NO 149
<211> LENGTH: 25
<212> TYPE: PRT
<213> ORGANISM: Escherichia coli

<400> SEQUENCE: 149

Val Tyr Asn Ile Gln Asp Glu Thr Gly Gln Phe Lys Pro Leu Pro Ala
1               5                   10                  15

Ser Ala Phe Ser Thr Ala Val Pro Gln
            20                  25

<210> SEQ ID NO 150
<211> LENGTH: 25
<212> TYPE: PRT
<213> ORGANISM: Escherichia coli

<400> SEQUENCE: 150

Val Tyr Asn Ile Gln Asp Glu Thr Gly Gln Phe Lys Pro Leu Pro Ala
1               5                   10                  15

Ser Ala Ala Ser Thr Ala Val Pro Gln
            20                  25

<210> SEQ ID NO 151
<211> LENGTH: 25
<212> TYPE: PRT
<213> ORGANISM: Escherichia coli

<400> SEQUENCE: 151

Val Tyr Asn Ile Gln Asp Glu Thr Gly Gln Phe Lys Pro Leu Pro Ala
1               5                   10                  15

Ser Ala Gly Ser Thr Ala Val Pro Gln
            20                  25

<210> SEQ ID NO 152
<211> LENGTH: 25
<212> TYPE: PRT
<213> ORGANISM: Escherichia coli

<400> SEQUENCE: 152

Val Tyr Asn Ile Gln Asp Glu Thr Gly Gln Phe Lys Pro Leu Pro Ala
1               5                   10                  15

Ser Ala Val Ser Thr Ala Val Pro Gln
            20                  25

<210> SEQ ID NO 153
<211> LENGTH: 24
<212> TYPE: PRT
<213> ORGANISM: Escherichia coli

<400> SEQUENCE: 153

Val Tyr Asn Ile Gln Asp Glu Thr Gly Gln Phe Lys Pro Leu Pro Ala
1               5                   10                  15

Ser Ala Ser Thr Ala Val Pro Gln
            20

<210> SEQ ID NO 154

```
<211> LENGTH: 25
<212> TYPE: PRT
<213> ORGANISM: Escherichia coli

<400> SEQUENCE: 154

Val Tyr Asn Ile Gln Asp Glu Thr Gly Gln Phe Lys Pro Leu Pro Ala
1               5                   10                  15

Ser Gly Phe Ser Thr Ala Val Pro Gln
            20                  25

<210> SEQ ID NO 155
<211> LENGTH: 25
<212> TYPE: PRT
<213> ORGANISM: Escherichia coli

<400> SEQUENCE: 155

Val Tyr Asn Ile Gln Asp Glu Thr Gly Gln Phe Lys Pro Leu Pro Ala
1               5                   10                  15

Ser Gly Ala Ser Thr Ala Val Pro Gln
            20                  25

<210> SEQ ID NO 156
<211> LENGTH: 25
<212> TYPE: PRT
<213> ORGANISM: Escherichia coli

<400> SEQUENCE: 156

Val Tyr Asn Ile Gln Asp Glu Thr Gly Gln Phe Lys Pro Leu Pro Ala
1               5                   10                  15

Ser Gly Gly Ser Thr Ala Val Pro Gln
            20                  25

<210> SEQ ID NO 157
<211> LENGTH: 25
<212> TYPE: PRT
<213> ORGANISM: Escherichia coli

<400> SEQUENCE: 157

Val Tyr Asn Ile Gln Asp Glu Thr Gly Gln Phe Lys Pro Leu Pro Ala
1               5                   10                  15

Ser Gly Val Ser Thr Ala Val Pro Gln
            20                  25

<210> SEQ ID NO 158
<211> LENGTH: 24
<212> TYPE: PRT
<213> ORGANISM: Escherichia coli

<400> SEQUENCE: 158

Val Tyr Asn Ile Gln Asp Glu Thr Gly Gln Phe Lys Pro Leu Pro Ala
1               5                   10                  15

Ser Gly Ser Thr Ala Val Pro Gln
            20

<210> SEQ ID NO 159
<211> LENGTH: 25
<212> TYPE: PRT
<213> ORGANISM: Escherichia coli

<400> SEQUENCE: 159

Val Tyr Asn Ile Gln Asp Glu Thr Gly Gln Phe Lys Pro Leu Pro Ala
1               5                   10                  15
```

Ser Val Phe Ser Thr Ala Val Pro Gln
            20                  25

<210> SEQ ID NO 160
<211> LENGTH: 25
<212> TYPE: PRT
<213> ORGANISM: Escherichia coli

<400> SEQUENCE: 160

Val Tyr Asn Ile Gln Asp Glu Thr Gly Gln Phe Lys Pro Leu Pro Ala
1               5                   10                  15

Ser Val Ala Ser Thr Ala Val Pro Gln
            20                  25

<210> SEQ ID NO 161
<211> LENGTH: 25
<212> TYPE: PRT
<213> ORGANISM: Escherichia coli

<400> SEQUENCE: 161

Val Tyr Asn Ile Gln Asp Glu Thr Gly Gln Phe Lys Pro Leu Pro Ala
1               5                   10                  15

Ser Val Gly Ser Thr Ala Val Pro Gln
            20                  25

<210> SEQ ID NO 162
<211> LENGTH: 25
<212> TYPE: PRT
<213> ORGANISM: Escherichia coli

<400> SEQUENCE: 162

Val Tyr Asn Ile Gln Asp Glu Thr Gly Gln Phe Lys Pro Leu Pro Ala
1               5                   10                  15

Ser Val Val Ser Thr Ala Val Pro Gln
            20                  25

<210> SEQ ID NO 163
<211> LENGTH: 24
<212> TYPE: PRT
<213> ORGANISM: Escherichia coli

<400> SEQUENCE: 163

Val Tyr Asn Ile Gln Asp Glu Thr Gly Gln Phe Lys Pro Leu Pro Ala
1               5                   10                  15

Ser Val Ser Thr Ala Val Pro Gln
            20

<210> SEQ ID NO 164
<211> LENGTH: 25
<212> TYPE: PRT
<213> ORGANISM: Escherichia coli

<400> SEQUENCE: 164

Val Tyr Asn Ile Gln Asp Glu Thr Gly Gln Phe Lys Pro Leu Pro Ala
1               5                   10                  15

Ser Ser Phe Ser Thr Ala Val Pro Gln
            20                  25

<210> SEQ ID NO 165
<211> LENGTH: 25
<212> TYPE: PRT
<213> ORGANISM: Escherichia coli

```
<400> SEQUENCE: 165

Val Tyr Asn Ile Gln Asp Glu Thr Gly Gln Phe Lys Pro Leu Pro Ala
1               5                   10                  15

Ser Ser Ala Ser Thr Ala Val Pro Gln
            20                  25

<210> SEQ ID NO 166
<211> LENGTH: 25
<212> TYPE: PRT
<213> ORGANISM: Escherichia coli

<400> SEQUENCE: 166

Val Tyr Asn Ile Gln Asp Glu Thr Gly Gln Phe Lys Pro Leu Pro Ala
1               5                   10                  15

Ser Ser Gly Ser Thr Ala Val Pro Gln
            20                  25

<210> SEQ ID NO 167
<211> LENGTH: 25
<212> TYPE: PRT
<213> ORGANISM: Escherichia coli

<400> SEQUENCE: 167

Val Tyr Asn Ile Gln Asp Glu Thr Gly Gln Phe Lys Pro Leu Pro Ala
1               5                   10                  15

Ser Ser Val Ser Thr Ala Val Pro Gln
            20                  25

<210> SEQ ID NO 168
<211> LENGTH: 24
<212> TYPE: PRT
<213> ORGANISM: Escherichia coli

<400> SEQUENCE: 168

Val Tyr Asn Ile Gln Asp Glu Thr Gly Gln Phe Lys Pro Leu Pro Ala
1               5                   10                  15

Ser Ser Ser Thr Ala Val Pro Gln
            20

<210> SEQ ID NO 169
<211> LENGTH: 25
<212> TYPE: PRT
<213> ORGANISM: Escherichia coli

<400> SEQUENCE: 169

Val Tyr Asn Ile Gln Asp Glu Thr Gly Gln Phe Lys Pro Leu Pro Ala
1               5                   10                  15

Ser Thr Phe Ser Thr Ala Val Pro Gln
            20                  25

<210> SEQ ID NO 170
<211> LENGTH: 25
<212> TYPE: PRT
<213> ORGANISM: Escherichia coli

<400> SEQUENCE: 170

Val Tyr Asn Ile Gln Asp Glu Thr Gly Gln Phe Lys Pro Leu Pro Ala
1               5                   10                  15

Ser Thr Ala Ser Thr Ala Val Pro Gln
            20                  25
```

```
<210> SEQ ID NO 171
<211> LENGTH: 25
<212> TYPE: PRT
<213> ORGANISM: Escherichia coli

<400> SEQUENCE: 171

Val Tyr Asn Ile Gln Asp Glu Thr Gly Gln Phe Lys Pro Leu Pro Ala
1               5                   10                  15

Ser Thr Gly Ser Thr Ala Val Pro Gln
            20                  25

<210> SEQ ID NO 172
<211> LENGTH: 25
<212> TYPE: PRT
<213> ORGANISM: Escherichia coli

<400> SEQUENCE: 172

Val Tyr Asn Ile Gln Asp Glu Thr Gly Gln Phe Lys Pro Leu Pro Ala
1               5                   10                  15

Ser Thr Val Ser Thr Ala Val Pro Gln
            20                  25

<210> SEQ ID NO 173
<211> LENGTH: 24
<212> TYPE: PRT
<213> ORGANISM: Escherichia coli

<400> SEQUENCE: 173

Val Tyr Asn Ile Gln Asp Glu Thr Gly Gln Phe Lys Pro Leu Pro Ala
1               5                   10                  15

Ser Thr Ser Thr Ala Val Pro Gln
            20

<210> SEQ ID NO 174
<211> LENGTH: 24
<212> TYPE: PRT
<213> ORGANISM: Escherichia coli

<400> SEQUENCE: 174

Val Tyr Asn Ile Gln Asp Glu Thr Gly Gln Phe Lys Pro Leu Pro Ala
1               5                   10                  15

Ser Phe Ser Thr Ala Val Pro Gln
            20

<210> SEQ ID NO 175
<211> LENGTH: 24
<212> TYPE: PRT
<213> ORGANISM: Escherichia coli

<400> SEQUENCE: 175

Val Tyr Asn Ile Gln Asp Glu Thr Gly Gln Phe Lys Pro Leu Pro Ala
1               5                   10                  15

Ser Ala Ser Thr Ala Val Pro Gln
            20

<210> SEQ ID NO 176
<211> LENGTH: 24
<212> TYPE: PRT
<213> ORGANISM: Escherichia coli

<400> SEQUENCE: 176

Val Tyr Asn Ile Gln Asp Glu Thr Gly Gln Phe Lys Pro Leu Pro Ala
1               5                   10                  15
```

```
Ser Gly Ser Thr Ala Val Pro Gln
            20

<210> SEQ ID NO 177
<211> LENGTH: 24
<212> TYPE: PRT
<213> ORGANISM: Escherichia coli

<400> SEQUENCE: 177

Val Tyr Asn Ile Gln Asp Glu Thr Gly Gln Phe Lys Pro Leu Pro Ala
1               5                   10                  15

Ser Val Ser Thr Ala Val Pro Gln
            20

<210> SEQ ID NO 178
<211> LENGTH: 23
<212> TYPE: PRT
<213> ORGANISM: Escherichia coli

<400> SEQUENCE: 178

Val Tyr Asn Ile Gln Asp Glu Thr Gly Gln Phe Lys Pro Leu Pro Ala
1               5                   10                  15

Ser Ser Thr Ala Val Pro Gln
            20

<210> SEQ ID NO 179
<211> LENGTH: 25
<212> TYPE: PRT
<213> ORGANISM: Escherichia coli

<400> SEQUENCE: 179

Val Tyr Asn Ile Gln Asp Glu Thr Gly Gln Phe Lys Pro Ile Pro Ala
1               5                   10                  15

Ser Asn Phe Ser Thr Ala Val Pro Gln
            20                  25

<210> SEQ ID NO 180
<211> LENGTH: 25
<212> TYPE: PRT
<213> ORGANISM: Escherichia coli

<400> SEQUENCE: 180

Val Tyr Asn Ile Gln Asp Glu Thr Gly Gln Phe Lys Pro Ile Pro Ala
1               5                   10                  15

Ser Asn Ala Ser Thr Ala Val Pro Gln
            20                  25

<210> SEQ ID NO 181
<211> LENGTH: 25
<212> TYPE: PRT
<213> ORGANISM: Escherichia coli

<400> SEQUENCE: 181

Val Tyr Asn Ile Gln Asp Glu Thr Gly Gln Phe Lys Pro Ile Pro Ala
1               5                   10                  15

Ser Asn Gly Ser Thr Ala Val Pro Gln
            20                  25

<210> SEQ ID NO 182
<211> LENGTH: 25
<212> TYPE: PRT
<213> ORGANISM: Escherichia coli
```

```
<400> SEQUENCE: 182

Val Tyr Asn Ile Gln Asp Glu Thr Gly Gln Phe Lys Pro Ile Pro Ala
1               5                   10                  15

Ser Asn Val Ser Thr Ala Val Pro Gln
            20                  25

<210> SEQ ID NO 183
<211> LENGTH: 24
<212> TYPE: PRT
<213> ORGANISM: Escherichia coli

<400> SEQUENCE: 183

Val Tyr Asn Ile Gln Asp Glu Thr Gly Gln Phe Lys Pro Ile Pro Ala
1               5                   10                  15

Ser Asn Ser Thr Ala Val Pro Gln
            20

<210> SEQ ID NO 184
<211> LENGTH: 25
<212> TYPE: PRT
<213> ORGANISM: Escherichia coli

<400> SEQUENCE: 184

Val Tyr Asn Ile Gln Asp Glu Thr Gly Gln Phe Lys Pro Ile Pro Ala
1               5                   10                  15

Ser Ala Phe Ser Thr Ala Val Pro Gln
            20                  25

<210> SEQ ID NO 185
<211> LENGTH: 25
<212> TYPE: PRT
<213> ORGANISM: Escherichia coli

<400> SEQUENCE: 185

Val Tyr Asn Ile Gln Asp Glu Thr Gly Gln Phe Lys Pro Ile Pro Ala
1               5                   10                  15

Ser Ala Ala Ser Thr Ala Val Pro Gln
            20                  25

<210> SEQ ID NO 186
<211> LENGTH: 25
<212> TYPE: PRT
<213> ORGANISM: Escherichia coli

<400> SEQUENCE: 186

Val Tyr Asn Ile Gln Asp Glu Thr Gly Gln Phe Lys Pro Ile Pro Ala
1               5                   10                  15

Ser Ala Gly Ser Thr Ala Val Pro Gln
            20                  25

<210> SEQ ID NO 187
<211> LENGTH: 25
<212> TYPE: PRT
<213> ORGANISM: Escherichia coli

<400> SEQUENCE: 187

Val Tyr Asn Ile Gln Asp Glu Thr Gly Gln Phe Lys Pro Ile Pro Ala
1               5                   10                  15

Ser Ala Val Ser Thr Ala Val Pro Gln
            20                  25
```

<210> SEQ ID NO 188
<211> LENGTH: 24
<212> TYPE: PRT
<213> ORGANISM: Escherichia coli

<400> SEQUENCE: 188

Val Tyr Asn Ile Gln Asp Glu Thr Gly Gln Phe Lys Pro Ile Pro Ala
1               5                   10                  15

Ser Ala Ser Thr Ala Val Pro Gln
            20

<210> SEQ ID NO 189
<211> LENGTH: 25
<212> TYPE: PRT
<213> ORGANISM: Escherichia coli

<400> SEQUENCE: 189

Val Tyr Asn Ile Gln Asp Glu Thr Gly Gln Phe Lys Pro Ile Pro Ala
1               5                   10                  15

Ser Gly Phe Ser Thr Ala Val Pro Gln
            20                  25

<210> SEQ ID NO 190
<211> LENGTH: 25
<212> TYPE: PRT
<213> ORGANISM: Escherichia coli

<400> SEQUENCE: 190

Val Tyr Asn Ile Gln Asp Glu Thr Gly Gln Phe Lys Pro Ile Pro Ala
1               5                   10                  15

Ser Gly Ala Ser Thr Ala Val Pro Gln
            20                  25

<210> SEQ ID NO 191
<211> LENGTH: 25
<212> TYPE: PRT
<213> ORGANISM: Escherichia coli

<400> SEQUENCE: 191

Val Tyr Asn Ile Gln Asp Glu Thr Gly Gln Phe Lys Pro Ile Pro Ala
1               5                   10                  15

Ser Gly Gly Ser Thr Ala Val Pro Gln
            20                  25

<210> SEQ ID NO 192
<211> LENGTH: 25
<212> TYPE: PRT
<213> ORGANISM: Escherichia coli

<400> SEQUENCE: 192

Val Tyr Asn Ile Gln Asp Glu Thr Gly Gln Phe Lys Pro Ile Pro Ala
1               5                   10                  15

Ser Gly Val Ser Thr Ala Val Pro Gln
            20                  25

<210> SEQ ID NO 193
<211> LENGTH: 24
<212> TYPE: PRT
<213> ORGANISM: Escherichia coli

<400> SEQUENCE: 193

Val Tyr Asn Ile Gln Asp Glu Thr Gly Gln Phe Lys Pro Ile Pro Ala

```
1               5                   10                  15
Ser Gly Ser Thr Ala Val Pro Gln
            20

<210> SEQ ID NO 194
<211> LENGTH: 25
<212> TYPE: PRT
<213> ORGANISM: Escherichia coli

<400> SEQUENCE: 194

Val Tyr Asn Ile Gln Asp Glu Thr Gly Gln Phe Lys Pro Ile Pro Ala
1               5                   10                  15

Ser Val Phe Ser Thr Ala Val Pro Gln
            20                  25

<210> SEQ ID NO 195
<211> LENGTH: 25
<212> TYPE: PRT
<213> ORGANISM: Escherichia coli

<400> SEQUENCE: 195

Val Tyr Asn Ile Gln Asp Glu Thr Gly Gln Phe Lys Pro Ile Pro Ala
1               5                   10                  15

Ser Val Ala Ser Thr Ala Val Pro Gln
            20                  25

<210> SEQ ID NO 196
<211> LENGTH: 25
<212> TYPE: PRT
<213> ORGANISM: Escherichia coli

<400> SEQUENCE: 196

Val Tyr Asn Ile Gln Asp Glu Thr Gly Gln Phe Lys Pro Ile Pro Ala
1               5                   10                  15

Ser Val Gly Ser Thr Ala Val Pro Gln
            20                  25

<210> SEQ ID NO 197
<211> LENGTH: 25
<212> TYPE: PRT
<213> ORGANISM: Escherichia coli

<400> SEQUENCE: 197

Val Tyr Asn Ile Gln Asp Glu Thr Gly Gln Phe Lys Pro Ile Pro Ala
1               5                   10                  15

Ser Val Val Ser Thr Ala Val Pro Gln
            20                  25

<210> SEQ ID NO 198
<211> LENGTH: 24
<212> TYPE: PRT
<213> ORGANISM: Escherichia coli

<400> SEQUENCE: 198

Val Tyr Asn Ile Gln Asp Glu Thr Gly Gln Phe Lys Pro Ile Pro Ala
1               5                   10                  15

Ser Val Ser Thr Ala Val Pro Gln
            20

<210> SEQ ID NO 199
<211> LENGTH: 25
<212> TYPE: PRT
```

-continued

<213> ORGANISM: Escherichia coli

<400> SEQUENCE: 199

Val Tyr Asn Ile Gln Asp Glu Thr Gly Gln Phe Lys Pro Ile Pro Ala
1               5                   10                  15

Ser Ser Phe Ser Thr Ala Val Pro Gln
            20                  25

<210> SEQ ID NO 200
<211> LENGTH: 25
<212> TYPE: PRT
<213> ORGANISM: Escherichia coli

<400> SEQUENCE: 200

Val Tyr Asn Ile Gln Asp Glu Thr Gly Gln Phe Lys Pro Ile Pro Ala
1               5                   10                  15

Ser Ser Ala Ser Thr Ala Val Pro Gln
            20                  25

<210> SEQ ID NO 201
<211> LENGTH: 25
<212> TYPE: PRT
<213> ORGANISM: Escherichia coli

<400> SEQUENCE: 201

Val Tyr Asn Ile Gln Asp Glu Thr Gly Gln Phe Lys Pro Ile Pro Ala
1               5                   10                  15

Ser Ser Gly Ser Thr Ala Val Pro Gln
            20                  25

<210> SEQ ID NO 202
<211> LENGTH: 25
<212> TYPE: PRT
<213> ORGANISM: Escherichia coli

<400> SEQUENCE: 202

Val Tyr Asn Ile Gln Asp Glu Thr Gly Gln Phe Lys Pro Ile Pro Ala
1               5                   10                  15

Ser Ser Val Ser Thr Ala Val Pro Gln
            20                  25

<210> SEQ ID NO 203
<211> LENGTH: 24
<212> TYPE: PRT
<213> ORGANISM: Escherichia coli

<400> SEQUENCE: 203

Val Tyr Asn Ile Gln Asp Glu Thr Gly Gln Phe Lys Pro Ile Pro Ala
1               5                   10                  15

Ser Ser Ser Thr Ala Val Pro Gln
            20

<210> SEQ ID NO 204
<211> LENGTH: 25
<212> TYPE: PRT
<213> ORGANISM: Escherichia coli

<400> SEQUENCE: 204

Val Tyr Asn Ile Gln Asp Glu Thr Gly Gln Phe Lys Pro Ile Pro Ala
1               5                   10                  15

Ser Thr Phe Ser Thr Ala Val Pro Gln
            20                  25

<210> SEQ ID NO 205
<211> LENGTH: 25
<212> TYPE: PRT
<213> ORGANISM: Escherichia coli

<400> SEQUENCE: 205

Val Tyr Asn Ile Gln Asp Glu Thr Gly Gln Phe Lys Pro Ile Pro Ala
1               5                   10                  15

Ser Thr Ala Ser Thr Ala Val Pro Gln
            20                  25

<210> SEQ ID NO 206
<211> LENGTH: 25
<212> TYPE: PRT
<213> ORGANISM: Escherichia coli

<400> SEQUENCE: 206

Val Tyr Asn Ile Gln Asp Glu Thr Gly Gln Phe Lys Pro Ile Pro Ala
1               5                   10                  15

Ser Thr Gly Ser Thr Ala Val Pro Gln
            20                  25

<210> SEQ ID NO 207
<211> LENGTH: 25
<212> TYPE: PRT
<213> ORGANISM: Escherichia coli

<400> SEQUENCE: 207

Val Tyr Asn Ile Gln Asp Glu Thr Gly Gln Phe Lys Pro Ile Pro Ala
1               5                   10                  15

Ser Thr Val Ser Thr Ala Val Pro Gln
            20                  25

<210> SEQ ID NO 208
<211> LENGTH: 24
<212> TYPE: PRT
<213> ORGANISM: Escherichia coli

<400> SEQUENCE: 208

Val Tyr Asn Ile Gln Asp Glu Thr Gly Gln Phe Lys Pro Ile Pro Ala
1               5                   10                  15

Ser Thr Ser Thr Ala Val Pro Gln
            20

<210> SEQ ID NO 209
<211> LENGTH: 24
<212> TYPE: PRT
<213> ORGANISM: Escherichia coli

<400> SEQUENCE: 209

Val Tyr Asn Ile Gln Asp Glu Thr Gly Gln Phe Lys Pro Ile Pro Ala
1               5                   10                  15

Ser Phe Ser Thr Ala Val Pro Gln
            20

<210> SEQ ID NO 210
<211> LENGTH: 24
<212> TYPE: PRT
<213> ORGANISM: Escherichia coli

<400> SEQUENCE: 210

Val Tyr Asn Ile Gln Asp Glu Thr Gly Gln Phe Lys Pro Ile Pro Ala
1               5                   10                  15

Ser Ala Ser Thr Ala Val Pro Gln
            20

<210> SEQ ID NO 211
<211> LENGTH: 24
<212> TYPE: PRT
<213> ORGANISM: Escherichia coli

<400> SEQUENCE: 211

Val Tyr Asn Ile Gln Asp Glu Thr Gly Gln Phe Lys Pro Ile Pro Ala
1               5                   10                  15

Ser Gly Ser Thr Ala Val Pro Gln
            20

<210> SEQ ID NO 212
<211> LENGTH: 24
<212> TYPE: PRT
<213> ORGANISM: Escherichia coli

<400> SEQUENCE: 212

Val Tyr Asn Ile Gln Asp Glu Thr Gly Gln Phe Lys Pro Ile Pro Ala
1               5                   10                  15

Ser Val Ser Thr Ala Val Pro Gln
            20

<210> SEQ ID NO 213
<211> LENGTH: 23
<212> TYPE: PRT
<213> ORGANISM: Escherichia coli

<400> SEQUENCE: 213

Val Tyr Asn Ile Gln Asp Glu Thr Gly Gln Phe Lys Pro Ile Pro Ala
1               5                   10                  15

Ser Ser Thr Ala Val Pro Gln
            20

<210> SEQ ID NO 214
<211> LENGTH: 25
<212> TYPE: PRT
<213> ORGANISM: Escherichia coli

<400> SEQUENCE: 214

Val Tyr Asn Ile Gln Asp Glu Thr Gly Gln Phe Lys Pro Asn Pro Ala
1               5                   10                  15

Ser Asn Phe Ser Thr Ala Val Pro Gln
            20                  25

<210> SEQ ID NO 215
<211> LENGTH: 25
<212> TYPE: PRT
<213> ORGANISM: Escherichia coli

<400> SEQUENCE: 215

Val Tyr Asn Ile Gln Asp Glu Thr Gly Gln Phe Lys Pro Asn Pro Ala
1               5                   10                  15

Ser Asn Ala Ser Thr Ala Val Pro Gln
            20                  25

<210> SEQ ID NO 216
<211> LENGTH: 25

```
<212> TYPE: PRT
<213> ORGANISM: Escherichia coli

<400> SEQUENCE: 216

Val Tyr Asn Ile Gln Asp Glu Thr Gly Gln Phe Lys Pro Asn Pro Ala
1               5                   10                  15

Ser Asn Gly Ser Thr Ala Val Pro Gln
            20                  25

<210> SEQ ID NO 217
<211> LENGTH: 25
<212> TYPE: PRT
<213> ORGANISM: Escherichia coli

<400> SEQUENCE: 217

Val Tyr Asn Ile Gln Asp Glu Thr Gly Gln Phe Lys Pro Asn Pro Ala
1               5                   10                  15

Ser Asn Val Ser Thr Ala Val Pro Gln
            20                  25

<210> SEQ ID NO 218
<211> LENGTH: 24
<212> TYPE: PRT
<213> ORGANISM: Escherichia coli

<400> SEQUENCE: 218

Val Tyr Asn Ile Gln Asp Glu Thr Gly Gln Phe Lys Pro Asn Pro Ala
1               5                   10                  15

Ser Asn Ser Thr Ala Val Pro Gln
            20

<210> SEQ ID NO 219
<211> LENGTH: 25
<212> TYPE: PRT
<213> ORGANISM: Escherichia coli

<400> SEQUENCE: 219

Val Tyr Asn Ile Gln Asp Glu Thr Gly Gln Phe Lys Pro Asn Pro Ala
1               5                   10                  15

Ser Ala Phe Ser Thr Ala Val Pro Gln
            20                  25

<210> SEQ ID NO 220
<211> LENGTH: 25
<212> TYPE: PRT
<213> ORGANISM: Escherichia coli

<400> SEQUENCE: 220

Val Tyr Asn Ile Gln Asp Glu Thr Gly Gln Phe Lys Pro Asn Pro Ala
1               5                   10                  15

Ser Ala Ala Ser Thr Ala Val Pro Gln
            20                  25

<210> SEQ ID NO 221
<211> LENGTH: 25
<212> TYPE: PRT
<213> ORGANISM: Escherichia coli

<400> SEQUENCE: 221

Val Tyr Asn Ile Gln Asp Glu Thr Gly Gln Phe Lys Pro Asn Pro Ala
1               5                   10                  15

Ser Ala Gly Ser Thr Ala Val Pro Gln
```

<210> SEQ ID NO 222
<211> LENGTH: 25
<212> TYPE: PRT
<213> ORGANISM: Escherichia coli

<400> SEQUENCE: 222

Val Tyr Asn Ile Gln Asp Glu Thr Gly Gln Phe Lys Pro Asn Pro Ala
1               5                   10                  15

Ser Ala Val Ser Thr Ala Val Pro Gln
            20                  25

<210> SEQ ID NO 223
<211> LENGTH: 24
<212> TYPE: PRT
<213> ORGANISM: Escherichia coli

<400> SEQUENCE: 223

Val Tyr Asn Ile Gln Asp Glu Thr Gly Gln Phe Lys Pro Asn Pro Ala
1               5                   10                  15

Ser Ala Ser Thr Ala Val Pro Gln
            20

<210> SEQ ID NO 224
<211> LENGTH: 25
<212> TYPE: PRT
<213> ORGANISM: Escherichia coli

<400> SEQUENCE: 224

Val Tyr Asn Ile Gln Asp Glu Thr Gly Gln Phe Lys Pro Asn Pro Ala
1               5                   10                  15

Ser Gly Phe Ser Thr Ala Val Pro Gln
            20                  25

<210> SEQ ID NO 225
<211> LENGTH: 25
<212> TYPE: PRT
<213> ORGANISM: Escherichia coli

<400> SEQUENCE: 225

Val Tyr Asn Ile Gln Asp Glu Thr Gly Gln Phe Lys Pro Asn Pro Ala
1               5                   10                  15

Ser Gly Ala Ser Thr Ala Val Pro Gln
            20                  25

<210> SEQ ID NO 226
<211> LENGTH: 25
<212> TYPE: PRT
<213> ORGANISM: Escherichia coli

<400> SEQUENCE: 226

Val Tyr Asn Ile Gln Asp Glu Thr Gly Gln Phe Lys Pro Asn Pro Ala
1               5                   10                  15

Ser Gly Gly Ser Thr Ala Val Pro Gln
            20                  25

<210> SEQ ID NO 227
<211> LENGTH: 25
<212> TYPE: PRT
<213> ORGANISM: Escherichia coli

<400> SEQUENCE: 227

Val Tyr Asn Ile Gln Asp Glu Thr Gly Gln Phe Lys Pro Asn Pro Ala
1               5                   10                  15

Ser Gly Val Ser Thr Ala Val Pro Gln
            20                  25

<210> SEQ ID NO 228
<211> LENGTH: 24
<212> TYPE: PRT
<213> ORGANISM: Escherichia coli

<400> SEQUENCE: 228

Val Tyr Asn Ile Gln Asp Glu Thr Gly Gln Phe Lys Pro Asn Pro Ala
1               5                   10                  15

Ser Gly Ser Thr Ala Val Pro Gln
            20

<210> SEQ ID NO 229
<211> LENGTH: 25
<212> TYPE: PRT
<213> ORGANISM: Escherichia coli

<400> SEQUENCE: 229

Val Tyr Asn Ile Gln Asp Glu Thr Gly Gln Phe Lys Pro Asn Pro Ala
1               5                   10                  15

Ser Val Phe Ser Thr Ala Val Pro Gln
            20                  25

<210> SEQ ID NO 230
<211> LENGTH: 25
<212> TYPE: PRT
<213> ORGANISM: Escherichia coli

<400> SEQUENCE: 230

Val Tyr Asn Ile Gln Asp Glu Thr Gly Gln Phe Lys Pro Asn Pro Ala
1               5                   10                  15

Ser Val Ala Ser Thr Ala Val Pro Gln
            20                  25

<210> SEQ ID NO 231
<211> LENGTH: 25
<212> TYPE: PRT
<213> ORGANISM: Escherichia coli

<400> SEQUENCE: 231

Val Tyr Asn Ile Gln Asp Glu Thr Gly Gln Phe Lys Pro Asn Pro Ala
1               5                   10                  15

Ser Val Gly Ser Thr Ala Val Pro Gln
            20                  25

<210> SEQ ID NO 232
<211> LENGTH: 25
<212> TYPE: PRT
<213> ORGANISM: Escherichia coli

<400> SEQUENCE: 232

Val Tyr Asn Ile Gln Asp Glu Thr Gly Gln Phe Lys Pro Asn Pro Ala
1               5                   10                  15

Ser Val Val Ser Thr Ala Val Pro Gln
            20                  25

<210> SEQ ID NO 233

```
<211> LENGTH: 24
<212> TYPE: PRT
<213> ORGANISM: Escherichia coli

<400> SEQUENCE: 233

Val Tyr Asn Ile Gln Asp Glu Thr Gly Gln Phe Lys Pro Asn Pro Ala
1               5                   10                  15

Ser Val Ser Thr Ala Val Pro Gln
            20

<210> SEQ ID NO 234
<211> LENGTH: 25
<212> TYPE: PRT
<213> ORGANISM: Escherichia coli

<400> SEQUENCE: 234

Val Tyr Asn Ile Gln Asp Glu Thr Gly Gln Phe Lys Pro Asn Pro Ala
1               5                   10                  15

Ser Ser Phe Ser Thr Ala Val Pro Gln
            20                  25

<210> SEQ ID NO 235
<211> LENGTH: 25
<212> TYPE: PRT
<213> ORGANISM: Escherichia coli

<400> SEQUENCE: 235

Val Tyr Asn Ile Gln Asp Glu Thr Gly Gln Phe Lys Pro Asn Pro Ala
1               5                   10                  15

Ser Ser Ala Ser Thr Ala Val Pro Gln
            20                  25

<210> SEQ ID NO 236
<211> LENGTH: 25
<212> TYPE: PRT
<213> ORGANISM: Escherichia coli

<400> SEQUENCE: 236

Val Tyr Asn Ile Gln Asp Glu Thr Gly Gln Phe Lys Pro Asn Pro Ala
1               5                   10                  15

Ser Ser Gly Ser Thr Ala Val Pro Gln
            20                  25

<210> SEQ ID NO 237
<211> LENGTH: 25
<212> TYPE: PRT
<213> ORGANISM: Escherichia coli

<400> SEQUENCE: 237

Val Tyr Asn Ile Gln Asp Glu Thr Gly Gln Phe Lys Pro Asn Pro Ala
1               5                   10                  15

Ser Ser Val Ser Thr Ala Val Pro Gln
            20                  25

<210> SEQ ID NO 238
<211> LENGTH: 24
<212> TYPE: PRT
<213> ORGANISM: Escherichia coli

<400> SEQUENCE: 238

Val Tyr Asn Ile Gln Asp Glu Thr Gly Gln Phe Lys Pro Asn Pro Ala
1               5                   10                  15
```

Ser Ser Ser Thr Ala Val Pro Gln
            20

<210> SEQ ID NO 239
<211> LENGTH: 25
<212> TYPE: PRT
<213> ORGANISM: Escherichia coli

<400> SEQUENCE: 239

Val Tyr Asn Ile Gln Asp Glu Thr Gly Gln Phe Lys Pro Asn Pro Ala
1               5                   10                  15

Ser Thr Phe Ser Thr Ala Val Pro Gln
            20                  25

<210> SEQ ID NO 240
<211> LENGTH: 25
<212> TYPE: PRT
<213> ORGANISM: Escherichia coli

<400> SEQUENCE: 240

Val Tyr Asn Ile Gln Asp Glu Thr Gly Gln Phe Lys Pro Asn Pro Ala
1               5                   10                  15

Ser Thr Ala Ser Thr Ala Val Pro Gln
            20                  25

<210> SEQ ID NO 241
<211> LENGTH: 25
<212> TYPE: PRT
<213> ORGANISM: Escherichia coli

<400> SEQUENCE: 241

Val Tyr Asn Ile Gln Asp Glu Thr Gly Gln Phe Lys Pro Asn Pro Ala
1               5                   10                  15

Ser Thr Gly Ser Thr Ala Val Pro Gln
            20                  25

<210> SEQ ID NO 242
<211> LENGTH: 25
<212> TYPE: PRT
<213> ORGANISM: Escherichia coli

<400> SEQUENCE: 242

Val Tyr Asn Ile Gln Asp Glu Thr Gly Gln Phe Lys Pro Asn Pro Ala
1               5                   10                  15

Ser Thr Val Ser Thr Ala Val Pro Gln
            20                  25

<210> SEQ ID NO 243
<211> LENGTH: 24
<212> TYPE: PRT
<213> ORGANISM: Escherichia coli

<400> SEQUENCE: 243

Val Tyr Asn Ile Gln Asp Glu Thr Gly Gln Phe Lys Pro Asn Pro Ala
1               5                   10                  15

Ser Thr Ser Thr Ala Val Pro Gln
            20

<210> SEQ ID NO 244
<211> LENGTH: 24
<212> TYPE: PRT
<213> ORGANISM: Escherichia coli

```
<400> SEQUENCE: 244

Val Tyr Asn Ile Gln Asp Glu Thr Gly Gln Phe Lys Pro Asn Pro Ala
1               5                   10                  15

Ser Phe Ser Thr Ala Val Pro Gln
            20

<210> SEQ ID NO 245
<211> LENGTH: 24
<212> TYPE: PRT
<213> ORGANISM: Escherichia coli

<400> SEQUENCE: 245

Val Tyr Asn Ile Gln Asp Glu Thr Gly Gln Phe Lys Pro Asn Pro Ala
1               5                   10                  15

Ser Ala Ser Thr Ala Val Pro Gln
            20

<210> SEQ ID NO 246
<211> LENGTH: 24
<212> TYPE: PRT
<213> ORGANISM: Escherichia coli

<400> SEQUENCE: 246

Val Tyr Asn Ile Gln Asp Glu Thr Gly Gln Phe Lys Pro Asn Pro Ala
1               5                   10                  15

Ser Gly Ser Thr Ala Val Pro Gln
            20

<210> SEQ ID NO 247
<211> LENGTH: 24
<212> TYPE: PRT
<213> ORGANISM: Escherichia coli

<400> SEQUENCE: 247

Val Tyr Asn Ile Gln Asp Glu Thr Gly Gln Phe Lys Pro Asn Pro Ala
1               5                   10                  15

Ser Val Ser Thr Ala Val Pro Gln
            20

<210> SEQ ID NO 248
<211> LENGTH: 23
<212> TYPE: PRT
<213> ORGANISM: Escherichia coli

<400> SEQUENCE: 248

Val Tyr Asn Ile Gln Asp Glu Thr Gly Gln Phe Lys Pro Asn Pro Ala
1               5                   10                  15

Ser Ser Thr Ala Val Pro Gln
            20

<210> SEQ ID NO 249
<211> LENGTH: 25
<212> TYPE: PRT
<213> ORGANISM: Escherichia coli

<400> SEQUENCE: 249

Val Tyr Asn Ile Gln Asp Glu Thr Gly Gln Phe Lys Pro Gln Pro Ala
1               5                   10                  15

Ser Asn Phe Ser Thr Ala Val Pro Gln
            20                  25
```

-continued

```
<210> SEQ ID NO 250
<211> LENGTH: 25
<212> TYPE: PRT
<213> ORGANISM: Escherichia coli

<400> SEQUENCE: 250

Val Tyr Asn Ile Gln Asp Glu Thr Gly Gln Phe Lys Pro Gln Pro Ala
1               5                   10                  15

Ser Asn Ala Ser Thr Ala Val Pro Gln
            20                  25

<210> SEQ ID NO 251
<211> LENGTH: 25
<212> TYPE: PRT
<213> ORGANISM: Escherichia coli

<400> SEQUENCE: 251

Val Tyr Asn Ile Gln Asp Glu Thr Gly Gln Phe Lys Pro Gln Pro Ala
1               5                   10                  15

Ser Asn Gly Ser Thr Ala Val Pro Gln
            20                  25

<210> SEQ ID NO 252
<211> LENGTH: 25
<212> TYPE: PRT
<213> ORGANISM: Escherichia coli

<400> SEQUENCE: 252

Val Tyr Asn Ile Gln Asp Glu Thr Gly Gln Phe Lys Pro Gln Pro Ala
1               5                   10                  15

Ser Asn Val Ser Thr Ala Val Pro Gln
            20                  25

<210> SEQ ID NO 253
<211> LENGTH: 24
<212> TYPE: PRT
<213> ORGANISM: Escherichia coli

<400> SEQUENCE: 253

Val Tyr Asn Ile Gln Asp Glu Thr Gly Gln Phe Lys Pro Gln Pro Ala
1               5                   10                  15

Ser Asn Ser Thr Ala Val Pro Gln
            20

<210> SEQ ID NO 254
<211> LENGTH: 25
<212> TYPE: PRT
<213> ORGANISM: Escherichia coli

<400> SEQUENCE: 254

Val Tyr Asn Ile Gln Asp Glu Thr Gly Gln Phe Lys Pro Gln Pro Ala
1               5                   10                  15

Ser Ala Phe Ser Thr Ala Val Pro Gln
            20                  25

<210> SEQ ID NO 255
<211> LENGTH: 25
<212> TYPE: PRT
<213> ORGANISM: Escherichia coli

<400> SEQUENCE: 255

Val Tyr Asn Ile Gln Asp Glu Thr Gly Gln Phe Lys Pro Gln Pro Ala
1               5                   10                  15
```

```
Ser Ala Ala Ser Thr Ala Val Pro Gln
            20                  25

<210> SEQ ID NO 256
<211> LENGTH: 25
<212> TYPE: PRT
<213> ORGANISM: Escherichia coli

<400> SEQUENCE: 256

Val Tyr Asn Ile Gln Asp Glu Thr Gly Gln Phe Lys Pro Gln Pro Ala
1               5                   10                  15

Ser Ala Gly Ser Thr Ala Val Pro Gln
            20                  25

<210> SEQ ID NO 257
<211> LENGTH: 25
<212> TYPE: PRT
<213> ORGANISM: Escherichia coli

<400> SEQUENCE: 257

Val Tyr Asn Ile Gln Asp Glu Thr Gly Gln Phe Lys Pro Gln Pro Ala
1               5                   10                  15

Ser Ala Val Ser Thr Ala Val Pro Gln
            20                  25

<210> SEQ ID NO 258
<211> LENGTH: 24
<212> TYPE: PRT
<213> ORGANISM: Escherichia coli

<400> SEQUENCE: 258

Val Tyr Asn Ile Gln Asp Glu Thr Gly Gln Phe Lys Pro Gln Pro Ala
1               5                   10                  15

Ser Ala Ser Thr Ala Val Pro Gln
            20

<210> SEQ ID NO 259
<211> LENGTH: 25
<212> TYPE: PRT
<213> ORGANISM: Escherichia coli

<400> SEQUENCE: 259

Val Tyr Asn Ile Gln Asp Glu Thr Gly Gln Phe Lys Pro Gln Pro Ala
1               5                   10                  15

Ser Gly Phe Ser Thr Ala Val Pro Gln
            20                  25

<210> SEQ ID NO 260
<211> LENGTH: 25
<212> TYPE: PRT
<213> ORGANISM: Escherichia coli

<400> SEQUENCE: 260

Val Tyr Asn Ile Gln Asp Glu Thr Gly Gln Phe Lys Pro Gln Pro Ala
1               5                   10                  15

Ser Gly Ala Ser Thr Ala Val Pro Gln
            20                  25

<210> SEQ ID NO 261
<211> LENGTH: 25
<212> TYPE: PRT
<213> ORGANISM: Escherichia coli
```

<400> SEQUENCE: 261

Val Tyr Asn Ile Gln Asp Glu Thr Gly Gln Phe Lys Pro Gln Pro Ala
1               5                   10                  15

Ser Gly Gly Ser Thr Ala Val Pro Gln
            20                  25

<210> SEQ ID NO 262
<211> LENGTH: 25
<212> TYPE: PRT
<213> ORGANISM: Escherichia coli

<400> SEQUENCE: 262

Val Tyr Asn Ile Gln Asp Glu Thr Gly Gln Phe Lys Pro Gln Pro Ala
1               5                   10                  15

Ser Gly Val Ser Thr Ala Val Pro Gln
            20                  25

<210> SEQ ID NO 263
<211> LENGTH: 24
<212> TYPE: PRT
<213> ORGANISM: Escherichia coli

<400> SEQUENCE: 263

Val Tyr Asn Ile Gln Asp Glu Thr Gly Gln Phe Lys Pro Gln Pro Ala
1               5                   10                  15

Ser Gly Ser Thr Ala Val Pro Gln
            20

<210> SEQ ID NO 264
<211> LENGTH: 25
<212> TYPE: PRT
<213> ORGANISM: Escherichia coli

<400> SEQUENCE: 264

Val Tyr Asn Ile Gln Asp Glu Thr Gly Gln Phe Lys Pro Gln Pro Ala
1               5                   10                  15

Ser Val Phe Ser Thr Ala Val Pro Gln
            20                  25

<210> SEQ ID NO 265
<211> LENGTH: 25
<212> TYPE: PRT
<213> ORGANISM: Escherichia coli

<400> SEQUENCE: 265

Val Tyr Asn Ile Gln Asp Glu Thr Gly Gln Phe Lys Pro Gln Pro Ala
1               5                   10                  15

Ser Val Ala Ser Thr Ala Val Pro Gln
            20                  25

<210> SEQ ID NO 266
<211> LENGTH: 25
<212> TYPE: PRT
<213> ORGANISM: Escherichia coli

<400> SEQUENCE: 266

Val Tyr Asn Ile Gln Asp Glu Thr Gly Gln Phe Lys Pro Gln Pro Ala
1               5                   10                  15

Ser Val Gly Ser Thr Ala Val Pro Gln
            20                  25

<210> SEQ ID NO 267
<211> LENGTH: 25
<212> TYPE: PRT
<213> ORGANISM: Escherichia coli

<400> SEQUENCE: 267

Val Tyr Asn Ile Gln Asp Glu Thr Gly Gln Phe Lys Pro Gln Pro Ala
1               5                   10                  15

Ser Val Val Ser Thr Ala Val Pro Gln
            20                  25

<210> SEQ ID NO 268
<211> LENGTH: 24
<212> TYPE: PRT
<213> ORGANISM: Escherichia coli

<400> SEQUENCE: 268

Val Tyr Asn Ile Gln Asp Glu Thr Gly Gln Phe Lys Pro Gln Pro Ala
1               5                   10                  15

Ser Val Ser Thr Ala Val Pro Gln
            20

<210> SEQ ID NO 269
<211> LENGTH: 25
<212> TYPE: PRT
<213> ORGANISM: Escherichia coli

<400> SEQUENCE: 269

Val Tyr Asn Ile Gln Asp Glu Thr Gly Gln Phe Lys Pro Gln Pro Ala
1               5                   10                  15

Ser Ser Phe Ser Thr Ala Val Pro Gln
            20                  25

<210> SEQ ID NO 270
<211> LENGTH: 25
<212> TYPE: PRT
<213> ORGANISM: Escherichia coli

<400> SEQUENCE: 270

Val Tyr Asn Ile Gln Asp Glu Thr Gly Gln Phe Lys Pro Gln Pro Ala
1               5                   10                  15

Ser Ser Ala Ser Thr Ala Val Pro Gln
            20                  25

<210> SEQ ID NO 271
<211> LENGTH: 25
<212> TYPE: PRT
<213> ORGANISM: Escherichia coli

<400> SEQUENCE: 271

Val Tyr Asn Ile Gln Asp Glu Thr Gly Gln Phe Lys Pro Gln Pro Ala
1               5                   10                  15

Ser Ser Gly Ser Thr Ala Val Pro Gln
            20                  25

<210> SEQ ID NO 272
<211> LENGTH: 25
<212> TYPE: PRT
<213> ORGANISM: Escherichia coli

<400> SEQUENCE: 272

Val Tyr Asn Ile Gln Asp Glu Thr Gly Gln Phe Lys Pro Gln Pro Ala

-continued

```
1               5                   10                  15

Ser Ser Val Ser Thr Ala Val Pro Gln
            20                  25

<210> SEQ ID NO 273
<211> LENGTH: 24
<212> TYPE: PRT
<213> ORGANISM: Escherichia coli

<400> SEQUENCE: 273

Val Tyr Asn Ile Gln Asp Glu Thr Gly Gln Phe Lys Pro Gln Pro Ala
1               5                   10                  15

Ser Ser Ser Thr Ala Val Pro Gln
            20

<210> SEQ ID NO 274
<211> LENGTH: 25
<212> TYPE: PRT
<213> ORGANISM: Escherichia coli

<400> SEQUENCE: 274

Val Tyr Asn Ile Gln Asp Glu Thr Gly Gln Phe Lys Pro Gln Pro Ala
1               5                   10                  15

Ser Thr Phe Ser Thr Ala Val Pro Gln
            20                  25

<210> SEQ ID NO 275
<211> LENGTH: 25
<212> TYPE: PRT
<213> ORGANISM: Escherichia coli

<400> SEQUENCE: 275

Val Tyr Asn Ile Gln Asp Glu Thr Gly Gln Phe Lys Pro Gln Pro Ala
1               5                   10                  15

Ser Thr Ala Ser Thr Ala Val Pro Gln
            20                  25

<210> SEQ ID NO 276
<211> LENGTH: 25
<212> TYPE: PRT
<213> ORGANISM: Escherichia coli

<400> SEQUENCE: 276

Val Tyr Asn Ile Gln Asp Glu Thr Gly Gln Phe Lys Pro Gln Pro Ala
1               5                   10                  15

Ser Thr Gly Ser Thr Ala Val Pro Gln
            20                  25

<210> SEQ ID NO 277
<211> LENGTH: 25
<212> TYPE: PRT
<213> ORGANISM: Escherichia coli

<400> SEQUENCE: 277

Val Tyr Asn Ile Gln Asp Glu Thr Gly Gln Phe Lys Pro Gln Pro Ala
1               5                   10                  15

Ser Thr Val Ser Thr Ala Val Pro Gln
            20                  25

<210> SEQ ID NO 278
<211> LENGTH: 24
<212> TYPE: PRT
```

<213> ORGANISM: Escherichia coli

<400> SEQUENCE: 278

Val Tyr Asn Ile Gln Asp Glu Thr Gly Gln Phe Lys Pro Gln Pro Ala
1               5                   10                  15

Ser Thr Ser Thr Ala Val Pro Gln
            20

<210> SEQ ID NO 279
<211> LENGTH: 24
<212> TYPE: PRT
<213> ORGANISM: Escherichia coli

<400> SEQUENCE: 279

Val Tyr Asn Ile Gln Asp Glu Thr Gly Gln Phe Lys Pro Gln Pro Ala
1               5                   10                  15

Ser Phe Ser Thr Ala Val Pro Gln
            20

<210> SEQ ID NO 280
<211> LENGTH: 24
<212> TYPE: PRT
<213> ORGANISM: Escherichia coli

<400> SEQUENCE: 280

Val Tyr Asn Ile Gln Asp Glu Thr Gly Gln Phe Lys Pro Gln Pro Ala
1               5                   10                  15

Ser Ala Ser Thr Ala Val Pro Gln
            20

<210> SEQ ID NO 281
<211> LENGTH: 24
<212> TYPE: PRT
<213> ORGANISM: Escherichia coli

<400> SEQUENCE: 281

Val Tyr Asn Ile Gln Asp Glu Thr Gly Gln Phe Lys Pro Gln Pro Ala
1               5                   10                  15

Ser Gly Ser Thr Ala Val Pro Gln
            20

<210> SEQ ID NO 282
<211> LENGTH: 24
<212> TYPE: PRT
<213> ORGANISM: Escherichia coli

<400> SEQUENCE: 282

Val Tyr Asn Ile Gln Asp Glu Thr Gly Gln Phe Lys Pro Gln Pro Ala
1               5                   10                  15

Ser Val Ser Thr Ala Val Pro Gln
            20

<210> SEQ ID NO 283
<211> LENGTH: 23
<212> TYPE: PRT
<213> ORGANISM: Escherichia coli

<400> SEQUENCE: 283

Val Tyr Asn Ile Gln Asp Glu Thr Gly Gln Phe Lys Pro Gln Pro Ala
1               5                   10                  15

Ser Ser Thr Ala Val Pro Gln
            20

<210> SEQ ID NO 284
<211> LENGTH: 25
<212> TYPE: PRT
<213> ORGANISM: Escherichia coli

<400> SEQUENCE: 284

Val Tyr Asn Ile Gln Asp Glu Thr Gly Gln Phe Lys Pro Phe Pro Ala
1               5                   10                  15

Ser Asn Phe Ser Thr Ala Val Pro Gln
            20                  25

<210> SEQ ID NO 285
<211> LENGTH: 25
<212> TYPE: PRT
<213> ORGANISM: Escherichia coli

<400> SEQUENCE: 285

Val Tyr Asn Ile Gln Asp Glu Thr Gly Gln Phe Lys Pro Phe Pro Ala
1               5                   10                  15

Ser Asn Ala Ser Thr Ala Val Pro Gln
            20                  25

<210> SEQ ID NO 286
<211> LENGTH: 25
<212> TYPE: PRT
<213> ORGANISM: Escherichia coli

<400> SEQUENCE: 286

Val Tyr Asn Ile Gln Asp Glu Thr Gly Gln Phe Lys Pro Phe Pro Ala
1               5                   10                  15

Ser Asn Gly Ser Thr Ala Val Pro Gln
            20                  25

<210> SEQ ID NO 287
<211> LENGTH: 25
<212> TYPE: PRT
<213> ORGANISM: Escherichia coli

<400> SEQUENCE: 287

Val Tyr Asn Ile Gln Asp Glu Thr Gly Gln Phe Lys Pro Phe Pro Ala
1               5                   10                  15

Ser Asn Val Ser Thr Ala Val Pro Gln
            20                  25

<210> SEQ ID NO 288
<211> LENGTH: 24
<212> TYPE: PRT
<213> ORGANISM: Escherichia coli

<400> SEQUENCE: 288

Val Tyr Asn Ile Gln Asp Glu Thr Gly Gln Phe Lys Pro Phe Pro Ala
1               5                   10                  15

Ser Asn Ser Thr Ala Val Pro Gln
            20

<210> SEQ ID NO 289
<211> LENGTH: 25
<212> TYPE: PRT
<213> ORGANISM: Escherichia coli

<400> SEQUENCE: 289

-continued

Val Tyr Asn Ile Gln Asp Glu Thr Gly Gln Phe Lys Pro Phe Pro Ala
1               5                   10                  15

Ser Ala Phe Ser Thr Ala Val Pro Gln
            20                  25

<210> SEQ ID NO 290
<211> LENGTH: 25
<212> TYPE: PRT
<213> ORGANISM: Escherichia coli

<400> SEQUENCE: 290

Val Tyr Asn Ile Gln Asp Glu Thr Gly Gln Phe Lys Pro Phe Pro Ala
1               5                   10                  15

Ser Ala Ala Ser Thr Ala Val Pro Gln
            20                  25

<210> SEQ ID NO 291
<211> LENGTH: 25
<212> TYPE: PRT
<213> ORGANISM: Escherichia coli

<400> SEQUENCE: 291

Val Tyr Asn Ile Gln Asp Glu Thr Gly Gln Phe Lys Pro Phe Pro Ala
1               5                   10                  15

Ser Ala Gly Ser Thr Ala Val Pro Gln
            20                  25

<210> SEQ ID NO 292
<211> LENGTH: 25
<212> TYPE: PRT
<213> ORGANISM: Escherichia coli

<400> SEQUENCE: 292

Val Tyr Asn Ile Gln Asp Glu Thr Gly Gln Phe Lys Pro Phe Pro Ala
1               5                   10                  15

Ser Ala Val Ser Thr Ala Val Pro Gln
            20                  25

<210> SEQ ID NO 293
<211> LENGTH: 24
<212> TYPE: PRT
<213> ORGANISM: Escherichia coli

<400> SEQUENCE: 293

Val Tyr Asn Ile Gln Asp Glu Thr Gly Gln Phe Lys Pro Phe Pro Ala
1               5                   10                  15

Ser Ala Ser Thr Ala Val Pro Gln
            20

<210> SEQ ID NO 294
<211> LENGTH: 25
<212> TYPE: PRT
<213> ORGANISM: Escherichia coli

<400> SEQUENCE: 294

Val Tyr Asn Ile Gln Asp Glu Thr Gly Gln Phe Lys Pro Phe Pro Ala
1               5                   10                  15

Ser Gly Phe Ser Thr Ala Val Pro Gln
            20                  25

<210> SEQ ID NO 295
<211> LENGTH: 25

```
<212> TYPE: PRT
<213> ORGANISM: Escherichia coli

<400> SEQUENCE: 295

Val Tyr Asn Ile Gln Asp Glu Thr Gly Gln Phe Lys Pro Phe Pro Ala
1               5                   10                  15
Ser Gly Ala Ser Thr Ala Val Pro Gln
            20                  25

<210> SEQ ID NO 296
<211> LENGTH: 25
<212> TYPE: PRT
<213> ORGANISM: Escherichia coli

<400> SEQUENCE: 296

Val Tyr Asn Ile Gln Asp Glu Thr Gly Gln Phe Lys Pro Phe Pro Ala
1               5                   10                  15
Ser Gly Gly Ser Thr Ala Val Pro Gln
            20                  25

<210> SEQ ID NO 297
<211> LENGTH: 25
<212> TYPE: PRT
<213> ORGANISM: Escherichia coli

<400> SEQUENCE: 297

Val Tyr Asn Ile Gln Asp Glu Thr Gly Gln Phe Lys Pro Phe Pro Ala
1               5                   10                  15
Ser Gly Val Ser Thr Ala Val Pro Gln
            20                  25

<210> SEQ ID NO 298
<211> LENGTH: 24
<212> TYPE: PRT
<213> ORGANISM: Escherichia coli

<400> SEQUENCE: 298

Val Tyr Asn Ile Gln Asp Glu Thr Gly Gln Phe Lys Pro Phe Pro Ala
1               5                   10                  15
Ser Gly Ser Thr Ala Val Pro Gln
            20

<210> SEQ ID NO 299
<211> LENGTH: 25
<212> TYPE: PRT
<213> ORGANISM: Escherichia coli

<400> SEQUENCE: 299

Val Tyr Asn Ile Gln Asp Glu Thr Gly Gln Phe Lys Pro Phe Pro Ala
1               5                   10                  15
Ser Val Phe Ser Thr Ala Val Pro Gln
            20                  25

<210> SEQ ID NO 300
<211> LENGTH: 25
<212> TYPE: PRT
<213> ORGANISM: Escherichia coli

<400> SEQUENCE: 300

Val Tyr Asn Ile Gln Asp Glu Thr Gly Gln Phe Lys Pro Phe Pro Ala
1               5                   10                  15
Ser Val Ala Ser Thr Ala Val Pro Gln
```

<210> SEQ ID NO 301
<211> LENGTH: 25
<212> TYPE: PRT
<213> ORGANISM: Escherichia coli

<400> SEQUENCE: 301

Val Tyr Asn Ile Gln Asp Glu Thr Gly Gln Phe Lys Pro Phe Pro Ala
1               5                   10                  15

Ser Val Gly Ser Thr Ala Val Pro Gln
            20                  25

<210> SEQ ID NO 302
<211> LENGTH: 25
<212> TYPE: PRT
<213> ORGANISM: Escherichia coli

<400> SEQUENCE: 302

Val Tyr Asn Ile Gln Asp Glu Thr Gly Gln Phe Lys Pro Phe Pro Ala
1               5                   10                  15

Ser Val Val Ser Thr Ala Val Pro Gln
            20                  25

<210> SEQ ID NO 303
<211> LENGTH: 24
<212> TYPE: PRT
<213> ORGANISM: Escherichia coli

<400> SEQUENCE: 303

Val Tyr Asn Ile Gln Asp Glu Thr Gly Gln Phe Lys Pro Phe Pro Ala
1               5                   10                  15

Ser Val Ser Thr Ala Val Pro Gln
            20

<210> SEQ ID NO 304
<211> LENGTH: 25
<212> TYPE: PRT
<213> ORGANISM: Escherichia coli

<400> SEQUENCE: 304

Val Tyr Asn Ile Gln Asp Glu Thr Gly Gln Phe Lys Pro Phe Pro Ala
1               5                   10                  15

Ser Ser Phe Ser Thr Ala Val Pro Gln
            20                  25

<210> SEQ ID NO 305
<211> LENGTH: 25
<212> TYPE: PRT
<213> ORGANISM: Escherichia coli

<400> SEQUENCE: 305

Val Tyr Asn Ile Gln Asp Glu Thr Gly Gln Phe Lys Pro Phe Pro Ala
1               5                   10                  15

Ser Ser Ala Ser Thr Ala Val Pro Gln
            20                  25

<210> SEQ ID NO 306
<211> LENGTH: 25
<212> TYPE: PRT
<213> ORGANISM: Escherichia coli

<400> SEQUENCE: 306

-continued

Val Tyr Asn Ile Gln Asp Glu Thr Gly Gln Phe Lys Pro Phe Pro Ala
1               5                   10                  15

Ser Ser Gly Ser Thr Ala Val Pro Gln
            20                  25

<210> SEQ ID NO 307
<211> LENGTH: 25
<212> TYPE: PRT
<213> ORGANISM: Escherichia coli

<400> SEQUENCE: 307

Val Tyr Asn Ile Gln Asp Glu Thr Gly Gln Phe Lys Pro Phe Pro Ala
1               5                   10                  15

Ser Ser Val Ser Thr Ala Val Pro Gln
            20                  25

<210> SEQ ID NO 308
<211> LENGTH: 24
<212> TYPE: PRT
<213> ORGANISM: Escherichia coli

<400> SEQUENCE: 308

Val Tyr Asn Ile Gln Asp Glu Thr Gly Gln Phe Lys Pro Phe Pro Ala
1               5                   10                  15

Ser Ser Ser Thr Ala Val Pro Gln
            20

<210> SEQ ID NO 309
<211> LENGTH: 25
<212> TYPE: PRT
<213> ORGANISM: Escherichia coli

<400> SEQUENCE: 309

Val Tyr Asn Ile Gln Asp Glu Thr Gly Gln Phe Lys Pro Phe Pro Ala
1               5                   10                  15

Ser Thr Phe Ser Thr Ala Val Pro Gln
            20                  25

<210> SEQ ID NO 310
<211> LENGTH: 25
<212> TYPE: PRT
<213> ORGANISM: Escherichia coli

<400> SEQUENCE: 310

Val Tyr Asn Ile Gln Asp Glu Thr Gly Gln Phe Lys Pro Phe Pro Ala
1               5                   10                  15

Ser Thr Ala Ser Thr Ala Val Pro Gln
            20                  25

<210> SEQ ID NO 311
<211> LENGTH: 25
<212> TYPE: PRT
<213> ORGANISM: Escherichia coli

<400> SEQUENCE: 311

Val Tyr Asn Ile Gln Asp Glu Thr Gly Gln Phe Lys Pro Phe Pro Ala
1               5                   10                  15

Ser Thr Gly Ser Thr Ala Val Pro Gln
            20                  25

<210> SEQ ID NO 312

<211> LENGTH: 25
<212> TYPE: PRT
<213> ORGANISM: Escherichia coli

<400> SEQUENCE: 312

Val Tyr Asn Ile Gln Asp Glu Thr Gly Gln Phe Lys Pro Phe Pro Ala
1               5                   10                  15

Ser Thr Val Ser Thr Ala Val Pro Gln
            20                  25

<210> SEQ ID NO 313
<211> LENGTH: 24
<212> TYPE: PRT
<213> ORGANISM: Escherichia coli

<400> SEQUENCE: 313

Val Tyr Asn Ile Gln Asp Glu Thr Gly Gln Phe Lys Pro Phe Pro Ala
1               5                   10                  15

Ser Thr Ser Thr Ala Val Pro Gln
            20

<210> SEQ ID NO 314
<211> LENGTH: 24
<212> TYPE: PRT
<213> ORGANISM: Escherichia coli

<400> SEQUENCE: 314

Val Tyr Asn Ile Gln Asp Glu Thr Gly Gln Phe Lys Pro Phe Pro Ala
1               5                   10                  15

Ser Phe Ser Thr Ala Val Pro Gln
            20

<210> SEQ ID NO 315
<211> LENGTH: 24
<212> TYPE: PRT
<213> ORGANISM: Escherichia coli

<400> SEQUENCE: 315

Val Tyr Asn Ile Gln Asp Glu Thr Gly Gln Phe Lys Pro Phe Pro Ala
1               5                   10                  15

Ser Ala Ser Thr Ala Val Pro Gln
            20

<210> SEQ ID NO 316
<211> LENGTH: 24
<212> TYPE: PRT
<213> ORGANISM: Escherichia coli

<400> SEQUENCE: 316

Val Tyr Asn Ile Gln Asp Glu Thr Gly Gln Phe Lys Pro Phe Pro Ala
1               5                   10                  15

Ser Gly Ser Thr Ala Val Pro Gln
            20

<210> SEQ ID NO 317
<211> LENGTH: 24
<212> TYPE: PRT
<213> ORGANISM: Escherichia coli

<400> SEQUENCE: 317

Val Tyr Asn Ile Gln Asp Glu Thr Gly Gln Phe Lys Pro Phe Pro Ala
1               5                   10                  15

```
Ser Val Ser Thr Ala Val Pro Gln
            20

<210> SEQ ID NO 318
<211> LENGTH: 23
<212> TYPE: PRT
<213> ORGANISM: Escherichia coli

<400> SEQUENCE: 318

Val Tyr Asn Ile Gln Asp Glu Thr Gly Gln Phe Lys Pro Phe Pro Ala
1               5                   10                  15

Ser Ser Thr Ala Val Pro Gln
            20

<210> SEQ ID NO 319
<211> LENGTH: 24
<212> TYPE: PRT
<213> ORGANISM: Escherichia coli

<400> SEQUENCE: 319

Val Tyr Asn Ile Gln Asp Glu Thr Gly Gln Phe Lys Pro Pro Ala Ser
1               5                   10                  15

Asn Phe Ser Thr Ala Val Pro Gln
            20

<210> SEQ ID NO 320
<211> LENGTH: 24
<212> TYPE: PRT
<213> ORGANISM: Escherichia coli

<400> SEQUENCE: 320

Val Tyr Asn Ile Gln Asp Glu Thr Gly Gln Phe Lys Pro Pro Ala Ser
1               5                   10                  15

Asn Ala Ser Thr Ala Val Pro Gln
            20

<210> SEQ ID NO 321
<211> LENGTH: 24
<212> TYPE: PRT
<213> ORGANISM: Escherichia coli

<400> SEQUENCE: 321

Val Tyr Asn Ile Gln Asp Glu Thr Gly Gln Phe Lys Pro Pro Ala Ser
1               5                   10                  15

Asn Gly Ser Thr Ala Val Pro Gln
            20

<210> SEQ ID NO 322
<211> LENGTH: 24
<212> TYPE: PRT
<213> ORGANISM: Escherichia coli

<400> SEQUENCE: 322

Val Tyr Asn Ile Gln Asp Glu Thr Gly Gln Phe Lys Pro Pro Ala Ser
1               5                   10                  15

Asn Val Ser Thr Ala Val Pro Gln
            20

<210> SEQ ID NO 323
<211> LENGTH: 23
<212> TYPE: PRT
<213> ORGANISM: Escherichia coli
```

```
<400> SEQUENCE: 323

Val Tyr Asn Ile Gln Asp Glu Thr Gly Gln Phe Lys Pro Pro Ala Ser
1               5                   10                  15

Asn Ser Thr Ala Val Pro Gln
            20

<210> SEQ ID NO 324
<211> LENGTH: 24
<212> TYPE: PRT
<213> ORGANISM: Escherichia coli

<400> SEQUENCE: 324

Val Tyr Asn Ile Gln Asp Glu Thr Gly Gln Phe Lys Pro Pro Ala Ser
1               5                   10                  15

Ala Phe Ser Thr Ala Val Pro Gln
            20

<210> SEQ ID NO 325
<211> LENGTH: 24
<212> TYPE: PRT
<213> ORGANISM: Escherichia coli

<400> SEQUENCE: 325

Val Tyr Asn Ile Gln Asp Glu Thr Gly Gln Phe Lys Pro Pro Ala Ser
1               5                   10                  15

Ala Ala Ser Thr Ala Val Pro Gln
            20

<210> SEQ ID NO 326
<211> LENGTH: 24
<212> TYPE: PRT
<213> ORGANISM: Escherichia coli

<400> SEQUENCE: 326

Val Tyr Asn Ile Gln Asp Glu Thr Gly Gln Phe Lys Pro Pro Ala Ser
1               5                   10                  15

Ala Gly Ser Thr Ala Val Pro Gln
            20

<210> SEQ ID NO 327
<211> LENGTH: 24
<212> TYPE: PRT
<213> ORGANISM: Escherichia coli

<400> SEQUENCE: 327

Val Tyr Asn Ile Gln Asp Glu Thr Gly Gln Phe Lys Pro Pro Ala Ser
1               5                   10                  15

Ala Val Ser Thr Ala Val Pro Gln
            20

<210> SEQ ID NO 328
<211> LENGTH: 23
<212> TYPE: PRT
<213> ORGANISM: Escherichia coli

<400> SEQUENCE: 328

Val Tyr Asn Ile Gln Asp Glu Thr Gly Gln Phe Lys Pro Pro Ala Ser
1               5                   10                  15

Ala Ser Thr Ala Val Pro Gln
            20
```

-continued

<210> SEQ ID NO 329
<211> LENGTH: 24
<212> TYPE: PRT
<213> ORGANISM: Escherichia coli

<400> SEQUENCE: 329

Val Tyr Asn Ile Gln Asp Glu Thr Gly Gln Phe Lys Pro Pro Ala Ser
1               5                   10                  15

Gly Phe Ser Thr Ala Val Pro Gln
            20

<210> SEQ ID NO 330
<211> LENGTH: 24
<212> TYPE: PRT
<213> ORGANISM: Escherichia coli

<400> SEQUENCE: 330

Val Tyr Asn Ile Gln Asp Glu Thr Gly Gln Phe Lys Pro Pro Ala Ser
1               5                   10                  15

Gly Ala Ser Thr Ala Val Pro Gln
            20

<210> SEQ ID NO 331
<211> LENGTH: 24
<212> TYPE: PRT
<213> ORGANISM: Escherichia coli

<400> SEQUENCE: 331

Val Tyr Asn Ile Gln Asp Glu Thr Gly Gln Phe Lys Pro Pro Ala Ser
1               5                   10                  15

Gly Gly Ser Thr Ala Val Pro Gln
            20

<210> SEQ ID NO 332
<211> LENGTH: 24
<212> TYPE: PRT
<213> ORGANISM: Escherichia coli

<400> SEQUENCE: 332

Val Tyr Asn Ile Gln Asp Glu Thr Gly Gln Phe Lys Pro Pro Ala Ser
1               5                   10                  15

Gly Val Ser Thr Ala Val Pro Gln
            20

<210> SEQ ID NO 333
<211> LENGTH: 23
<212> TYPE: PRT
<213> ORGANISM: Escherichia coli

<400> SEQUENCE: 333

Val Tyr Asn Ile Gln Asp Glu Thr Gly Gln Phe Lys Pro Pro Ala Ser
1               5                   10                  15

Gly Ser Thr Ala Val Pro Gln
            20

<210> SEQ ID NO 334
<211> LENGTH: 24
<212> TYPE: PRT
<213> ORGANISM: Escherichia coli

<400> SEQUENCE: 334

Val Tyr Asn Ile Gln Asp Glu Thr Gly Gln Phe Lys Pro Pro Ala Ser
1               5                   10                  15

```
Val Phe Ser Thr Ala Val Pro Gln
            20

<210> SEQ ID NO 335
<211> LENGTH: 24
<212> TYPE: PRT
<213> ORGANISM: Escherichia coli

<400> SEQUENCE: 335

Val Tyr Asn Ile Gln Asp Glu Thr Gly Gln Phe Lys Pro Pro Ala Ser
1               5                   10                  15

Val Ala Ser Thr Ala Val Pro Gln
            20

<210> SEQ ID NO 336
<211> LENGTH: 24
<212> TYPE: PRT
<213> ORGANISM: Escherichia coli

<400> SEQUENCE: 336

Val Tyr Asn Ile Gln Asp Glu Thr Gly Gln Phe Lys Pro Pro Ala Ser
1               5                   10                  15

Val Gly Ser Thr Ala Val Pro Gln
            20

<210> SEQ ID NO 337
<211> LENGTH: 24
<212> TYPE: PRT
<213> ORGANISM: Escherichia coli

<400> SEQUENCE: 337

Val Tyr Asn Ile Gln Asp Glu Thr Gly Gln Phe Lys Pro Pro Ala Ser
1               5                   10                  15

Val Val Ser Thr Ala Val Pro Gln
            20

<210> SEQ ID NO 338
<211> LENGTH: 23
<212> TYPE: PRT
<213> ORGANISM: Escherichia coli

<400> SEQUENCE: 338

Val Tyr Asn Ile Gln Asp Glu Thr Gly Gln Phe Lys Pro Pro Ala Ser
1               5                   10                  15

Val Ser Thr Ala Val Pro Gln
            20

<210> SEQ ID NO 339
<211> LENGTH: 24
<212> TYPE: PRT
<213> ORGANISM: Escherichia coli

<400> SEQUENCE: 339

Val Tyr Asn Ile Gln Asp Glu Thr Gly Gln Phe Lys Pro Pro Ala Ser
1               5                   10                  15

Ser Phe Ser Thr Ala Val Pro Gln
            20

<210> SEQ ID NO 340
<211> LENGTH: 24
<212> TYPE: PRT
<213> ORGANISM: Escherichia coli
```

-continued

```
<400> SEQUENCE: 340

Val Tyr Asn Ile Gln Asp Glu Thr Gly Gln Phe Lys Pro Pro Ala Ser
1               5                   10                  15

Ser Ala Ser Thr Ala Val Pro Gln
            20

<210> SEQ ID NO 341
<211> LENGTH: 24
<212> TYPE: PRT
<213> ORGANISM: Escherichia coli

<400> SEQUENCE: 341

Val Tyr Asn Ile Gln Asp Glu Thr Gly Gln Phe Lys Pro Pro Ala Ser
1               5                   10                  15

Ser Gly Ser Thr Ala Val Pro Gln
            20

<210> SEQ ID NO 342
<211> LENGTH: 24
<212> TYPE: PRT
<213> ORGANISM: Escherichia coli

<400> SEQUENCE: 342

Val Tyr Asn Ile Gln Asp Glu Thr Gly Gln Phe Lys Pro Pro Ala Ser
1               5                   10                  15

Ser Val Ser Thr Ala Val Pro Gln
            20

<210> SEQ ID NO 343
<211> LENGTH: 23
<212> TYPE: PRT
<213> ORGANISM: Escherichia coli

<400> SEQUENCE: 343

Val Tyr Asn Ile Gln Asp Glu Thr Gly Gln Phe Lys Pro Pro Ala Ser
1               5                   10                  15

Ser Ser Thr Ala Val Pro Gln
            20

<210> SEQ ID NO 344
<211> LENGTH: 24
<212> TYPE: PRT
<213> ORGANISM: Escherichia coli

<400> SEQUENCE: 344

Val Tyr Asn Ile Gln Asp Glu Thr Gly Gln Phe Lys Pro Pro Ala Ser
1               5                   10                  15

Thr Phe Ser Thr Ala Val Pro Gln
            20

<210> SEQ ID NO 345
<211> LENGTH: 24
<212> TYPE: PRT
<213> ORGANISM: Escherichia coli

<400> SEQUENCE: 345

Val Tyr Asn Ile Gln Asp Glu Thr Gly Gln Phe Lys Pro Pro Ala Ser
1               5                   10                  15

Thr Ala Ser Thr Ala Val Pro Gln
            20
```

<210> SEQ ID NO 346
<211> LENGTH: 24
<212> TYPE: PRT
<213> ORGANISM: Escherichia coli

<400> SEQUENCE: 346

Val Tyr Asn Ile Gln Asp Glu Thr Gly Gln Phe Lys Pro Pro Ala Ser
1               5                   10                  15

Thr Gly Ser Thr Ala Val Pro Gln
            20

<210> SEQ ID NO 347
<211> LENGTH: 24
<212> TYPE: PRT
<213> ORGANISM: Escherichia coli

<400> SEQUENCE: 347

Val Tyr Asn Ile Gln Asp Glu Thr Gly Gln Phe Lys Pro Pro Ala Ser
1               5                   10                  15

Thr Val Ser Thr Ala Val Pro Gln
            20

<210> SEQ ID NO 348
<211> LENGTH: 23
<212> TYPE: PRT
<213> ORGANISM: Escherichia coli

<400> SEQUENCE: 348

Val Tyr Asn Ile Gln Asp Glu Thr Gly Gln Phe Lys Pro Pro Ala Ser
1               5                   10                  15

Thr Ser Thr Ala Val Pro Gln
            20

<210> SEQ ID NO 349
<211> LENGTH: 23
<212> TYPE: PRT
<213> ORGANISM: Escherichia coli

<400> SEQUENCE: 349

Val Tyr Asn Ile Gln Asp Glu Thr Gly Gln Phe Lys Pro Pro Ala Ser
1               5                   10                  15

Phe Ser Thr Ala Val Pro Gln
            20

<210> SEQ ID NO 350
<211> LENGTH: 23
<212> TYPE: PRT
<213> ORGANISM: Escherichia coli

<400> SEQUENCE: 350

Val Tyr Asn Ile Gln Asp Glu Thr Gly Gln Phe Lys Pro Pro Ala Ser
1               5                   10                  15

Ala Ser Thr Ala Val Pro Gln
            20

<210> SEQ ID NO 351
<211> LENGTH: 23
<212> TYPE: PRT
<213> ORGANISM: Escherichia coli

<400> SEQUENCE: 351

Val Tyr Asn Ile Gln Asp Glu Thr Gly Gln Phe Lys Pro Pro Ala Ser

-continued

```
                1               5                  10                 15
Gly Ser Thr Ala Val Pro Gln
            20

<210> SEQ ID NO 352
<211> LENGTH: 23
<212> TYPE: PRT
<213> ORGANISM: Escherichia coli

<400> SEQUENCE: 352

Val Tyr Asn Ile Gln Asp Glu Thr Gly Gln Phe Lys Pro Pro Ala Ser
1               5                  10                 15

Val Ser Thr Ala Val Pro Gln
            20

<210> SEQ ID NO 353
<211> LENGTH: 22
<212> TYPE: PRT
<213> ORGANISM: Escherichia coli

<400> SEQUENCE: 353

Val Tyr Asn Ile Gln Asp Glu Thr Gly Gln Phe Lys Pro Pro Ala Ser
1               5                  10                 15

Ser Thr Ala Val Pro Gln
            20

<210> SEQ ID NO 354
<211> LENGTH: 23
<212> TYPE: PRT
<213> ORGANISM: Escherichia coli

<400> SEQUENCE: 354

Val Tyr Asn Ile Gln Asp Glu Thr Gly Gln Phe Lys Gly Gly Ser Asn
1               5                  10                 15

Phe Ser Thr Ala Val Pro Gln
            20

<210> SEQ ID NO 355
<211> LENGTH: 23
<212> TYPE: PRT
<213> ORGANISM: Escherichia coli

<400> SEQUENCE: 355

Val Tyr Asn Ile Gln Asp Glu Thr Gly Gln Phe Lys Gly Gly Ser Asn
1               5                  10                 15

Ala Ser Thr Ala Val Pro Gln
            20

<210> SEQ ID NO 356
<211> LENGTH: 23
<212> TYPE: PRT
<213> ORGANISM: Escherichia coli

<400> SEQUENCE: 356

Val Tyr Asn Ile Gln Asp Glu Thr Gly Gln Phe Lys Gly Gly Ser Asn
1               5                  10                 15

Gly Ser Thr Ala Val Pro Gln
            20

<210> SEQ ID NO 357
<211> LENGTH: 23
<212> TYPE: PRT
```

<213> ORGANISM: Escherichia coli

<400> SEQUENCE: 357

Val Tyr Asn Ile Gln Asp Glu Thr Gly Gln Phe Lys Gly Gly Ser Asn
1               5                   10                  15

Val Ser Thr Ala Val Pro Gln
            20

<210> SEQ ID NO 358
<211> LENGTH: 22
<212> TYPE: PRT
<213> ORGANISM: Escherichia coli

<400> SEQUENCE: 358

Val Tyr Asn Ile Gln Asp Glu Thr Gly Gln Phe Lys Gly Gly Ser Asn
1               5                   10                  15

Ser Thr Ala Val Pro Gln
            20

<210> SEQ ID NO 359
<211> LENGTH: 23
<212> TYPE: PRT
<213> ORGANISM: Escherichia coli

<400> SEQUENCE: 359

Val Tyr Asn Ile Gln Asp Glu Thr Gly Gln Phe Lys Gly Gly Ser Ala
1               5                   10                  15

Phe Ser Thr Ala Val Pro Gln
            20

<210> SEQ ID NO 360
<211> LENGTH: 23
<212> TYPE: PRT
<213> ORGANISM: Escherichia coli

<400> SEQUENCE: 360

Val Tyr Asn Ile Gln Asp Glu Thr Gly Gln Phe Lys Gly Gly Ser Ala
1               5                   10                  15

Ala Ser Thr Ala Val Pro Gln
            20

<210> SEQ ID NO 361
<211> LENGTH: 23
<212> TYPE: PRT
<213> ORGANISM: Escherichia coli

<400> SEQUENCE: 361

Val Tyr Asn Ile Gln Asp Glu Thr Gly Gln Phe Lys Gly Gly Ser Ala
1               5                   10                  15

Gly Ser Thr Ala Val Pro Gln
            20

<210> SEQ ID NO 362
<211> LENGTH: 23
<212> TYPE: PRT
<213> ORGANISM: Escherichia coli

<400> SEQUENCE: 362

Val Tyr Asn Ile Gln Asp Glu Thr Gly Gln Phe Lys Gly Gly Ser Ala
1               5                   10                  15

Val Ser Thr Ala Val Pro Gln
            20

<210> SEQ ID NO 363
<211> LENGTH: 22
<212> TYPE: PRT
<213> ORGANISM: Escherichia coli

<400> SEQUENCE: 363

Val Tyr Asn Ile Gln Asp Glu Thr Gly Gln Phe Lys Gly Gly Ser Ala
1               5                   10                  15

Ser Thr Ala Val Pro Gln
            20

<210> SEQ ID NO 364
<211> LENGTH: 23
<212> TYPE: PRT
<213> ORGANISM: Escherichia coli

<400> SEQUENCE: 364

Val Tyr Asn Ile Gln Asp Glu Thr Gly Gln Phe Lys Gly Gly Ser Gly
1               5                   10                  15

Phe Ser Thr Ala Val Pro Gln
            20

<210> SEQ ID NO 365
<211> LENGTH: 23
<212> TYPE: PRT
<213> ORGANISM: Escherichia coli

<400> SEQUENCE: 365

Val Tyr Asn Ile Gln Asp Glu Thr Gly Gln Phe Lys Gly Gly Ser Gly
1               5                   10                  15

Ala Ser Thr Ala Val Pro Gln
            20

<210> SEQ ID NO 366
<211> LENGTH: 23
<212> TYPE: PRT
<213> ORGANISM: Escherichia coli

<400> SEQUENCE: 366

Val Tyr Asn Ile Gln Asp Glu Thr Gly Gln Phe Lys Gly Gly Ser Gly
1               5                   10                  15

Gly Ser Thr Ala Val Pro Gln
            20

<210> SEQ ID NO 367
<211> LENGTH: 23
<212> TYPE: PRT
<213> ORGANISM: Escherichia coli

<400> SEQUENCE: 367

Val Tyr Asn Ile Gln Asp Glu Thr Gly Gln Phe Lys Gly Gly Ser Gly
1               5                   10                  15

Val Ser Thr Ala Val Pro Gln
            20

<210> SEQ ID NO 368
<211> LENGTH: 22
<212> TYPE: PRT
<213> ORGANISM: Escherichia coli

<400> SEQUENCE: 368

Val Tyr Asn Ile Gln Asp Glu Thr Gly Gln Phe Lys Gly Gly Ser Gly
1               5                   10                  15

Ser Thr Ala Val Pro Gln
            20

<210> SEQ ID NO 369
<211> LENGTH: 23
<212> TYPE: PRT
<213> ORGANISM: Escherichia coli

<400> SEQUENCE: 369

Val Tyr Asn Ile Gln Asp Glu Thr Gly Gln Phe Lys Gly Gly Ser Val
1               5                   10                  15

Phe Ser Thr Ala Val Pro Gln
            20

<210> SEQ ID NO 370
<211> LENGTH: 23
<212> TYPE: PRT
<213> ORGANISM: Escherichia coli

<400> SEQUENCE: 370

Val Tyr Asn Ile Gln Asp Glu Thr Gly Gln Phe Lys Gly Gly Ser Val
1               5                   10                  15

Ala Ser Thr Ala Val Pro Gln
            20

<210> SEQ ID NO 371
<211> LENGTH: 23
<212> TYPE: PRT
<213> ORGANISM: Escherichia coli

<400> SEQUENCE: 371

Val Tyr Asn Ile Gln Asp Glu Thr Gly Gln Phe Lys Gly Gly Ser Val
1               5                   10                  15

Gly Ser Thr Ala Val Pro Gln
            20

<210> SEQ ID NO 372
<211> LENGTH: 23
<212> TYPE: PRT
<213> ORGANISM: Escherichia coli

<400> SEQUENCE: 372

Val Tyr Asn Ile Gln Asp Glu Thr Gly Gln Phe Lys Gly Gly Ser Val
1               5                   10                  15

Val Ser Thr Ala Val Pro Gln
            20

<210> SEQ ID NO 373
<211> LENGTH: 22
<212> TYPE: PRT
<213> ORGANISM: Escherichia coli

<400> SEQUENCE: 373

Val Tyr Asn Ile Gln Asp Glu Thr Gly Gln Phe Lys Gly Gly Ser Val
1               5                   10                  15

Ser Thr Ala Val Pro Gln
            20

<210> SEQ ID NO 374
<211> LENGTH: 23

```
<212> TYPE: PRT
<213> ORGANISM: Escherichia coli

<400> SEQUENCE: 374

Val Tyr Asn Ile Gln Asp Glu Thr Gly Gln Phe Lys Gly Gly Ser Ser
1               5                   10                  15

Phe Ser Thr Ala Val Pro Gln
            20

<210> SEQ ID NO 375
<211> LENGTH: 23
<212> TYPE: PRT
<213> ORGANISM: Escherichia coli

<400> SEQUENCE: 375

Val Tyr Asn Ile Gln Asp Glu Thr Gly Gln Phe Lys Gly Gly Ser Ser
1               5                   10                  15

Ala Ser Thr Ala Val Pro Gln
            20

<210> SEQ ID NO 376
<211> LENGTH: 23
<212> TYPE: PRT
<213> ORGANISM: Escherichia coli

<400> SEQUENCE: 376

Val Tyr Asn Ile Gln Asp Glu Thr Gly Gln Phe Lys Gly Gly Ser Ser
1               5                   10                  15

Gly Ser Thr Ala Val Pro Gln
            20

<210> SEQ ID NO 377
<211> LENGTH: 23
<212> TYPE: PRT
<213> ORGANISM: Escherichia coli

<400> SEQUENCE: 377

Val Tyr Asn Ile Gln Asp Glu Thr Gly Gln Phe Lys Gly Gly Ser Ser
1               5                   10                  15

Val Ser Thr Ala Val Pro Gln
            20

<210> SEQ ID NO 378
<211> LENGTH: 22
<212> TYPE: PRT
<213> ORGANISM: Escherichia coli

<400> SEQUENCE: 378

Val Tyr Asn Ile Gln Asp Glu Thr Gly Gln Phe Lys Gly Gly Ser Ser
1               5                   10                  15

Ser Thr Ala Val Pro Gln
            20

<210> SEQ ID NO 379
<211> LENGTH: 23
<212> TYPE: PRT
<213> ORGANISM: Escherichia coli

<400> SEQUENCE: 379

Val Tyr Asn Ile Gln Asp Glu Thr Gly Gln Phe Lys Gly Gly Ser Thr
1               5                   10                  15

Phe Ser Thr Ala Val Pro Gln
```

<210> SEQ ID NO 380
<211> LENGTH: 23
<212> TYPE: PRT
<213> ORGANISM: Escherichia coli

<400> SEQUENCE: 380

Val Tyr Asn Ile Gln Asp Glu Thr Gly Gln Phe Lys Gly Gly Ser Thr
1               5                   10                  15

Ala Ser Thr Ala Val Pro Gln
            20

<210> SEQ ID NO 381
<211> LENGTH: 23
<212> TYPE: PRT
<213> ORGANISM: Escherichia coli

<400> SEQUENCE: 381

Val Tyr Asn Ile Gln Asp Glu Thr Gly Gln Phe Lys Gly Gly Ser Thr
1               5                   10                  15

Gly Ser Thr Ala Val Pro Gln
            20

<210> SEQ ID NO 382
<211> LENGTH: 23
<212> TYPE: PRT
<213> ORGANISM: Escherichia coli

<400> SEQUENCE: 382

Val Tyr Asn Ile Gln Asp Glu Thr Gly Gln Phe Lys Gly Gly Ser Thr
1               5                   10                  15

Val Ser Thr Ala Val Pro Gln
            20

<210> SEQ ID NO 383
<211> LENGTH: 22
<212> TYPE: PRT
<213> ORGANISM: Escherichia coli

<400> SEQUENCE: 383

Val Tyr Asn Ile Gln Asp Glu Thr Gly Gln Phe Lys Gly Gly Ser Thr
1               5                   10                  15

Ser Thr Ala Val Pro Gln
            20

<210> SEQ ID NO 384
<211> LENGTH: 22
<212> TYPE: PRT
<213> ORGANISM: Escherichia coli

<400> SEQUENCE: 384

Val Tyr Asn Ile Gln Asp Glu Thr Gly Gln Phe Lys Gly Gly Ser Phe
1               5                   10                  15

Ser Thr Ala Val Pro Gln
            20

<210> SEQ ID NO 385
<211> LENGTH: 22
<212> TYPE: PRT
<213> ORGANISM: Escherichia coli

<400> SEQUENCE: 385

Val Tyr Asn Ile Gln Asp Glu Thr Gly Gln Phe Lys Gly Gly Ser Ala
1               5                   10                  15

Ser Thr Ala Val Pro Gln
            20

<210> SEQ ID NO 386
<211> LENGTH: 22
<212> TYPE: PRT
<213> ORGANISM: Escherichia coli

<400> SEQUENCE: 386

Val Tyr Asn Ile Gln Asp Glu Thr Gly Gln Phe Lys Gly Gly Ser Gly
1               5                   10                  15

Ser Thr Ala Val Pro Gln
            20

<210> SEQ ID NO 387
<211> LENGTH: 22
<212> TYPE: PRT
<213> ORGANISM: Escherichia coli

<400> SEQUENCE: 387

Val Tyr Asn Ile Gln Asp Glu Thr Gly Gln Phe Lys Gly Gly Ser Val
1               5                   10                  15

Ser Thr Ala Val Pro Gln
            20

<210> SEQ ID NO 388
<211> LENGTH: 21
<212> TYPE: PRT
<213> ORGANISM: Escherichia coli

<400> SEQUENCE: 388

Val Tyr Asn Ile Gln Asp Glu Thr Gly Gln Phe Lys Gly Gly Ser Ser
1               5                   10                  15

Thr Ala Val Pro Gln
        20

<210> SEQ ID NO 389
<211> LENGTH: 786
<212> TYPE: DNA
<213> ORGANISM: Escherichia coli

<400> SEQUENCE: 389
tgtctgaccg caccgccgaa agaagcggca cgtccgaccc tgatgccgcg tgcacagtct      60
tataaagatc tgacccatct gccggctccg acgggcaaaa tttttgttag cgtctataac     120
atccaggacg aaaccggtca atttaaaccg tacccggcga gtaatttctc cacggccgtt     180
ccgcagagtg caaccgctat gctggtcacg gcactgaaag attcccgttg gttcattccg     240
ctggaacgcc agggcctgca aaacctgctg aatgaacgta aaattatccg cgcagctcag     300
gaaaacggta ccgtggccat taacaatcgt attccgctgc aaagcctgac cgccgcaaac     360
atcatggttg aaggctctat catcggttac gaatcaaacg tcaaatcggg cggtgtgggc     420
gcacgttatt ttggcattgg tgctgatacc cagtaccaac tggaccagat cgcagttaac     480
ctgcgcgtgg ttaatgtcag caccggcgaa attctgagct ctgtgaatac cagcaaaacg     540
atcctgtctt acgaagtgca ggctggtgtt tttcgtttca ttgattatca acgcctgctg     600
gaaggcgaag tcggttacac ctcaaacgaa ccggtgatgc tgtgtctgat gtcggcgatt     660

```
gaaacgggtg ttattttcct gatcaatgat ggcatcgacc gtggtctgtg ggatctgcag    720
aacaaagccg aacgtcaaaa tgacattctg gtgaaatacc gccacatgag tgttccgccg    780
gaatcc                                                               786
```

<210> SEQ ID NO 390
<211> LENGTH: 262
<212> TYPE: PRT
<213> ORGANISM: Escherichia coli

<400> SEQUENCE: 390

```
Cys Leu Thr Ala Pro Lys Glu Ala Arg Pro Thr Leu Met Pro
1               5                   10                  15

Arg Ala Gln Ser Tyr Lys Asp Leu Thr His Leu Pro Ala Pro Thr Gly
                20                  25                  30

Lys Ile Phe Val Ser Val Tyr Asn Ile Gln Asp Glu Thr Gly Gln Phe
            35                  40                  45

Lys Pro Tyr Pro Ala Ser Asn Phe Ser Thr Ala Val Pro Gln Ser Ala
        50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260
```

<210> SEQ ID NO 391
<211> LENGTH: 248
<212> TYPE: PRT
<213> ORGANISM: Citrobacter koseri

<400> SEQUENCE: 391

```
Met Pro Arg Ala Gln Ser Tyr Lys Asp Leu Thr His Leu Pro Met Pro
1               5                   10                  15

Thr Gly Lys Ile Phe Val Ser Val Tyr Asn Ile Gln Asp Glu Thr Gly
                20                  25                  30
```

```
Gln Phe Lys Pro Tyr Pro Ala Ser Asn Phe Ser Thr Ala Val Pro Gln
             35                  40                  45

Ser Ala Thr Ala Met Leu Val Thr Ala Leu Lys Asp Ser Arg Trp Phe
 50                  55                  60

Ile Pro Leu Glu Arg Gln Gly Leu Gln Asn Leu Leu Asn Glu Arg Lys
 65                  70                  75                  80

Ile Ile Arg Ala Ala Gln Glu Asn Gly Thr Val Ala Ile Asn Asn Arg
                 85                  90                  95

Ile Pro Leu Gln Ser Leu Thr Ala Ala Asn Ile Met Val Glu Gly Ser
                100                 105                 110

Ile Ile Gly Tyr Glu Ser Asn Val Lys Ser Gly Gly Val Gly Ala Arg
                115                 120                 125

Tyr Phe Gly Ile Gly Ala Asp Thr Gln Tyr Gln Leu Asp Gln Ile Ala
130                 135                 140

Val Asn Leu Arg Val Val Asn Val Ser Thr Gly Glu Ile Leu Ser Ser
145                 150                 155                 160

Val Asn Thr Ser Lys Thr Ile Leu Ser Tyr Glu Val Gln Ala Gly Val
                165                 170                 175

Phe Arg Phe Ile Asp Tyr Gln Arg Leu Leu Glu Gly Glu Ile Gly Tyr
                180                 185                 190

Thr Ser Asn Glu Pro Val Met Leu Cys Leu Met Ser Ala Ile Glu Thr
                195                 200                 205

Gly Val Ile Phe Leu Ile Asn Asp Gly Ile Asp Arg Gly Leu Trp Asp
                210                 215                 220

Leu Gln Asn Lys Ala Glu Arg Gln Asn Asp Ile Leu Val Lys Tyr Arg
225                 230                 235                 240

His Met Ser Val Pro Pro Glu Ser
                245

<210> SEQ ID NO 392
<211> LENGTH: 223
<212> TYPE: PRT
<213> ORGANISM: Salmonella enterica

<400> SEQUENCE: 392

Cys Leu Thr Ala Pro Pro Lys Gln Ala Ala Lys Pro Thr Leu Met Pro
 1               5                  10                  15

Arg Ala Gln Ser Tyr Lys Asp Leu Thr His Leu Pro Ala Pro Thr Gly
                 20                  25                  30

Lys Ile Phe Val Ser Val Tyr Asn Ile Gln Asp Glu Thr Gly Gln Phe
             35                  40                  45

Lys Pro Tyr Pro Ala Ser Asn Phe Ser Thr Ala Val Pro Gln Ser Ala
 50                  55                  60

Thr Ala Met Leu Val Thr Ala Leu Lys Asp Ser Arg Trp Phe Ile Pro
 65                  70                  75                  80

Leu Glu Arg Gln Gly Leu Gln Asn Leu Leu Asn Glu Arg Lys Ile Ile
                 85                  90                  95

Arg Ala Ala Gln Glu Asn Gly Thr Val Ala Met Asn Asn Arg Ile Pro
                100                 105                 110

Leu Gln Ser Leu Thr Ala Ala Asn Ile Met Val Glu Gly Ser Ile Ile
                115                 120                 125

Gly Tyr Glu Ser Asn Val Lys Ser Gly Gly Val Gly Ala Arg Tyr Phe
130                 135                 140

Gly Ile Gly Ala Asp Thr Gln Tyr Gln Leu Asp Gln Ile Ala Val Asn
145                 150                 155                 160
```

```
Leu Arg Val Val Asn Val Ser Thr Gly Glu Ile Leu Ser Ser Val Asn
            165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Ile Gly Tyr Thr Ser
            195                 200                 205

Asn Glu Pro Val Met Leu Cys Leu Met Ser Ala Ile Glu Thr Gly
    210                 215                 220
```

<210> SEQ ID NO 393
<211> LENGTH: 262
<212> TYPE: PRT
<213> ORGANISM: Citrobacter amalonaticus

<400> SEQUENCE: 393

```
Cys Leu Thr Ala Pro Lys Glu Ala Ala Lys Pro Thr Leu Met Pro
1               5                   10                  15

Arg Ala Gln Ser Tyr Lys Asp Leu Thr His Leu Pro Ile Pro Thr Gly
            20                  25                  30

Lys Ile Phe Val Ser Val Tyr Asn Ile Gln Asp Glu Thr Gly Gln Phe
            35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Val Pro
65                  70                  75                  80

Leu Glu Arg Gln Gly Leu Gln Asn Leu Leu Asn Glu Arg Lys Ile Ile
            85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
            115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
            165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Ile Gly Tyr Thr Ser
            195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Asp Arg Gln Asn Asp Ile Leu Val Lys Tyr Arg His Met
            245                 250                 255

Ser Val Pro Pro Glu Ser
            260
```

<210> SEQ ID NO 394
<211> LENGTH: 262
<212> TYPE: PRT
<213> ORGANISM: Citrobacter rodentium

<400> SEQUENCE: 394

Cys Leu Thr Thr Pro Pro Lys Glu Ala Ala Lys Pro Thr Leu Met Pro
1               5                   10                  15

Arg Ala Gln Ser Tyr Lys Asp Leu Thr His Leu Pro Val Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
                100                 105                 110

Leu Pro Ser Leu Thr Ala Ala Asn Ile Met Val Glu Gly Ser Ile Ile
            115                 120                 125

Gly Tyr Glu Ser Asn Val Lys Ser Gly Gly Ala Gly Ala Arg Tyr Phe
        130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Ile Gly Tyr Thr Ser
        195                 200                 205

Asn Glu Pro Val Met Leu Cys Leu Met Ser Ala Ile Glu Thr Gly Val
210                 215                 220

Ile Phe Leu Ile Asn Asp Gly Ile Asp Arg Gly Leu Trp Asp Leu Gln
225                 230                 235                 240

Asn Lys Ala Asp Arg Gln Asn Asp Ile Leu Val Lys Tyr Arg Gln Met
                245                 250                 255

Ser Val Pro Pro Glu Ser
            260

<210> SEQ ID NO 395
<211> LENGTH: 262
<212> TYPE: PRT
<213> ORGANISM: Enterobacter asburiae

<400> SEQUENCE: 395

Cys Leu Thr Ala Pro Pro Lys Glu Ala Ala Lys Pro Thr Leu Met Pro
1               5                   10                  15

Arg Ala Gln Ser Tyr Arg Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
50                  55                  60

Thr Ala Met Leu Val Thr Ala Leu Lys Asp Ser His Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Asn Asn Asn Arg Met Pro

```
            100                 105                 110
Leu Gln Ser Leu Ala Ala Ala Asn Val Met Ile Glu Gly Ser Ile Ile
        115                 120                 125
Gly Tyr Glu Ser Asn Val Lys Ser Gly Gly Val Gly Ala Arg Tyr Phe
    130                 135                 140
Gly Ile Gly Ala Asp Thr Gln Tyr Gln Leu Asp Gln Ile Ala Val Asn
145                 150                 155                 160
Leu Arg Val Val Asn Val Ser Thr Gly Glu Val Leu Ser Ser Val Asn
                165                 170                 175
Thr Ser Lys Thr Ile Leu Ser Tyr Glu Val Gln Ala Gly Val Phe Arg
            180                 185                 190
Phe Ile Asp Tyr Gln Arg Leu Leu Glu Gly Glu Ile Gly Tyr Thr Ser
        195                 200                 205
Asn Glu Pro Val Met Met Cys Leu Met Ser Ala Ile Glu Thr Gly Val
    210                 215                 220
Ile Phe Leu Ile Asn Asp Gly Ile Asp Arg Gly Leu Trp Asp Leu Gln
225                 230                 235                 240
Asn Lys Ala Asp Ala Gln Asn Pro Val Leu Val Lys Tyr Arg Asp Met
                245                 250                 255
Ser Val Pro Pro Glu Ser
            260

<210> SEQ ID NO 396
<211> LENGTH: 1830
<212> TYPE: DNA
<213> ORGANISM: Bacillus subtilis phage phi29

<400> SEQUENCE: 396
atgaaacaca tgccgcgtaa aatgtatagc tgcgcgtttg aaaccacgac caaagtggaa      60
gattgtcgcg tttgggccta tggctacatg aacatcgaag atcattctga atacaaaatc     120
ggtaacagtc tggatgaatt tatggcatgg gtgctgaaag ttcaggcgga tctgtacttc     180
cacaacctga atttgatgg cgcattcatt atcaactggc tggaacgtaa tggctttaaa     240
tggagcgcgg atggtctgcc gaacacgtat aataccatta tctctcgtat gggccagtgg     300
tatatgattg atatctgcct gggctacaaa ggtaaacgca aaattcatac cgtgatctat     360
gatagcctga aaaactgcc gtttccggtg aagaaaattg cgaaagattt caaactgacg     420
gttctgaaag gcgatattga ttatcacaaa gaacgtccgg ttggttacaa aatcaccccg     480
gaagaatacg catacatcaa aaacgatatc cagatcatcg cagaagcgct gctgattcag     540
tttaaacagg gcctggatcg catgaccgcg ggcagtgata gcctgaaagg tttcaaagat     600
atcatcacga ccaaaaaatt caaaaaagtg ttcccgacgc tgagcctggg tctggataaa     660
gaagttcgtt atgcctaccg cggcggtttt acctggctga cgatcgtttt caaagaaaaa     720
gaaattggcg agggtatggt gtttgatgtt aatagtctgt atccggcaca gatgtacagc     780
cgcctgctgc cgtatggcga accgatcgtg ttcgagggta atatgtttg ggatgaagat     840
tacccgctgc atattcagca catccgttgt gaatttgaac tgaaagaagg ctatattccg     900
accattcaga tcaaacgtag tcgcttctat aagggtaacg aatacctgaa agctctggc     960
ggtgaaatcg cggatctgtg gctgagtaac gtggatctgg aactgatgaa agaacactac    1020
gatctgtaca acgttgaata catcagcggc ctgaaattta agccacgac cggtctgttc    1080
aaagatttca tcgataaatg gacctacatc aaaacgacct gaaggcgc gattaaacag    1140
ctggccaaac tgatgctgaa cagcctgtat ggcaaattcg cctctaatcc ggatgtgacc    1200
```

-continued

```
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg gtgtggttct ggtggatgat acgtttacca ttaaatctgg cggtagtgcg   1740
tggagccatc cgcagttcga aaaggcggt ggctctggtg gcggttctgg cggtagtgcc   1800
tggagccacc cgcagtttga aaataataa                                     1830
```

<210> SEQ ID NO 397
<211> LENGTH: 608
<212> TYPE: PRT
<213> ORGANISM: Bacillus subtilis phage phi29

<400> SEQUENCE: 397

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255
```

```
Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605

<210> SEQ ID NO 398
<211> LENGTH: 1390
<212> TYPE: DNA
<213> ORGANISM: Escherichia coli

<400> SEQUENCE: 398
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat tgcaaaccgg ccgatgatta tctgccgcag     180
```

```
ccgggtgcgg tgctgattac cggtattacc ccgcaggaag cgcgcgcgaa aggtgaaaac      240
gaagcggcgt tgccgcgcg cattcatagc ctgtttaccg tgccgaaaac ctgcattctg      300
ggctataaca atgtgcgctt cgatgatgaa gttacccgta atatctttta tcgtaacttt      360
tatgatccgt atgcgtggag ctggcagcat gataacagcc gttgggatct gctggatgtg      420
atgcgcgcgt gctatgcgct gcgcccggaa ggcattaatt ggccggaaaa cgatgatggc      480
ctgccgagct ttcgtctgga acatctgacc aaagccaacg gcattgaaca tagcaatgcc      540
catgatgcga tggccgatgt ttatgcgacc attgcgatgg cgaaactggt taaaacccgt      600
cagccgcgcc tgtttgatta tctgtttacc accgtaaca aacacaaact gatggcgctg      660
attgatgttc gcagatgaa accgctggtg catgtgagcg gcatgtttgg cgcctggcgc      720
ggcaacacca gctgggtggc cccgctggcc tggcacccgg aaaatcgtaa cgccgtgatt      780
atggttgatc tggccggtga tattagcccg ctgctggaac tggatagcga taccctgcgt      840
gaacgcctgt ataccgccaa aaccgatctg ggcgataatg ccgccgtgcc ggtgaaactg      900
gttcacatta caaatgccc ggtgctggcc caggcgaaca ccctgcgccc ggaagatgcg      960
gatcgtctgg gtattaatcg ccagcattgt ctggataatc tgaaaatcct gcgtgaaaac     1020
ccgcaggtgc gtgaaaaagt ggtggcgatc ttcgcggaag cggaaccgtt caccccgagc     1080
gataacgtgg atgcgcagct gtataacggc ttctttagcg atgccgatcg cgcggcgatg     1140
aaaatcgttc tggaaaccga accgcgcaat ctgccggcgc tggatattac ctttgttgat     1200
aaacgtattg aaaaactgct gtttaattat cgtgcgcgca attttccggg tacccctggat     1260 tatgccgaac agcagcgttg gctggaacat cgtcgtcagg ttttcacccc ggaatttctg     1320
cagggttatg cggatgaact gcagatgctg gttcagcagt atgccgatga taaagaaaaa     1380
gtggcgctgc                                                            1390
```

<210> SEQ ID NO 399
<211> LENGTH: 485
<212> TYPE: PRT
<213> ORGANISM: Escherichia coli

<400> SEQUENCE: 399

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
                20                  25                  30

Ala Ile Arg Thr Asp Ser Glu Phe Asn Val Ile Gly Glu Pro Glu Val
            35                  40                  45

Phe Tyr Cys Lys Pro Ala Asp Asp Tyr Leu Pro Gln Pro Gly Ala Val
        50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
```

```
            145                 150                 155                 160
Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 400
<211> LENGTH: 804
<212> TYPE: DNA
<213> ORGANISM: Escherichia coli

<400> SEQUENCE: 400
atgaaatttg tctctttttaa tatcaacggc ctgcgcgcca gacctcacca gcttgaagcc      60
atcgtcgaaa agcaccaacc ggatgtgatt ggcctgcagg agacaaaagt tcatgacgat     120
atgtttccgc tcgaagaggt ggcgaagctc ggctacaacg tgttttatca cgggcagaaa     180
```

-continued

```
ggccattatg gcgtggcgct gctgaccaaa gagacgccga ttgccgtgcg tcgcggcttt      240
cccggtgacg acgaagaggc gcagcggcgg attattatgg cggaaatccc ctcactgctg      300
ggtaatgtca ccgtgatcaa cggttacttc ccgcagggtg aaagccgcga ccatccgata      360
aaattcccgg caaaagcgca gttttatcag aatctgcaaa actacctgga aaccgaactc      420
aaacgtgata atccggtact gattatgggc gatatgaata tcagccctac agatctggat      480
atcggcattg gcgaagaaaa ccgtaagcgc tggctgcgta ccggtaaatg ctctttcctg      540
ccggaagagc gcgaatggat ggacaggctg atgagctggg ggttggtcga taccttccgc      600
catgcgaatc cgcaaacagc agatcgtttc tcatggtttg attaccgctc aaaaggtttt      660
gacgataacc gtggtctgcg catcgacctg ctgctcgcca gccaaccgct ggcagaatgt      720
tgcgtagaaa ccggcatcga ctatgaaatc gcagcatgg aaaaaccgtc cgatcacgcc      780
cccgtctggg cgaccttccg ccgc                                             804
```

<210> SEQ ID NO 401
<211> LENGTH: 268
<212> TYPE: PRT
<213> ORGANISM: Escherichia coli

<400> SEQUENCE: 401

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
```

<210> SEQ ID NO 402
<211> LENGTH: 1275
<212> TYPE: DNA
<213> ORGANISM: Thermus thermophilus

<400> SEQUENCE: 402

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat tcgtgttcac     120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact gcgcgaactg ctggaaaatg gcgtggaagt cattgttacc     360
gatcatcata cgccgggcaa aacgccgccg ccgggtctgg tcgtgcatcc ggcgctgacg     420
ccggatctga agaaaaaacc gaccggcgca ggcgtggcgt tctgctgctg tgggcactg     480
catgaacgcc tgggcctgcc gccgccgctg aatacgcgg acctggcagc cgttggcacc     540
attgccgacg ttgccccgct gtggggttgg aatcgtgcac tggtgaaaga aggtctggca     600
cgcatcccgg cttcatcttg ggtgggcctg cgtctgctgg ctgaagccgt gggctatacc     660
ggcaaagcgt cgaagtcgc tttccgcatc gcgccgcgca tcaatgcggc ttcccgcctg     720
ggcgaagcgg aaaaagccct gcgcctgctg ctgacggatg atgcggcaga gctcaggcg     780
ctggtcggcg aactgcaccg tctgaacgcc gtcgtcaga ccctggaaga gcgatgctg     840
cgcaaactgc tgccgcaggc cgaccccgga gcgaaagcca tcgttctgct ggacccggaa     900
ggccatccgg tgttatggg tattgtggcc tctcgcatcc tggaagcgac cctgcgcccg     960
gtctttctgg tggcccaggg caaaggcacc gtgcgttcgc tggctccgat tccgccgtc    1020
gaagcactgc gcagcgcgga agatctgctg ctgcgttatg gtggtcataa agaagcggcg    1080
ggtttcgcaa tggatgaagc gctgtttccg gcgttcaaag cacgcgttga agcgtatgcc    1140
gcacgttttc cggatccggt tcgtgaagtg cactgctgg atctgctgcc ggaaccgggc    1200
ctgctgccgc aggtgttccg tgaactggca ctgctggaac cgtatggtga aggtaacccg    1260
gaaccgctgt cctg                                                     1275
```

<210> SEQ ID NO 403
<211> LENGTH: 425
<212> TYPE: PRT
<213> ORGANISM: Thermus thermophilus

<400> SEQUENCE: 403

```
Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95
```

```
Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
        130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
                180                 185                 190

Ala Leu Val Lys Glu Gly Leu Ala Arg Ile Pro Ala Ser Ser Trp Val
            195                 200                 205

Gly Leu Arg Leu Leu Ala Glu Ala Val Gly Tyr Thr Gly Lys Ala Val
            210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
                260                 265                 270

Gln Thr Leu Glu Glu Ala Met Leu Arg Lys Leu Leu Pro Gln Ala Asp
            275                 280                 285

Pro Glu Ala Lys Ala Ile Val Leu Leu Asp Pro Glu Gly His Pro Gly
            290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
                340                 345                 350

Tyr Gly Gly His Lys Glu Ala Ala Gly Phe Ala Met Asp Glu Ala Leu
            355                 360                 365

Phe Pro Ala Phe Lys Ala Arg Val Glu Ala Tyr Ala Ala Arg Phe Pro
            370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
                420                 425

<210> SEQ ID NO 404
<211> LENGTH: 738
<212> TYPE: DNA
<213> ORGANISM: Bacteriophage lambda

<400> SEQUENCE: 404
tccggaagcg gctctggtag tggttctggc atgacaccgg acattatcct gcagcgtacc    60
gggatcgatg tgagagctgt cgaacagggg gatgatgcgt ggcacaaatt acggctcggc   120
gtcatcaccg cttcagaagt tcacaacgtg atagcaaaac cccgctccgg aaagaagtgg   180
cctgacatga aaatgtccta cttccacacc ctgcttgctg aggtttgcac cggtgtggct   240
```

```
ccggaagtta acgctaaagc actggcctgg ggaaaacagt acgagaacga cgccagaacc      300
ctgtttgaat tcacttccgg cgtgaatgtt actgaatccc cgatcatcta tcgcgacgaa      360
agtatgcgta ccgcctgctc tcccgatggt ttatgcagtg acggcaacgg ccttgaactg      420
aaatgcccgt ttacctcccg ggatttcatg aagttccggc tcggtggttt cgaggccata      480
aagtcagctt acatggccca ggtgcagtac agcatgtggg tgacgcgaaa aaatgcctgg      540
tactttgcca actatgaccc gcgtatgaag cgtgaaggcc tgcattatgt cgtgattgag      600
cgggatgaaa agtacatggc gagttttgac gagatcgtgc cggagttcat cgaaaaaatg      660
gacgaggcac tggctgaaat tggttttgta tttggggagc aatggcgatc tggctctggt      720
tccggcagcg gttccgga                                                    738
```

```
<210> SEQ ID NO 405
<211> LENGTH: 226
<212> TYPE: PRT
<213> ORGANISM: Bacteriophage lambda

<400> SEQUENCE: 405
```

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

```
<210> SEQ ID NO 406
<211> LENGTH: 760
<212> TYPE: PRT
<213> ORGANISM: Methanococcoides burtonii

<400> SEQUENCE: 406
```

```
Met Met Ile Arg Glu Leu Asp Ile Pro Arg Asp Ile Gly Phe Tyr
1               5                   10                  15

Glu Asp Ser Gly Ile Lys Glu Leu Tyr Pro Pro Gln Ala Glu Ala Ile
                20                  25                  30

Glu Met Gly Leu Leu Glu Lys Lys Asn Leu Leu Ala Ala Ile Pro Thr
            35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
                100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
        130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415
```

-continued

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
            435                 440                 445

Gly Ala Thr Phe Phe Ala Tyr Gln Gln Asp Lys Trp Met Leu Glu Glu
450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
            515                 520                 525

Asn Met Gly Ser Leu Glu Asp Asp Lys Gly Asp Asp Ile Thr Val Thr
            530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
            595                 600                 605

Glu Trp Val Thr Glu Val Ser Ala Glu Asp Ile Thr Arg His Phe Asn
610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
            675                 680                 685

Arg Lys Leu Tyr Asn Ala Gly Phe Val Ser Val Ala Lys Leu Lys Gly
690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
            755                 760

<210> SEQ ID NO 407
<211> LENGTH: 707
<212> TYPE: PRT
<213> ORGANISM: Cenarchaeum symbiosum

<400> SEQUENCE: 407

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

-continued

Lys Ala Gly Leu Thr Asp Gly Lys Ser Val Leu Val Ser Ala Pro Thr
            35                  40                  45

Ala Ser Gly Lys Thr Leu Ile Ala Ala Ile Ala Met Ile Ser His Leu
 50                  55                  60

Ser Arg Asn Arg Gly Lys Ala Val Tyr Leu Ser Pro Leu Arg Ala Leu
 65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
               100                 105                 110

Gly Arg Ser Leu Gly Asn Asn Asp Ile Leu Val Leu Thr Asn Glu Arg
               115                 120                 125

Met Asp Ser Leu Ile Arg Arg Arg Pro Asp Trp Met Asp Glu Val Gly
           130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
                180                 185                 190

Ala Gly Trp Leu Asp Cys Thr Leu Val His Ser Thr Trp Arg Pro Val
            195                 200                 205

Pro Leu Ser Glu Gly Val Tyr Gln Asp Gly Glu Val Ala Met Gly Asp
            210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
        275                 280                 285

Lys Lys Ile Ile Ser Ser Gly Glu Thr Lys Leu Ala Lys Thr Leu
290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
            325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
            435                 440                 445

Val Thr Glu Phe Phe Leu Gly Thr Leu Gly Gly Gln Gln Ser Gly Glu
450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
                500                 505                 510

Leu Arg Asp Ala Val Gly Glu Ala Ser Pro Gly Arg Met His Thr Leu
                515                 520                 525

Gly Phe Leu His Leu Val Ser Glu Cys Ser Glu Phe Met Pro Arg Phe
                530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
                580                 585                 590

Leu Ala Glu Asp Leu Lys Phe Glu Ser Gly Asp Val His Arg Met Val
                595                 600                 605

Glu Ser Ser Gly Trp Leu Leu Arg Cys Ile Trp Glu Ile Ser Lys His
610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
                660                 665                 670

Gly Pro Gly Asp Leu Ala Ala Val Pro Val Glu Arg Leu Ser Arg Val
                675                 680                 685

Glu Gly Ile Gly Ala Thr Leu Ala Asn Asn Ile Lys Ser Gln Leu Arg
                690                 695                 700

Lys Gly Gly
705

<210> SEQ ID NO 408
<211> LENGTH: 720
<212> TYPE: PRT
<213> ORGANISM: Thermococcus gammatolerans

<400> SEQUENCE: 408

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
                20                  25                  30

Lys Ser Gly Ala Leu Glu Gly Arg Asn Leu Val Leu Ala Ile Pro Thr
                35                  40                  45

Ala Ser Gly Lys Thr Leu Val Ser Glu Ile Val Met Val Asn Lys Leu
50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
                100                 105                 110

Gly Arg Tyr Asp Ile Ile Val Ala Thr Ala Glu Lys Phe Asp Ser Leu
            115                 120                 125

Leu Arg His Gly Ala Arg Trp Ile Asn Asp Val Lys Leu Val Val Ala
130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Val Ala Phe His His Ala Gly
290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

```
Leu Thr Ala Arg Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Glu Leu Ala Asp Trp Leu
        595                 600                 605

Met Tyr Ser Leu Ile Glu Leu Tyr Lys Leu Phe Glu Pro Lys Glu Glu
    610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
                660                 665                 670

Ala Asn Ala Lys Pro Ala Glu Leu Leu Ala Val Glu Gly Ile Gly Ala
            675                 680                 685

Lys Ile Leu Asp Gly Ile Tyr Arg His Leu Gly Ile Glu Lys Arg Val
    690                 695                 700

Thr Glu Glu Lys Pro Lys Arg Lys Gly Thr Leu Glu Asp Phe Leu Arg
705                 710                 715                 720

<210> SEQ ID NO 409
<211> LENGTH: 799
<212> TYPE: PRT
<213> ORGANISM: Methanospirillum hungatei

<400> SEQUENCE: 409

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190
```

```
Leu Ile Thr Ser Thr Trp Arg Pro Val Asp Leu Arg Gln Gly Val Tyr
            195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Arg Arg Asn Ala Glu Gly
                245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
            275                 280                 285

Asn Val Leu Ala Asp Cys Val Glu Arg Gly Ala Ala Phe His His Ala
        290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
        370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
        450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
            485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
        515                 520                 525

Arg Leu Tyr Leu Lys Ala Ala Asp Thr Gln Leu Leu Arg Thr Phe Leu
        530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
            595                 600                 605
```

```
Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                    645                 650                 655

Arg Thr Leu Tyr Asn Ala Gly Tyr Pro Asp Pro Glu Ala Val Ala Arg
                660                 665                 670

Ala Gly Leu Ser Thr Ile Ala Arg Ile Ile Gly Glu Gly Ile Ala Arg
            675                 680                 685

Gln Val Ile Asp Glu Ile Thr Gly Val Lys Arg Ser Gly Ile His Ser
690                 695                 700

Ser Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                    725                 730                 735

Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
            755                 760                 765

Ser Glu Lys Glu Asn Ser Ser Ser Asp Lys Thr Glu Glu Ile Pro Asp
770                 775                 780

Thr Gln Lys Ile Arg Gly Gln Ser Ser Trp Glu Asp Phe Gly Cys
785                 790                 795
```

<210> SEQ ID NO 410
<211> LENGTH: 1756
<212> TYPE: PRT
<213> ORGANISM: Escherichia coli

<400> SEQUENCE: 410

```
Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
                20                  25                  30

Trp Ala Gly Lys Gly Ala Glu Gln Leu Gly Leu Gln Gly Ser Val Asp
            35                  40                  45

Lys Asp Val Phe Thr Arg Leu Leu Glu Gly Arg Leu Pro Asp Gly Ala
50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
                100                 105                 110

Ala Val Arg Gln Val Glu Ala Leu Ala Ser Thr Arg Val Met Thr Asp
            115                 120                 125

Gly Gln Ser Glu Thr Val Leu Thr Gly Asn Leu Val Met Ala Leu Phe
130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
                180                 185                 190
```

```
Gln Ile Ala Phe Gly Arg Leu Tyr Arg Glu Lys Leu Lys Glu Gln Val
            195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605
```

```
Ile Leu Thr Gln Ala Ile Arg Ser Glu Leu Lys Thr Gln Gly Val Leu
610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
                660                 665                 670

Arg Val Thr Ala Gln Ser His Ser Leu Thr Leu Arg Asp Ala Gln Gly
                675                 680                 685

Glu Thr Gln Val Val Arg Ile Ser Ser Leu Asp Ser Ser Trp Ser Leu
690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Pro Gly Arg
                740                 745                 750

Ala Glu Pro Ala Ser Leu Pro Val Ser Asp Ser Pro Phe Thr Ala Leu
                755                 760                 765

Lys Leu Glu Asn Gly Trp Val Glu Thr Pro Gly His Ser Val Ser Asp
770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
                820                 825                 830

Phe Thr Val Val Ser Glu Gln Ile Lys Ala Arg Ala Gly Glu Thr Leu
                835                 840                 845

Leu Glu Thr Ala Ile Ser Leu Gln Lys Ala Gly Leu His Thr Pro Ala
850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
                900                 905                 910

Lys Arg Gly Asp Leu Leu Tyr Val Asp Val Ala Lys Gly Tyr Gly Thr
                915                 920                 925

Gly Leu Leu Val Ser Arg Ala Ser Tyr Glu Ala Glu Lys Ser Ile Leu
930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
                980                 985                 990

Tyr Ala Gly Val Gly Lys Thr Thr  Gln Phe Arg Ala Val  Met Ser Ala
                995                1000                1005

Val Asn Met Leu Pro Ala Ser  Glu Arg Pro Arg Val  Val Gly Leu
            1010                1015                1020

Gly Pro Thr His Arg Ala Val  Gly Glu Met Arg Ser  Ala Gly Val
```

```
              1025                1030                1035

Asp Ala Gln Thr Leu Ala Ser Phe Leu His Asp Thr Gln Leu Gln
              1040                1045                1050

Gln Arg Ser Gly Glu Thr Pro Asp Phe Ser Asn Thr Leu Phe Leu
              1055                1060                1065

Leu Asp Glu Ser Ser Met Val Gly Asn Thr Glu Met Ala Arg Ala
              1070                1075                1080

Tyr Ala Leu Ile Ala Ala Gly Gly Gly Arg Ala Val Ala Ser Gly
              1085                1090                1095

Asp Thr Asp Gln Leu Gln Ala Ile Ala Pro Gly Gln Ser Phe Arg
              1100                1105                1110

Leu Gln Gln Thr Arg Ser Ala Ala Asp Val Val Ile Met Lys Glu
              1115                1120                1125

Ile Val Arg Gln Thr Pro Glu Leu Arg Glu Ala Val Tyr Ser Leu
              1130                1135                1140

Ile Asn Arg Asp Val Glu Arg Ala Leu Ser Gly Leu Glu Ser Val
              1145                1150                1155

Lys Pro Ser Gln Val Pro Arg Leu Glu Gly Ala Trp Ala Pro Glu
              1160                1165                1170

His Ser Val Thr Glu Phe Ser His Ser Gln Glu Ala Lys Leu Ala
              1175                1180                1185

Glu Ala Gln Gln Lys Ala Met Leu Lys Gly Glu Ala Phe Pro Asp
              1190                1195                1200

Ile Pro Met Thr Leu Tyr Glu Ala Ile Val Arg Asp Tyr Thr Gly
              1205                1210                1215

Arg Thr Pro Glu Ala Arg Glu Gln Thr Leu Ile Val Thr His Leu
              1220                1225                1230

Asn Glu Asp Arg Arg Val Leu Asn Ser Met Ile His Asp Ala Arg
              1235                1240                1245

Glu Lys Ala Gly Glu Leu Gly Lys Glu Gln Val Met Val Pro Val
              1250                1255                1260

Leu Asn Thr Ala Asn Ile Arg Asp Gly Glu Leu Arg Arg Leu Ser
              1265                1270                1275

Thr Trp Glu Lys Asn Pro Asp Ala Leu Ala Leu Val Asp Asn Val
              1280                1285                1290

Tyr His Arg Ile Ala Gly Ile Ser Lys Asp Asp Gly Leu Ile Thr
              1295                1300                1305

Leu Gln Asp Ala Glu Gly Asn Thr Arg Leu Ile Ser Pro Arg Glu
              1310                1315                1320

Ala Val Ala Glu Gly Val Thr Leu Tyr Thr Pro Asp Lys Ile Arg
              1325                1330                1335

Val Gly Thr Gly Asp Arg Met Arg Phe Thr Lys Ser Asp Arg Glu
              1340                1345                1350

Arg Gly Tyr Val Ala Asn Ser Val Trp Thr Val Thr Ala Val Ser
              1355                1360                1365

Gly Asp Ser Val Thr Leu Ser Asp Gly Gln Gln Thr Arg Val Ile
              1370                1375                1380

Arg Pro Gly Gln Glu Arg Ala Glu Gln His Ile Asp Leu Ala Tyr
              1385                1390                1395

Ala Ile Thr Ala His Gly Ala Gln Gly Ala Ser Glu Thr Phe Ala
              1400                1405                1410

Ile Ala Leu Glu Gly Thr Glu Gly Asn Arg Lys Leu Met Ala Gly
              1415                1420                1425
```

-continued

```
Phe Glu Ser Ala Tyr Val Ala Leu Ser Arg Met Lys Gln His Val
    1430            1435                1440
Gln Val Tyr Thr Asp Asn Arg Gln Gly Trp Thr Asp Ala Ile Asn
    1445            1450                1455
Asn Ala Val Gln Lys Gly Thr Ala His Asp Val Leu Glu Pro Lys
    1460            1465                1470
Pro Asp Arg Glu Val Met Asn Ala Gln Arg Leu Phe Ser Thr Ala
    1475            1480                1485
Arg Glu Leu Arg Asp Val Ala Ala Gly Arg Ala Val Leu Arg Gln
    1490            1495                1500
Ala Gly Leu Ala Gly Gly Asp Ser Pro Ala Arg Phe Ile Ala Pro
    1505            1510                1515
Gly Arg Lys Tyr Pro Gln Pro Tyr Val Ala Leu Pro Ala Phe Asp
    1520            1525                1530
Arg Asn Gly Lys Ser Ala Gly Ile Trp Leu Asn Pro Leu Thr Thr
    1535            1540                1545
Asp Asp Gly Asn Gly Leu Arg Gly Phe Ser Gly Glu Gly Arg Val
    1550            1555                1560
Lys Gly Ser Gly Asp Ala Gln Phe Val Ala Leu Gln Gly Ser Arg
    1565            1570                1575
Asn Gly Glu Ser Leu Leu Ala Asp Asn Met Gln Asp Gly Val Arg
    1580            1585                1590
Ile Ala Arg Asp Asn Pro Asp Ser Gly Val Val Arg Ile Ala
    1595            1600                1605
Gly Glu Gly Arg Pro Trp Asn Pro Gly Ala Ile Thr Gly Gly Arg
    1610            1615                1620
Val Trp Gly Asp Ile Pro Asp Asn Ser Val Gln Pro Gly Ala Gly
    1625            1630                1635
Asn Gly Glu Pro Val Thr Ala Glu Val Leu Ala Gln Arg Gln Ala
    1640            1645                1650
Glu Glu Ala Ile Arg Arg Glu Thr Glu Arg Arg Ala Asp Glu Ile
    1655            1660                1665
Val Arg Lys Met Ala Glu Asn Lys Pro Asp Leu Pro Asp Gly Lys
    1670            1675                1680
Thr Glu Leu Ala Val Arg Asp Ile Ala Gly Gln Glu Arg Asp Arg
    1685            1690                1695
Ser Ala Ile Ser Glu Arg Glu Thr Ala Leu Pro Glu Ser Val Leu
    1700            1705                1710
Arg Glu Ser Gln Arg Glu Arg Glu Ala Val Arg Glu Val Ala Arg
    1715            1720                1725
Glu Asn Leu Leu Gln Glu Arg Leu Gln Gln Met Glu Arg Asp Met
    1730            1735                1740
Val Arg Asp Leu Gln Lys Glu Lys Thr Leu Gly Gly Asp
    1745            1750                1755

<210> SEQ ID NO 411
<211> LENGTH: 726
<212> TYPE: PRT
<213> ORGANISM: Methanococcoides burtonii

<400> SEQUENCE: 411

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
```

```
            20                  25                  30
Gln Gln Gln Leu Val Leu Phe Glu Gly Ala Cys Gly Thr Gly Lys Thr
            35                  40                  45
Leu Ser Ala Leu Val Pro Ala Leu His Val Gly Lys Met Leu Gly Lys
 50                  55                  60
Thr Val Ile Ile Ala Thr Asn Val His Gln Met Val Gln Phe Ile
 65                  70                  75                  80
Asn Glu Ala Arg Asp Ile Lys Lys Val Gln Asp Val Lys Val Ala Val
                 85                  90                  95
Ile Lys Gly Lys Thr Ala Met Cys Pro Gln Glu Ala Asp Tyr Glu Glu
                100                 105                 110
Cys Ser Val Lys Arg Glu Asn Thr Phe Glu Leu Met Glu Thr Glu Arg
                115                 120                 125
Glu Ile Tyr Leu Lys Arg Gln Glu Leu Asn Ser Ala Arg Asp Ser Tyr
                130                 135                 140
Lys Lys Ser His Asp Pro Ala Phe Val Thr Leu Arg Asp Glu Leu Ser
145                 150                 155                 160
Lys Glu Ile Asp Ala Val Glu Lys Ala Arg Gly Leu Arg Asp Arg
                165                 170                 175
Ala Cys Asn Asp Leu Tyr Glu Val Leu Arg Ser Asp Ser Glu Lys Phe
                180                 185                 190
Arg Glu Trp Leu Tyr Lys Glu Val Arg Ser Pro Glu Glu Ile Asn Asp
                195                 200                 205
His Ala Ile Lys Asp Gly Met Cys Gly Tyr Glu Leu Val Lys Arg Glu
                210                 215                 220
Leu Lys His Ala Asp Leu Leu Ile Cys Asn Tyr His His Val Leu Asn
225                 230                 235                 240
Pro Asp Ile Phe Ser Thr Val Leu Gly Trp Ile Glu Lys Glu Pro Gln
                245                 250                 255
Glu Thr Ile Val Ile Phe Asp Glu Ala His Asn Leu Glu Ser Ala Ala
                260                 265                 270
Arg Ser His Ser Ser Leu Ser Leu Thr Glu His Ser Ile Glu Lys Ala
                275                 280                 285
Ile Thr Glu Leu Glu Ala Asn Leu Asp Leu Leu Ala Asp Asp Asn Ile
                290                 295                 300
His Asn Leu Phe Asn Ile Phe Leu Glu Val Ile Ser Asp Thr Tyr Asn
305                 310                 315                 320
Ser Arg Phe Lys Phe Gly Glu Arg Glu Arg Val Arg Lys Asn Trp Tyr
                325                 330                 335
Asp Ile Arg Ile Ser Asp Pro Tyr Glu Arg Asn Asp Ile Val Arg Gly
                340                 345                 350
Lys Phe Leu Arg Gln Ala Lys Gly Asp Phe Gly Glu Lys Asp Ile
                355                 360                 365
Gln Ile Leu Leu Ser Glu Ala Ser Glu Leu Gly Ala Lys Leu Asp Glu
                370                 375                 380
Thr Tyr Arg Asp Gln Tyr Lys Lys Gly Leu Ser Ser Val Met Lys Arg
385                 390                 395                 400
Ser His Ile Arg Tyr Val Ala Asp Phe Met Ser Ala Tyr Ile Glu Leu
                405                 410                 415
Ser His Asn Leu Asn Tyr Tyr Pro Ile Leu Asn Val Arg Arg Asp Met
                420                 425                 430
Asn Asp Glu Ile Tyr Gly Arg Val Glu Leu Phe Thr Cys Ile Pro Lys
                435                 440                 445
```

Asn Val Thr Glu Pro Leu Phe Asn Ser Leu Phe Ser Val Ile Leu Met
            450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Leu Phe Ala Lys Asn
            500                 505                 510

Arg Asp Asp Arg His Val Thr Glu Leu Leu Glu Gln Val Leu Leu Asp
            515                 520                 525

Ser Ile Glu Asn Ser Lys Gly Asn Val Ile Leu Phe Phe Gln Ser Ala
            530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Asn Gly Lys Ala Val Leu Leu Ser
            580                 585                 590

Tyr Leu Trp Gly Thr Leu Ser Glu Gly Ile Asp Tyr Arg Asp Gly Arg
            595                 600                 605

Gly Arg Thr Val Ile Ile Ile Gly Val Gly Tyr Pro Ala Leu Asn Asp
610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
            675                 680                 685

Lys Phe Ser Val Phe Glu Val Phe Pro Pro Ala Glu Arg Ser Glu Phe
690                 695                 700

Val Asp Val Asp Pro Glu Lys Val Lys Tyr Ser Leu Met Asn Phe Phe
705                 710                 715                 720

Met Asp Asn Asp Glu Gln
                725

<210> SEQ ID NO 412
<211> LENGTH: 439
<212> TYPE: PRT
<213> ORGANISM: Bacteriophage T4

<400> SEQUENCE: 412

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val

```
                85                  90                  95
Leu Phe Glu Gln Lys Glu Val Pro Asp Leu Ala Lys Cys Arg Val Leu
            100                 105                 110
Ile Cys Asp Glu Val Ser Met Tyr Asp Arg Lys Leu Phe Lys Ile Leu
            115                 120                 125
Leu Ser Thr Ile Pro Pro Trp Cys Thr Ile Ile Gly Ile Gly Asp Asn
            130                 135                 140
Lys Gln Ile Arg Pro Val Asp Pro Gly Glu Asn Thr Ala Tyr Ile Ser
145                 150                 155                 160
Pro Phe Phe Thr His Lys Asp Phe Tyr Gln Cys Glu Leu Thr Glu Val
                165                 170                 175
Lys Arg Ser Asn Ala Pro Ile Ile Asp Val Ala Thr Asp Val Arg Asn
                180                 185                 190
Gly Lys Trp Ile Tyr Asp Lys Val Val Asp Gly His Gly Val Arg Gly
                195                 200                 205
Phe Thr Gly Asp Thr Ala Leu Arg Asp Phe Met Val Asn Tyr Phe Ser
            210                 215                 220
Ile Val Lys Ser Leu Asp Asp Leu Phe Glu Asn Arg Val Met Ala Phe
225                 230                 235                 240
Thr Asn Lys Ser Val Asp Lys Leu Asn Ser Ile Ile Arg Lys Lys Ile
                245                 250                 255
Phe Glu Thr Asp Lys Asp Phe Ile Val Gly Glu Ile Ile Val Met Gln
            260                 265                 270
Glu Pro Leu Phe Lys Thr Tyr Lys Ile Asp Gly Lys Pro Val Ser Glu
            275                 280                 285
Ile Ile Phe Asn Asn Gly Gln Leu Val Arg Ile Ile Glu Ala Glu Tyr
290                 295                 300
Thr Ser Thr Phe Val Lys Ala Arg Gly Val Pro Gly Glu Tyr Leu Ile
305                 310                 315                 320
Arg His Trp Asp Leu Thr Val Glu Thr Tyr Gly Asp Asp Glu Tyr Tyr
                325                 330                 335
Arg Glu Lys Ile Lys Ile Ile Ser Ser Asp Glu Glu Leu Tyr Lys Phe
            340                 345                 350
Asn Leu Phe Leu Gly Lys Thr Ala Glu Thr Tyr Lys Asn Trp Asn Lys
        355                 360                 365
Gly Gly Lys Ala Pro Trp Ser Asp Phe Trp Asp Ala Lys Ser Gln Phe
    370                 375                 380
Ser Lys Val Lys Ala Leu Pro Ala Ser Thr Phe His Lys Ala Gln Gly
385                 390                 395                 400
Met Ser Val Asp Arg Ala Phe Ile Tyr Thr Pro Cys Ile His Tyr Ala
                405                 410                 415
Asp Val Glu Leu Ala Gln Gln Leu Leu Tyr Val Gly Val Thr Arg Gly
            420                 425                 430
Arg Tyr Asp Val Phe Tyr Val
            435

<210> SEQ ID NO 413
<211> LENGTH: 970
<212> TYPE: PRT
<213> ORGANISM: Citromicrobium bathyomarinum

<400> SEQUENCE: 413

Met Leu Ser Val Ala Asn Val Arg Ser Pro Ser Ala Ala Ala Ser Tyr
1               5                   10                  15
```

```
Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
 50                  55                  60

Ser Ser Val Gly Asn Pro Gly Gln Ala His Arg Pro Gly Thr Asp Leu
 65                  70                  75                  80

Thr Phe Ser Val Pro Lys Ser Trp Ser Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
 130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
        180                 185                 190

Ala Arg Phe Arg Val Ala Val Glu Lys Leu Gly Tyr Glu Pro Gly Pro
 195                 200                 205

Val Leu Lys His Gly Asn Phe Glu Ala Arg Gly Ile Ser Arg Glu Gln
 210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
        260                 265                 270

Glu Ala Ala Gln Ser Ile Gly Leu Asp Leu Lys Pro Leu Val Asp Arg
 275                 280                 285

Ala Arg Thr Lys Ala Leu Gly Gln Gly Met Glu Ala Thr Arg Ile Gly
 290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                325                 330                 335

Gln Asp Arg Gln Thr Ile Ala Ala Ala Gln Ala Val Ala Ser Ala Val
        340                 345                 350

Arg His Leu Ser Gln Arg Glu Ala Phe Glu Arg Thr Ala Leu Tyr
 355                 360                 365

Lys Ala Ala Leu Asp Phe Gly Leu Pro Thr Thr Ile Ala Asp Val Glu
 370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
        420                 425                 430

Ala Ile Thr Pro Gln Lys Ala Ala Ala Ser Val Gln Ala Ala Ala Leu
```

```
                    435                 440                 445
Thr Gly Gln Gly Phe Arg Leu Asn Glu Gly Gln Leu Ala Ala Ala Arg
450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                    485                 490                 495

Asp Glu Gly His Pro Val Ile Gly Leu Ala Ile Gln Asn Thr Leu Val
                500                 505                 510

Gln Met Leu Glu Arg Asp Thr Gly Ile Gly Ser Gln Thr Leu Ala Arg
                515                 520                 525

Phe Leu Gly Gly Trp Asn Lys Leu Leu Asp Asp Pro Gly Asn Val Ala
530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
                580                 585                 590

Lys Gln Leu Gly Ala Val Asp Ala Gly Lys Pro Phe Ala Leu Leu Gln
                595                 600                 605

Arg Ala Gly Ile Ala Arg Ala Glu Met Ala Thr Asn Leu Arg Ala Arg
610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
                660                 665                 670

Thr Arg Ala Arg Thr Ser Ile Tyr Ala Ser Gly Arg Ala Ile Arg Ser
                675                 680                 685

Ala Val Asn Ala Ala Val Gln Gln Gly Leu Leu Ala Ser Arg Glu Ile
                690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
                740                 745                 750

Arg Val Ile Gly Gln Asp Arg Lys Gly Lys Leu Val Glu Val Glu Asp
                755                 760                 765

Lys Arg Gly Lys Arg Phe Arg Phe Asp Pro Ala Arg Ile Arg Ala Gly
                770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
                820                 825                 830

Val Thr Phe Glu Thr Ser Lys Gly Asp Leu Val Glu Leu Lys Lys Asp
                835                 840                 845

Asp Pro Met Leu Lys Arg Ile Asp Leu Ala Tyr Ala Leu Asn Val His
                850                 855                 860
```

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
            885                 890                 895

Arg Leu Arg Asp His Leu Thr Leu Val Val Asp Ser Ala Asp Lys Leu
        900                 905                 910

Gly Ala Ala Val Ala Arg Asn Lys Gly Glu Lys Ala Ser Ala Ile Glu
            915                 920                 925

Val Thr Gly Ser Val Lys Pro Thr Ala Thr Lys Gly Ser Gly Val Asp
930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 414
<211> LENGTH: 262
<212> TYPE: PRT
<213> ORGANISM: Yokenella regensburgei

<400> SEQUENCE: 414

Cys Leu Thr Ala Pro Pro Lys Glu Ala Ala Lys Pro Thr Leu Met Pro
1               5                   10                  15

Arg Ala Gln Ser Tyr Arg Asp Leu Thr His Leu Pro Leu Pro Ser Gly
            20                  25                  30

Lys Val Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Val Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Asp Asn Asn Arg Ile Pro
            100                 105                 110

Leu Gln Ser Leu Thr Ala Ala Asn Val Met Ile Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Val Leu Ser Ser Val Asn
                165                 170                 175

Thr Ser Lys Thr Ile Leu Ser Tyr Glu Val Gln Ala Gly Val Phe Arg
            180                 185                 190

Phe Val Asp Tyr Gln Arg Leu Leu Glu Gly Ile Gly Tyr Thr Ser
        195                 200                 205

Asn Glu Pro Val Met Leu Cys Leu Met Ser Ala Ile Glu Thr Gly Val
    210                 215                 220

Ile Tyr Leu Ile Asn Asp Gly Ile Glu Arg Gly Leu Trp Asp Leu Gln
225                 230                 235                 240

Gln Lys Ala Asp Val Asp Asn Pro Ile Leu Ala Arg Tyr Arg Asn Met
                245                 250                 255

Ser Ala Pro Pro Glu Ser

<210> SEQ ID NO 415
<211> LENGTH: 262
<212> TYPE: PRT
<213> ORGANISM: Cronobacter pulveris

<400> SEQUENCE: 415

Cys Leu Thr Ala Pro Pro Lys Glu Ala Ala Lys Pro Thr Leu Met Pro
1               5                   10                  15

Arg Ala Gln Ser Tyr Arg Asp Leu Thr Asn Leu Pro Asp Pro Lys Gly
            20                  25                  30

Lys Leu Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ser Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Glu Asn Asn Arg Met Pro
            100                 105                 110

Leu Gln Ser Leu Val Ala Ala Asn Val Met Ile Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Gly Asp Thr Gln Tyr Gln Leu Asp Gln Ile Ala Val Asn
145                 150                 155                 160

Leu Arg Val Val Asn Val Ser Thr Gly Glu Val Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Ile Gly Tyr Thr Ala
        195                 200                 205

Asn Glu Pro Val Met Leu Cys Leu Met Ser Ala Ile Glu Thr Gly Val
    210                 215                 220

Ile His Leu Ile Asn Asp Gly Ile Asn Arg Gly Leu Trp Glu Leu Lys
225                 230                 235                 240

Asn Lys Gly Asp Ala Lys Asn Thr Ile Leu Ala Lys Tyr Arg Ser Met
                245                 250                 255

Ala Val Pro Pro Glu Ser
            260

<210> SEQ ID NO 416
<211> LENGTH: 262
<212> TYPE: PRT
<213> ORGANISM: Rahnella aquatilis

<400> SEQUENCE: 416

Cys Leu Thr Ala Ala Pro Lys Glu Ala Ala Arg Pro Thr Leu Leu Pro
1               5                   10                  15

Arg Ala Pro Ser Tyr Thr Asp Leu Thr His Leu Pro Ser Pro Gln Gly
            20                  25                  30

Arg Ile Phe Val Ser Val Tyr Asn Ile Gln Asp Glu Thr Gly Gln Phe
        35                  40                  45

Lys Pro Tyr Pro Ala Cys Asn Phe Ser Thr Ala Val Pro Gln Ser Ala

```
            50                  55                  60
Thr Ala Met Leu Val Ser Ala Leu Lys Asp Ser Lys Trp Phe Ile Pro
 65                  70                  75                  80

Leu Glu Arg Gln Gly Leu Gln Asn Leu Leu Asn Glu Arg Lys Ile Ile
                 85                  90                  95

Arg Ala Ala Gln Glu Asn Gly Ser Val Ala Ile Asn Asn Gln Arg Pro
            100                 105                 110

Leu Ser Ser Leu Val Ala Ala Asn Ile Leu Ile Glu Gly Ser Ile Ile
        115                 120                 125

Gly Tyr Glu Ser Asn Val Lys Ser Gly Gly Val Gly Ala Arg Tyr Phe
130                 135                 140

Gly Ile Gly Ala Ser Thr Gln Tyr Gln Leu Asp Gln Ile Ala Val Asn
145                 150                 155                 160

Leu Arg Ala Val Asp Val Asn Thr Gly Glu Val Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Leu Gly Tyr Thr Thr
        195                 200                 205

Asn Glu Pro Val Met Leu Cys Leu Met Ser Ala Ile Glu Ser Gly Val
210                 215                 220

Ile Tyr Leu Val Asn Asp Gly Ile Glu Arg Asn Leu Trp Gln Leu Gln
225                 230                 235                 240

Asn Pro Ser Glu Ile Asn Ser Pro Ile Leu Gln Arg Tyr Lys Asn Asn
                245                 250                 255

Ile Val Pro Ala Glu Ser
                260

<210> SEQ ID NO 417
<211> LENGTH: 259
<212> TYPE: PRT
<213> ORGANISM: Kluyvera ascorbata

<400> SEQUENCE: 417

Cys Ile Thr Ser Pro Pro Lys Gln Ala Ala Lys Pro Thr Leu Leu Pro
  1               5                  10                  15

Arg Ser Gln Ser Tyr Gln Asp Leu Thr His Leu Pro Glu Pro Gln Gly
                 20                  25                  30

Arg Leu Phe Val Ser Val Tyr Asn Ile Ser Asp Glu Thr Gly Gln Phe
            35                  40                  45

Lys Pro Tyr Pro Ala Ser Asn Phe Ser Thr Ser Val Pro Gln Ser Ala
 50                  55                  60

Thr Ala Met Leu Val Ser Ala Leu Lys Asp Ser Asn Trp Phe Ile Pro
 65                  70                  75                  80

Leu Glu Arg Gln Gly Leu Gln Asn Leu Leu Asn Glu Arg Lys Ile Ile
                 85                  90                  95

Arg Ala Ala Gln Glu Asn Gly Thr Val Ala Val Asn Asn Arg Thr Gln
            100                 105                 110

Leu Pro Ser Leu Val Ala Ala Asn Ile Leu Ile Glu Gly Ser Ile Ile
        115                 120                 125

Gly Tyr Glu Ser Asn Val Lys Ser Gly Gly Ala Gly Ala Arg Tyr Phe
130                 135                 140

Gly Ile Gly Ala Ser Thr Gln Tyr Gln Leu Asp Gln Ile Ala Val Asn
145                 150                 155                 160
```

```
Leu Arg Val Val Asn Val Ser Thr Gly Glu Val Leu Ser Ser Val Asn
                165                 170                 175

Thr Ser Lys Thr Ile Leu Ser Tyr Glu Phe Gln Ala Gly Val Phe Arg
            180                 185                 190

Tyr Ile Asp Tyr Gln Arg Leu Leu Glu Gly Glu Val Gly Tyr Thr Val
        195                 200                 205

Asn Glu Pro Val Met Leu Cys Leu Met Ser Ala Ile Glu Thr Gly Val
    210                 215                 220

Ile Tyr Leu Val Asn Asp Gly Ile Ser Arg Asn Leu Trp Gln Leu Lys
225                 230                 235                 240

Asn Ala Ser Asp Ile Asn Ser Pro Val Leu Glu Lys Tyr Lys Ser Ile
                245                 250                 255

Ile Val Pro

<210> SEQ ID NO 418
<211> LENGTH: 259
<212> TYPE: PRT
<213> ORGANISM: Hafnia alvei

<400> SEQUENCE: 418

Cys Leu Thr Ala Pro Pro Lys Gln Ala Ala Lys Pro Thr Leu Met Pro
1               5                   10                  15

Arg Ala Gln Ser Tyr Gln Asp Leu Thr His Leu Pro Glu Pro Ala Gly
            20                  25                  30

Lys Leu Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Ser Ala Leu Lys Asp Ser Gly Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Ala Ala Val Asn Asn Gln His Gln
            100                 105                 110

Leu Ser Ser Leu Val Ala Ala Asn Val Leu Val Glu Gly Ser Ile Ile
        115                 120                 125

Gly Tyr Glu Ser Asn Val Lys Ser Gly Gly Ala Gly Ala Arg Phe Phe
    130                 135                 140

Gly Ile Gly Ala Ser Thr Gln Tyr Gln Leu Asp Gln Ile Ala Val Asn
145                 150                 155                 160

Leu Arg Val Val Asp Val Asn Thr Gly Gln Val Leu Ser Ser Val Asn
                165                 170                 175

Thr Ser Lys Thr Ile Leu Ser Tyr Glu Val Gln Ala Gly Val Phe Arg
            180                 185                 190

Tyr Ile Asp Tyr Gln Arg Leu Leu Glu Gly Glu Ile Gly Tyr Thr Thr
        195                 200                 205

Asn Glu Pro Val Met Leu Cys Val Met Ser Ala Ile Glu Thr Gly Val
    210                 215                 220

Ile Tyr Leu Val Asn Asp Gly Ile Asn Arg Asn Leu Trp Thr Leu Lys
225                 230                 235                 240

Asn Pro Gln Asp Ala Lys Ser Ser Val Leu Glu Arg Tyr Lys Ser Thr
                245                 250                 255

Ile Val Pro
```

```
<210> SEQ ID NO 419
<211> LENGTH: 255
<212> TYPE: PRT
<213> ORGANISM: Enterobacteriaceae bacterium strain FGI 57

<400> SEQUENCE: 419

Cys Ile Thr Thr Pro Pro Gln Glu Ala Ala Lys Pro Thr Leu Leu Pro
1               5                   10                  15

Arg Asp Ala Thr Tyr Lys Asp Leu Val Ser Leu Pro Gln Pro Arg Gly
            20                  25                  30

Lys Ile Tyr Val Ala Val Tyr Asn Ile Gln Asp Glu Thr Gly Gln Phe
        35                  40                  45

Gln Pro Tyr Pro Ala Ser Asn Phe Ser Thr Ser Val Pro Gln Ser Ala
    50                  55                  60

Thr Ala Met Leu Val Ser Ser Leu Lys Asp Ser Arg Trp Phe Val Pro
65                  70                  75                  80

Leu Glu Arg Gln Gly Leu Asn Asn Leu Leu Asn Glu Arg Lys Ile Ile
                85                  90                  95

Arg Ala Ala Gln Gln Asn Gly Thr Val Gly Asp Asn Asn Ala Ser Pro
            100                 105                 110

Leu Pro Ser Leu Tyr Ser Ala Asn Val Ile Val Glu Gly Ser Ile Ile
        115                 120                 125

Gly Tyr Ala Ser Asn Val Lys Thr Gly Gly Phe Gly Ala Arg Tyr Phe
    130                 135                 140

Gly Ile Gly Gly Ser Thr Gln Tyr Gln Leu Asp Gln Val Ala Val Asn
145                 150                 155                 160

Leu Arg Ile Val Asn Val His Thr Gly Glu Val Leu Ser Ser Val Asn
                165                 170                 175

Thr Ser Lys Thr Ile Leu Ser Tyr Glu Ile Gln Ala Gly Val Phe Arg
            180                 185                 190

Phe Ile Asp Tyr Gln Arg Leu Leu Glu Gly Glu Ala Gly Phe Thr Thr
        195                 200                 205

Asn Glu Pro Val Met Thr Cys Leu Met Ser Ala Ile Glu Glu Gly Val
    210                 215                 220

Ile His Leu Ile Asn Asp Gly Ile Asn Lys Lys Leu Trp Ala Leu Ser
225                 230                 235                 240

Asn Ala Ala Asp Ile Asn Ser Glu Val Leu Thr Arg Tyr Arg Lys
                245                 250                 255

<210> SEQ ID NO 420
<211> LENGTH: 258
<212> TYPE: PRT
<213> ORGANISM: Plesiomonas shigelloides

<400> SEQUENCE: 420

Ile Thr Glu Val Pro Lys Glu Ala Ala Lys Pro Thr Leu Met Pro Arg
1               5                   10                  15

Ala Ser Thr Tyr Lys Asp Leu Val Ala Leu Pro Lys Pro Asn Gly Lys
            20                  25                  30

Ile Ile Val Ser Val Tyr Ser Val Gln Asp Glu Thr Gly Gln Phe Lys
        35                  40                  45

Pro Leu Pro Ala Ser Asn Phe Ser Thr Ala Val Pro Gln Ser Gly Asn
    50                  55                  60

Ala Met Leu Thr Ser Ala Leu Lys Asp Ser Gly Trp Phe Val Pro Leu
65                  70                  75                  80

Glu Arg Glu Gly Leu Gln Asn Leu Leu Asn Glu Arg Lys Ile Ile Arg
```

-continued

```
                85                  90                  95
Ala Ala Gln Glu Asn Gly Thr Val Ala Ala Asn Asn Gln Gln Pro Leu
            100                 105                 110

Pro Ser Leu Leu Ser Ala Asn Val Val Ile Glu Gly Ala Ile Ile Gly
            115                 120                 125

Tyr Asp Ser Asp Ile Lys Thr Gly Ala Gly Ala Arg Tyr Phe Gly
        130                 135                 140

Ile Gly Ala Asp Gly Lys Tyr Arg Val Asp Gln Val Ala Val Asn Leu
145                 150                 155                 160

Arg Ala Val Asp Val Arg Thr Gly Glu Val Leu Leu Ser Val Asn Thr
                165                 170                 175

Ser Lys Thr Ile Leu Ser Ser Glu Leu Ser Ala Gly Val Phe Arg Phe
                180                 185                 190

Ile Glu Tyr Gln Arg Leu Leu Glu Leu Glu Ala Gly Tyr Thr Thr Asn
                195                 200                 205

Glu Pro Val Met Met Cys Met Met Ser Ala Leu Glu Ala Gly Val Ala
            210                 215                 220

His Leu Ile Val Glu Gly Ile Arg Gln Asn Leu Trp Ser Leu Gln Asn
225                 230                 235                 240

Pro Ser Asp Ile Asn Asn Pro Ile Ile Gln Arg Tyr Met Lys Glu Asp
                245                 250                 255

Val Pro

<210> SEQ ID NO 421
<211> LENGTH: 248
<212> TYPE: PRT
<213> ORGANISM: Vibrio fischeri

<400> SEQUENCE: 421

Pro Glu Thr Ser Glu Ser Pro Thr Leu Met Gln Arg Gly Ala Asn Tyr
1               5                   10                  15

Ile Asp Leu Ile Ser Leu Pro Lys Pro Gln Gly Lys Ile Phe Val Ser
                20                  25                  30

Val Tyr Asp Phe Arg Asp Gln Thr Gly Gln Tyr Lys Pro Gln Pro Asn
            35                  40                  45

Ser Asn Phe Ser Thr Ala Val Pro Gln Gly Gly Thr Ala Leu Leu Thr
    50                  55                  60

Met Ala Leu Leu Asp Ser Glu Trp Phe Tyr Pro Leu Glu Arg Gln Gly
65                  70                  75                  80

Leu Gln Asn Leu Leu Thr Glu Arg Lys Ile Ile Arg Ala Ala Gln Lys
                85                  90                  95

Lys Gln Glu Ser Ile Ser Asn His Gly Ser Thr Leu Pro Ser Leu Leu
            100                 105                 110

Ser Ala Asn Val Met Ile Glu Gly Gly Ile Val Ala Tyr Asp Ser Asn
            115                 120                 125

Ile Lys Thr Gly Gly Ala Gly Ala Arg Tyr Leu Gly Ile Gly Gly Ser
        130                 135                 140

Gly Gln Tyr Arg Ala Asp Gln Val Thr Val Asn Ile Arg Ala Val Asp
145                 150                 155                 160

Val Arg Ser Gly Lys Ile Leu Thr Ser Val Thr Thr Ser Lys Thr Ile
                165                 170                 175

Leu Ser Tyr Glu Val Ser Ala Gly Ala Phe Arg Phe Val Asp Tyr Lys
                180                 185                 190

Glu Leu Leu Glu Val Glu Leu Gly Tyr Thr Asn Asn Glu Pro Val Asn
```

```
                    195                 200                 205

Ile Ala Leu Met Ser Ala Ile Asp Ser Ala Val Ile His Leu Ile Val
    210                 215                 220

Lys Gly Val Gln Gln Gly Leu Trp Arg Pro Ala Asn Leu Asp Thr Arg
225                 230                 235                 240

Asn Asn Pro Ile Phe Lys Lys Tyr
                245

<210> SEQ ID NO 422
<211> LENGTH: 248
<212> TYPE: PRT
<213> ORGANISM: Aliivibrio logei

<400> SEQUENCE: 422

Pro Asp Ala Ser Glu Ser Pro Thr Leu Met Gln Arg Gly Ala Thr Tyr
1               5                   10                  15

Leu Asp Leu Ile Ser Leu Pro Lys Pro Gln Gly Lys Ile Tyr Val Ser
            20                  25                  30

Val Tyr Asp Phe Arg Asp Gln Thr Gly Gln Tyr Lys Pro Gln Pro Asn
        35                  40                  45

Ser Asn Phe Ser Thr Ala Val Pro Gln Gly Gly Thr Ala Leu Leu Thr
    50                  55                  60

Met Ala Leu Leu Asp Ser Glu Trp Phe Tyr Pro Leu Glu Arg Gln Gly
65                  70                  75                  80

Leu Gln Asn Leu Leu Thr Glu Arg Lys Ile Ile Arg Ala Ala Gln Lys
                85                  90                  95

Lys Gln Glu Ser Ile Ser Asn His Gly Ser Thr Leu Pro Ser Leu Leu
            100                 105                 110

Ser Ala Asn Val Met Ile Glu Gly Gly Ile Val Ala Tyr Asp Ser Asn
        115                 120                 125

Ile Lys Thr Gly Gly Ala Gly Ala Arg Tyr Leu Gly Ile Gly Gly Ser
    130                 135                 140

Gly Gln Tyr Arg Ala Asp Gln Val Thr Val Asn Ile Arg Ala Val Asp
145                 150                 155                 160

Val Arg Ser Gly Lys Ile Leu Thr Ser Val Thr Thr Ser Lys Thr Ile
                165                 170                 175

Leu Ser Tyr Glu Leu Ser Ala Gly Ala Phe Arg Phe Val Asp Tyr Lys
            180                 185                 190

Glu Leu Leu Glu Val Glu Leu Gly Tyr Thr Asn Asn Glu Pro Val Asn
        195                 200                 205

Ile Ala Leu Met Ser Ala Ile Asp Ser Ala Val Ile His Leu Ile Val
    210                 215                 220

Lys Gly Ile Glu Glu Gly Leu Trp Arg Pro Glu Asn Gln Asn Gly Lys
225                 230                 235                 240

Glu Asn Pro Ile Phe Arg Lys Tyr
                245

<210> SEQ ID NO 423
<211> LENGTH: 254
<212> TYPE: PRT
<213> ORGANISM: Photobacterium sp. AK15

<400> SEQUENCE: 423

Pro Glu Thr Ser Lys Glu Pro Thr Leu Met Ala Arg Gly Thr Ala Tyr
1               5                   10                  15

Gln Asp Leu Val Ser Leu Pro Leu Pro Lys Gly Lys Val Tyr Val Ser
```

```
                20                  25                  30
Val Tyr Asp Phe Arg Asp Gln Thr Gly Gln Tyr Lys Pro Gln Pro Asn
            35                  40                  45
Ser Asn Phe Ser Thr Ala Val Pro Gln Gly Gly Ala Ala Leu Leu Thr
        50                  55                  60
Thr Ala Leu Leu Asp Ser Arg Trp Phe Met Pro Leu Glu Arg Glu Gly
65                  70                  75                  80
Leu Gln Asn Leu Thr Glu Arg Lys Ile Ile Arg Ala Ala Gln Lys
                85                  90                  95
Lys Asp Glu Ile Pro Thr Asn His Gly Val His Leu Pro Ser Leu Ala
            100                 105                 110
Ser Ala Asn Ile Met Val Glu Gly Gly Ile Val Ala Tyr Asp Thr Asn
        115                 120                 125
Ile Gln Thr Gly Gly Ala Gly Ala Arg Tyr Leu Gly Val Gly Ala Ser
        130                 135                 140
Gly Gln Tyr Arg Thr Asp Gln Val Thr Val Asn Ile Arg Ala Val Asp
145                 150                 155                 160
Val Arg Thr Gly Arg Ile Leu Leu Ser Val Thr Thr Ser Lys Thr Ile
                165                 170                 175
Leu Ser Lys Glu Leu Gln Thr Gly Val Phe Lys Phe Val Asp Tyr Lys
            180                 185                 190
Asp Leu Leu Glu Ala Glu Leu Gly Tyr Thr Thr Asn Glu Pro Val Asn
        195                 200                 205
Leu Ala Val Met Ser Ala Ile Asp Ala Ala Val Val His Val Ile Val
        210                 215                 220
Asp Gly Ile Lys Thr Gly Leu Trp Glu Pro Leu Arg Gly Glu Asp Leu
225                 230                 235                 240
Gln His Pro Ile Ile Gln Glu Tyr Met Asn Arg Ser Lys Pro
                245                 250

<210> SEQ ID NO 424
<211> LENGTH: 261
<212> TYPE: PRT
<213> ORGANISM: Aeromonas veronii

<400> SEQUENCE: 424

Cys Ala Thr His Ile Gly Ser Pro Val Ala Asp Glu Lys Ala Thr Leu
1               5                   10                  15
Met Pro Arg Ser Val Ser Tyr Lys Glu Leu Ile Ser Leu Pro Lys Pro
            20                  25                  30
Lys Gly Lys Ile Val Ala Ala Val Tyr Asp Phe Arg Asp Gln Thr Gly
        35                  40                  45
Gln Tyr Leu Pro Ala Pro Ala Ser Asn Phe Ser Thr Ala Val Thr Gln
    50                  55                  60
Gly Gly Val Ala Met Leu Ser Thr Ala Leu Trp Asp Ser Gln Trp Phe
65              70                  75                  80
Val Pro Leu Glu Arg Glu Gly Leu Gln Asn Leu Leu Thr Glu Arg Lys
                85                  90                  95
Ile Val Arg Ala Ala Gln Asn Lys Pro Asn Val Pro Gly Asn Asn Ala
            100                 105                 110
Asn Gln Leu Pro Ser Leu Val Ala Ala Asn Ile Leu Ile Glu Gly Gly
        115                 120                 125
Ile Val Ala Tyr Asp Ser Asn Val Arg Thr Gly Gly Ala Gly Ala Lys
        130                 135                 140
```

```
Tyr Phe Gly Ile Gly Ala Ser Gly Glu Tyr Arg Val Asp Gln Val Thr
145                 150                 155                 160

Val Asn Leu Arg Ala Val Asp Ile Arg Ser Gly Arg Ile Leu Asn Ser
                165                 170                 175

Val Thr Thr Ser Lys Thr Val Met Ser Gln Val Gln Ala Gly Val
                180                 185                 190

Phe Arg Phe Val Glu Tyr Lys Arg Leu Leu Glu Ala Glu Gly Phe
                195                 200                 205

Ser Thr Asn Glu Pro Val Gln Met Cys Val Met Ser Ala Ile Glu Ser
                210                 215                 220

Gly Val Ile Arg Leu Ile Ala Asn Gly Val Arg Asp Asn Leu Trp Gln
225                 230                 235                 240

Leu Ala Asp Gln Arg Asp Ile Asp Asn Pro Ile Leu Gln Glu Tyr Leu
                245                 250                 255

Gln Asp Asn Ala Pro
                260

<210> SEQ ID NO 425
<211> LENGTH: 239
<212> TYPE: PRT
<213> ORGANISM: Shewanella sp. ECSMB14101

<400> SEQUENCE: 425

Ala Ser Ser Leu Met Pro Lys Gly Glu Ser Tyr Tyr Asp Leu Ile
1               5                   10                  15

Asn Leu Pro Ala Pro Gln Gly Val Met Leu Ala Ala Val Tyr Asp Phe
                20                  25                  30

Arg Asp Gln Thr Gly Gln Tyr Lys Pro Ile Pro Ser Ser Asn Phe Ser
                35                  40                  45

Thr Ala Val Pro Gln Ser Gly Thr Ala Phe Leu Ala Gln Ala Leu Asn
50                  55                  60

Asp Ser Ser Trp Phe Ile Pro Val Glu Arg Glu Gly Leu Gln Asn Leu
65                  70                  75                  80

Leu Thr Glu Arg Lys Ile Val Arg Ala Gly Leu Lys Gly Asp Ala Asn
                85                  90                  95

Lys Leu Pro Gln Leu Asn Ser Ala Gln Ile Leu Met Glu Gly Gly Ile
                100                 105                 110

Val Ala Tyr Asp Thr Asn Val Arg Thr Gly Gly Ala Gly Ala Arg Tyr
                115                 120                 125

Leu Gly Ile Gly Ala Ala Thr Gln Phe Arg Val Asp Thr Val Thr Val
130                 135                 140

Asn Leu Arg Ala Val Asp Ile Arg Thr Gly Arg Leu Leu Ser Ser Val
145                 150                 155                 160

Thr Thr Thr Lys Ser Ile Leu Ser Lys Glu Ile Thr Ala Gly Val Phe
                165                 170                 175

Lys Phe Ile Asp Ala Gln Glu Leu Leu Glu Ser Glu Leu Gly Tyr Thr
                180                 185                 190

Ser Asn Glu Pro Val Ser Leu Cys Val Ala Ser Ala Ile Glu Ser Ala
                195                 200                 205

Val Val His Met Ile Ala Asp Gly Ile Trp Lys Gly Ala Trp Asn Leu
                210                 215                 220

Ala Asp Gln Ala Ser Gly Leu Arg Ser Pro Val Leu Gln Lys Tyr
225                 230                 235

<210> SEQ ID NO 426
```

<211> LENGTH: 233
<212> TYPE: PRT
<213> ORGANISM: Pseudomonas putida

<400> SEQUENCE: 426

Gln Asp Ser Glu Thr Pro Thr Leu Thr Pro Arg Ala Ser Thr Tyr Tyr
1               5                   10                  15

Asp Leu Ile Asn Met Pro Arg Pro Lys Gly Arg Leu Met Ala Val Val
            20                  25                  30

Tyr Gly Phe Arg Asp Gln Thr Gly Gln Tyr Lys Pro Thr Pro Ala Ser
        35                  40                  45

Ser Phe Ser Thr Ser Val Thr Gln Gly Ala Ala Ser Met Leu Met Asp
    50                  55                  60

Ala Leu Ser Ala Ser Gly Trp Phe Val Val Leu Glu Arg Glu Gly Leu
65                  70                  75                  80

Gln Asn Leu Leu Thr Glu Arg Lys Ile Ile Arg Ala Ser Gln Lys Lys
                85                  90                  95

Pro Asp Val Ala Glu Asn Ile Met Gly Glu Leu Pro Pro Leu Gln Ala
            100                 105                 110

Ala Asn Leu Met Leu Glu Gly Gly Ile Ile Ala Tyr Asp Thr Asn Val
        115                 120                 125

Arg Ser Gly Gly Glu Gly Ala Arg Tyr Leu Gly Ile Asp Ile Ser Arg
    130                 135                 140

Glu Tyr Arg Val Asp Gln Val Thr Val Asn Leu Arg Ala Val Asp Val
145                 150                 155                 160

Arg Thr Gly Gln Val Leu Ala Asn Val Met Thr Ser Lys Thr Ile Tyr
                165                 170                 175

Ser Val Gly Arg Ser Ala Gly Val Phe Lys Phe Ile Glu Phe Lys Lys
            180                 185                 190

Leu Leu Glu Ala Glu Val Gly Tyr Thr Thr Asn Glu Pro Ala Gln Leu
        195                 200                 205

Cys Val Leu Ser Ala Ile Glu Ser Ala Val Gly His Leu Leu Ala Gln
    210                 215                 220

Gly Ile Glu Gln Arg Leu Trp Gln Val
225                 230

<210> SEQ ID NO 427
<211> LENGTH: 234
<212> TYPE: PRT
<213> ORGANISM: Shewanella violacea DSS12

<400> SEQUENCE: 427

Met Pro Lys Ser Asp Thr Tyr Tyr Asp Leu Ile Gly Leu Pro His Pro
1               5                   10                  15

Gln Gly Ser Met Leu Ala Ala Val Tyr Asp Phe Arg Asp Gln Thr Gly
            20                  25                  30

Gln Tyr Lys Ala Ile Pro Ser Ser Asn Phe Ser Thr Ala Val Pro Gln
        35                  40                  45

Ser Gly Thr Ala Phe Leu Ala Gln Ala Leu Asn Asp Ser Ser Trp Phe
    50                  55                  60

Val Pro Val Glu Arg Glu Gly Leu Gln Asn Leu Leu Thr Glu Arg Lys
65                  70                  75                  80

Ile Val Arg Ala Gly Leu Lys Gly Glu Ala Asn Gln Leu Pro Gln Leu
                85                  90                  95

Ser Ser Ala Gln Ile Leu Met Glu Gly Gly Ile Val Ala Tyr Asp Thr
            100                 105                 110

```
Asn Ile Lys Thr Gly Gly Ala Gly Ala Arg Tyr Leu Gly Ile Gly Val
        115                 120                 125

Asn Ser Lys Phe Arg Val Asp Thr Val Thr Val Asn Leu Arg Ala Val
        130                 135                 140

Asp Ile Arg Thr Gly Arg Leu Leu Ser Ser Val Thr Thr Thr Lys Ser
145                 150                 155                 160

Ile Leu Ser Lys Glu Val Ser Ala Gly Val Phe Lys Phe Ile Asp Ala
                165                 170                 175

Gln Asp Leu Leu Glu Ser Glu Leu Gly Tyr Thr Ser Asn Glu Pro Val
            180                 185                 190

Ser Leu Cys Val Ala Gln Ala Ile Glu Ser Ala Val Val His Met Ile
            195                 200                 205

Ala Asp Gly Ile Trp Lys Arg Ala Trp Asn Leu Ala Asp Thr Ala Ser
210                 215                 220

Gly Leu Asn Asn Pro Val Leu Gln Lys Tyr
225                 230

<210> SEQ ID NO 428
<211> LENGTH: 245
<212> TYPE: PRT
<213> ORGANISM: Marinobacterium jannaschii

<400> SEQUENCE: 428

Leu Thr Arg Arg Met Ser Thr Tyr Gln Asp Leu Ile Asp Met Pro Ala
1               5                   10                  15

Pro Arg Gly Lys Ile Val Thr Ala Val Tyr Ser Phe Arg Asp Gln Ser
                20                  25                  30

Gly Gln Tyr Lys Pro Ala Pro Ser Ser Ser Phe Ser Thr Ala Val Thr
            35                  40                  45

Gln Gly Ala Ala Ala Met Leu Val Asn Val Leu Asn Asp Ser Gly Trp
50                  55                  60

Phe Ile Pro Leu Glu Arg Glu Gly Leu Gln Asn Ile Leu Thr Glu Arg
65                  70                  75                  80

Lys Ile Ile Arg Ala Ala Leu Lys Lys Asp Asn Val Pro Val Asn Asn
                85                  90                  95

Ser Ala Gly Leu Pro Ser Leu Leu Ala Ala Asn Ile Met Leu Glu Gly
            100                 105                 110

Gly Ile Val Gly Tyr Asp Ser Asn Ile His Thr Gly Gly Ala Gly Ala
        115                 120                 125

Arg Tyr Phe Gly Ile Gly Ala Ser Glu Lys Tyr Arg Val Asp Glu Val
        130                 135                 140

Thr Val Asn Leu Arg Ala Ile Asp Ile Arg Thr Gly Arg Ile Leu His
145                 150                 155                 160

Ser Val Leu Thr Ser Lys Lys Ile Leu Ser Arg Glu Ile Arg Ser Asp
                165                 170                 175

Val Tyr Arg Phe Ile Glu Phe Lys His Leu Leu Glu Met Glu Ala Gly
            180                 185                 190

Ile Thr Thr Asn Asp Pro Ala Gln Leu Cys Val Leu Ser Ala Ile Glu
        195                 200                 205

Ser Ala Val Ala His Leu Ile Val Asp Gly Val Ile Lys Lys Ser Trp
        210                 215                 220

Ser Leu Ala Asp Pro Asn Glu Leu Asn Ser Pro Val Ile Gln Ala Tyr
225                 230                 235                 240

Gln Gln Gln Arg Ile
            245
```

<210> SEQ ID NO 429
<211> LENGTH: 234
<212> TYPE: PRT
<213> ORGANISM: Chryseobacterium oranimense G311

<400> SEQUENCE: 429

```
Pro Ser Asp Pro Glu Arg Ser Thr Met Gly Glu Leu Thr Pro Ser Thr
1               5                   10                  15

Ala Glu Leu Arg Asn Leu Pro Leu Pro Asn Glu Lys Ile Val Ile Gly
            20                  25                  30

Val Tyr Lys Phe Arg Asp Gln Thr Gly Gln Tyr Lys Pro Ser Glu Asn
        35                  40                  45

Gly Asn Asn Trp Ser Thr Ala Val Pro Gln Gly Thr Thr Thr Ile Leu
    50                  55                  60

Ile Lys Ala Leu Glu Asp Ser Arg Trp Phe Ile Pro Ile Glu Arg Glu
65                  70                  75                  80

Asn Ile Ala Asn Leu Leu Asn Glu Arg Gln Ile Ile Arg Ser Thr Arg
                85                  90                  95

Gln Glu Tyr Met Lys Asp Ala Asp Lys Asn Ser Gln Ser Leu Pro Pro
            100                 105                 110

Leu Leu Tyr Ala Gly Ile Leu Leu Glu Gly Gly Val Ile Ser Tyr Asp
        115                 120                 125

Ser Asn Thr Met Thr Gly Gly Phe Gly Ala Arg Tyr Phe Gly Ile Gly
    130                 135                 140

Ala Ser Thr Gln Tyr Arg Gln Asp Arg Ile Thr Ile Tyr Leu Arg Ala
145                 150                 155                 160

Val Ser Thr Leu Asn Gly Glu Ile Leu Lys Thr Val Tyr Thr Ser Lys
                165                 170                 175

Thr Ile Leu Ser Thr Ser Val Asn Gly Ser Phe Phe Arg Tyr Ile Asp
            180                 185                 190

Thr Glu Arg Leu Leu Glu Ala Glu Val Gly Leu Thr Gln Asn Glu Pro
        195                 200                 205

Val Gln Leu Ala Val Thr Glu Ala Ile Glu Lys Ala Val Arg Ser Leu
    210                 215                 220

Ile Ile Glu Gly Thr Arg Asp Lys Ile Trp
225                 230
```

<210> SEQ ID NO 430
<211> LENGTH: 12
<212> TYPE: DNA
<213> ORGANISM: artificial sequence
<220> FEATURE:
<223> OTHER INFORMATION: polynucleotide sequence used in Example 18

<400> SEQUENCE: 430
tttttttttt tt                                                                12

<210> SEQ ID NO 431
<211> LENGTH: 27
<212> TYPE: DNA
<213> ORGANISM: artificial sequence
<220> FEATURE:
<223> OTHER INFORMATION: polynucleotide sequence used in Example 18

<400> SEQUENCE: 431
ggttgtttct gttggtgctg atattgc                                                27

<210> SEQ ID NO 432
<211> LENGTH: 3635
<212> TYPE: DNA
<213> ORGANISM: artificial sequence
<220> FEATURE:
<223> OTHER INFORMATION: polynucleotide sequence used in Example 18

<400> SEQUENCE: 432

| | | | | | |
|---|---|---|---|---|---|
| gccatcagat | tgtgtttgtt | agtcgctgcc | atcagattgt | gtttgttagt | cgctttttttt | 60 |
| ttttggaatt | ttttttttgg | aattttttttt | ttgcgctaac | aacctcctgc | cgttttgccc | 120 |
| gtgcatatcg | gtcacgaaca | aatctgatta | ctaaacacag | tagcctggat | ttgttctatc | 180 |
| agtaatcgac | cttattccta | attaaataga | gcaaatcccc | ttattggggg | taagacatga | 240 |
| agatgccaga | aaacatgac | ctgttggccg | ccattctcgc | ggcaaaggaa | caaggcatcg | 300 |
| gggcaatcct | tgcgtttgca | atggcgtacc | ttcgcggcag | atataatggc | ggtgcgttta | 360 |
| caaaaacagt | aatcgacgca | acgatgtgcg | ccattatcgc | ctagttcatt | cgtgaccttc | 420 |
| tcgacttcgc | cggactaagt | agcaatctcg | cttatataac | gagcgtgttt | atcggctaca | 480 |
| tcggtactga | ctcgattggt | tcgcttatca | aacgcttcgc | tgctaaaaaa | gccggagtag | 540 |
| aagatggtag | aaatcaataa | tcaacgtaag | gcgttcctcg | atatgctggc | gtggtcggag | 600 |
| ggaactgata | acggacgtca | gaaaaccaga | aatcatggtt | atgacgtcat | tgtaggcgga | 660 |
| gagctattta | ctgattactc | cgatcaccct | cgcaaacttg | tcacgctaaa | cccaaaactc | 720 |
| aaatcaacag | gcgccggacg | ctaccagctt | cttttcccgtt | ggtgggatgc | ctaccgcaag | 780 |
| cagcttggcc | tgaaagactt | ctctccgaaa | agtcaggacg | ctgtggcatt | gcagcagatt | 840 |
| aaggagcgtg | gcgctttacc | tatgattgat | cgtggtgata | ccgtcaggc | aatcgaccgt | 900 |
| tgcagcaata | tctgggcttc | actgccgggc | gctggttatg | gtcagttcga | gcataaggct | 960 |
| gacagcctga | ttgcaaaatt | caaagaagcg | ggcggaacgg | tcagagagat | tgatgtatga | 1020 |
| gcagagtcac | cgcgattatc | tccgctctgg | ttatctgcat | catcgtctgc | ctgtcatggg | 1080 |
| ctgttaatca | ttaccgtgat | aacgccatta | cctacaaagc | ccagcgcgac | aaaaatgcca | 1140 |
| gagaactgaa | gctggcgaac | gcggcaatta | ctgacatgca | gatgcgtcag | cgtgatgttg | 1200 |
| ctgcgctcga | tgcaaaatac | acgaaggagt | tagctgatgc | taaagctgaa | aatgatgctc | 1260 |
| tgcgtgatga | tgttgccgct | ggtcgtcgtc | ggttgcacat | caaagcagtc | tgtcagtcag | 1320 |
| tgcgtgaagc | caccaccgcc | tccggcgtgg | ataatgcagc | ctcccccga | ctggcagaca | 1380 |
| ccgctgaacg | ggattatttc | accctcagag | agaggctgat | cactatgcaa | aaacaactgg | 1440 |
| aaggaaccca | gaagtatatt | aatgagcagt | gcagatagag | ttgcccatat | cgatgggcaa | 1500 |
| ctcatgcaat | tattgtgagc | aatacacacg | cgcttccagc | ggagtataaa | tgcctaaagt | 1560 |
| aataaaaccg | agcaatccat | ttacgaatgt | ttgctgggtt | tctgttttaa | caacattttc | 1620 |
| tgcgccgcca | caaattttgg | ctgcatcgac | agtttttcttc | tgcccaattc | cagaaacgaa | 1680 |
| gaaatgatgg | gtgatggttt | cctttggtgc | tactgctgcc | ggtttgtttt | gaacagtaaa | 1740 |
| cgtctgttga | gcacatcctg | taataagcag | ggccagcgca | gtagcgagta | gcattttttt | 1800 |
| catggtgtta | ttcccgatgc | ttttttgaagt | tcgcagaatc | gtatgtgtag | aaaattaaac | 1860 |
| aaaccctaaa | caatgagttg | aaatttcata | ttgttaatat | ttattaatgt | atgtcaggtg | 1920 |
| cgatgaatcg | tcattgtatt | cccggattaa | ctatgtccac | agccctgacg | ggaacttct | 1980 |
| ctgcgggagt | gtccgggaat | aattaaaacg | atgcacacag | gtttagcgc | gtacacgtat | 2040 |
| tgcattatgc | caacgccccg | gtgctgacac | ggaagaaacc | ggacgttatg | atttagcgtg | 2100 |

```
gaaagatttg tgtagtgttc tgaatgctct cagtaaatag taatgaatta tcaaaggtat    2160
agtaatatct tttatgttca tggatatttg taacccatcg gaaaactcct gctttagcaa    2220
gattttccct gtattgctga aatgtgattt ctcttgattt caacctatca taggacgttt    2280
ctataagatg cgtgtttctt gagaatttaa catttacaac ctttttaagt ccttttatta    2340
acacggtgtt atcgtttcct aacacgatgt gaatattatc tgtggctaga tagtaaatat    2400
aatgtgagac gttgtgacgt tttagttcag aataaaacaa ttcacagtct aaatcttttc    2460
gcacttgatc gaatatttct ttaaaaatgg caacctgagc cattggtaaa accttccatg    2520
tgatacgagg gcgcgtagtt tgcattatcg tttttatcgt ttcaatctgg tctgacctcc    2580
ttgtgttttg ttgatgattt atgtcaaata ttaggaatgt tttcacttaa tagtattggt    2640
tgcgtaacaa agtgcggtcc tgctggcatt ctggagggaa atacaaccga cagatgtatg    2700
taaggccaac gtgctcaaat cttcatacag aaagatttga agtaatattt taaccgctag    2760
atgaagagca agcgcatgga gcgacaaaat gaataaagaa caatctgctg atgatccctc    2820
cgtggatctg attcgtgtaa aaaatatgct taatagcacc atttctatga gttaccctga    2880
tgttgtaatt gcatgtatag aacataaggt gtctctggaa gcattcagag caattgaggc    2940
agcgttggtg aagcacgata ataatatgaa ggattattcc ctggtggttg actgatcacc    3000
ataactgcta atcattcaaa ctatttagtc tgtgacagag ccaacacgca gtctgtcact    3060
gtcaggaaag tggtaaaact gcaactcaat tactgcaatg ccctcgtaat taagtgaatt    3120
tacaatatcg tcctgttcgg agggaagaac gcgggatgtt cattcttcat cacttttaat    3180
tgatgtatat gctctctttt ctgacgttag tctccgacgg caggcttcaa tgacccaggc    3240
tgagaaattc ccggacccct tttgctcaag agcgatgtta atttgttcaa tcatttggtt    3300
aggaaagcgg atgttgcggg ttgttgttct gcgggttctg ttcttcgttg acatgaggtt    3360
gccccgtatt cagtgtcgct gatttgtatt gtctgaagtt gtttttacgt taagttgatg    3420
cagatcaatt aatacgatac ctgcgtcata attgattatt tgacgtggtt tgatggcctc    3480
cacgcacgtt gtgatatgta gatgataatc attatcactt tacgggtcct ttccggtgaa    3540
aaaaaaggta ccaaaaaaaa catcgtcgtg agtagtgaac cgtaagccgt tctgtttatg    3600
tttcttggac actgattgac acggtttagt agaac                              3635
```

<210> SEQ ID NO 433
<211> LENGTH: 3636
<212> TYPE: DNA
<213> ORGANISM: artificial sequence
<220> FEATURE:
<223> OTHER INFORMATION: polynucleotide sequence used in Example 18

<400> SEQUENCE: 433

```
tttttttttt tttttttttt tttttttttca agaaacataa acagaacgtg cttacggttc      60
actactcacg acgatgtttt ttttggtacc ttttttttca ccggaaagga cccgtaaagt     120
gataatgatt atcatctaca tatcacaacg tgcgtggagg ccatcaaacc acgtcaaata     180
atcaattatg acgcaggtat cgtattaatt gatctgcatc aacttaacgt aaaaacaact     240
tcagacaata caaatcagcg acactgaata cggggcaacc tcatgtcaac gaagaacaga     300
acccgcagaa caacaacccg caacatccgc tttcctaacc aaatgattga acaaattaac     360
atcgctcttg agcaaaaagg gtccgggaat ttctcagcct gggtcattga agcctgccgt     420
cggagactaa cgtcagaaaa gagagcatat acatcaatta aagtgatgag agaatgaaca     480
```

-continued

| | | |
|---|---|---|
| tcccgcgttc ttccctccga acaggacgat attgtaaatt cacttaatta cgagggcatt | 540 |
| gcagtaattg agttgcagtt ttaccacttt cctgacagtg acagactgcg tgttggctct | 600 |
| gtcacagact aaatagtttg aatgattagc agttatggtg atcagtcaac caccagggaa | 660 |
| taatccttca tattattatc gtgcttcacc aacgctgcct caattgctct gaatgcttcc | 720 |
| agagacacct tatgttctat acatgcaatt acaacatcag ggtaactcat agaaatggtg | 780 |
| ctattaagca tattttttac acgaatcaga tccacggagg gatcatcagc agattgttct | 840 |
| ttattcattt tgtcgctcca tgcgcttgct cttcatctag cggttaaaat attacttcaa | 900 |
| atctttctgt atgaagattt gagcacgttg gccttacata catctgtcgg ttgtatttcc | 960 |
| ctccagaatg ccagcaggac cgcactttgt tacgcaacca atactattaa gtgaaaacat | 1020 |
| tcctaatatt tgacataaat catcaacaaa acacaaggag gtcagaccag attgaaacga | 1080 |
| taaaaacgat aatgcaaact acgcgccctc gtatcacatg gaaggtttta ccaatggctc | 1140 |
| aggttgccat ttttaaagaa atattcgatc aagtgcgaaa agatttagac tgtgaattgt | 1200 |
| tttattctga actaaaacgt cacaacgtct cacattatat ttactatcta gccacagata | 1260 |
| atattcacat cgtgttagaa aacgataaca ccgtgttaat aaaaggactt aaaaaggttg | 1320 |
| taaatgttaa attctcaaga aacacgcatc ttatagaaac gtcctatgat aggttgaaat | 1380 |
| caagagaaat cacatttcag caatacaggg aaaatcttgc taaagcagga gttttccgat | 1440 |
| gggttacaaa tatccatgaa cataaaagat attactatac ctttgataat tcattactat | 1500 |
| ttactgagag cattcagaac actacacaaa tctttccacg ctaaatcata acgtccggtt | 1560 |
| tcttccgtgt cagcaccggg gcgttggcat aatgcaatac gtgtacgcgc taaaccctgt | 1620 |
| gtgcatcgtt ttaattattc ccggacactc ccgcagagaa gttccccgtc agggctgtgg | 1680 |
| acatagttaa tccgggaata caatgacgat tcatcgcacc tgacatacat taataaatat | 1740 |
| taacaatatg aaatttcaac tcattgtttta gggtttgttt aattttctac acatacgatt | 1800 |
| ctgcgaactt caaaaagcat cgggaataac accatgaaaa aaatgctact cgctactgcg | 1860 |
| ctggccctgc ttattacagg atgtgctcaa cagacgttta ctgttcaaaa caaaccggca | 1920 |
| gcagtagcac caaaggaaac catcacccat catttcttcg tttctggaat tgggcagaag | 1980 |
| aaaactgtcg atgcagccaa aatttgtggc ggcgcagaaa atgttgttaa aacagaaacc | 2040 |
| cagcaaacat tcgtaaatgg attgctcggt tttattactt taggcattta tactccgctg | 2100 |
| gaagcgcgtg tgtattgctc acaataattg catgagttgc ccatcgatat gggcaactct | 2160 |
| atctgcactg ctcattaata tacttctggg ttccttccag ttgttttttgc atagtgatca | 2220 |
| gcctctctct gagggtgaaa taatcccgtt cagcggtgtc tgccagtcgg ggggaggctg | 2280 |
| cattatccac gccggaggcg gtggtggctt cacgcactga ctgacagact gctttgatgt | 2340 |
| gcaaccgacg acgaccagcg gcaacatcat cacgcagagc atcattttca gctttagcat | 2400 |
| cagctaactc cttcgtgtat tttgcatcga gcgcagcaac atcacgctga cgcatctgca | 2460 |
| tgtcagtaat tgccgcgttc gccagcttca gttctctggc attttttgtcg cgctgggctt | 2520 |
| tgtaggtaat ggcgttatca cggtaatgat taacagccca tgacaggcag acgatgatgc | 2580 |
| agataaccag agcggagata atcgcggtga ctctgctcat acatcaatct ctctgaccgt | 2640 |
| tccgcccgct tctttgaatt ttgcaatcag gctgtcagcc ttatgctcga actgaccata | 2700 |
| accagcgccc ggcagtgaag cccagatatt gctgcaacgg tcgattgcct gacggatatc | 2760 |
| accacgatca atcataggta aagcgccacg ctccttaatc tgctgcaatg ccacagcgtc | 2820 |
| ctgacttttc ggagagaagt ctttcaggcc aagctgcttg cggtaggcat cccaccaacg | 2880 |

-continued

```
ggaaagaagc tggtagcgtc cggcgcctgt tgatttgagt tttgggttta gcgtgacaag    2940
tttgcgaggg tgatcggagt aatcagtaaa tagctctccg cctacaatga cgtcataacc    3000
atgatttctg gttttctgac gtccgttatc agttccctcc gaccacgcca gcatatcgag    3060
gaacgcctta cgttgattat tgatttctac catcttctac tccggctttt ttagcagcga    3120
agcgtttgat aagcgaacca atcgagtcag taccgatgta gccgataaac acgctcgtta    3180
tataagcgag attgctactt agtccggcga agtcgagaag gtcacgaatg aactaggcga    3240
taatggcgca catcgttgcg tcgattactg ttttgtaaa cgcaccgcca ttatatctgc     3300
cgcgaaggta cgccattgca aacgcaagga ttgccccgat gccttgttcc tttgccgcga    3360
gaatggcggc aacaggtca tgttttctg gcatcttcat gtcttacccc caataagggg      3420
atttgctcta tttaattagg aataaggtcg attactgata gaacaaatcc aggctactgt    3480
gtttagtaat cagatttgtt cgtgaccgat atgcacgggc aaaacggcag gaggttgtta    3540
gcgcaaaaaa aaaattccaa aaaaaaaatt ccaaaaaaaa aaagcgacta acaaacacaa    3600
tctgatggca gcgactaaca aacacaatct gatggc                              3636
```

<210> SEQ ID NO 434
<211> LENGTH: 28
<212> TYPE: DNA
<213> ORGANISM: artificial sequence
<220> FEATURE:
<223> OTHER INFORMATION: polynucleotide sequence used in Example 18

<400> SEQUENCE: 434
gcaatatcag caccaacaga aacaacct                                        28

<210> SEQ ID NO 435
<211> LENGTH: 10
<212> TYPE: PRT
<213> ORGANISM: artificial sequence
<220> FEATURE:
<223> OTHER INFORMATION: amino acid sequence of StepII(C)

<400> SEQUENCE: 435

Ser Ala Trp Ser His Pro Gln Phe Glu Lys
1               5                   10

<210> SEQ ID NO 436
<211> LENGTH: 15
<212> TYPE: PRT
<213> ORGANISM: artificial sequence
<220> FEATURE:
<223> OTHER INFORMATION: amino acid sequence of Pro

<400> SEQUENCE: 436

Met Gln Arg Leu Phe Leu Leu Val Ala Val Met Leu Leu Ser Gly
1               5                   10                  15

<210> SEQ ID NO 437
<211> LENGTH: 22
<212> TYPE: DNA
<213> ORGANISM: artificial sequence
<220> FEATURE:
<223> OTHER INFORMATION: Primer

<400> SEQUENCE: 437
tctttaaccg ccccgcctaa ag                                              22

<210> SEQ ID NO 438

```
<211> LENGTH: 20
<212> TYPE: DNA
<213> ORGANISM: artificial sequence
<220> FEATURE:
<223> OTHER INFORMATION: Primer

<400> SEQUENCE: 438 catttttgc cctcgttatc                                              20

<210> SEQ ID NO 439
<211> LENGTH: 67
<212> TYPE: DNA
<213> ORGANISM: artificial sequence
<220> FEATURE:
<223> OTHER INFORMATION: Primer

<400> SEQUENCE: 439
aataactcaa ccgattttta agccccagct tcataaggaa ataatcgtg taggctggag   60 ctgcttc                                                           67

<210> SEQ ID NO 440
<211> LENGTH: 66
<212> TYPE: DNA
<213> ORGANISM: artificial sequence
<220> FEATURE:
<223> OTHER INFORMATION: Primer

<400> SEQUENCE: 440
cgcttaaaca gtaaaatgcc ggatgataat tccggctttt ttatctgcat atgaatatcc   60
tcctta                                                            66

<210> SEQ ID NO 441
<211> LENGTH: 78
<212> TYPE: DNA
<213> ORGANISM: artificial sequence
<220> FEATURE:
<223> OTHER INFORMATION: Hairpin

<400> SEQUENCE: 441
gcggggagcg tattagagtt ggatcggatg cagctggcta ctgacgtcat gacgtcagta   60
gccagcatgc atccgatc                                               78

<210> SEQ ID NO 442
<211> LENGTH: 239
<212> TYPE: PRT
<213> ORGANISM: Pseudoalteromonas sp. (strain SM9913)

<400> SEQUENCE: 442

Met Gly Asn Leu Ile Pro Pro Ser Lys Gln Ser Ala Val Thr Leu Glu
1               5                   10                  15

Pro Thr Asp Val Phe Ser Asp Leu Lys Ser Leu Pro Lys Pro Ala Gly
                20                  25                  30

Ser Ile Pro Val Ser Val Tyr Ser Phe Arg Asp Gln Thr Gly Gln Tyr
            35                  40                  45

Lys Pro Gln Thr Asn Val Ser Ser Phe Ser Thr Ala Val Thr Gln Gly
        50                  55                  60

Ala Asn Ser Ile Leu Val Gln Ala Leu His Glu Ser Asp Trp Phe Thr
65                  70                  75                  80

Pro Val Glu Arg Glu Gly Leu Gln Asn Ile Leu Thr Glu Arg Lys Ile
                85                  90                  95

Ile Arg Ala Ala Gln Ala Thr Asn Pro Asn Gln Gly Glu Leu Pro Pro
```

```
                100             105             110
Leu Thr Thr Ala Lys Ile Ile Leu Glu Gly Gly Ile Ile Ser Tyr Asp
            115                 120                 125

Thr Asn Val Lys Thr Gly Gly Leu Gly Met Glu Tyr Phe Gly Ile Gly
            130                 135             140

Ala Ser Glu Leu Tyr Arg Glu Asp Ala Ile Ser Ile Tyr Leu Arg Ala
145                     150                 155                 160

Val Asp Val Arg Thr Gly Gln Val Leu Leu Ser Val Ala Thr Ser Lys
                    165                 170                 175

Lys Val Leu Ser Gln Glu Met Arg Ala Gly Phe Phe Arg Tyr Val Ser
                180                 185                 190

Tyr Lys Arg Leu Ala Glu Ala Glu Ala Gly Phe Ser Asp Asn Glu Pro
            195                 200                 205

Met Ser Ile Cys Val Thr Gln Ala Ile Glu Lys Ala Leu Thr Asp Leu
            210                 215                 220

Ile Thr Lys Gly Ile Asp Lys Gly Leu Trp Ala Lys Gln Ala Thr
225                 230                 235
```

<210> SEQ ID NO 443
<211> LENGTH: 252
<212> TYPE: PRT
<213> ORGANISM: Shewanella baltica

<400> SEQUENCE: 443

```
Cys Ser Leu Ile Pro Lys Pro Asp Leu Asn Ile Thr Pro Ala Glu Val
1               5                   10                  15

Asn Pro Leu Ser Glu Val Met Arg Gly Leu Gln Thr Gln Pro Gly Pro
                20                  25                  30

Lys Phe Pro Ile Pro Val Ala Val Tyr Ser Phe Arg Asp Gln Thr Gly
            35                  40                  45

Gln Tyr Lys Pro Gln Ala Asn Val Ser Ser Phe Ser Thr Ala Val Thr
        50                  55                  60

Gly Gly Ala Thr Ser Met Leu Met Gln Thr Leu Leu Asp Ser Lys Trp
65                  70                  75                  80

Phe Thr Pro Val Glu Arg Glu Gly Leu Gln Asn Leu Leu Thr Glu Arg
                85                  90                  95

Lys Ile Ser Asn Lys Gln Ser Gly Thr Lys Gly Asp Asp Val Pro Val
            100                 105                 110

Leu Ser Thr Ala Arg Leu Leu Leu Glu Gly Gly Val Ile Ser Tyr Glu
            115                 120                 125

Thr Asn Thr Ser Thr Gly Gly Ser Gly Val Glu Tyr Tyr Gly Ile Gly
            130                 135             140

Ala Ser Glu Met Tyr Arg Glu Asp Gln Val Thr Ile Tyr Leu Arg Ala
145                     150                 155                 160

Val Asp Val His Thr Gly Lys Val Met Met Ser Val Ser Thr Ser Lys
                    165                 170                 175

Arg Val Leu Ser Gln Glu Met Arg Ala Gly Leu Phe Arg Tyr Thr Ser
                180                 185                 190

Leu Asn Arg Leu Ala Glu Ala Glu Ile Gly Phe Thr Thr Asn Glu Pro
            195                 200                 205

Val Gln Phe Cys Val Leu Gln Ala Ile Glu Leu Ala Val Ala Glu Leu
            210                 215                 220

Ile Asp Lys Gly Ile Lys Gln Gly Tyr Trp Ser Pro Thr Gln Val Thr
225                 230                 235                 240
```

-continued

Gln Pro Val Glu Lys Ala Gln Glu Leu Ser Gln Ser
                245                 250

<210> SEQ ID NO 444
<211> LENGTH: 264
<212> TYPE: PRT
<213> ORGANISM: Pseudomonas entomophila

<400> SEQUENCE: 444

Cys Gly Leu Arg Glu Pro Met Pro Ala Glu Gln Asp Ala Glu Thr Pro
1               5                   10                  15

Thr Leu Thr Pro Arg Ala Ser Thr Tyr Tyr Asp Leu Ile Asn Met Pro
            20                  25                  30

Arg Pro Arg Gly Arg Leu Met Ala Val Val Tyr Gly Phe Arg Asp Gln
        35                  40                  45

Thr Gly Gln Tyr Lys Pro Thr Pro Ala Ser Ser Phe Ser Thr Ser Val
    50                  55                  60

Thr Gln Gly Ala Ala Ser Met Leu Met Asp Ala Leu Asn Ala Ser Gly
65                  70                  75                  80

Trp Phe Val Val Leu Glu Arg Glu Gly Leu Gln Asn Leu Leu Thr Glu
                85                  90                  95

Arg Lys Ile Ile Arg Ala Ser Gln Lys Lys Pro Asp Val Ala Glu Asn
            100                 105                 110

Ile Gln Gly Glu Leu Pro Pro Leu Gln Ala Ala Asn Leu Met Leu Glu
        115                 120                 125

Gly Gly Ile Ile Ala Tyr Asp Thr Asn Val Arg Ser Gly Gly Glu Gly
    130                 135                 140

Ala Arg Tyr Leu Gly Ile Asp Ile Ser Arg Glu Tyr Arg Val Asp Gln
145                 150                 155                 160

Val Thr Val Asn Leu Arg Ala Val Asp Val Arg Thr Gly Gln Val Leu
                165                 170                 175

Ala Asn Val Met Thr Ser Lys Thr Ile Tyr Ser Val Gly Arg Ser Ala
            180                 185                 190

Gly Val Phe Lys Phe Ile Glu Phe Lys Lys Leu Leu Glu Ala Glu Val
        195                 200                 205

Gly Tyr Thr Thr Asn Glu Pro Ala Gln Leu Cys Val Leu Ser Ala Ile
    210                 215                 220

Glu Ala Ala Val Gly His Leu Leu Ala Gln Gly Ile Glu Arg Arg Leu
225                 230                 235                 240

Trp Gln Val Ala Ala Asp Gly Ala Gly Asp Lys Ala Leu Leu Asp Lys
                245                 250                 255

Tyr Leu Ser Gln Tyr Gln Gln Pro
            260

<210> SEQ ID NO 445
<211> LENGTH: 261
<212> TYPE: PRT
<213> ORGANISM: Hafnia alvei

<400> SEQUENCE: 445

Cys Ala Gly Met Val Ala Thr Ser Glu Asn Leu Glu Gly Ala Glu Ala
1               5                   10                  15

Thr Leu Thr Pro Arg Gly Ala Thr Tyr Gln Asp Leu Val Ser Leu Pro
            20                  25                  30

Pro Pro Ser Gly Lys Ile Phe Ser Val Tyr Asp Phe Arg Asp Gln
        35                  40                  45

```
Thr Gly Gln Tyr Arg Pro Ala Pro Ala Ser Thr Phe Ser Thr Ala Val
 50                  55                  60

Thr Gln Gly Ala Ala Met Leu Thr Gly Ser Leu Ser Asp Ser Gly
 65                  70                  75                  80

Trp Phe Ile Pro Leu Glu Arg Val Gly Leu Gln Asn Leu Leu Thr Glu
                 85                  90                  95

Arg Arg Ile Ile Arg Ala Glu Phe Glu Arg Phe Gly Gln Pro Asp Thr
                100                 105                 110

Leu Pro Ser Leu Arg Ala Ala Ser Val Met Leu Glu Gly Ile Ile
            115                 120                 125

Ala Tyr Glu Ser Asn Ile Arg Thr Gly Gly Ala Gly Ala Glu Tyr Phe
130                 135                 140

Gly Ile Gly Ala Ser Gly Gln Tyr Gln Val Asp Gln Val Thr Val Asn
145                 150                 155                 160

Leu Arg Ala Val Glu Ile Ser Thr Gly Glu Ile Leu Ala Asn Val Thr
                165                 170                 175

Thr Thr Lys Thr Ile Tyr Ser Lys Glu Leu Arg Ala Gly Val Tyr Arg
                180                 185                 190

Phe Ile Asp Phe Ser Arg Leu Leu Glu Ala Glu Ala Gly Ile Thr Ala
                195                 200                 205

Asn Glu Pro Val Gln Leu Ala Val Met Ser Ala Ile Glu Ser Ala Val
210                 215                 220

Ile His Leu Ile Ala Arg Gly Ile Glu Asn Arg Leu Trp Asn Leu Ala
225                 230                 235                 240

Pro Gly Val Ser Leu Gln Glu Ser Ile Leu Asn Asp Tyr Leu Asn Ala
                245                 250                 255

Pro Ile Pro Met Leu
                260

<210> SEQ ID NO 446
<211> LENGTH: 262
<212> TYPE: PRT
<213> ORGANISM: Escherichia coli

<400> SEQUENCE: 446

Cys Leu Thr Ala Pro Pro Lys Glu Ala Ala Arg Pro Thr Leu Met Pro
 1               5                  10                  15

Arg Ala Gln Ser Tyr Lys Asp Leu Thr His Leu Pro Ala Pro Thr Gly
                20                  25                  30

Lys Ile Phe Val Ser Val Tyr Asn Ile Gln Asp Glu Thr Gly Gln Phe
             35                  40                  45

Lys Pro Tyr Pro Ala Ser Asn Phe Ser Thr Ala Val Pro Gln Ser Ala
 50                  55                  60

Thr Ala Met Leu Val Thr Ala Leu Lys Asp Ser Arg Trp Phe Ile Pro
 65                  70                  75                  80

Leu Glu Arg Gln Gly Leu Gln Asn Leu Leu Asn Glu Arg Lys Ile Ile
                 85                  90                  95

Arg Ala Ala Gln Glu Asn Gly Thr Val Ala Ile Asn Asn Arg Ile Pro
                100                 105                 110

Leu Gln Ser Leu Thr Ala Ala Asn Ile Met Val Glu Gly Ser Ile Ile
            115                 120                 125

Gly Tyr Glu Ser Asn Val Lys Ser Gly Gly Val Gly Ala Arg Tyr Phe
130                 135                 140

Gly Ile Gly Ala Asp Thr Gln Tyr Gln Leu Asp Gln Ile Ala Val Asn
145                 150                 155                 160
```

```
Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260

<210> SEQ ID NO 447
<211> LENGTH: 263
<212> TYPE: PRT
<213> ORGANISM: Vibrio orientalis

<400> SEQUENCE: 447

Cys Ser Asn Ser Met Thr Ile Pro Asp Ala Asp Glu Ala Pro Thr Leu
1               5                   10                  15

Met Pro Arg Gly Ala Thr Tyr Gln Asp Leu Val Gln Leu Pro Glu Pro
            20                  25                  30

Lys Gly Arg Ile Leu Val Ser Val Tyr Asp Phe Arg Asp Gln Thr Gly
        35                  40                  45

Gln Tyr Lys Pro Gln Pro Asn Ser Asn Phe Ser Thr Ala Val Pro Gln
    50                  55                  60

Gly Gly Thr Ala Leu Leu Thr Ala Ser Leu Leu Asp Ser Arg Trp Phe
65                  70                  75                  80

Ile Pro Leu Glu Arg Glu Gly Leu Gln Asn Leu Leu Thr Glu Arg Lys
                85                  90                  95

Ile Ile Arg Ala Ala Gln Lys Lys Gly Gln Ala Ala Ser Asn His Gly
            100                 105                 110

Asp Asp Leu Ser Ala Leu Ser Ser Ala Asn Val Val Ile Glu Gly Gly
        115                 120                 125

Ile Val Ala Tyr Asp Ser Asn Ile Lys Thr Gly Gly Leu Gly Ala Arg
    130                 135                 140

Tyr Leu Gly Ile Gly Ser Ser Gly Lys Tyr Arg Thr Asp Gln Val Thr
145                 150                 155                 160

Val Asn Leu Arg Ala Val Asn Val Arg Thr Gly Gln Ile Leu Leu Ser
                165                 170                 175

Val Thr Thr Ser Lys Thr Ile Phe Ser His Glu Leu Thr Ala Gly Ala
            180                 185                 190

Phe Arg Phe Ile Asp Tyr Lys Asp Leu Leu Val Glu Met Gly Tyr
        195                 200                 205

Thr Asn Asn Glu Pro Val Asn Val Ala Val Met Ser Ala Ile Asp Ala
    210                 215                 220

Ala Val Ile His Leu Ile Val Lys Gly Ile Gly Arg Gly Leu Trp Gln
225                 230                 235                 240

Pro Glu Asn Lys Glu Asp Leu Gln Asp Glu Thr Ile Gln Arg Tyr Ala
                245                 250                 255

Lys Gln Thr His Gln Ile Leu
```

```
                    260

<210> SEQ ID NO 448
<211> LENGTH: 267
<212> TYPE: PRT
<213> ORGANISM: Shewanella pealeana

<400> SEQUENCE: 448

Cys Ser Thr Met Ser Glu Ile Glu Gln Ile Thr Pro Ser Ser Leu
1               5                   10                  15

Met Pro Lys Ser Glu Thr Tyr Tyr Asp Leu Ile Gly Leu Pro Ala Pro
            20                  25                  30

Gln Gly Ser Met Val Ala Ala Val Tyr Asp Phe Arg Asp Gln Thr Gly
        35                  40                  45

Gln Tyr Lys Pro Ile Pro Ser Ser Asn Phe Ser Thr Ala Val Pro Gln
    50                  55                  60

Ser Gly Thr Ala Phe Leu Ala Gln Ala Leu Asn Asp Ser Ser Trp Phe
65                  70                  75                  80

Thr Pro Val Glu Arg Glu Gly Leu Gln Asn Leu Leu Thr Glu Arg Lys
                85                  90                  95

Ile Val Arg Ala Gly Leu Lys Gly Asp Ala Ala Ser Leu Ser Gln Leu
            100                 105                 110

Asn Ser Ala Gln Ile Leu Met Glu Gly Gly Ile Val Ala Tyr Asp Thr
        115                 120                 125

Asn Ile Arg Thr Gly Gly Ala Gly Ala Arg Tyr Leu Gly Ile Gly Ala
    130                 135                 140

Ser Gly Gln Phe Arg Val Asp Ser Ile Thr Val Asn Leu Arg Ala Val
145                 150                 155                 160

Asp Ile Arg Thr Gly Arg Leu Leu Ser Ser Val Thr Thr Thr Lys Ser
                165                 170                 175

Val Leu Ser Lys Glu Leu Thr Ala Gly Val Phe Lys Phe Ile Asp Ala
            180                 185                 190

Gln Glu Leu Leu Glu Ser Glu Ile Gly Tyr Thr Ser Asn Glu Pro Val
        195                 200                 205

Ser Leu Cys Val Ala Gln Ala Ile Glu Ser Ala Val Val His Met Ile
    210                 215                 220

Ala Asp Gly Ile Trp Lys Arg Ala Trp Asn Leu Ala Asp Ser Gln Thr
225                 230                 235                 240

Gly Leu Glu Asn Pro Ile Leu Lys Lys Tyr Trp Leu Glu Ala His Ser
                245                 250                 255

Val Glu Arg Val Gln Ala Arg Leu Glu Gln Gly
            260                 265

<210> SEQ ID NO 449
<211> LENGTH: 21
<212> TYPE: PRT
<213> ORGANISM: artificial sequence
<220> FEATURE:
<223> OTHER INFORMATION: TM1 hairpin (figure 43)

<400> SEQUENCE: 449

Val Lys Ser Gly Gly Val Gly Ala Arg Tyr Phe Gly Ile Gly Ala Asp
1               5                   10                  15

Thr Gln Tyr Gln Leu
            20

<210> SEQ ID NO 450
```

```
<211> LENGTH: 27
<212> TYPE: PRT
<213> ORGANISM: artificial sequence
<220> FEATURE:
<223> OTHER INFORMATION: TM2 hairpin (figure 43)

<400> SEQUENCE: 450

Leu Ser Tyr Glu Val Gln Ala Gly Val Phe Arg Phe Ile Asp Tyr Gln
1               5                   10                  15

Arg Leu Leu Glu Gly Glu Val Gly Tyr Thr Ser
            20                  25

<210> SEQ ID NO 451
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 451

Met Gly Asn Leu Ile Pro Pro Ser Lys Gln Ser Ala Val Thr Leu Glu
1               5                   10                  15

Pro Thr Asp Val Phe Ser Asp Leu Lys Ser Leu Pro Lys Pro Ala Gly
            20                  25                  30

Ser Ile Pro Val Ser Val Tyr Ser Phe Arg Asp Gln Thr Gly Gln Tyr
        35                  40                  45

Lys Pro Gln Thr Asn Val Ser Ser Phe Ser Thr Ala Val Thr Gln Gly
    50                  55                  60

Ala Asn
65

<210> SEQ ID NO 452
<211> LENGTH: 68
<212> TYPE: PRT
<213> ORGANISM: Artificial Sequence
<220> FEATURE:
<223> OTHER INFORMATION: Synthetic polypeptide

<400> SEQUENCE: 452

Cys Ser Leu Ile Pro Lys Pro Asp Leu Asn Ile Thr Pro Ala Glu Val
1               5                   10                  15

Asn Pro Leu Ser Glu Val Met Arg Gly Leu Gln Thr Gln Pro Gly Pro
            20                  25                  30

Lys Phe Pro Ile Pro Val Ala Val Tyr Ser Phe Arg Asp Gln Thr Gly
        35                  40                  45

Gln Tyr Lys Pro Gln Ala Asn Val Ser Ser Phe Ser Thr Ala Val Thr
    50                  55                  60

Gln Gly Ala Thr
65

<210> SEQ ID NO 453
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 453

Cys Gly Leu Arg Glu Pro Met Pro Ala Glu Gln Asp Ala Glu Thr Pro
1               5                   10                  15

Thr Leu Thr Pro Arg Ala Ser Thr Tyr Tyr Asp Leu Ile Asn Met Pro
            20                  25                  30
```

Arg Pro Arg Gly Arg Leu Met Ala Val Val Tyr Gly Phe Arg Asp Gln
            35                  40                  45

Thr Gly Gln Tyr Lys Pro Thr Pro Ala Ser Ser Phe Ser Thr Ser Val
        50                  55                  60

Thr Gln Gly Ala Ala
65

<210> SEQ ID NO 454
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 454

Cys Ala Gly Met Val Ala Thr Ser Glu Asn Leu Glu Gly Ala Glu Ala
1               5                   10                  15

Thr Leu Thr Pro Arg Gly Ala Thr Tyr Gln Asp Leu Val Ser Leu Pro
            20                  25                  30

Pro Pro Ser Gly Lys Ile Phe Val Ser Val Tyr Asp Phe Arg Asp Gln
        35                  40                  45

Thr Gly Gln Tyr Arg Pro Ala Pro Ala Ser Thr Phe Ser Thr Ala Val
    50                  55                  60

Thr Gln Gly Ala Ala
65

<210> SEQ ID NO 455
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 455

Cys Leu Thr Ala Pro Pro Lys Gln Ala Ala Lys Pro Thr Leu Met Pro
1               5                   10                  15

Arg Ala Gln Ser Tyr Gln Asp Leu Thr His Leu Pro Glu Pro Ala Gly
            20                  25                  30

Lys Leu Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr
65

<210> SEQ ID NO 456
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 456

Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

-continued

Lys Pro Tyr Pro Ala Ser Asn Phe Ser Thr Ala Val Pro Gln Ser Ala
            50                  55                  60

Thr
65

<210> SEQ ID NO 457
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 457

Cys Ser Asn Ser Met Thr Ile Pro Asp Ala Asp Glu Ala Pro Thr Leu
1               5                   10                  15

Met Pro Arg Gly Ala Thr Tyr Gln Asp Leu Val Gln Leu Pro Glu Pro
            20                  25                  30

Lys Gly Arg Ile Leu Val Ser Val Tyr Asp Phe Arg Asp Gln Thr Gly
        35                  40                  45

Gln Tyr Lys Pro Gln Pro Asn Ser Asn Phe Ser Thr Ala Val Pro Gln
    50                  55                  60

Gly Gly Thr
65

<210> SEQ ID NO 458
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 458

Cys Ser Thr Met Ser Glu Ile Glu Gln Ile Thr Pro Ser Ser Ser Leu
1               5                   10                  15

Met Pro Lys Ser Glu Thr Tyr Tyr Asp Leu Ile Gly Leu Pro Ala Pro
            20                  25                  30

Gly Ser Met Val Ala Ala Val Tyr Asp Phe Arg Asp Gln Thr Gln Tyr
        35                  40                  45

Lys Pro Ile Pro Ser Ser Asn Phe Ser Thr Ala Val Pro Gln Ser Gly
    50                  55                  60

Thr
65

<210> SEQ ID NO 459
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 459

Ser Ile Leu Val Gln Ala Leu His Glu Ser Asp Trp Phe Thr Pro Val
1               5                   10                  15

Glu Arg Glu Gly Leu Gln Asn Ile Leu Thr Glu Arg Lys Ile Ile Arg
            20                  25                  30

Ala Ala Gln Ala Thr Asn Pro Asn Gln Gly Glu Leu Pro Pro Leu Thr
        35                  40                  45

Thr Ala Lys Ile Ile Leu Glu Gly Gly Ile Ile Ser Tyr Asp Thr Asn
    50                  55                  60

Val Lys

<210> SEQ ID NO 460
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 460

```
Ser Met Leu Met Gln Thr Leu Leu Asp Ser Lys Trp Phe Thr Pro Val
1               5                   10                  15
Glu Arg Glu Gly Leu Gln Asn Leu Leu Thr Glu Arg Lys Ile Ser Asn
            20                  25                  30
Lys Gln Ser Gly Thr Lys Gly Asp Asp Val Pro Val Leu Ser Thr Ala
        35                  40                  45
Arg Leu Leu Glu Gly Gly Val Ile Ser Tyr Glu Thr Asn Thr Ser
    50                  55                  60
```

<210> SEQ ID NO 461
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 461

```
Ser Met Leu Met Asp Ala Leu Asn Ala Ser Gly Trp Phe Val Val Leu
1               5                   10                  15
Glu Arg Glu Gly Leu Gln Asn Leu Leu Thr Glu Arg Lys Ile Ile Arg
            20                  25                  30
Ala Ser Gln Lys Lys Pro Asp Val Ala Glu Asn Ile Gln Gly Glu Leu
        35                  40                  45
Pro Pro Leu Gln Ala Ala Asn Leu Met Leu Glu Gly Ile Ile Ala
    50                  55                  60
Tyr Asp Thr Asn Val Arg
65                  70
```

<210> SEQ ID NO 462
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 462

```
Ala Met Leu Thr Gly Ser Leu Ser Asp Ser Gly Trp Phe Ile Pro Leu
1               5                   10                  15
Glu Arg Val Gly Leu Gln Asn Leu Leu Thr Glu Arg Arg Ile Ile Arg
            20                  25                  30
Ala Glu Phe Glu Arg Phe Gly Gln Pro Asp Thr Leu Pro Ser Leu Arg
        35                  40                  45
Ala Ser Val Met Leu Glu Gly Gly Ile Ile Ala Tyr Glu Ser Asn Ile
    50                  55                  60
Arg
65
```

<210> SEQ ID NO 463
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 463

Ala Met Leu Val Ser Ala Leu Lys Asp Ser Gly Trp Phe Ile Pro Leu
1               5                   10                  15

Glu Arg Gln Gly Leu Gln Asn Leu Leu Asn Glu Arg Lys Ile Ile Arg
            20                  25                  30

Ala Ala Gln Glu Asn Gly Thr Val Ala Val Asn Asn Gln Arg Gln Leu
        35                  40                  45

Ser Ser Leu Val Ala Ala Asn Val Leu Ile Glu Gly Ser Ile Gly
    50                  55                  60

Tyr Glu Ser Asn Val Lys
65                  70

<210> SEQ ID NO 464
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 464

Ala Met Leu Val Thr Ala Leu Lys Asp Ser Arg Trp Phe Ile Pro Leu
1               5                   10                  15

Glu Arg Gln Gly Leu Gln Asn Leu Leu Asn Glu Arg Lys Ile Ile Arg
            20                  25                  30

Ala Ala Gln Glu Asn Gly Thr Val Ala Ile Asn Asn Arg Ile Pro Leu
        35                  40                  45

Gln Ser Leu Thr Ala Ala Asn Ile Met Val Glu Gly Ser Ile Ile Gly
    50                  55                  60

Tyr Glu Ser Asn Val Lys
65                  70

<210> SEQ ID NO 465
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 465

Ala Leu Leu Thr Ala Ser Leu Leu Asp Ser Arg Trp Phe Ile Pro Leu
1               5                   10                  15

Glu Arg Glu Gly Leu Gln Asn Leu Leu Thr Glu Arg Lys Ile Ile Arg
            20                  25                  30

Ala Ala Gln Lys Lys Gly Gln Ala Ala Ser Asn His Gly Asp Asp Leu
        35                  40                  45

Ser Ala Leu Ser Ser Ala Asn Val Val Ile Glu Gly Gly Ile Val Ala
    50                  55                  60

Tyr Asp Ser Asn Ile Lys
65                  70

<210> SEQ ID NO 466
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 466

```
Ala Phe Leu Ala Gln Ala Leu Asn Asp Ser Ser Trp Phe Thr Pro Val
1               5                   10                  15

Glu Arg Glu Gly Leu Gln Asn Leu Leu Thr Glu Arg Lys Ile Val Arg
            20                  25                  30

Ala Gly Leu Lys Gly Asp Ala Ala Ser Leu Ser Gln Leu Asn Ser Ala
            35                  40                  45

Gln Ile Leu Met Glu Gly Gly Ile Val Ala Tyr Asp Thr Asn Ile Arg
    50                  55                  60
```

<210> SEQ ID NO 467
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 467

```
Thr Gly Gly Leu Gly Met Glu Tyr Phe Gly Ile Gly Ala Ser Glu Leu
1               5                   10                  15

Tyr Arg Glu Asp Ala Ile Ser Ile Tyr Leu Arg Ala Val Asp Val Arg
            20                  25                  30

Thr Gly Gln Val Leu Leu Ser Val Ala Thr Ser Lys Lys Val Leu Ser
            35                  40                  45

Gln Glu Met Arg Ala Gly Phe Phe Arg Tyr Val Ser Tyr Lys Arg Leu
    50                  55                  60

Ala Glu Ala Glu Ala Gly
65                  70
```

<210> SEQ ID NO 468
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 468

```
Thr Gly Gly Ser Gly Val Glu Tyr Tyr Gly Ile Gly Ala Ser Glu Met
1               5                   10                  15

Tyr Arg Glu Asp Gln Val Thr Ile Tyr Leu Arg Ala Val Asp Val His
            20                  25                  30

Thr Gly Lys Val Met Met Ser Val Ser Thr Ser Lys Arg Val Leu Ser
            35                  40                  45

Gln Glu Met Arg Ala Gly Leu Phe Arg Tyr Thr Ser Leu Asn Arg Leu
    50                  55                  60

Ala Glu Ala Glu Ile Gly
65                  70
```

<210> SEQ ID NO 469
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 469

```
Ser Gly Gly Glu Gly Ala Arg Tyr Leu Gly Ile Asp Ile Ser Arg Glu
1               5                   10                  15

Tyr Arg Val Asp Gln Val Thr Val Asn Leu Arg Ala Val Asp Val Arg
            20                  25                  30
```

Thr Gly Gln Val Leu Ala Asn Val Met Thr Ser Lys Thr Ile Tyr Ser
            35                  40                  45

Val Gly Arg Ser Ala Gly Val Phe Lys Phe Ile Glu Phe Lys Lys Leu
 50                  55                  60

Leu Glu Ala Val Gly
 65

<210> SEQ ID NO 470
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 470

Thr Gly Gly Ala Gly Ala Glu Tyr Phe Gly Ile Gly Ala Ser Gly Gln
 1               5                  10                  15

Tyr Gln Val Asp Gln Val Thr Val Asn Leu Arg Ala Val Glu Ile Ser
                20                  25                  30

Thr Gly Glu Ile Leu Ala Asn Val Thr Thr Lys Thr Ile Tyr Ser Lys
            35                  40                  45

Glu Leu Arg Ala Gly Val Tyr Arg Phe Ile Asp Phe Ser Arg Leu Leu
 50                  55                  60

Glu Ala Glu Ala Gly
 65

<210> SEQ ID NO 471
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 471

Ser Gly Gly Ala Gly Ala Arg Phe Phe Gly Ile Gly Ala Ser Thr Gln
 1               5                  10                  15

Tyr Gln Leu Asp Gln Ile Ala Val Asn Leu Arg Val Val Asp Val Asn
                20                  25                  30

Thr Gly Gln Val Leu Ser Ser Val Asn Thr Ser Lys Thr Ile Leu Ser
            35                  40                  45

Tyr Glu Val Gln Ala Gly Val Phe Arg Tyr Ile Asp Tyr Gln Arg Leu
 50                  55                  60

Leu Glu Gly Lys Ile Gly
 65                  70

<210> SEQ ID NO 472
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 472

Ser Gly Gly Val Gly Ala Arg Tyr Phe Gly Ile Gly Ala Asp Thr Gln
 1               5                  10                  15

Tyr Gln Leu Asp Gln Ile Ala Val Asn Leu Arg Val Val Asn Val Ser
                20                  25                  30

Thr Gly Glu Ile Leu Ser Ser Val Asn Thr Ser Lys Thr Ile Leu Ser
            35                  40                  45

Tyr Glu Val Gln Ala Gly Val Phe Arg Phe Ile Asp Tyr Gln Arg Leu

```
                 50                  55                  60

Leu Glu Gly Glu Val Gly
 65                  70

<210> SEQ ID NO 473
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 473

Thr Gly Gly Leu Gly Ala Arg Tyr Leu Gly Ile Gly Ser Ser Gly Lys
  1               5                  10                  15

Tyr Arg Thr Asp Gln Val Thr Val Asn Leu Arg Ala Val Asn Val Arg
                 20                  25                  30

Thr Gly Gln Ile Leu Leu Ser Val Thr Thr Ser Lys Thr Ile Phe Ser
             35                  40                  45

His Glu Leu Thr Ala Gly Ala Phe Arg Phe Ile Asp Tyr Lys Asp Leu
         50                  55                  60

Leu Glu Val Glu Met Gly
 65                  70

<210> SEQ ID NO 474
<211> LENGTH: 70
<212> TYPE: PRT
<213> ORGANISM: Artificial Sequence
<220> FEATURE:
<223> OTHER INFORMATION: Synthetic polypeptide

<400> SEQUENCE: 474

Thr Gly Gly Ala Gly Ala Arg Tyr Leu Gly Ile Gly Ala Ser Gly Gln
  1               5                  10                  15

Phe Arg Val Asp Ser Ile Thr Val Asn Leu Arg Ala Val Asp Ile Arg
                 20                  25                  30

Thr Gly Arg Leu Leu Ser Ser Val Thr Thr Lys Ser Val Leu Ser
             35                  40                  45

Lys Glu Leu Thr Ala Gly Val Phe Lys Phe Ile Asp Ala Gln Glu Leu
         50                  55                  60

Leu Glu Ser Glu Ile Gly
 65                  70

<210> SEQ ID NO 475
<211> LENGTH: 37
<212> TYPE: PRT
<213> ORGANISM: Artificial Sequence
<220> FEATURE:
<223> OTHER INFORMATION: Synthetic polypeptide

<400> SEQUENCE: 475

Phe Ser Asp Asn Glu Pro Met Ser Ile Cys Val Thr Gln Ala Ile Glu
  1               5                  10                  15

Lys Ala Leu Thr Asp Leu Ile Thr Lys Gly Ile Asp Lys Gly Leu Trp
                 20                  25                  30

Ala Lys Gln Ala Thr
             35

<210> SEQ ID NO 476
<211> LENGTH: 50
<212> TYPE: PRT
<213> ORGANISM: Artificial Sequence
```

```
<220> FEATURE:
<223> OTHER INFORMATION: Synthetic polypeptide

<400> SEQUENCE: 476

Phe Thr Thr Asn Glu Pro Val Gln Phe Cys Val Leu Gln Ala Ile Glu
1               5                   10                  15

Leu Ala Val Ala Glu Leu Ile Asp Lys Gly Ile Lys Gln Gly Tyr Trp
            20                  25                  30

Ser Pro Thr Gln Val Thr Gln Pro Val Glu Lys Ala Gln Glu Leu Ser
        35                  40                  45

Gln Ser
    50

<210> SEQ ID NO 477
<211> LENGTH: 55
<212> TYPE: PRT
<213> ORGANISM: Artificial Sequence
<220> FEATURE:
<223> OTHER INFORMATION: Synthetic polypeptide

<400> SEQUENCE: 477

Tyr Thr Thr Asn Glu Pro Ala Gln Leu Cys Val Leu Ser Ala Ile Glu
1               5                   10                  15

Ala Ala Val Gly His Leu Leu Ala Gln Gly Ile Glu Arg Arg Leu Trp
            20                  25                  30

Gln Val Ala Ala Asp Gly Ala Gly Asp Lys Ala Leu Leu Asp Lys Tyr
        35                  40                  45

Leu Ser Gln Tyr Gln Gln Pro
    50                  55

<210> SEQ ID NO 478
<211> LENGTH: 56
<212> TYPE: PRT
<213> ORGANISM: Artificial Sequence
<220> FEATURE:
<223> OTHER INFORMATION: Synthetic polypeptide

<400> SEQUENCE: 478

Ile Thr Ala Asn Glu Pro Val Gln Leu Ala Val Met Ser Ala Ile Glu
1               5                   10                  15

Ser Ala Val Ile His Leu Ile Ala Glu Gly Ile Glu Asn Arg Leu Trp
            20                  25                  30

Asn Leu Ala Pro Gly Val Ser Leu Gln Glu Ser Ile Leu Asn Asp Tyr
        35                  40                  45

Leu Asn Ala Pro Ile Pro Met Leu
    50                  55

<210> SEQ ID NO 479
<211> LENGTH: 57
<212> TYPE: PRT
<213> ORGANISM: Artificial Sequence
<220> FEATURE:
<223> OTHER INFORMATION: Synthetic polypeptide

<400> SEQUENCE: 479

Tyr Thr Thr Asn Glu Pro Val Met Leu Cys Val Met Ser Ala Ile Glu
1               5                   10                  15

Thr Gly Val Ile Tyr Leu Val Asn Asp Gly Ile Thr Arg Asn Leu Trp
            20                  25                  30

Ser Leu Lys Asn Ala Lys Asp Val Thr Ser Pro Ile Leu Glu Arg Tyr
        35                  40                  45
```

```
Lys Ser Thr Ile Val Pro Ile Ala Ser
    50                  55

<210> SEQ ID NO 480
<211> LENGTH: 57
<212> TYPE: PRT
<213> ORGANISM: Artificial Sequence
<220> FEATURE:
<223> OTHER INFORMATION: Synthetic polypeptide

<400> SEQUENCE: 480

Tyr Thr Ser Asn Glu Pro Val Met Leu Cys Leu Met Ser Ala Ile Glu
1               5                   10                  15

Thr Gly Val Ile Phe Leu Ile Asn Asp Gly Ile Asp Arg Gly Leu Trp
            20                  25                  30

Asp Leu Gln Asn Lys Ala Glu Arg Gln Asn Asp Ile Leu Val Lys Tyr
        35                  40                  45

Arg His Met Ser Val Pro Pro Glu Ser
    50                  55

<210> SEQ ID NO 481
<211> LENGTH: 56
<212> TYPE: PRT
<213> ORGANISM: Artificial Sequence
<220> FEATURE:
<223> OTHER INFORMATION: Synthetic polypeptide

<400> SEQUENCE: 481

Tyr Thr Asn Asn Glu Pro Val Asn Val Ala Val Met Ser Ala Ile Asp
1               5                   10                  15

Ala Ala Val Ile His Leu Ile Val Lys Gly Ile Gly Arg Gly Leu Trp
            20                  25                  30

Gln Pro Glu Asn Lys Glu Asp Leu Gln Asp Glu Thr Ile Gln Arg Tyr
        35                  40                  45

Ala Lys Gln Thr His Gln Ile Leu
    50                  55

<210> SEQ ID NO 482
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 482

Tyr Thr Ser Asn Glu Pro Val Ser Leu Cys Val Ala Gln Ala Ile Glu
1               5                   10                  15

Ser Ala Val Val His Met Ile Ala Asp Gly Ile Trp Lys Arg Ala Trp
            20                  25                  30

Asn Leu Ala Asp Ser Gln Thr Gly Leu Glu Asn Pro Ile Leu Lys Lys
        35                  40                  45

Tyr Trp Leu Glu Ala His Ser Val Glu Arg Val Gln Ala Arg Leu Glu
    50                  55                  60

Gln Gly
65
```